(12) United States Patent
Draper et al.

(10) Patent No.: US 7,045,507 B2
(45) Date of Patent: May 16, 2006

(54) SUBSTITUTED TETRACYCLINE COMPOUNDS AS SYNERGISTIC ANTIFUNGAL AGENTS

(75) Inventors: Michael Draper, Plaistow, NH (US); Mark L. Nelson, Wellesley, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 366 days.

(21) Appl. No.: 10/097,634

(22) Filed: Mar. 14, 2002

(65) Prior Publication Data

US 2003/0166585 A1 Sep. 4, 2003

Related U.S. Application Data

(60) Provisional application No. 60/275,899, filed on Mar. 14, 2001.

(51) Int. Cl.
*A61K 31/70* (2006.01)
*A61K 31/65* (2006.01)
*A61K 31/415* (2006.01)

(52) U.S. Cl. .................. 514/31; 514/152; 514/394; 514/395

(58) Field of Classification Search .............. 514/31, 514/152, 394, 395
See application file for complete search history.

(56) References Cited

U.S. PATENT DOCUMENTS

| | | | |
|---|---|---|---|
| 2,980,584 A | 4/1961 | Hammer | 167/65 |
| 2,990,331 A | 6/1961 | Neumann et al. | 167/65 |
| 3,062,717 A | 11/1962 | Hammer | 167/65 |
| 3,165,531 A | 1/1965 | Blackwood et al. | 260/330.5 |
| 3,454,697 A | 7/1969 | Joyner et al. | 424/227 |
| 3,557,280 A | 1/1971 | Weber et al. | 424/80 |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 4,168,206 A | 9/1979 | Boyer | |
| 5,362,754 A | 11/1994 | Raad et al. | |
| 5,532,227 A | 7/1996 | Golub et al. | 514/152 |
| 5,639,742 A | 6/1997 | Lee et al. | 514/152 |
| 5,688,516 A | 11/1997 | Raad et al. | |
| 5,789,395 A | 8/1998 | Amin et al. | 514/152 |
| 5,834,450 A | 11/1998 | Su | 514/152 |
| 6,509,319 B1 | 1/2003 | Raad et al. | |

FOREIGN PATENT DOCUMENTS

| | | |
|---|---|---|
| DE | 28 14 974 A | 10/1978 |
| DE | 28 20 983 A1 | 10/1979 |

OTHER PUBLICATIONS

Koza, D.J. et al. "Synthesis of 7–Substituted Tetracycline Derivatives," *Organic Letters* 2(6):815–817 (2000).
Koza, D.J. et al. "Synthesis and biological evaluation of 9–substituted tetracycline derivatives," *Bioorganic & Medicinal Chemistry Letters* 12:2163–65 (2002).
Lew, M.A. et al. Combined activity of minocycline and amphotericin B in vitro against medically imported yeasts. *Antimicrob. Agents Chemother*. 1978 Sep.;14(3):465–469.
Nelson, M.L. et al. Inhibition of the tetracycline efflux antiport protein by 13–thio–substituted 5–hydroxy–6–deoxytetracyclines. *J. Med. Chem*. 1993 Feb. 5;36(3):370–377.
Roy, S. Use of tetracycline sorbate for the treatment of *Aspergillus fumigatus* infection in broiler chicks. *Br. Vet. J.* 1991;147:549–555.
Schwartz, S.N. et al. Antifungal properties of polymyxin B and its potentiation of tetracycline as an antifungal agent. *Antimicrobial agents and chemotherapy* 1972 Jul;2:36–40.
Thong, Y.H. et al. Synergism between tetracycline and amphotericin B in experimental amoebic meningoencephalitis. *Med. J. Aust*. 1978 Jun. 17;1:663–664.
Waterworth, P.M. The effect of minocycline on *Candida albicans*. *J. Clin. Path*. 1974;24:269–272.
Hughes, C.E. et al. Enhancement of the in vitro activity of amphotericin B against *Aspergillus* spp. by tetracycline analogs. *Antimicrob. Agents Chemother*. Dec. 1984;26(6):837–40.
Huppert, M. et al. Combined amphotericin B–tetracycline therpy for experimental coccidioidomycosis. *Antimicrob. Agents Chemother*. May 1974;5(5):473–478.
Kwan, C.N. et al. Potentiation of the antifungal effects of antibiotics by amphotericin B. *Antimicrob. Agents Chemother*. 1972 Aug. 1972;2(2):61–65.
Lavarde, V. et al. [Effect of minocycline on Candida albicans. "In vitro" study: comparison with tetracycline] *Pathol. Biol*. (French). Nov. 1975;23(9):725–728 (English abstr. provided).
Lew, M.A. et al. Antifungal activity of four tetracycline analogues against *Candida albicans* in vitro: Potentiation by amphotericin B. *J. Infect. Dis*. Aug. 1977;136(2):263–270.

*Primary Examiner*—Kevin E. Weddington
(74) *Attorney, Agent, or Firm*—Lahive & Cockfield, LLP; Elizabeth A. Hanley, Esq.; Cynthia M. Soroos, Esq.

(57) ABSTRACT

Methods and compositions for treating for the synergistic treatment of fungal associated disorders are discussed.

75 Claims, No Drawings

SUBSTITUTED TETRACYCLINE COMPOUNDS AS SYNERGISTIC ANTIFUNGAL AGENTS

RELATED APPLICATIONS

This application claims priority to U.S. Provisional Patent Application Ser. No. 60/275,899, entitled "Substituted Tetracycline Compounds as Synergistic Antifungal Agents," filed Mar. 14, 2001, incorporated herein by reference in its entirety.

BACKGROUND OF THE INVENTION

For many years, the development of effective therapeutic agents for fungal diseases (mycoses) has lacked the attention devoted to drugs effective against other infective organisms. The most common mycotic infections are superficial in nature, are not life threatening, and provide little medical impetus to pharmaceutical companies to develop novel treatments. This scenario is changing, however, and while death from fungal disease is not new, the incidence of systemic fungal infections that cause these fatalities is increasing. Ironically, advances in modern medical techniques in other fields (immunosuppressive and/or cytotoxic therapy) and the advent of disease such as Acquired Immuno Deficiency Syndrome (AIDS) are major contributing causes to the increased number of serious fungal infections.

Fungal disorders can, thus, be divided into the life-threatening systemic infections, such as histoplasmosis, systemic candidiasis, aspergillosis, blastomycosis, coccidioidomycosis, paracoccidioidomycosis, and cryptococcosis, and the more common superficial ones, such as dermatophyte (ringworm) infections, for example, tinea pedis (athlete's foot) and tinea cruris (jock itch), candidiasis, and actinomycosis. The life-threatening fungal infections are a growing problem not only for immunosuppressed or immunocompromised individuals as noted above but individuals with other viral infections, such as cytomegalovirus (CMV), and influenza, for cancer patients receiving chemotherapy or radiotherapy, for transplant patients receiving antirejection agents, and for patients that have received toxic chemicals, metals and radiation exposure.

Mycoses are often caused by fungi which are opportunists, rather than pathogens. Candidiasis, aspergillosis, phycomycosis, nocardiosis, and cryptococcosis are typically opportunistic fungal infections. For example, *Candida albicans*, is normally found in the alimentary tract as a commensal, yet it is a major cause of systemic fungal infections in immunocomprised patients and topical infections in healthy individuals.

Most drugs currently available for the treatment of mycoses have limited efficacy or are poorly tolerated. A persistent and vexatious problem with antifungal agents, largely unattended by the prior art, is the lack of an agent that is easy and economical to synthesize, and possesses high activity and broad spectrum activity against organisms, low toxicity and limited adverse effects.

Moreover, many known agents merely have fungistatic properties, rather than fungicidal properties. Fungistatic activity is the ability to prevent growth of fungi, while fungicidal (fungitoxic) activity is the ability to kill the fingi. Many agents used in the treatment of superficial mycoses are virtually devoid of either fungistatic or fungicidal actions in the concentrations used, and their beneficial effects probably depend upon factors not related to any direct effect on fungi.

Despite a plethora of agents which have or are alleged to have antifungal properties, most are simply fungistatic and not fungitoxic. For those that are fungicidal, for example, amphotericin B, there are severe adverse side effects which limit their use and their chemical properties, e.g., solubility, limit drug delivery method.

SUMMARY OF THE INVENTION

The invention pertains, at least in part, to methods foe increasing the antifungal activity of an antifungal agent. The method includes administering the antifungal agent with an effective amount of a substituted tetracycline compound, such that the antifungal activity of the antifungal agent is increased. Examples of antifungal agents include polyenes such as amphotericin B. Examples of substituted tetracycline compounds include compounds of formula I:

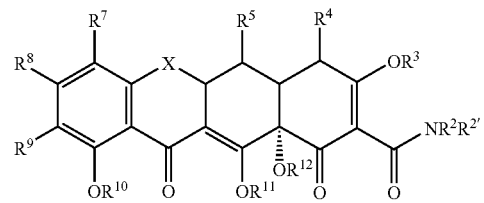

X is $CHC(R^{13}Y'Y)$, $C=CR^{13}Y$, $CR^{6'}R^6$, S, $NR^6$, or O;

$R^2$, $R^{2'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^4R^{4''}$, alkyl, alkenyl, alkynyl, hydroxyl, halogen, or hydrogen;

$R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or $-(CH_2)_{0-3}NR^{7c}C(=W')WR^{7a}$;

$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., $-N=S$), or $-(CH_2)_{0-3}NR^{9c}C(=Z')ZR^{9a}$;

Z is $CR^{9d}R^{9e}$, S, $NR^{9b}$ or O;

Z' is O, S, or NR;

W is $CR^{7d}R^{7e}$, S, $NR^{7b}$ or O;

W' is O, $NR^{7f}$ S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

In an embodiment, the invention includes methods for treating fungal associated disorders in subjects. The methods include administering to a subject an effective amount of a substituted tetracycline compound in combination with an antifungal agent such that the subject is treated for the fungal associated disorder.

The invention also pertains, at least in part, to methods for treating fungal associated disorders in mammals. The method includes administering to the mammal a synergistically effective amount of a substituted tetracycline compound in combination with an effective amount of amphotericin B, such that the mammal is treated for the fungal associated disorder.

In another embodiment, the invention pertains to a pharmaceutical composition which contains a synergistically effective amount of a substituted tetracycline compound, an effective amount of an antifungal agent, and, optionally, a pharmaceutically acceptable carrier.

The invention also pertains, at least in part, to a method for killing fungus. The method includes contacting the fungus with a synergistically effective amount of a substituted tetracycline compound and a effective amount of an antifingal agent.

DETAILED DESCRIPTION OF THE INVENTION

Although opportunistic systemic fungal infections have a high morbidity and mortality and their incidence is increasing, the art has yet to provide a safe, effective water soluble, simple-to-synthesize, fungitoxic agent with a broad antifungal spectrum of activity coupled with limited adverse effects and low toxicity.

The invention pertains, at least in part, to methods for increasing the antifungal activity of an antifungal agent, by administering an antifungal agent in combination with an effective amount of a substituted tetracycline compound. Previously, unsubstituted minocycline and doxycycline have been shown to possess limited antifungal activity both alone and in synergy with amphotericin B (*Antimicrob. Agents Chemother*. (1984), 26(6)837–40; *Pathol. Biol.* (1975) 23(9): 725–8). However, both unsubstituted minocycline and doxycycline are limited by both low synergistic activity as well as high levels of cytotoxicity.

The terms "fungus" or "fungi" include a variety of nucleated, sporebearing organisms which are devoid of chlorophyll. Examples include yeasts, mildews, molds, rusts, and mushrooms. Examples of fungi include, but are not limited to *Aspergillus fumigatus, Aspergillus flavus, Aspergillus nidulans, Candida albicans, Candida glabrata, Candida guilliermondii, Candida krusei, Candida lusitaniae, Candida parapsilosis, Candida tropicalis, Cryptococcus neoformans, Issatchenkia orientalis, Coccidioides, Paracoccidioides, Histoplasma, Blastomyces,* and *Neurospora crassa*. In one embodiment, the fungi of the invention includes fungi of the genus *Candida* (e.g., *C. tropicalis, C. parapsilosis, C. lusitaniae, C. krusei, C. guilliermondii, C. glabrata, C. dubliniensis,* and *C. albicans*).

The term "antifungal agent" includes agents which are known in the art to have fungistatic or fungicidal activity, which can be synergistically increased using the compounds of the invention. Examples of antifungal agents include but are not limited to, azoles (e.g., Fluconazole®, Itraconazole®, Ketoconazole®, Miconazole®, Clortrimazole®, Voriconazole ®, Posaconazole®, Rovuconazole®, etc.), polyenes (e.g., natamycin, lucensomycin, nystatin, amphotericin B, etc.), echinocandins (e.g., Cancidas®), pradimicins (e.g., beanomicins, nikkomycins, sordarins, allylamines, etc.) and derivatives and analogs thereof.

The term "antifungal activity" includes inhibiting the growth of a fungus (e.g., fungistatic activity), killing at least a portion of the fungus (e.g., fungicidal activity), limiting the ability of the fungus to reproduce, etc.

The term "inhibiting the growth of a fungus" includes both fungistatic and fungicidal activity. Fungistatic activity includes any decrease in the rate of growth of a fungal colony. Fungistatic activity may be manifested by a fungus maintaining its present size or failing to colonize the surrounding areas. Fungistatic activity may be a result of inhibition of the fungal reproductive processes. Fungicidal activity generally includes, for example, irraditication of a fungus or fungal colony, killing a fungus or fungal colony or, in one embodiment, a decrease in the mass or size of a fungus or fungal colony.

In one embodiment, the antifungal activity of the antifungal agent is increased when administered in combination with a substituted tetracycline compound of the invention, thereby reducing the effective amount of the antifungal agent required as compared to the amount required when the antifungal agent is administered alone. In one embodiment, the coadministration of a substituted tetracycline compound of the invention reduces the effective amount of the antifungal agent by 1 fold, 2 fold, 3 fold, 4 fold, 5 fold, 6 fold, 7 fold, 8 fold, 9 fold, or 10 fold, as compared to the effective amount of the antifungal agent alone, e.g., without the aid of a substituted tetracycline compound or another synergistic agent. Advantageously, the substituted tetracycline compound has low cell toxicity and may exhibit low (or, in some embodiments, no) antibacterial activity, e.g., as measured in Example 4. Substituted tetracycline compounds with low antibacterial activity may be compounds with MIC of 4 µm or greater. In certain embodiments, the substituted tetracycline compounds of the invention may have anti-inflammatory activity, e.g., as measured by art recognized assays. The cell toxicity of particular substituted tetracycline compounds, antifungal agents, and combinations thereof can be measured using the assay given in Example 3.

The language "effective amount" of the antifungal agent is the amount necessary or sufficient to inhibit the growth of fungus, or in certain instances, to kill the fungus. In an embodiment, the effective amount of the antifungal agent is reduced when administered in combination with a substituted tetracycline compound of the invention.

The term "tetracycline compounds" includes tetracycline family members such as methacycline, sancycline, apicycline, clomocycline, guamecycline, meglucycline, mepylcycline, penimepicycline, pipacycline, etamocycline, penimocycline, etc. as well as other tetracycline compounds having the characteristic naphthacene A-B-C-D ring structure. Additional tetracycline compounds can be found, for example, in U.S. patent application Ser. No. 09/234,847, and U.S. Pat. Nos. 5,834,450; 5,532,227; 5,789,395; 5,639,742 and German patents DE 28 14 974 and DE 28 20 983. The entire contents of the aforementioned applications and patents are hereby expressly incorporated herein by reference.

Recent research efforts have focused on developing new tetracycline compositions effective under varying therapeutic conditions and routes of administration; and for developing new tetracycline analogues which might prove to be equal or more effective as antibiotics than the originally introduced tetracycline families (See, U.S. Pat. Nos. 3,957, 980; 3,674,859; 2,980,584; 2,990,331; 3,062,717; 3,557, 280; 4,018,889; 4,024,272; 4,126,680; 3,454,697; and 3,165,531).

The term "substituted tetracycline compounds" includes tetracycline compounds which have at least one substitution, e.g., at the 2, 3, 4, 5, 6, 7, 8, 9, 10, 11, 11a, 12, 12a, or, for methacycline, the 13 position, which allows the compound to perform its intended function, e.g., synergistically inhibit the growth of fungus. In an embodiment, the term "substituted tetracycline compounds" does not include unsubstituted tetracycline, minocycline, or doxycycline. In an embodiment, the substituted tetracycline compounds of the invention reduce the MIC of amphotericin B to a larger extent than unsubstituted doxycycline, tetracycline, or minocycline. The term "substituted tetracycline compound" includes, for example, substituted sancycline compounds, substituted minocycline compounds and substituted doxycycline compounds. In one embodiment, the FIC of a substituted tetracycline compound of the invention is 0.125 or less, 0.09 or less, 0.08 or less, 0.07 or less, 0.063 or less, etc. Values and ranges included and/or intermediate within the ranges set forth herein are also intended to be within the scope of the present invention.

Substituted tetracycline compounds used in the methods and compositions of the invention include compounds of Formula I:

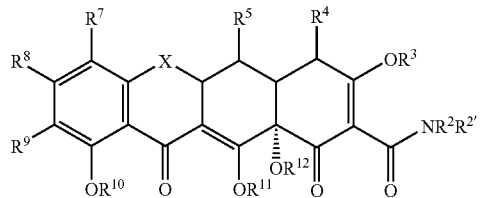

X is CHC($R^{13}$Y'Y), C=C$R^{13}$Y, C$R^{6'}R^6$, S, N$R^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is N$R^{4'}R^{4''}$, alkyl, alkenyl, alkynyl, hydroxyl, halogen, or hydrogen;

$R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$N$R^{7c}$C(=W')W$R^{7a}$;

$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso (e.g., —N=S), or —(CH$_2$)$_{0-3}$N$R^{9c}$C(=Z')ZR$^{9a}$;

Z is C$R^{9d}R^{9e}$, S, N$R^{9f}$ or O;

Z'is O, S, or N$R^{9f}$;

W is C$R^{7d}R^{7e}$, S, N$R^{7b}$ or O;

W' is O, N$R^{7f}$ S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, aryl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In an embodiment, the substituted tetracycline compounds used in the methods and compositions of the invention are substituted sancycline compounds, e.g., with substitution at the, for example, 2, 5, 6, 7, 8, 9, 10, 11, 11a, 12 12a position and/or, in the case of minocycline, 13. In substituted sancycline compounds of the invention, $R^2$, $R^3$, $R^{10}$, $R^{11}$, and $R^{12}$ are each hydrogen or a prodrug moiety; $R^{4'}$ and $R^{4''}$ are each alkyl (e.g., lower alkyl, e.g., methyl); X is C$R^6R^{6'}$; and $R^2$, $R^5$, $R^6$, $R^{6'}$, and $R^8$ are each, generally, hydrogen. In other embodiments, In an embodiment, the substituted tetracycline compound is a substituted tetracycline (e.g., generally, wherein $R^4$ is N$R^{4'}R^{4''}$, $R^{4'}$ and $R^{4''}$ are methyl, $R^5$ is hydrogen and X is C$R^6R^{6'}$, wherein $R^6$ is methyl and $R^{6'}$ is hydroxy); substituted doxycycline (e.g., wherein $R^4$ is N$R^{4'}R^{4''}$, $R^{4'}$ and $R^{4''}$ are methyl, $R^5$ is hydroxyl and X is C$R^6R^{6'}$, wherein $R^6$ is methyl and $R^{6'}$ is hydrogen); substituted minocycline (e.g., wherein $R^4$ is N$R^{4'}R^{4''}$, $R^{4'}$ and $R^{4''}$ are methyl; $R^5$ is hydrogen and X is C$R^6R^{6'}$ wherein $R^6$ and $R^{6'}$ are hydrogen atoms and $R^7$ is dimethylamino) or substituted sancycline (wherein $R^4$ is N$R^{4'}R^{4''}$, $R^{4'}$ and $R^{4''}$ are methyl; $R^5$ is hydrogen and X is C$R^6R^{6'}$ wherein $R^6$ and $R^{6'}$ are hydrogen atoms).

In one embodiment, $R^5$ is substituted, e.g., not hydrogen or hydroxy. In a further embodiment $R^5$ is an ester (alkcarbonyloxy). In an embodiment, $R^5$ is an alkyl ester. Examples of $R^5$ include alkyl esters such as $C_1$–$C_{12}$ alkyl, alkenyl, alkynyl, or aryl esters. The alkyl groups may be straight chains, branched chains, and/or contain rings. Examples of esters include, but are not limited to, tetracycline esters of ethanoic acid, propanoic acid, pentanoic acid, hexanoic acid, 2-cyclopentane ethanoic acid, cyclopentanoic acid, cycloheptanoic acid, 2-methyl propanoic acid, cyclohexanoic acid, and adamantane 2-carboxylic acid. In other embodiments, $R^5$ is hydrogen.

In an embodiment, the substituted tetracycline compounds used in the methods and compositions of the invention are substituted sancycline compounds, e.g., with substitution at the, for example, 2, 7 and/or 9 position. In substituted sancycline compounds of the invention, $R^{2'}$, $R^3$, $R^{10}$, $R^{11}$, and $R^{12}$ are each hydrogen or a prodrug moiety; $R^4$ is dialkylamino and $R^{4'}$ is hydrogen; X is C$R^6R^{6'}$; and $R^2$, $R^5$, $R^6$, $R^{6'}$, and $R^8$ are each, generally, hydrogen. For 7-substituted sancycline compounds, $R^9$ may be hydrogen. In another embodiment, $R^4$ is hydrogen.

In one embodiment, $R^7$ is substituted or unsubstituted aryl, e.g., heteroaryl, phenyl, etc. Examples of $R^7$ substituents include substituents which allow the substituted tetracycline compound to perform its intended function. Examples of such substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the phenyl is substituted with at least one alkyl, amino, heterocycle, alkoxy, halogen, nitro, alkoxycarbonyl, dialkylamino, or alkylamino.

In another embodiment, $R^7$ is substituted or unsubstituted heteroaryl. Examples of heteroaromatic groups include both monocyclic and polycyclic (e.g., multicylic rings), such as, but not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In an embodiment, $R^7$ is benzofuranyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In an embodiment, $R^7$ is thienyl. $R^7$ may also be substituted or unsubstituted heterocyclic, e.g., morpholinyl, piperazinyl, piperidinyl, etc.

In another embodiment, $R^7$ is substituted or unsubstituted, branched, straight chain or cyclic alkyl. Examples of substituents include substituents which allow the substituted tetracycline compound to perform its intended function, such as, but not limited to, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, trialkylsilyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the substituents include heterocycles, substituted and unsubstituted phenyl, a hydroxy, and combinations thereof. The substituents of the alkyl $R^7$ may also be further substituted, if chemically possible, with the substituents for $R^7$ groups listed above. Examples of alkyl $R^7$ groups include $C_1$–$C_{15}$ groups, $C_1$–$C_{10}$ groups, $C_1$–$C_7$ groups, etc., such as, but not limited to, 2-ethyl pentyl, methyl, ethyl, propyl, pentyl, hexyl, heptyl, etc. Values and ranges included and/or intermediate within the ranges set forth herein are also intended to be within the scope of the present invention. For example, a $C_1$–$C_7$ group includes groups with 1, 2, 3, 4, 5, 6, and 7 carbons.

In one embodiment, $R^7$ is substituted or unsubstituted alkenyl. Examples of substituents include substituents which allow the substituted tetracycline compound to perform its intended function. Examples of such substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In one embodiment, an alkenyl $R^7$ moiety is substituted with a substituted or unsubstituted cyclic moiety. Cyclic moieties include both carbocyclic, heterocyclic, aryl, heteroaryl, cycloalkenyl, and cycloalkyl groups. Examples of cyclic moieties include, for example, cyclobutane, cylopentane, cyclohexane, phenyl, etc. The cyclic moiety can be substituted, e.g., with any substituent listed above for alkenyl $R^7$ moieties.

$R^7$ may also be linked to another tetracycline ring structure through a linking moiety. The linking moiety can be any length which allows the substituted tetracycline compound to perform its intended function. The linking moiety can be attached to the second tetracycline ring structure at any position that allows for such a substitution. In certain embodiments, the linker is alkyl, alkenyl, or alkynyl. The linker may be from about $C_1$–$C_{25}$, $C_1$–$C_{20}$, $C_1$–$C_{15}$, etc. In certain embodiments, the linker is alkynyl and the second tetracycline ring structure is sancyclyl. The term "tetracycline dimer" refers to compounds wherein two tetracycline ring structures are connected through chemical, e.g., covalent bonds, e.g., a linking moiety.

In another embodiment, $R^7$ is substituted or unsubstituted alkynyl. Examples of substituents include substituents which allow the substituted tetracycline compound to perform its intended function, such as but are not limited to, for alkynyl $R^7$ moieties include alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

The $R^7$ alkynyl moiety may be substituted with a substituted or unsubstituted cyclic moiety. Cyclic moieties include both carbocyclic, heterocyclic, aryl, heteroaryl, cycloalkenyl, and cycloalkyl groups. Examples of cyclic moieties include, for example, cycloalkyls such as cyclobutane, cylopentane, cyclohexane, etc. The cyclic moiety can be substituted, e.g., with any substituent listed above for alkynyl $R^7$ moieties. Examples of cyclic substituents for alkynyl $R^7$ moieties include, but are not limited to, phenyl, cyclohexyl, p-nitro phenyl, p-methyl phenyl, cyclohexene, and 1-hydroxy cyclohexane.

Other examples of $R^7$ groups include substituted and unsubstituted alkyl carbonyl groups. These groups can be further substituted with aryl, alkyl, arylamino, alkenyl, alkoxy, or other substituents which allow the substituted tetracycline compound to perform its intended function. Another example of an $R^7$ moiety includes substituted and unsubstituted amino. The amino group can be dialkylamino, alkylamino, alkenylamino, arylamino, arylalkylamino, etc. or any other combination of substituents which allow it to perform its intended function, e.g., reduce the effective amount of a antifungal agent.

The invention also pertains to methods and pharmaceutical compositions comprising 7,9-disubstituted tetracycline compounds, e.g., tetracycline compounds wherein the 7 and 9 position are substituted. For example, the invention pertains to 7, 9-substituted sancycline compounds, e.g., compounds wherein X is $CR^6R^{6'}$; and $R^2$, $R^5$, $R^6$, $R^{6'}$, and $R^8$ are each hydrogen. The invention includes compounds wherein $R^9$ is alkyl and R is substituted or unsubstituted aminomethyl. The invention includes compounds with any combination of substituents as described above for $R^7$ combined with any possible other substituent at another position, e.g., $R^9$.

In another embodiment, the invention pertains to substituted doxycycline compounds wherein $R^5$ is hydroxy or alkylcarbonyloxy; X is $CHR^6$; $R^6$ is alkyl (e.g., lower alkyl, e.g., methyl); and $R^8$ is hydrogen. $R^7$ may be hydrogen or alkyl. $R^2$ may be hydrogen or alkyl.

In one embodiment, $R^9$ is substituted or unsubstituted alkenyl. Examples of substituents include substituents which allow the substituted tetracycline compound to perform its intended function. Examples of such substituents include alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Other examples of $R^9$ include substituted or unsubstituted alkyl (e.g., methyl, ethyl, propyl, t-butyl, n-butyl, i-butyl, pentyl, etc.), aryl, or any other substituent which allows the compound to perform its intended function.

In another embodiment, the invention pertains to methods and compositions which the substituted tetracycline compound is a substituted minocycline compound. Examples of these compounds include compounds wherein X is $CR^6R^{6'}$; $R^2$, $R^5$, $R^6$, $R^{6'}$, and $R^8$ are each hydrogen, and $R^7$ is dialkyl amino, e.g., dimethyl amino. In certain embodiments, the substituent may comprise one or more nitrogen atoms.

In an embodiment, $R^9$ is substituted or unsubstituted aryl (e.g., phenyl biaryl, heteroaryl, etc.) or araalkyl. $R^9$ may be substituted or unsubstituted heteroaryl. Examples of heteroaromatic groups include both monocyclic and polycyclic (e.g., multicylic rings), such as, but not limited to, furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl. In an embodiment, $R^7$ is benzofuranyl. Examples of substituents include all substituents which allow the tetracycline compound to perform its intended function, such as but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In an embodiment, $R^7$ is thienyl. $R^7$ may also be substituted or unsubstituted heterocyclic, e.g., morpholinyl, piperazinyl, piperidinyl, etc. In one embodiment, the aryl $R^9$ moiety is substituted or unsubstituted phenyl.

Other examples of $R^9$ moieties include substituted and unsubstituted, cyclic, branched or straight chain alkyl (e.g., $C_1$–$C_{15}$, $C_1$–$C_{10}$, e.g., methyl, ethyl, propyl, butyl, pentyl, hexyl, 2-cyclopentane ethyl, etc.). Examples of substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonatmido, nitro, cyano, azido, heterocyclyl, alkylaryl, aryl and heteroaryl. Examples of substituents include those listed above substituents selected from the group consisting of amido, alkyl, aminoalkyl, heterocycle, carboxylic acid, formyl, chlorine, fluorine, or acetyl.

Other examples of $R^9$ include both substituted and unsubstituted or unsubstituted alkenyl or alkynyl. Examples of substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In one embodiment, the alkynyl $R^9$ moiety is substituted with one or more substituents selected from the group consisting of substituted and unsubstituted aryl, substituted and unsubstituted alkyl, carboxylic acid, cycloalkyl, cycloalkenyl, or alkoxycarbonyl.

In another embodiment, $R^9$ is substituted or unsubstituted alkyl or alkylamino. For example, $R^9$ may be $C_1$–$C_{15}$ alkyl, $C_1$–$C_{10}$ alkyl, etc. In other embodiment, $R^9$ may be substituted with groups such as aminoalkyl, hydroxy, halogens and other substituents which allow the substituted tetracycline compounds to perform their intended function. Examples of substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In another embodiment, $R^{9c}$ is hydrogen, Z is S or O, and Z is NH. In an embodiment, $R^{9a}$ comprises substituted or unsubstituted phenyl. Examples of substituents for the substituted phenyl include, for example, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In other embodiments, $R^9$ may be heterocyclic, e.g., morpholinyl, pyridinyl, pyrazinyl, piperdinyl, etc. These substituents may further be substituted with substituents such as, but not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the substituted tetracycline compound of the invention include substituted methacycline compounds, e.g., wherein X is $C$=$CR^{13}Y$; and $R^2$, $R^5$, $R^6$, $R^{6'}$, $R^8$, and Y are each hydrogen. $R^7$ and $R^9$ may also be hydrogen or another moiety which allows for the substituted tetracycline compounds of the invention to perform their intended function.

In one embodiment, $R^{13}$ is substituted or unsubstituted aryl, e.g., phenyl, biaryl, heteroaryl, etc. Examples of substituents include those which allow the substituted tetracycline compound to perform its intended function. Examples, include but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In a further embodiment, the substituent is methyl or alkoxy.

In a further embodiment, the substituted tetracycline compounds of Formula (I) include compounds with large hydrophobic moieties at the 7, 9 or 13 position. The hydrophobic moieties may be partially sterically rigid (e.g., contain double or triple bonds, or contain one or more rings). For example, the compounds may comprise a substituted or unsubstituted aryl (e.g., heteroaryl, phenyl, etc. ring) group or one or more alkyl groups. In another embodiment, the compounds may comprise a group with one or more nitrogen or other other heteroatoms. In a further embodiment, the compound may be a 9-substituted minocycline compound. The substituted tetracycline compounds may comprise any combination of substituents shown in Table 2.

In another embodiment, the invention also pertains to 4-dedimethylaminotetracycline compounds with the substituents described herein or shown in Table 2 (e.g., compounds with the same substituents as described herein or in Table 2, except at the $R^4$ position where the shown dimethylamino group is a hydrogen.)

Examples of substituted tetracycline compounds which can be used in the methods of the invention are shown below and in Table 2.

13                                          14
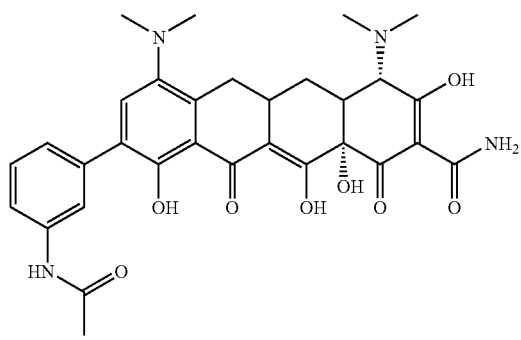
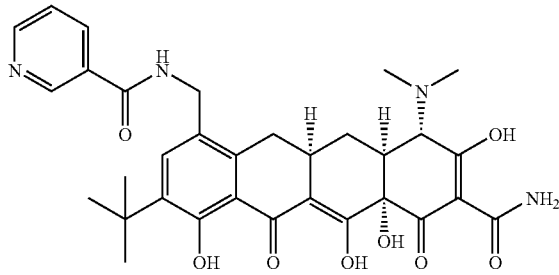
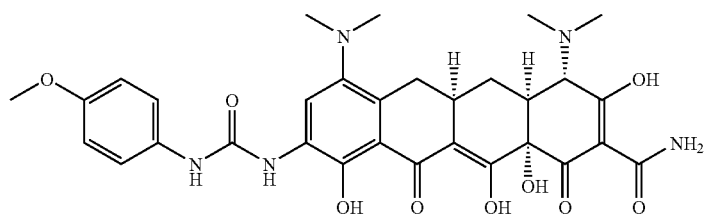
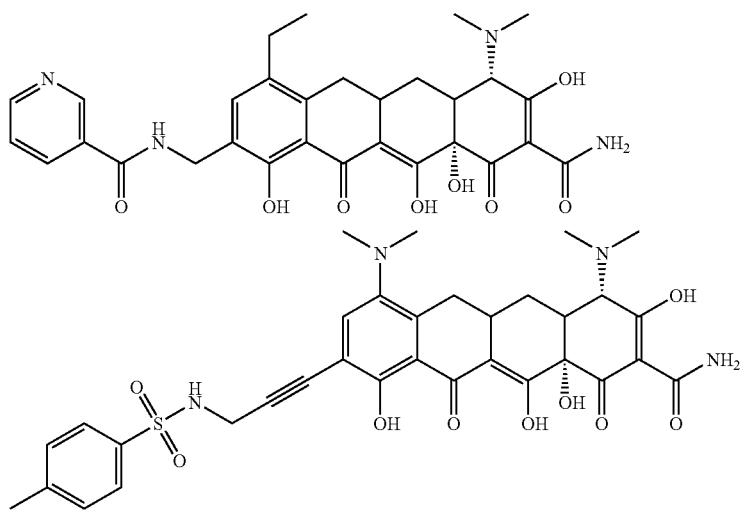
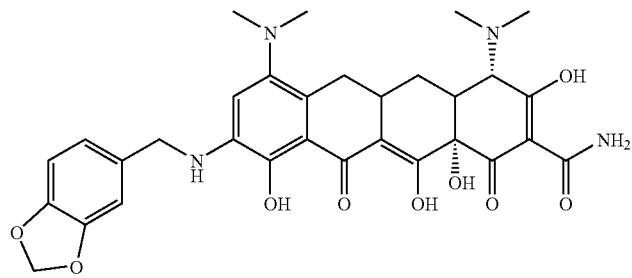
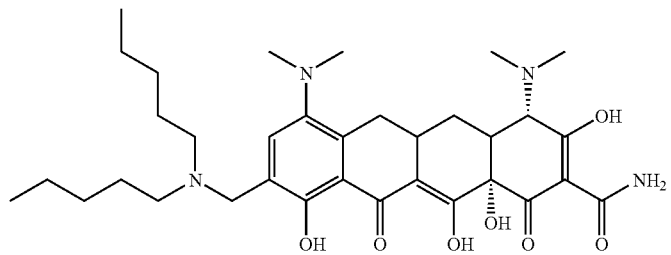

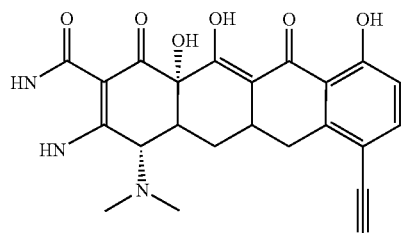
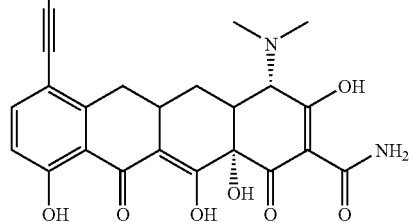
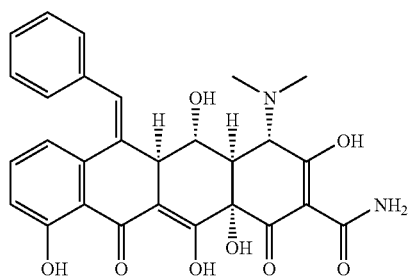
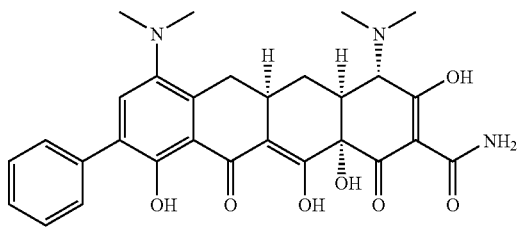
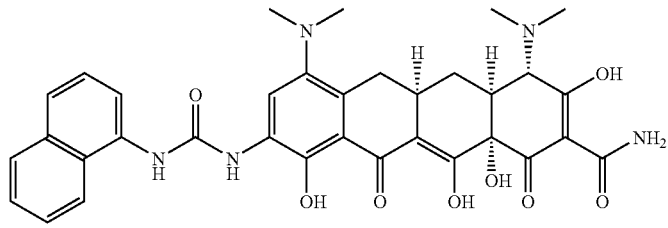
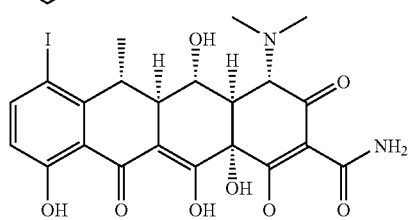
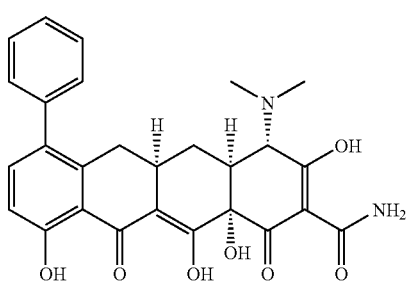
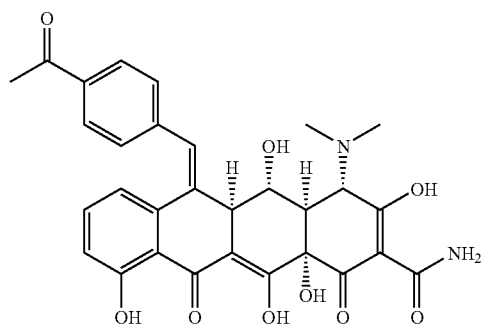
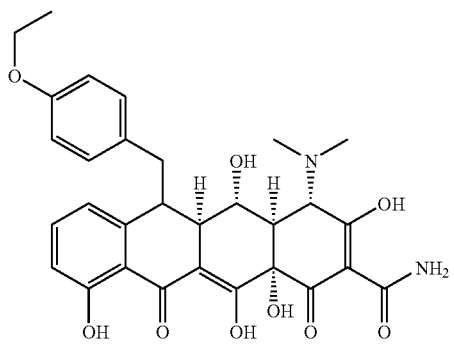

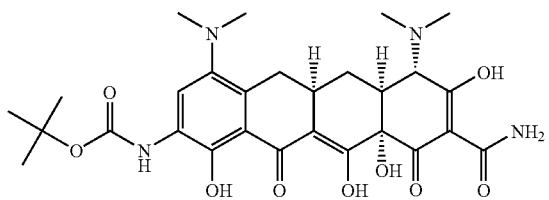
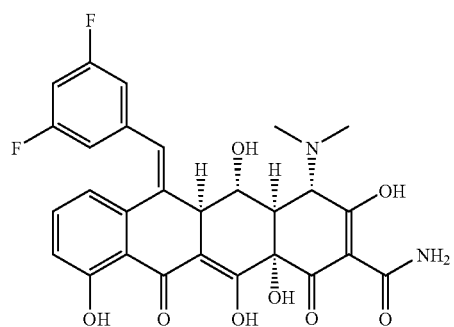
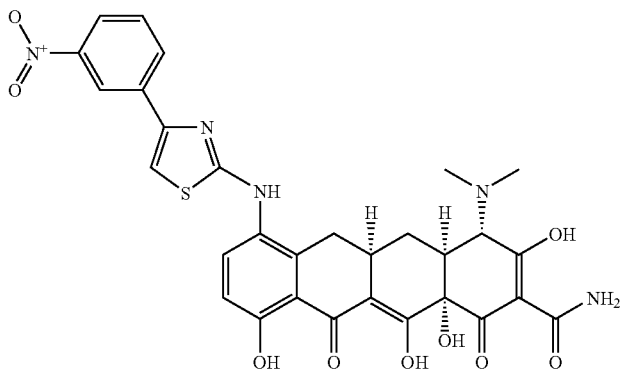
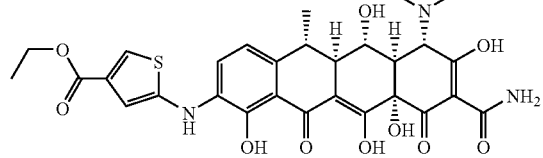
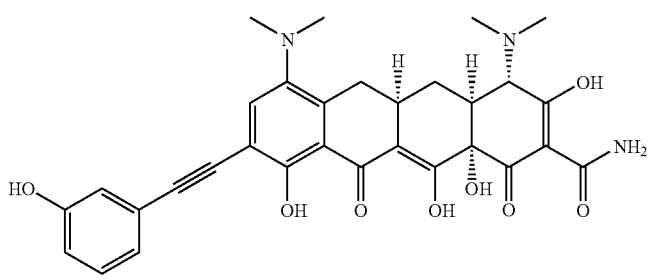
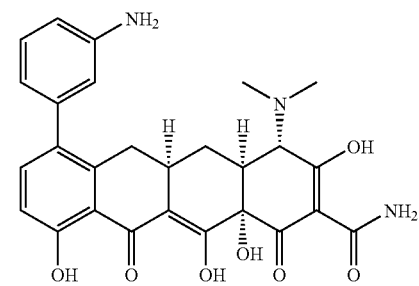
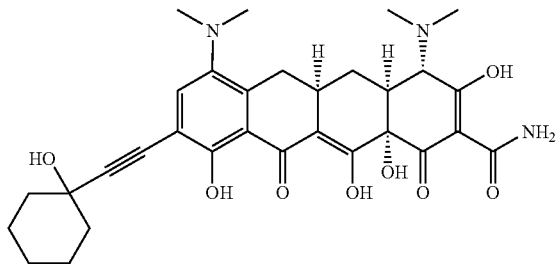
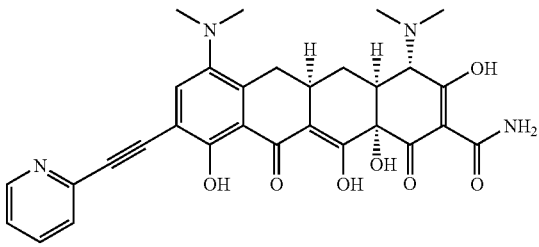
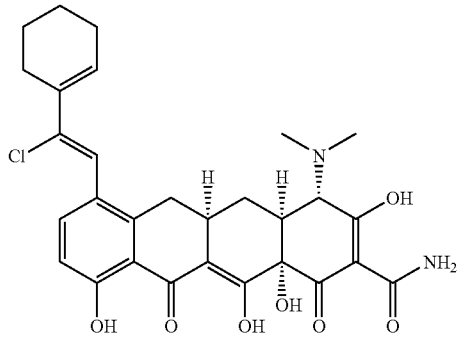
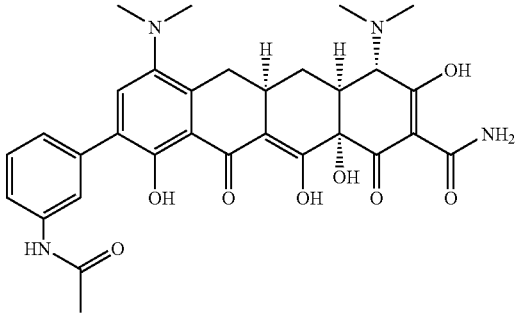

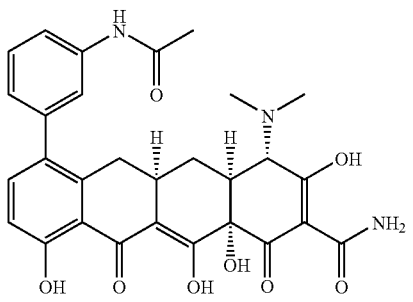
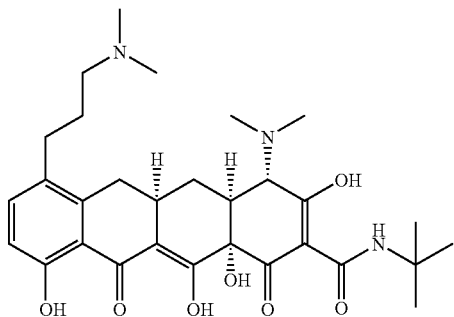
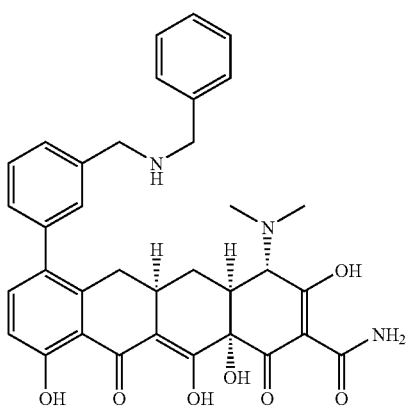
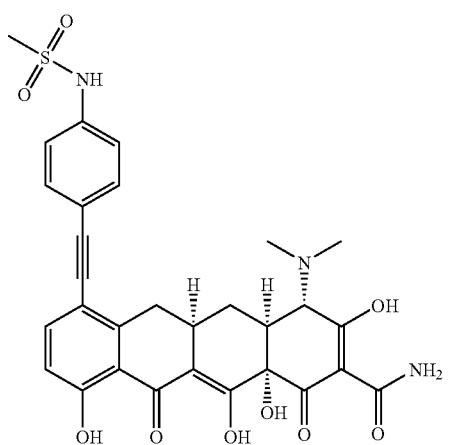
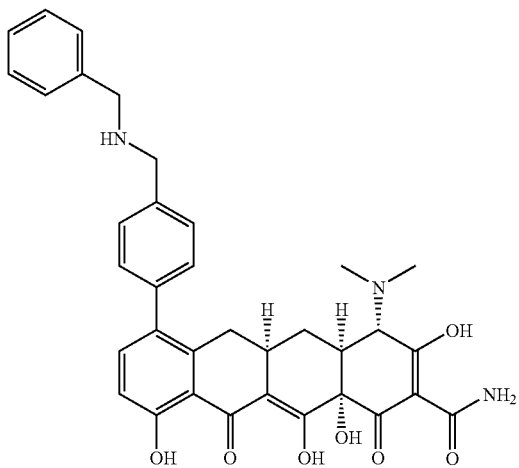
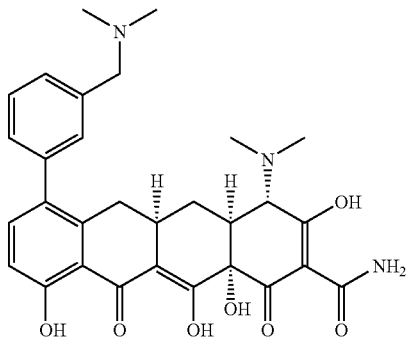
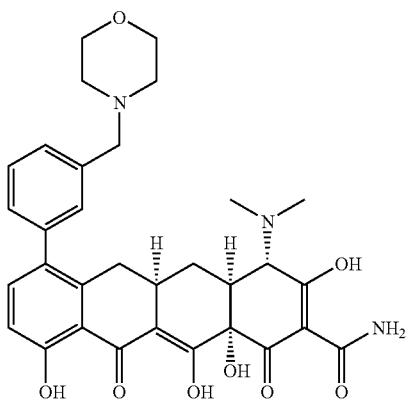
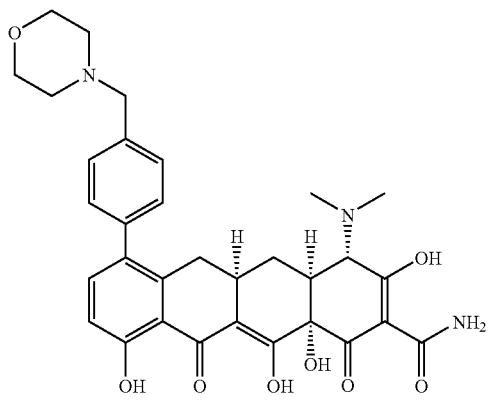

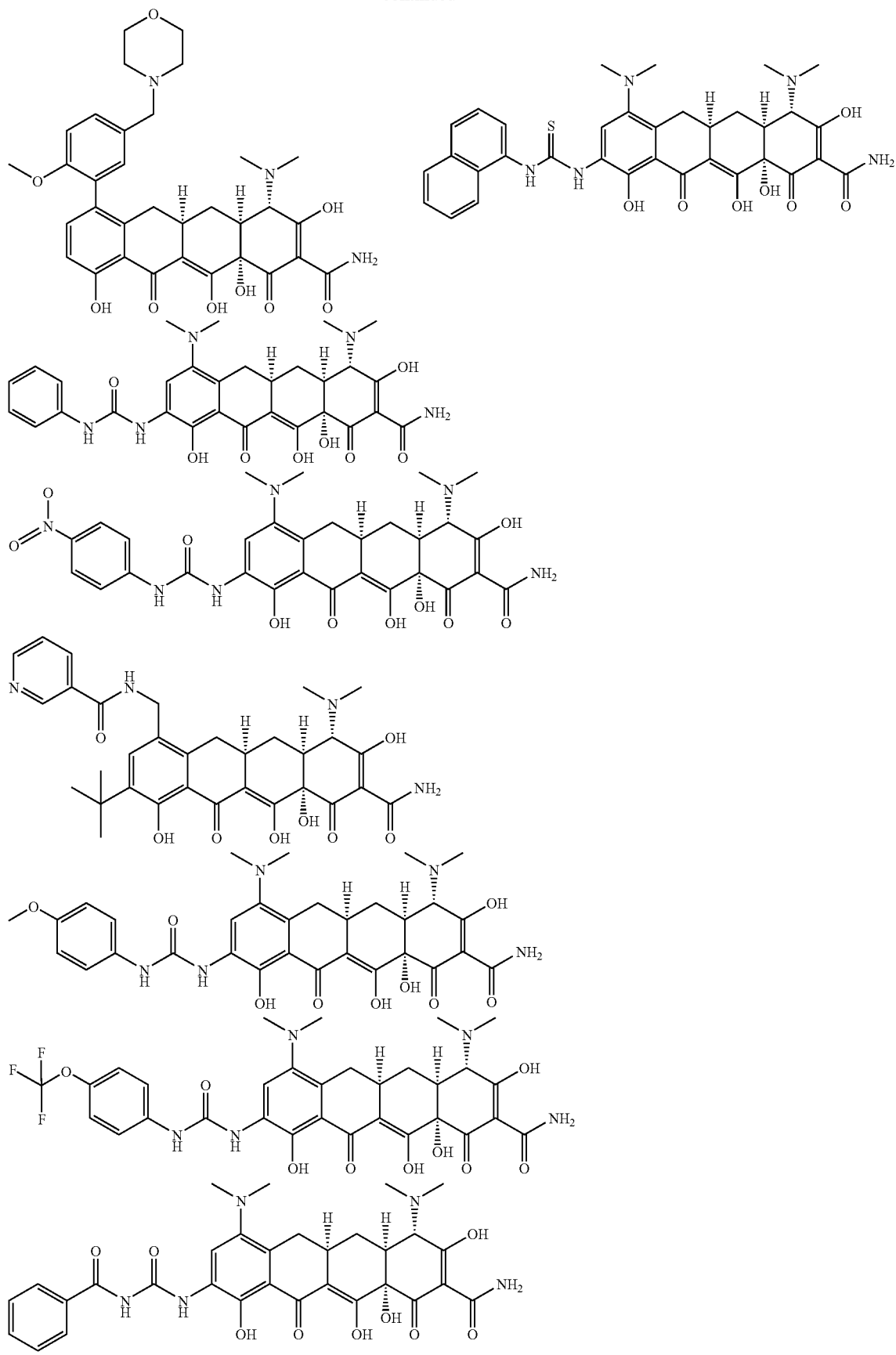

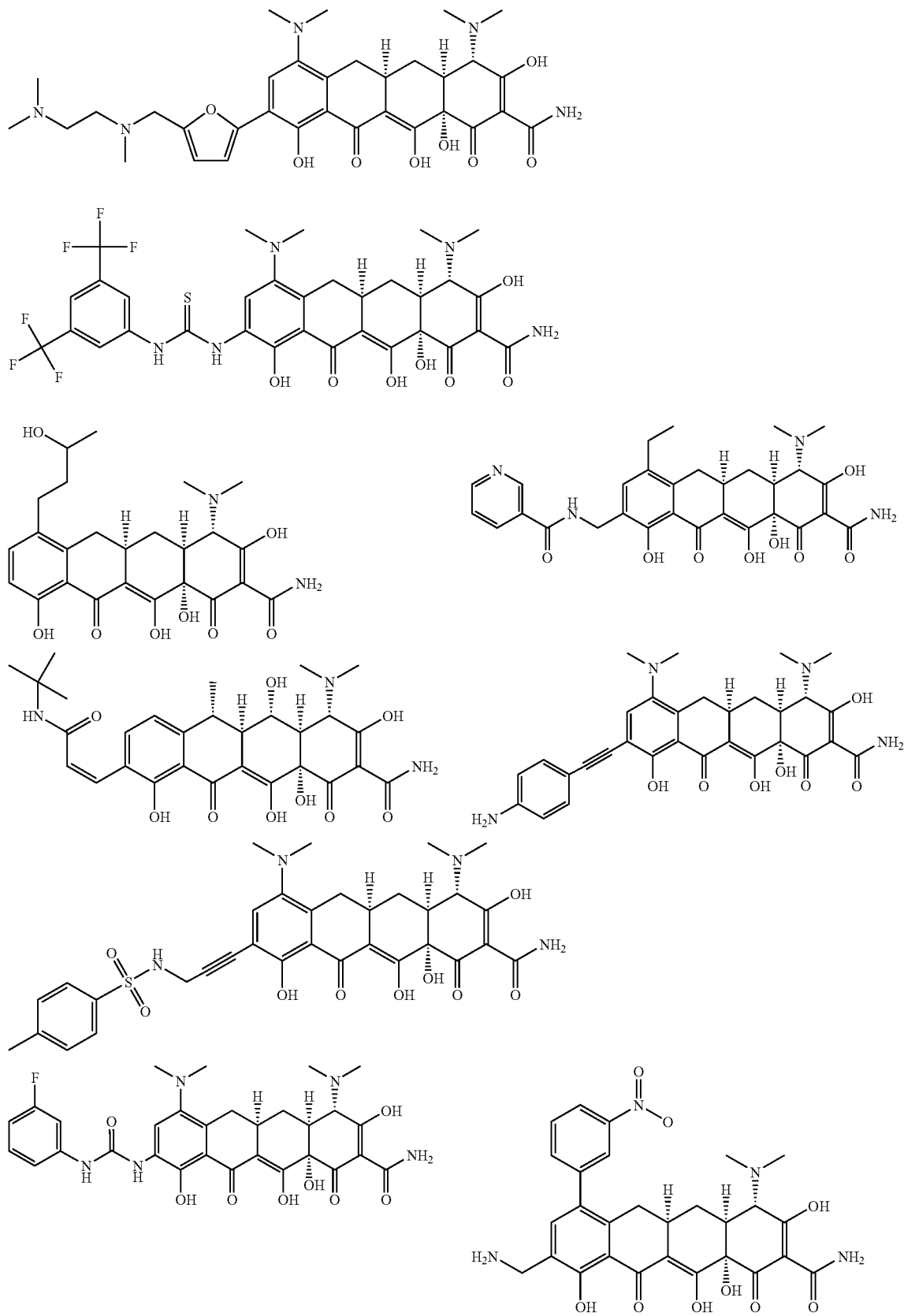

-continued
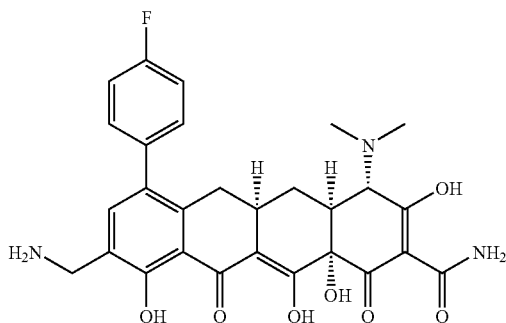
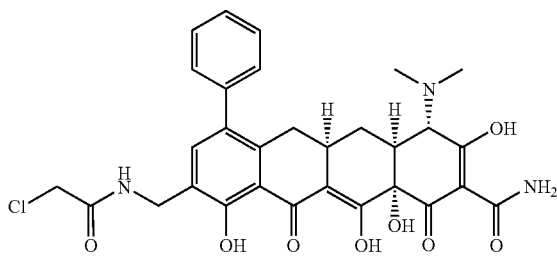
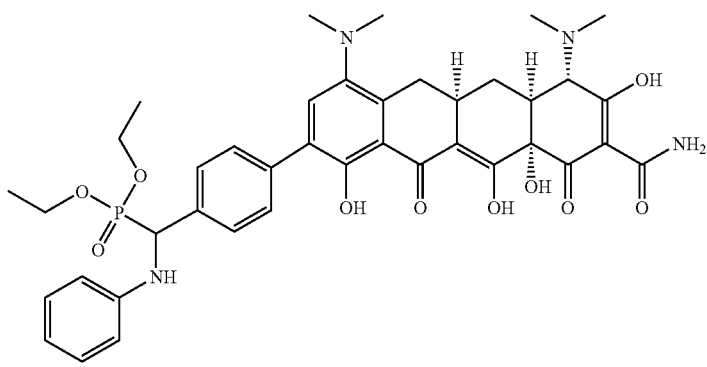
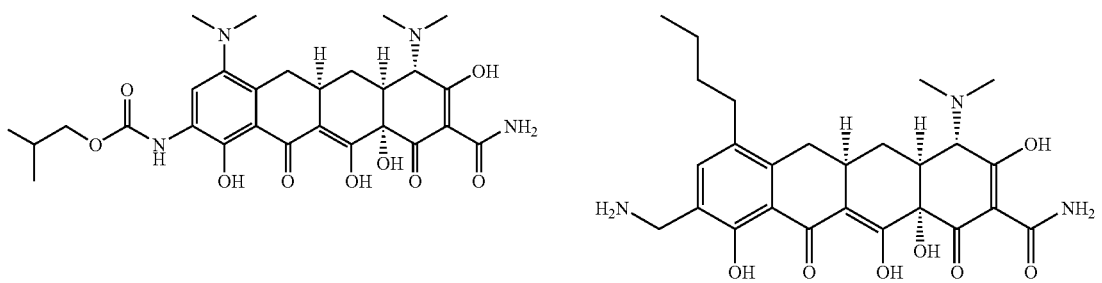
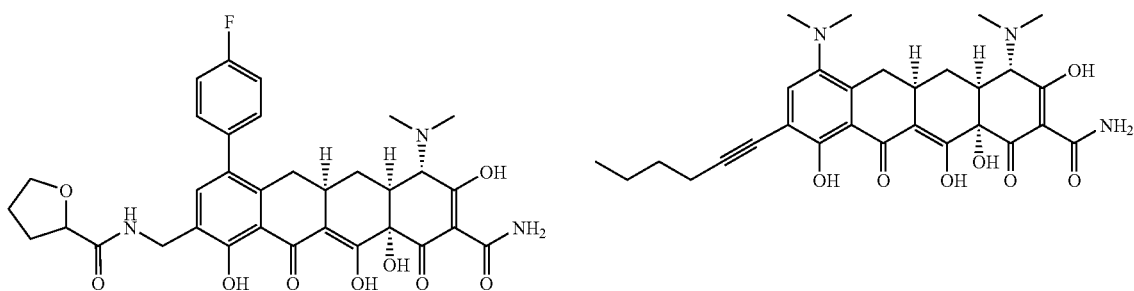
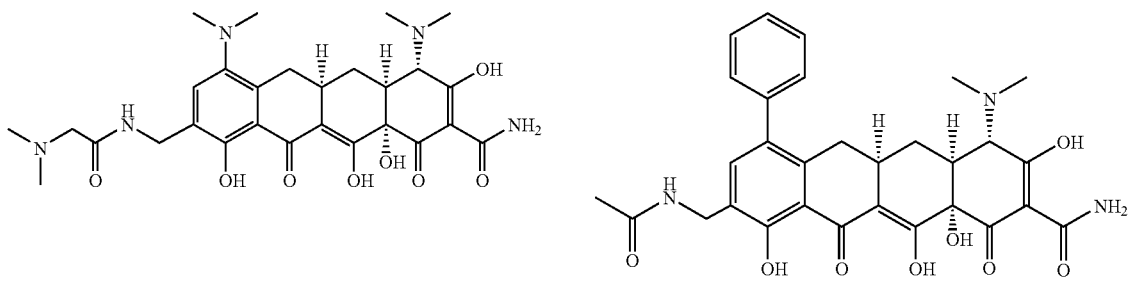

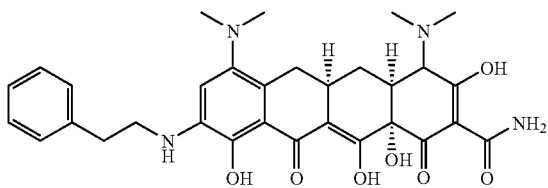
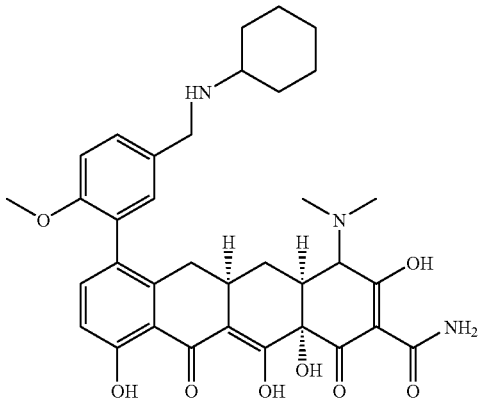
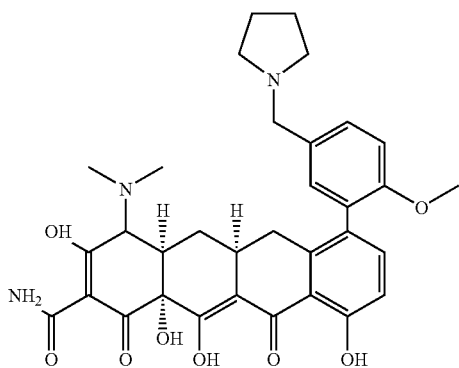
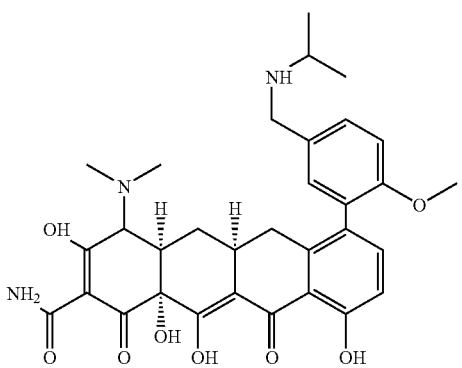
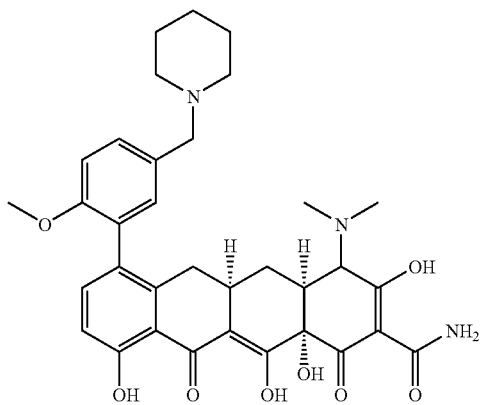
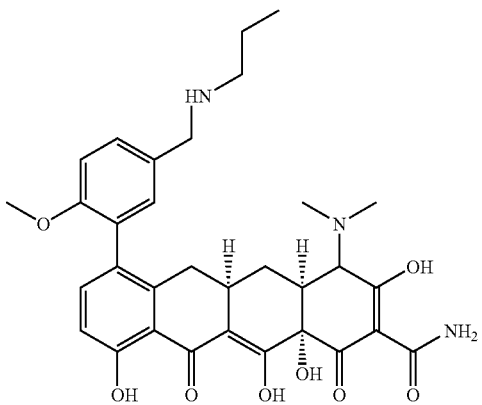
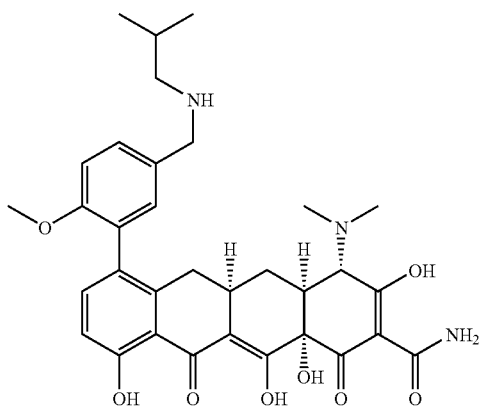

-continued
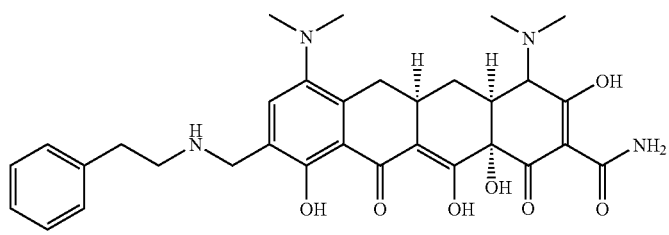
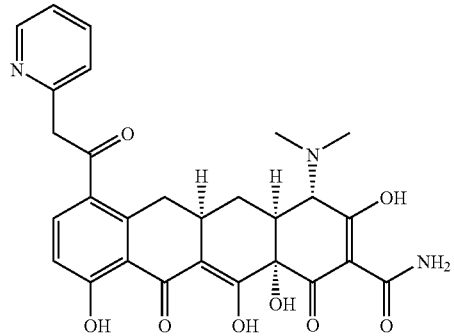
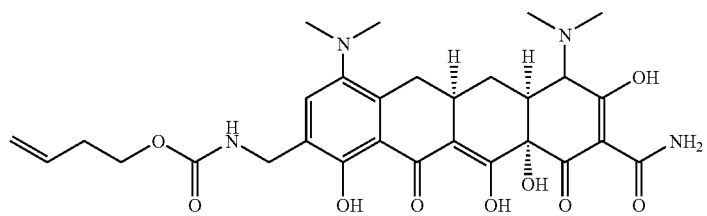
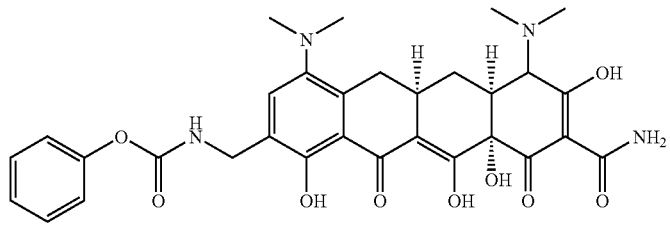
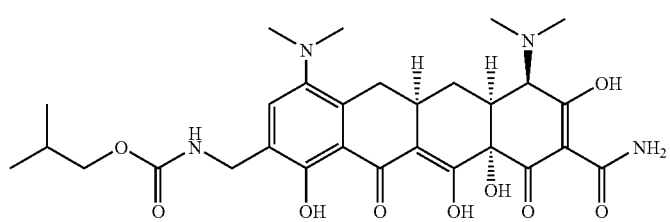
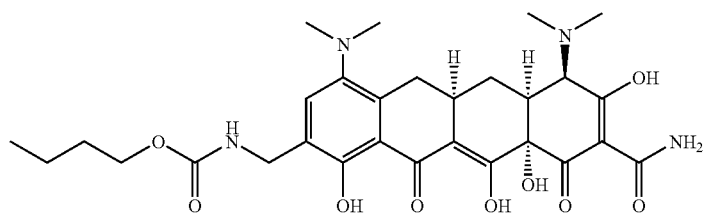
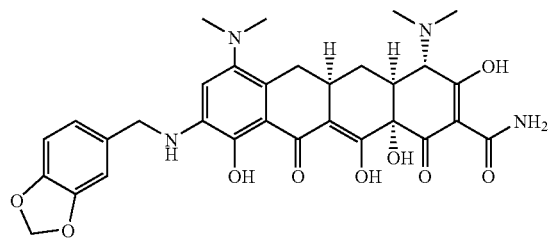
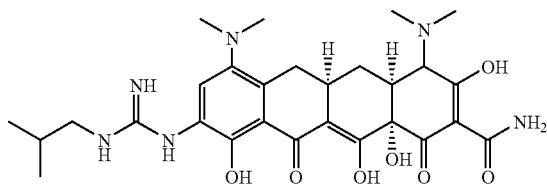

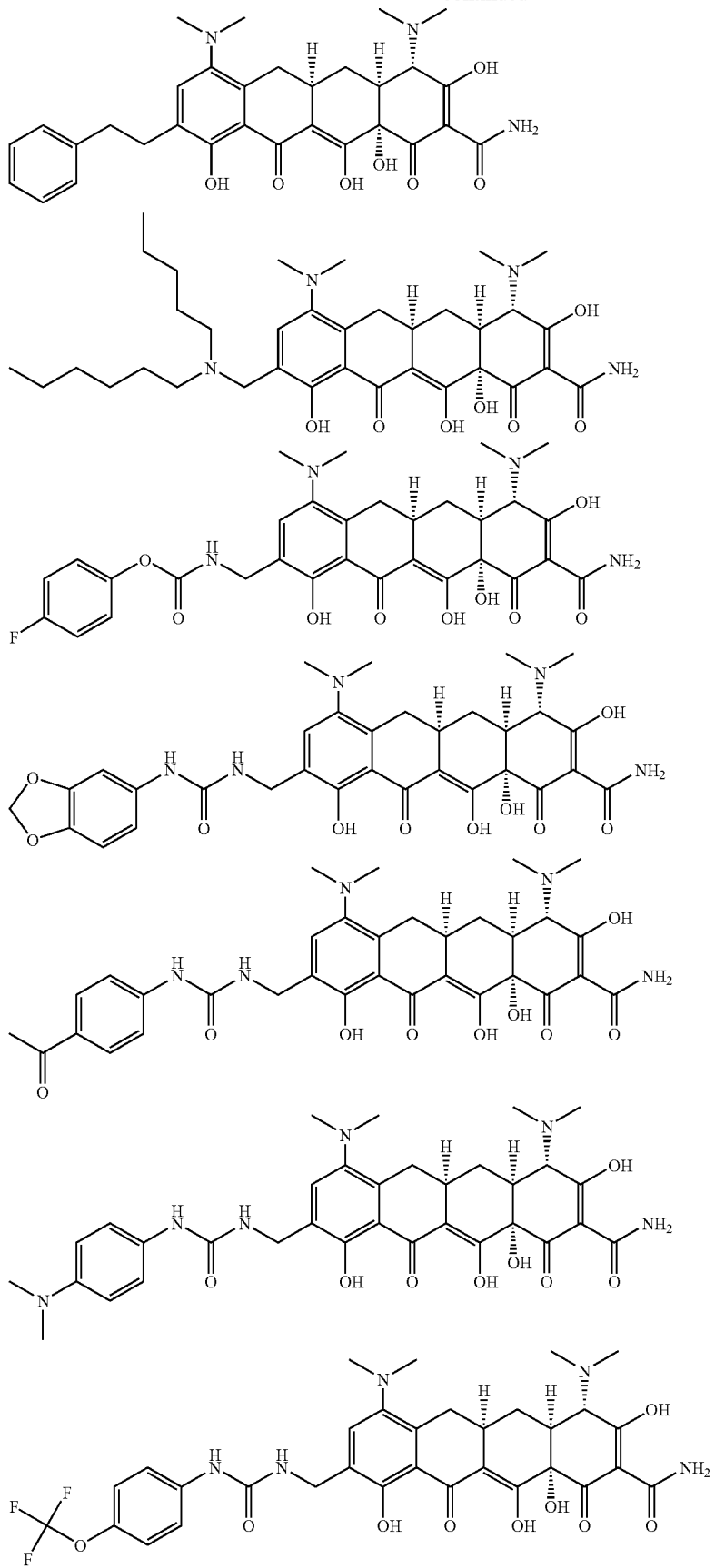

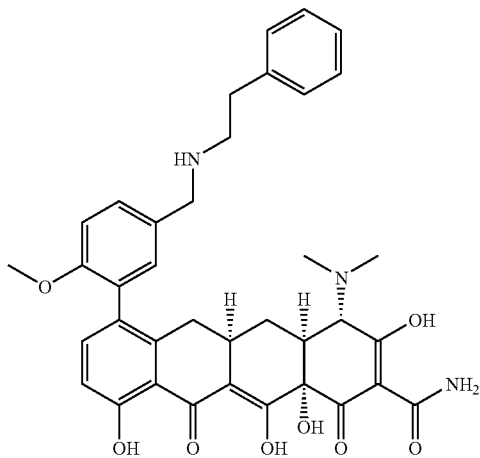
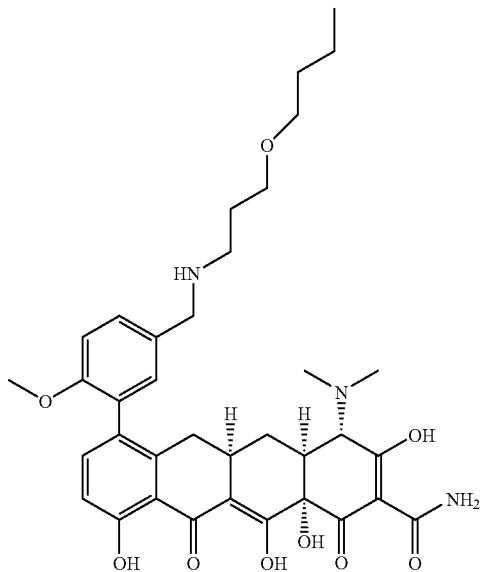
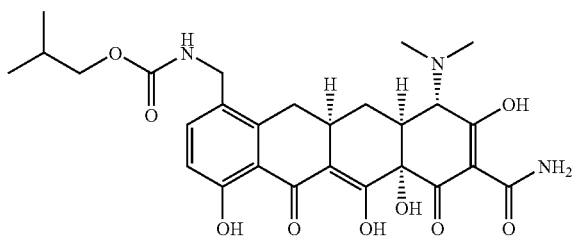
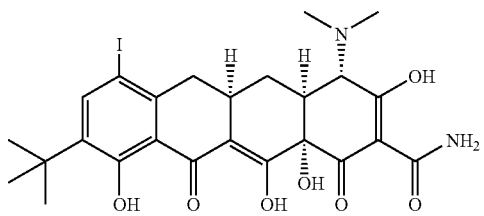
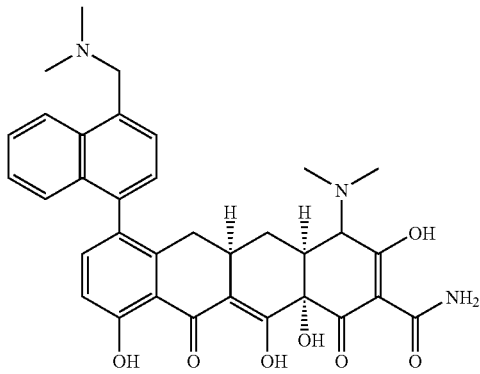
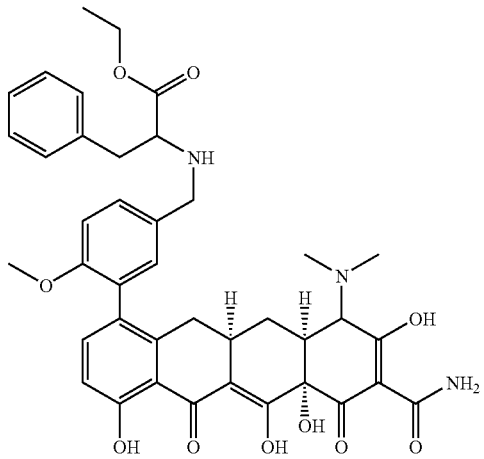
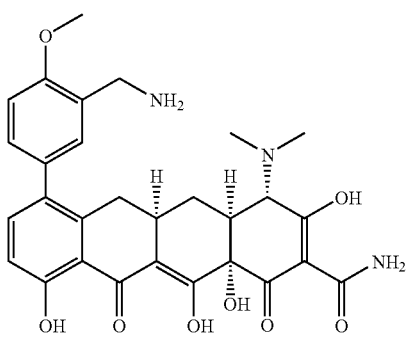
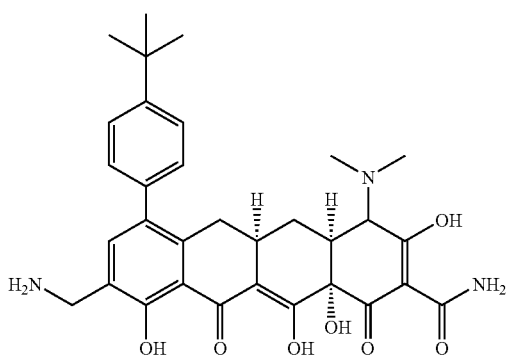

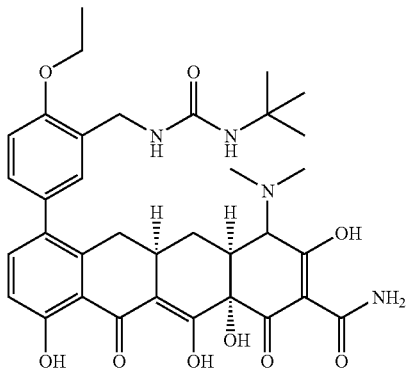
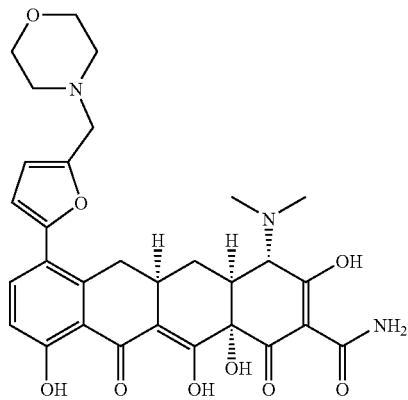
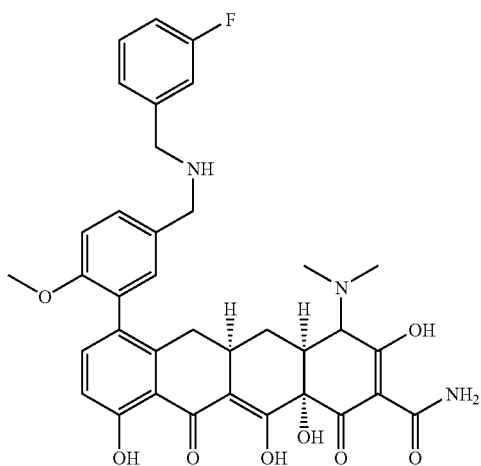
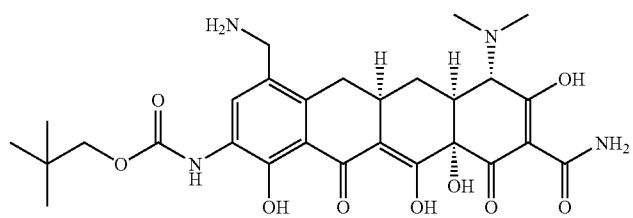
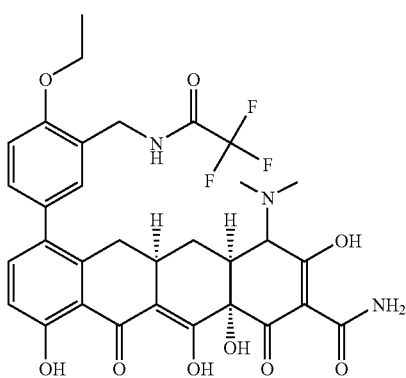
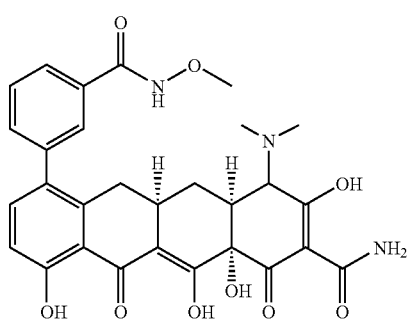
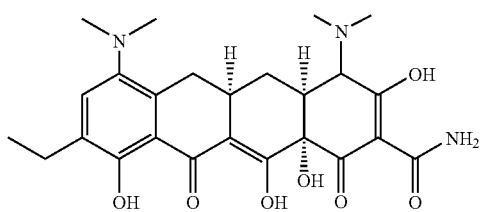
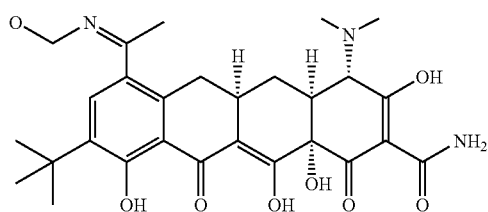

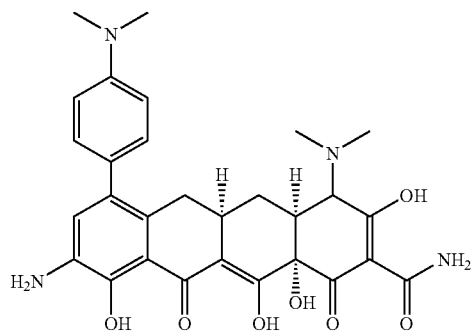
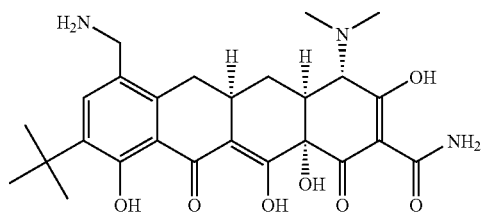
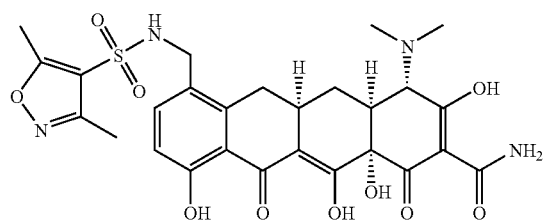
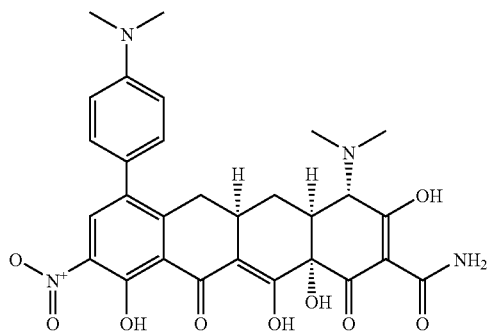
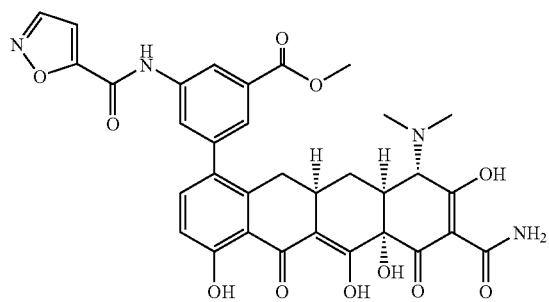
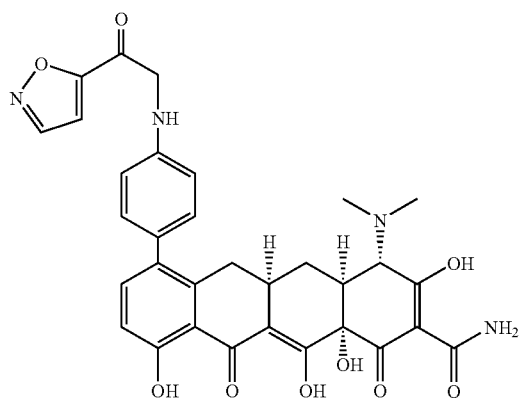
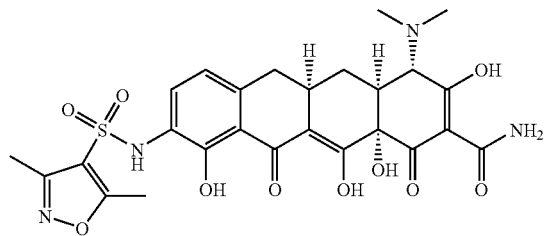
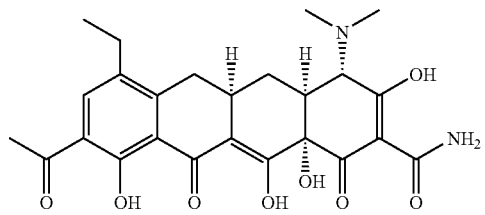
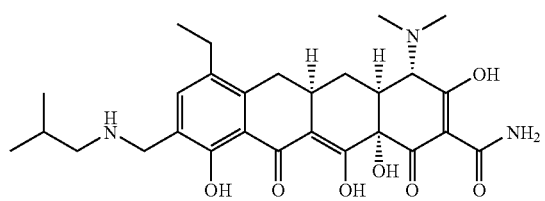
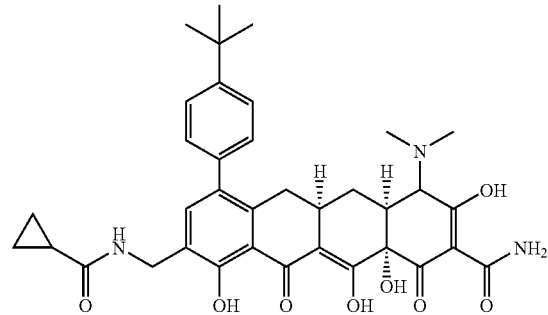

39
-continued
40
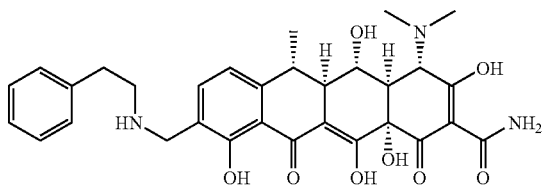
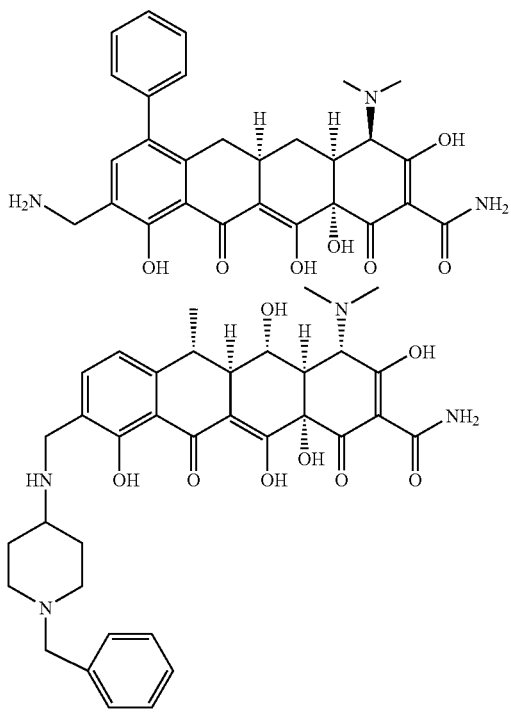
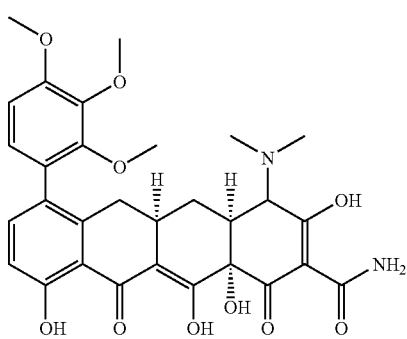
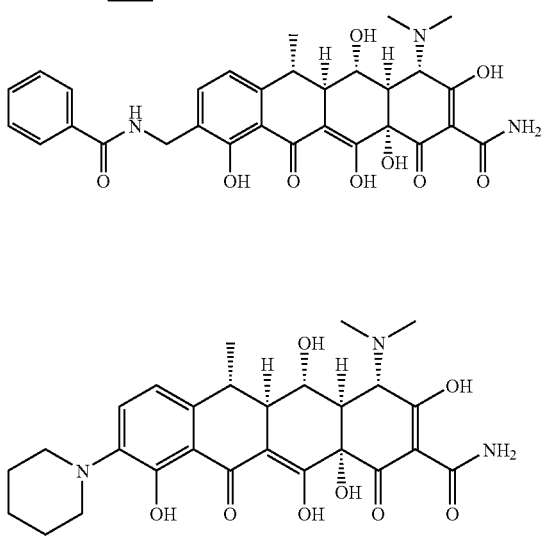
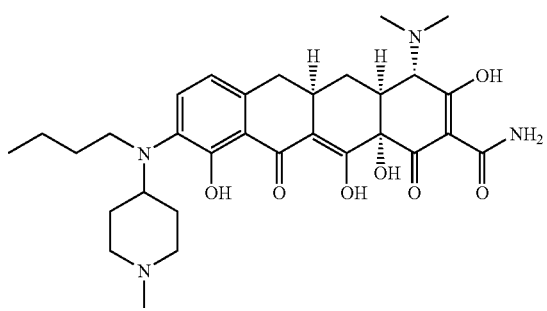
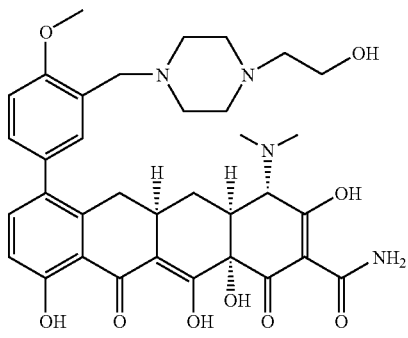
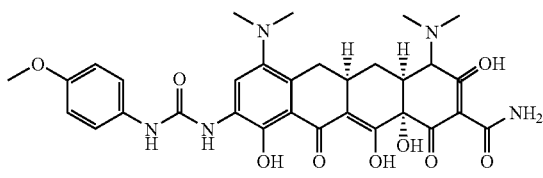
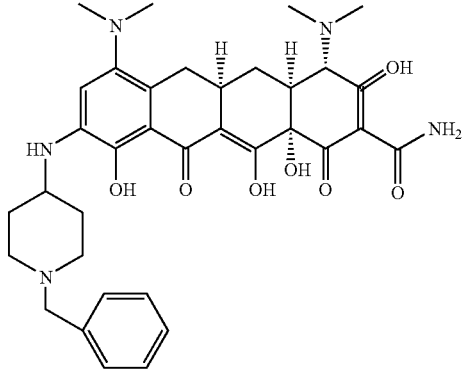

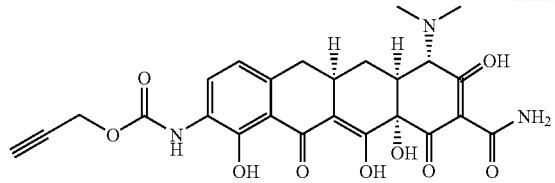
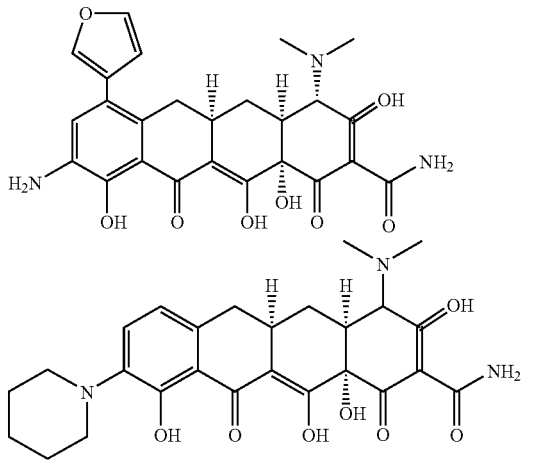
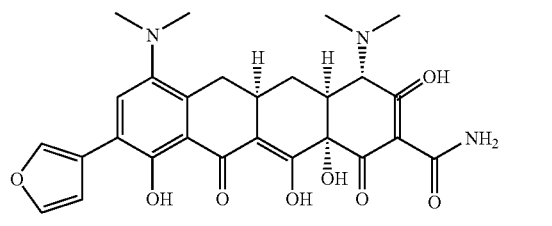
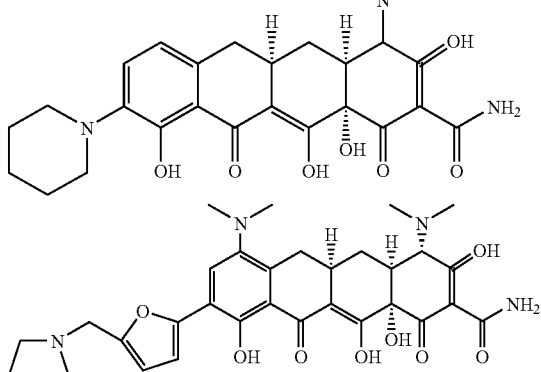
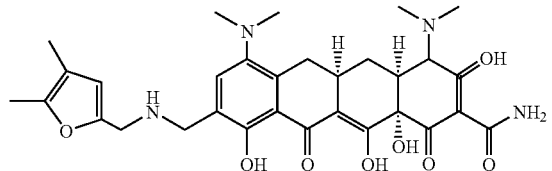
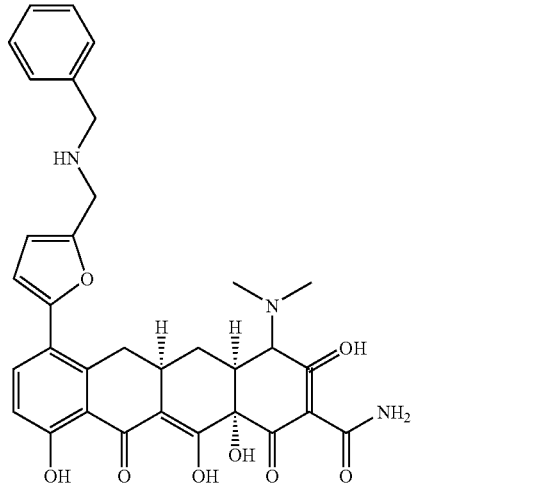
The substituted tetracycline compounds of the invention can be synthesized using the methods described in Example 1, the following schemes, and art recognized techniques. All novel substituted tetracycline compounds described herein are included in the invention as compounds.
SCHEME 1
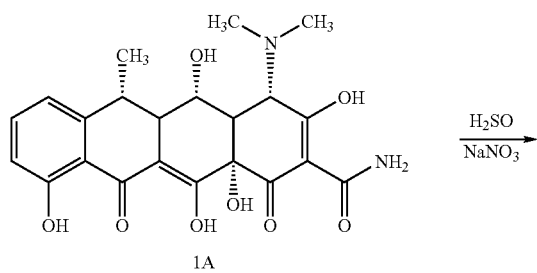

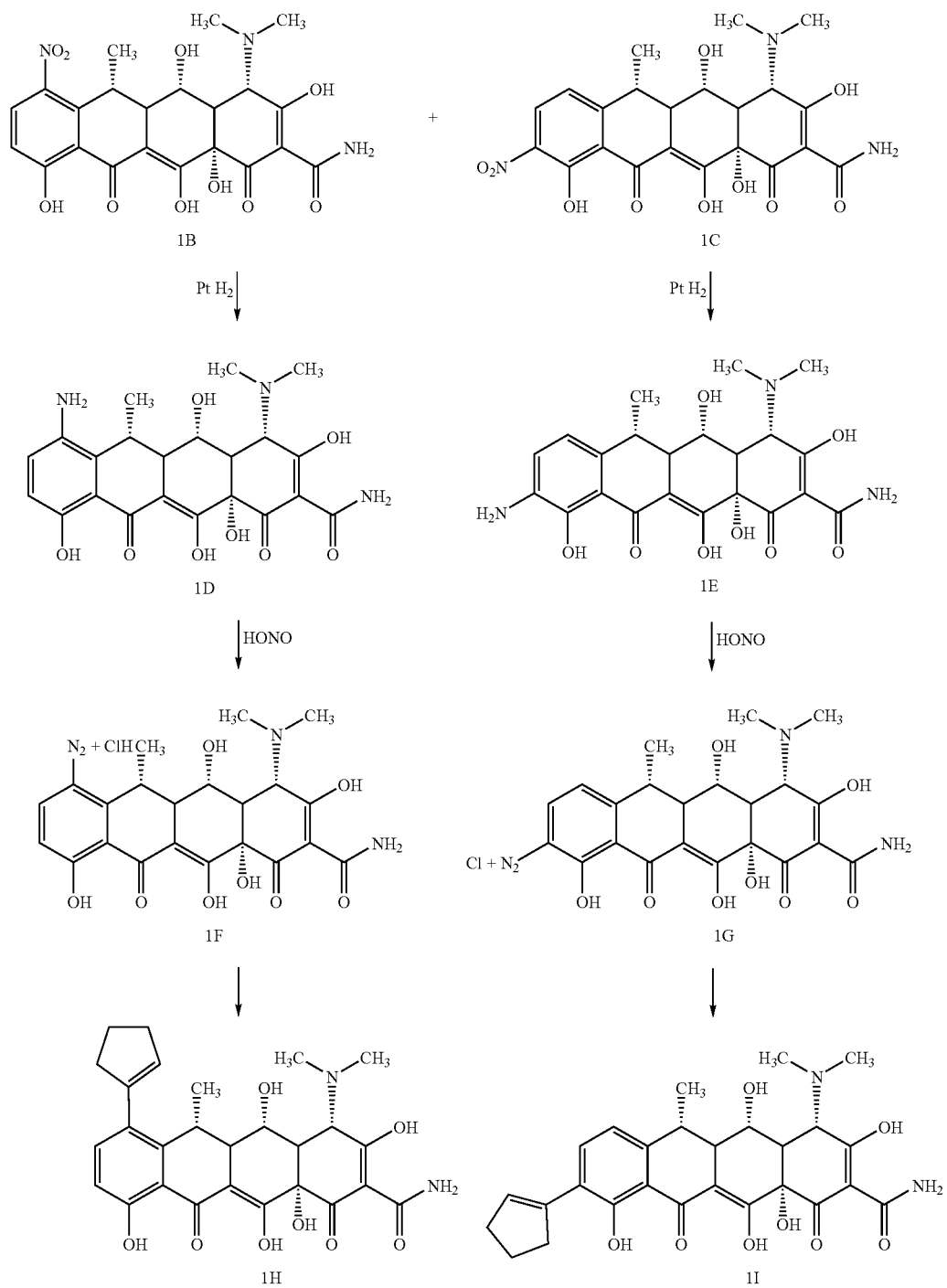

9- and 7-substituted tetracyclines can be synthesized by the method shown in Scheme 1. As shown in Scheme 1, 9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate halogenated reagent (e.g., $R^{9b}Br$, wherein $R^9$ is an aryl, alkenyl, or alkynyl moiety) to yield the desired compound (e.g., in Scheme 1, 7-cyclopent-1-enyl doxycycline (1H) and 9-cyclopent-1-enyl doxycycline (1I)).

SCHEME 2

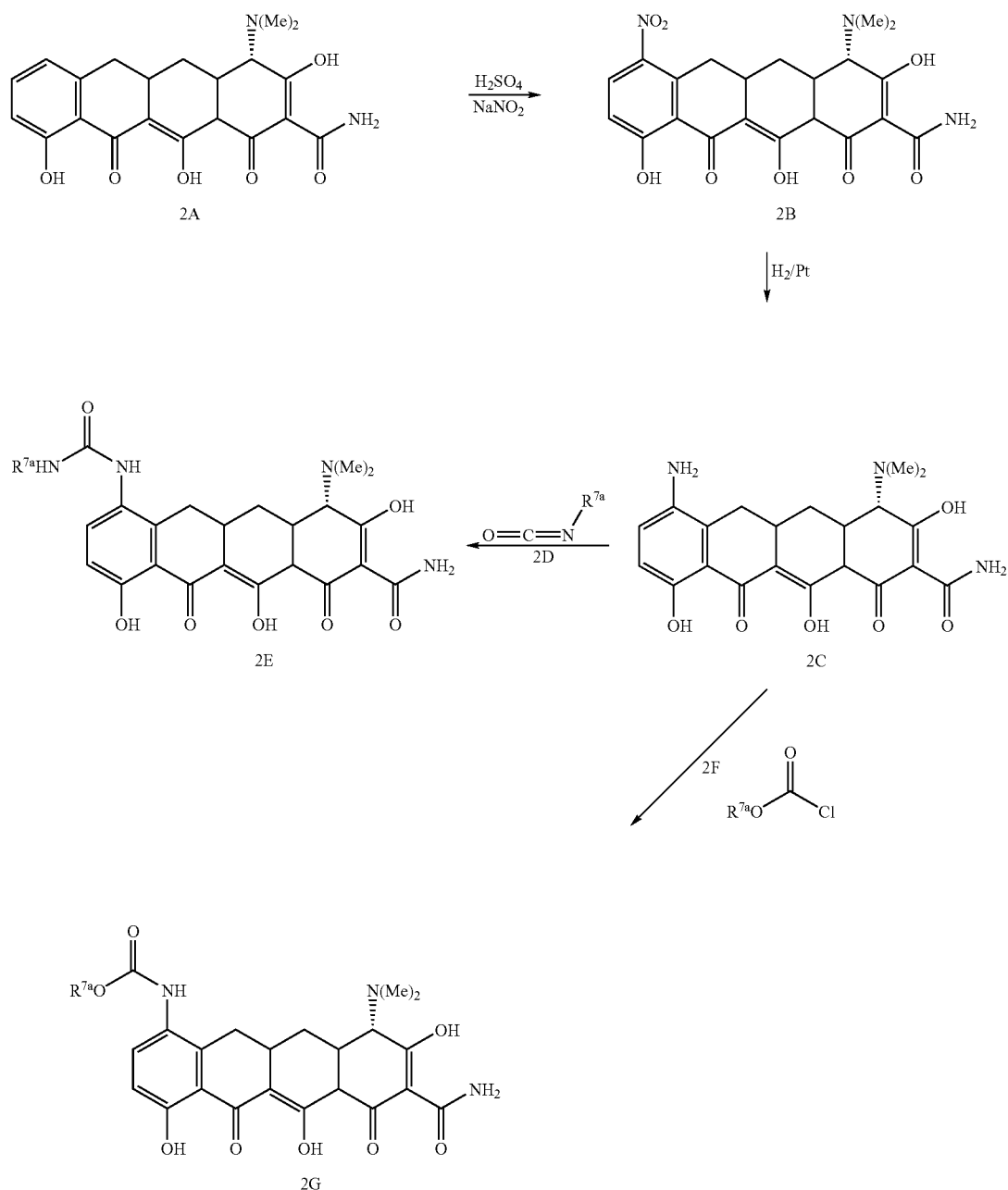

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

SCHEME 3

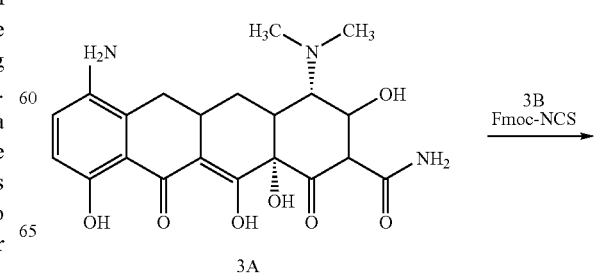

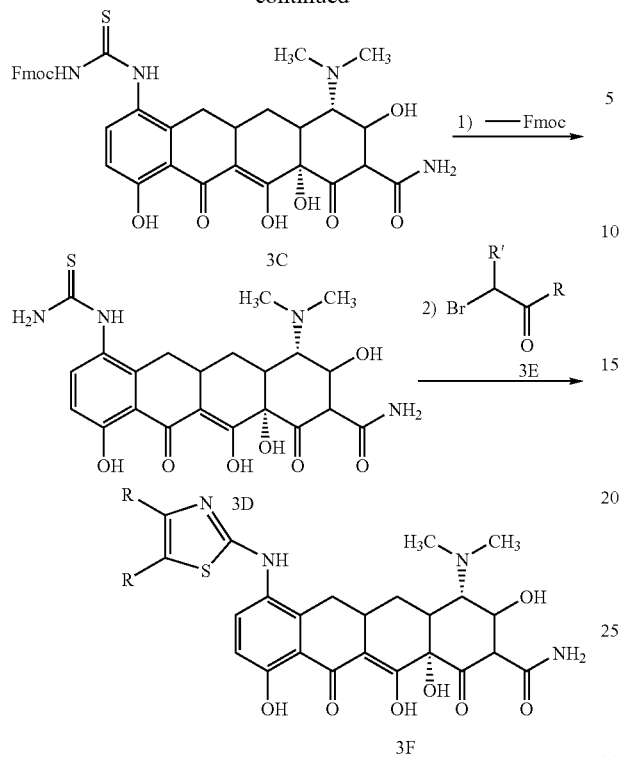

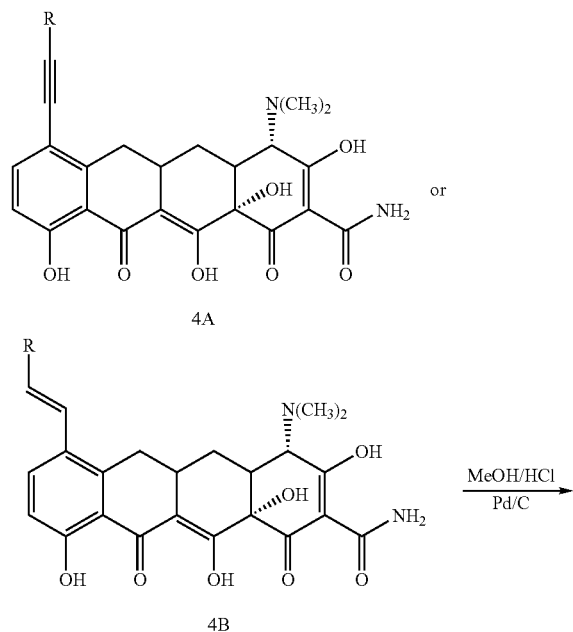

As shown in Scheme 3, tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

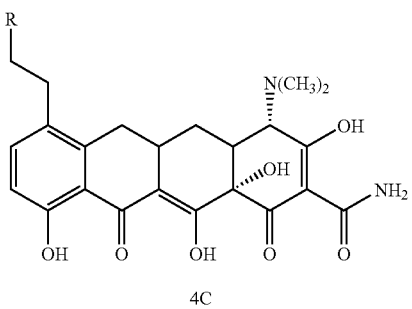

7-alkenyl tetracycline compounds, such as 7-alkynyl sancycline (4A) and 7-alkenyl sancycline (4B), can be hydrogenated to form alkyl 7-substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

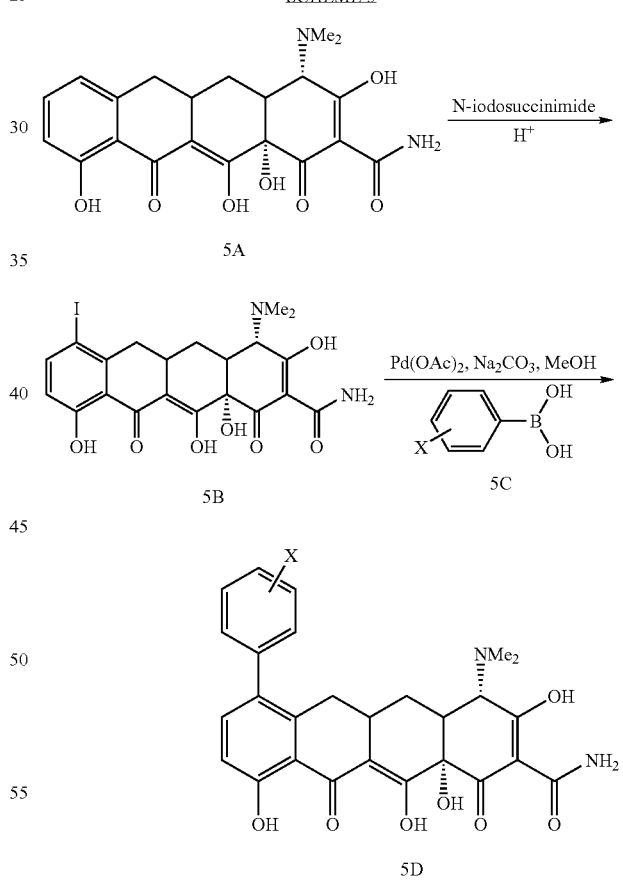

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., Na₂CO₃) and an appropriate boronic acid (5C) and under an inert atmosphere. The reaction is catalyzed with a palladium catalyst (e.g., Pd(OAc)₂). The product (5D) can be purified by methods known in the art (such as HPLC). Other 7-aryl and alkynyl tetracycline compounds can be synthesized using similar protocols. Furthermore, 7and 9-carbonylated compounds can be synthesized using art recognized techniques.

The 7-substituted tetracycline compounds of the invention can also be synthesized using Stille cross couplings. Stille cross couplings can be performed using an appropriate tin reagent (e.g., R—SnBu₃) and a halogenated tetracycline compound, (e.g., 7-iodosancycline). The tin reagent and the iodosancycline compound can be treated with a palladium catalyst (e.g., Pd(PPh₃)₂Cl₂ or Pd(AsPh₃)₂Cl₂) and, optionally, with an additional copper salt, e.g., CuI. The resulting compound can then be purified using techniques known in the art.

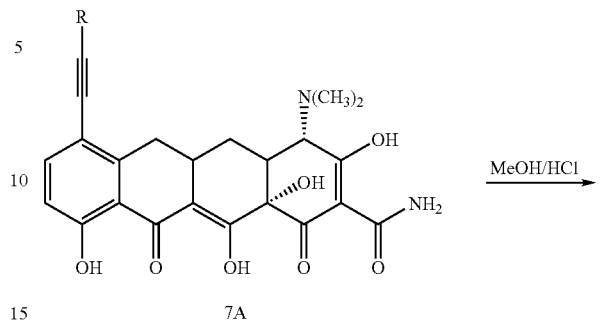

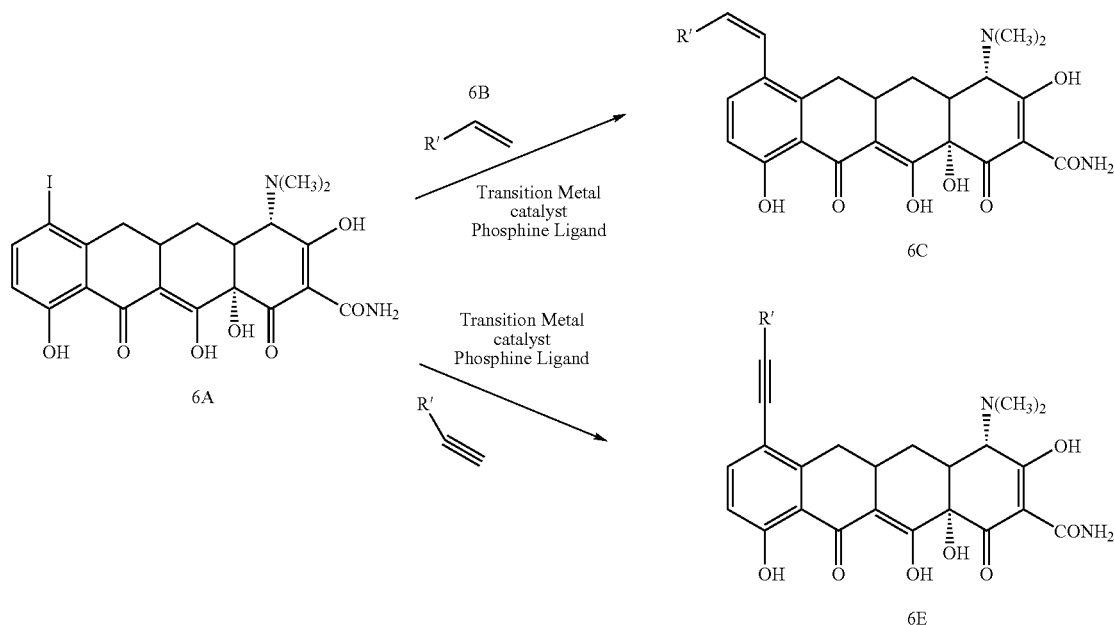

The compounds of the invention can also be synthesized using Heck-type cross coupling reactions. As shown in Scheme 6, Heck-type cross-couplings can be performed by suspending a halogenated tetracycline compound (e.g., 6-iodosancycline, 6A) and an appropriate palladium or other transition metal catalyst (e.g., Pd(OAc)₂ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art

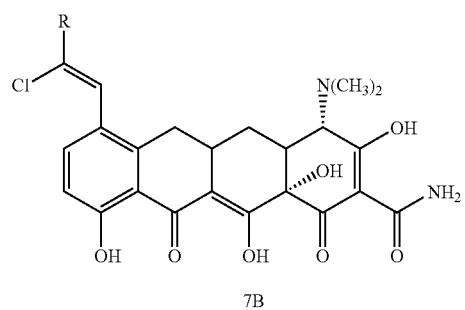

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

SCHEME 8

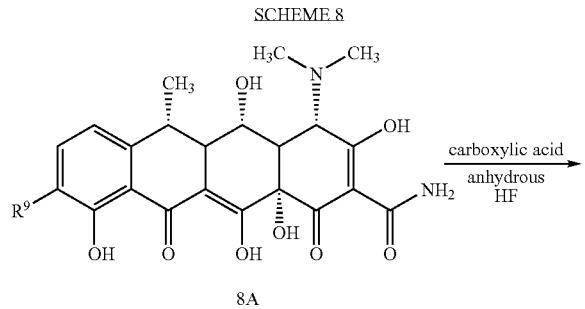

8A

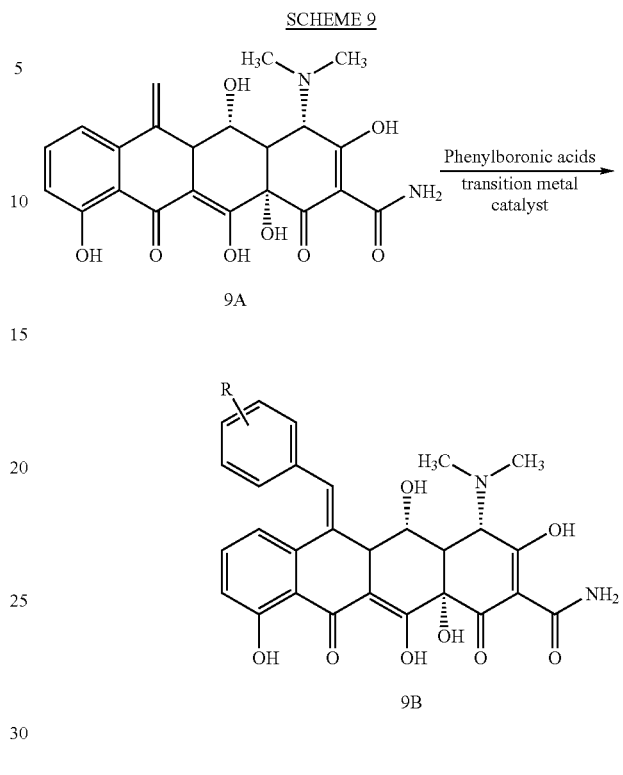

SCHEME 9

9A

9B

As depicted in Scheme 8, 5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

As shown in Scheme 9, methacycline (9A) can be reacted with a phenylboronic acid in the presence of a palladium catalyst such as Pd(OAc)$_2$ to form a 13 aryl substituted methacycline compound. The resulting compound can then be purified using techniques known in the art such as preparative HPLC and characterized.

As shown in Scheme 10 below, 7 and 9 aminomethyl tetracyclines may be synthesized using reagents such as hydroxymethyl-carbamic acid benzyl ester.

SCHEME 10

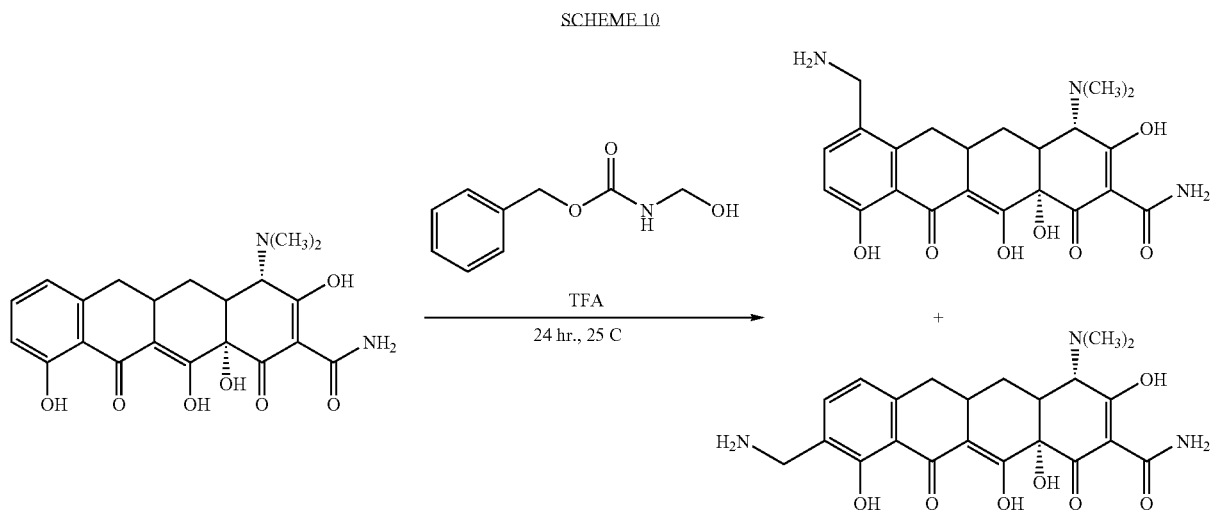

The term "alkenyl" includes unsaturated aliphatic groups, including straight-chain alkenyl groups, branched-chain alkenyl groups, cycloalkenyl (alicyclic) groups, alkenyl substituted cycloalkyl or cycloalkenyl groups, and cycloalkenyl substituted alkyl or alkenyl groups. The term alkenyl further includes alkenyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkenyl group has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkenyl groups have from 4–7 carbon atoms in their ring structure, and more preferably have 5 or 6 carbons in the ring structure, e.g., cyclopentene or cyclohexene.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkyls have from 4–7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acyl amino (including alkylcarbonyl amino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively. Examples of substituents of alkynyl groups include, for example alkyl, alkenyl (e.g., cycloalkenyl, e.g., cyclohenxenyl), and aryl groups.

Unless the number of carbons is otherwise specified, "lower alkyl" as used herein means an alkyl group, as defined above, but having from one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "alkylsulfinyl" include groups which have one or more sulfinyl (SO) linkages, typically 1 to about 5 or 6 sulfinyl linkages. Advantageous alkylsulfinyl groups include groups having 1 to about 12 carbon atoms, preferably from 1 to about 6 carbon atoms.

The term "alkylsulfonyl" includes groups which have one or more sulfonyl ($SO_2$) linkages, typically 1 to about 5 or 6 sulfonyl linkages. Advantageous alkylsulfonyl groups include groups having 1 to about 12 carbon atoms, preferably from 1 to about 6 carbon atoms.

The term "alkanoyl" includes groups having 1 to about 4 or 5 carbonyl groups. The term "aroyl" includes aryl groups, such as phenyl and other carbocyclic aryls, which have carbonyl substituents. The term "alkaroyl" includes aryl groups with alkylcarbonyl substituents, e.g., phenylaetyl.

The structures of some of the substituted tetracycline compounds used in the methods and compositions of the invention include asymmetric carbon atoms. The isomers arising from the chiral atoms (e.g., all enantiomers and diastereomers) are included within the scope of this invention, unless indicated otherwise. Such isomers can be obtained in substantially pure form by classical separation techniques and by stereochemically controlled synthesis.

In one embodiment, the invention pertains to methods for treating fungal associated disorder in a subject. The method includes administering to the subject an effective amount of a substituted tetracycline compound in combination with an antifungal agent such that the subject is treated for the fungal associated disorder.

The language "effective amount" of a substituted tetracycline compound and/or an antifungal agent is that amount necessary or sufficient to inhibit the growth of fungus, or treat a fungus associated disorder, e.g., in a subject, e.g., prevent the various morphological and somatic symptoms of a fungal associated disorder. The effective amount can vary depending on such factors as the size and weight of the subject, the type of disorder, or the particular substituted tetracycline compound and/or antifungal agent. For example, the choice of the substituted tetracycline compound and/or antifungal agent can affect what constitutes an "effective amount". One of ordinary skill in the art would be able to study the aforementioned factors and make the determination regarding the effective amount of the substituted tetracycline compound and/or antifungal agent without undue experimentation. An in vitro assay as described in Example 2 below or an assay similar thereto (e.g., differing in choice of fungus) also can be used to determine an "effective amount" of a substituted tetracycline compound and/or antifungal agent. The ordinarily skilled artisan would select an appropriate amount of a substituted tetracycline compound for use in the aforementioned in vitro assay.

The term "subject" any organism which may benefit from the inhibition of a fungus or which is capable of having a fungal associated disorder. Examples of subjects include not only animals, such as mammals, birds, fish, etc., but plants which may be adversely effected by the presence of a fungus.

The term "mammal" includes, but is not limited to, ruminants (e.g., cattle and goats), mice, rats, hamsters, dogs, cats, horses, pigs, sheep, lions, tigers, bears, monkeys, chimpanzees, and, in a preferred embodiment, humans. The mammal may be immunocompetent or immunocompromised, e.g., suffering from an immunodeficiency. For example, the mammal may have AIDS or may have previously or concurrently undergone chemotherapy. In another embodiment, the mammal may be elderly or young. The mammal may or may not be suffering from a fungal associated disorder. The tetracycline compounds may be administered to a mammal susceptible to a fungal associated disorder to prevent the occurrence of the disorder.

The language "fungal associated disorder" includes disorders which are related to the presence of fungus in a subject Examples of fungal associated disorders in animals include topical fungal infections caused by, e.g., *Candida*, and dermatophytes such as *Trichophyton, Microsporum* or *Epidermophyton*, or in mucosal infections caused by *Candida albicans* (e.g., oral thrush and vaginal candidiasis). The substituted tetracycline compounds of the invention are also useful for treatment of systemic fungal infections caused by, for example, *Candida albicans, Cryptococcus neoformans, Aspergillus flavus, Aspergillus fumigatus, Coccidioides, Paracoccidioides, Histoplasma* or *Blastomyces*. The substituted tetracycline compounds of the invention are particularly useful for treating fungal infections in immunocompromised patients such as patients with viral infections such as AIDS, CMV, and influenza, cancer patients receiving chemotherapy or radiotherapy, transplant patients receiving antirejection agents, and patients that have received toxic chemicals, metals and radiation exposure.

Other fungal associated disorders include aspergillosis, candidosis, chromomycosis, coccidioidiocycosis, cryptocococcosis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, and sprotrichiosis in animals. In an embodiment, the substituted tetracycline compounds of the invention can be included in feed for the livestock, such that normal consumption of said feed provides about 1 mg to about 200 mg of at least one of the substituted tetracycline compounds of the invention per kg of animal per day.

The term "in combination with" an antifungal agent is intended to include simultaneous administration of the substituted tetracycline compound and the antifungal agent, administration of the antifungal agent first, followed by the substituted tetracycline compound and administration of the substituted tetracycline compound first, followed by the antifungal agent. The antifungal agent can be administered by the same or one or more different routes than the tetracycline. The antifungal agent and the tetracycline compound may be administered at an appropriate interval (e.g., an interval selected such that the compounds of the invention are allowed to perform their intended function, e.g., the substituted tetracycline compound and the antifungal agent are allowed to interact synergistically).

The invention also pertains to a method for treating a fungal associated disorder in a mammal. The method includes administering to a mammal a synergistically effective amount of a substituted tetracycline compound in combination with an effective amount amphotericin B, such that said mammal is treated for said fungal associated disorder. In one embodiment, the tetracycline compound is a compound of formula (I). In another embodiment, the tetracycline compound is a tetracycline compound shown in Table 2.

The invention also pertains to pharmaceutical compositions comprising a synergistically effective amount of a substituted tetracycline compound, an effective amount of an antifungal agent, and, optionally, a pharmaceutically acceptable carrier.

The term "synergistically effective amount" is the amount of a substituted tetracycline compound of the invention necessary to increase the antifungal activity of the antifungal agent, such that the fungal associated disorder is treated.

The language "pharmaceutically acceptable carrier" includes substances capable of being coadministered with the substituted tetracycline compound and the antifungal agent, and which allows the antifungal agent and the substituted tetracycline compounds to perform their intended function, e.g., treat or prevent a fungal associated disorder. Examples of such carriers include solutions, solvents, dispersion media, delay agents, emulsions and the like. The use of such media for pharmaceutically active substances are well known in the art. Any other conventional carrier suitable for use with the tetracycline compounds of the present invention are included. The pharmaceutically acceptable carrier may be formulated such that it releases one or more of the active components over a desireable length of time, e.g., time release, by methods known in the art.

For example, one or more compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Substituted tetracycline compounds and antifungal agents may be administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an appropriate acidic group is present on a substituted tetracycline compound or antifungal agent of the invention, a pharmaceutically acceptable salt of an organic or inorganic base can be employed such as an ammonium salt, or salt of an organic amine, or a salt of an alkali metal or alkaline earth metal such as a potassium, calcium or sodium salt.

Therapeutic compounds can be administered to a subject in accordance with the invention by any of a variety of routes. Topical (including transdermal, buccal or sublingual), oral, parenteral (including intraperitoneal, subcutaneous, intravenous, intradermal or intramuscular injection) are generally preferred.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral application, particularly suitable are solutions, preferably oily or aqueous solutions as well as suspensions, emulsions, or implants, including suppositories. Therapeutic compositions will be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For topical applications, the substituted tetracycline compound and antifungal agents can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

The actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the Physicians' Desk Reference. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines and antifungal agents generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

In a still further aspect, the substituted tetracycline compounds and antifungal agents of the present invention can also be used in agricultural compositions, for example, compositions for plants and seeds to treat or prevent a variety of plant pathogenic fungi, including rusts, mildews, and molds. Generally, the compounds of the present invention are dispensed in the form of dusting powders, granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture, and they are manufactured in accordance with conventional procedures. The compositions typically contain from 0.01 to 10 wt %, preferably 0.1 to 1 wt. % of the active ingredient. The compositions may also incorporate other active ingredients, for example, compounds having herbicidal or insecticidal activity or a further fungicide. The compounds and compositions can be applied in a number of ways, for example, they can be applied directly to the plant foliage, stems, branches, seeds or roots or to the soil or other growing medium and they may be used not only to eradicate disease, but also prophylactically to protect the plants or seeds from attack. For field use, likely application rates of active ingredient are about 100 to 10,000 g/acre.

The invention also pertains to methods of killing fungus, by contacting the fungus with a synergistically effective amount of a substituted tetracycline compound and a effective amount of an antifungal agent, such that said fungus is killed.

The present invention is further illustrated by the following examples. These examples are provided to aid in the understanding of the invention and are not to be construed as limitations thereof.

Exemplification of the Invention

EXAMPLE 1

Synthesis of Tetracycline Compounds

The following example discusses methods of synthesizing the tetracycline compounds of the invention. Other compounds of the invention can be synthesized using techniques discussed in the application and/or by using art recognized methods.

Experimental

Melting points were taken on a Mel-Temp capillary melting point apparatus and are uncorrected. Nuclear magnetic resonance ($^1$H NMR) spectra were recorded at 300 MHz on a Bruker Avance spectrometer. The chemical shift values are expressed in δ values (ppm) relative to tetramethylsilane or 3-(trimethylsilyl)-1-propanesulfonic acid, sodium salt, as either an internal or external standard using $CDCl_3$, $DMSO-d_6$, or $MeOH-d_4$ as the solvent. Column chromatography was performed according to the method of Still using Baker "flash" grade silica gel (40 μm) that was treated with a saturated solution of $Na_2EDTA$, washed with water, filtered and dried in an oven at 130° C. for three hours prior to use. Analytical TLC separations employed the use of 0.25 mm silica gel plates with florescence indicator obtained from J. T. Baker Chemical Co., Phillipsburg, N.J., that were pretreated by immersion into a saturated solution of $Na_2EDTA$ for five minutes and reactivated at 130° C. for three hours. Solvent systems used were as follows: 50:50:5 $CHCl_3/MeOH/5\%$ $Na_2EDTA$ (lower phase) (I), 65:20:5, $CHCl_3/MeOH/Na_2EDTA$ (lower phase) (II). Visualization of TLC was accomplished by 0.5% aqueous Fast Blue BB salt and heating at 130° C. for 5 minutes. Analytical HPLC was performed on a Waters Bondapak C18 reverse phase column by using two Varian SD 100 HPLC pumps at a 1.6 mL/min flow rate controlled by software, Detection was by UV absorption with Model 441 absorbance detector operating at 280 nm. Mobile phases used followed a linear gradient from 30% to 100% methanol over 30 minutes at 1.6 mL/min flow rate followed by isocratic elution with MeOH; solvent system A: 0.02 M $Na_2HPO_4$+0.001 M $Na_2EDTA$ adjusted to pH 4.5 with $H_3PO_3$; solvent system B: 100% MeOH. Semipreparative HPLC separations used a Waters semipreparative C18 reverse-phase column at a flow rate of 6.4 mL/min. Low and high resolution mass spectra were performed on a PE Mariner spectrometer (Nelson et al., *J. Med. Chem.* (1993) 36(3):374).

7 Iodo Sancycline

One gram of sancycline was dissolved in 25 mL of TFA (trifluoroacetic acid) that was cooled to 0 C (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal., filtering through Celite, and subsequent removal of the solvent in vacuo to produce the 7-isomer compound as a pure yellow solid in 75% yield.

MS(M+H) (formic acid solvent) 541.3.

\Rt: Hypersil C18 BDS Column, 11.73.

$^1$H NMR (Methanol $d_4$-300 MHz) δ 7.87–7.90 (d, 1H), 6.66–6.69 (d, 1H), 4.06 (s, 1H), 2.98 (s, 6H), 2.42 (m, 1H), 2.19 (m, 1H), 1.62 (m, 4H), 0.99 (m, 2H).

Compound B (13-(4'-Trifluoromethylphenyl) Methacycline)

Methacycline (1.0 mmol), $PdCl_2$ (0.14 mmol), and $CuCl_2$ (0.90 mmol) were dissolved in 20 ml of MeOH and heated under nitrogen atmosphere. After 1 hour, the 4-trifluoromethylphenyl boronic acid (2.0 mmol) was added to it and the reaction mixture was heated for another 6–10 hours. The reactions was monitored by TLC, and analytical HPLC. The reaction mixture was then cooled down to the room temperature and was passed through a bed of celite. Evaporation of the solvent gave a yellow-brown solid, which was purified using preparative HPLC ($CH_3CN:MeOH:H_2O$). Evaporation of the solvent from the fractions indicated the right peak for the expected product, gave a yellow solid, which was again dissolved in MeOH and purged with HCl gas. After evaporation of MeOH, the yellow material was dried under vacuum for several hours.

Compound HF (7-(3',4'-Dimethoxy-Phenyl Sancycline)

7-iodosancycline (0.28 mM), $Pd(OAc)_2$ and 10 mL of MeOH are added to a flask with a stir bar and the system degassed 3× using argon. $Na_2CO_3$ (0.8 mM) dissolved in water and argon degassed is added via syringe is added along with 2,5-dimethoxy phenylboronic acid (0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The solvent was removed in vacuo to yield the product plus salts. The salts were removed by extraction into 50:25:25 water, butanol, ethyl acetate and dried in vacuo. This solid was dissolved in MeOH and the HCl salt made by bubbling in HCl gas.

Compound FN (7-(3'-aminophenyl) Sancycline)

To a solution of 200 mg of 7-(3-nitrophenyl) sancycline in 50 mL methanol, 10 mg of 10% palladium on charcoal catalyst was added. The reaction mixture was shaken under 40 psi hydrogen pressure for 2 hours and was then filtered followed by concentration. The residue was further purified by preparative HPLC. 35 mg was isolated as the HCl salt and the structure was proved by MNR and LC-MS to be 7-(3-aminophenyl) sancycline.

Compound NB (1,8-Di-7-Sancyclinyl-1,8-Heptyne)

A flask was charged with 7-iodosancycline (3.0 g, 4.57 mmol,), Pd(OAc)$_2$ (0.102 g, 0.46 mmol), CuI (0.044 g, 0.23 mmol), and P(o-Tol)$_3$ (0.278 g, 0.91 mmol) and the contents were suspended in anhydrous acetonitrile. After purging this mixture with dinitrogen at 60° C. (bath temperature), 1,7-octadiyne (0.305 mL, 2.29 mmol) was added to it, followed by the addition of triethylamine. The dark colored solution was stirred at 60° C. for 3 h, filtered through a bed of celite, dried. A methanol: DMF: TFA (90:8:2) solution of the product (9C) was purified on-preparative HPLC column. Compound AN was characterized by HPLC, MS, and $^1$H NMR spectroscopy.

Compound EN (7-(2',4'-Difluorophenyl) Sancycline)

7-iodosancycline, (0.3 mM), Pd(OAc)$_2$, and 10 mL of MeOH was added to a flask with a stir bar and the system degassed 3× using argon. Na$_2$CO$_3$ (1.1 mM) dissolved in water and argon degassed was added via syringe is added along with 2,4-difluoro-phenylboronic acid (0.7 mM) in MeOH that was also degassed. The reaction was followed by HPLC for 20 minutes and cooled to room temperature. The solution was filtered, and dried to produce a crude mixture. The solid was dissolved in dimethylformamide and injected onto a preparative HPLC system using C18 reverse-phase silica. The solvent was removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product.

Compound FO (9-Cyclohexenylethynyl-Minocycline)

To a solution of 9-iodo-minocycline (1.13 mmol), 50 mg tetrakis-triphenylphosphino-palladate, 50 mg copper(I) iodide, 10 mg palladium acetate and 3 ml triethylamine, 0.1 ml cyclohexenyl-acetylene was added. The reaction mixture was stirred at 60° C. for one hour, filtered through a celite bed and concentrated. The dry material was dissolved in methanol and filtered. The solution was then concentrated and purified using preparative liquid chromatography. The preparative liquid chromatography used a C$_{18}$ stationary phase with eluent A: 0.1% TFA in water and eluent B: 0.1% TFA in acetonitrile. The resulting compound was determined to be compound BE as determined by standard techniques.

Compound HC (7-(Propynyl)-Sancycline

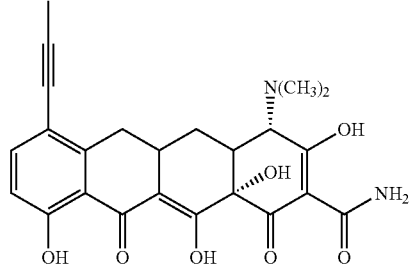

7-I-Sancycline (1 gm, 1.86 mmol), taken in 25 mL of acetonitrile was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen for few minutes. Propyne (3.72 mmol) and triethylamine (1 mL) were added to the suspension. It was turned into a brown solution upon addition of Et$_3$N. The reaction mixture was then heated to 70° C. for 3 hours. Progress of the reaction was monitored by HPLC. It was then cooled down to room temperature and was filtered through celite. Evaporation of the solvent gave a brown solid, which was then purified on preparative HPLC to give a yellow solid. The structure of this compound has been characterized using 1H NMR, HPLC, and MS.

Compound HG (7-(2-Methylphenylethyl)-Sancycline)

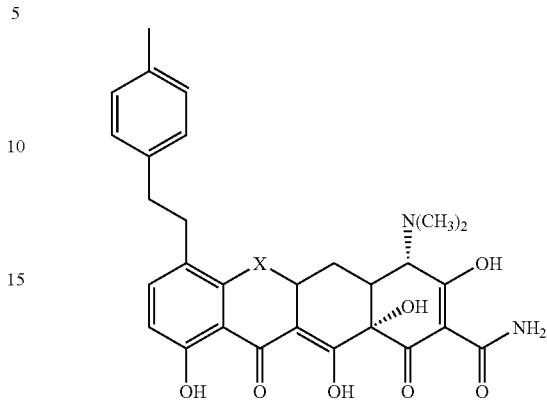

7-(2-Methylphenylethynyl)-sancycline (1 mmol) was taken in saturated solution of MeOH/HCl. To this solution 10% Pd/C was added and was subjected to hydrogenation at 50 psi for 12 hrs. It was then filtered through celite. The solvent was evaporated to give a yellow powder. Finally, it was precipitated from MeOH/diethylether. The structure of this compound has been characterized using 1H NMR, HPLC, and MS.

Compound HJ (9-(4'-Acetyl Phenyl) Minocycline)

In a clean, dry reaction vessel, was placed 9-iodominocycline (0.762 mmoles) bis HCl salt, palladium (II) acetate (0.076 mmoles) along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution, followed by a solution of p-acetylphenyl boronic acid (1.53 mmoles) in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed the pad with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoro-acetic acid.

Compound IO (7-n-Propyl-Sancycline)

7-propynyl sancycline was dissolved in a saturated methanol hydrochloric acid solvent. The mixture was placed in a hydrogenator under 50 psi hydrogen pressure. The reaction was completed in ~8 hours. The catalyst was filtered off, and the resulting solution was concentrated. The crude product was purified by preparative liquid chromatography using a C$_{18}$ stationary phase with eluent A: 0.1% TFA in water and eluent B: 0.1% TFA in acetonitrile. The combined clean fractions are concentrated and hydrochloric acid saturated isopropanol added. The pure product is precipitated by addition of diethylether and filtered off.

Compound OU (N-Benzyl-9'-minocyclinyl Guanidine)

To a stirred solution of 9-aminominocycline (1.6 mmol) in 30 mL of acetonitrile, benzylcyanimide (6.0 mmol) was added in one portion. The reaction mixture was first heated to refluxed at 60° C. for several hours, and continued at room temperature for 4–5 days. The guanidino product was subsequently isolated, and identified using MS, NMR and HPLC.

Compound QE (7-(para-tert-butyl phenyl)-9-aminomethyl Sancycline)

7-para-tert-butyl phenyl sancycline (5.0 g) was dissolved in trifluoroacetic acid (300 mL). Three equivalents of HMBC was added and the reaction was stirred at room temperature. After 72 hours, HPLC indicated that the reaction was complete. The reaction mixture was filtered to give a brown liquid which was subsequently dissolved in methanol and precipitated in diethyl ether. The solid was then purified using HPLC and the product was identified using NMR and mass spectra.

Compound QS (7-Furanyl Sancycline)

7-iodo sancycline (1.3 mg) and Pd(OAc)$_2$ were taken in 100 mL of methanol and purged with argon for five minutes at 70° C. To this solution was added a solution of sodium carbonate (44 mg) in water (previously purged with argon). A yellow precipitate was obtained and the mixture was heated for another ten minutes. 3-Furanyl boronic acid (333 mg, solution in DMF, purged with argon) was then added and the mixture was heated for another two hours at 70° C. The reaction was monitored by MPLC/MS. When the reaction was complete, the mixture was filtered through celite and the solvent was removed to give a crude material. The crude material was purified by precipitating it with ether (200 ml). The yellow precipitate was filtered and purified using preparative HPLC. The hydrochloride salt was made by disolving the material in MeOH/HCl and evaporating to dryness. The identity of the resulting solid was confirmed using HPLC, MS, and NMR.

Compound RR (9-(2'phenyl ethyl amino methyl)-Doxycycline)

Under a N$_2$ atmosphere, a stirred solution of 9-aminomethyldoxycycline dihydrochloride (1.21 g, 2.21 mmol) in DMF (10 mL) was treated with InCl$_3$ (0.076 g, 0.34 mmol) and phenylacetaldehyde (0.511 mL, 4.4 mmol). HPLC and LC-MS monitoring of the reaction indicated the complete consumption of the starting material over the course of twelve hours; the products being both mono- (major) and bis- (minor) substituted aminomethyldoxycycline. Methanol (10 mL) was added to quench this reaction. The reaction mixture was filtered through a bed of celite. The celite bed was subsequently washed with 5 mL of methanol twice. The combined organic washes were concentrated to about 7–8 mL and diluted with ether. The resulting amorphous solid was filtered, washed with ether (6×15 mL) and dried under vacuum to afford a red powder, which was purified by preparative HPLC. The final product, Compound RR, was charachterized by HPLC, MS, and $^1$H NMR spectroscopic methods. MS(m/z): Theor. 577.24; Found: 578.17 (M+1).

Compound SF (7-Ethyl-9-Iso-butyl Amino Sancycline)

7-ethyl-9-amino sancycline (390 mg) was dissolved in 10 mL of DMF. Triethylamine (237 µL), isobutyraldehyde (77 µL), and InCl$_3$ (19 mg) were then added and the reaction mixture was stirred for several minutes at room temperature. Then, NaBH(OAc)$_3$ (360 mg) was added and the reaction was continued at room temperature. LC-MS showed that the reaction was completed after two hours. The reaction was quenched with methanol and dried. The resulting solid was redissolved in methanol and purified. The product was then converted to the HCl salt. The identity of the product was confirmed using NMR, HPLC, and MS.

Compound SM (7-Furanyl-9-nitro-Sancycline)

500 milligrams of 9-NO$_2$ sancycline was taken in 20 mL of TFA and cooled down in an ice bath. To this solution, NIS (300 mg) was added in portions and stirred at room temperature for three hours. Once the reaction was completed, 7-iodo-9-NO$_2$ sancycline was precipitated in diethyl ether. The yellow powder was then filtered and dried in vacuo.

7-Iodo-9-nitro-sancycline (585 mg) and PD(OAc)$_2$ (22 mg) were taken in 20 mL of methanol and purged with argon for five minutes. To this solution, Na$_2$CO$_3$ (420 mg, solution in 5 mL H$_2$O, purgen with argon), was added and a yellow precipitate was obtained. The solution was stirred at 55–60° C. for five minutes. To this solution, 3-furanyl boronic acid (160 mg in 5 mL of DMF, purged with argon) was added and the reaction mixture was heated at 70° C. for three hours. The reaction mixture was then passed through celite. Evaporation of the solvent gave a brown solid, which was then recrystallized using a mixture of methanol and ether to yield 7-furanyl 9-nitro sancycline.

7-Furanyl 9-nitro sancycline (500 mg) was taken in 30 ml of methanol. To this solution, PtO$_2$ (15 mg) was added and hydrogenated at 40 psi for three hours. It was then filtered through celite. The crude material was purified using preparative HPLC to yield 7-furanyl 9-amino sancycline.

Compound TC (9-Minocycline Methyl Ester)

In the Parr apparatus were placed: 9-iodosancycline trifluoroacetic acid salt (0.8 g, 1.17 mmol), NaOAc (0.64 g, 4 eq.), Pd(dppf)$_2$Cl$_2$, and CH$_2$Cl$_2$ (48 mg, 5%). The apparatus was closed, purged with CO, and then filled with CO under 450 psi. The reaction mixture was stirred for four hours at 80° C. It was then acidified with TFA and concentrated in vacuo. The product was purified by HPLC. A mixture of 3:1 epimers was obtained. The yield was 188 mg of product.

Compound TI (7-Cyano Sancycline)

7-iodo sancycline (1.3 g) was dissolved in NMP (15 mL) and CuCN (344 mg) was added. The reaction mixture was stirred at 80° C. for 15/16 hours overnight. The reaction mixture was diluted with methanol and centrifuged to yield a grey white precipitate. The reaction mixture was then passed through Celite and washed with additional methanol. The filtrate was then concentrated and precipitated with ether. The solid obtained was then purified using preparative HPLC to yield 7-cyano sancycline in a 50/50 mixture of epimers. The structure of the product was confirmed using mass spectra and NMR.

Compound TP (9-N-piperdinyl-minocycline)

Concentrated H$_2$SO$_4$ (2 mL) was added slowly to a stirred solution of gluteraldehyde (1 mL). Water (0.8 g) was added and stirred at room temperature for eighteen hours and heater to 70° C. for two hours. The mixture was then cooled to room temperature. The solution was then transferred to a solution of 9-amino minocycline in DMF (5 ml) and stirred at room temperature for two days until all starting material was consumed, as indicated by HPLC. The product was isolated and purified using standard techniques. The structure of the product was confirmed by NMR and mass spec.

Compound UC (2-[4-(5-Minocyclin-9-yl-furan-2-ylmethyl)-piperazin-1-yl]-ethanol)

Na$_2$CO$_3$ (0.64 g) in water (5 mL) was added to a degassed solution of 9-iodo-minocycline hydrochloride (1 g) and Pd(OAc)$_2$ (100 mg) in methanol (10 mL). The reaction was stirred for five minutes at 60° C. 2-Formyl furan-5-boronic acid (0.3 g) in methanol (10 mL) was then added, and the reaction was allowed to proceed for four hours. The mixture was then filtered and concentrated to give a brown solid (9-(2'formyl furanyl)-minocycline).

The brown solid (9-(2'formyl furanyl)-minocycline, 1 g) was dissolved in 20 mL of methanol and acetic acid (2 mL) and hydroxyethyl piperazine (1 mL) was added and stirred for ten minutes at room temperature. The reaction was quenched with ether (200 mL), and the organic layer was then washed and concentrated to yield a brown oil. The brown oil was the dissolved in methanol (10 mL) and water. The mixture was the chromatographed using a CH$_3$CN gradient to yield the product, 2-[4-(9-Minocyclin-2-yl-furan-2-ylmethyl)-piperazin-1-yl]-ethanol. The product was confirmed using MS, NMR, and HPLC.

Compound UD (9-N-morpholinyl Minocycline)

NaCNBH$_3$ (200 mg) was added to a stirred solution of 9-amino minoccycline H$_2$SO$_4$ (1 g) in methanol (4.9 mL) and acetic acid 91 mL) and stirred for five minutes at room temperature. (2-Oxo-ethoxy)-acetaldehyde (10 mL) was added dropwise and stirred for fifteen minutes at room temperature. The reaction mixture was concentrated with out heat and the residue was dissolved in 20 mL of methanol and TFA (0.5 mL). The product was obtained using preparative HPLC and converted to the HCl salt. The product was confirmed using mass spectra and NMR.

Compound UK (N-Benzyl-N',N'-dimethyl-N-(5-minocyclin-9-yl-furan-2-ylmethyl)-ethane-1,2-diamine)

Na$_2$CO$_3$ (0.64 g) in water (5 mL) was added to a degassed solution of 9-iodo-minocycline hydrochloride (1 g) and Pd(OAc)$_2$ (100 mg) in methanol (10 mL). The reaction was stirred for five minutes at 60° C. 2-Formyl furan-5-boronic acid (0.3 g) in methanol (10 mL) was then added, and the reaction was allowed to proceed for four hours. The mixture was then filtered and concentrated to give a brown solid (9-(2'formyl furanyl)-minocycline).

The brown solid (9-(2'formyl furanyl)-minocycline, 1 g) was dissolved in 20 mL of methanol and acetic acid (2 mL) and N'-benzyl-N,N-dimethyl ethylenediamine (1 mL) was added and stirred for ten minutes at room temperature. The reaction was quenched with ether (200 mL), and the organic layer was then washed and concentrated to yield a brown oil. The brown oil was the dissolved in methanol (10 mL) and water. The mixture was the chromatographed using a CH$_3$CN gradient to yield the product, N-Benzyl-N',N'-dimethyl-N-(5-minocyclin-9-yl-furan-2-ylmethyl)-ethane-1,2-diamine. The product was confirmed using MS, NMR, and HPLC.

EXAMPLE 2

Synergetic Antifungal Activity of Substituted Tetracycline Compounds with Amphotericin B Synergetic antifungal activity of the substituted tetracycline compounds was determined by a broth microdillution technique following NCCLS (1997) Standards. Assays were setup using a Tecan Genesis robotic workstation. All drugs were dissolved in DMSO and diluted appropriately. Drug concentration ranged from 0.125 to 64 μg/mL in 2 fold serial dilutions. Each tetracycline was tested at 10 concentrations ranging from 0.125 to 64 μg/mL. The compounds were tested for their antifingal activity against *Candida albicans* (ATCC#90028). Amphotericin B was added to all wells of the plate at a concentration of 10 fold less than the amphotericin B MIC (0.5 μg/mL).

The strains tested include those listed in Table 1.

TABLE 1

| Genus | Species | ATCC/FGSC # |
|---|---|---|
| Aspergillus | fumigatus | ATCC 13073 (Fresenius) |
| Aspergillus | nidulans | FGSCA991 (wt) |
| Candida | albicans | ATCC90028 |
| Candida | albicans | PCI-1 |
| Candida | albicans | PCI-17 |
| Candida | albicans | ATCC 36082 |
| Candida | glabrata | ATCC 90030 |
| Candida | guilliermondii | ATCC 14242 |
| Candida | krusei | ATCC 96685 |
| Candida | krusei | ATCC 90878 |
| Candida | lusitaniae | ATCC 24347 |
| Candida | parapsilosis | ATCC 22109 |
| Candida | tropicalis | ATCC 14246 |
| Candida | tropicalis | ATCC 28707 |
| Cryptococcus | neoformans | ATCC 90012 |
| Cryptococcus | neoformans | ATCC 90013 |
| Issatchenkia | orientalis | ATCC 6258 |
| Neurospora | crassa | FGSC853 |

The results are shown in Table 2. For each compound, * represents good antifungal activity against the particular fungus,  represents very good inhibition of the fungus, and  * represents excellent inhibition of a particular fungus. Each of the compounds in Table 2 exhibited synergistic behavior with amphotericin B for at least one strain of fungi.

A number of derivatives exhibited fractional inhibitory concentrations (FIC) values in the range of 0.063–0.125. The fractional inhibition values are a measure of the enhancement of the amphotericin B antifungal activity. Compounds which exhibit FIC's in the range of 0.063–0.125 allows for a 8–10 fold reduction in the effective amount of amphotericin required for antifungal activity.

TABLE 2

| ID | STRUCTURE | *Aspergillus flavus* | *Aspergillus fumigatus* | *Aspergillus terreus* |
|---|---|---|---|---|
| A | 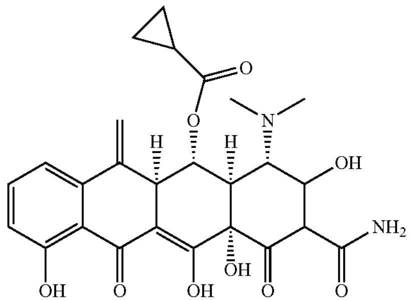 | | | |
| B | 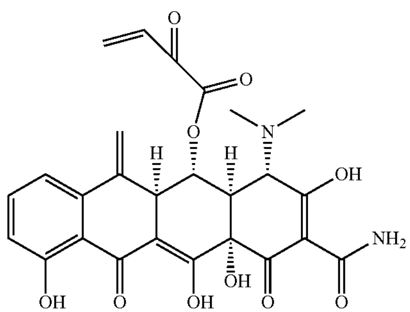 | | | |
| C | 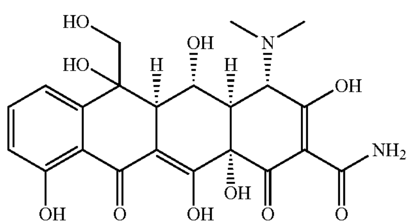 | | | |

TABLE 2-continued
| D | E | F | G |
|---|---|---|---|
| 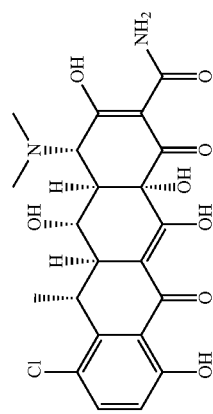 | 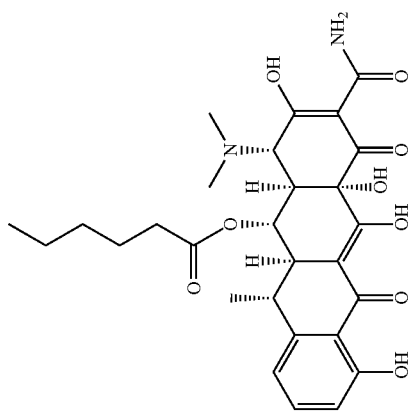 | 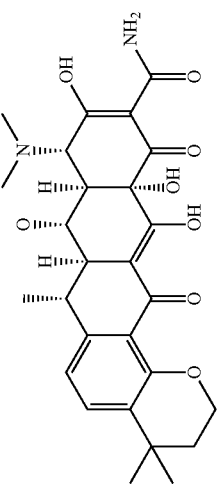 | 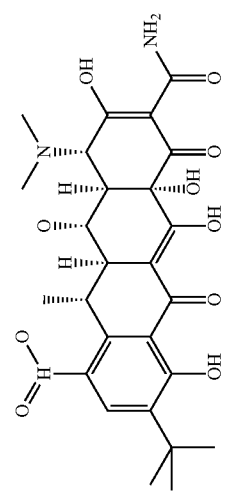 |

TABLE 2-continued
| H | I | J |
|---|---|---|
| 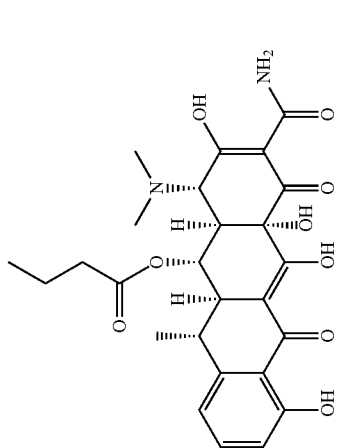 | 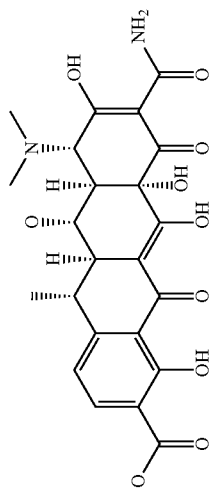 | 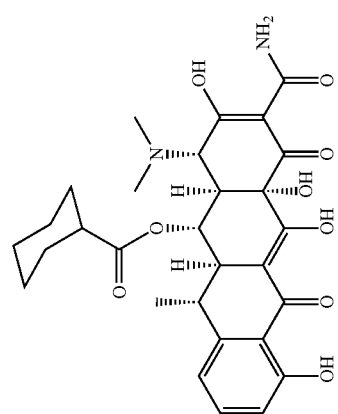 |

TABLE 2-continued
| K | L | M | N |
|---|---|---|---|
| 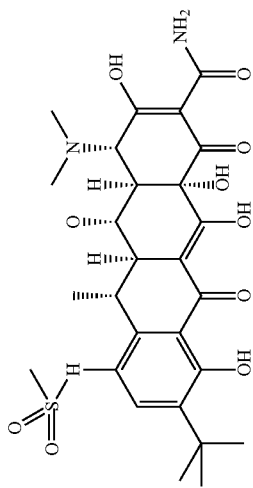 | 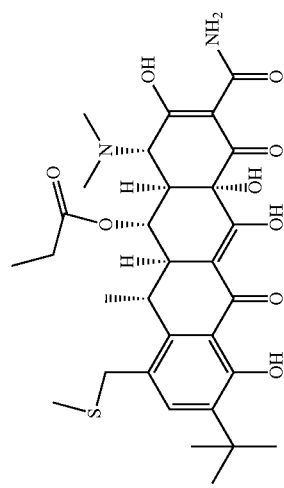 | 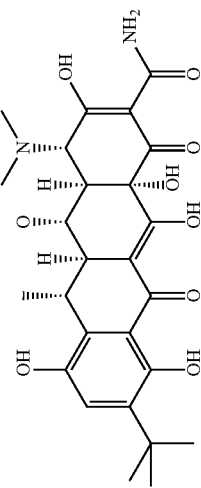 | 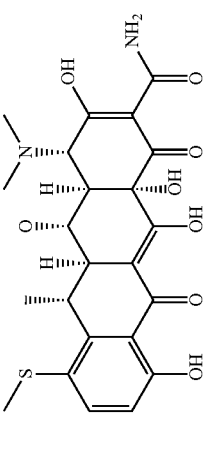 |

TABLE 2-continued
O 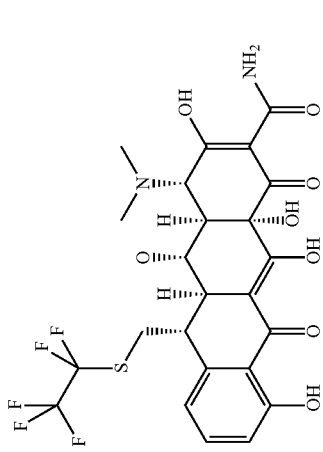
P 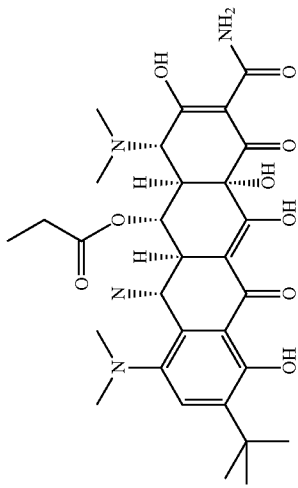
Q 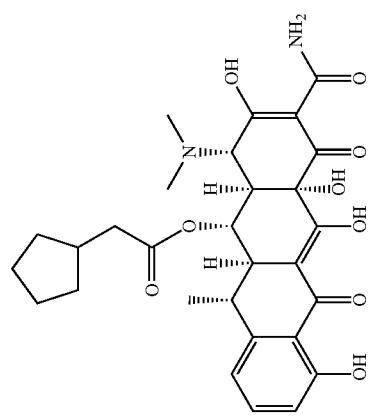

TABLE 2-continued
| R | S | T |
|---|---|---|
| 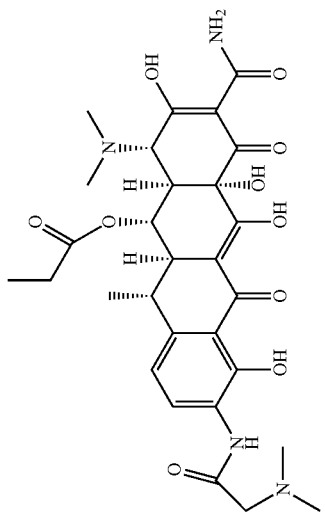 | 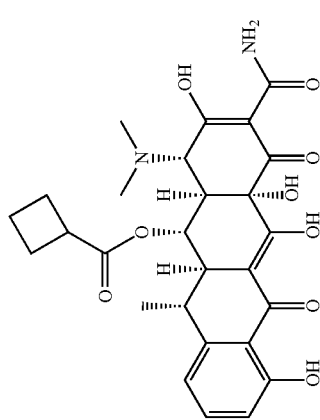 | 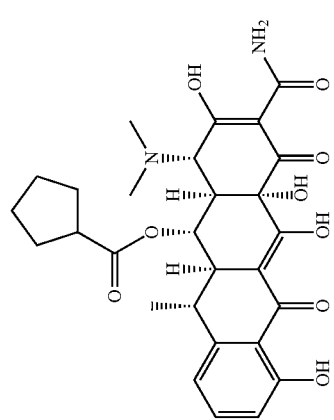 |

TABLE 2-continued
| U | V | W | X |
|---|---|---|---|
| 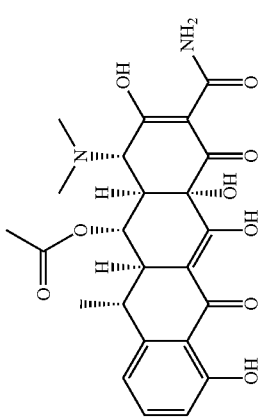 | 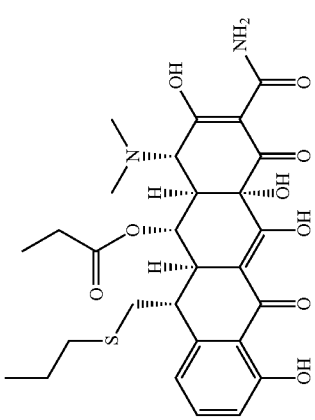 | 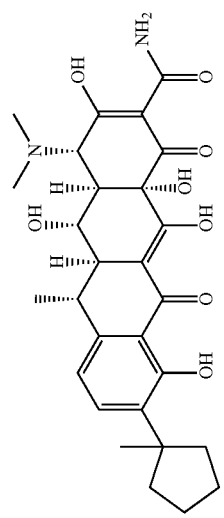 | 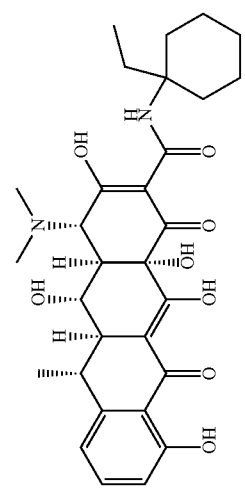 |

TABLE 2-continued
| Y | Z | AA |
|---|---|---|
| 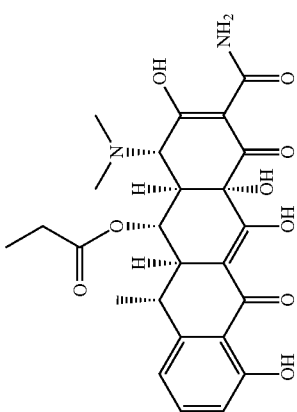 | 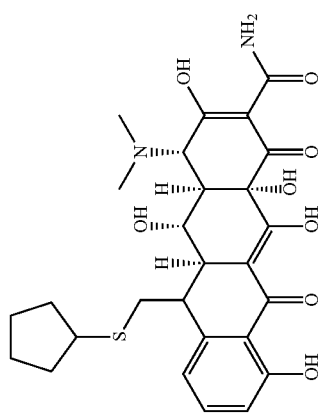 | 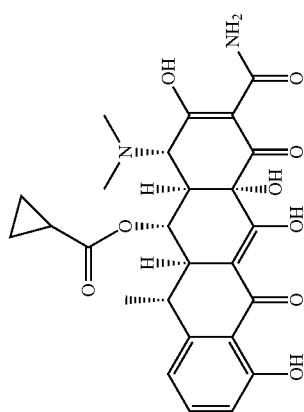 |

TABLE 2-continued
| AB | 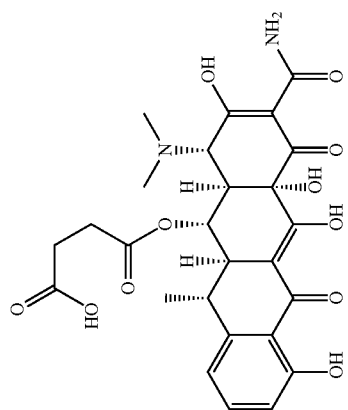 |
| --- | --- |
| AC | 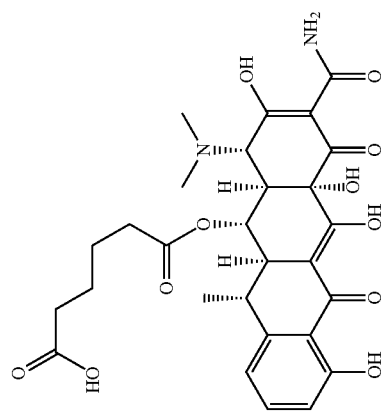 |

TABLE 2-continued
| AD | AE | AF |
|---|---|---|
| 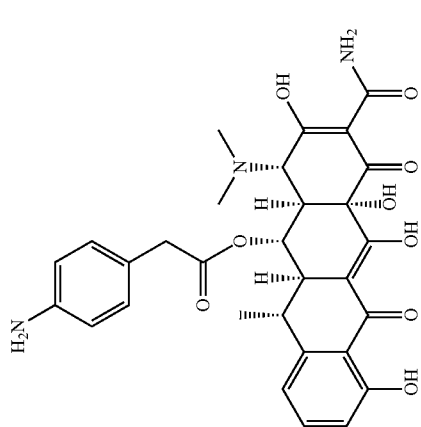 | 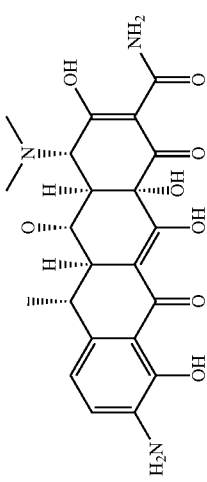 | 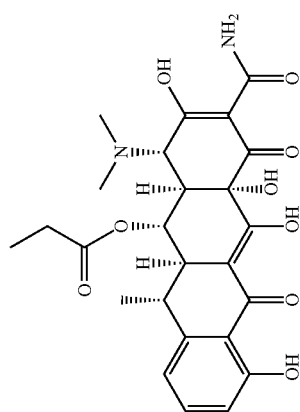 |

TABLE 2-continued
| | |
|---|---|
| AG | 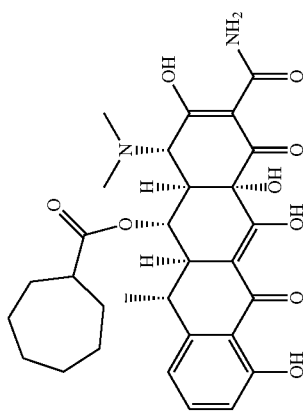 |
| AH | 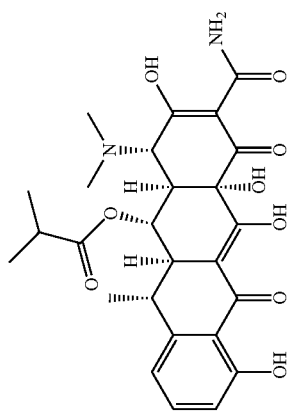 |
| AI | 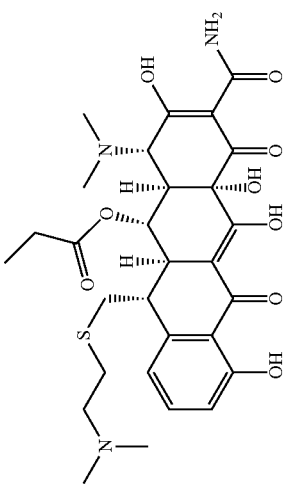 |

TABLE 2-continued
| AJ | 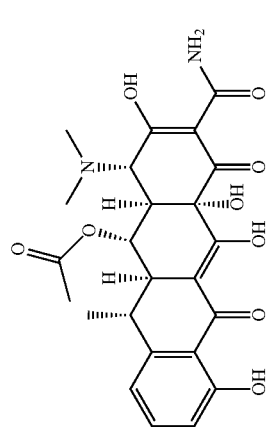 |
| AK | 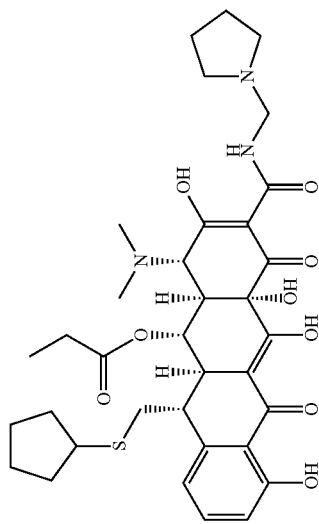 |
| AL | 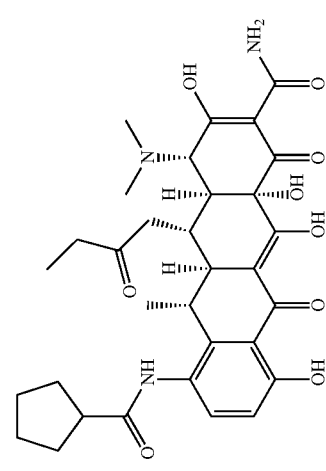 |

TABLE 2-continued
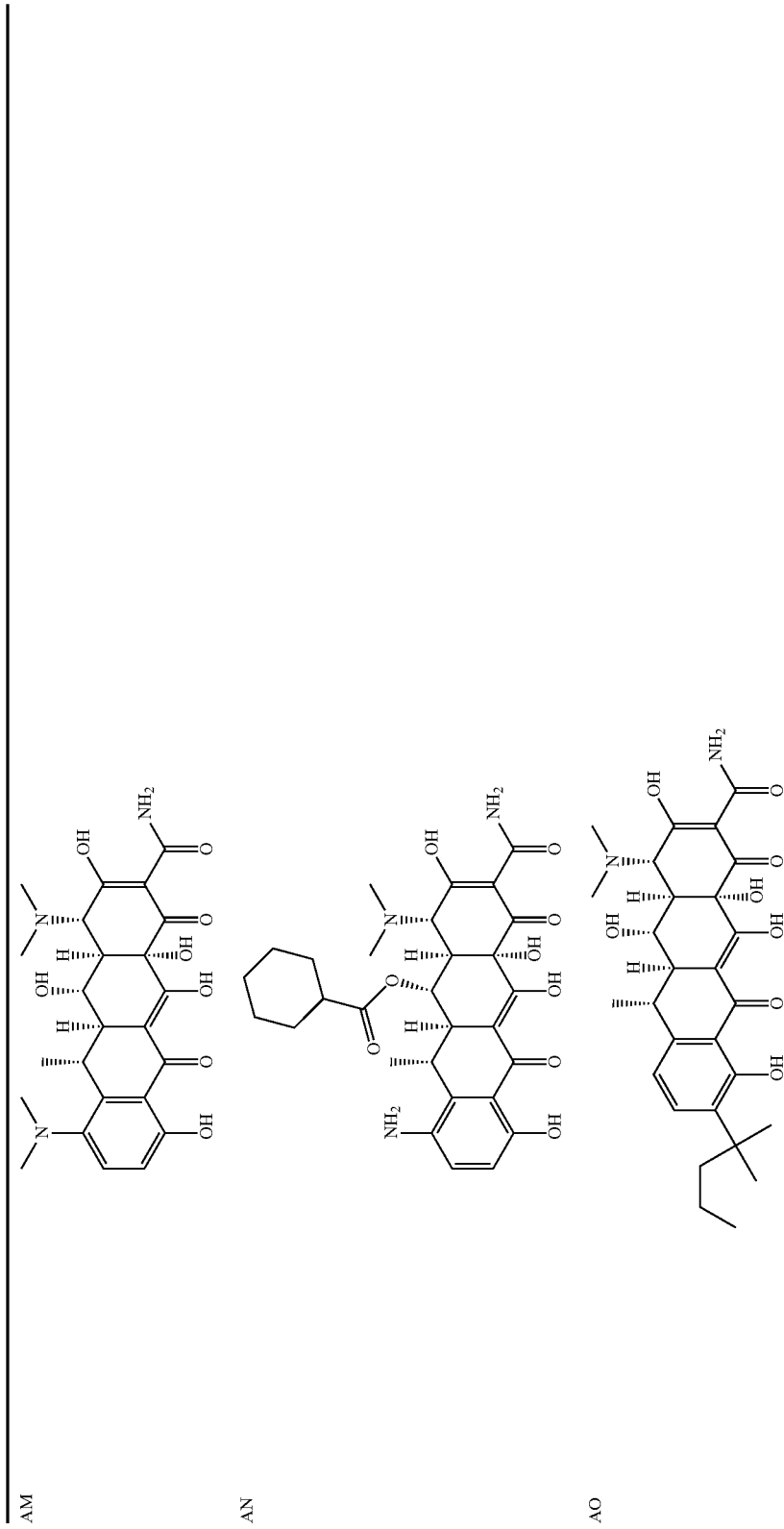
AM
AN
AO

TABLE 2-continued
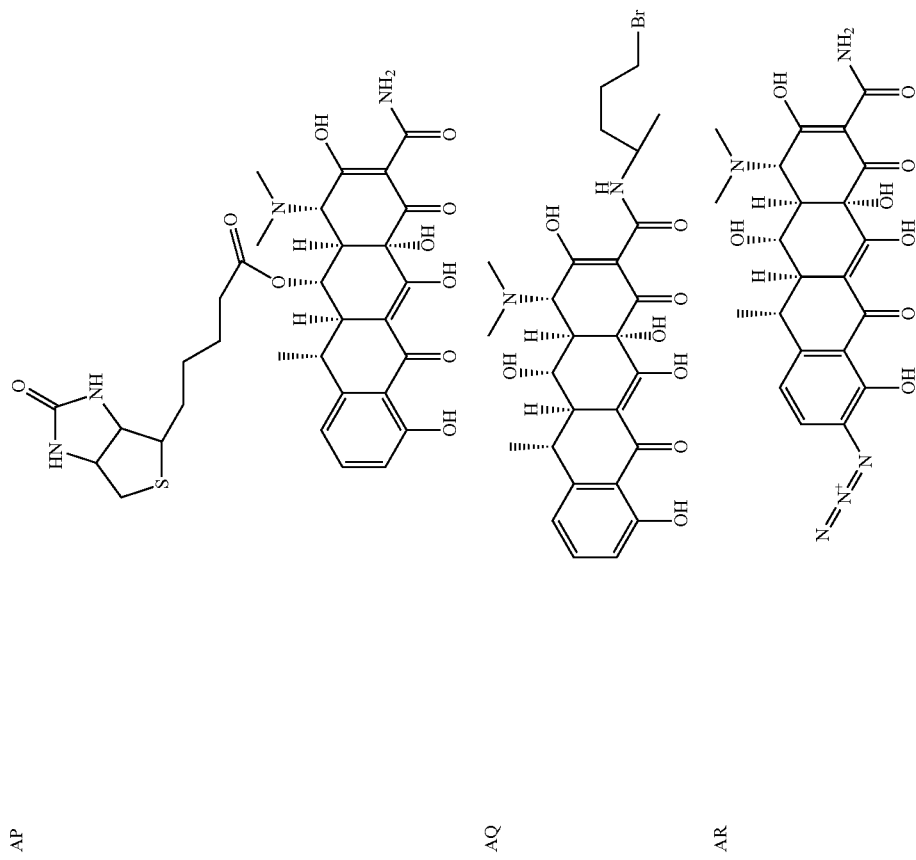
AP
AQ
AR

TABLE 2-continued
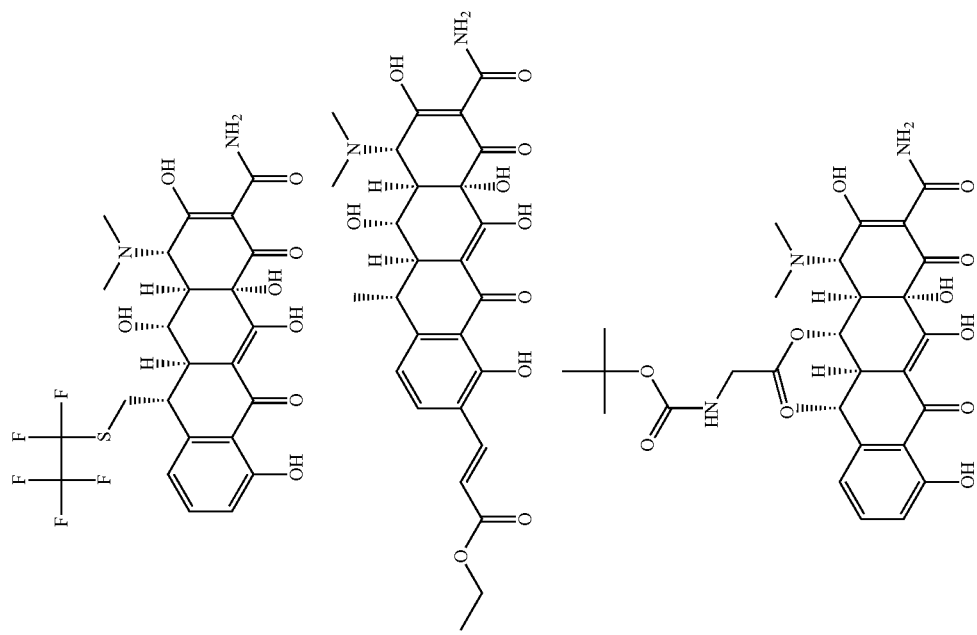
AS
AT
AU

TABLE 2-continued
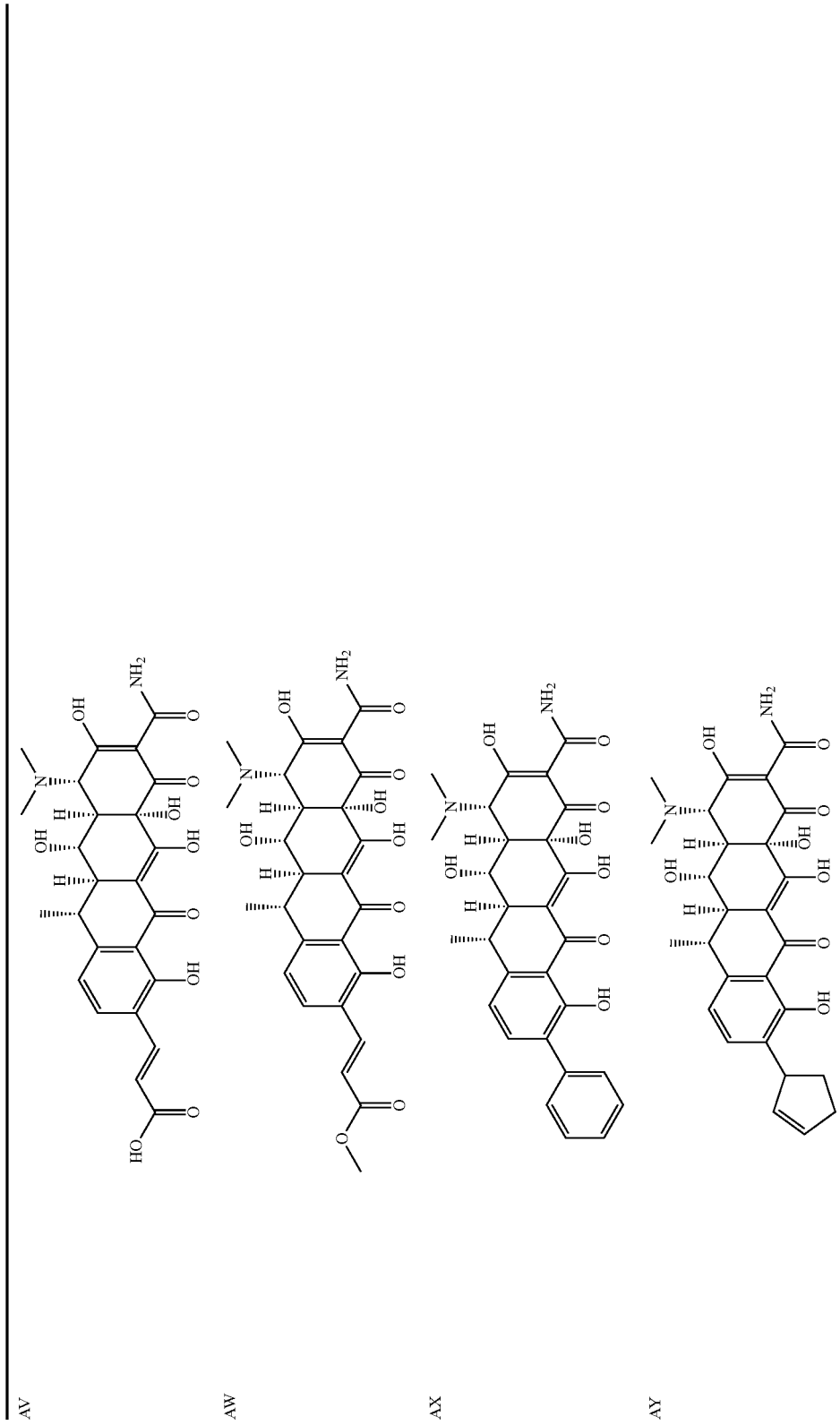
AV
AW
AX
AY

TABLE 2-continued
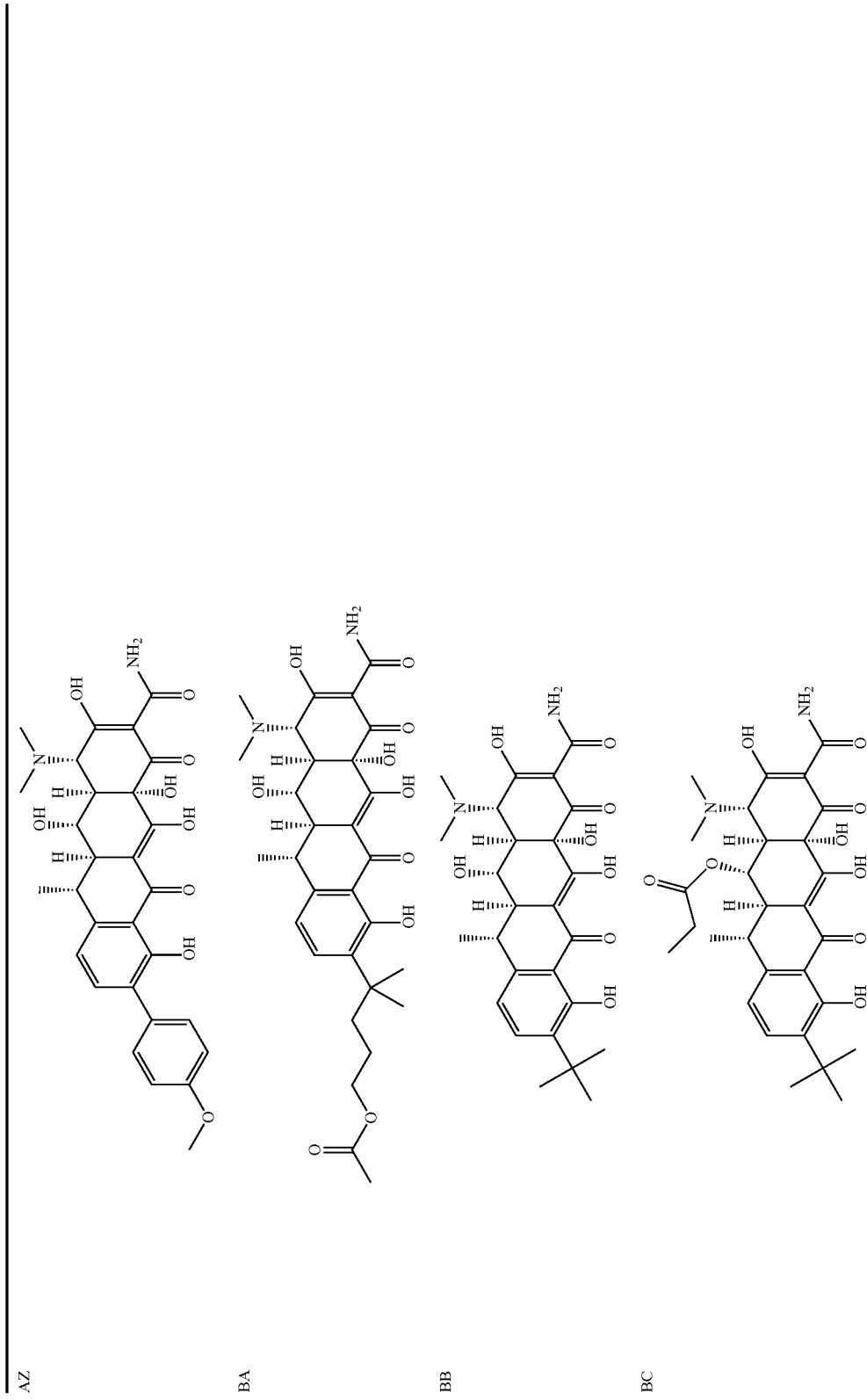
AZ
BA
BB
BC

TABLE 2-continued
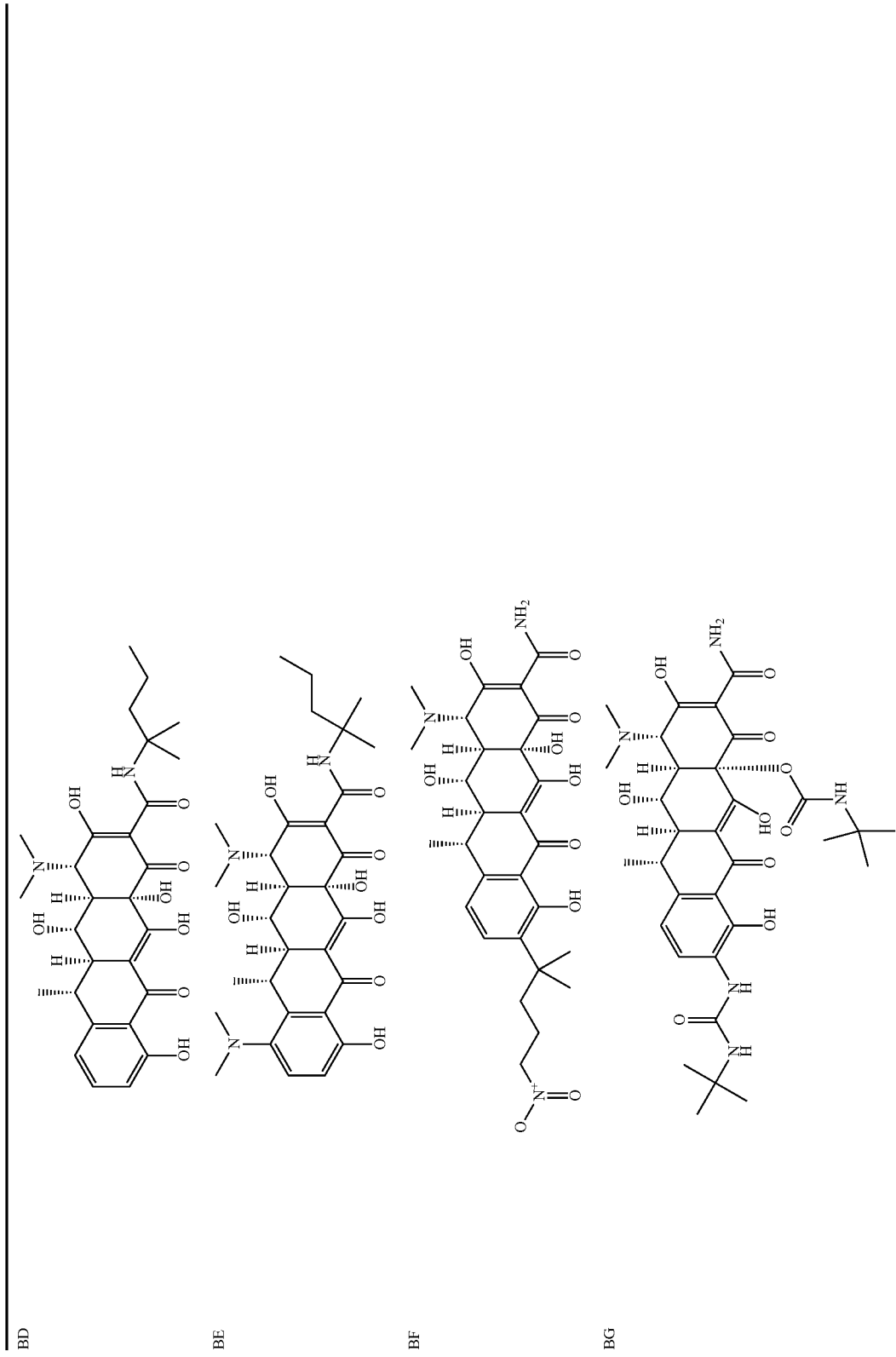

TABLE 2-continued
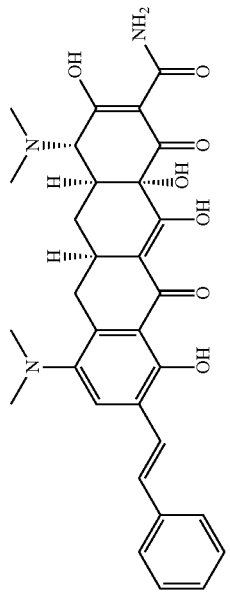
BH
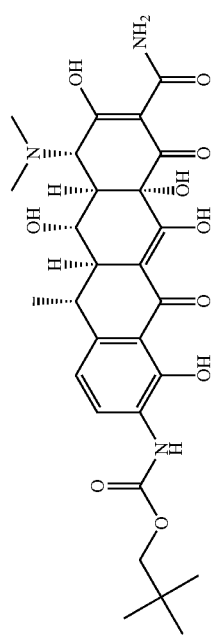
BI
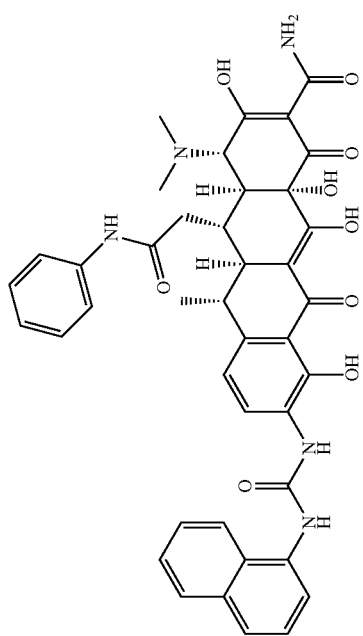
BJ

TABLE 2-continued
| | |
|---|---|
| BK | 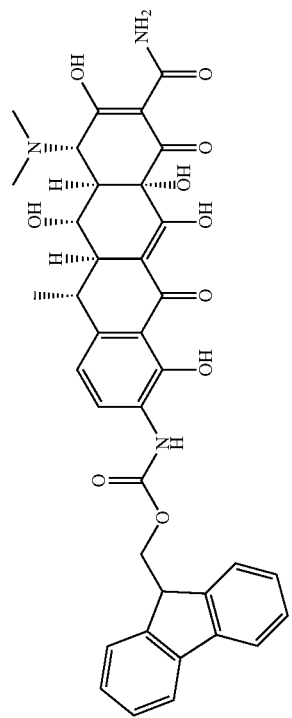 |
| BL | 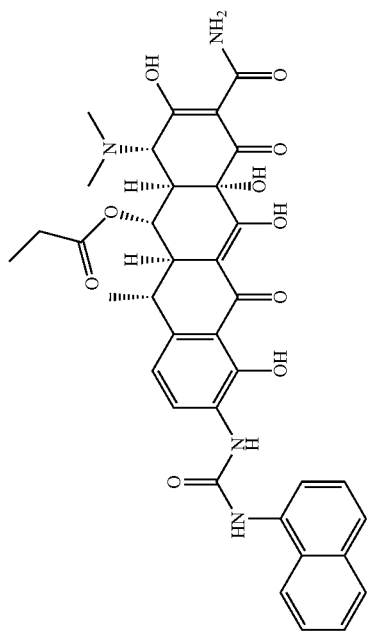 |
| BM | 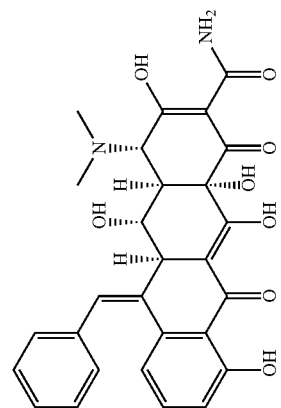 |

TABLE 2-continued
| | |
|---|---|
| BN | 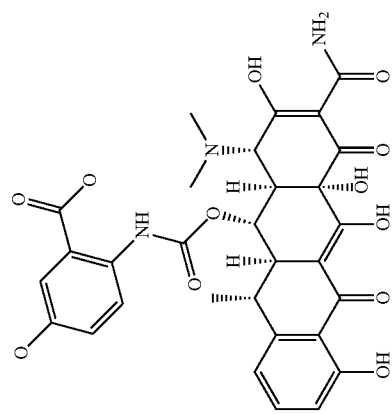 |
| BO | 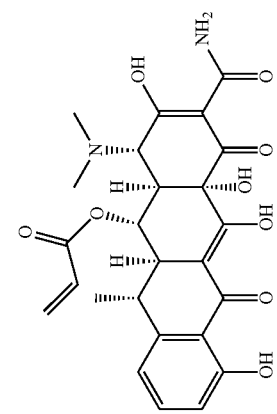 |
| BP | 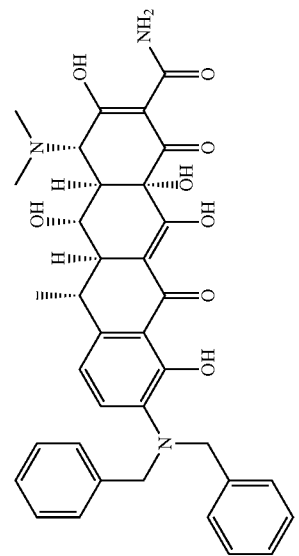 |

TABLE 2-continued
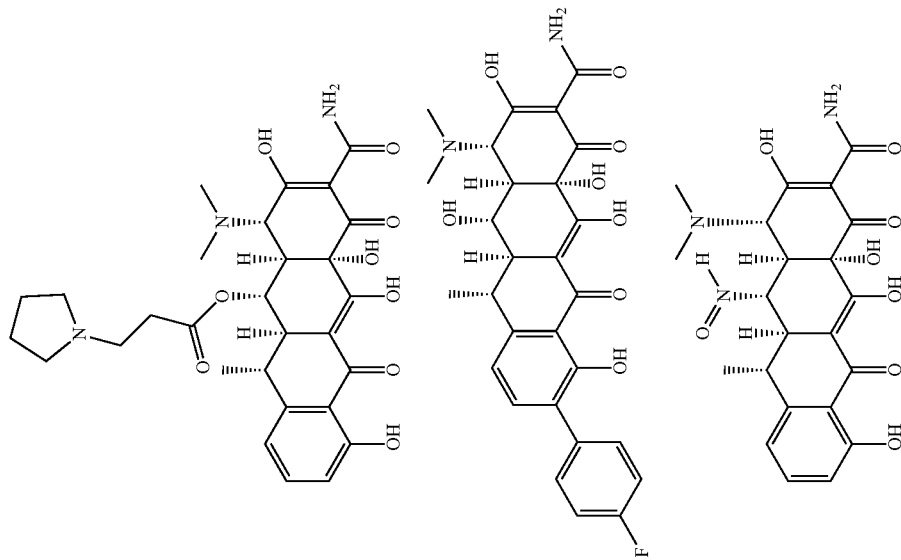
BQ
BR
BS

TABLE 2-continued
| BT | 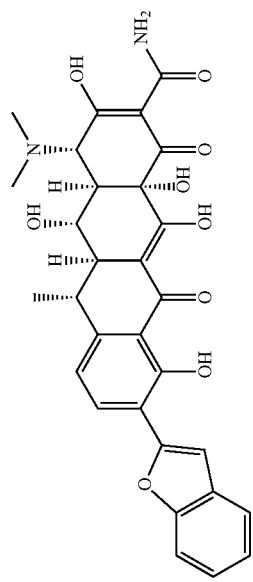 |
| BU | 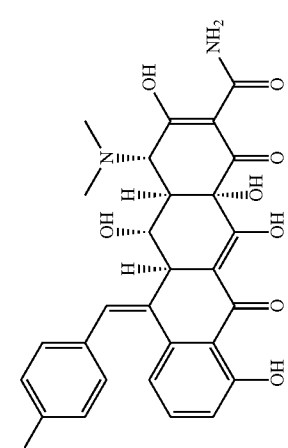 |
| BV | 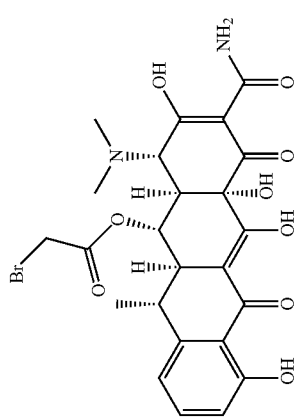 |

TABLE 2-continued
| | |
|---|---|
| BW | 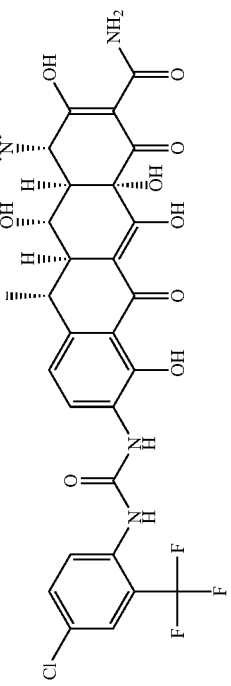 |
| BX | 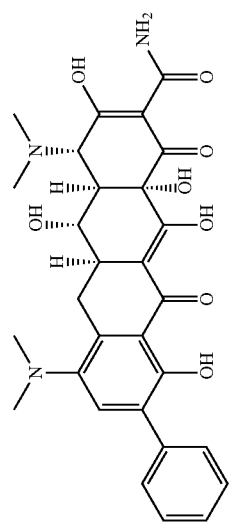 |
| BY | 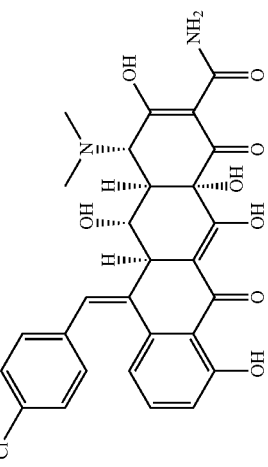 |

TABLE 2-continued
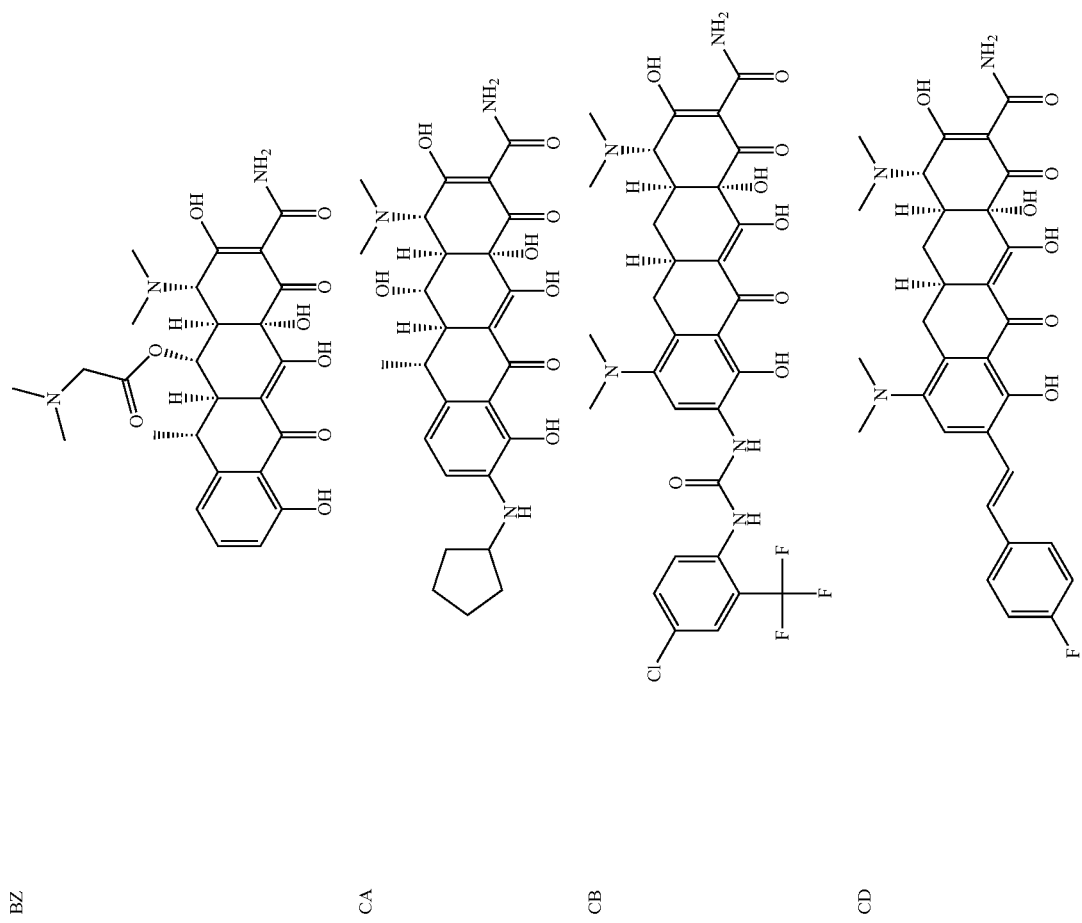
BZ
CA
CB
CD

TABLE 2-continued
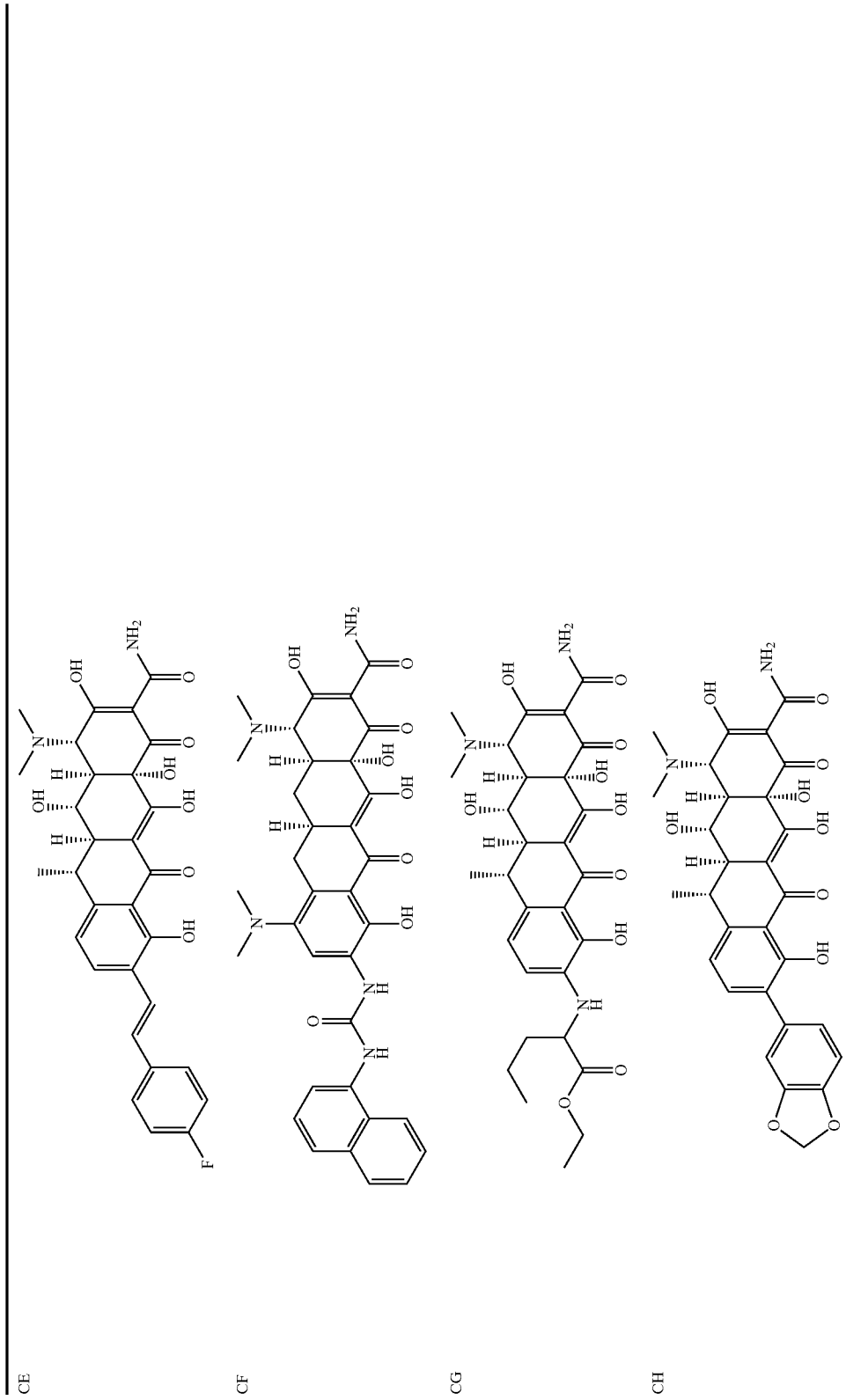
CE
CF
CG
CH

TABLE 2-continued
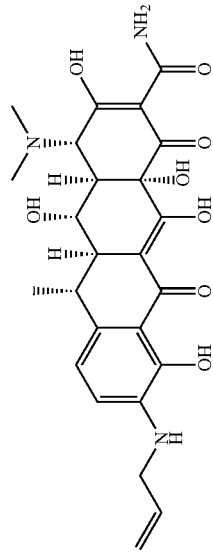
CI
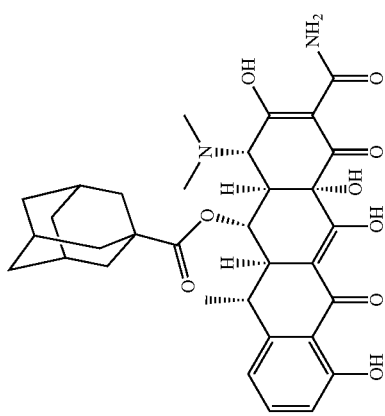
CJ
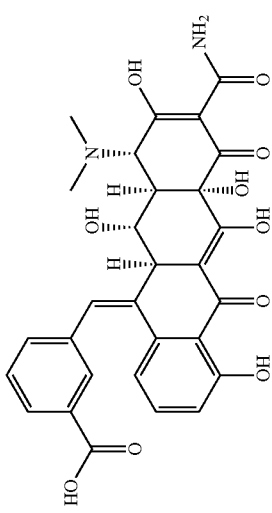
CK

TABLE 2-continued
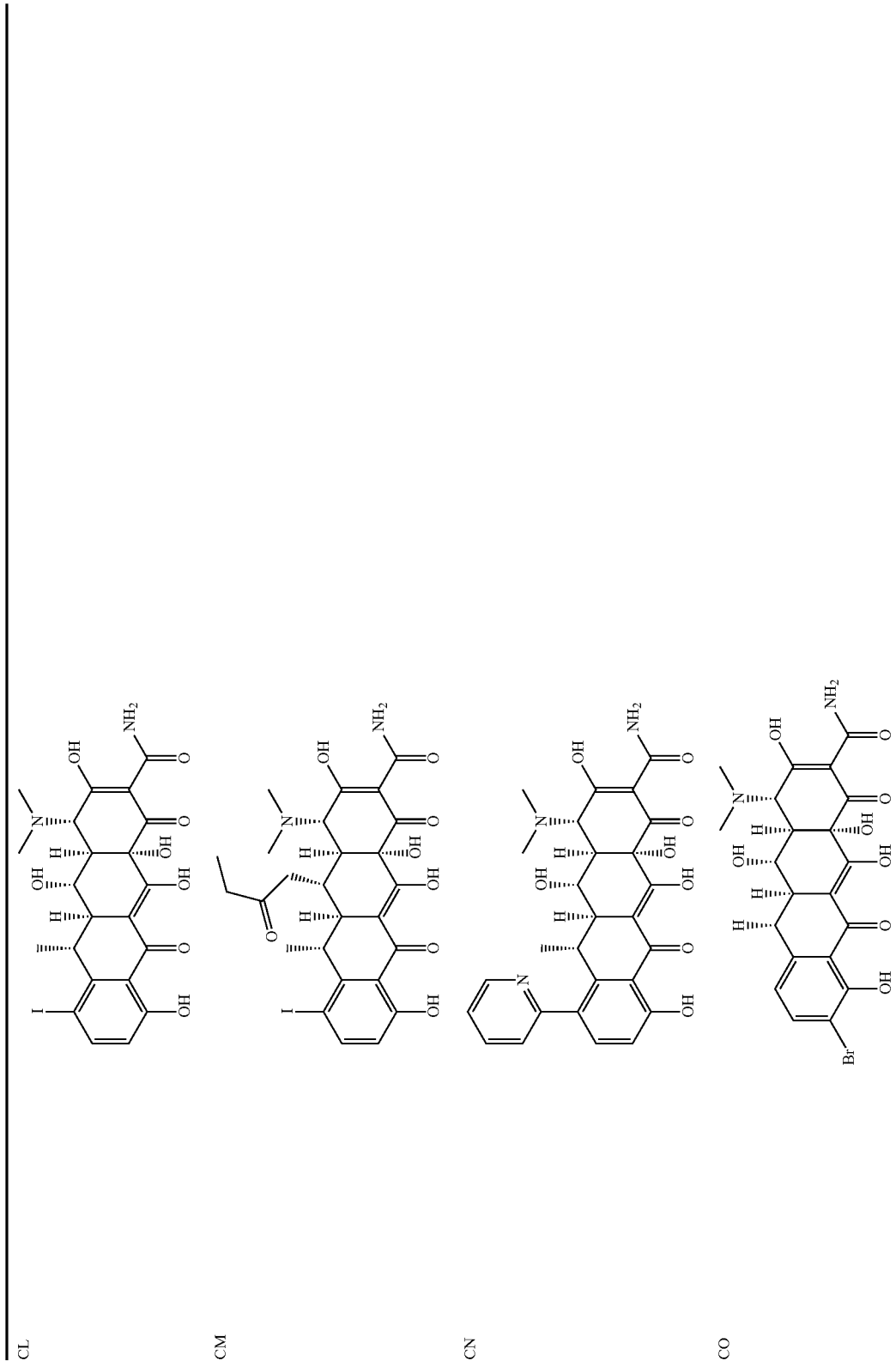
CL
CM
CN
CO

TABLE 2-continued
| | |
|---|---|
| CQ | 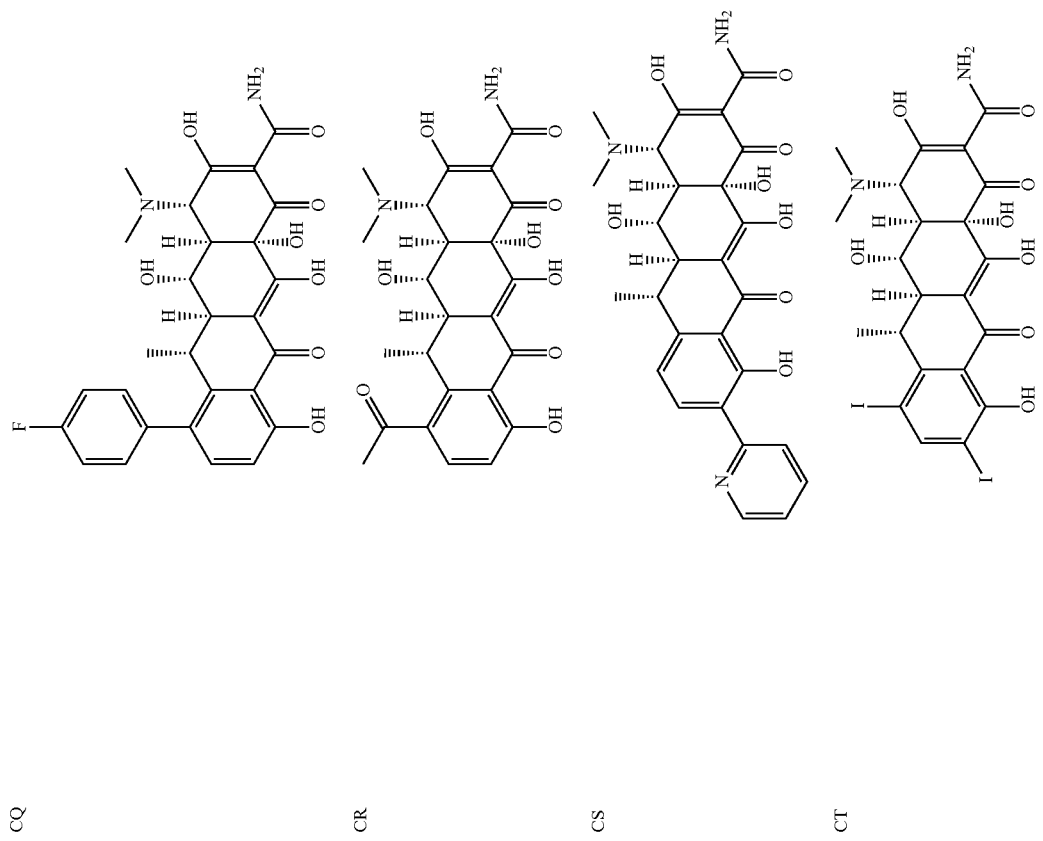 |
| CR | |
| CS | |
| CT | |

TABLE 2-continued
| CU | CV | CW |
|---|---|---|
| 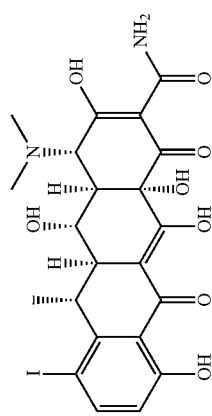 | 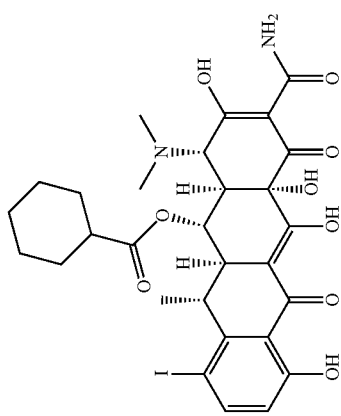 | 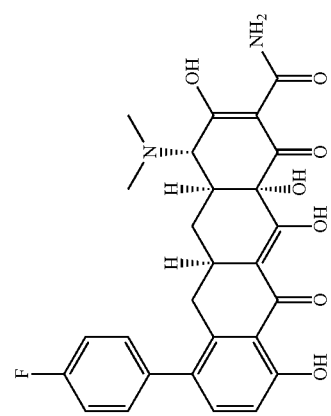 |

TABLE 2-continued
| | |
|---|---|
| CX | 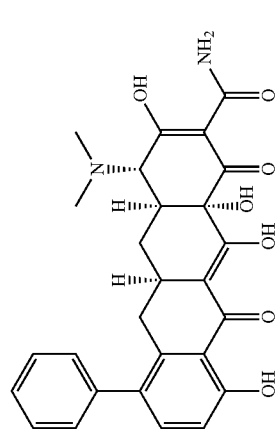 |
| CY | 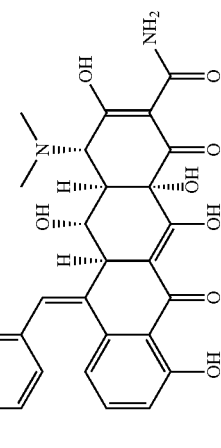 |
| CZ | 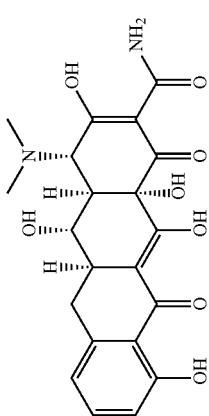 |
| DA | 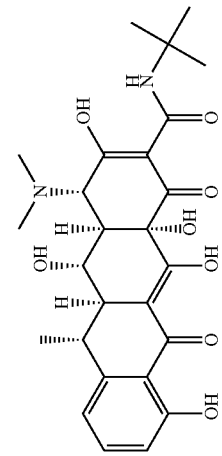 |

TABLE 2-continued

| | |
|---|---|
| DB | [structure] |
| DC | [structure] |
| DD | [structure] |
| DE | [structure] |

TABLE 2-continued
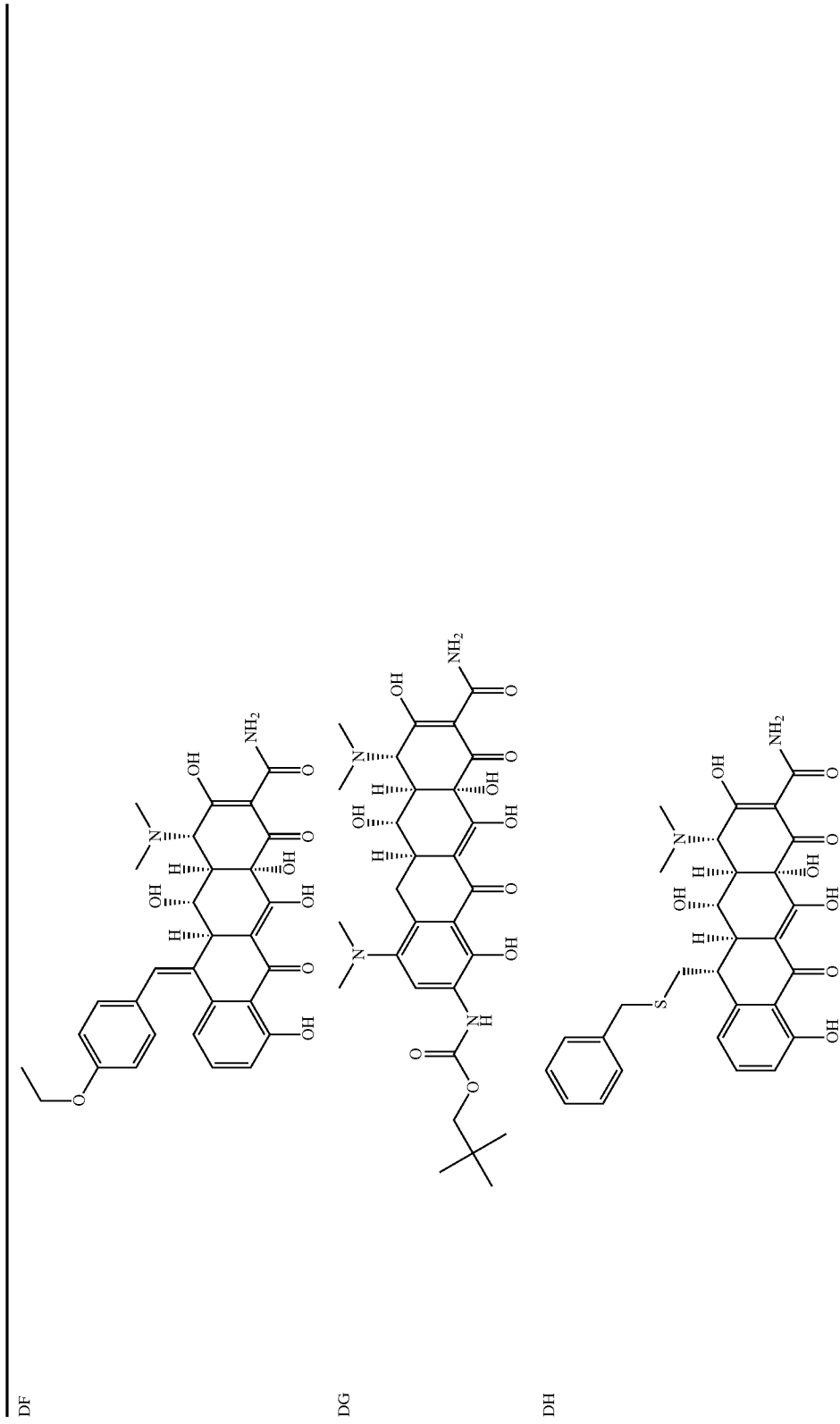
DF
DG
DH

TABLE 2-continued
| DI | 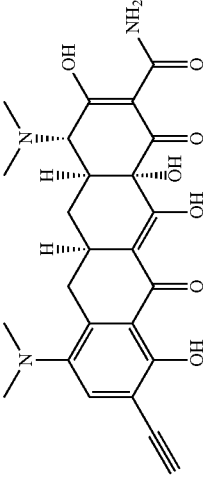 |
| DK | 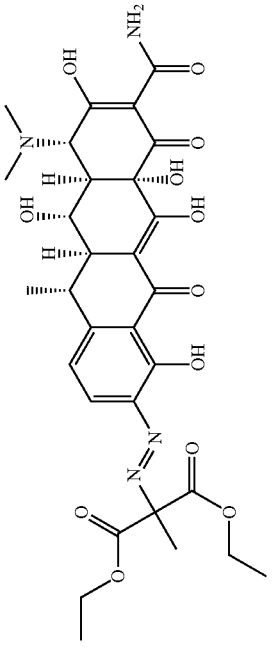 |
| DL | 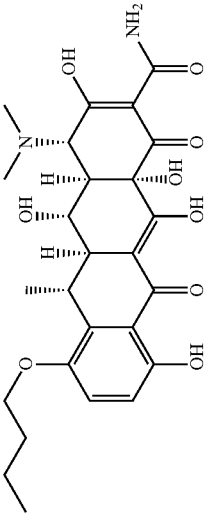 |
| DM | 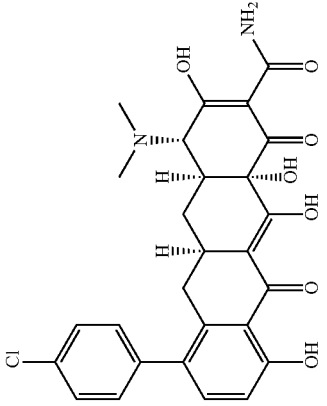 |

TABLE 2-continued
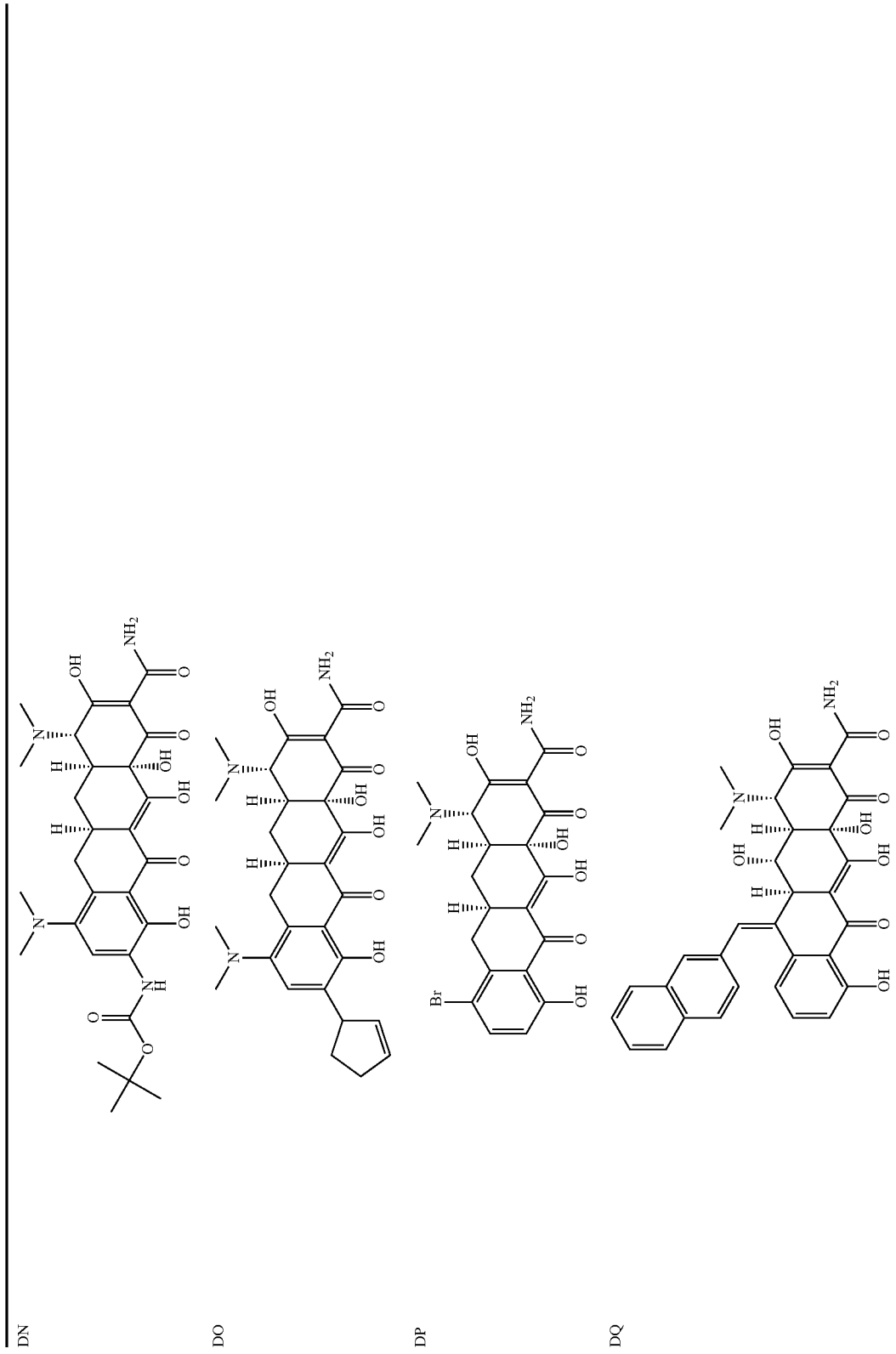
DN
DO
DP
DQ

TABLE 2-continued
| DR | DS | DT |
|---|---|---|
| 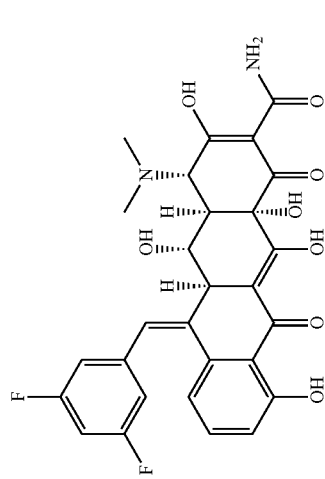 | 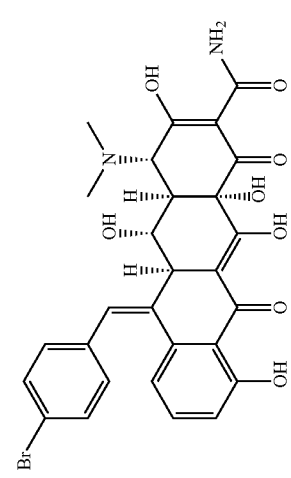 | 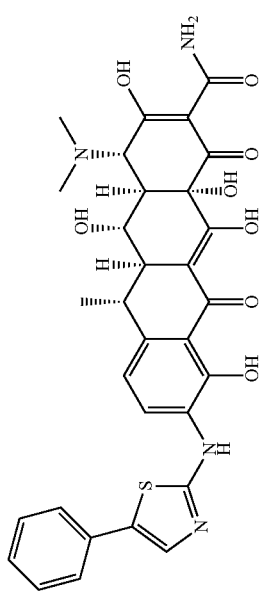 |

TABLE 2-continued
| | |
|---|---|
| DU | 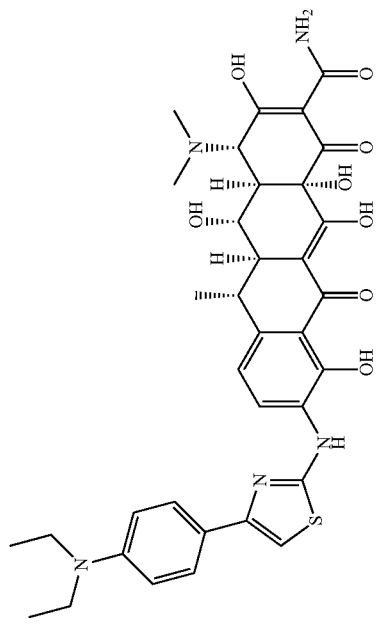 |
| DV | 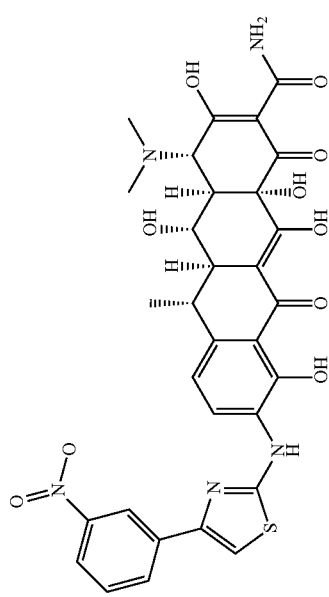 |
| DW | 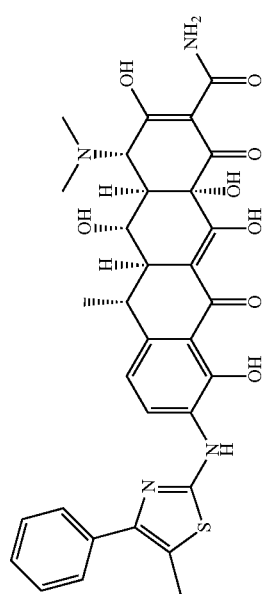 |

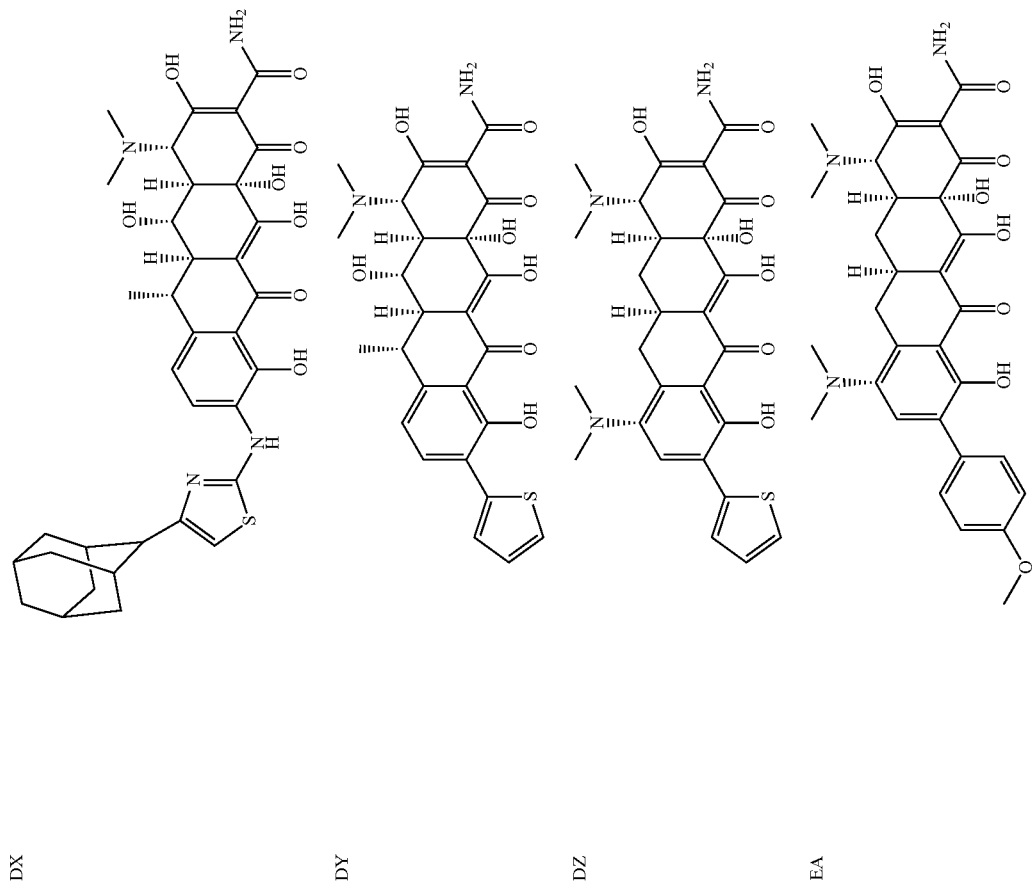

TABLE 2-continued
| EB | EC | ED |
|---|---|---|
| 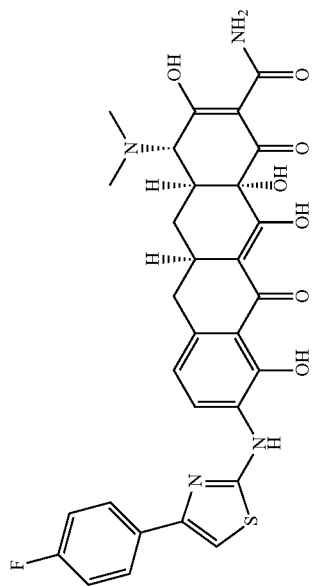 | 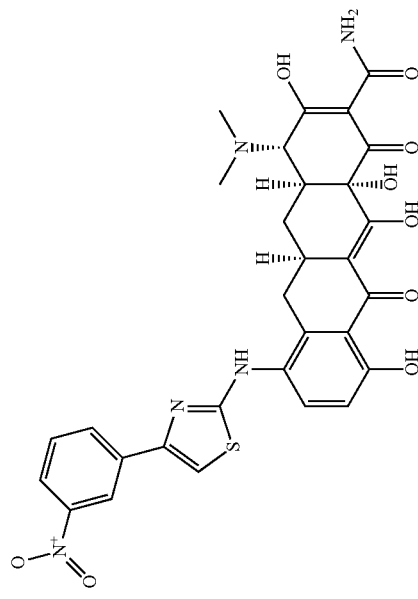 | 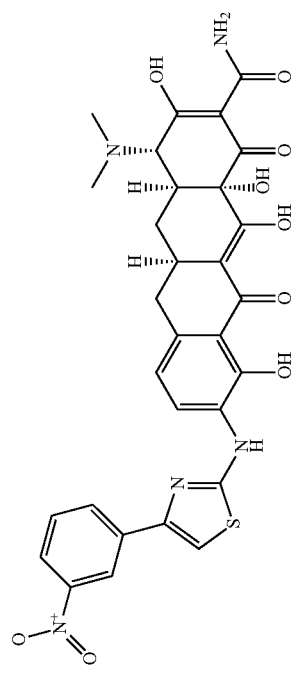 |

TABLE 2-continued
| | | |
|---|---|---|
| 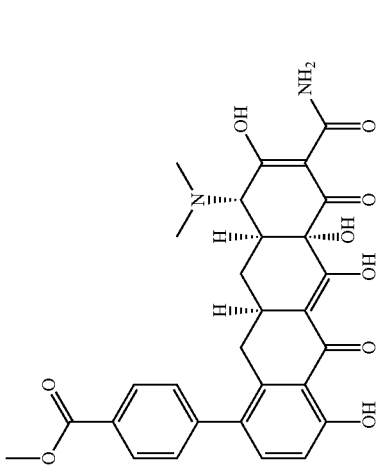 | 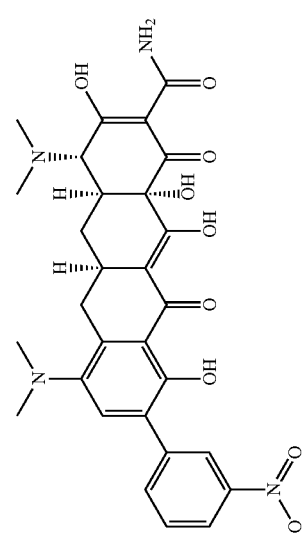 | 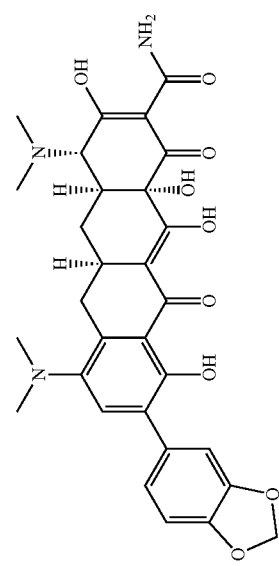 |
| EF | EG | EH |

TABLE 2-continued
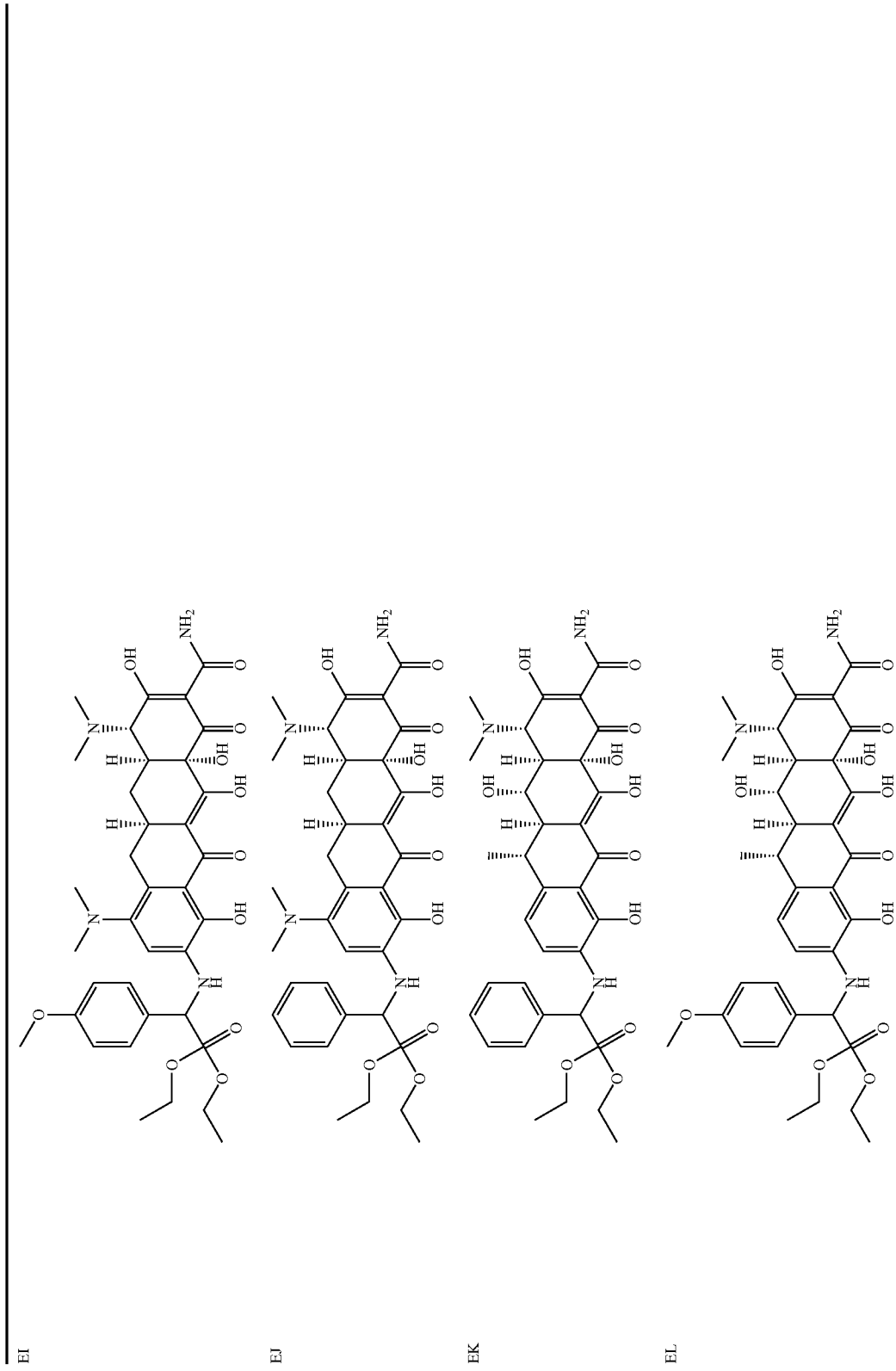
EI
EJ
EK
EL

TABLE 2-continued
| | |
|---|---|
| EM | 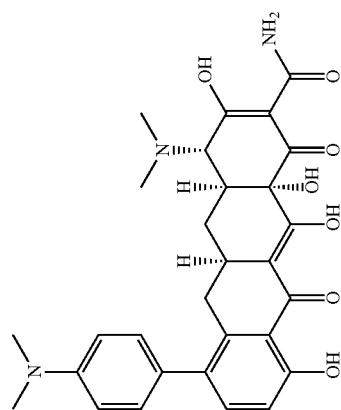 |
| EN | 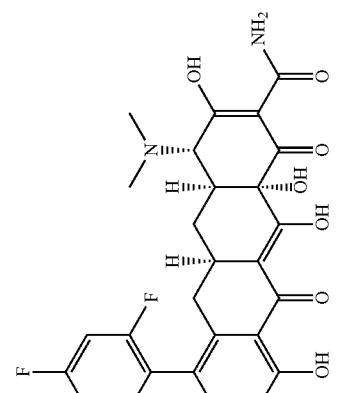 |
| EO | 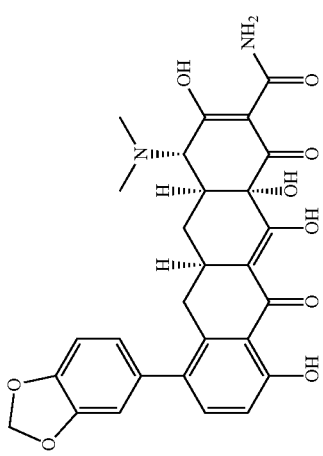 |

TABLE 2-continued
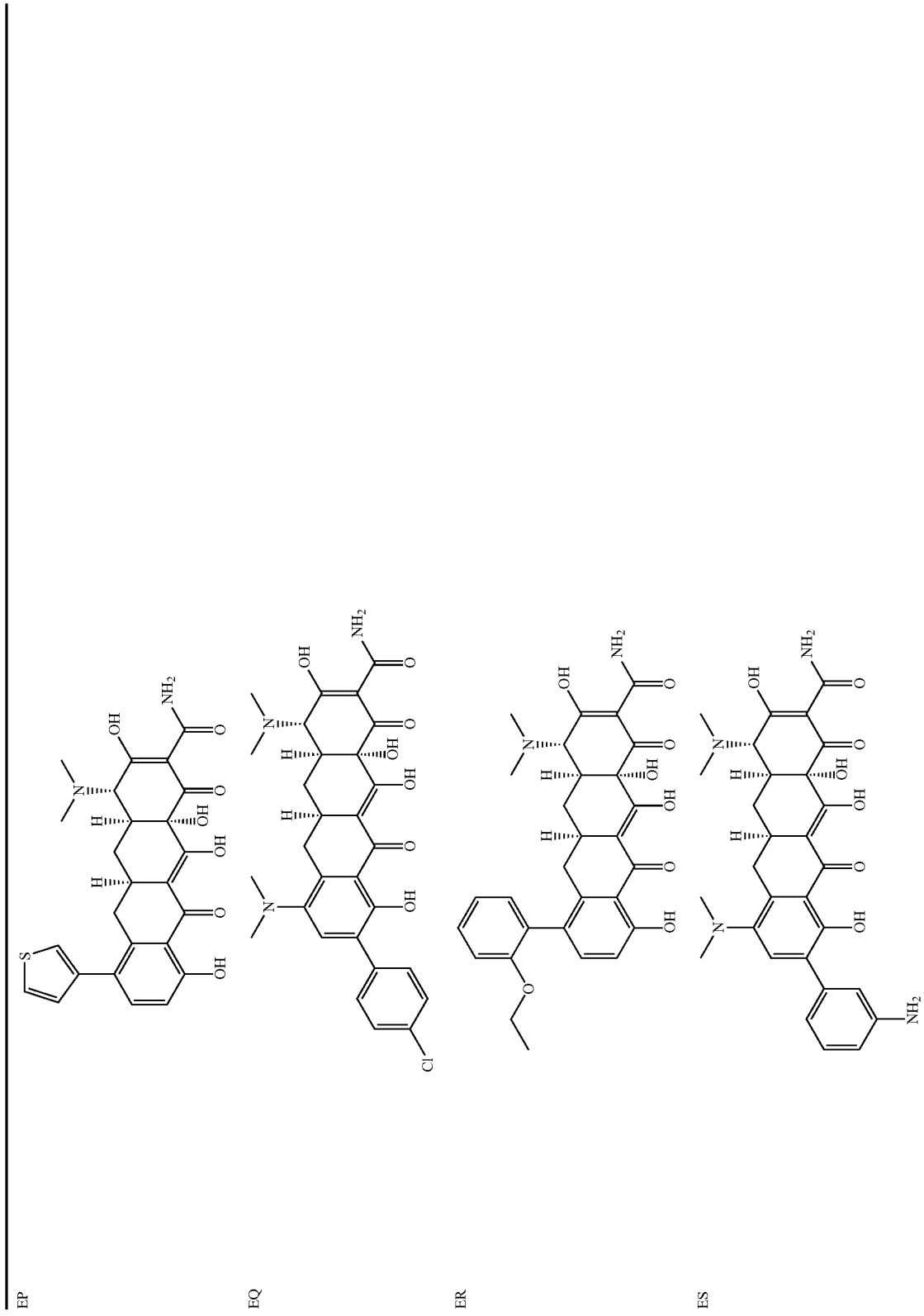
EP
EQ
ER
ES

TABLE 2-continued
| ET | 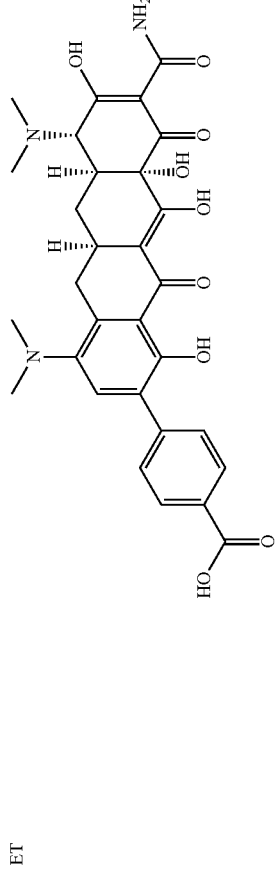 |
| EU | 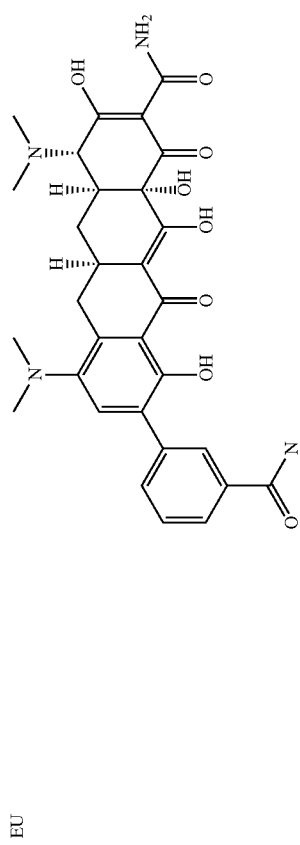 |
| EV | 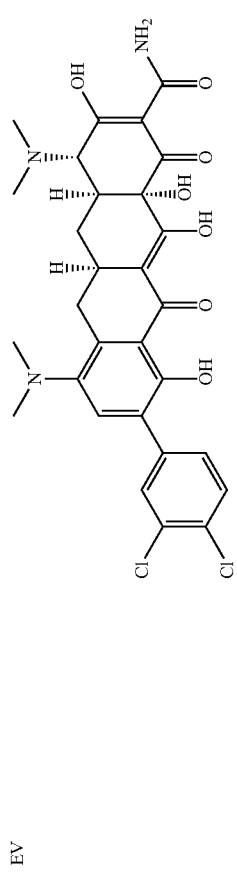 |
| EW | 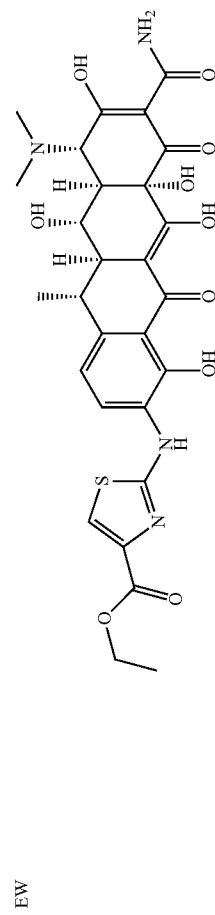 |

TABLE 2-continued

| EX | EY | EZ |

TABLE 2-continued
FA 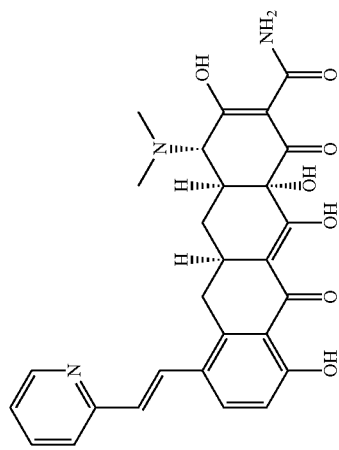
FB 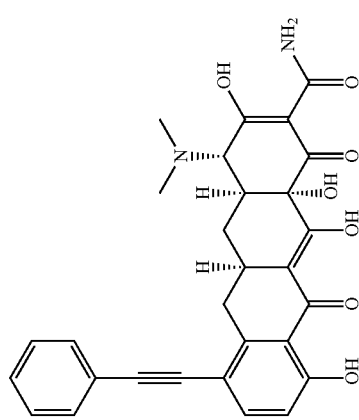
FC 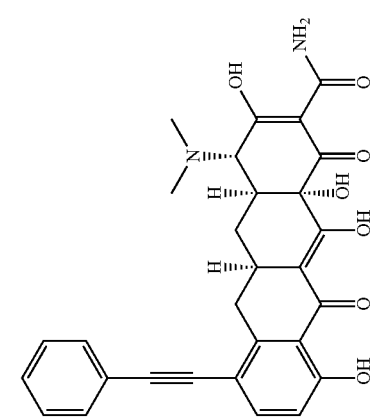

TABLE 2-continued
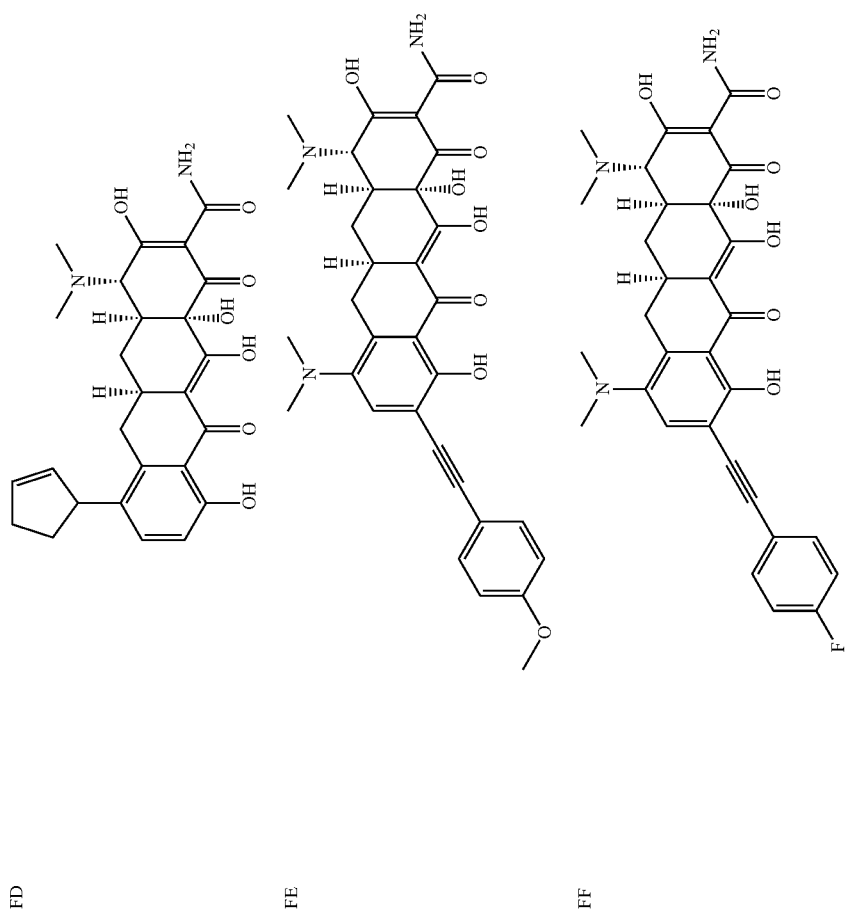
FD
FE
FF

TABLE 2-continued
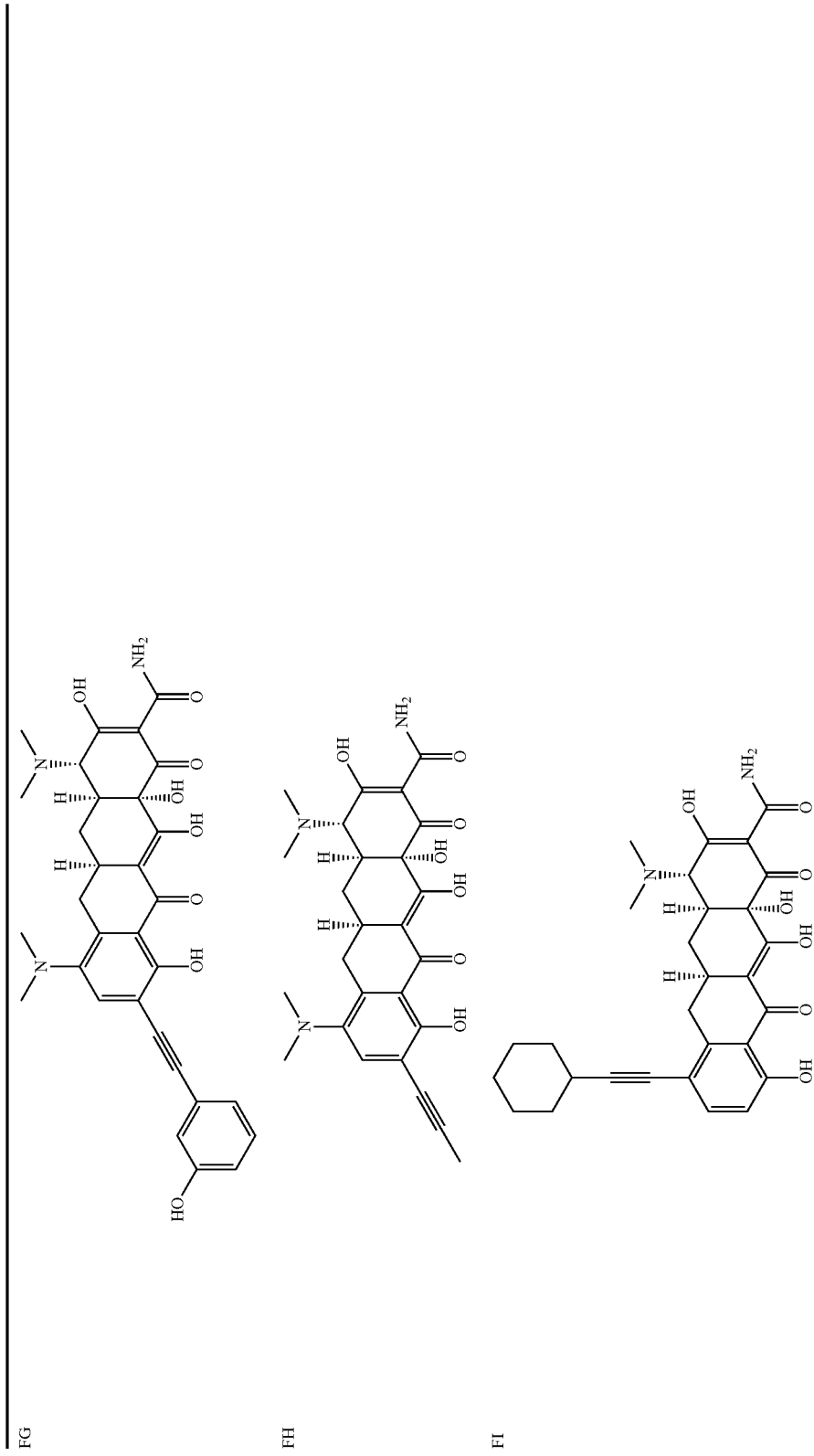
FG
FH
FI

TABLE 2-continued
| FJ | FK | FL *** |
|---|---|---|
| 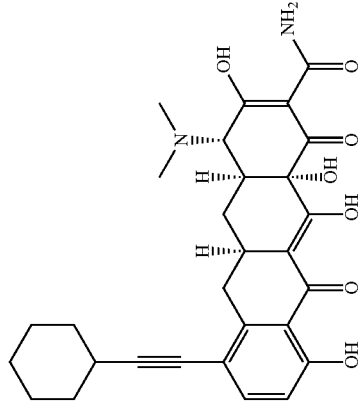 | 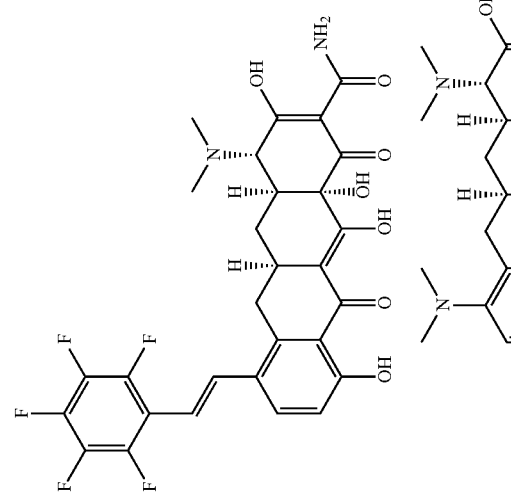 | 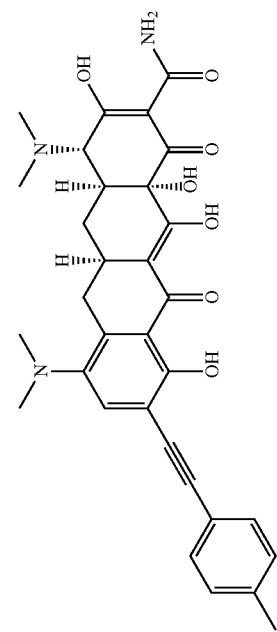 |

TABLE 2-continued
| FM | FN | FO |
|---|---|---|
| 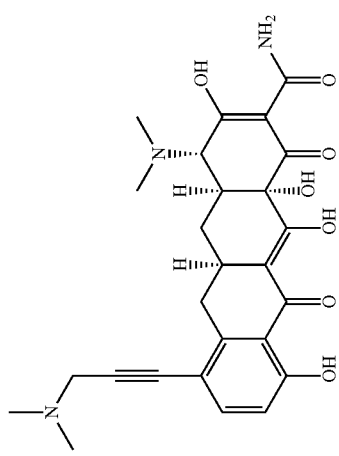 | 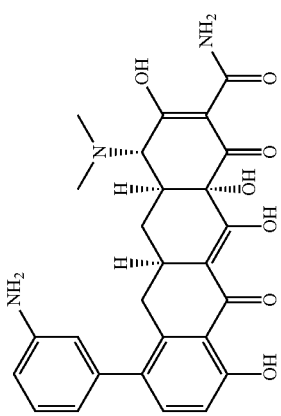 | 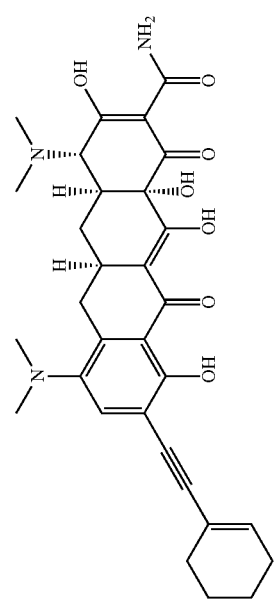 |

TABLE 2-continued
| FP | 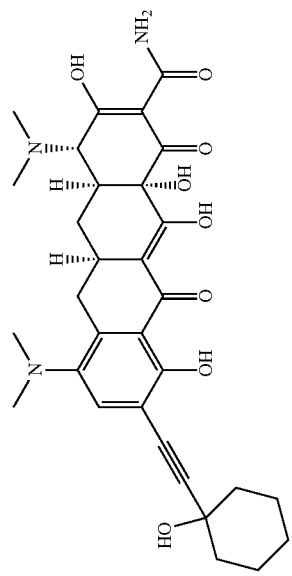 |
| FQ | 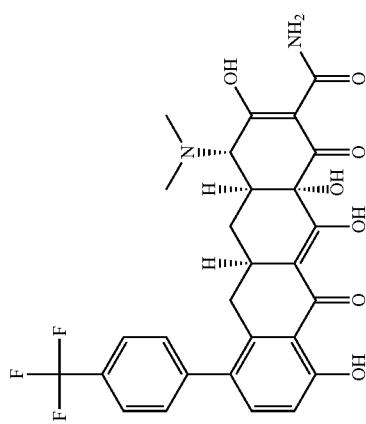 |
| FR | 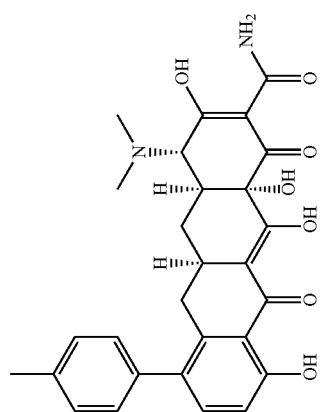 |

TABLE 2-continued
| | | |
|---|---|---|
| 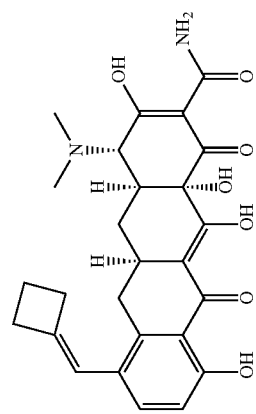 | 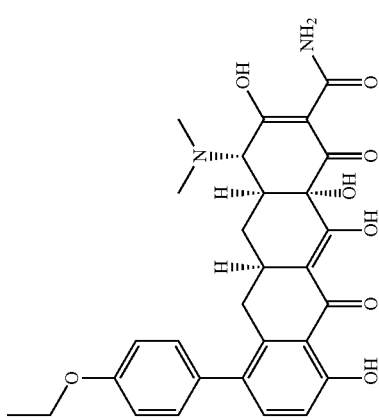 | 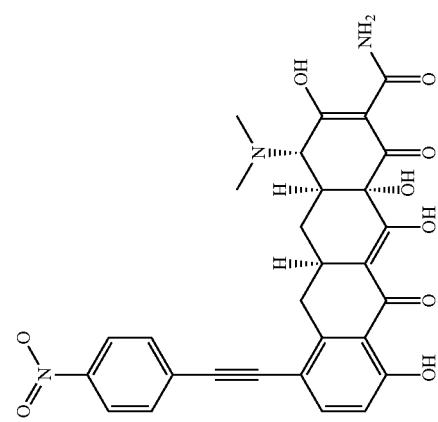 |
| FS | FT | FU |

TABLE 2-continued
| FV | FW | FX |
|----|----|-----|
| 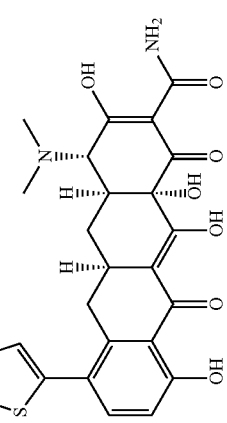 | * | ** |

TABLE 2-continued
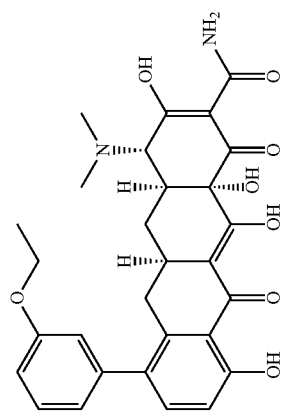
FY
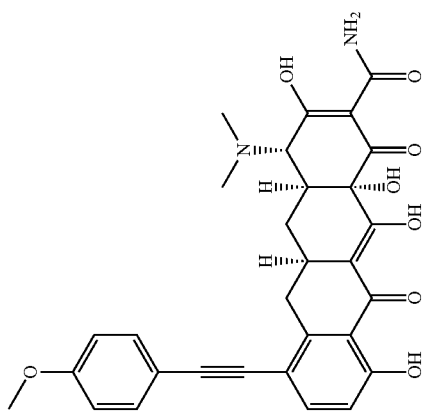
FZ
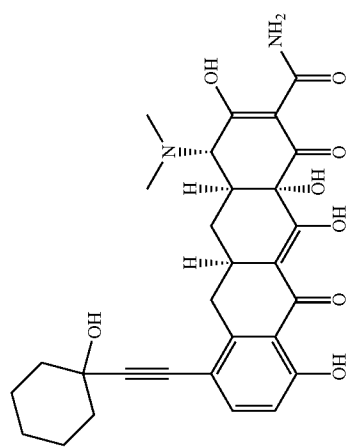
GA

TABLE 2-continued
| | |
|---|---|
| GB | 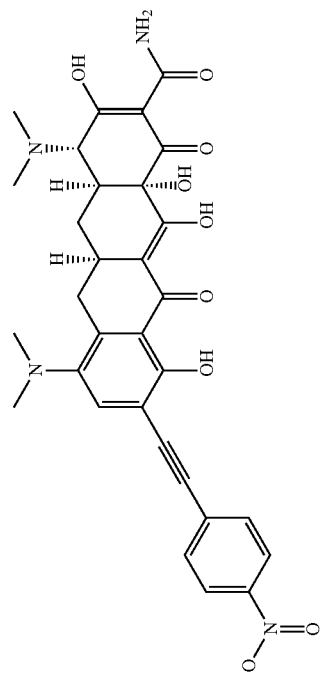 |
| GC | 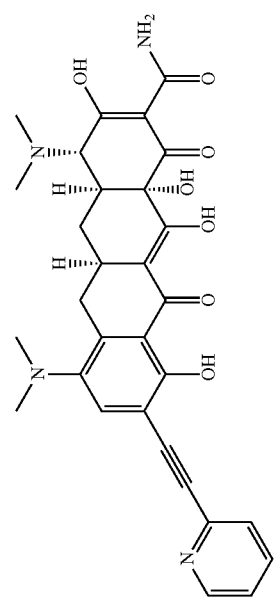 |
| GD | 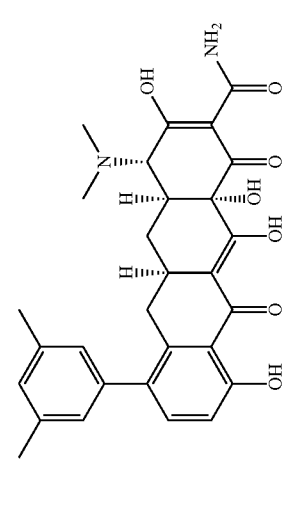 |

TABLE 2-continued
| GE | GF | GG |
|---|---|---|
| 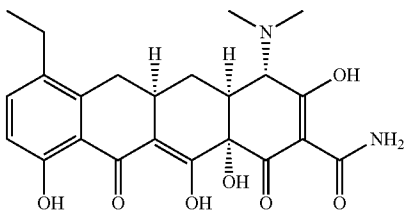 | 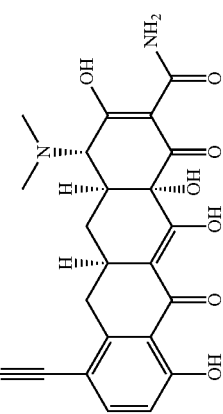 | 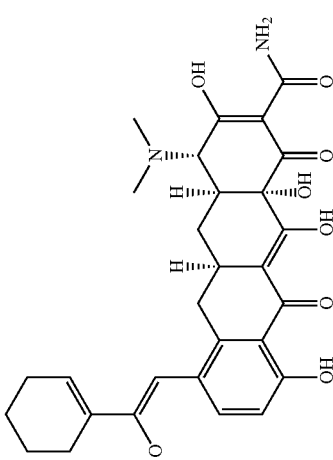 |

TABLE 2-continued
| GH | GI | GJ |
|---|---|---|
| 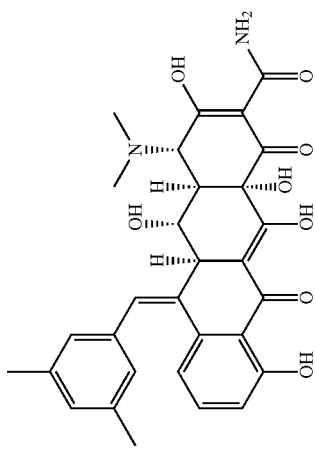 | 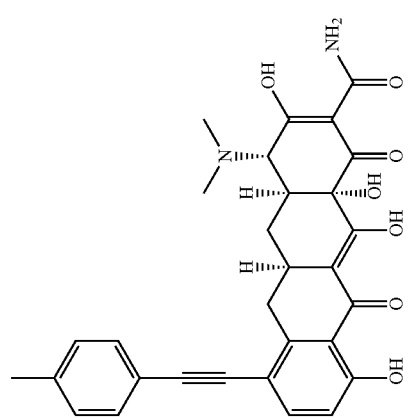 | 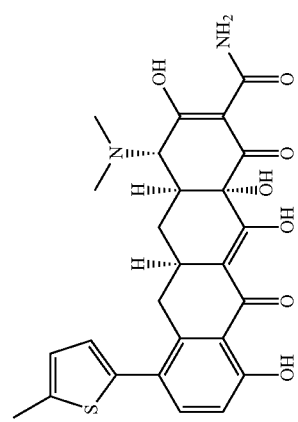 |

TABLE 2-continued
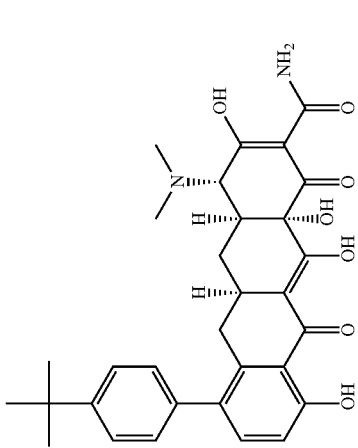
GK
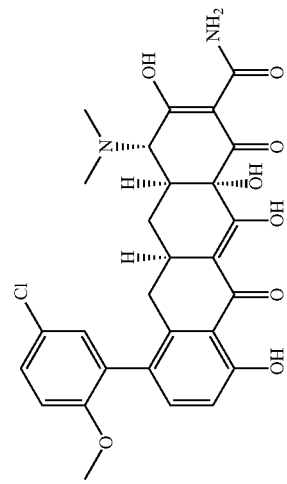
GL
GM

TABLE 2-continued
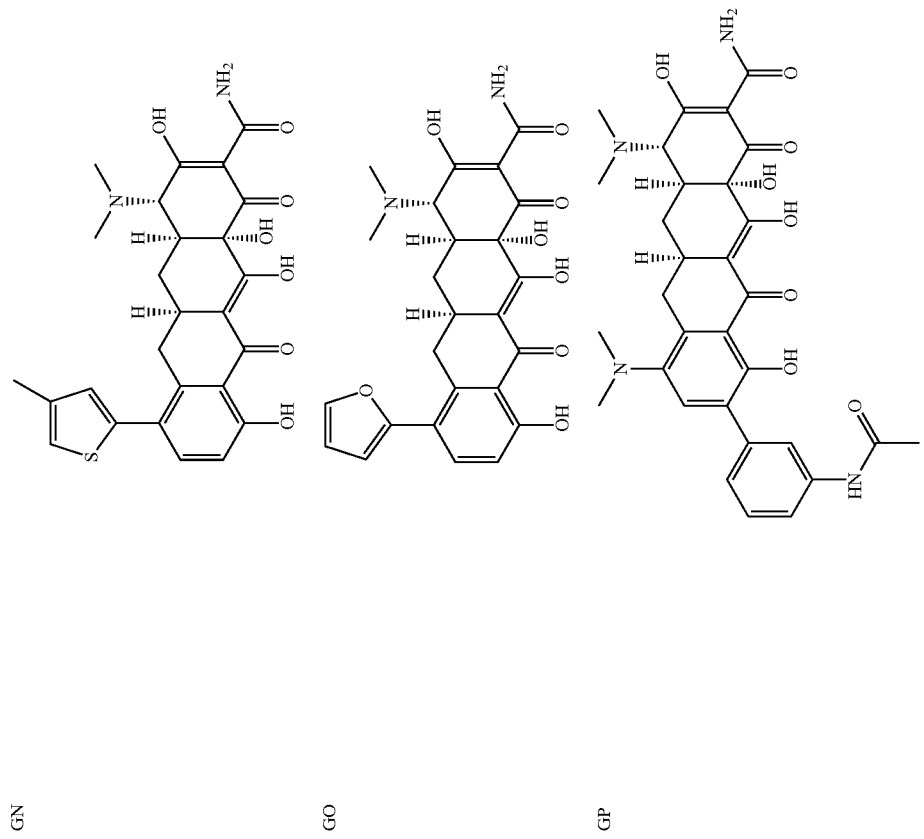
GN
GO
GP

TABLE 2-continued
| GQ | 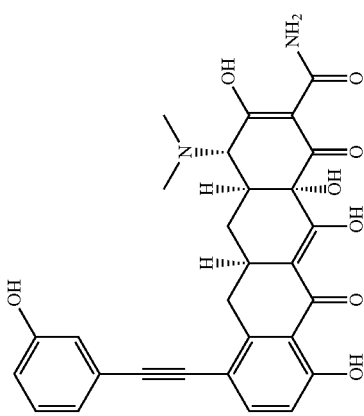 |
| GR | 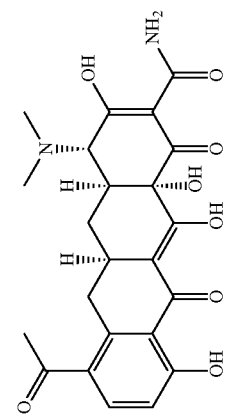 |
| GS | 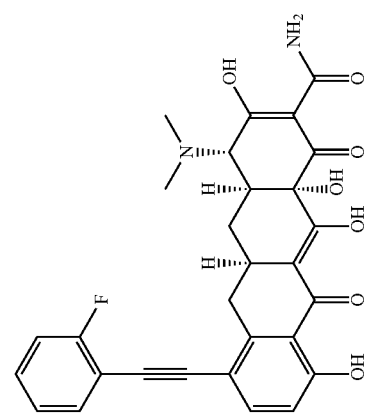 |

TABLE 2-continued
| GT | GU | GV |
|---|---|---|
| 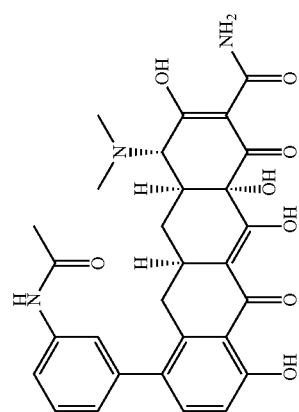 | 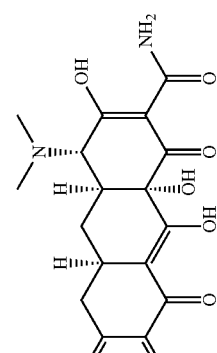 | 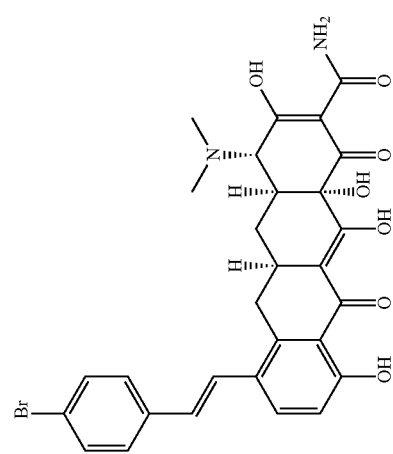 |

TABLE 2-continued
| | |
|---|---|
| GW | 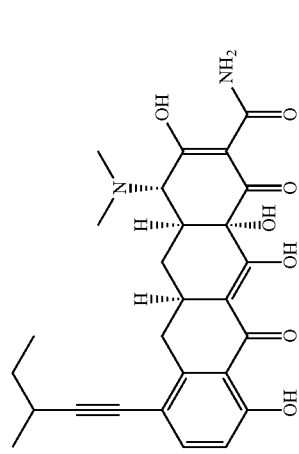 |
| GX | 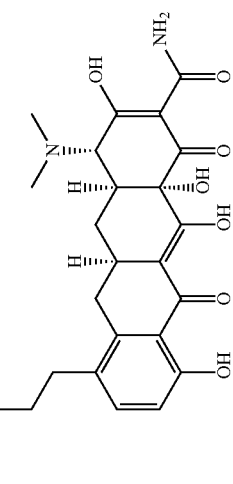 |

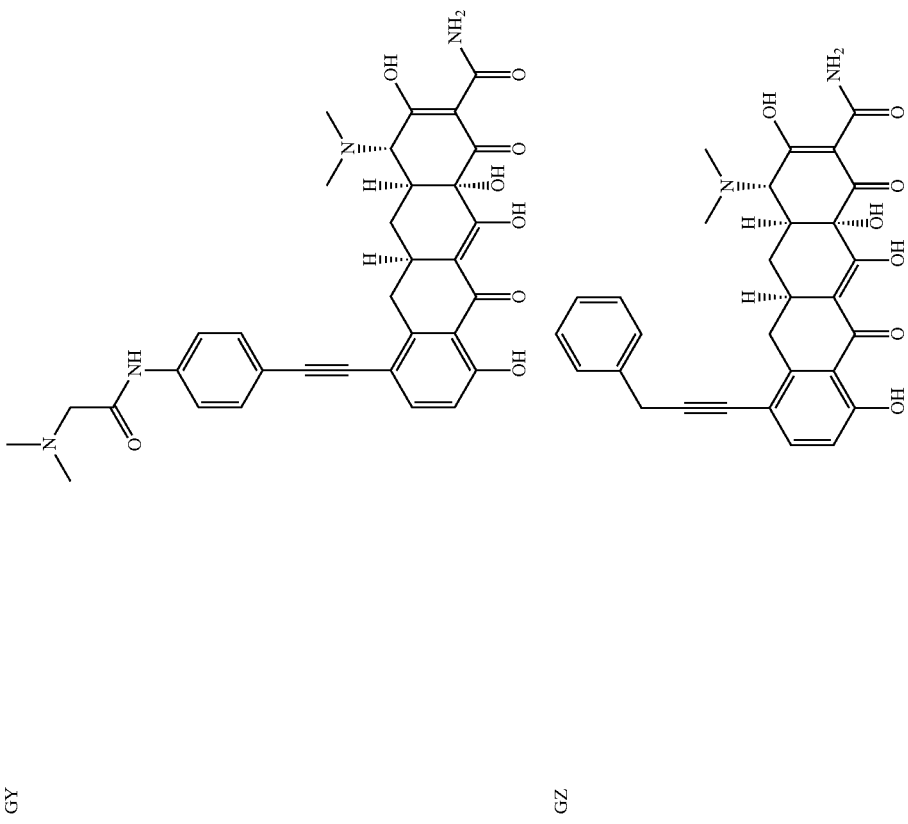

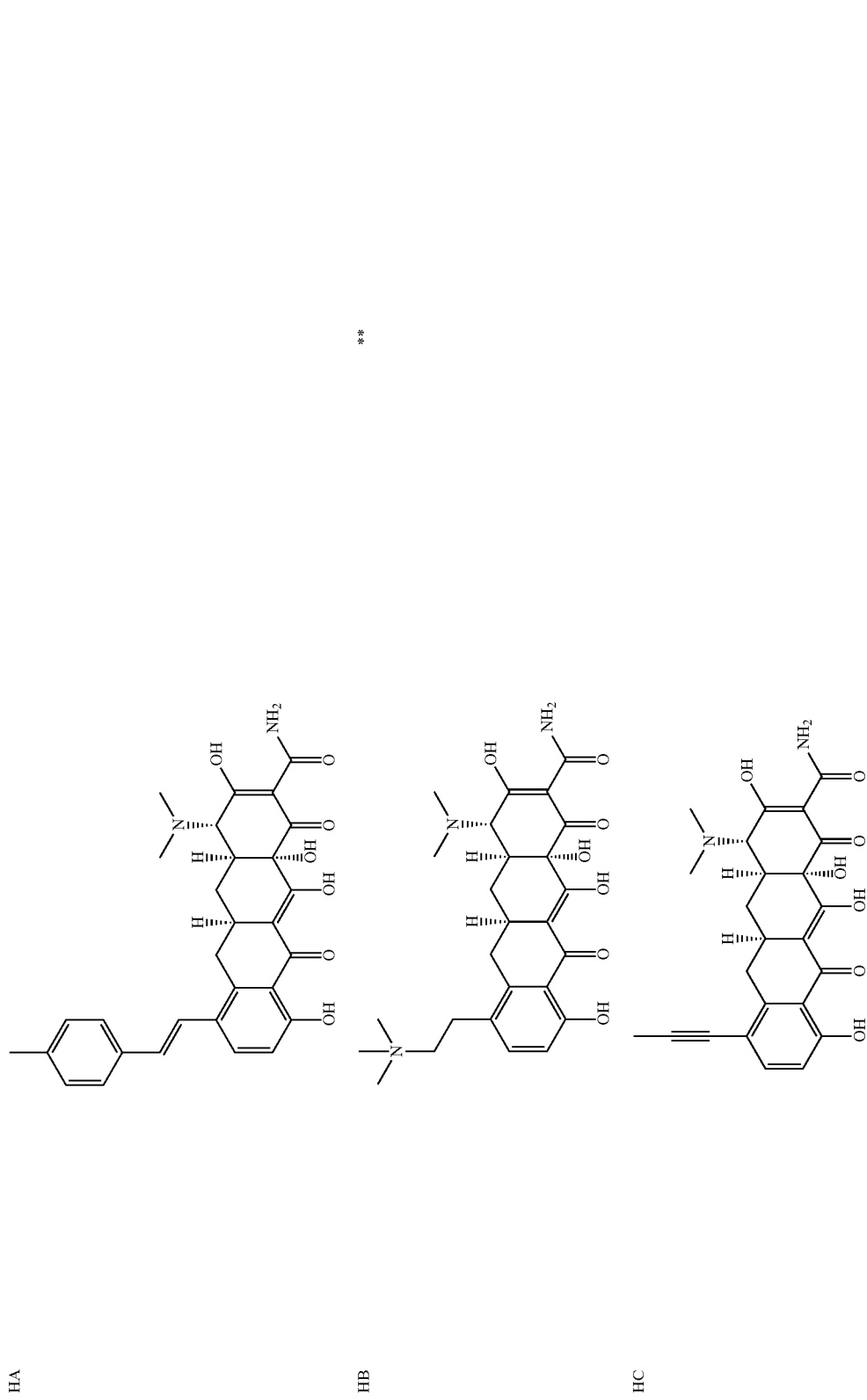

TABLE 2-continued
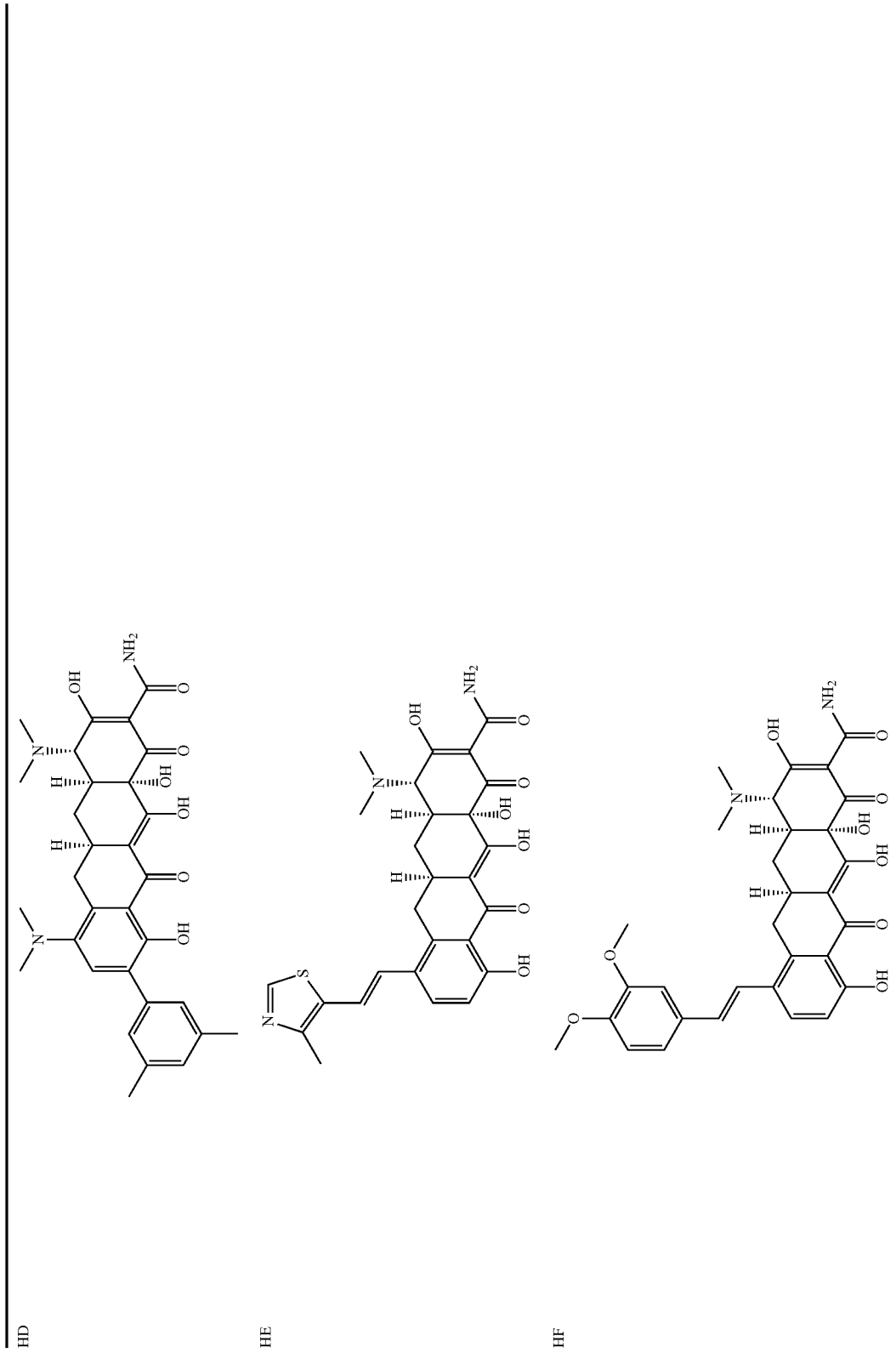
HD
HE
HF

TABLE 2-continued
| HG | HH | HI |
|---|---|---|
| 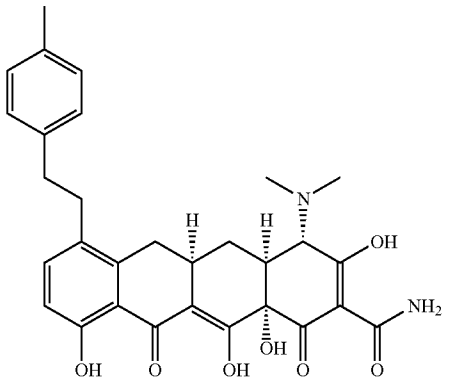 | 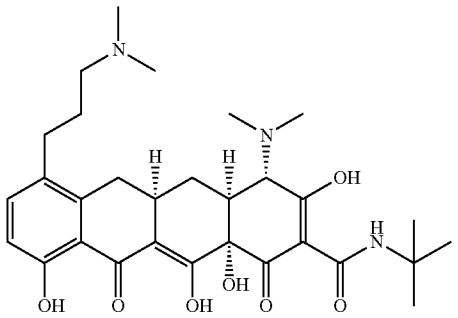 | 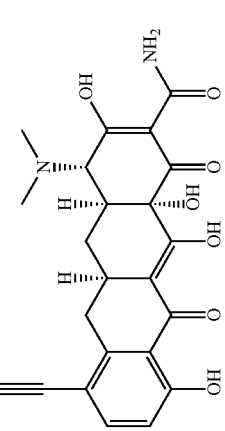 |

TABLE 2-continued
| HJ | HK |
|---|---|
| 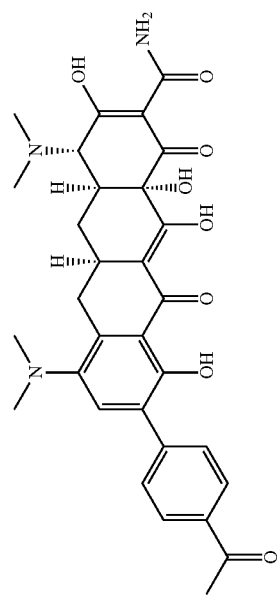 | 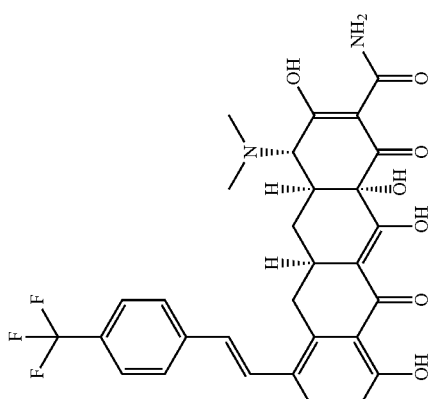 |

TABLE 2-continued
| HL | HM |
|---|---|
| 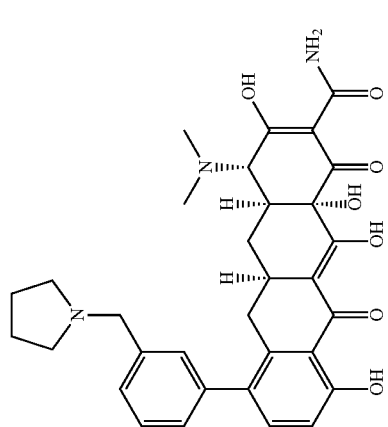 | 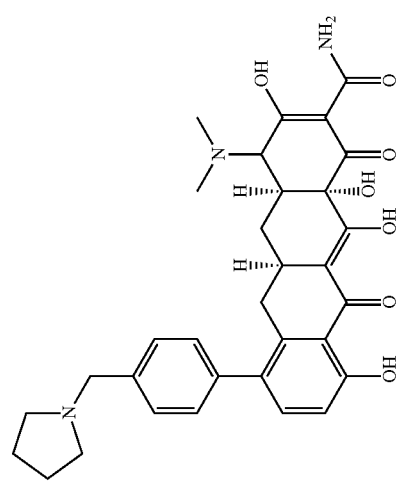 |

TABLE 2-continued
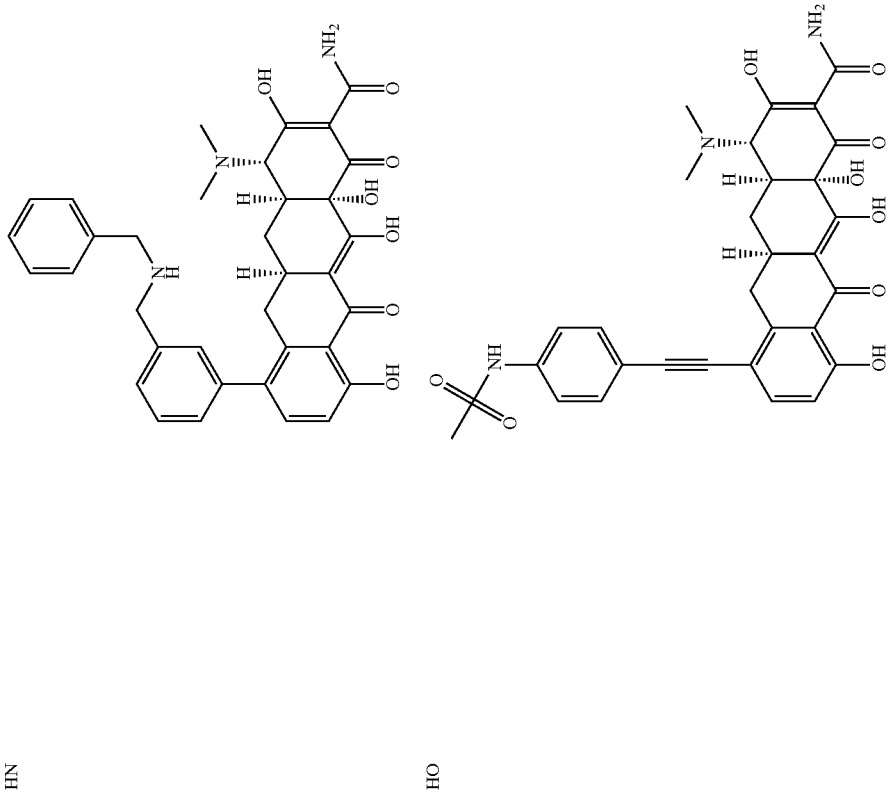

TABLE 2-continued
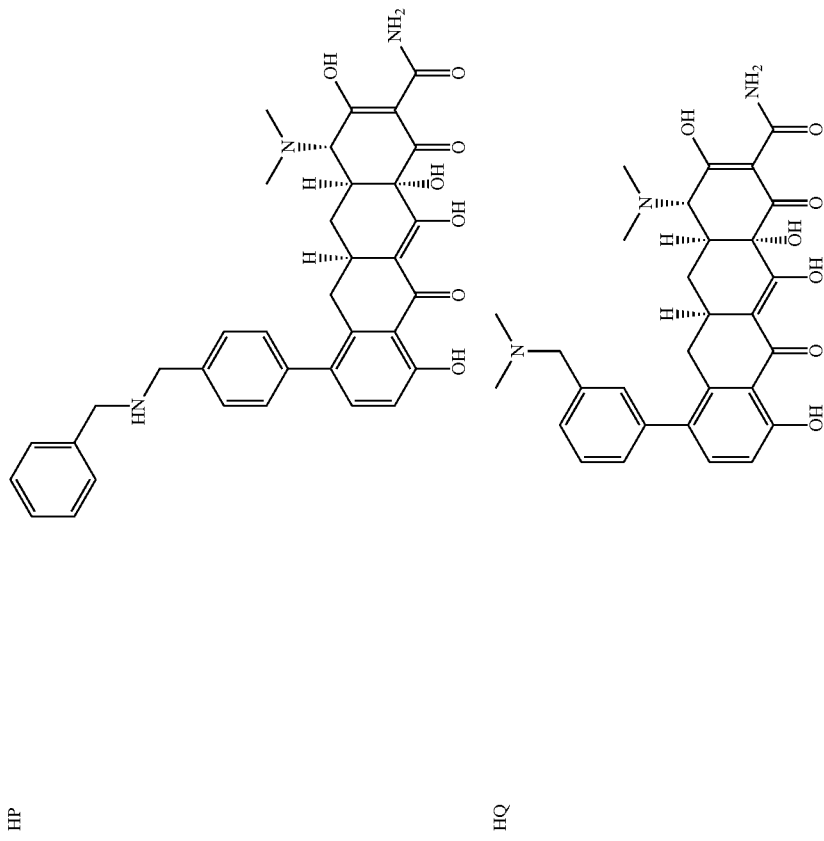

TABLE 2-continued
| HR | HS |
|---|---|
| 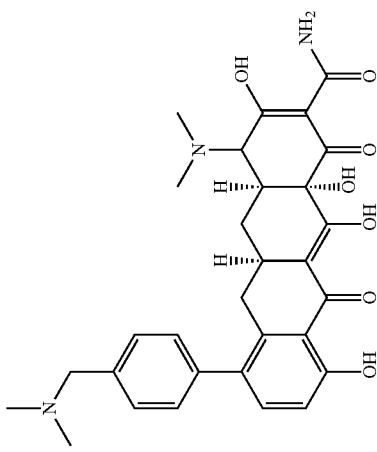 | 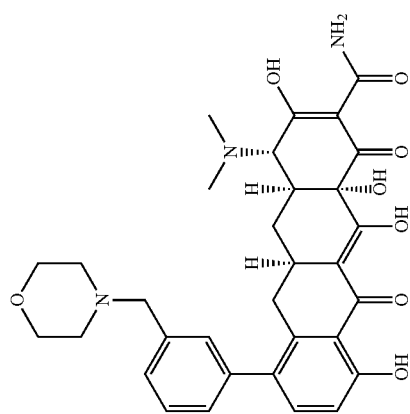 |

TABLE 2-continued
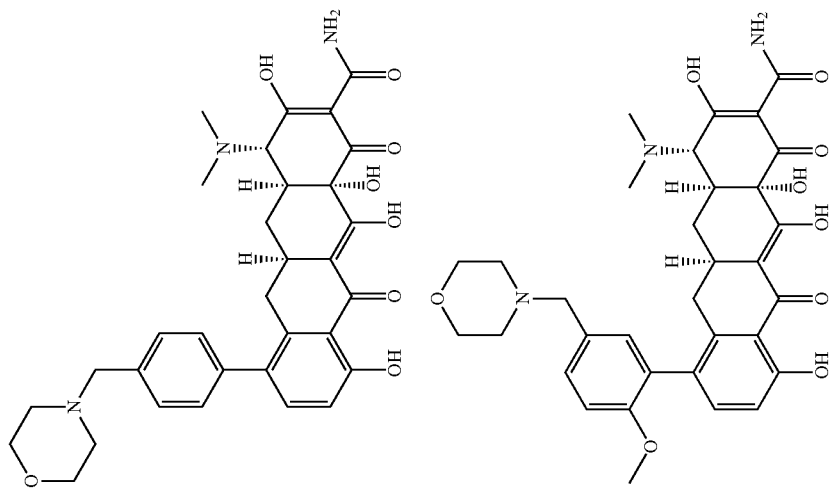
HT
HU

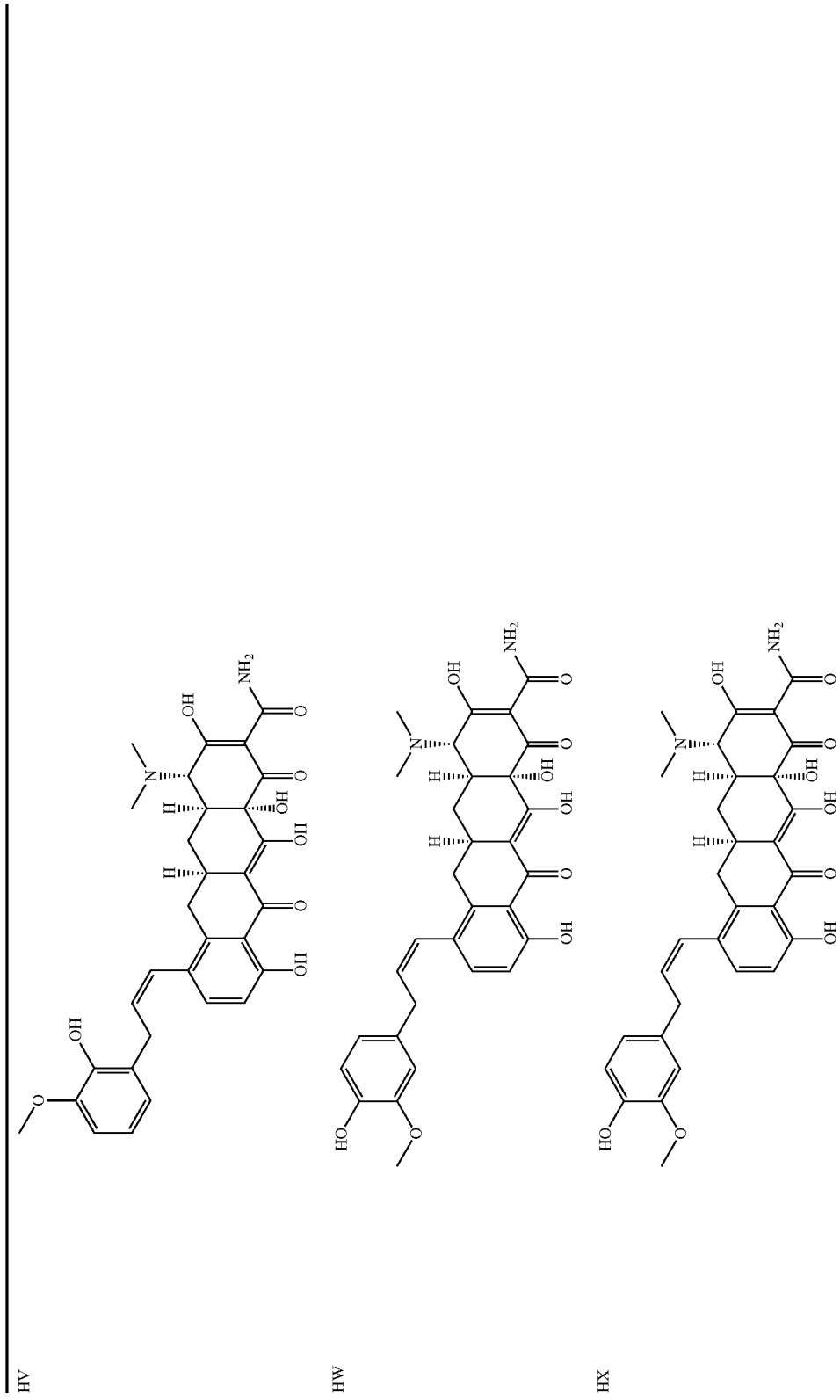

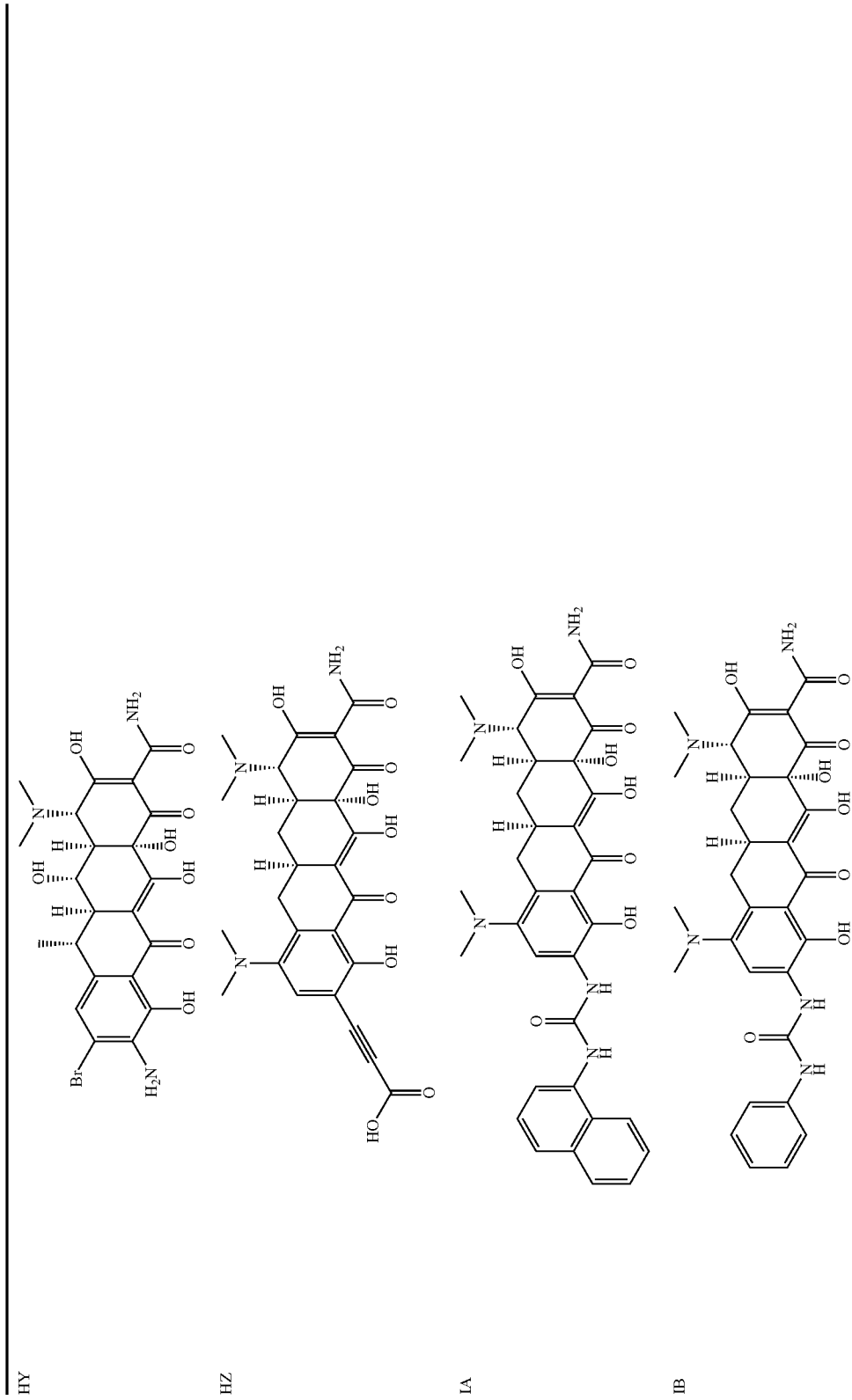

TABLE 2-continued
| | |
|---|---|
| IC | 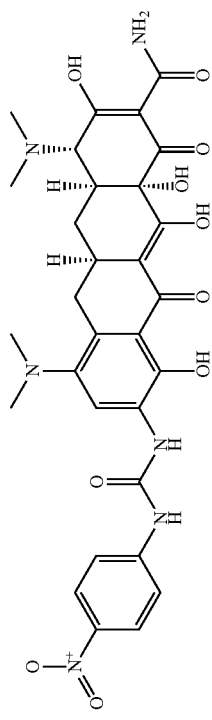 |
| ID | 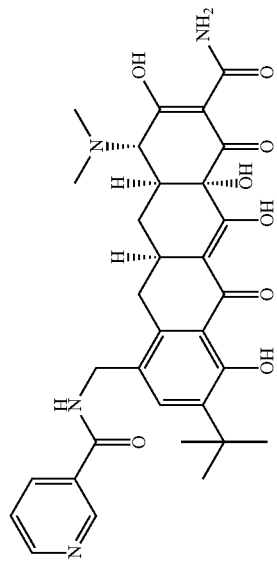 |
| IE | 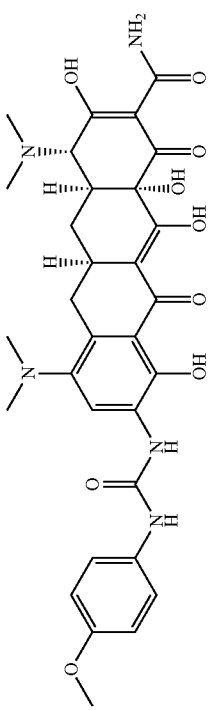 |
| IF | 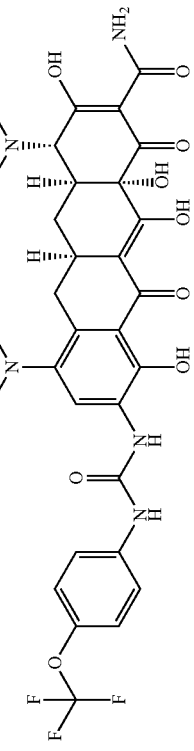 |

TABLE 2-continued
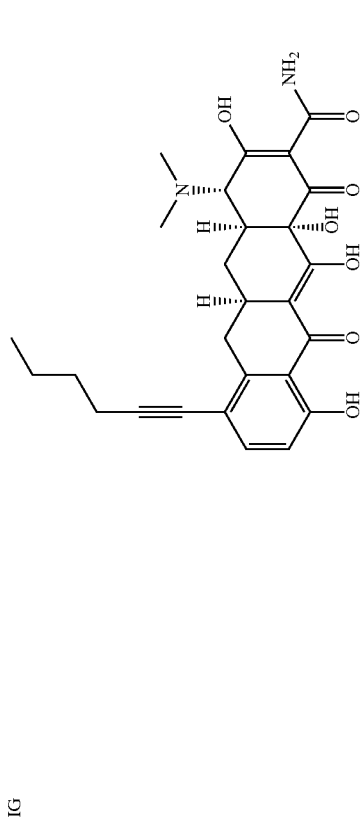
IG
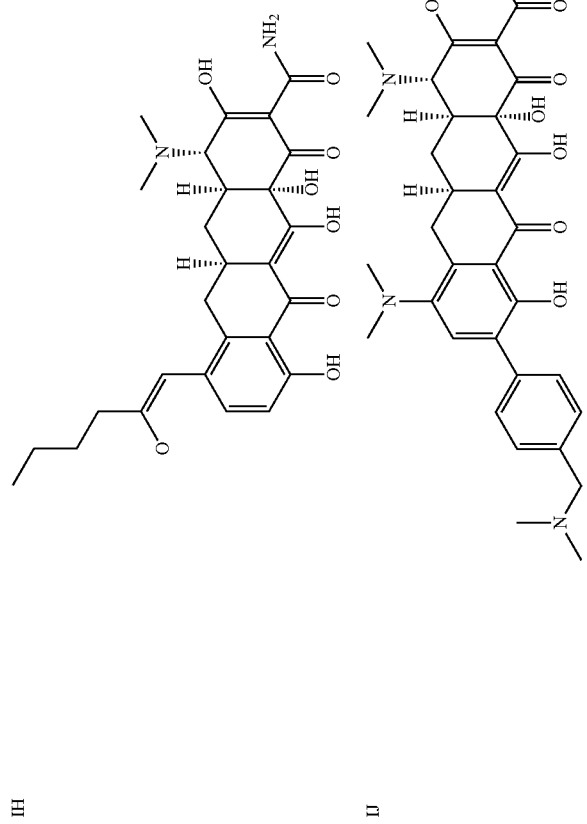
IH    II

TABLE 2-continued
| | |
|---|---|
| IK | 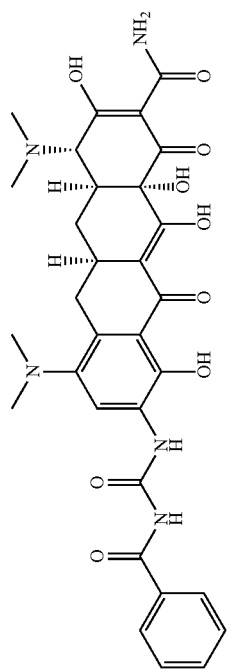 |
| IL | 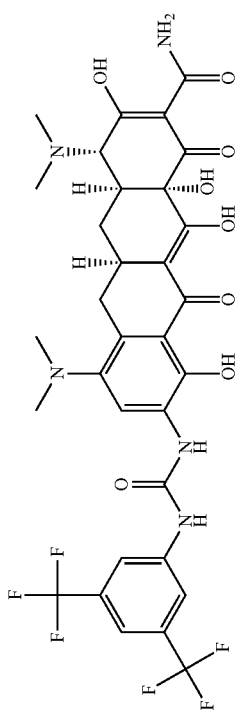 |
| IM | 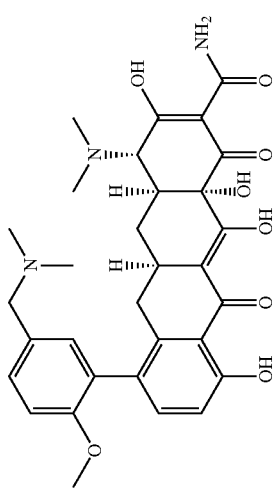 |

TABLE 2-continued
| | |
|---|---|
| IN | 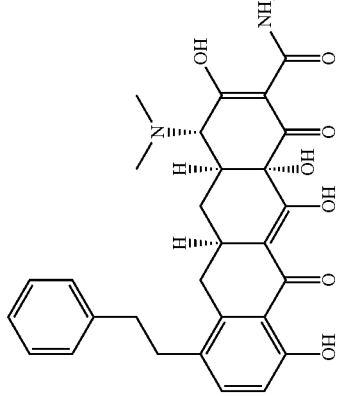 |
| IO | |
| IP | 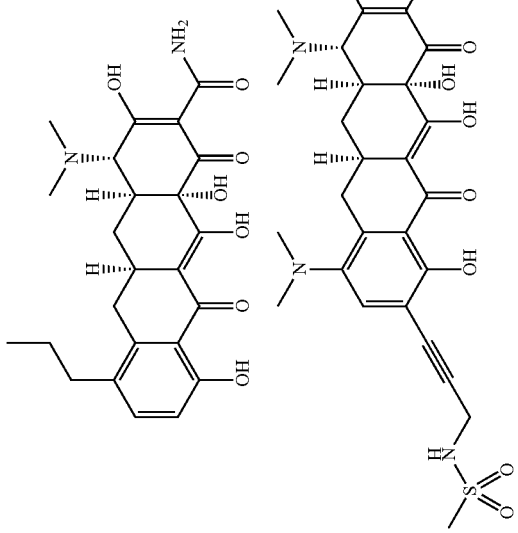 |

TABLE 2-continued
| | |
|---|---|
| IQ | 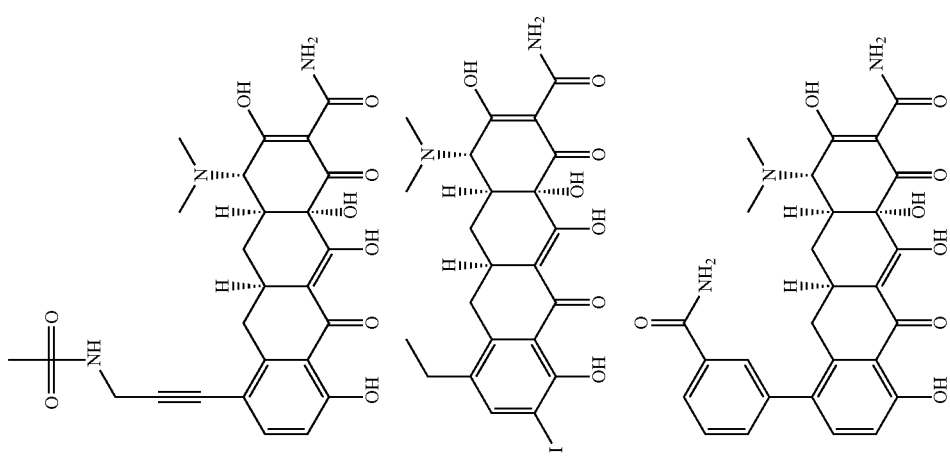 |
| IR | |
| IS | |

TABLE 2-continued
| | | |
|---|---|---|
| 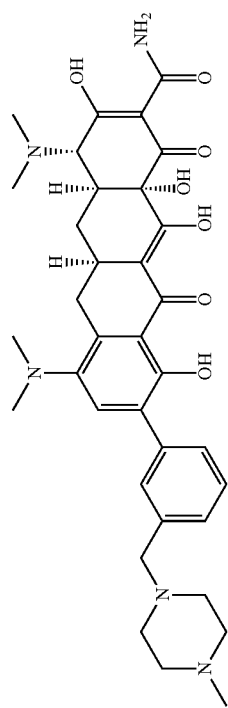 | 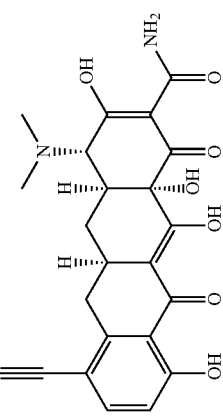 | 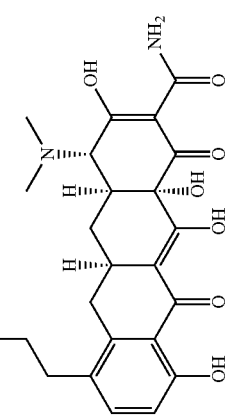 |
| IT | IU | IV |

TABLE 2-continued
| IW | IX | IY | IZ |
|---|---|---|---|
| 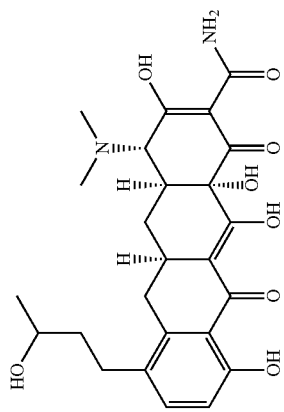 | 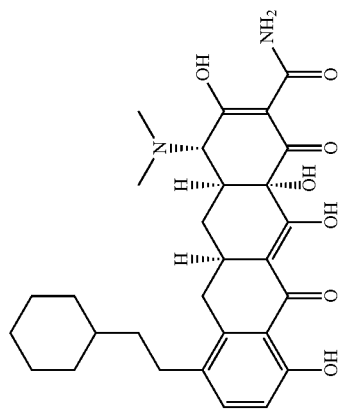 | 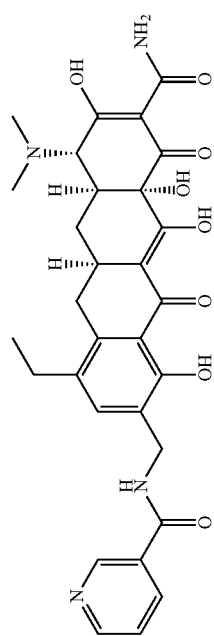 | 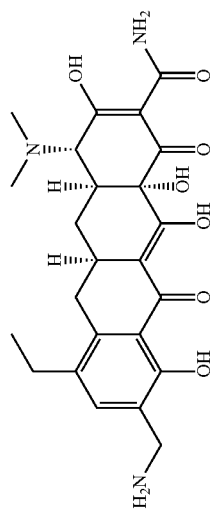 |

TABLE 2-continued
JA 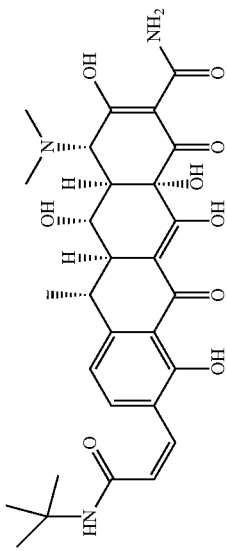
JB 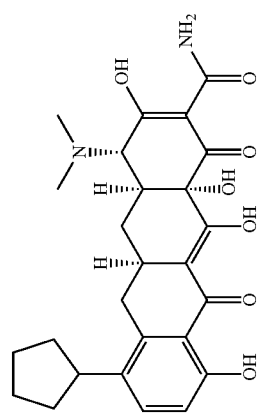
JC 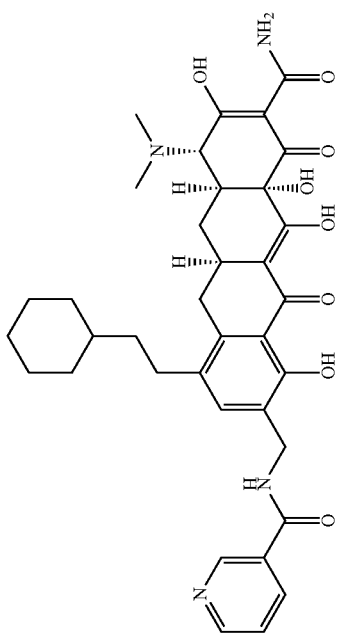

TABLE 2-continued
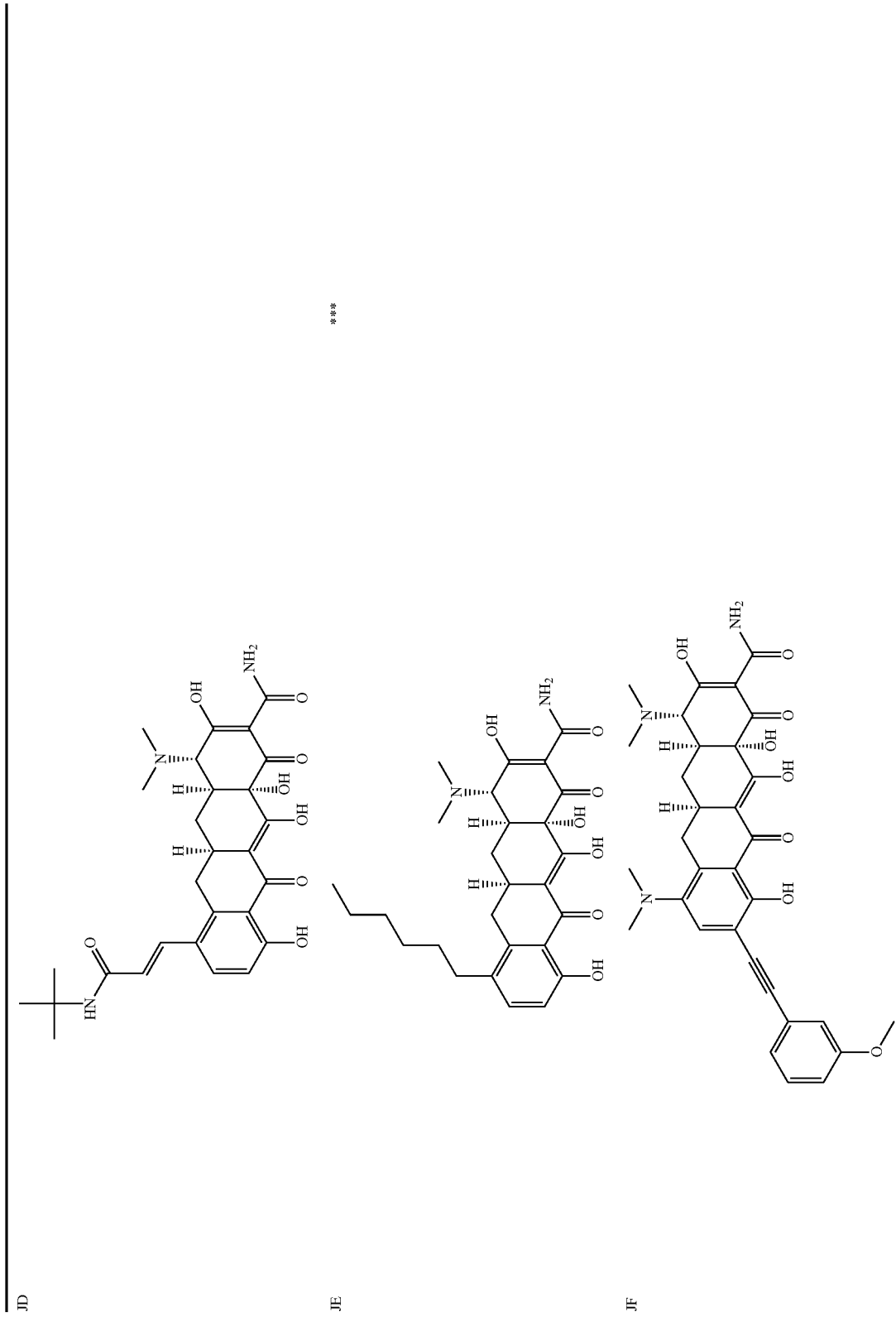
JD
JE
JF

TABLE 2-continued
| JG | JH | JI |
|---|---|---|
| 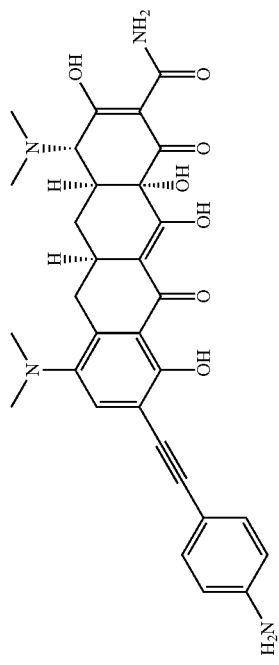 | 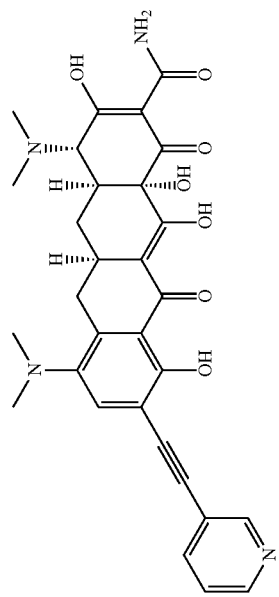 | 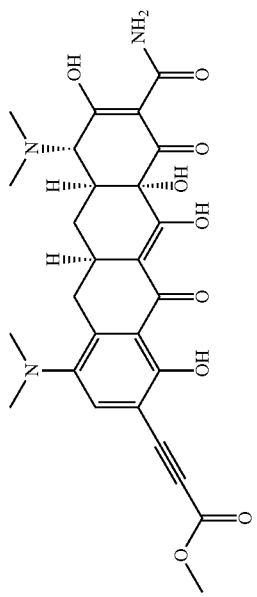 |

TABLE 2-continued
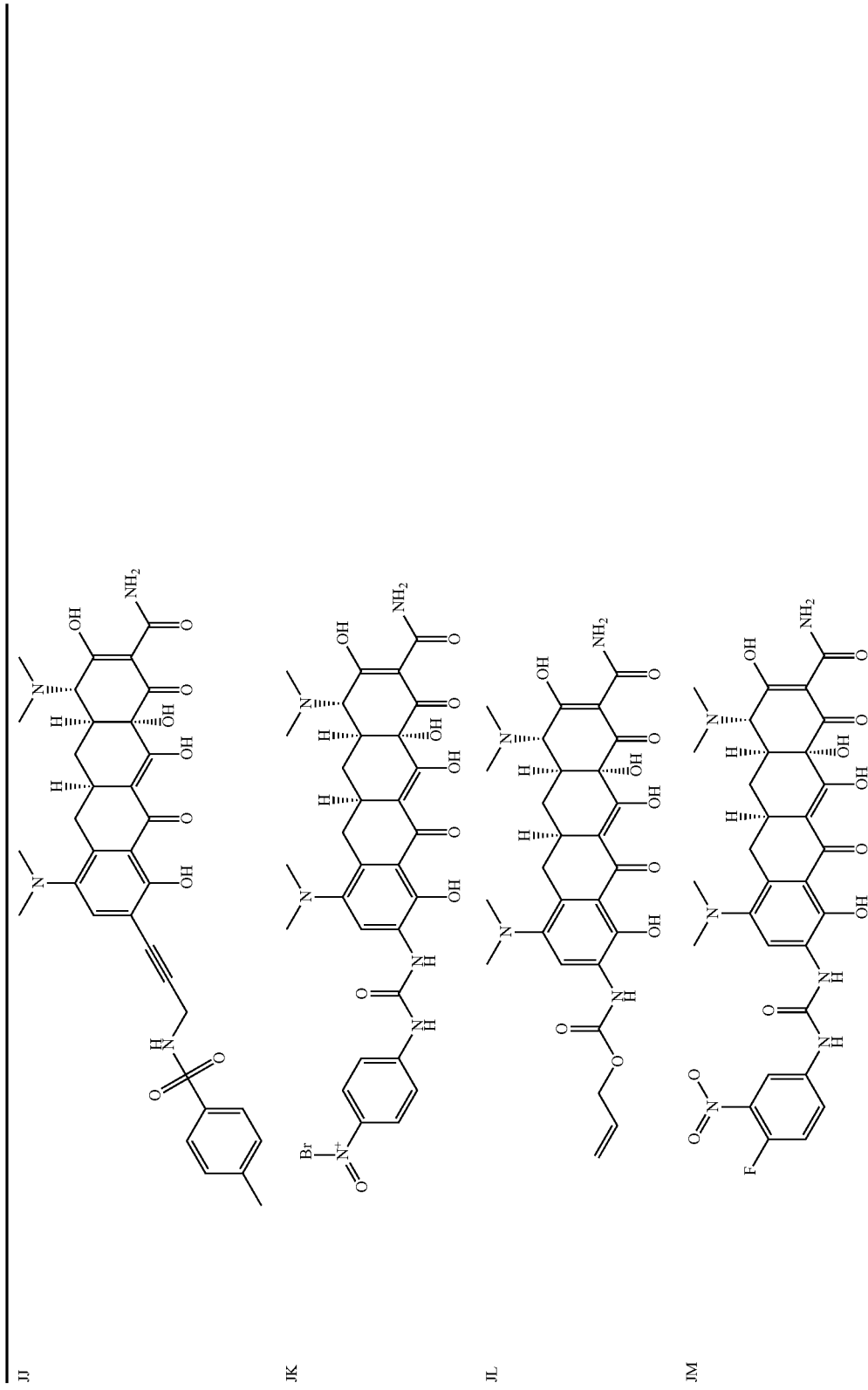

TABLE 2-continued
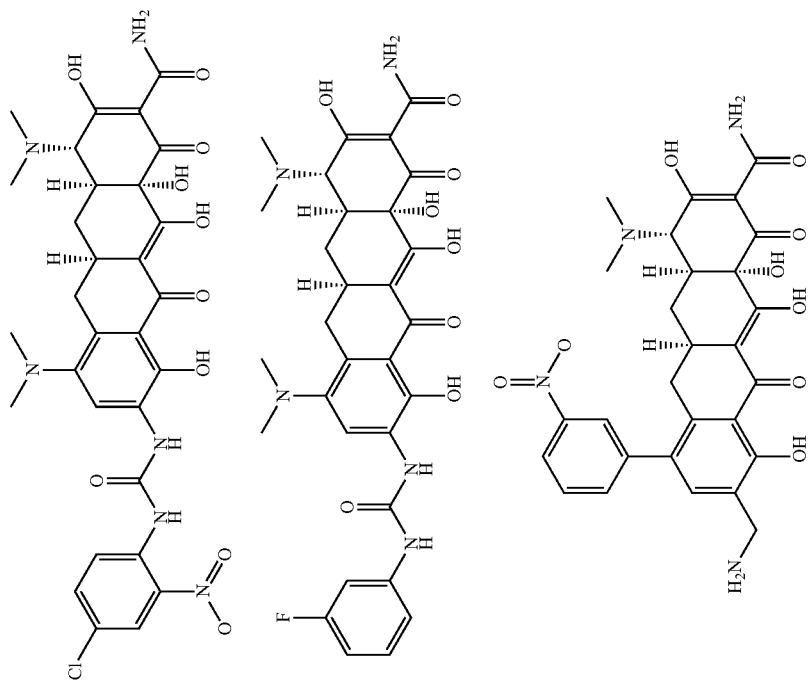
JN
JO
JP

TABLE 2-continued
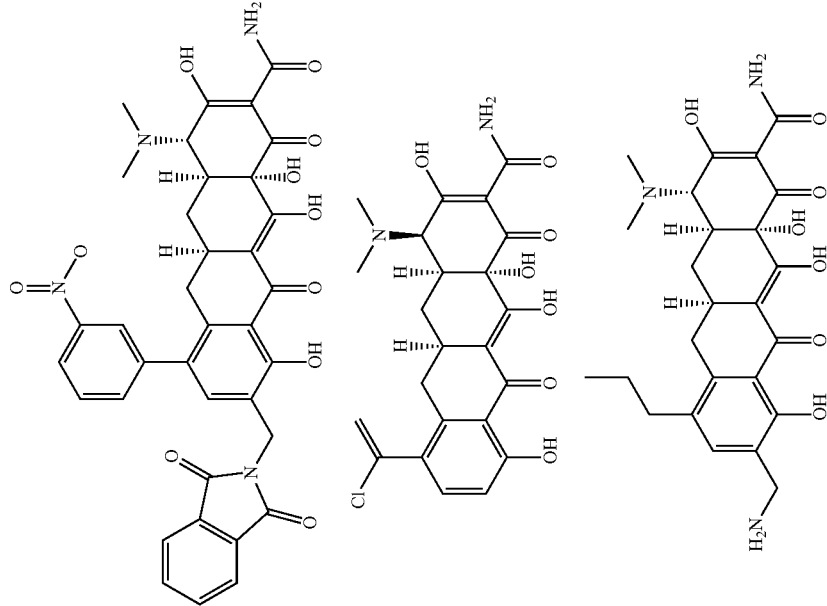
JQ JR JS

TABLE 2-continued
| JT | JU | JV |
|----|----|----|
| 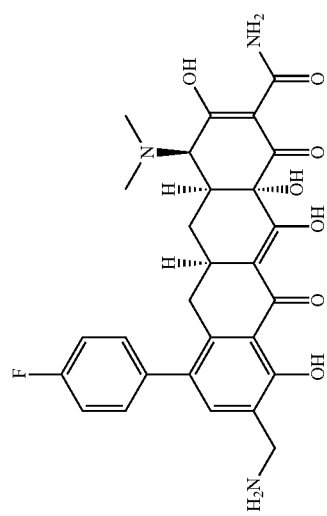 | 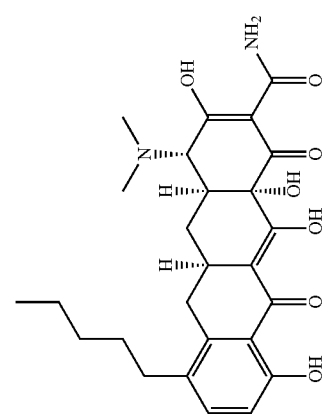 | 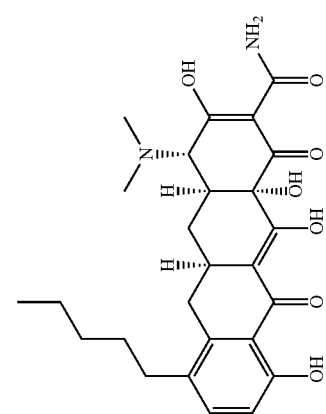 |
| 241 | | 242 |
**

TABLE 2-continued
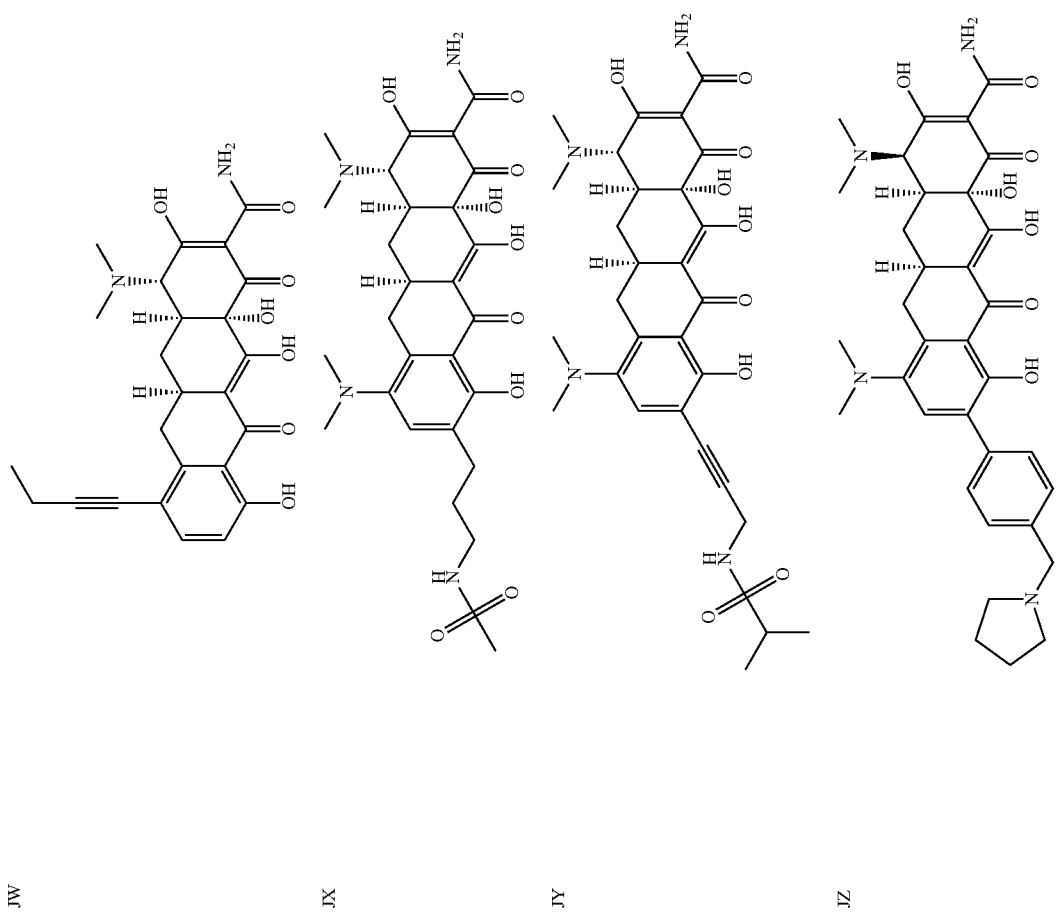
JW
JX
JY
JZ

TABLE 2-continued
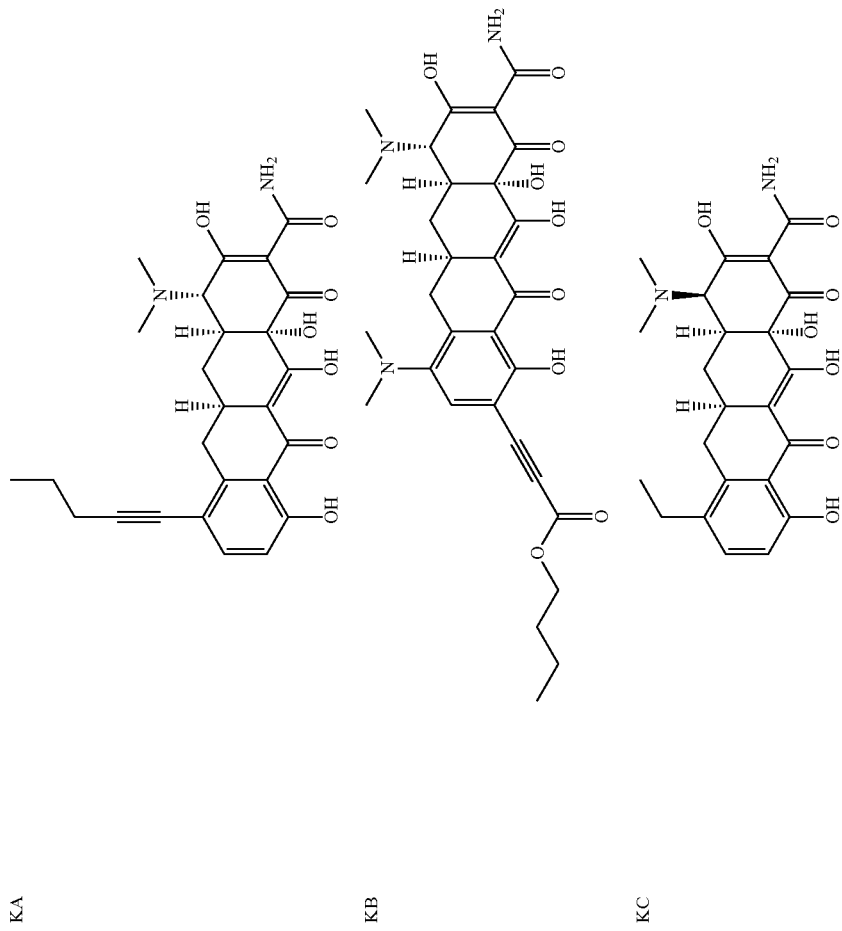
KA
KB
KC

TABLE 2-continued
| KD | KE | KF | KG |
|---|---|---|---|
| 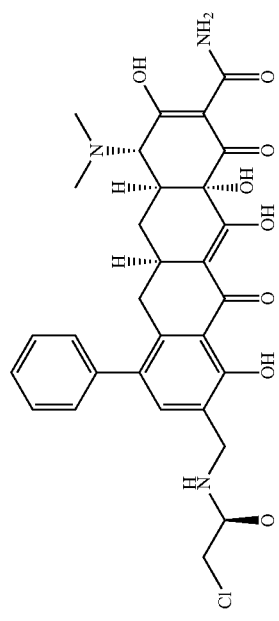 | 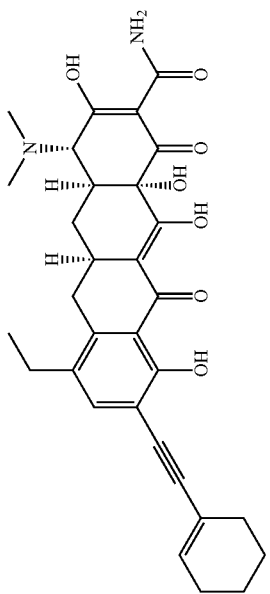 | 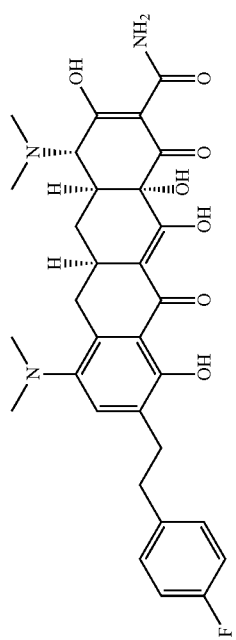 | 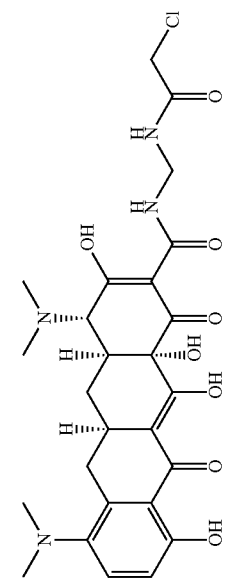 |

TABLE 2-continued
| KH | KI | KJ | KK |
|---|---|---|---|
| 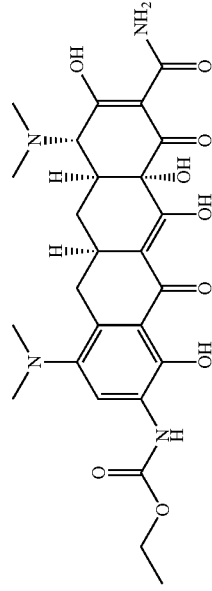 | 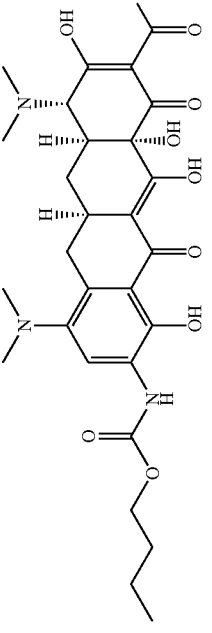 | 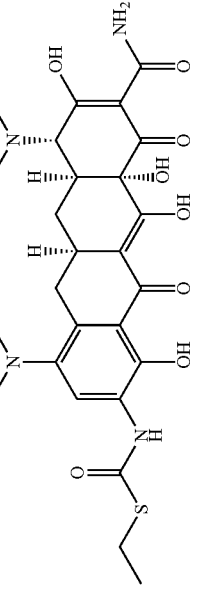 | 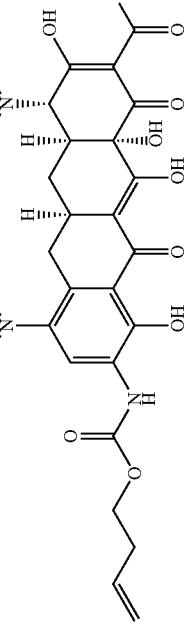 |

TABLE 2-continued
| KL | 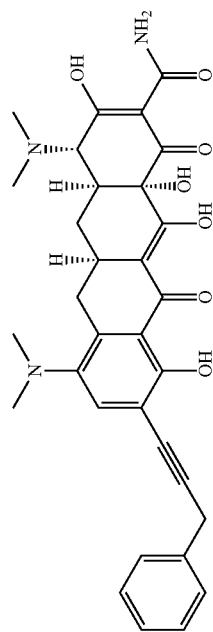 |
| KM | 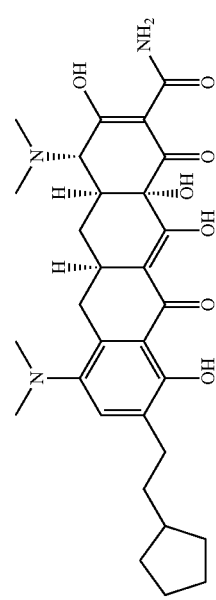 |
| KN | 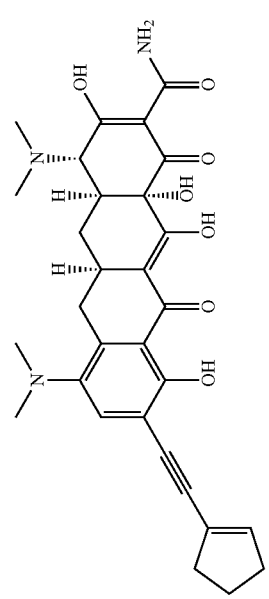 |

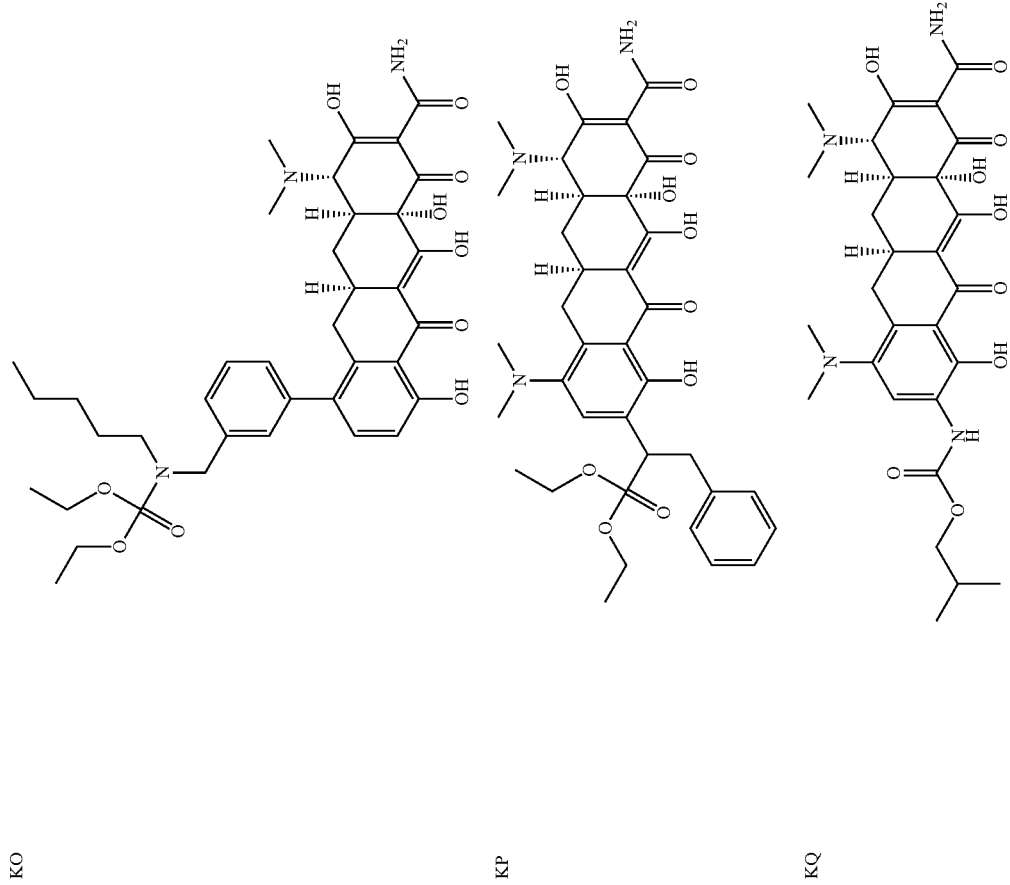

TABLE 2-continued
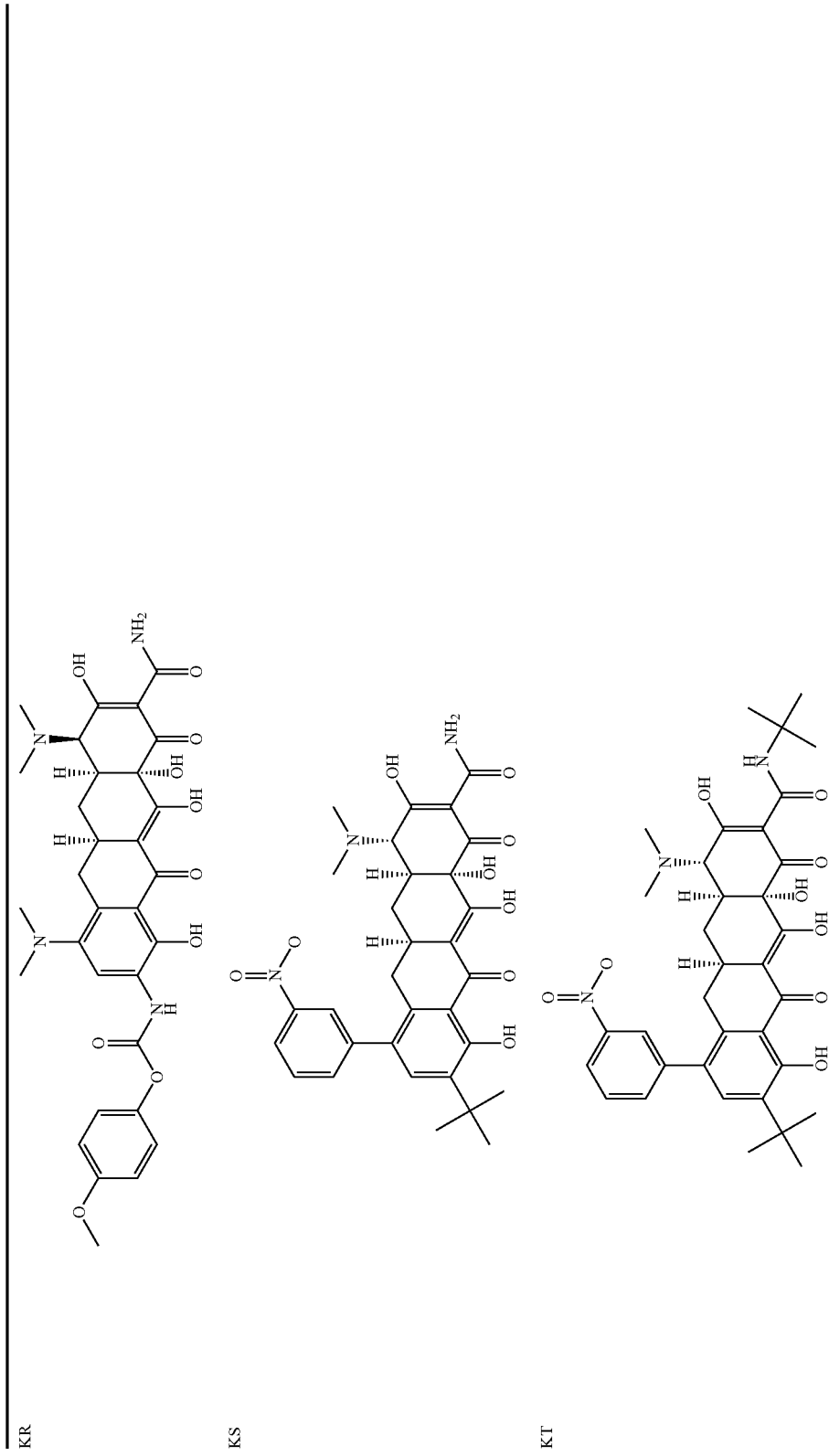
KR
KS
KT

TABLE 2-continued

| KU | KV | KW | KX |

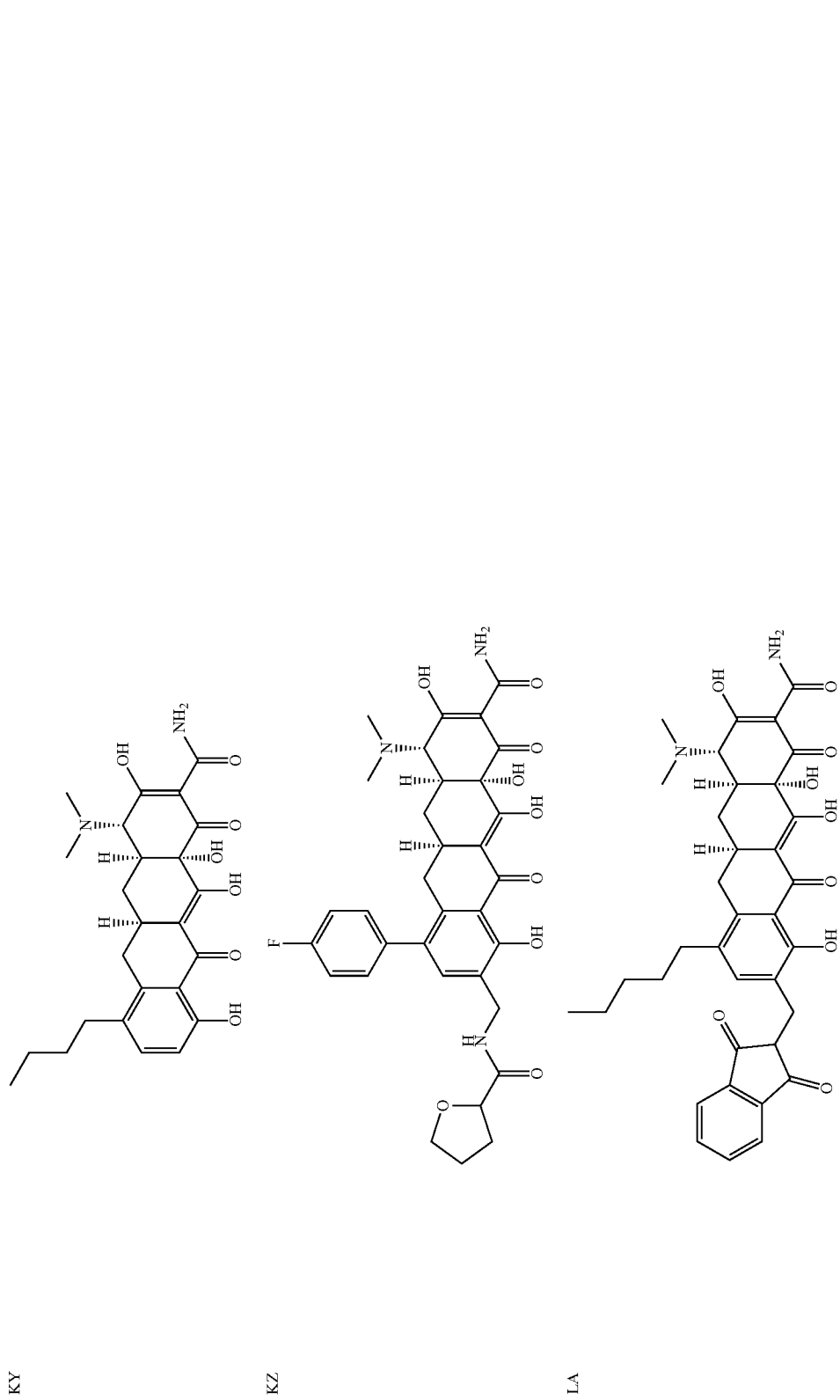

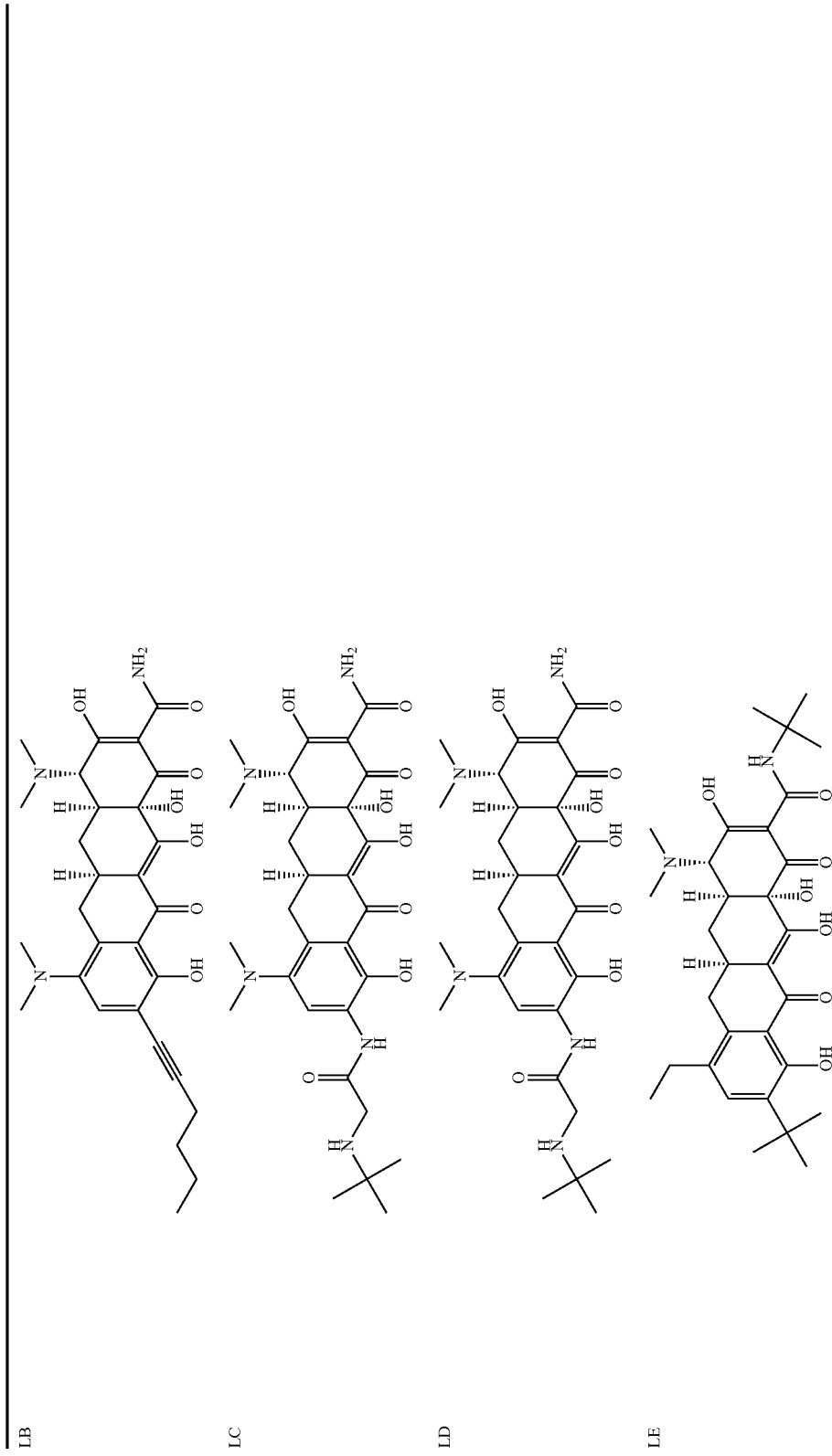

TABLE 2-continued
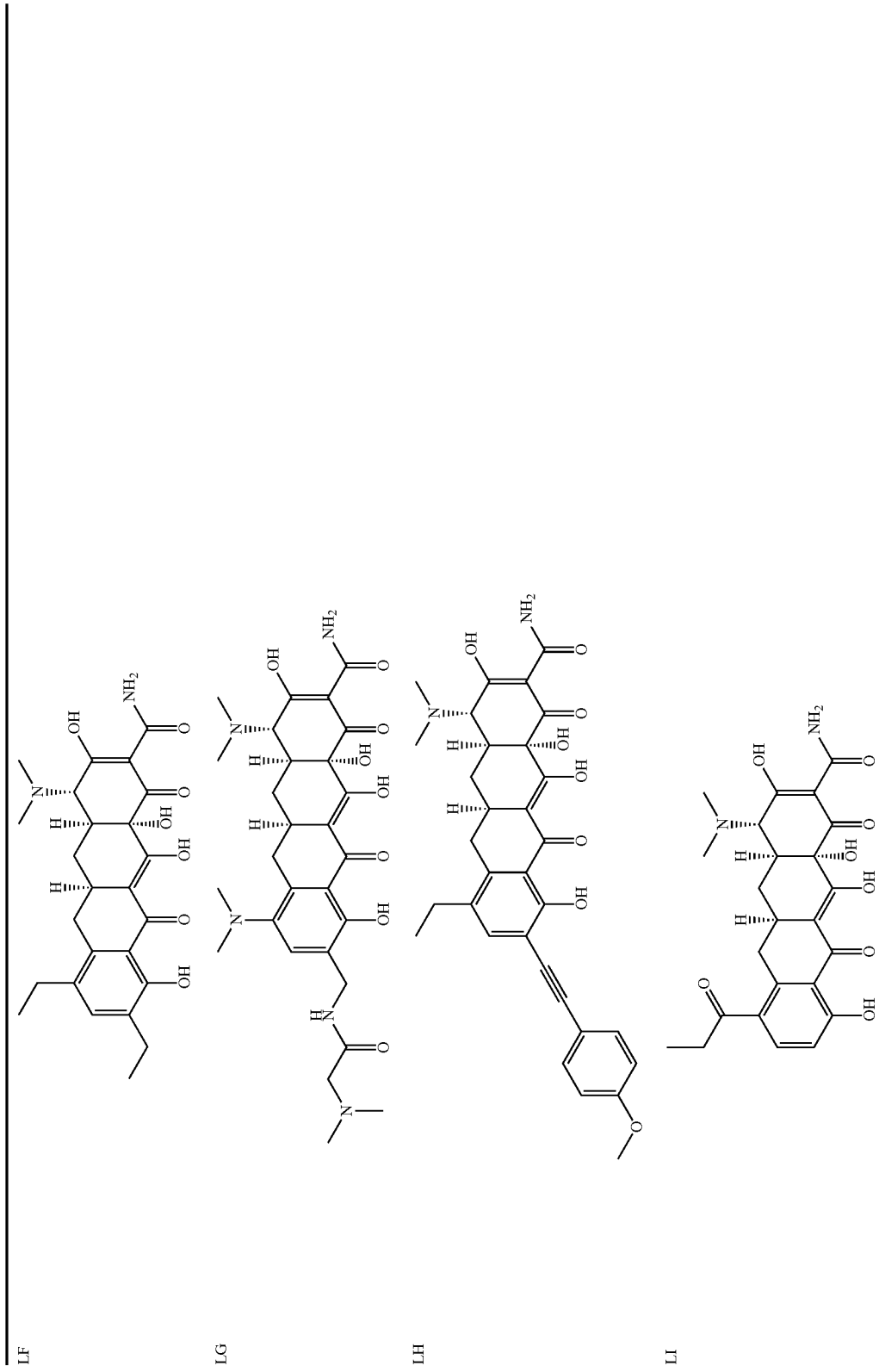
LF
LG
LH
LI

TABLE 2-continued
| LJ | 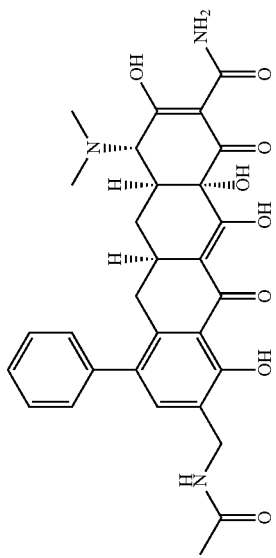 |
| LK | 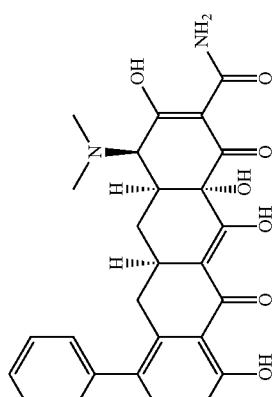 |
| LL | 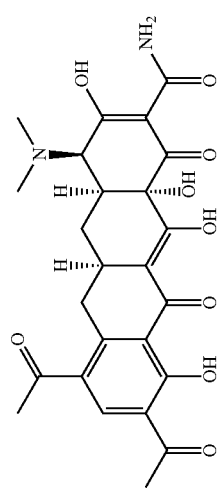 |

TABLE 2-continued
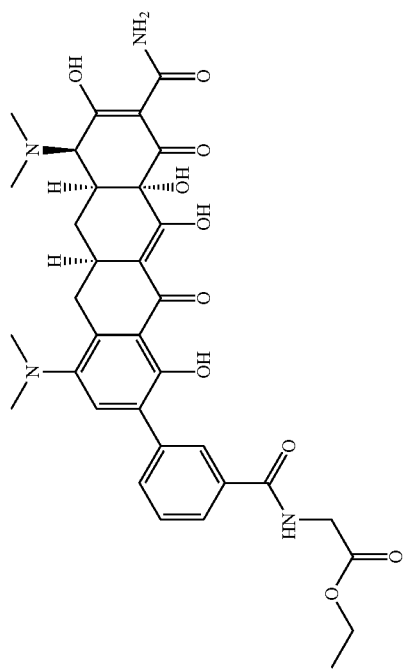
LM
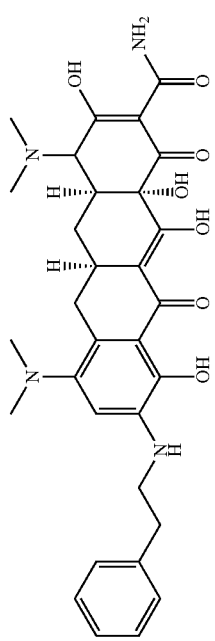
LN
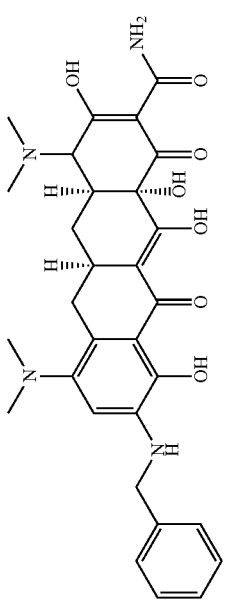
LO

TABLE 2-continued
| LP | 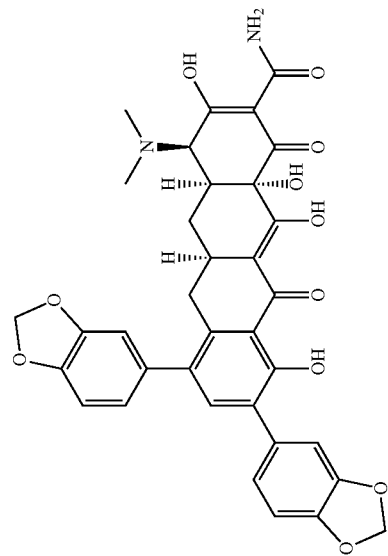 |
| LQ | 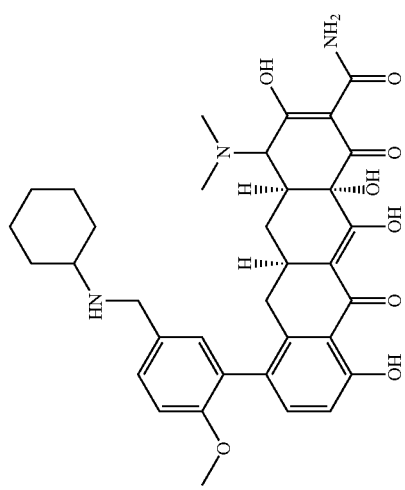 |

TABLE 2-continued
| LR | LS |
|---|---|
| 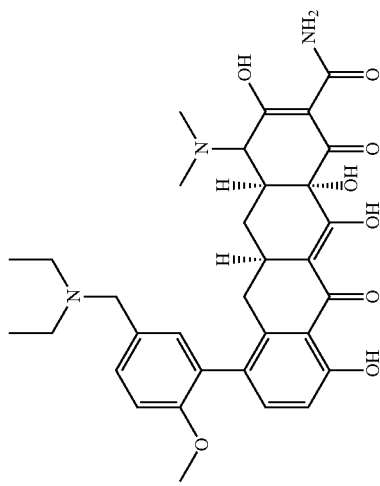 | 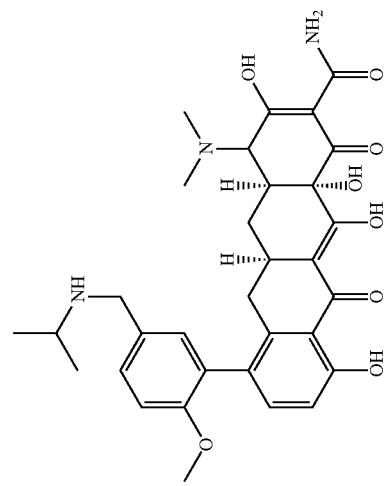 |

TABLE 2-continued
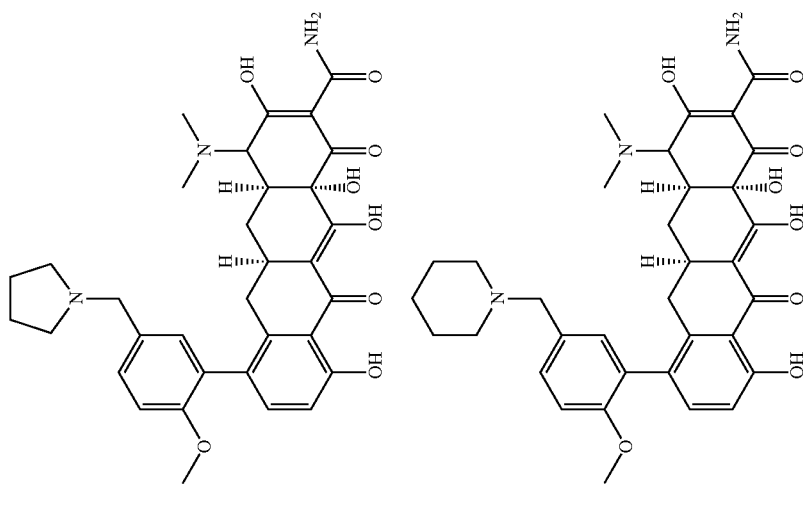
LT
LU

TABLE 2-continued
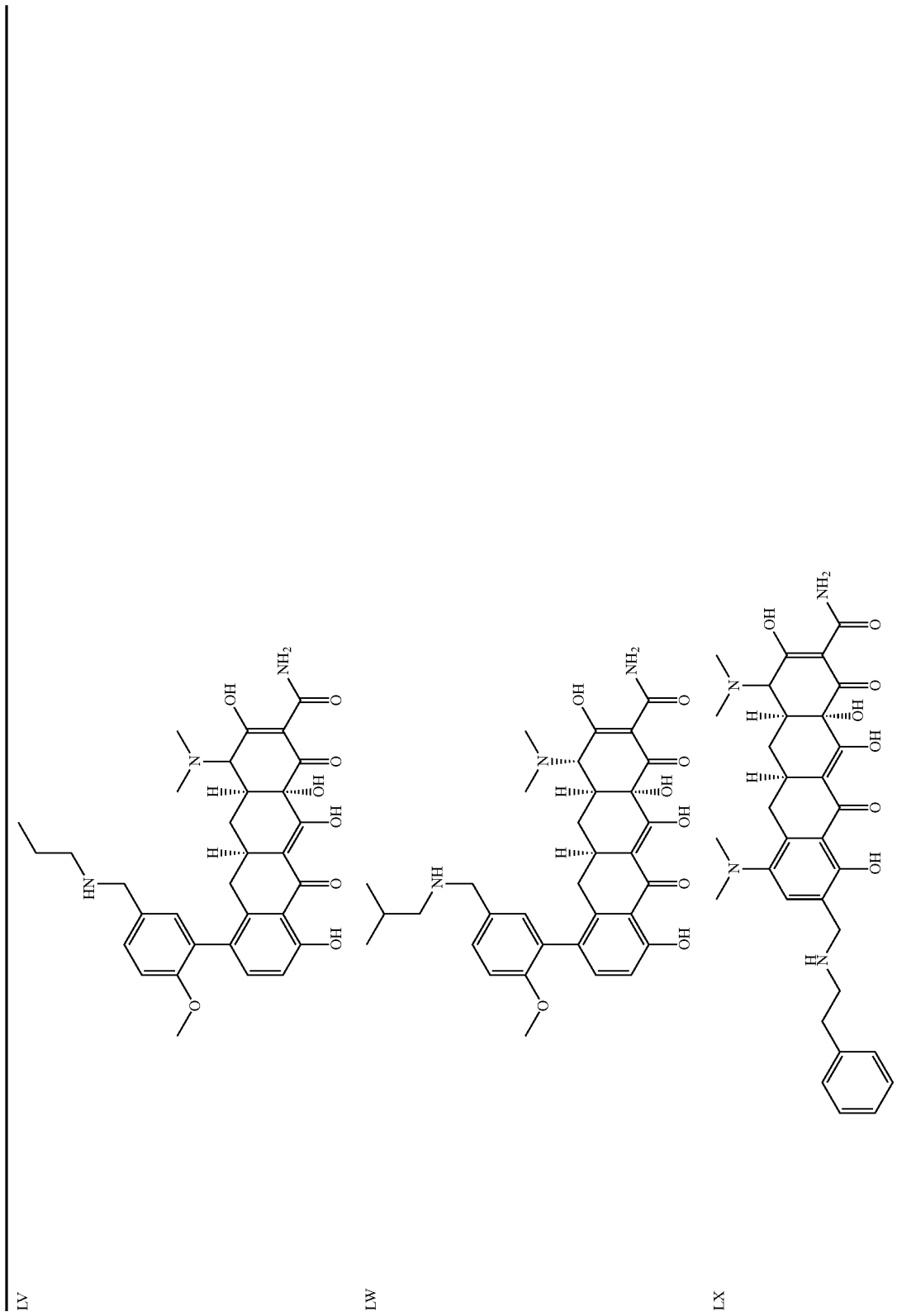
LV
LW
LX

TABLE 2-continued
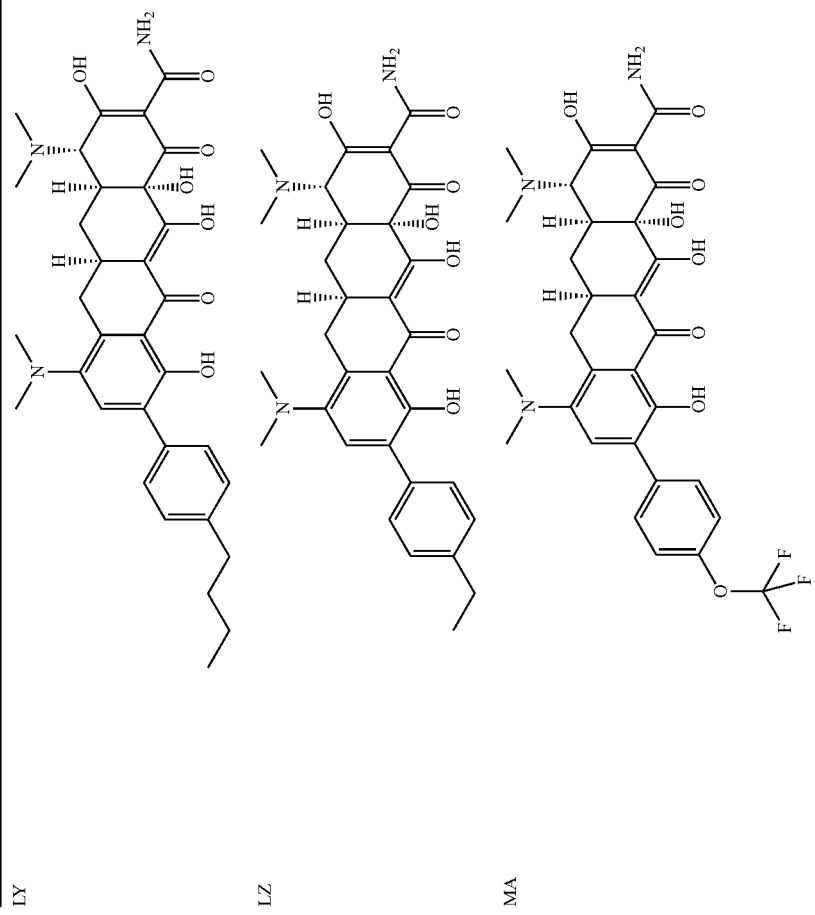
LY
LZ
MA

TABLE 2-continued
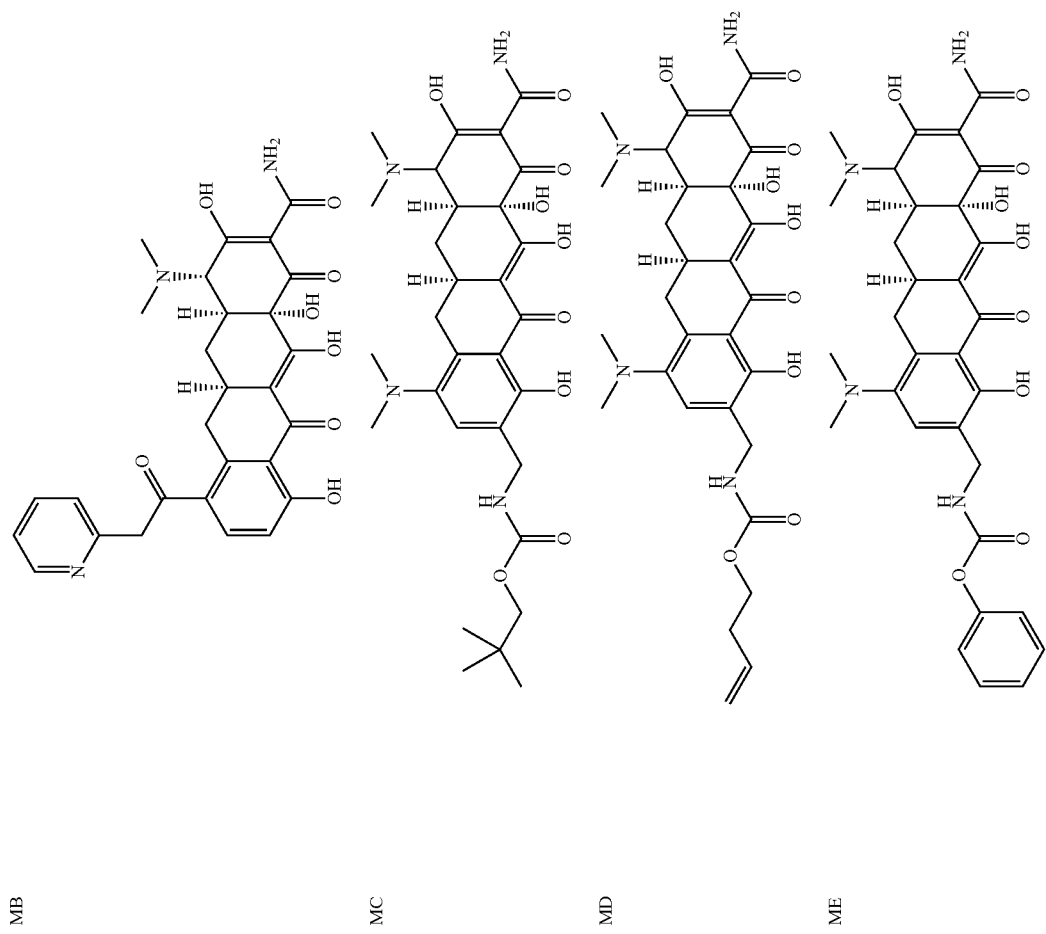
MB
MC
MD
ME

TABLE 2-continued
| MF | 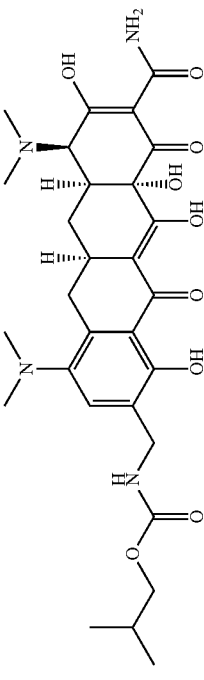 |
| MG | 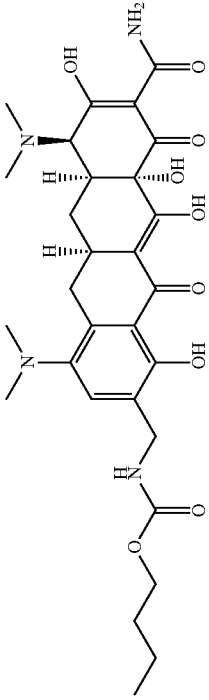 |
| MH | 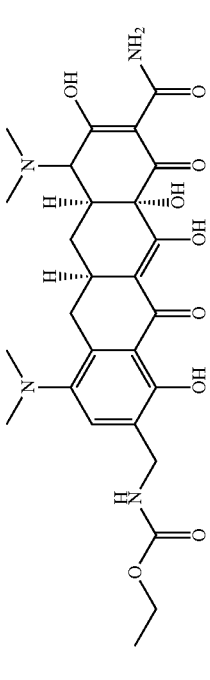 |
| MI | 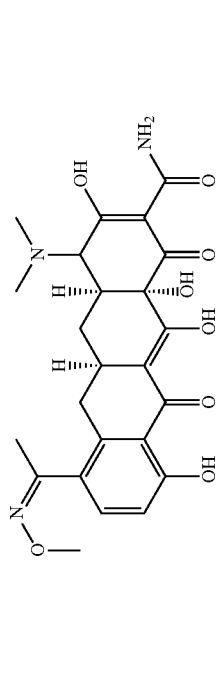 |

TABLE 2-continued
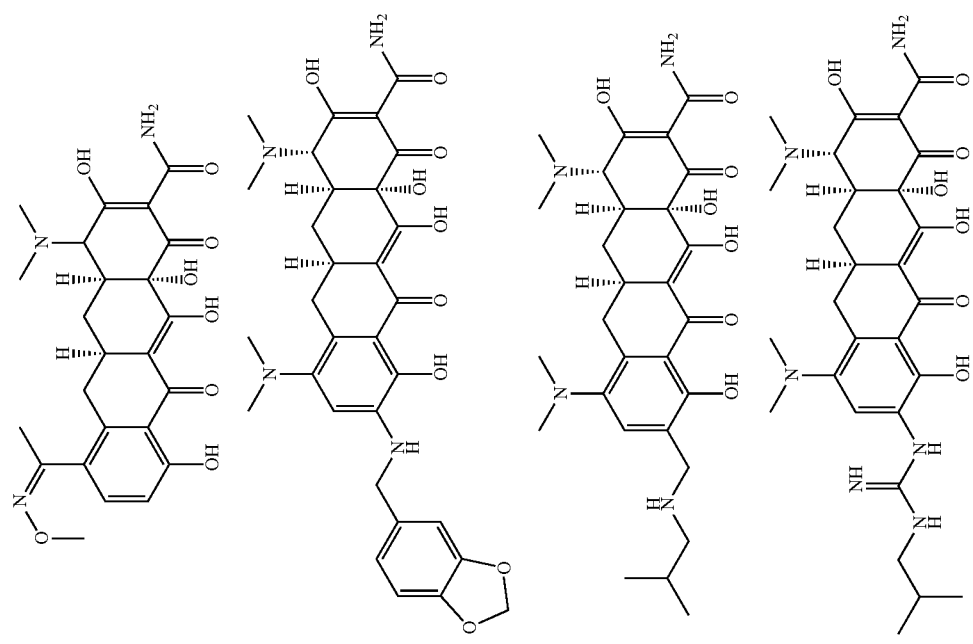
MJ
MK
ML
MM

TABLE 2-continued

| MN | MO | MP | MQ |

TABLE 2-continued
| MR | MS | MT | MU |
|----|----|----|----|
| 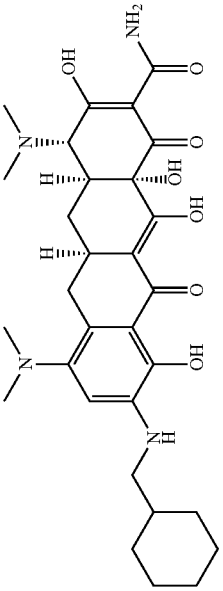 | 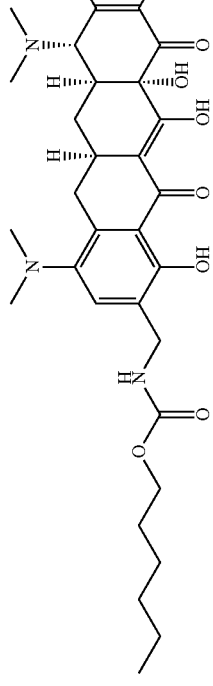 | 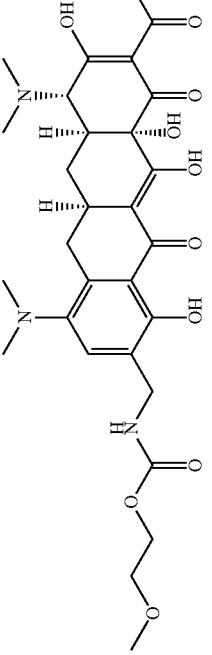 | 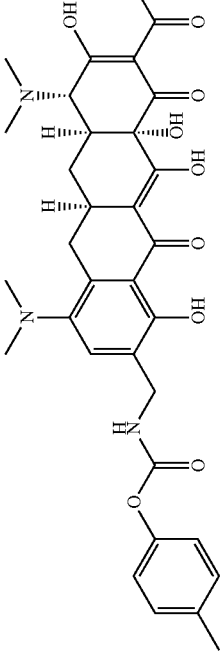 |

TABLE 2-continued

| MV | MW | MX | MY |

TABLE 2-continued
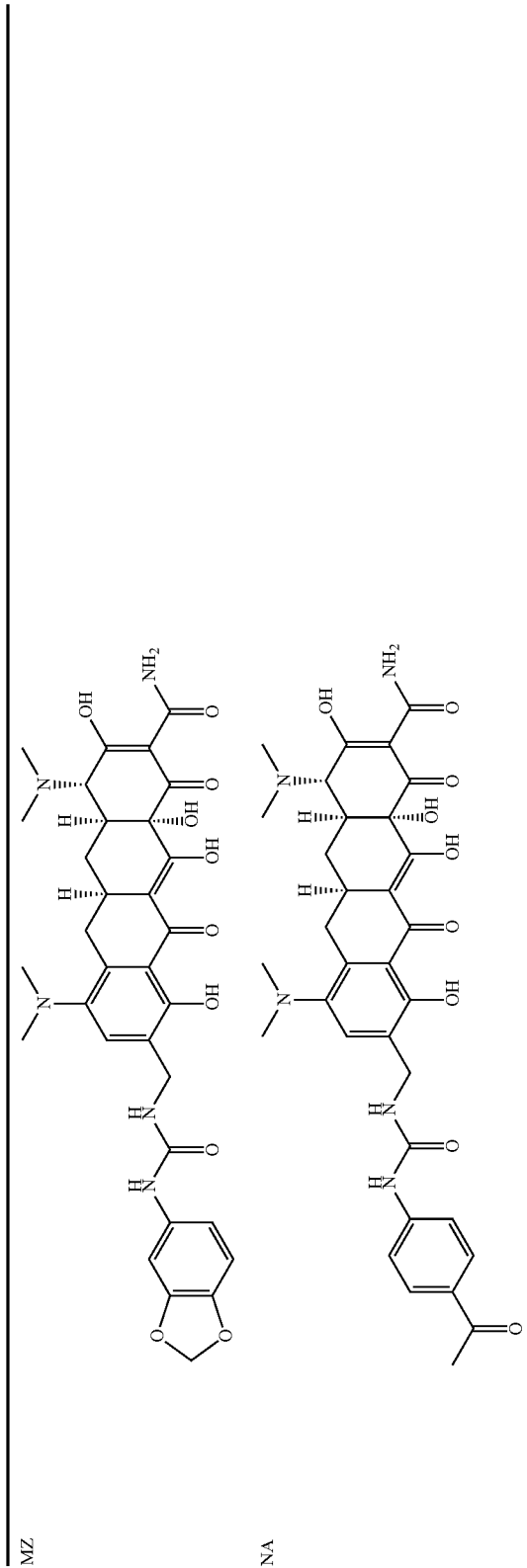
MZ
NA

TABLE 2-continued
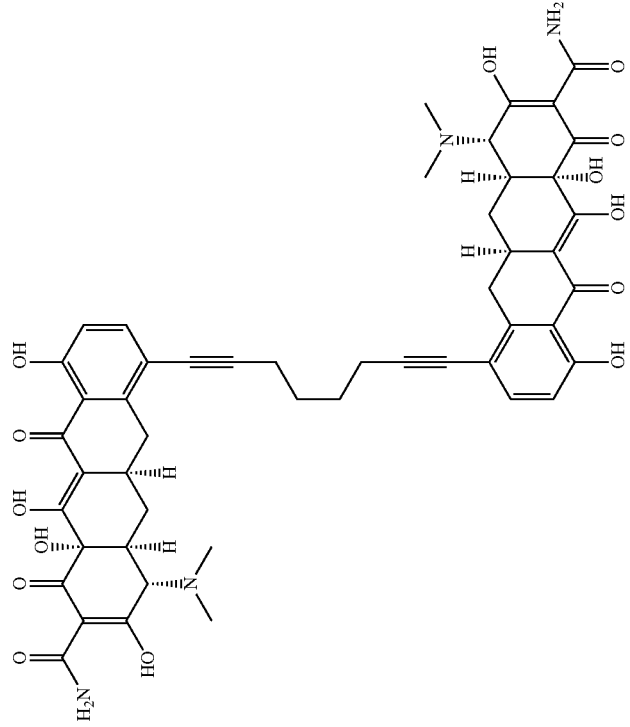
NB

TABLE 2-continued
| NC | 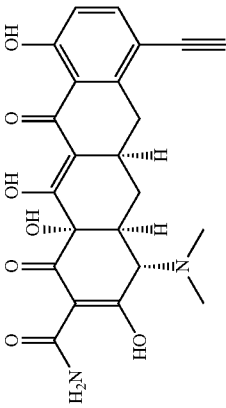 |
| ND | 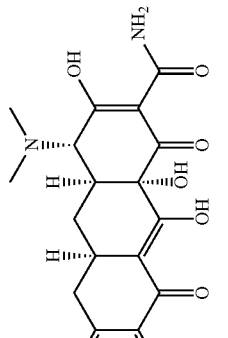 |
| NE | 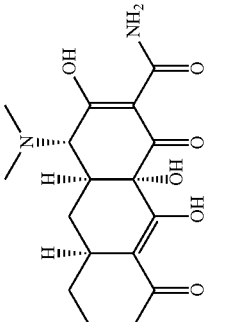 |

TABLE 2-continued
| | |
|---|---|
| NF | 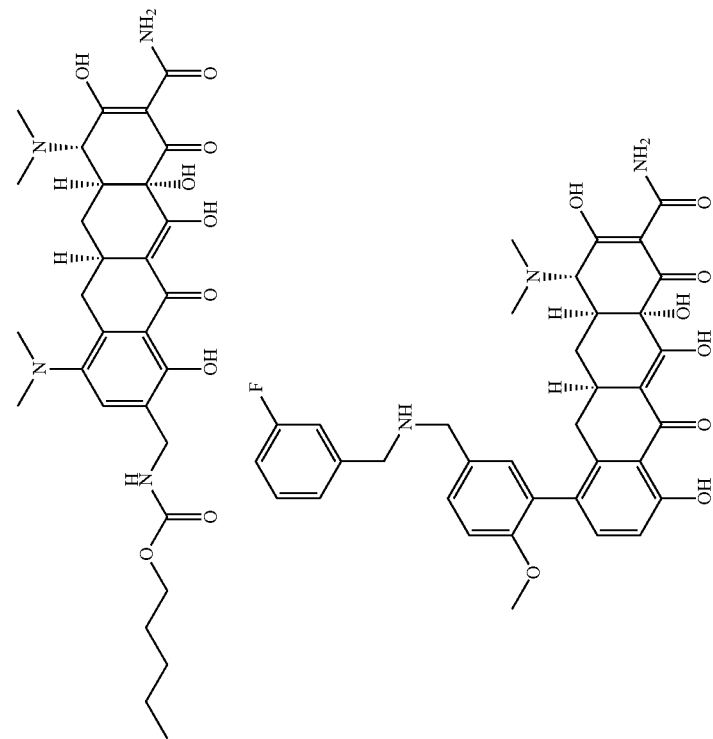 |
| NG | |

TABLE 2-continued
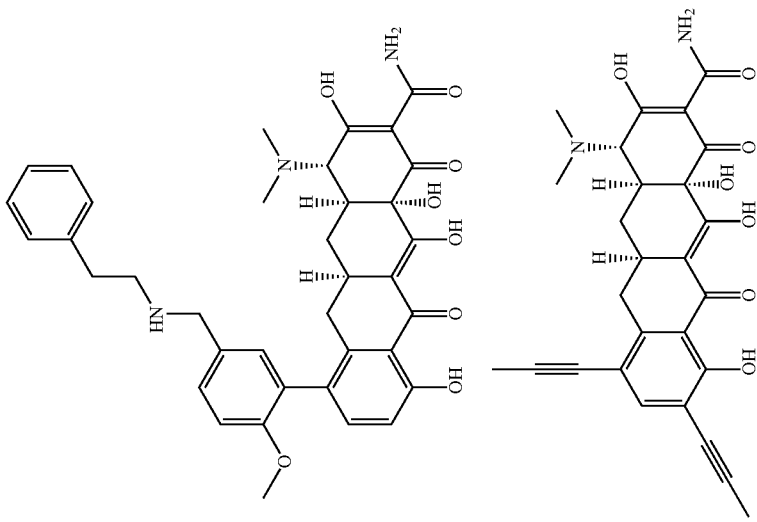

TABLE 2-continued
| NJ | 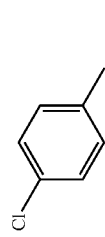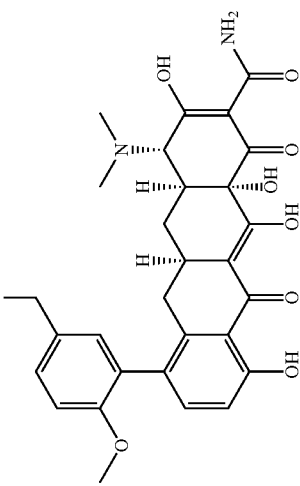 |
| NK | 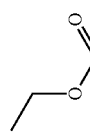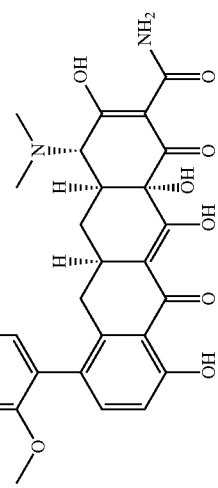 |

TABLE 2-continued
| NL | 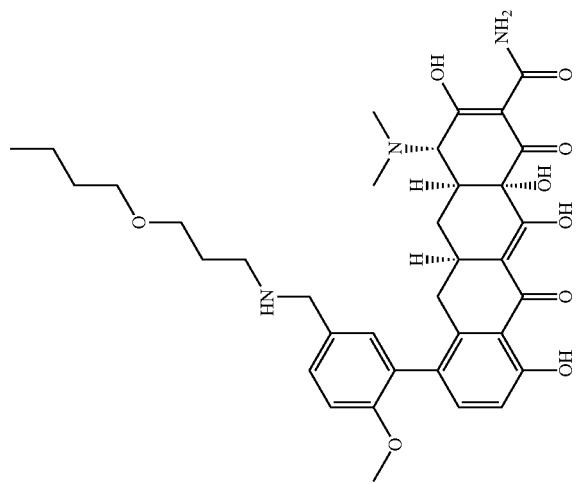 |
| NM | 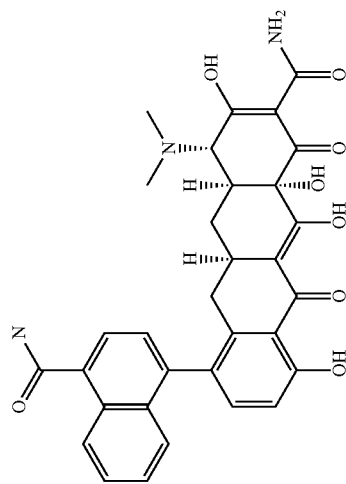 |

TABLE 2-continued

| NN | NO | NP | NQ |

TABLE 2-continued

| | |
|---|---|
| NR | (structure) |
| NS | (structure) |
| NT | (structure) |
| NU | (structure) |

TABLE 2-continued
| | |
|---|---|
| NV | 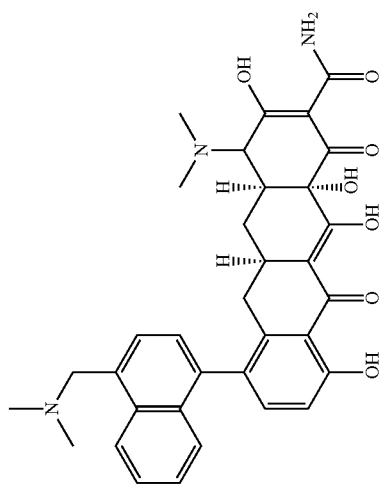 |
| NW | 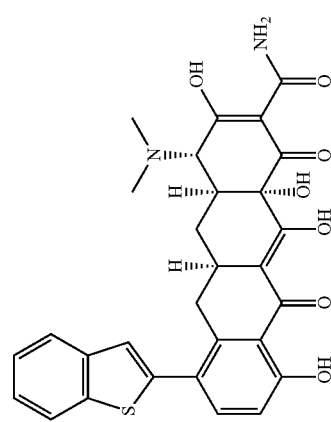 |
| NX | 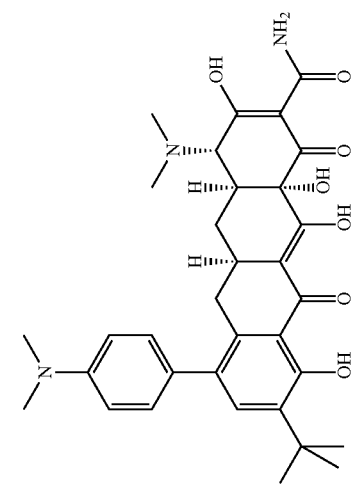 |

TABLE 2-continued
| | |
|---|---|
| NY | 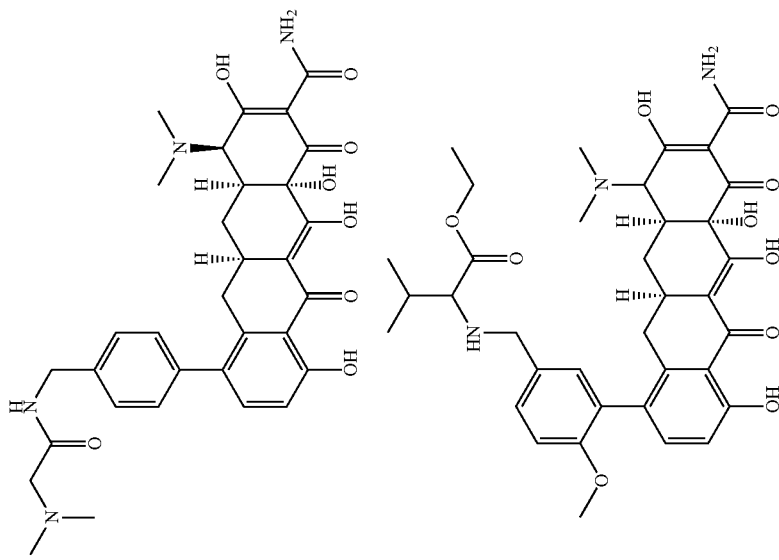 |
| NZ | |

TABLE 2-continued
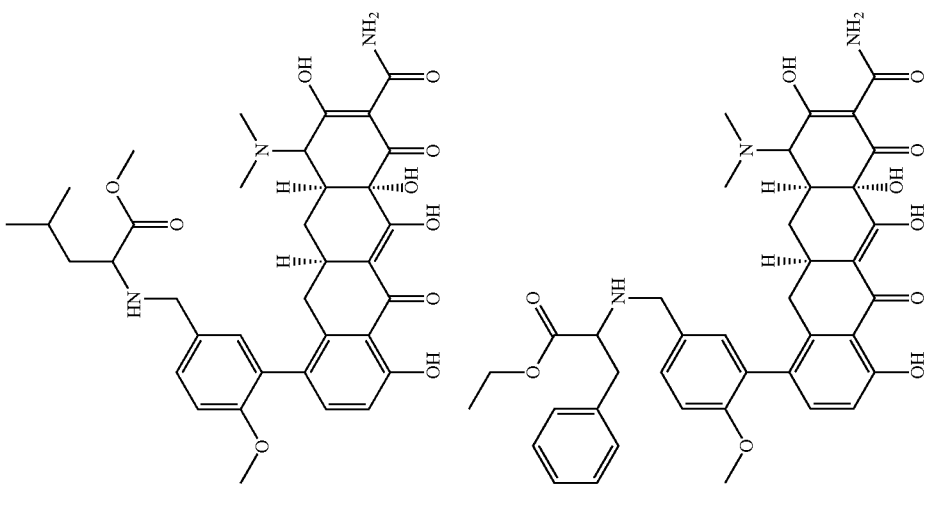
OA
OB

TABLE 2-continued
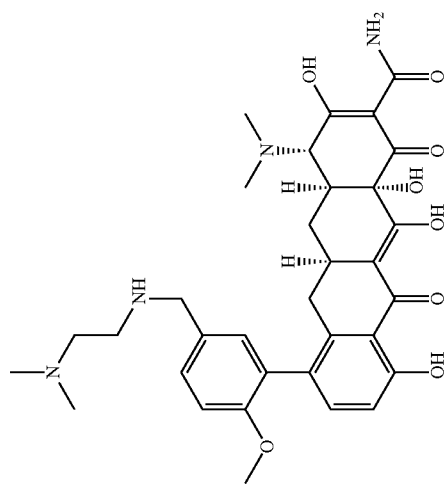
OC
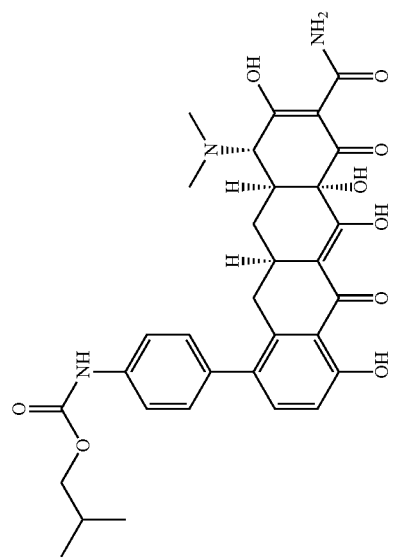
OD

TABLE 2-continued
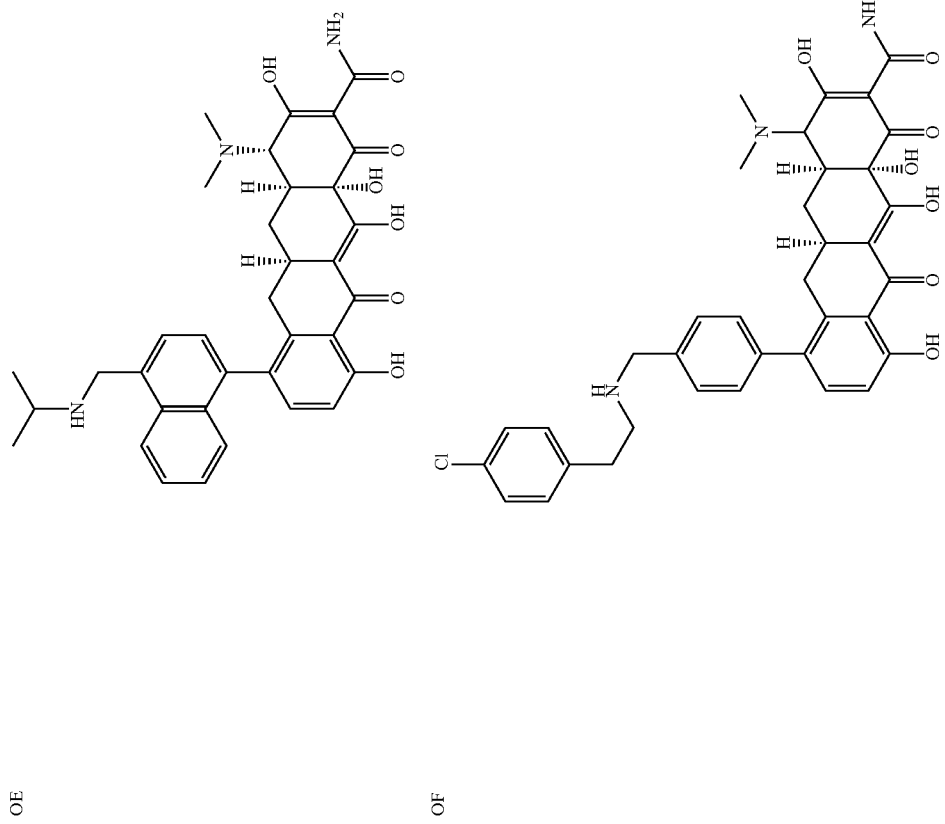
OE
OF

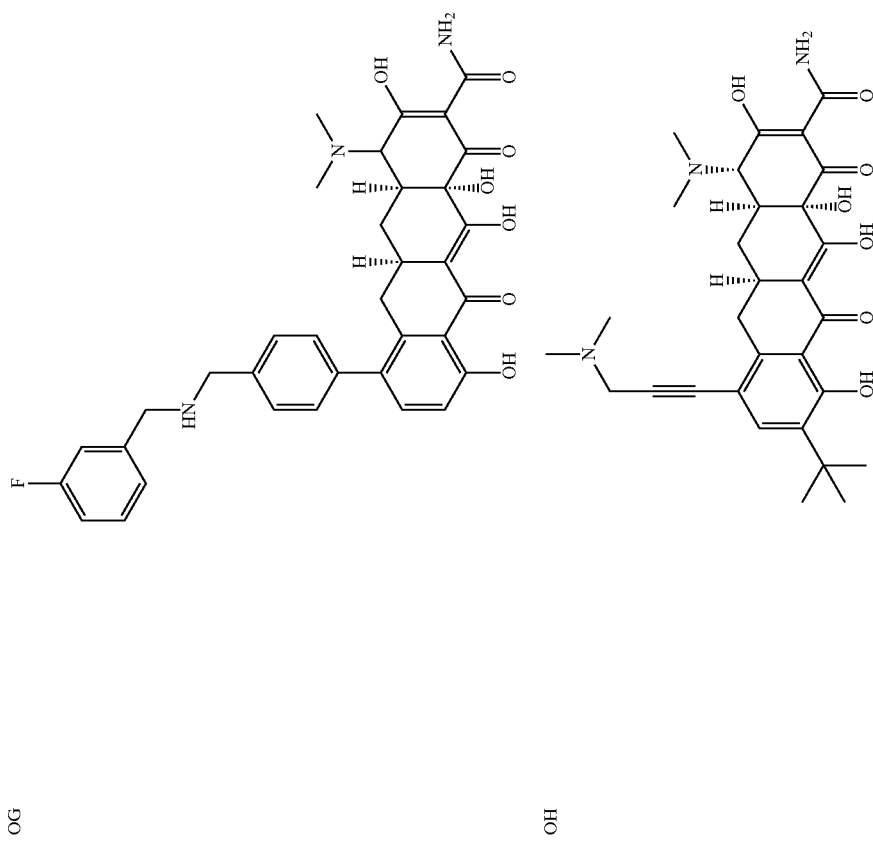

TABLE 2-continued
| 321 | 322 |
|---|---|
| 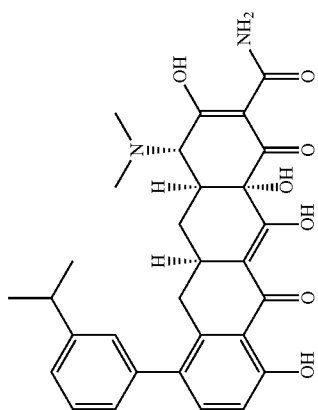 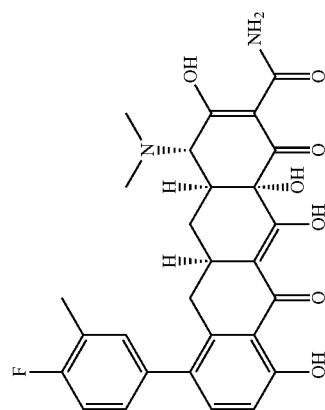 | 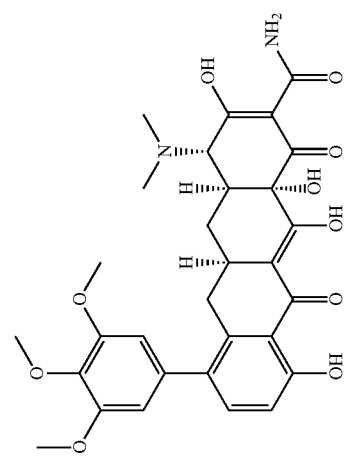 |
| IO  IO | OK |

TABLE 2-continued
| 323 | 324 | |
|---|---|---|
| 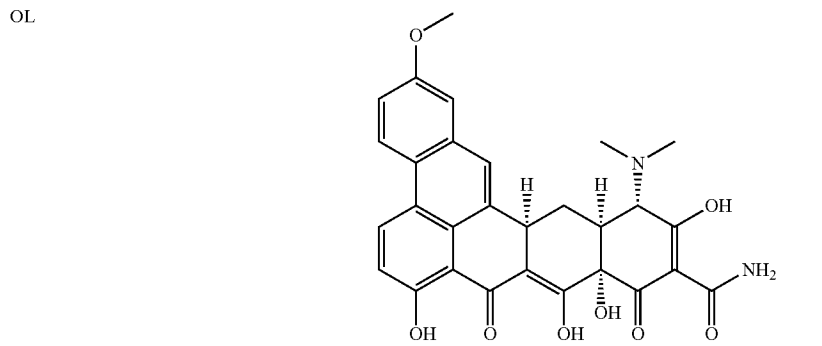 | 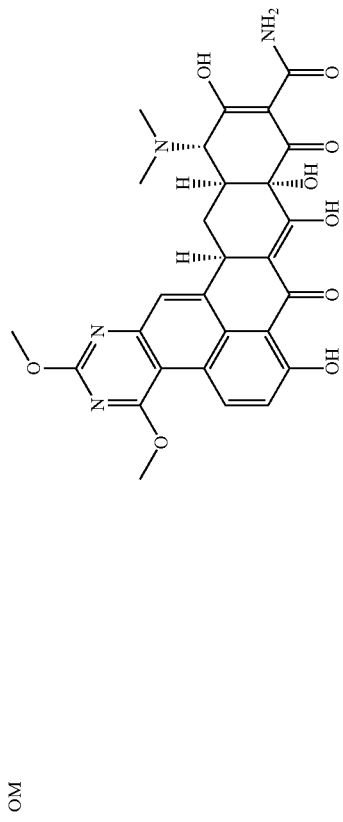 | 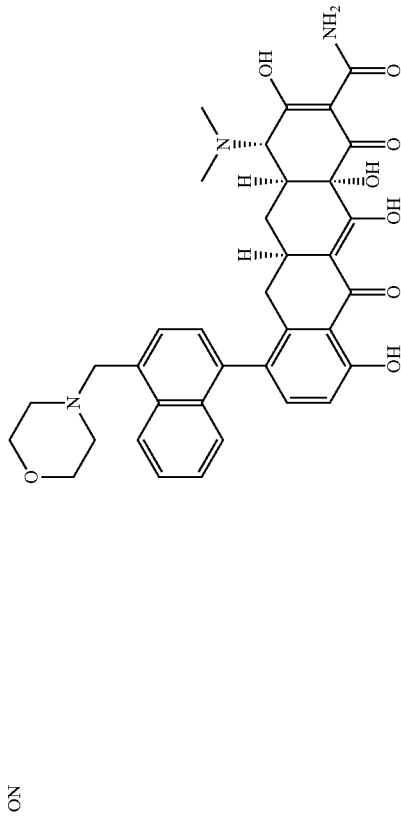 |
| OL | OM | ON |

TABLE 2-continued
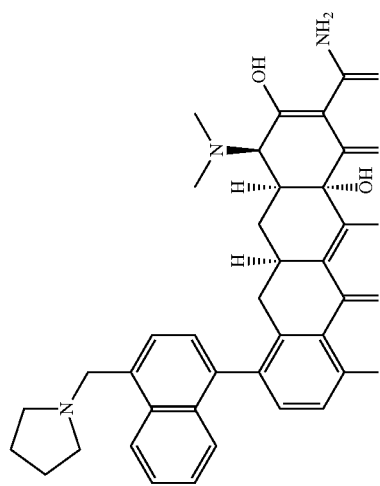
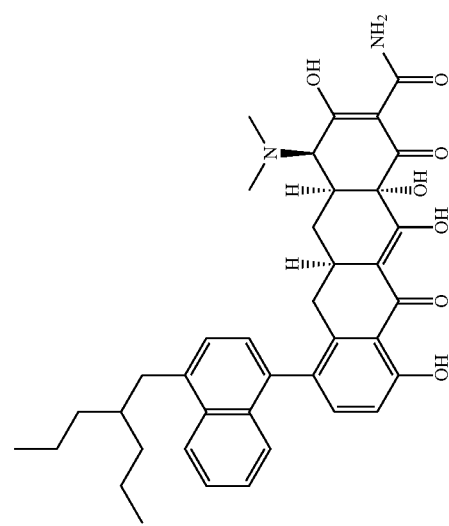

TABLE 2-continued
| OQ | OR |
|---|---|
| 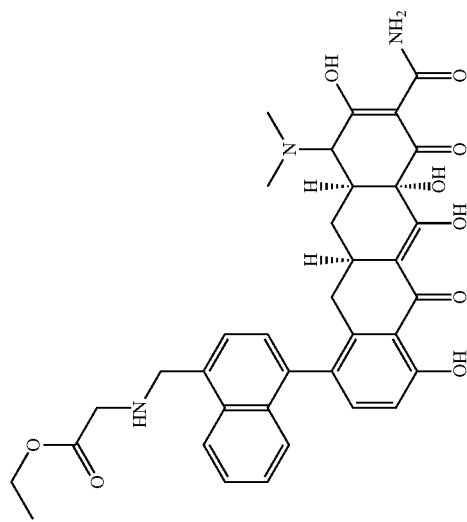 | 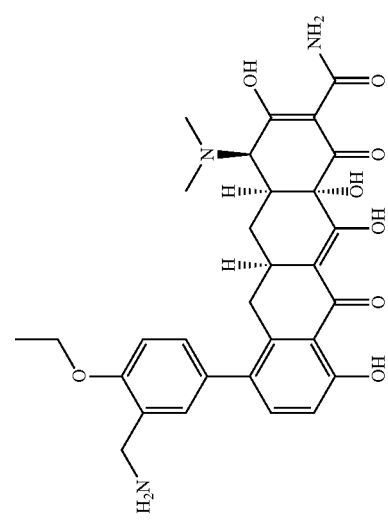 |

TABLE 2-continued
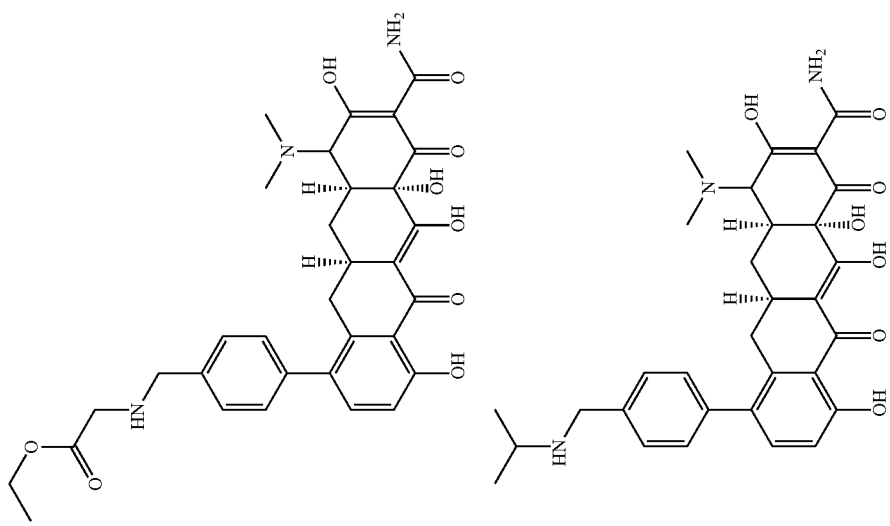

TABLE 2-continued
OU 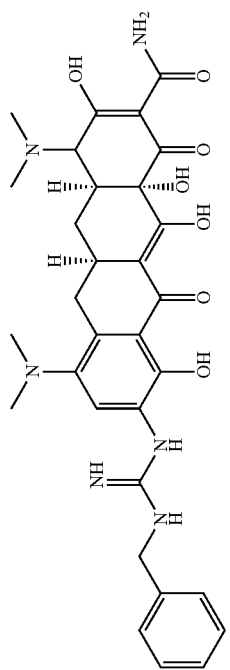
OV 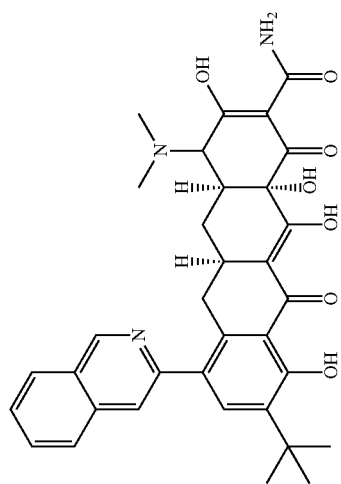
OW 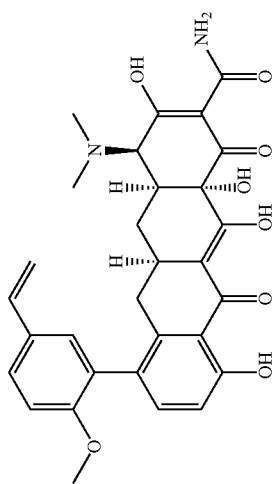

TABLE 2-continued
| OX | OY | OZ |
|----|----|----|
| 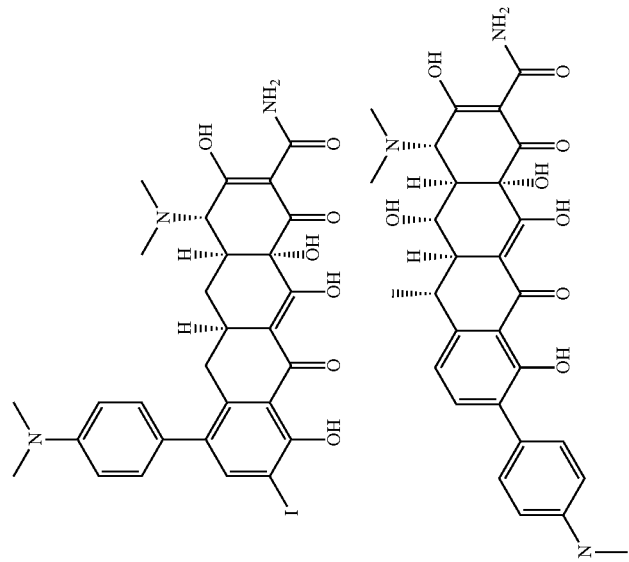 | | 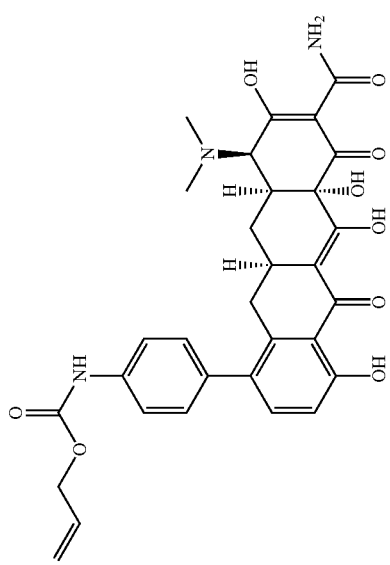 |

TABLE 2-continued
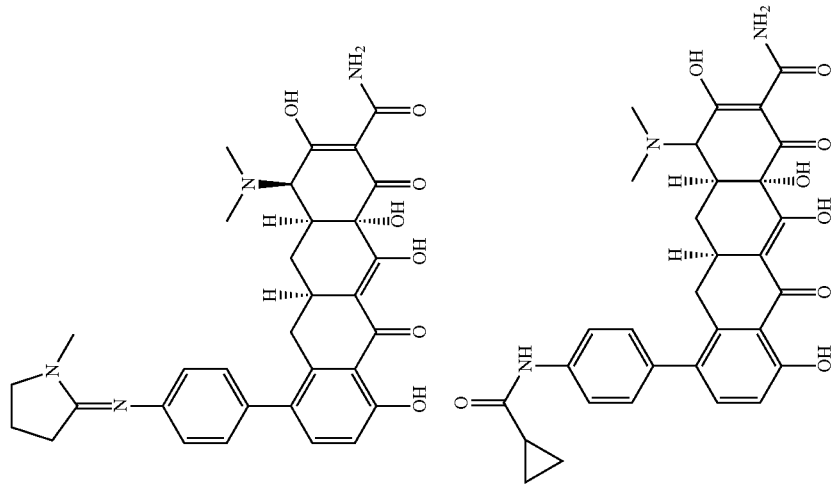
PA
PB

TABLE 2-continued
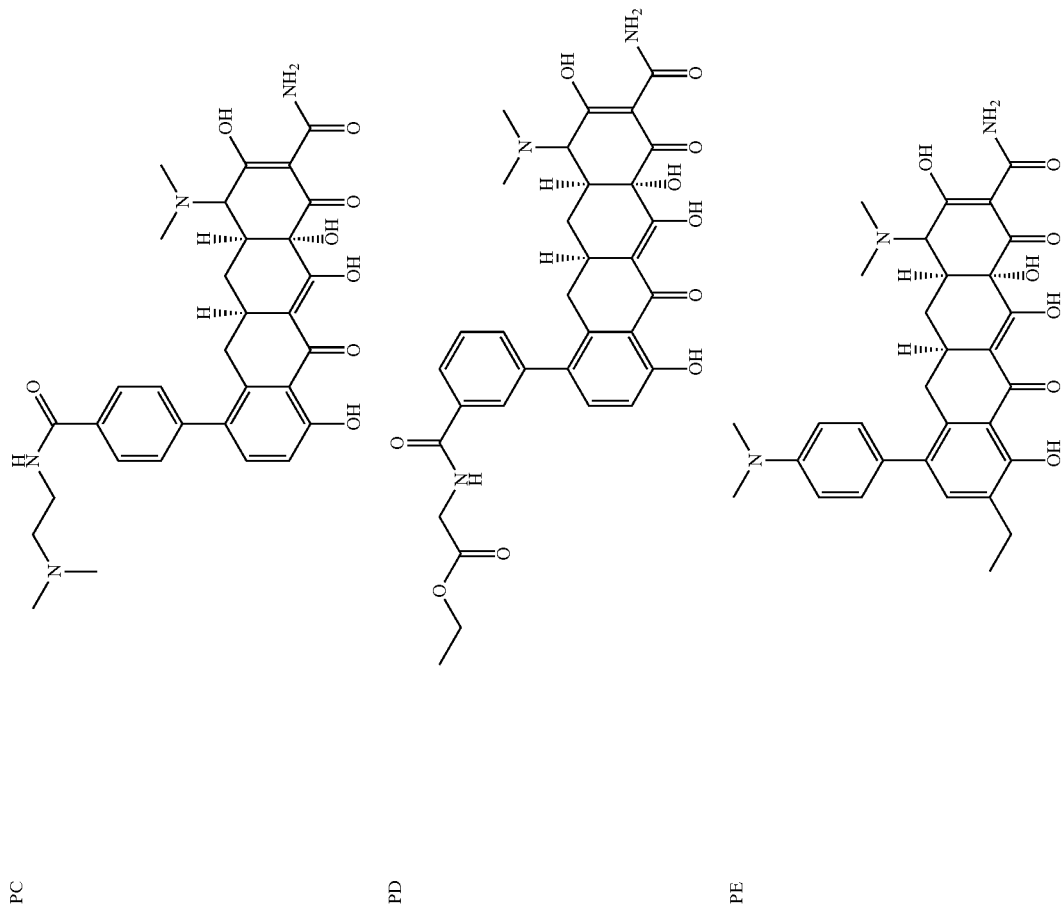
PC
PD
PE

TABLE 2-continued
| PF | PG |
|---|---|
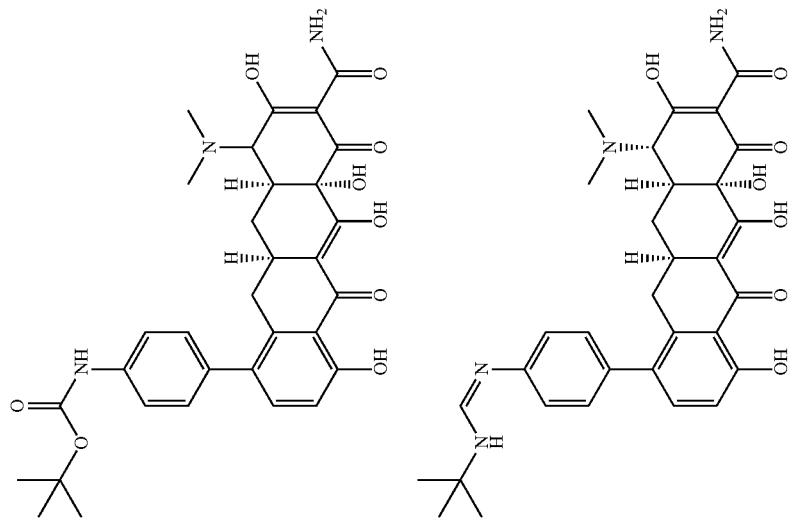

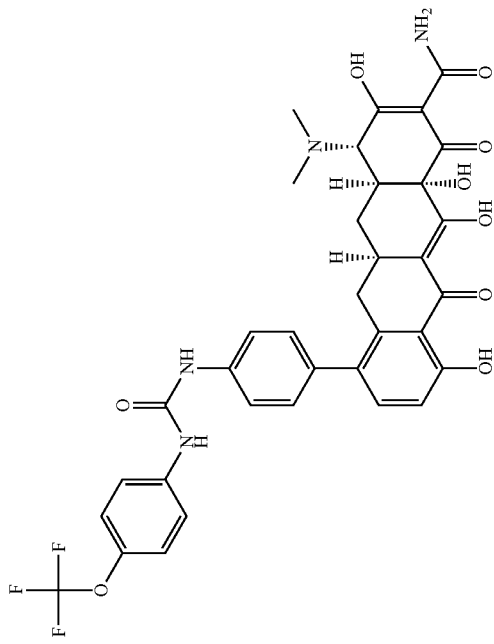

TABLE 2-continued
| PJ | PK | PL |
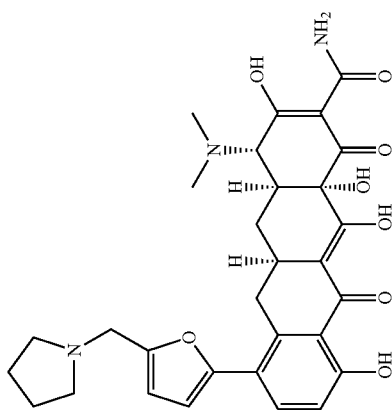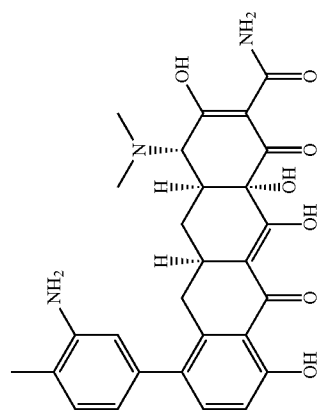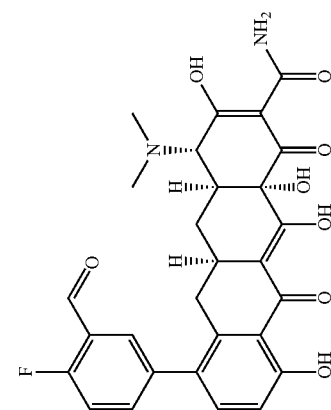

TABLE 2-continued
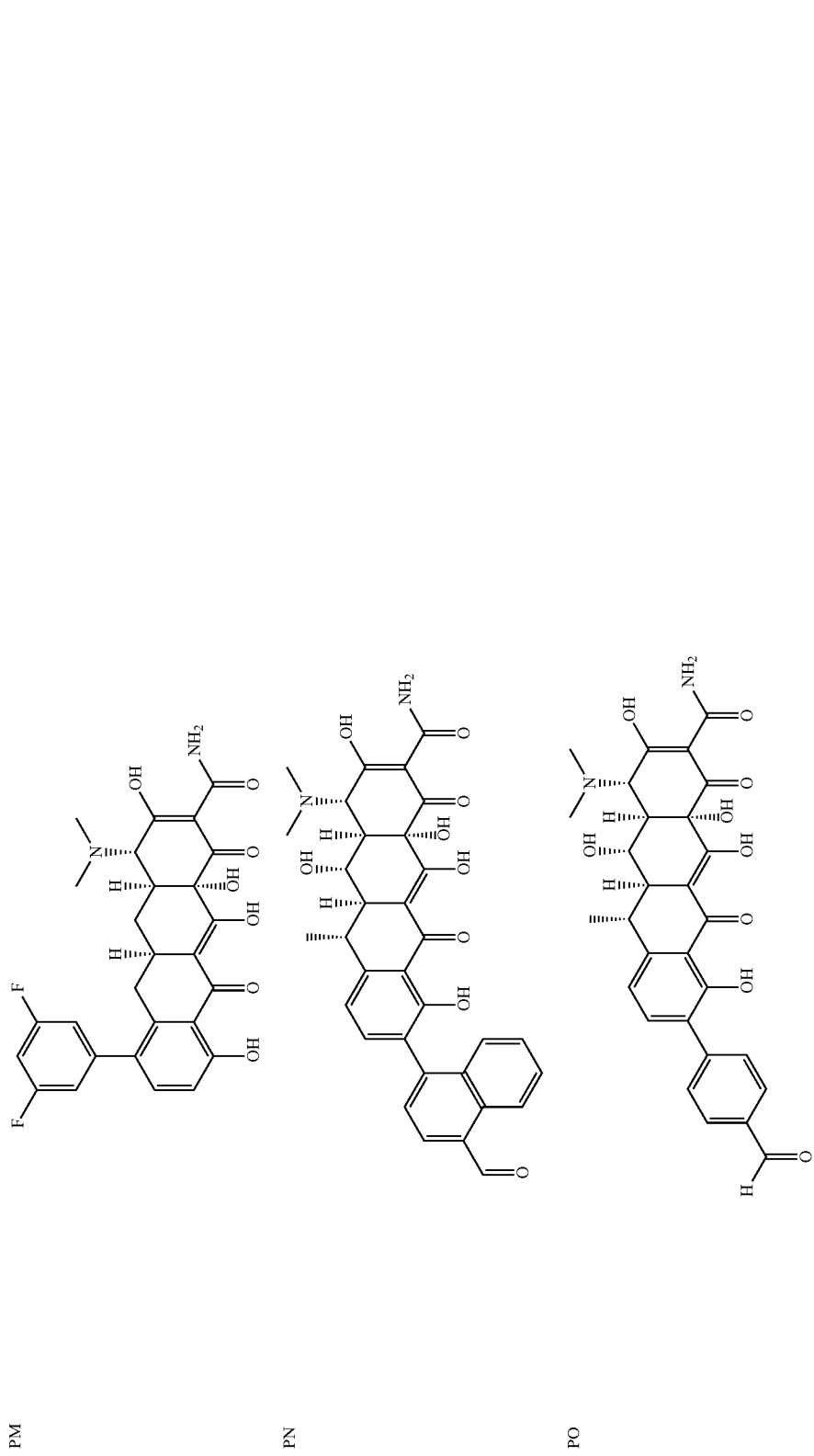
PM
PN
PO

TABLE 2-continued

| PP | PQ | PR | PS |

TABLE 2-continued
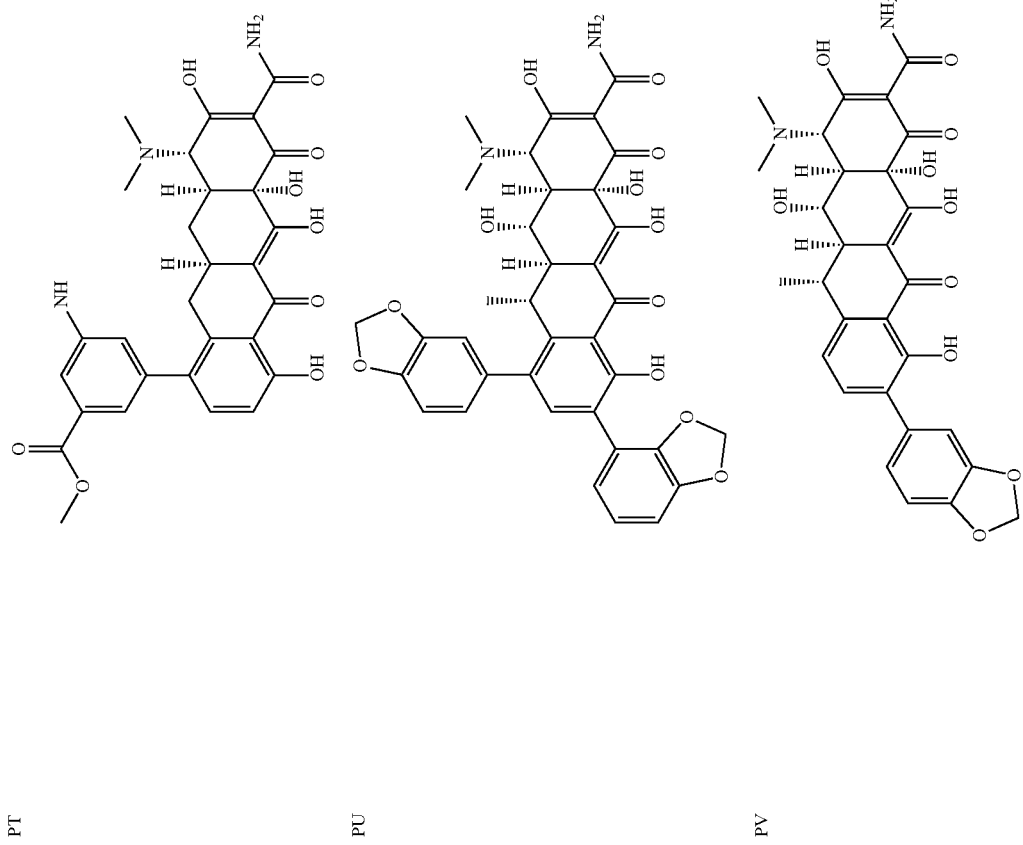
PT
PU
PV

TABLE 2-continued
| | | |
|---|---|---|
| 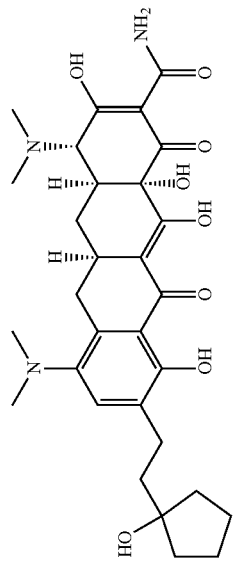 | 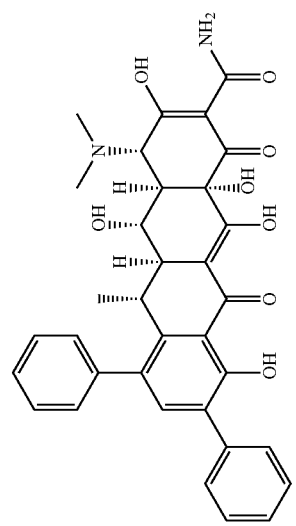 | 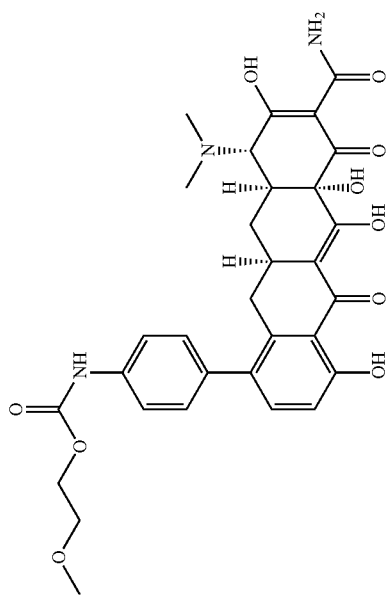 |
| PW | PX | PY |

TABLE 2-continued
| PZ | 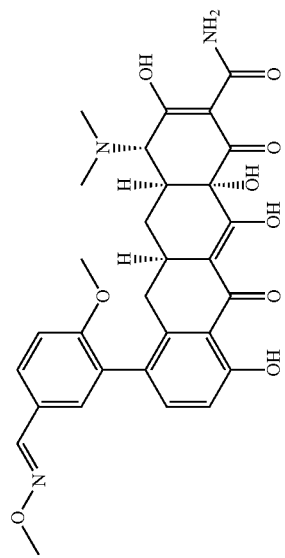 |
| QA | 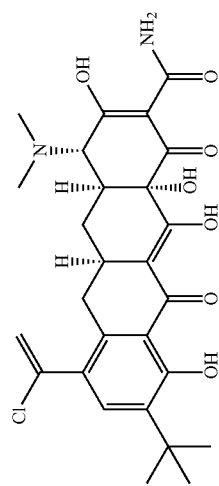 |
| QB | 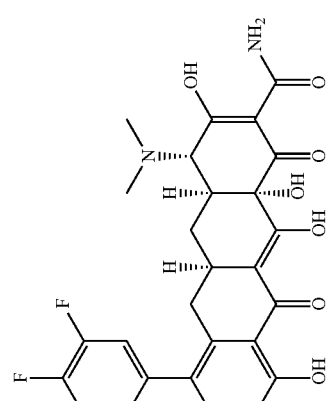 |

TABLE 2-continued
| | |
|---|---|
| QC | 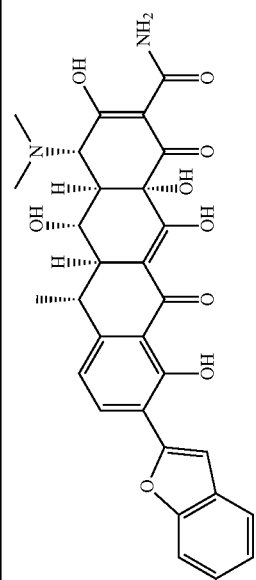 |
| QD | 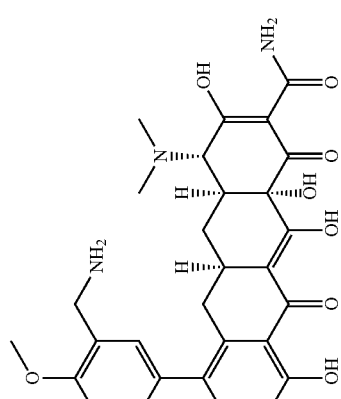 |
| QE | 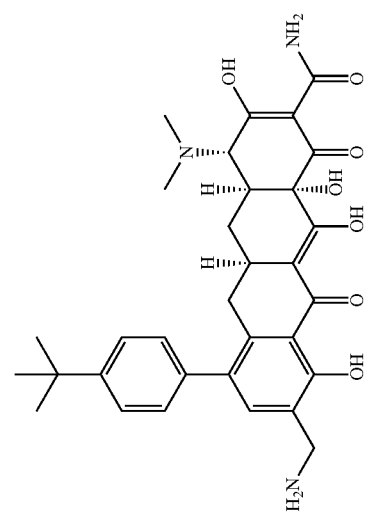 |

TABLE 2-continued
| QF | QG | QH |
|---|---|---|
| 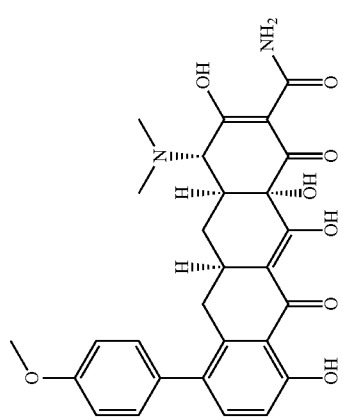 | 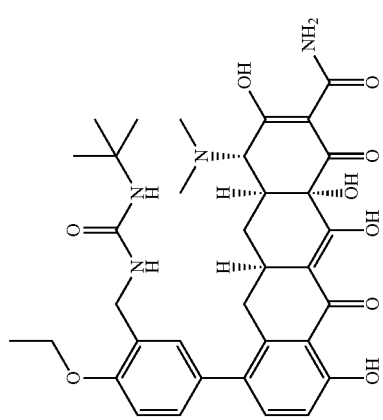 | 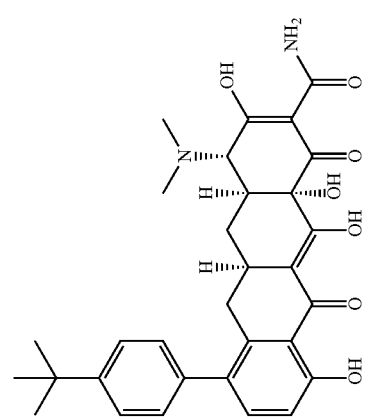 |

TABLE 2-continued
| Q1 | Q2 |
|---|---|
| 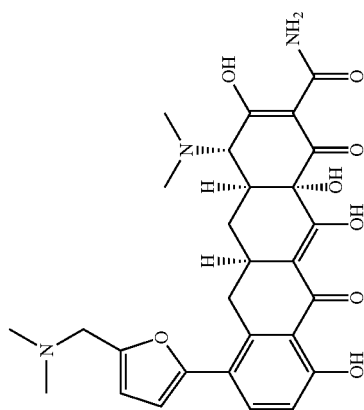 | 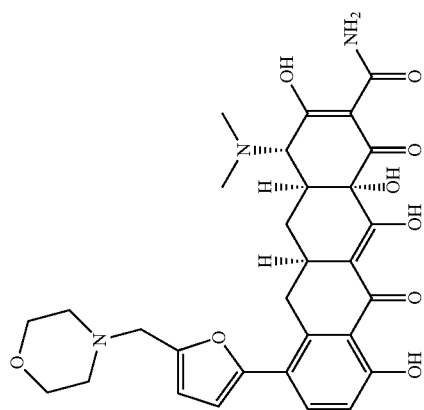 |

TABLE 2-continued
| QK | QL |
|---|---|
| 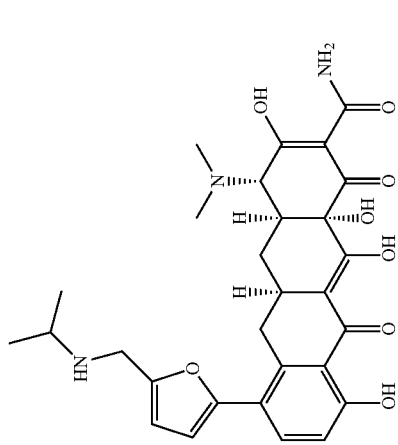 | 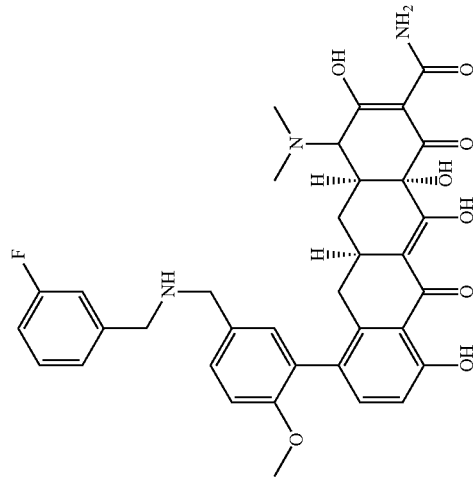 |

TABLE 2-continued
| QM | QN | QO |
|---|---|---|
| 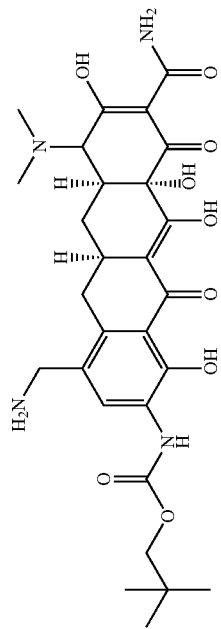 | 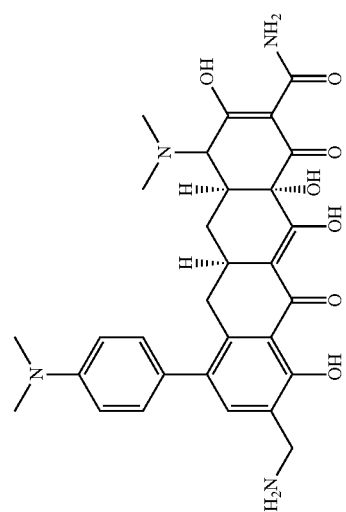 | 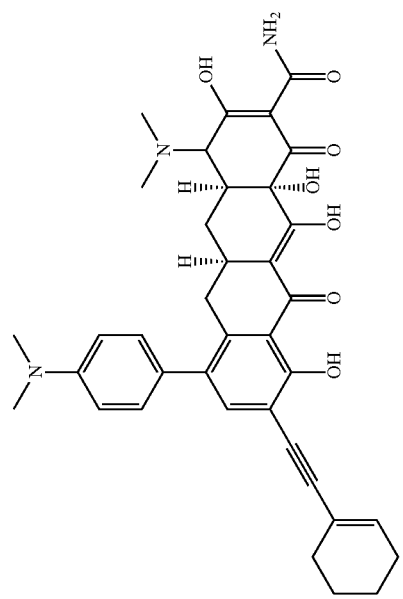 |

TABLE 2-continued
| QP | QQ | QR |
|---|---|---|
| 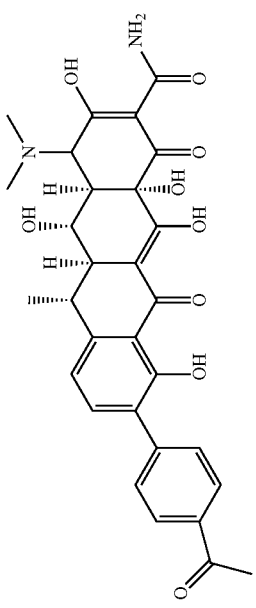 | 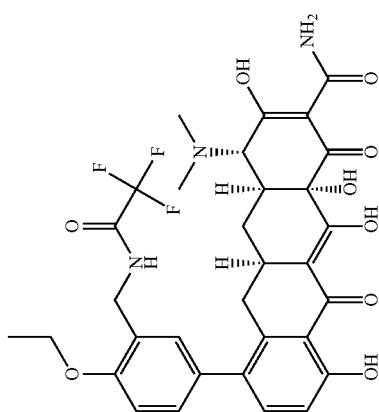 | 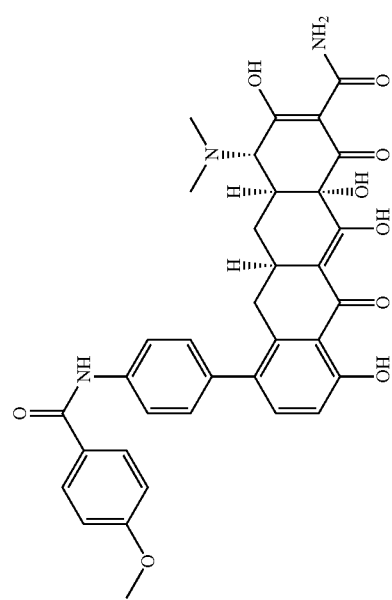 |

TABLE 2-continued
QS 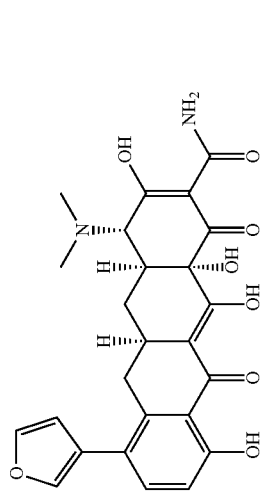
QT 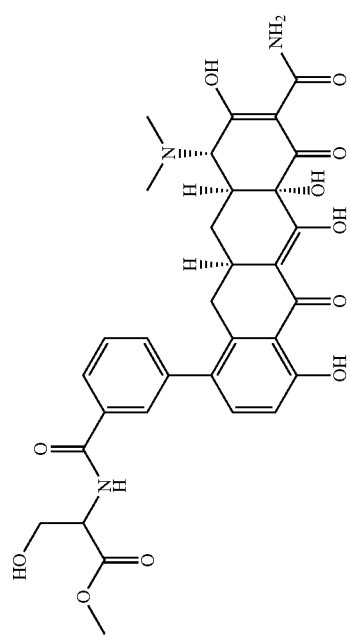
QU 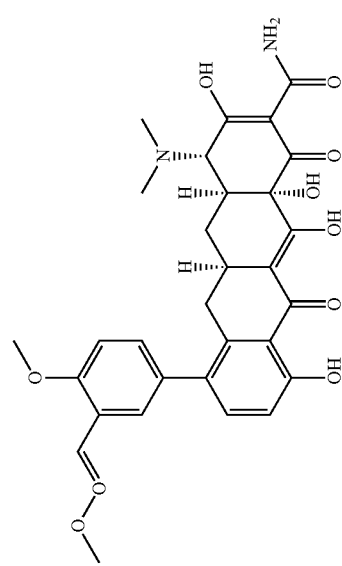

TABLE 2-continued
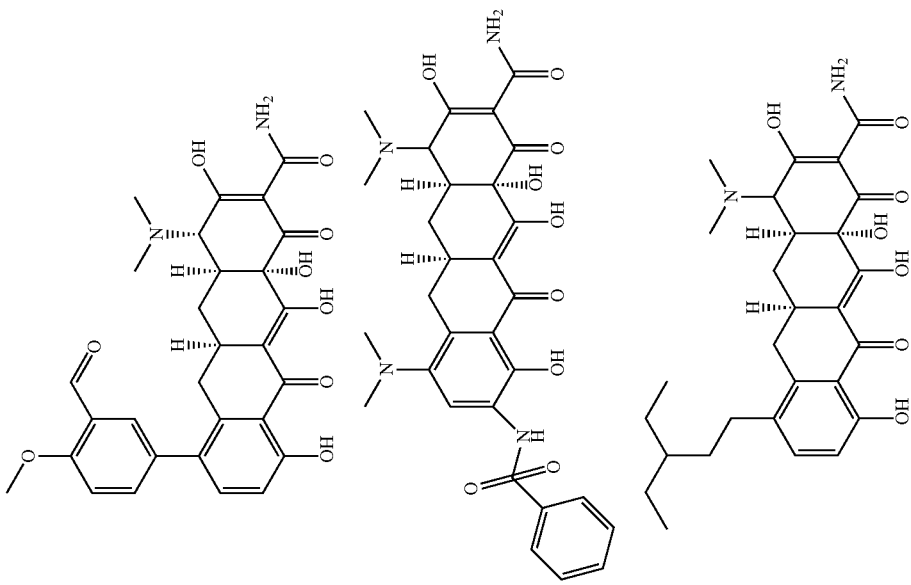
QV
QW
QX

TABLE 2-continued
| QY | QZ | RA |
|---|---|---|
| 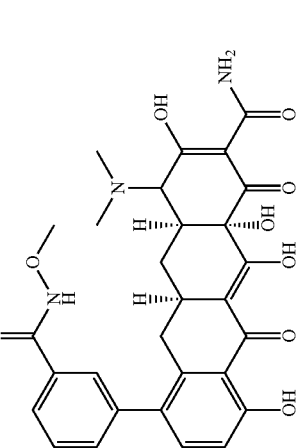 | 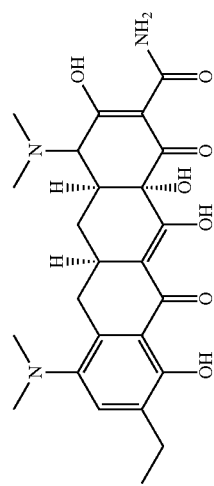 | 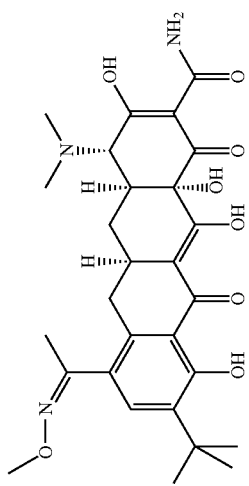 |

TABLE 2-continued
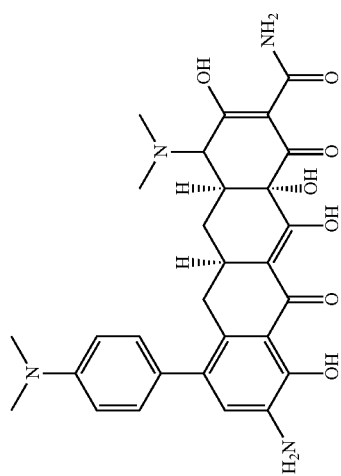
RB
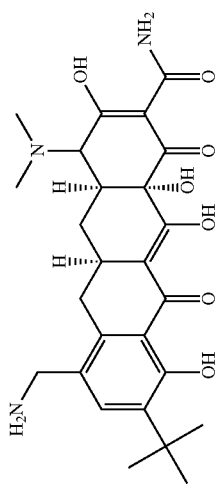
RC
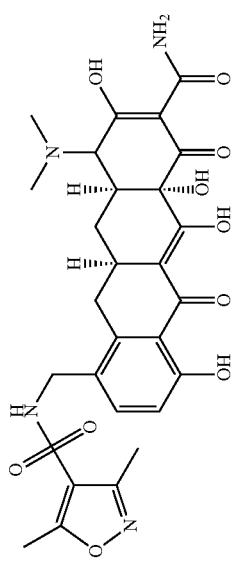
RD

TABLE 2-continued
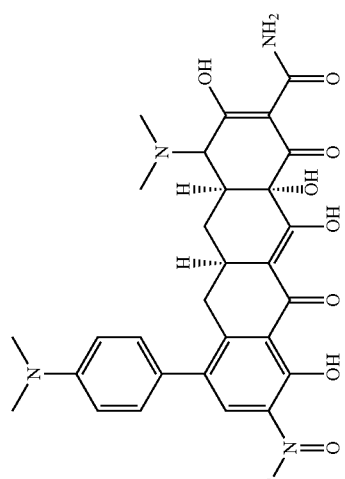
RE
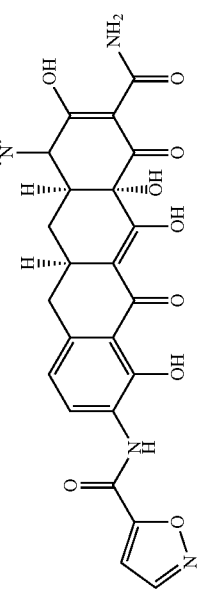
RF
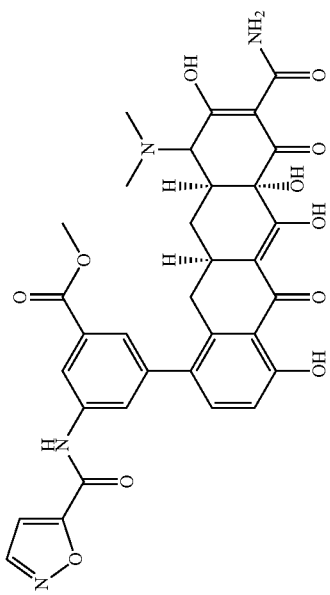
RG

TABLE 2-continued
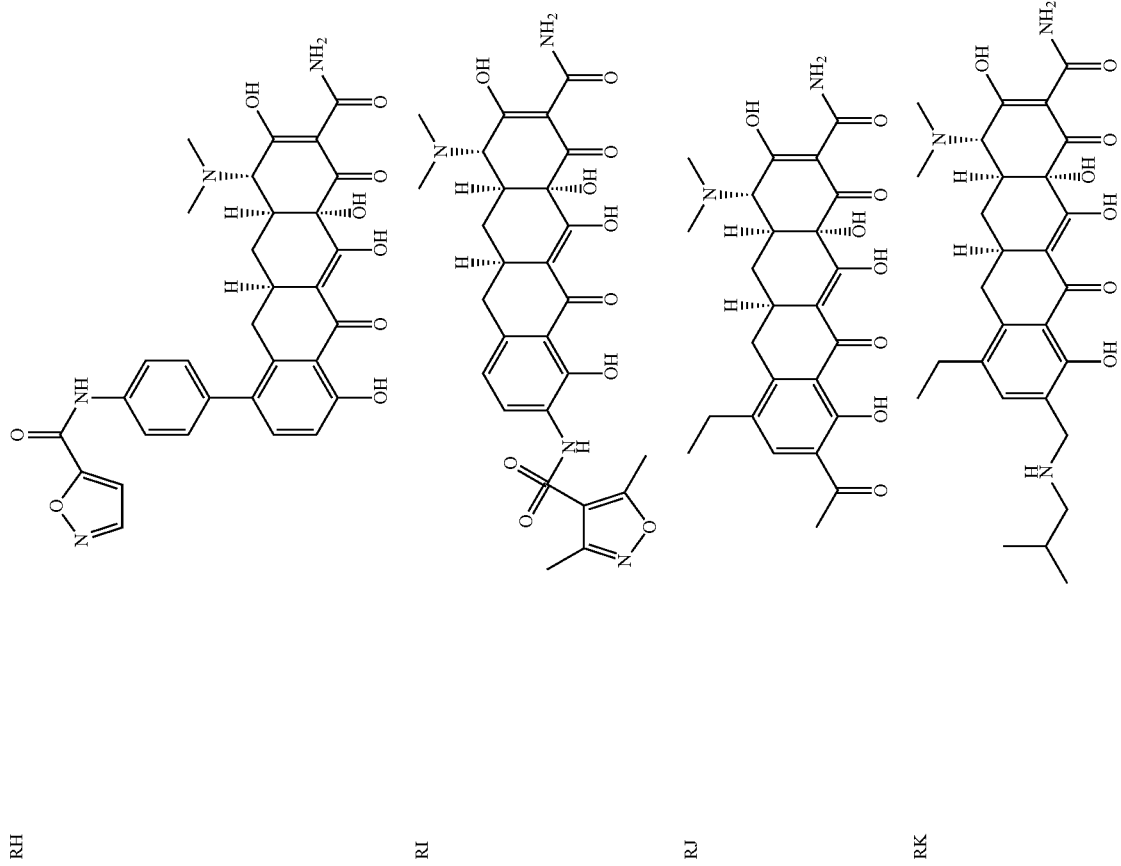
RH
RJ
RJ
RK

TABLE 2-continued
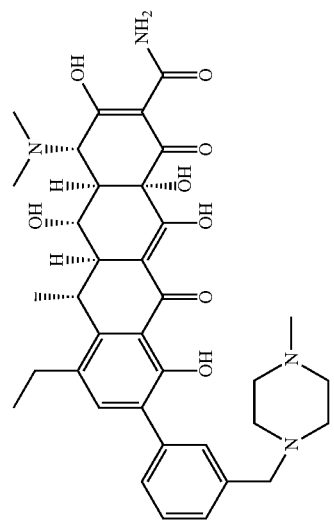
RL
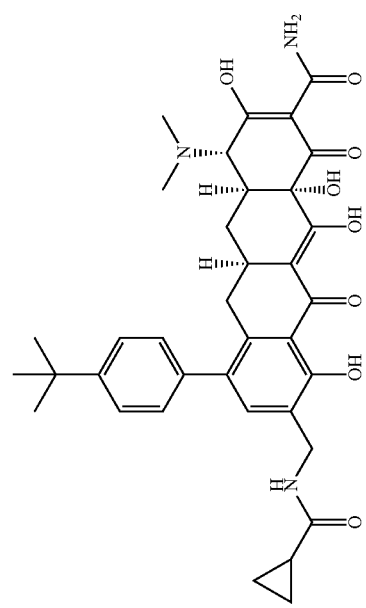
RM
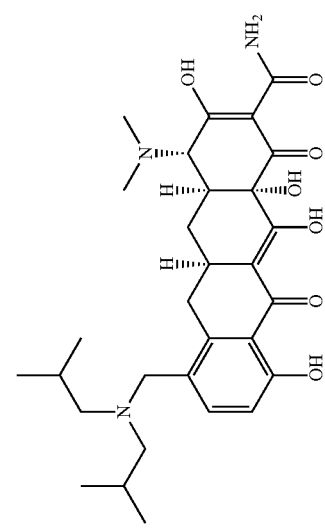
RN

TABLE 2-continued
| | | | |
|---|---|---|---|
| 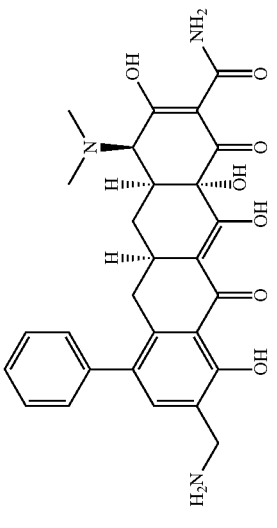 | 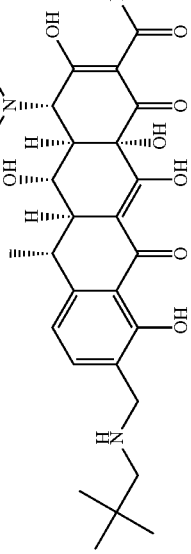 | 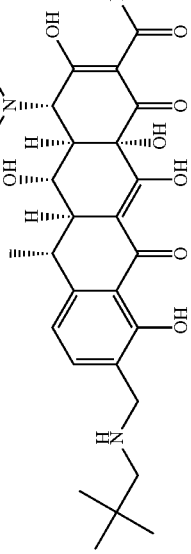 | 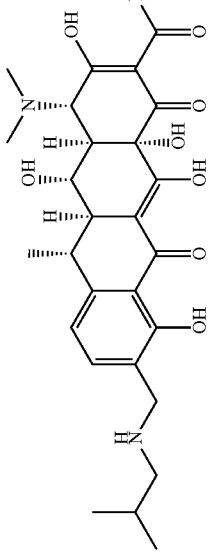 |
| RO | RP | RQ | RR |

TABLE 2-continued
| RS | RT |
|---|---|
| 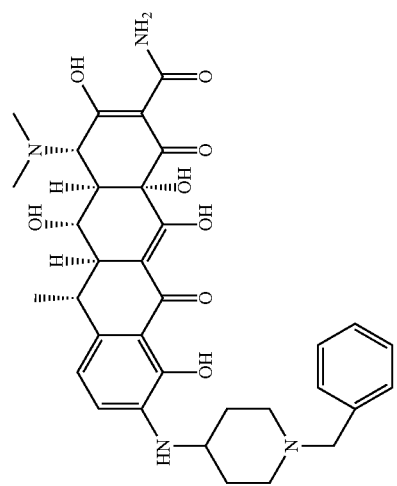 | 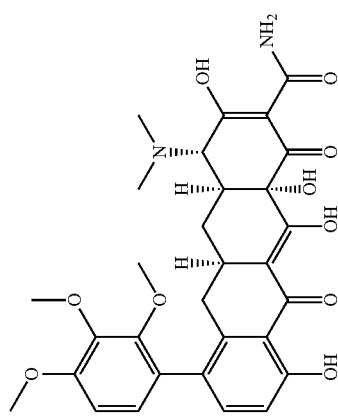 ** |

TABLE 2-continued
| | |
|---|---|
| RU | 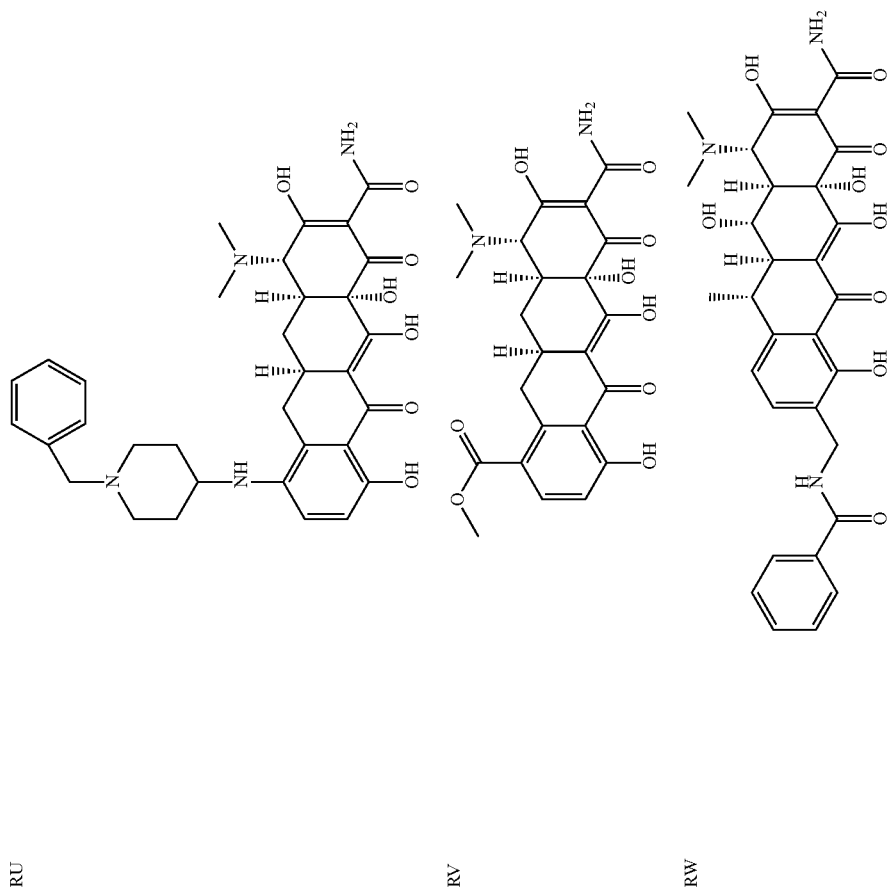 |
| RV | |
| RW | |

TABLE 2-continued
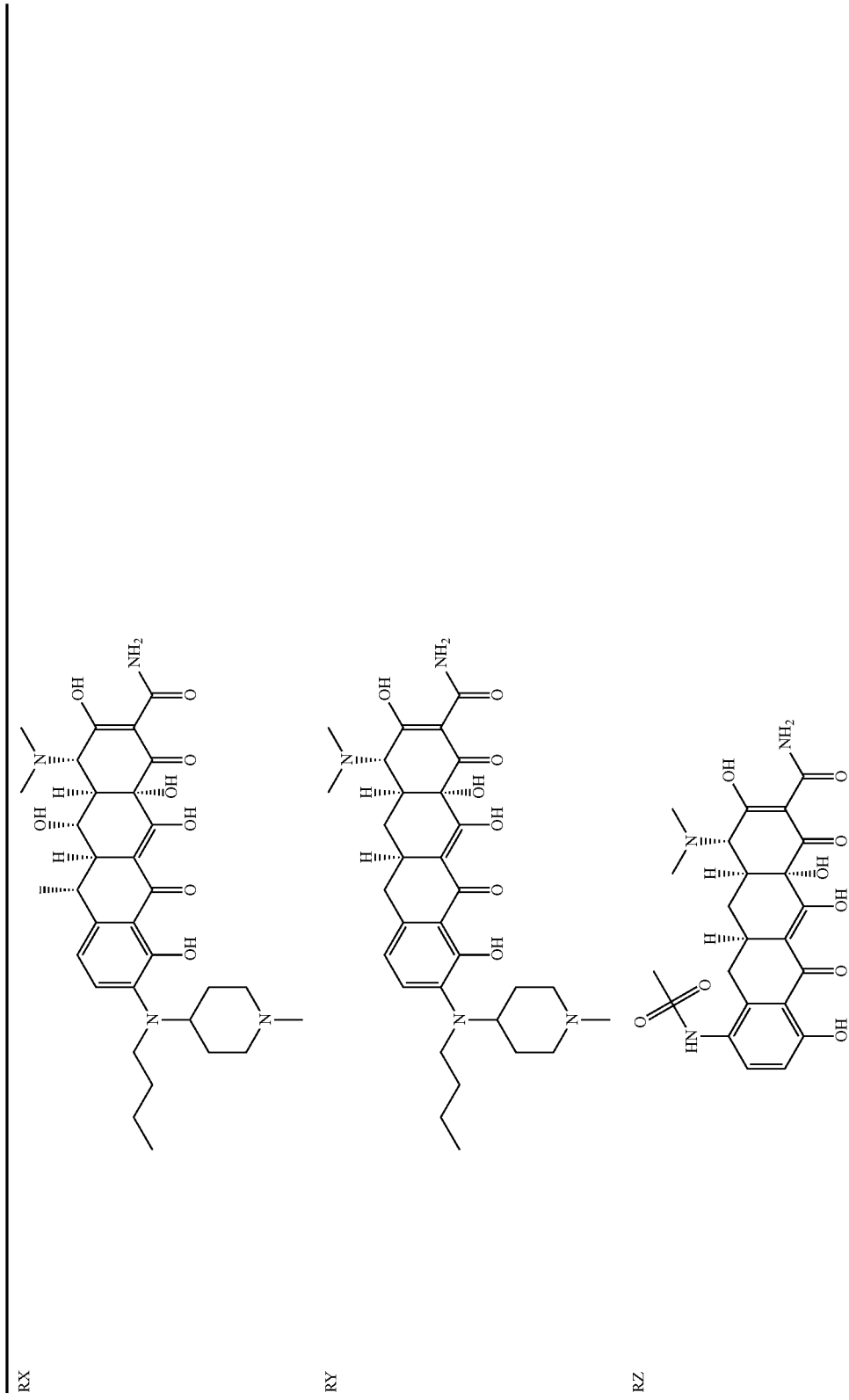
RX
RY
RZ

TABLE 2-continued
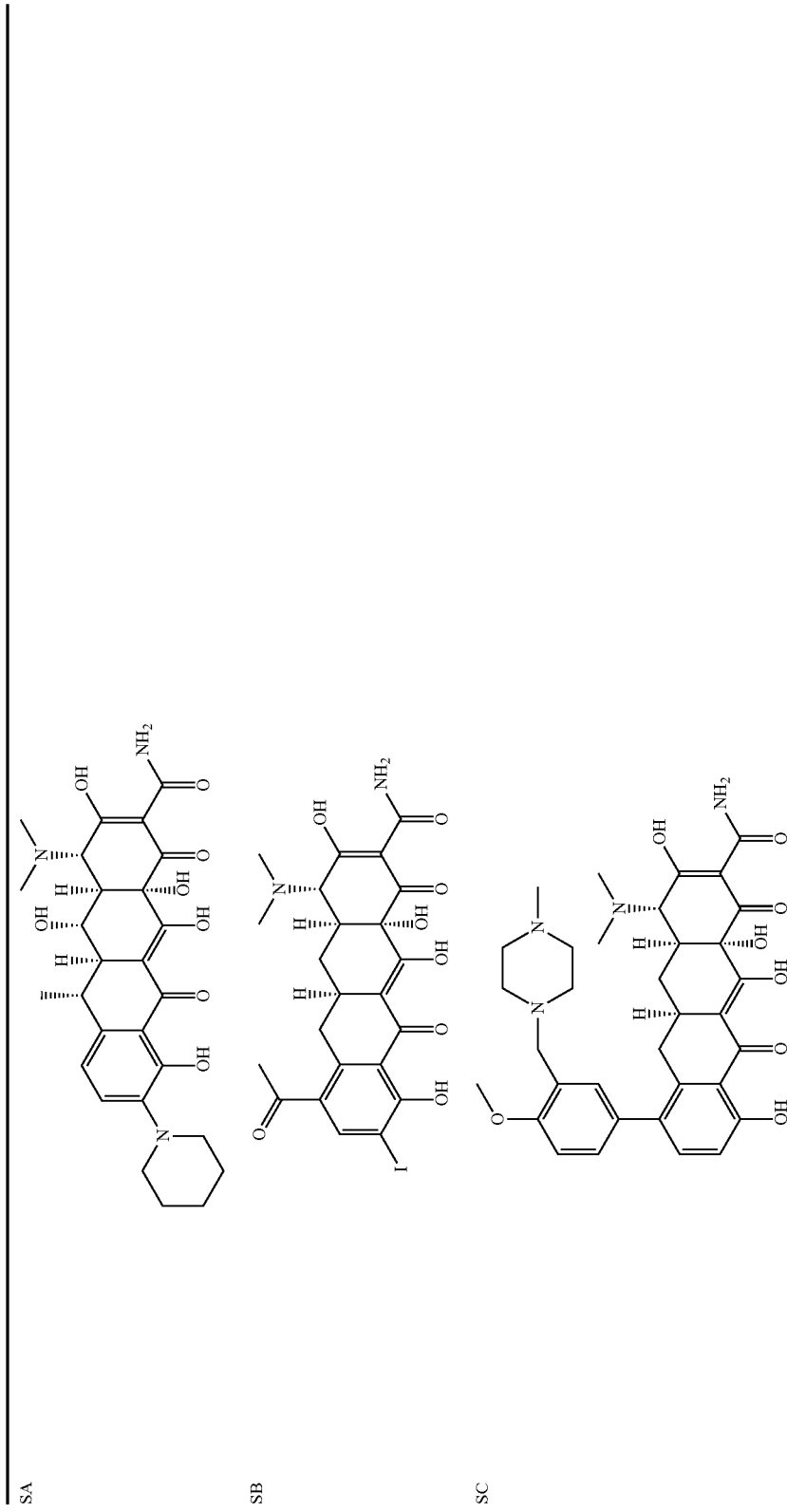
SA
SB
SC

TABLE 2-continued
| | |
|---|---|
| SD | 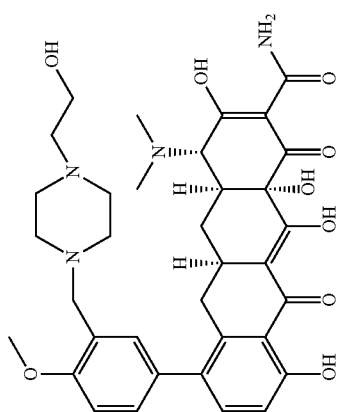 |
| SE | 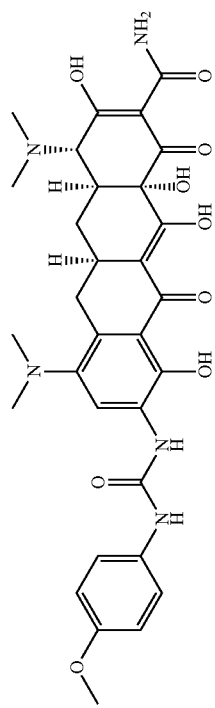 |
| SF | 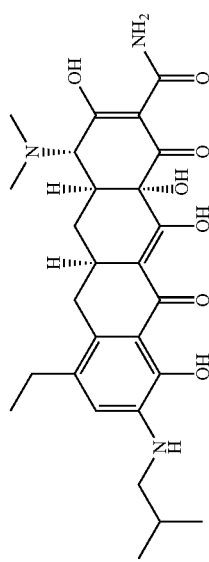 |

TABLE 2-continued
| SG | SH | SI |
|---|---|---|
| 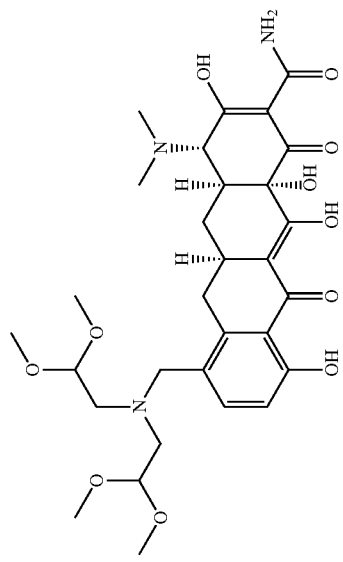 | 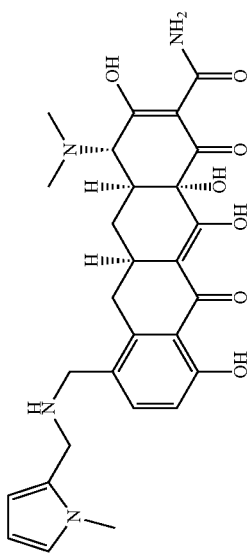 | 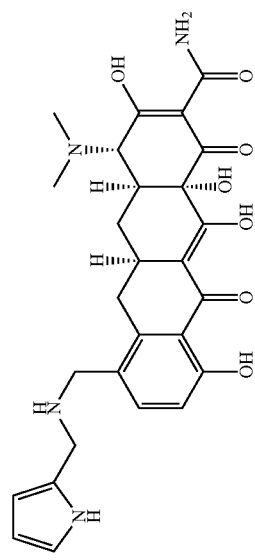 |

TABLE 2-continued
| | |
|---|---|
| SJ | 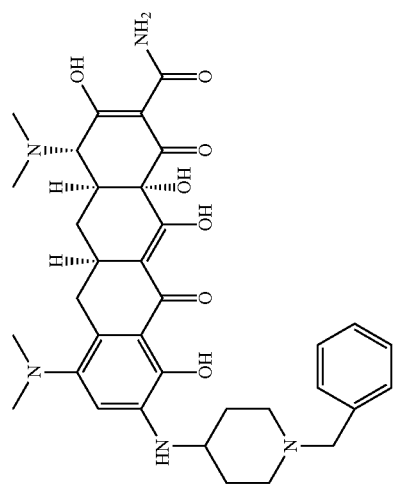 |
| SK | 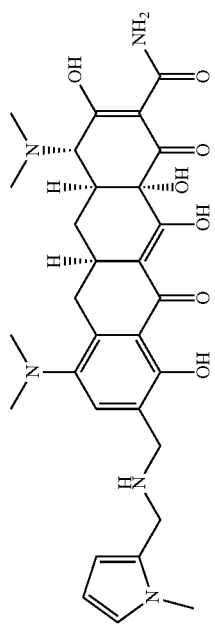 |
| SL | 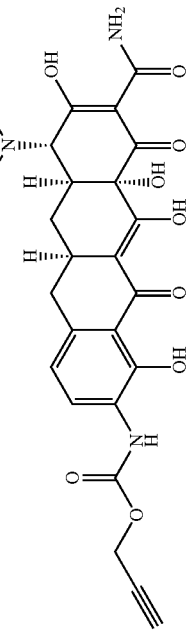 |

TABLE 2-continued

| | |
|---|---|
| SM | [structure of tetracycline derivative with furan substituent and H₂N group] |
| SN | [structure of tetracycline derivative with thiophene substituent and dimethylamino group] |
| SO | [structure of tetracycline derivative with piperidine substituent] |
| SP | [structure of tetracycline derivative with (4,5-dimethylfuran-2-yl)methylaminomethyl substituent and dimethylamino group] |

TABLE 2-continued
| SQ | 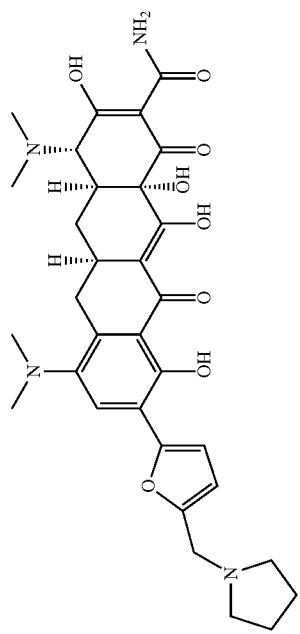 |
| SR | 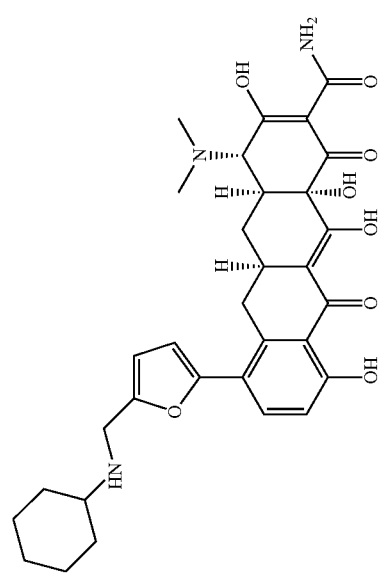 |

TABLE 2-continued
SS 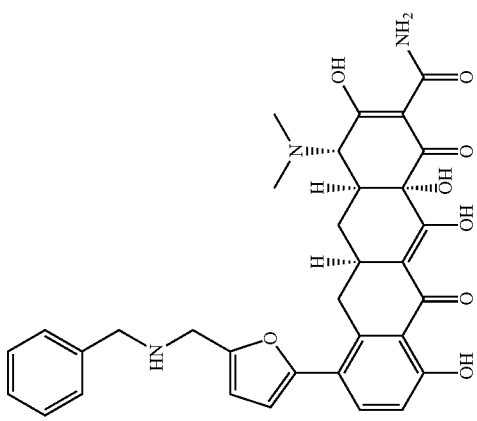
ST 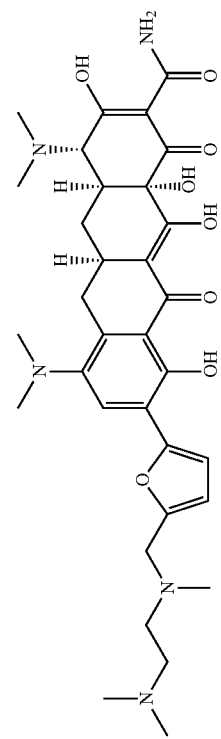
SU 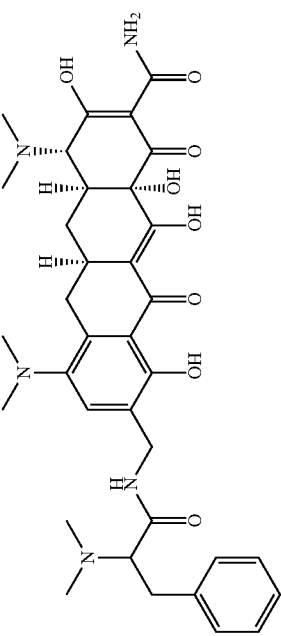

TABLE 2-continued
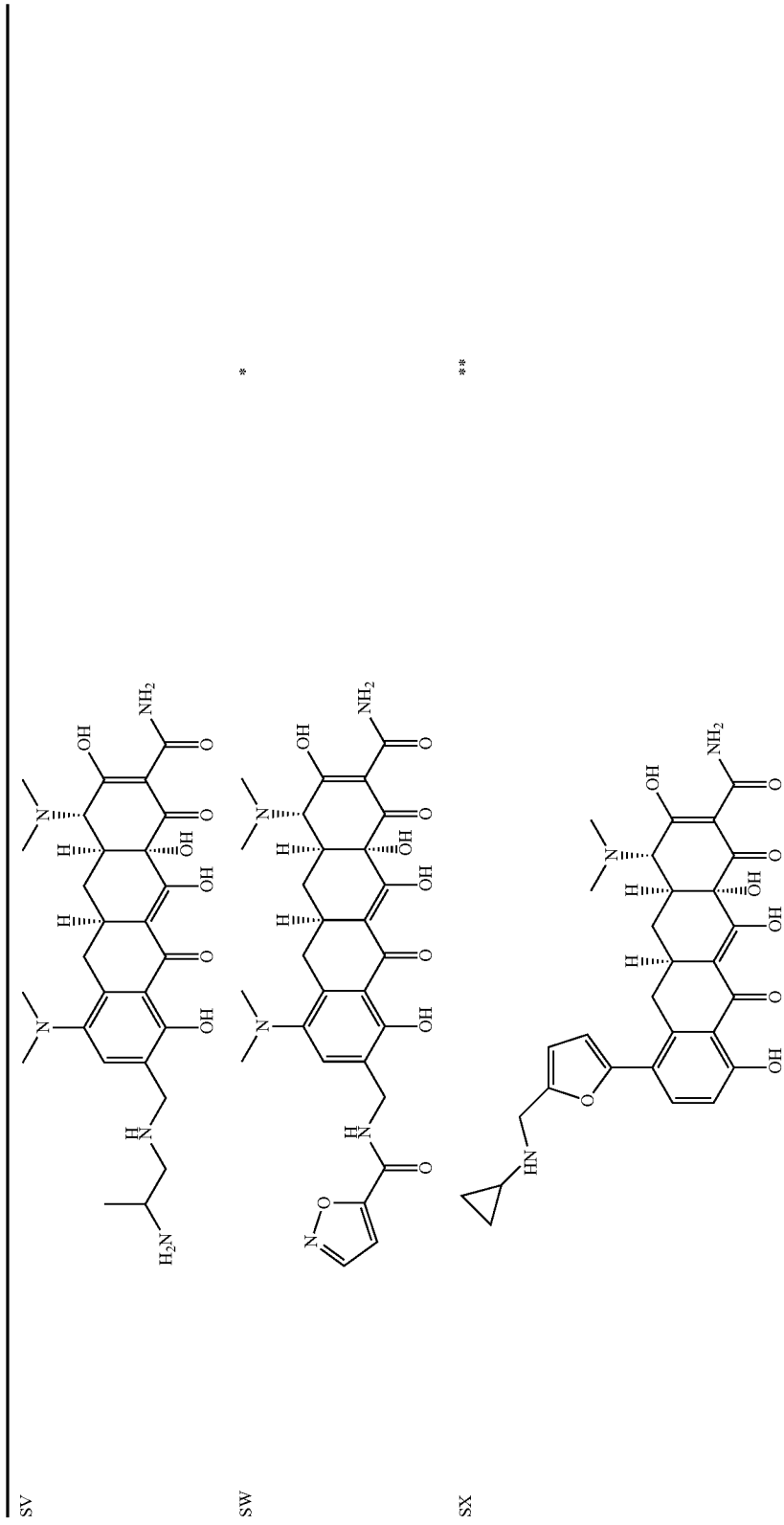

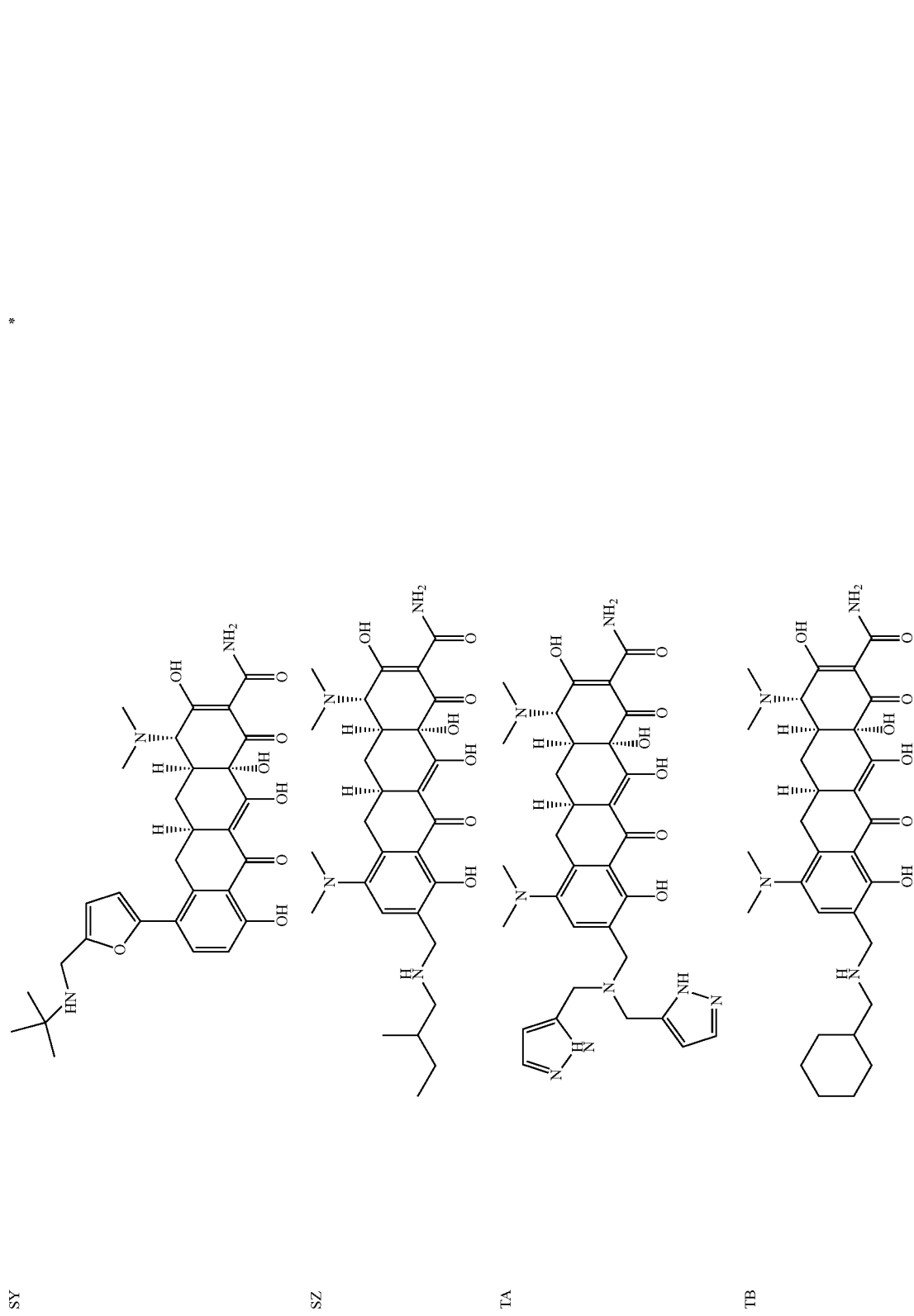

TABLE 2-continued

TC

TD

TE

TF

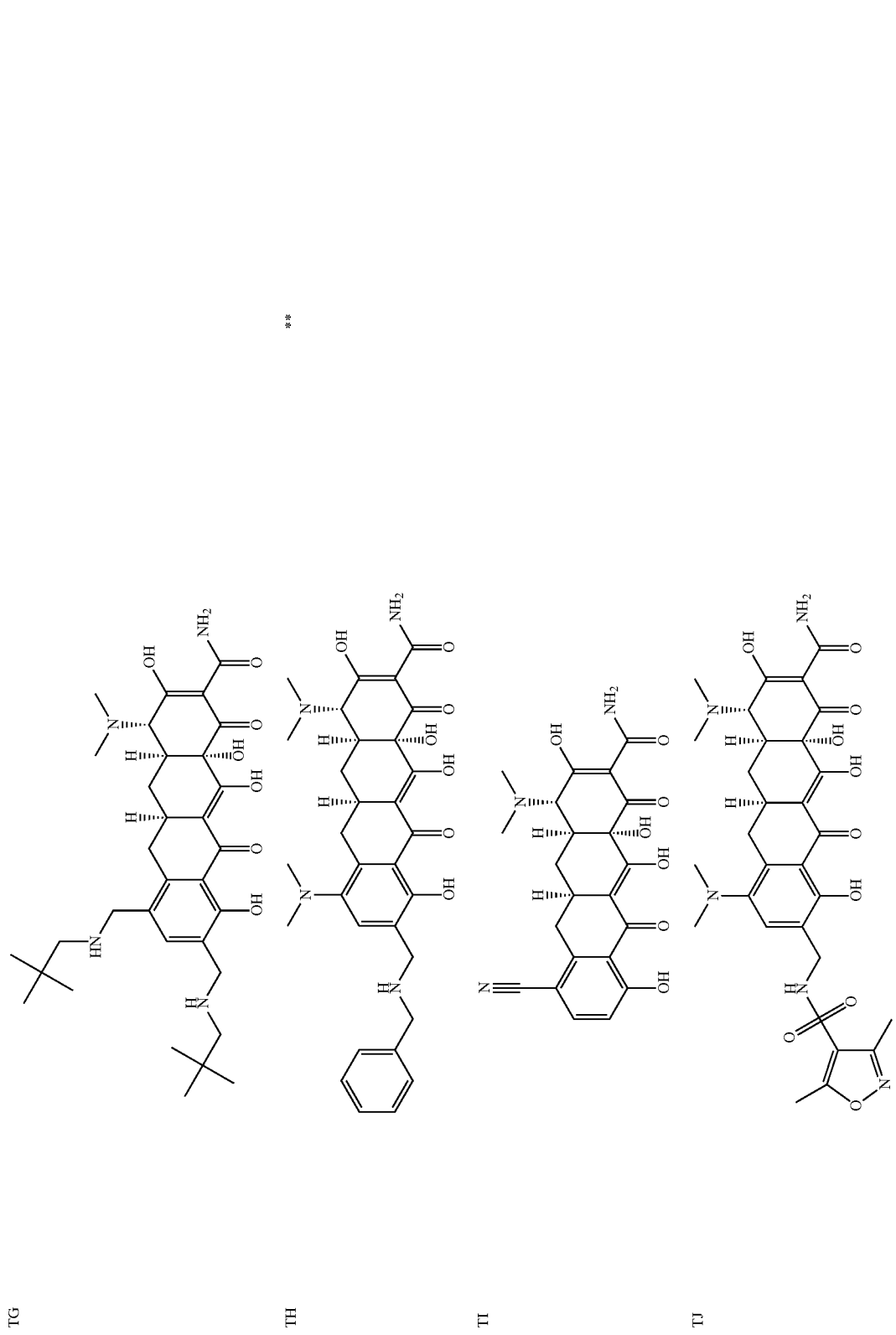

TABLE 2-continued
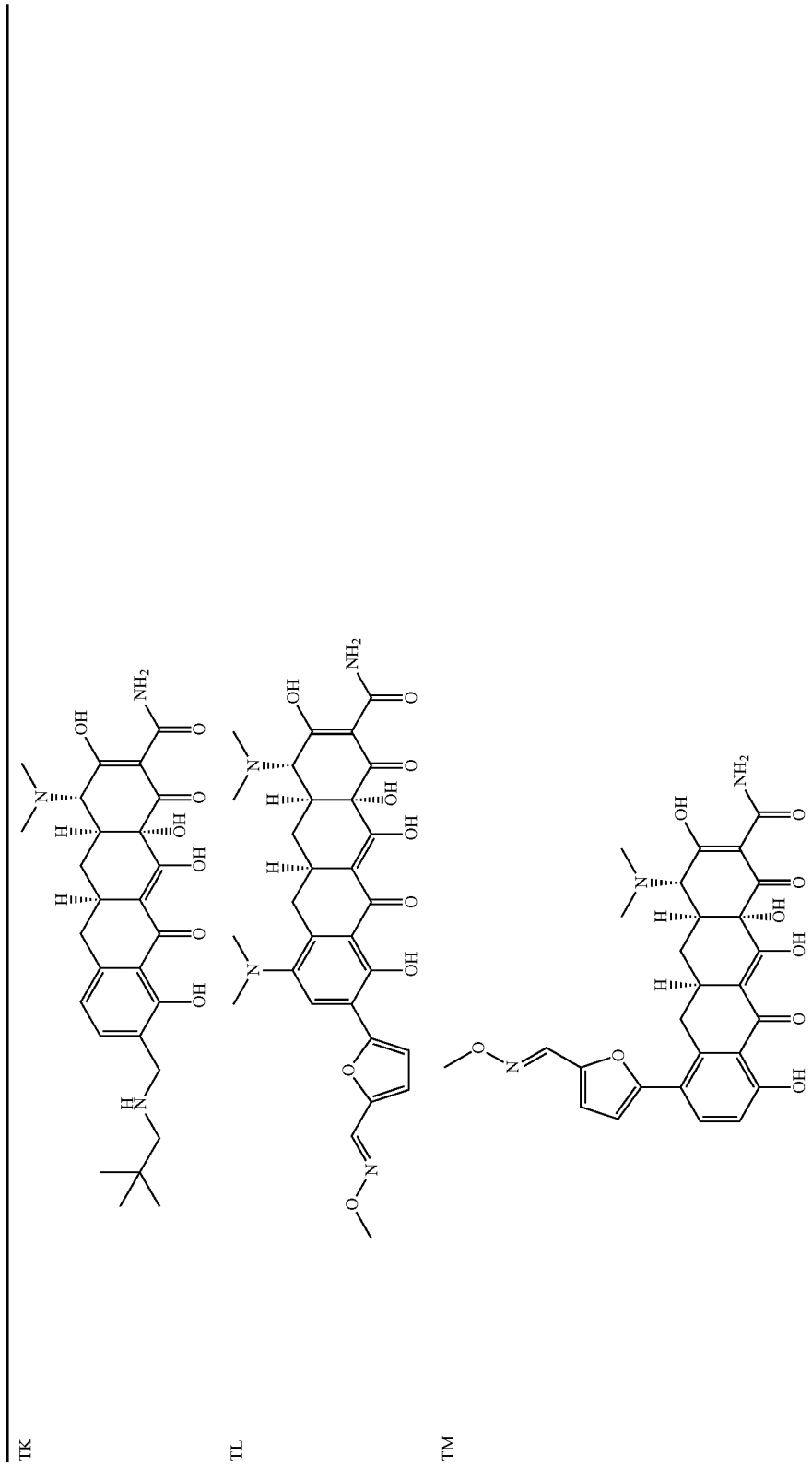
TK
TL
TM

TABLE 2-continued
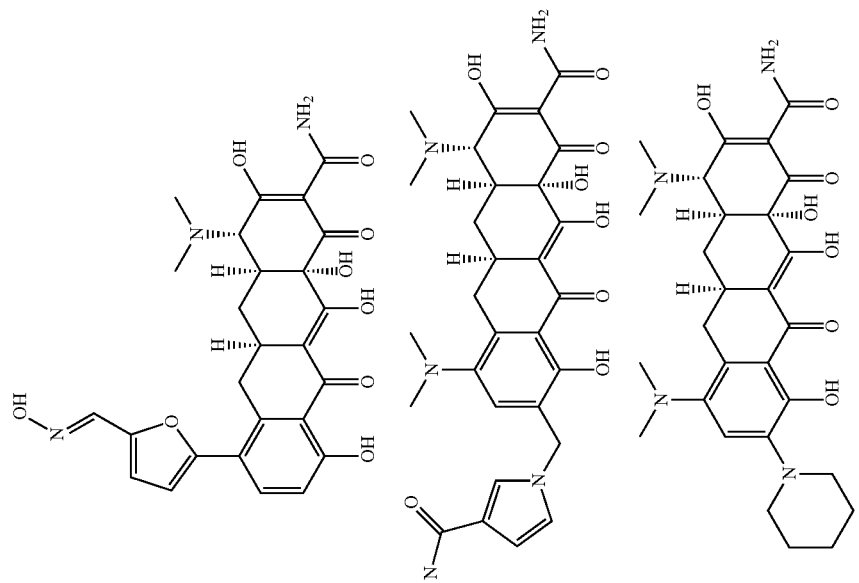
TN
TO
TP

TABLE 2-continued
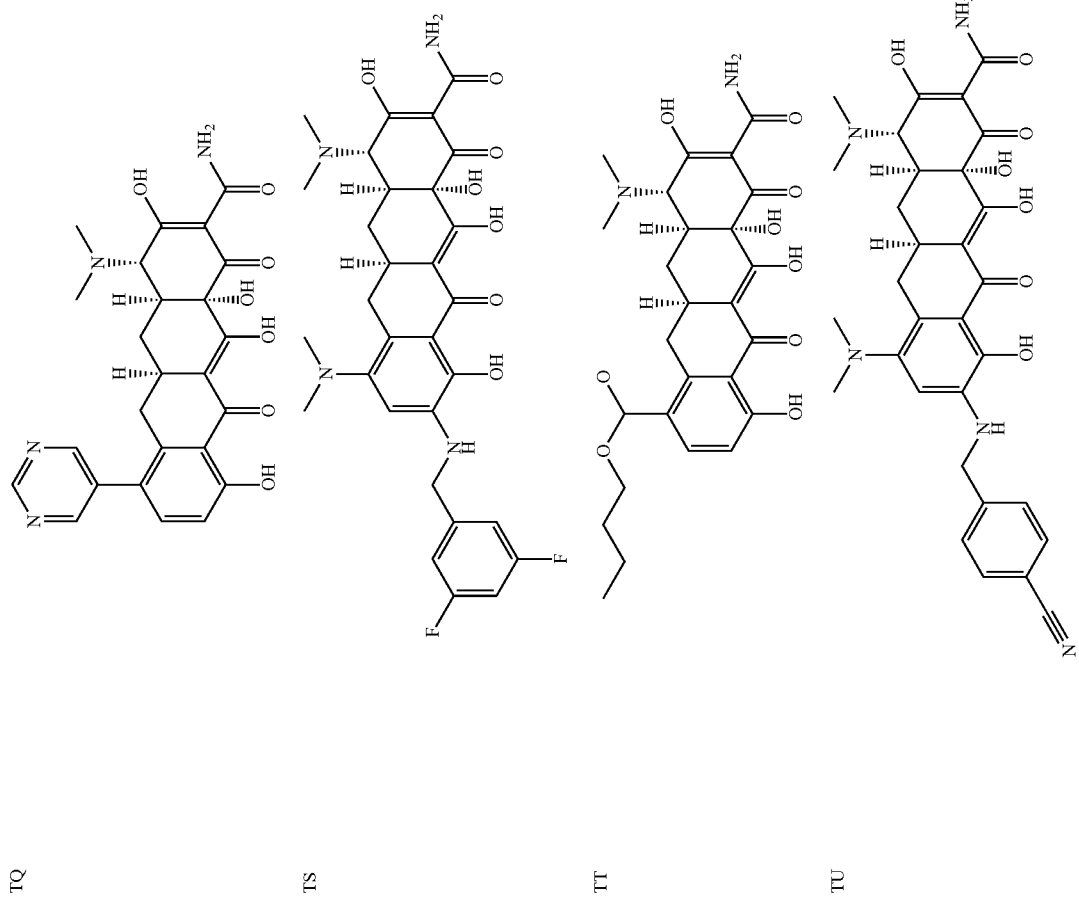
TQ
TS
TT
TU

TABLE 2-continued
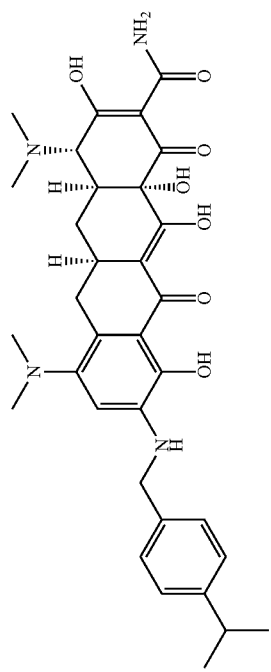
TV
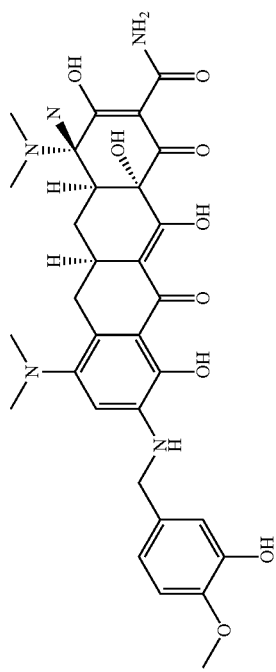
TW
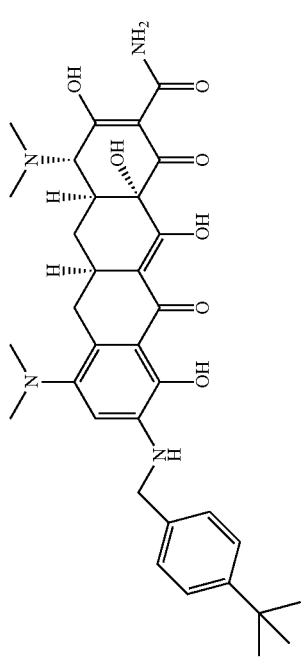
TX

TABLE 2-continued
| TY | TZ | UC | UD |
|---|---|---|---|
| 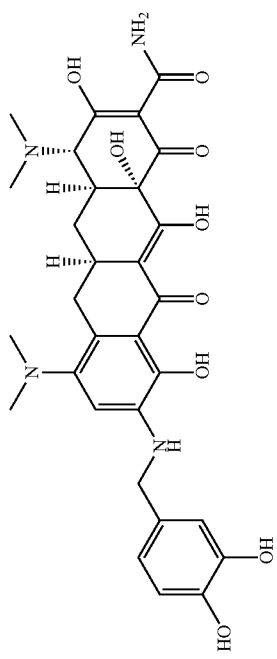 | 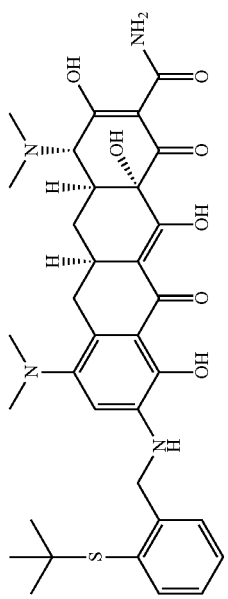 | 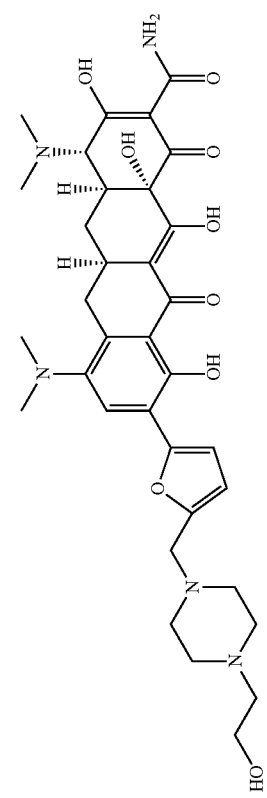 | 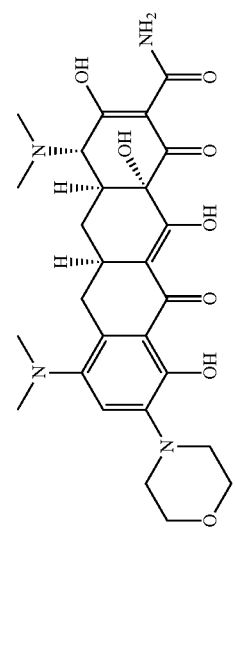 |

TABLE 2-continued
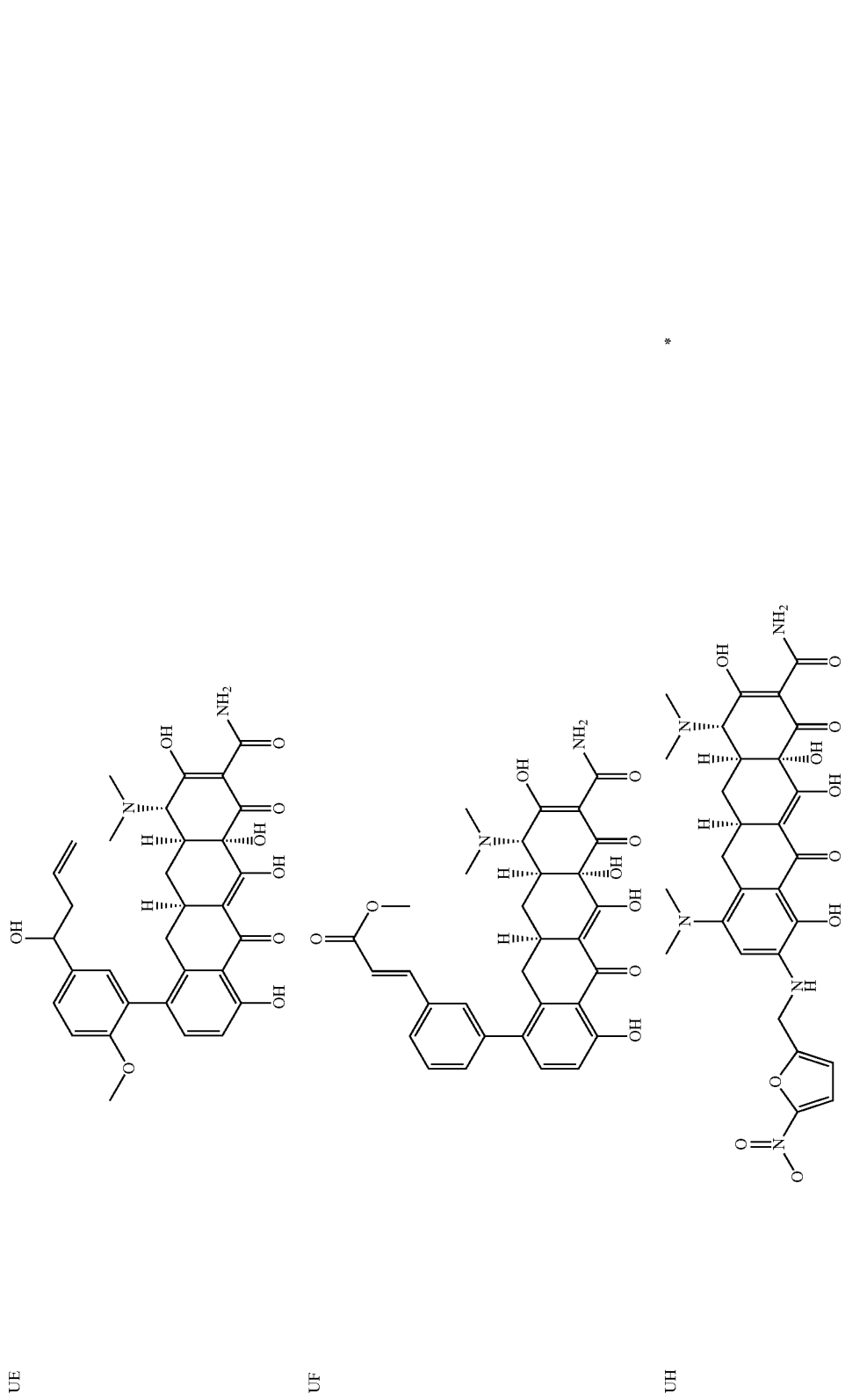
UE
UF
UH

TABLE 2-continued
| UI | *** | 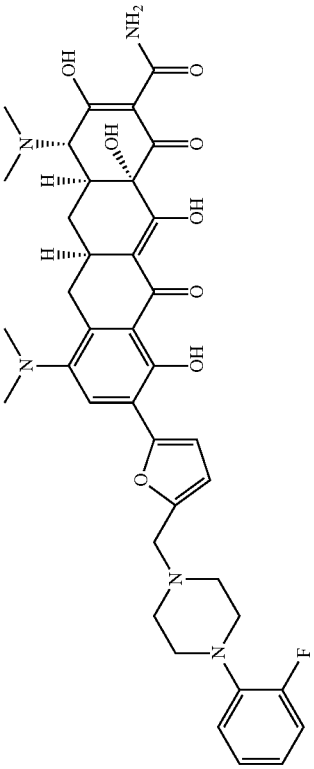 |
| UJ | ** | 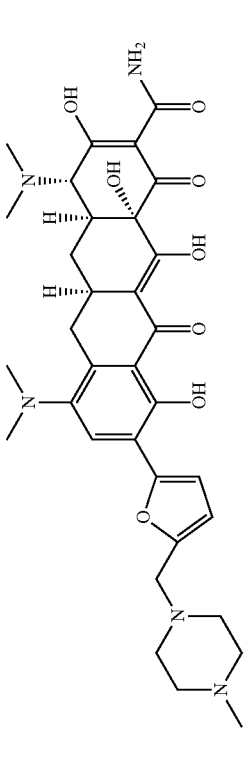 |
| UK | *** | 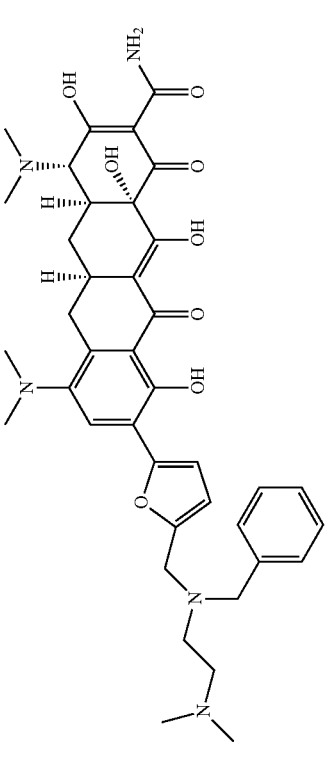 |

TABLE 2-continued
UL 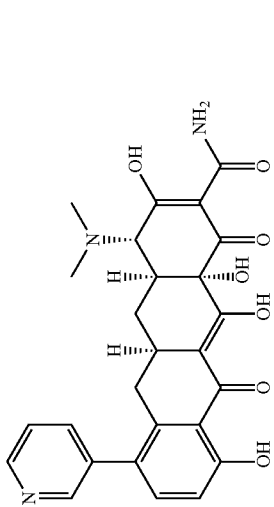
UM 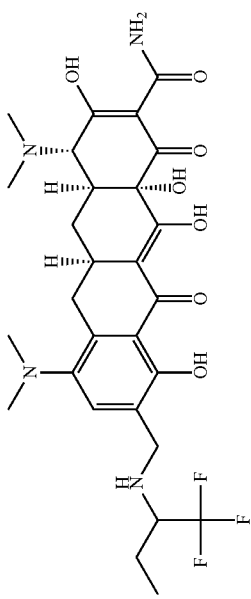
UN 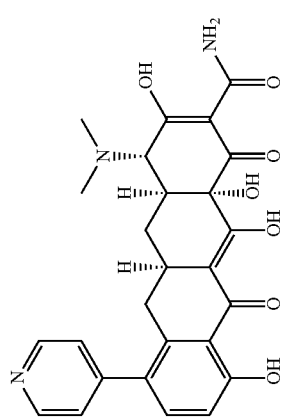

TABLE 2-continued
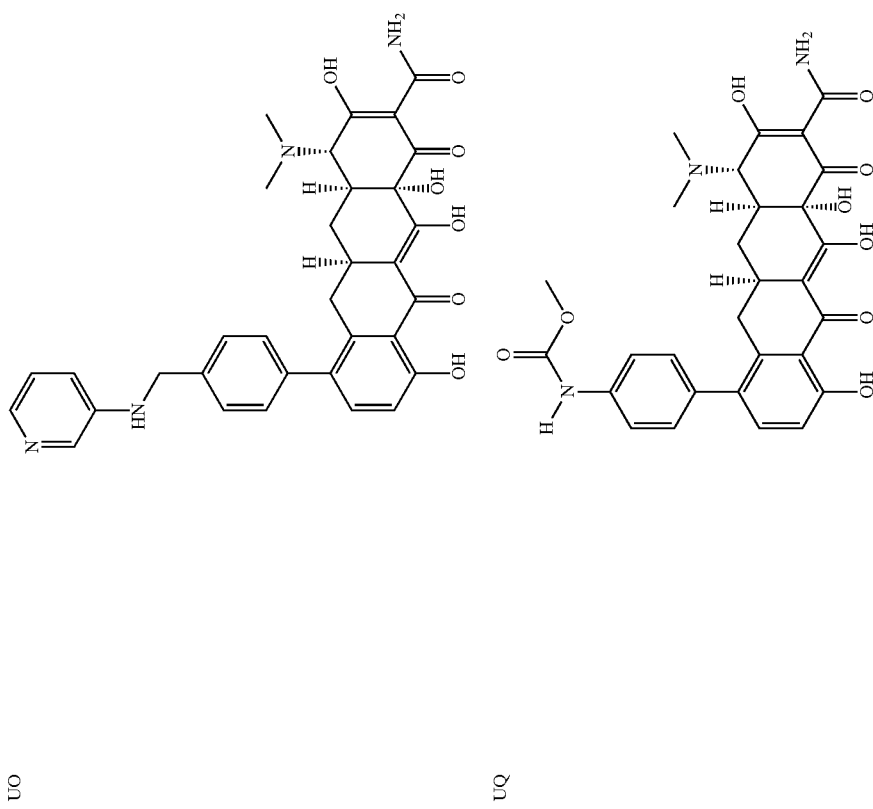

TABLE 2-continued
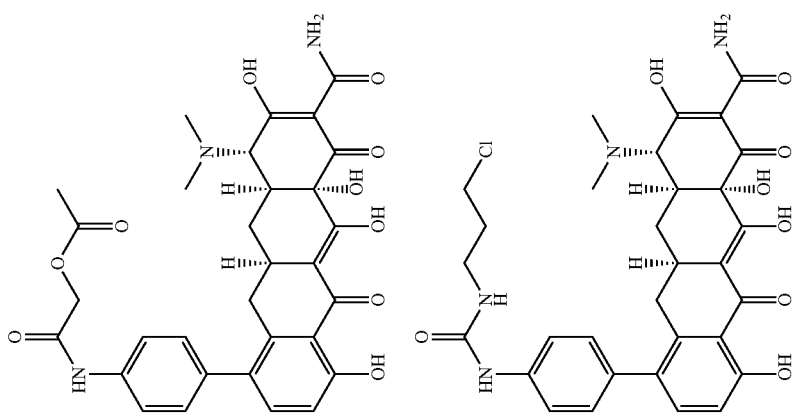

TABLE 2-continued
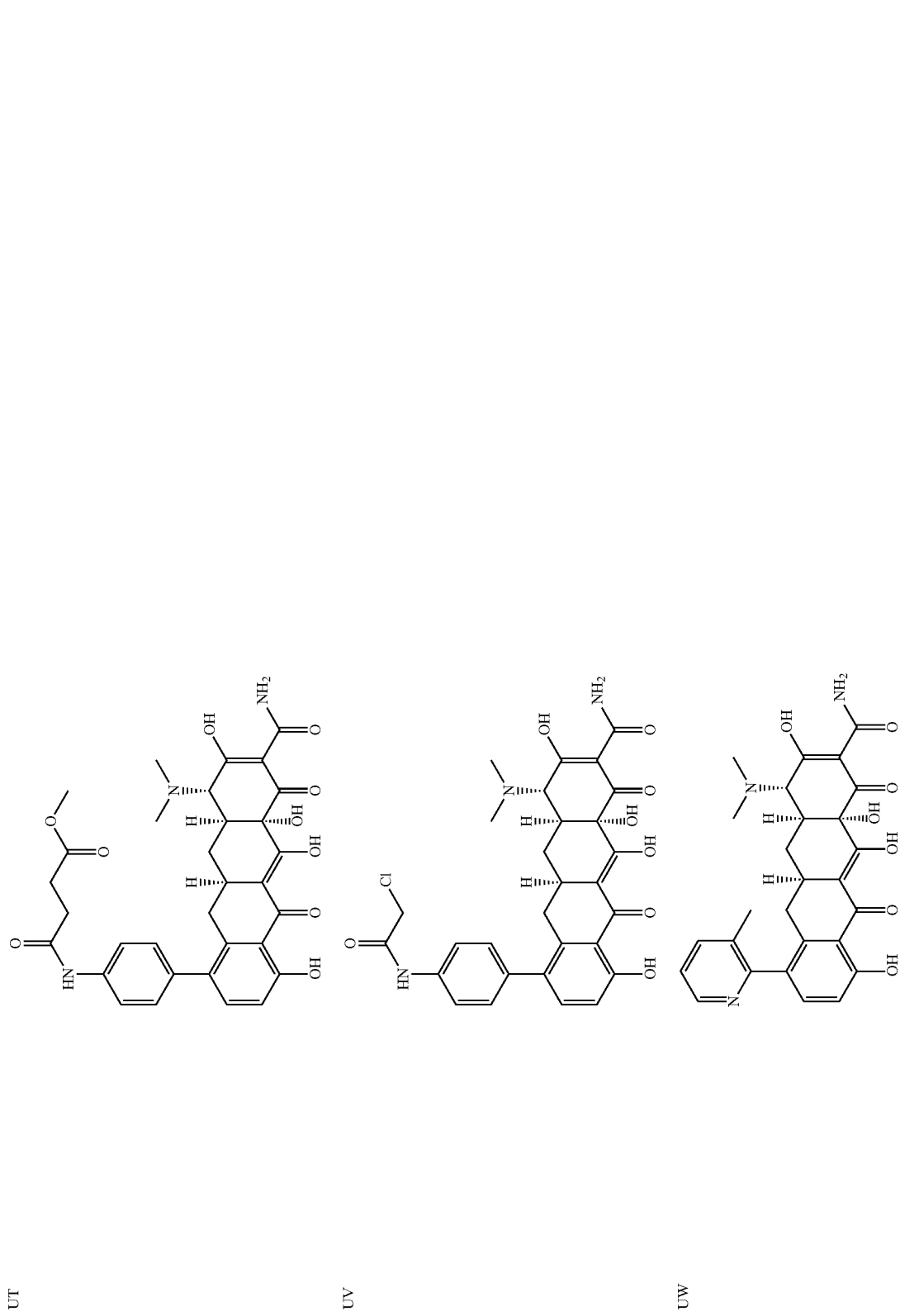
UT
UV
UW

TABLE 2-continued
| | |
|---|---|
| UX | 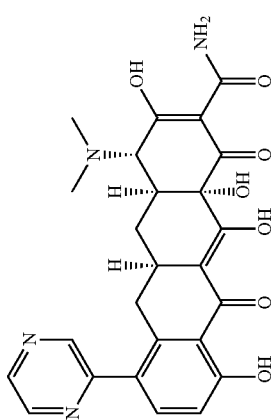 |
| UY | 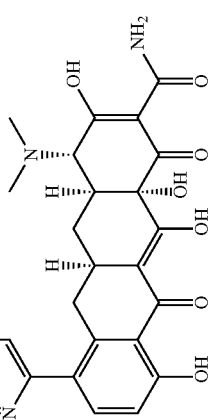 |
| UZ | 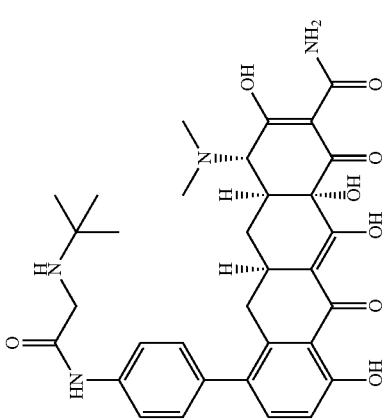 |

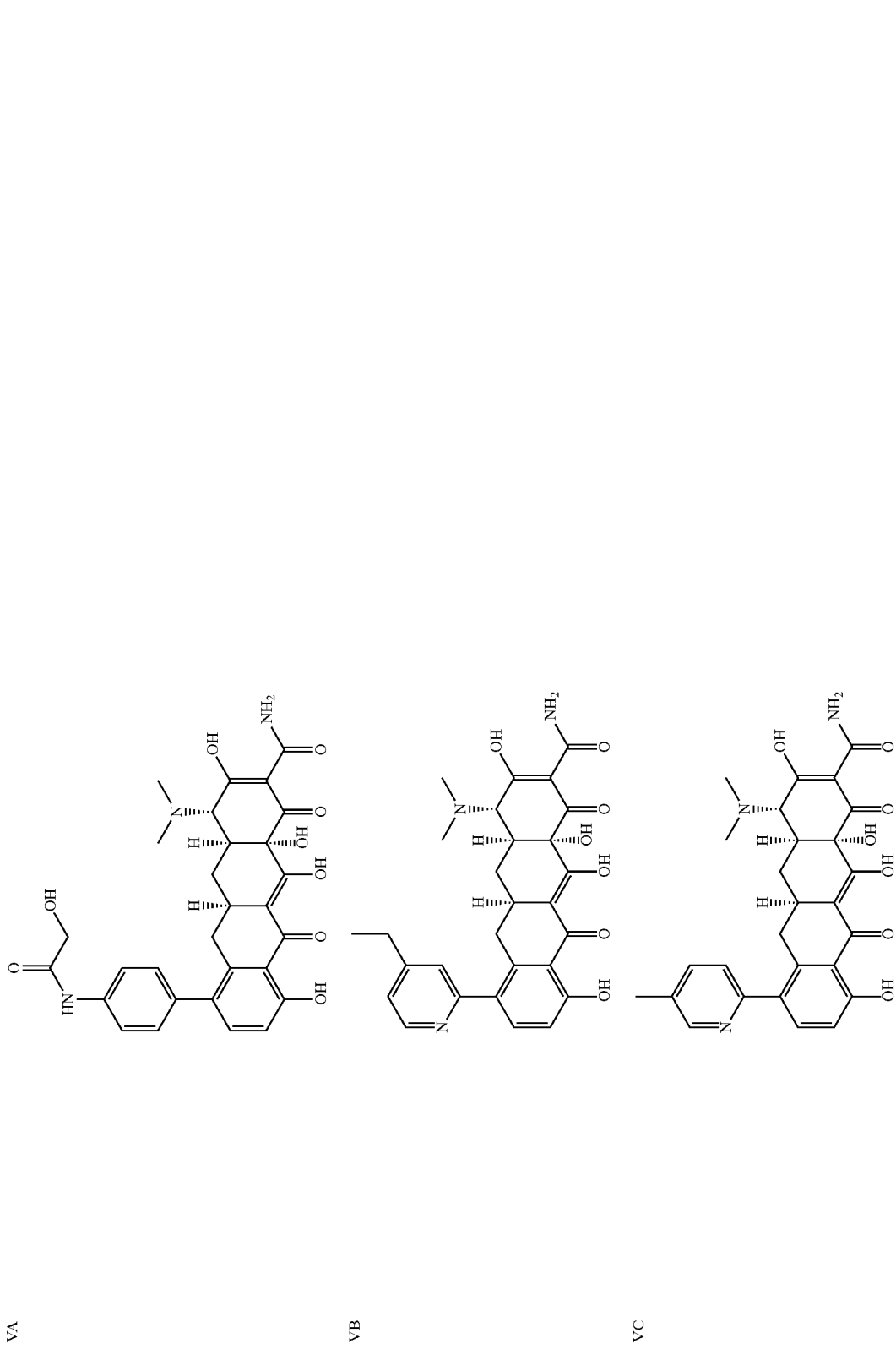

TABLE 2-continued
| | | |
|---|---|---|
| 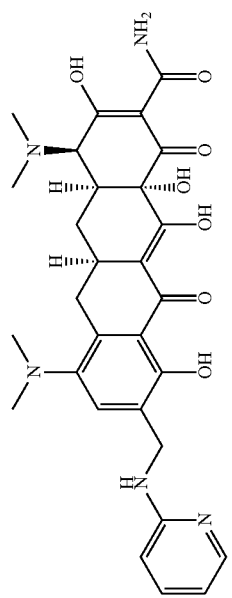 | 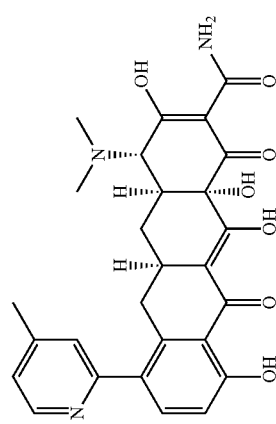 | 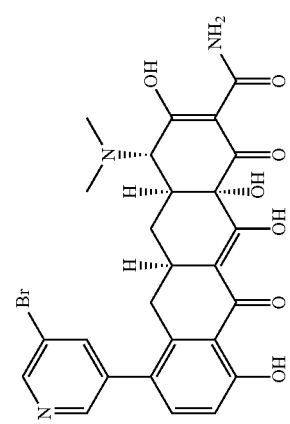 |
| VD | VE | VF |

TABLE 2-continued
| VG | VH | VJ |
|---|---|---|
| 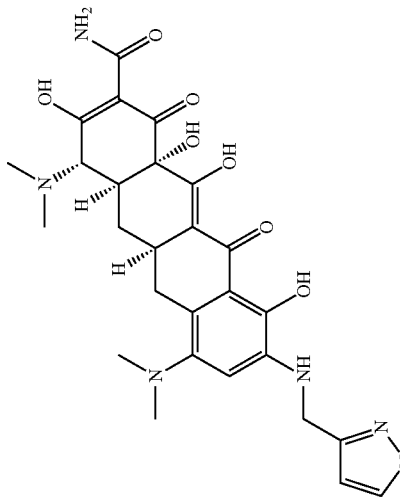 | 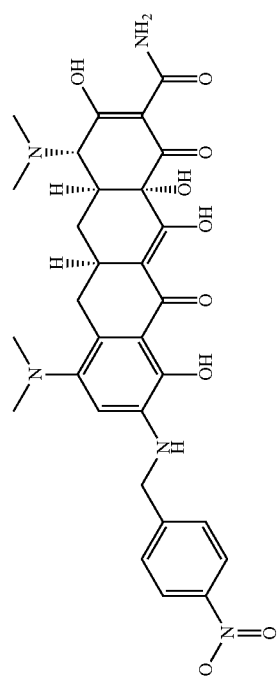 | 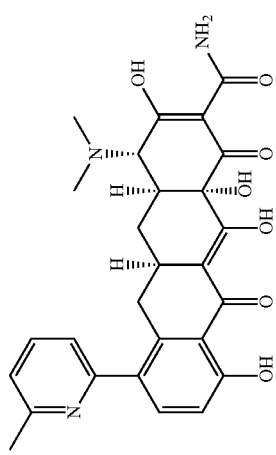 |

TABLE 2-continued
VK
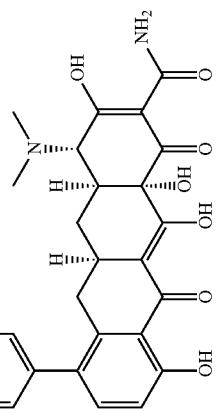
| ID | Candida albicans | Candida glabrata | Candida guilliermondii | Candida krusei | Candida lusitaniae | Candida parapsilosis | Candida tropicalis | Cryptococcus neoformans | Issatchenkia orientalis | Saccharomyces cerevisiae | In Vitro Cytotoxicity |
|---|---|---|---|---|---|---|---|---|---|---|---|
| A | *** | | | | | | | | | | ** |
| B | *** | | | | | | | | | | *** |
| C | ** | | | | | | | | | | *** |
| D | *** | | | | | | | | | | *** |
| E | ** | | | | | | | | | | *** |
| F | ** | | | | | | | | | | *** |
| G | * | | | | | | | | | | *** |
| H | *** | | | | | | | | | | *** |
| I | ** | | | | | | | | | | *** |
| J | *** | | | | | | | | | | *** |
| K | *** | | | | | | | | | | *** |
| L | * | | | | | | | | | | *** |
| M | ** | | | | | | | | | | *** |
| N | ** | | | | | | | | | | *** |
| O | *** | | | | | | | | | | *** |
| P | *** | | | | | | | | | | *** |
| Q | * | | | | | | | | | | *** |
| R | *** | | | | | | | | | | *** |
| S | *** | | | | | | | | | | *** |
| T | ** | | | | | | | | | | *** |
| U | ** | | | | | | | | | | *** |
| V | ** | | | | | | | | | | *** |
| W | *** | | | | | | | | | | *** |
| X | *** | | | | | | | | | | *** |
| Y | *** | | | | | | | | | | * |
| Z | ** | ** | | | | | | | | | *** |
| AA | * | | | | | | | | | | *** |
| AB | *** | | | | | | | | | | *** |
| AC | *** | | | | | | | | | | ** |
| AD | *** | | | | | | | | | | |

TABLE 2-continued

| | |
|---|---|
| AE | * |
| AF | ** |
| AG | *** |
| AH | ** |
| AI | *** |
| AJ | ** |
| AK | *** |
| AL | *** |
| AM | *** |
| AN | *** |
| AO | *** |
| AP | *** |
| AQ | *** |
| AR | *** |
| AS | ** |
| AT | *** |
| AU | *** |
| AV | * |
| AW | ** |
| AX | *** |
| AY | *** |
| AZ | *** |
| BA | *** |
| BB | *** |
| BC | *** |
| BD | *** |
| BE | *** |
| BF | ** |
| BG | *** |
| BH | *** |
| BI | *** |
| BJ | *** |
| BK | *** |
| BL | *** |
| BM | *** |
| BN | *** |
| BO | *** |
| BP | *** |
| BQ | *** |
| BR | *** |
| BS | * |
| BT | *** |
| BU | *** |
| BV | ** |
| BW | *** |
| BX | *** |
| BY | *** |
| BZ | * |
| CA | *** |
| CB | ** |
| CD | ** |
| CE | * |

TABLE 2-continued

| | | | | | | |
|---|---|---|---|---|---|---|
| CF | * | | | | | *** |
| CG | **** | | | | | *** |
| CH | *** | | | | | *** |
| CI | *** | | | | | *** |
| CJ | *** | | | | | * |
| CK | *** | | | | | *** |
| CL | *** | | | | | *** |
| CM | . | | | | | *** |
| CN | *** | | | | | *** |
| CO | *** | | | | | *** |
| CQ | *** | | | | | *** |
| CR | *** | | | | | *** |
| CS | *** | | | | | *** |
| CT | *** | | | | | *** |
| CU | *** | | | | | * |
| CV | *** | | | | | *** |
| CW | *** | | | | | *** |
| CX | *** | | | | | *** |
| CY | *** | | | | | *** |
| CZ | *** | | | | | * |
| DA | *** | | | | | *** |
| DB | *** | *** | | | | *** |
| DC | *** | | | | | *** |
| DD | *** | | | | | *** |
| DE | *** | | | | | *** |
| DF | *** | | | | | *** |
| DG | *** | | | | | *** |
| DH | *** | | | | | *** |
| DI | *** | | | | | *** |
| DK | *** | | | | | *** |
| DL | *** | | | | | *** |
| DM | . | | | | | *** |
| DN | *** | | | | | *** |
| DO | *** | | | | | *** |
| DP | *** | | | | | *** |
| DQ | *** | | | | | *** |
| DR | *** | | | | | *** |
| DS | *** | | | | | *** |
| DT | *** | | | | | *** |
| DU | *** | | | | | *** |
| DV | *** | | | | | *** |
| DW | *** | | | | | *** |
| DX | *** | | | | | *** |
| DY | *** | | | | | *** |
| DZ | *** | | | | | *** |
| EA | *** | | | | | * |
| EB | ** | ** | | | | . |
| EC | *** | *** | *** | *** | *** | *** |
| ED | * | | | | | |
| EF | *** | | | | | *** |
| EG | *** | | | | | *** |
| EH | *** | | | | | *** |

TABLE 2-continued

| | | | | | | | | |
|---|---|---|---|---|---|---|---|---|
| EI | *** | | | | | | | |
| EJ | **** | | | | | | | |
| EK | *** | | | | | | | |
| EL | **** | | | | | | | |
| EM | ** | | | | | | | |
| EN | **** | | | | | | | |
| EO | *** | | | | | | | |
| EP | **** | | | | | | | |
| EQ | *** | | | | | | | |
| ER | **** | | | | | | | |
| ES | *** | | | | | | | |
| ET | **** | | | | | | | |
| EU | ** | | | | | | | |
| EV | **** | | | | | | | |
| EW | ** | | | | | | | |
| EX | **** | | | | | | | |
| EY | ** | | | | | | | |
| EZ | ** | | | | | | | |
| FA | **** | | | | | | | |
| FB | **** | | | | | | | |
| FC | *** | | | | | | | |
| FD | **** | | | | | | | |
| FE | *** *** | | | | | | | |
| FF | **** | | | | | | | |
| FG | *** | | | | | | | |
| FH | **** | | | | | | | |
| FI | ** | | | | | | | |
| FJ | **** | | | | | | | |
| FK | *** | | | | | | | |
| FL | **** | | | | | | | |
| FM | *** | | | | | | | |
| FN | **** | | | | | | | |
| FO | *** | | | | | | | |
| FP | * | | | | | | | |
| FQ | *** | | | | | | | |
| FR | **** | | | | | | | |
| FS | *** | | | | | | | |
| FT | **** | | | | | | | |
| FU | *** | | | | | | | |
| FV | **** | | | | | | | |
| FW | *** | | | | | | | |
| FX | * | | | | | | | |
| FY | * | | | | | | | |
| FZ | ** | | | | | | | |
| GA | *** | | | | | | | |
| GB | **** | | | | | | | |
| GC | *** | | | | | | | |
| GD | **** | | | | | | | |
| GE | ** | | | | | | | |
| GF | ** | | | | | | | |
| GG | ** | | | | | | | |
| GH | *** | | | | | | | |

TABLE 2-continued

TABLE 2-continued

| | | | | | | | |
|---|---|---|---|---|---|---|---|
| IJ | ** | | | | | | *** |
| IK | **** | | | | | | |
| IL | * | | | | | | |
| IM | | | | | | | |
| IN | *** | | | | | | |
| IO | * | | | | | | |
| IP | * | | | | | | |
| IQ | *** | ** | | | | | |
| IR | *** | | | | | | |
| IS | *** | *** | *** | | | | *** |
| IT | *** | | | | | | |
| IU | *** | | | | | | |
| IV | *** | *** | *** | | | | *** |
| IW | *** | | | | | | |
| IX | *** | *** | *** | ** | | | *** |
| IY | ** | | | | | | |
| IZ | *** | | *** | | | | *** |
| JA | *** | *** | *** | | | | *** |
| JB | | | | | | | |
| JC | *** | | | | | | |
| JD | *** | ** | ** | | | | *** |
| JE | *** | *** | *** | ** | | | *** |
| JF | | | | | | | |
| JG | | *** | | | | | *** |
| JH | | | | | | | |
| JI | *** | *** | *** | *** | *** | | *** |
| JJ | *** | | | | | | *** |
| JK | *** | ** | | | | | |
| JL | | | | | | | |
| JM | ** | | | | | | |
| JN | * | | | | | | |
| JO | ** | | | | | | |
| JP | ** | * | | | | | |
| JQ | *** | | | | | | |
| JR | *** | | | | | | |
| JS | * | | | | | | |
| JT | *** | | | | | | |
| JU | *** | | | | | | |
| JV | *** | ** | | | | | |
| JW | *** | | | | | | |
| JX | *** | | | | | | |
| JY | *** | | | | | | |
| JZ | *** | | | | | | |
| KA | *** | | | | | | |
| KB | **** | | | | | | |
| KC | *** | | | | | | |
| KD | *** | | | | | | |
| KE | *** | | | | | | |
| KF | *** | | | | | | |
| KG | ** | | | | | | |
| KH | ** | ** | | | | | |
| KI | *** | | | | | | |

TABLE 2-continued

| | | |
|---|---|---|
| KJ | ** | |
| KK | **** | |
| KL | ** | *** |
| KM | **** | ** |
| KN | **** | * |
| KO | **** | |
| KP | *. | ** |
| KQ | *. | *** |
| KR | * | ** |
| KS | * | *** |
| KT | ** | *** |
| KU | ** | *** |
| KV | ** | *** |
| KW | ** | *** |
| KX | ** | *** |
| KY | ** | *** |
| KZ | ** | *** |
| LA | ** | *** |
| LB | | *** |
| LC | * | *** |
| LD | | *** |
| LE | ** | *** |
| LF | ** | *** |
| LG | ** | *** |
| LH | ** | *** |
| LI | ** | *** |
| LJ | ** | *** |
| LK | ** | *** |
| LL | ** | *** |
| LM | ** | *** |
| LN | ** | *** |
| LO | ** | ** |
| LP | ** | ** |
| LQ | ** | * |
| LR | ** | * |
| LS | * | * |
| LT | * | * |
| LU | * | * |
| LV | ** | * |
| LW | ** | * |
| LX | ** | * |
| LY | ** | * |
| LZ | ** | * |
| MA | *** | |
| MB | *** | |
| MC | *** | |
| MD | ** | |
| ME | ** | |
| MF | ** | |
| MG | ** | |
| MH | ** | |
| MI | * | |

TABLE 2-continued

| | | | | | | | | |
|---|---|---|---|---|---|---|---|---|
| MJ | ** | | | | | | | |
| MK | . | | | | ** | | * | ** |
| ML | . | | | | | | | * |
| MM | * | | | | | | | *** |
| MN | *** | ** | | | | | | **** |
| MO | *** | | | | | | | *** |
| MP | *** | | | | | * | | *** |
| MQ | *** | | | | | | | *** |
| MR | *** | | | | | | | *** |
| MS | ** | | | | | | | *** |
| MT | *** | | | | | | | *** |
| MU | *** | | | | | | | *** |
| MV | *** | | | | | | | *** |
| MW | *** | | | | | | | *** |
| MX | *** | | | | | | | *** |
| MY | * | *** | *** | | * | | | *** |
| MZ | * | | | | | | | *** |
| NA | ** | | | | | | | *** |
| NB | *** | | *** | | | | | *** |
| NC | . | | | | | | | *** |
| ND | * | | *** | | | | | *** |
| NE | *** | | | ** | | | | *** |
| NF | ** | | | | | | | *** |
| NG | *** | | | | | | | *** |
| NH | *** | | | | | | | *** |
| NI | *** | | | | | | | *** |
| NJ | *** | | *** | | | | | *** |
| NK | . | | | | | | | *** |
| NL | * | | | | | | | *** |
| NM | ** | | | | | | | *** |
| NN | *** | | | | | | | *** |
| NO | *** | | | | | | | *** |
| NP | *** | | | | | | | *** |
| NQ | *** | | | | | | | *** |
| NR | *** | | | | | | | *** |
| NS | *** | | | | | | | *** |
| NT | *** | | | | | | | *** |
| NU | *** | | | | | | | *** |
| NV | *** | | | | | | | *** |
| NW | ** | | | | | | | *** |
| NX | . | | | | | | | *** |
| NY | *** | | | | | | | *** |
| NZ | **** | | | | | | | *** |
| OA | *** | *** | | | | | | *** |
| OB | *** | | | | | | | *** |
| OC | *** | | | | | | | *** |
| OD | *** | | | | | | | *** |
| OE | *** | | | | | | | *** |
| OF | * | | | | | | | *** |
| OG | *** | | | | | | | *** |
| OH | * | | | | | | | *** |
| OI | ** | | | | | | | *** |

TABLE 2-continued

| | | |
|---|---|---|
| OJ | *** | *** |
| OK | *** | *** |
| OL | ** | ** |
| OM | *** | *** |
| ON | ** | ** |
| OO | *** | *** |
| OP | *** | *** |
| OQ | *** | *** |
| OR | *** | *** |
| OS | ** | - |
| OT | *** | - |
| OU | ** | - |
| OV | *** | *** |
| OW | *** | *** |
| OX | ** | * |
| OY | ** | - |
| OZ | * | - |
| PA | * | - |
| PB | ** | - |
| PC | ** | *** |
| PD | *** | * |
| PE | *** | - |
| PF | *** | *** |
| PG | *** | *** |
| PH | ** | - |
| PI | ** | * |
| PJ | *** | - |
| PK | *** | *** |
| PL | *** | *** |
| PM | *** | *** |
| PN | *** | - |
| PO | *** | - |
| PP | *** | *** |
| PQ | ** | - |
| PR | * | - |
| PS | ** | * |
| PT | *** | - |
| PU | *** | *** |
| PV | *** | *** |
| PW | *** | *** |
| PX | *** | *** |
| PY | *** | - |
| PZ | *** | * |
| QA | *** | *** |
| QB | *** | *** |
| QC | *** | *** |
| QD | *** | - ** |
| QE | *** | *** |
| QF | *** | *** |
| QG | *** | - * |
| QH | *** | |
| QI | ** | |

TABLE 2-continued

| | | | |
|---|---|---|---|
| QJ | * | | * |
| QK | **** | | * |
| QL | ** | ** | * |
| QM | **** | | * |
| QN | ** | | * |
| QO | **** | ** | * |
| QP | **** | | * |
| QQ | **** | | * |
| QR | *** | ** | * |
| QS | *** | | * |
| QT | *** | | * |
| QU | *** | | * |
| QV | *** | ** | * |
| QW | *** | | * |
| QX | *** | ** | * |
| QY | *** | ** | * |
| QZ | **** | **** | * |
| RA | ** | ** | * |
| RB | **** | | * |
| RC | *** | | * |
| RD | **** | | * |
| RE | **** | | * |
| RF | *** | **** | * |
| RG | **** | | * |
| RH | ***** | | * |
| RI | *** | *** | *** |
| RJ | ** | **** | * |
| RK | *** | | * |
| RL | ** | | * |
| RM | | | * |
| RN | | | |
| RO | | | * |
| RP | | | * |
| RQ | | ** | * |
| RR | *** | | * |
| RS | *** | * | |
| RT | ** | | * |
| RU | *** | | * |
| RV | *** | *** | * |
| RW | ** | * | * |
| RX | ** | | * |
| RY | ** | | * |
| RZ | *** | *** | * |
| SA | ** | | * |
| SB | ** | | * |
| SC | *** | | * |
| SD | **** | | ** |
| SE | *** | | * |
| SF | **** | | * |
| SG | * | | * |
| SH | * | | * |
| SI | * | | * |

TABLE 2-continued

| | | | | | |
|---|---|---|---|---|---|
| SJ | | | | * | |
| SK | * | | ** | | ** |
| SL | *** | | | | |
| SM | | | | | |
| SN | *** | | | | |
| SO | **** | | * | | * |
| SP | * | | | | |
| SQ | *** | | | | |
| SR | **** | | | | |
| SS | * | | | | |
| ST | ** | | ** | | ** |
| SU | *** | | | | * |
| SV | *** | | ** | | *** |
| SW | *** | | *** | ** | |
| SX | *** | | ** | *** | |
| SY | ** | | | ** | |
| SZ | ** | | ** | *** | |
| TA | ** | | *** | **** | |
| TB | * | | | * | |
| TC | *** | | ** | *** | |
| TD | *** | | *** | **** | |
| TE | * | | * | *** | |
| TF | ** | | *** | **** | |
| TG | *** | | | *** | |
| TH | *** | | ** | | |
| TI | **** | | ** | *** | |
| TJ | **** | | ** | **** | |
| TK | | | | | |
| TL | **** | | ** | **** | |
| TM | **** | | *** | **** | * |
| TN | *** | | | *** | * |
| TO | *** | | *** | **** | * |
| TP | **** | | *** | **** | * |
| TQ | *** | | | **** | * |
| TR | **** | | ** | | * |
| TS | **** | | *** | | * |
| TT | *** | | ** | | * |
| TU | **** | | *** | *** | ** |
| TV | **** | | | *** | ** |
| TW | *** | | * | ** | ** |
| TX | *** | | * | * | ** |
| TY | **** | | | | ** |
| TZ | **** | | | | ** |
| UC | **** | | ** | *** | ** |
| UD | **** | | *** | **** | ** |
| UE | **** | | *** | **** | ** |
| UF | **** | | ** | *** | ** |
| UH | *** | | ** | *** | ** |
| UI | **** | | | | ** |
| UJ | *** | | | | |
| UK | **** | | *** | ** | |
| UL | **** | | ** | ** | |
| UM | **** | | *** | *** | |

TABLE 2-continued

| | | | | |
|---|---|---|---|---|
| UN | ** | | | |
| UO | *** | | ** | ** |
| UQ | *** | *** | | *** |
| UR | *** | | | *** |
| US | *** | | | *** |
| UT | *** | ** | | *** |
| UV | ** | | | * |
| UW | | | | |
| UX | ** | *** | | *** |
| UY | ** | ** | | *** |
| UZ | ** | ** | | *** |
| VA | ** | ** | * | ** |
| VB | ** | ** | | ** |
| VC | | | | |
| VD | ** | ** | ** | ** |
| VE | | | * | |
| VF | ** | ** | ** | *** |
| VG | | | | |
| VH | ** | ** | | ** |
| VJ | ** | | | ** |
| VK | *** | *** | | *** |

EXAMPLE 3

In Vitro Cytotoxicity Assay of Tetracycline Compounds Mammalian Cytotoxicity Assay COS-1 and CHO Cell suspensions were prepared, seeded into 96-well tissue culture treated black-walled microtiter plates (density determined by cell line), and incubated overnight at 37° C., in 5% $CO_2$ and approximately 95% humidity. The following day serial dilutions of drug were prepared under sterile conditions and transferred to cell plates. Cell/Drug plates were incubated under the above conditions for 24 hours. Following the incubation period, media/drug was aspirated and 50 ml of Resazurin was added. Plates were then incubated under the above conditions for 2 hours and then in the dark at room temperature for an additional 30 minutes. Fluorescence measurements were taken (excitation 535 nm, emission 590 nm). The $IC_{50}$ (concentration of drug causing 50% growth inhibition) was then calculated for each compound.

In Table 2, toxicities greater than >25 µg/ml are represented by * and toxicities less than 25 µg/mL are represented by **.

EXAMPLE 4

In vitro Anti-Bacterial Activity Assay

The following assay is used to determine the efficacy of the tetracycline compounds against common bacteria 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1 \times 10^6$ CFU/ml. At OD=1, cell densities for different genera should be approximately:

*E coli* $1 \times 10^9$ CFU/ml

*S. aureus* $5 \times 10^8$ CFU/ml

*Enterococcus* sp. $2.5 \times 10^9$ CFU/ml.

50 µl of the cell suspensions are added to each well of microtiter plates. The final cell density should be approximately $5 \times 10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A method for increasing the antifungal activity of an antifungal agent, comprising administering said antifungal agent in combination with an effective amount of a substituted tetracycline compound, such that the antifungal activity of said antifungal agent is increased, wherein said substituted tetracycline compound is of formula I:

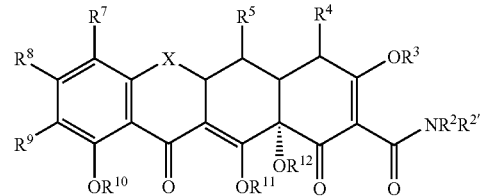

X is $CHC(R^{13}Y'Y)$, $C=CR^{13}Y$, $CR^{6'}R^6$, S, $NR^6$, or O;

$R^2$, $R^{2'}$, $R^4$, and $R^{4'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is bromine, fluorine, iodine, nitro, alkyl, alkenyl, alkynyl, aryl, alkoxy, alkylthio, alkylsulfinyl, alkylsulfonyl, arylalkyl, amino, arylalkenyl, arylalkynyl, or $-(CH_2)_{0-3}NR^{7c}C(=W')WR^{7a}$;

$R^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$ S;

$R^{7a}$, $R^{7b}$, $R^{7c}$, $R^{7d}$, $R^{7e}$, $R^{7f}$ $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof, wherein said tetracycline compound is not minocycline.

2. A method for treating a fungal associated disorder in a subject, comprising administering to said subject an effective amount of a substituted tetracycline compound in combination with an antifungal agent such that said subject is treated for said fungal associated disorder, wherein said substituted tetracycline compound is of formula I:

467

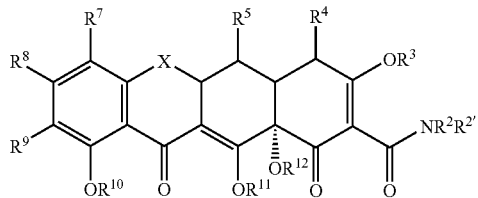

X is CHC(R$^{13}$Y'Y), C=CR$^{13}$Y, CR$^{6'}$R$^6$, S, NR$^6$, or O;

R$^2$, R$^{2'}$, R$^4$, and R$^{4'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is bromine, fluorine, iodine, nitro, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$NR$^{7c}$C(=W')WR$^{7a}$;

R$^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH$_2$)$_{0-3}$NR$^{9c}$C(=Z')ZR$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$ S;

R$^{7a}$, R$^{7b}$, R$^{7c}$, R$^{7d}$, R$^{7e}$, R$^{7f}$ R$^{9a}$, R$^{9b}$, R$^{9c}$, R$^{9d}$, R$^{9e}$, and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof, wherein said tetracycline compound is not minocycline.

3. A method for treating a fungal associated disorder in a mammal, comprising administering to said mammal a synergistically effective amount of a substituted tetracycline compound in combination with an effective amount amphotericin B, such that said mammal is treated for said fungal associated disorder, wherein said substituted tetracycline compound is of formula I:

468

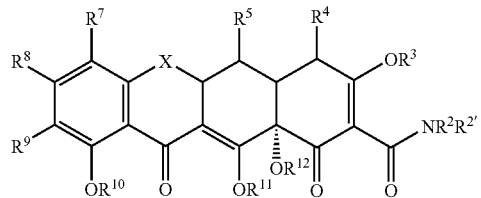

X is CHC(R$^{13}$Y'Y), C=CR$^{13}$Y, CR$^{6'}$R$^6$, S, NR$^6$, or O;

R$^2$, R$^{2'}$, R$^4$, and R$^{4'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is bromine, fluorine, iodine, nitro, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$NR$^{7c}$C(=W')WR$^{7a}$;

R$^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH$_2$)$_{0-3}$NR$^{9c}$C(=Z')ZR$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$ S;

R$^{7a}$, R$^{7b}$, R$^{7c}$, R$^{7d}$, R$^{7e}$, R$^{7f}$, R$^{9a}$, R$^{9b}$, R$^{9c}$, R$^{9d}$, R$^{9e}$, and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof, wherein said tetracycline compound is not minocycline.

4. A method for increasing the antifungal activity of an antifungal agent, comprising administering said antifungal agent in combination with an effective amount of a substituted tetracycline compound, such that the antifungal activity of said antifungal agent is increased, wherein said substituted tetracycline compound is of formula I:

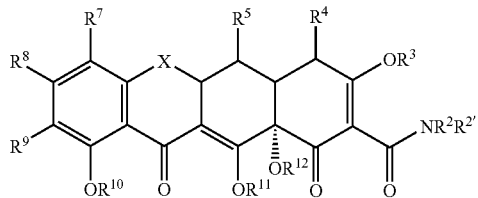

X is C=CR¹³Y;

R², R²', R⁴, and R⁴' are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R³, R¹⁰, R¹¹ and R¹² are each hydrogen or a pro-drug moiety;

R⁵ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R⁶ and R⁶' are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R⁷ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —(CH₂)₀₋₃NR⁷ᶜC(=W')WR⁷ᵃ;

R⁹ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH₂)₀₋₃NR⁹ᶜC(=Z')ZR⁹ᵃ;

Z is CR⁹ᵈR⁹ᵉ, S, NR⁹ᵇ or O;

Z' is O, S, or NR⁹ᶠ;

W is CR⁷ᵈR⁷ᵉ, S, NR⁷ᵇ or O;

W' is O, NR⁷ᶠ S;

R⁷ᵃ, R⁷ᵇ, R⁷ᶜ, R⁷ᵈ, R⁷ᵉ, R⁷ᶠ, R⁹ᵃ, R⁹ᵇ, R⁹ᶜ, R⁹ᵈ, R⁹ᵉ, and R⁹ᶠ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R⁸ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R¹³ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

5. A method for increasing the antifungal activity of an antifungal agent, comprising administering said antifungal agent in combination with an effective amount of a substituted tetracycline compound, such that the antifungal activity of said antifungal agent is increased, wherein said substituted tetracycline compound is of formula I:

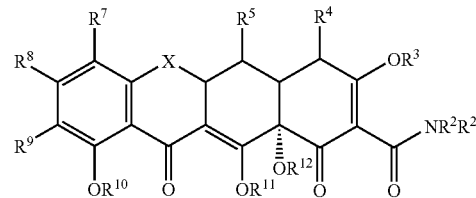

X is CHC(R¹³Y'Y), C=CR¹³Y, CR⁶R⁶', S, NR⁶, or O;

R², R²', R⁴, and R⁴' are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R³, R¹⁰, R¹¹ and R¹² are each hydrogen or a pro-drug moiety;

R⁵ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R⁶ and R⁶' are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R⁷ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —(CH₂)₀₋₃NR⁷ᶜC(=W')ZR⁷ᵃ;

R⁹ is halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH₂)₀₋₃NR⁹ᶜC(=Z')ZR⁹ᵃ;

Z is CR⁹ᵈR⁹ᵉ, S, NR⁹ᵇ or O;

Z'is O, S, or NR⁹ᶠ;

W is CR⁷ᵈ, R⁷ᵉ, S, NR⁷ᵇ or O;

W' is O, NR⁷ S;

R⁷ᵃ, R⁷ᵇ, R⁷ᶜ, R⁷ᵈ, R⁷ᵉ, R⁷ᶠ, R⁹ᵃ, R⁹ᵇ, R⁹ᶜ, R⁹ᵈ, R⁹ᵉ and R⁹ᶠ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R⁸ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R¹³ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

6. A method for treating a fungal associated disorder in a subject, comprising administering to said subject an effective amount of a substituted tetracycline compound in combination with an antifungal agent such that said subject is treated for said fungal associated disorder, wherein said substituted tetracycline compound is of formula I:

471

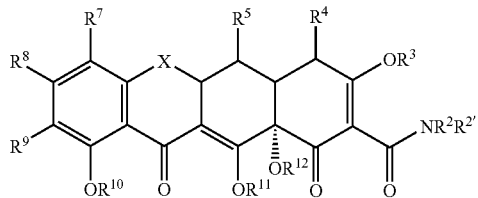

X is C=CR$^{13}$Y;

R$^2$, R$^{2'}$, R$^4$, and R$^{4'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$NR$^{7c}$(=W')WR$^{7a}$;

R$^9$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH$_2$)$_{0-3}$NR$^{9c}$C(=Z')ZR$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$ S;

R$^{7a}$, R$^{7b}$, R$^{7c}$, R$^{7d}$, R$^{7e}$, R$^{7f}$, R$^{9a}$, R$^{9b}$, R$^{9c}$, R$^{9d}$, R$^{9e}$, and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

7. A method for treating a fungal associated disorder in a subject, comprising administering to said subject an effective amount of a substituted tetracycline compound in combination with an antifungal agent such that said subject is treated for said fungal associated disorder, wherein said substituted tetracycline compound is of formula I:

472

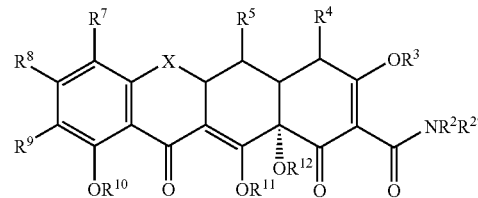

X is CHC(R$^{13}$Y'Y), C=CR$^{13}$Y, CR$^6$R$^{6'}$, S, NR$^6$, or O;

R$^2$, R$^{2'}$, R$^4$, and R$^{4'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{10}$, R$^{11}$ and R$^{12}$ are each hydrogen or a pro-drug moiety;

R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^7$ is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —(CH$_2$)$_{0-3}$NR$^{7c}$C(=W')WR$^{7a}$;

R$^9$ is halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —(CH$_2$)$_{0-3}$NR$^{9c}$C(=Z')ZR$^{9a}$;

Z is CR$^{9d}$R$^{9e}$, S, NR$^{9b}$ or O;

Z' is O, S, or NR$^{9f}$;

W is CR$^{7d}$R$^{7e}$, S, NR$^{7b}$ or O;

W' is O, NR$^{7f}$ S;

R$^{7a}$ R$^{7b}$, R$^{7c}$R$^{7d}$, R$^{7e}$, R$^{7f}$, R$^{9a}$, R$^{9b}$, R$^{9c}$, R$^{9d}$, R$^{9e}$, and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

8. A method for treating a fungal associated disorder in a mammal, comprising administering to said mammal a synergistically effective amount of a substituted tetracycline compound in combination with an effective amount amphotericin B, such that said mammal is treated for said fungal associated disorder, wherein said substituted tetracycline compound is of formula I:

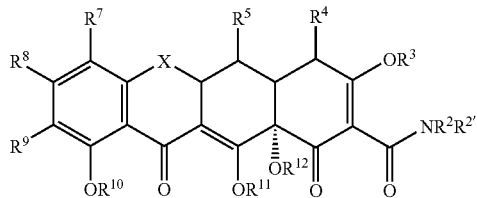

X is C=CR[13]Y;

R[2], R[2'], R[4], and R[4'] are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R[3], R[10], R[11] and R[12] are each hydrogen or a pro-drug moiety;

R[5] is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R[6] and R[6'] are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R[7] is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —$(CH_2)_{0-3}$NR[7c]C(=W')WR[7a];

R[9] is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}$NR[9c]C(=Z')ZR[9a];

Z is CR[9d]R[9e], S, NR[9b] or O;

Z' is O, S, or NR[9f];

W is CR[7d]R[7e], S, NR[7b] or O;

W' is O, NR[7f] S;

R[7a], R[7b], R[7c], R[7d], R[7e], R[7f] R[9a], R[9b], R[9c], R[9d], R[9e] and R[9f] are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R[8] is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R[13] is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

9. A method for treating a fungal associated disorder in a mammal, comprising administering to said mammal a synergistically effective amount of a substituted tetracycline compound in combination with an effective amount amphotericin B, such that said mammal is treated for said fungal associated disorder, wherein said substituted tetracycline compound is of formula I:

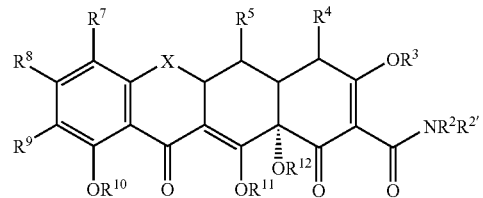

X is CHC(R[13]Y'Y), C=CR[13]Y, CR[6]R[6'], S, NR[6], or O;

R[2], R[2'], R[4], and R[4'] are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R[3], R[10], R[11] and R[12] are each hydrogen or a pro-drug moiety;

R[5] is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R[6] and R[6'] are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R[7] is hydrogen, halogen, nitro, alkyl, alkenyl, alkynyl, aryl, alkoxy, alkylthio, alkylsulfinyl, alkylsulfonyl, arylalkyl, amino, arylalkenyl, arylalkynyl, or —$(CH_2)_{0-3}$NR[7c]C(=W')WR[7a];

R[9] is halogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}$NR[9c]C(=Z')ZR[9a];

Z is CR[9d]R[9e], S, NR[9b] or O;

Z' is O, S, or NR[9f];

W is CR[7d]R[7e], S, NR[7b] or O;

W' is O, NR[7f] S;

R[7a], R[7b], R[7c], R[7d], R[7e], R[7f], R[9a], R[9b], R[9c], R[9d], R[9e], and R[9f] are each independently hydrogen, acyl, alkyl, alkenyl, alkynyl, alkoxy, alkylthio, alkylsulfinyl, alkylsulfonyl, alkylamino arylalkyl, aryl, heterocyclic, heteroaromatic or a prodrug moiety;

R[8] is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R[13] is hydrogen, hydroxy, alkyl, alkenyl, alkynyl, alkoxy, alkylthio, aryl, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts and enantiomers thereof.

10. A method for increasing the antifungal activity of an antifungal agent, comprising administering said antifungal agent in combination with an effective amount of a substituted tetracycline compound, such that the antifungal activity of said antifungal agent is increased, wherein said tetracycline compound is:

475
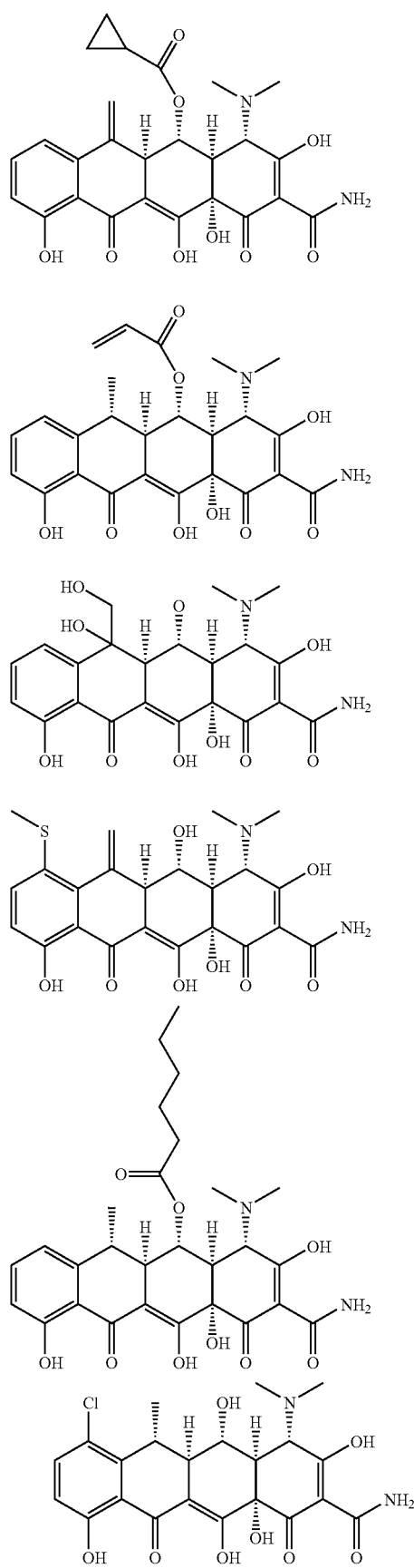
476
-continued
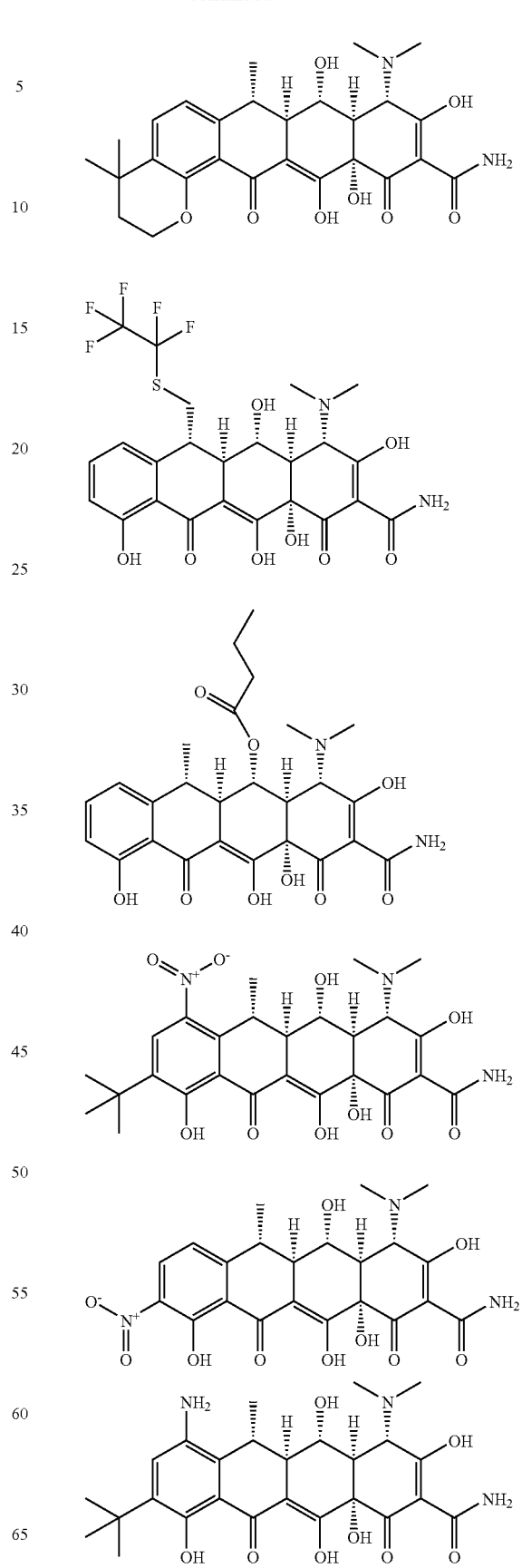

477
-continued
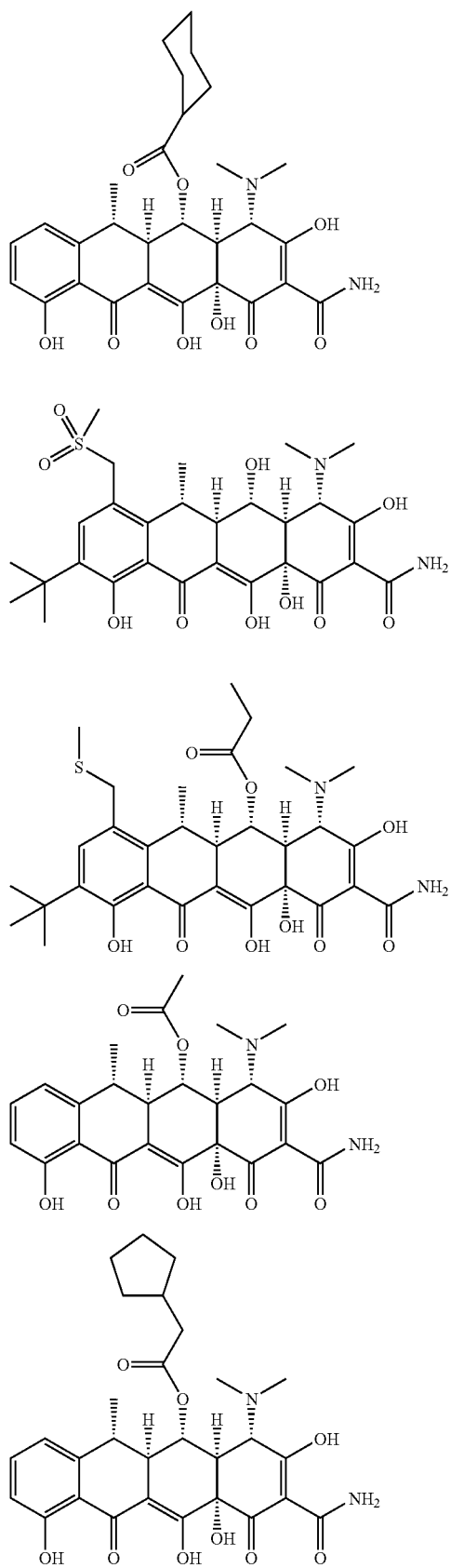
478
-continued
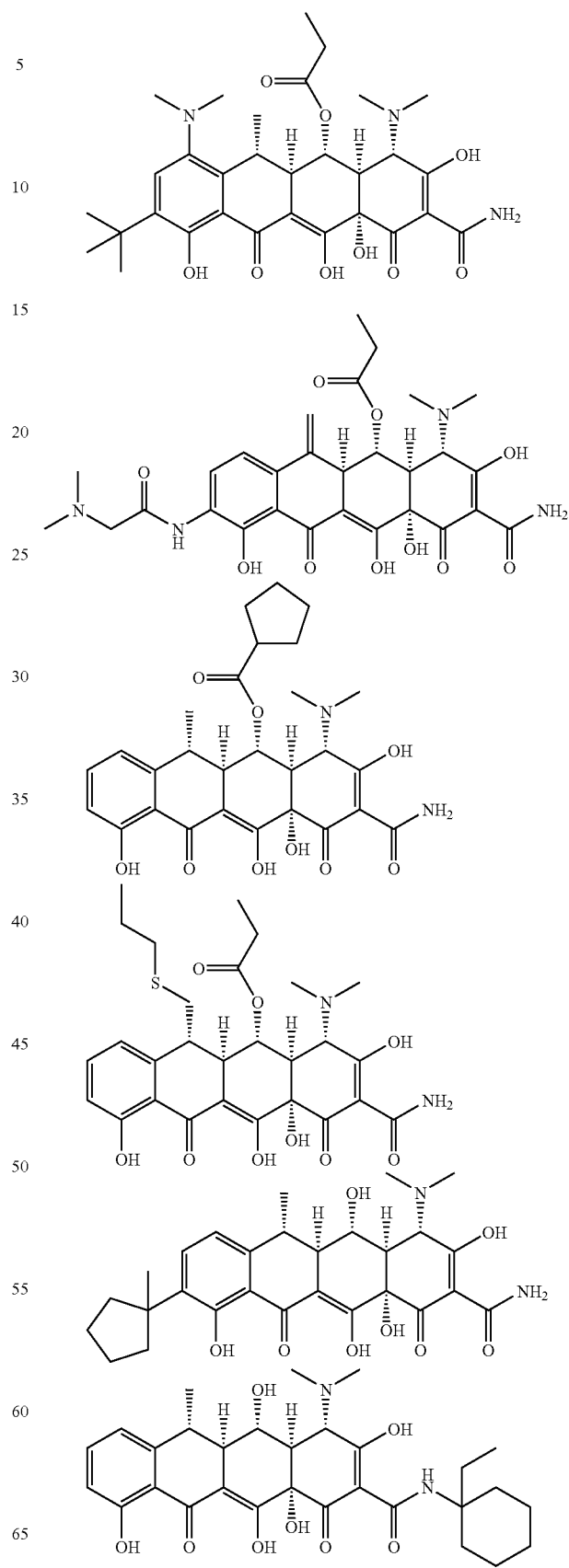

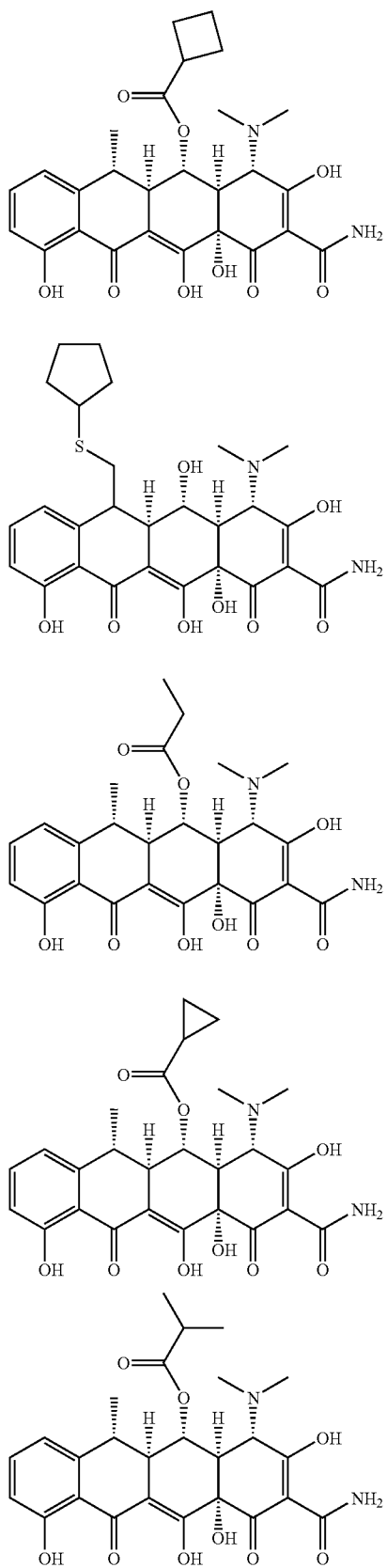
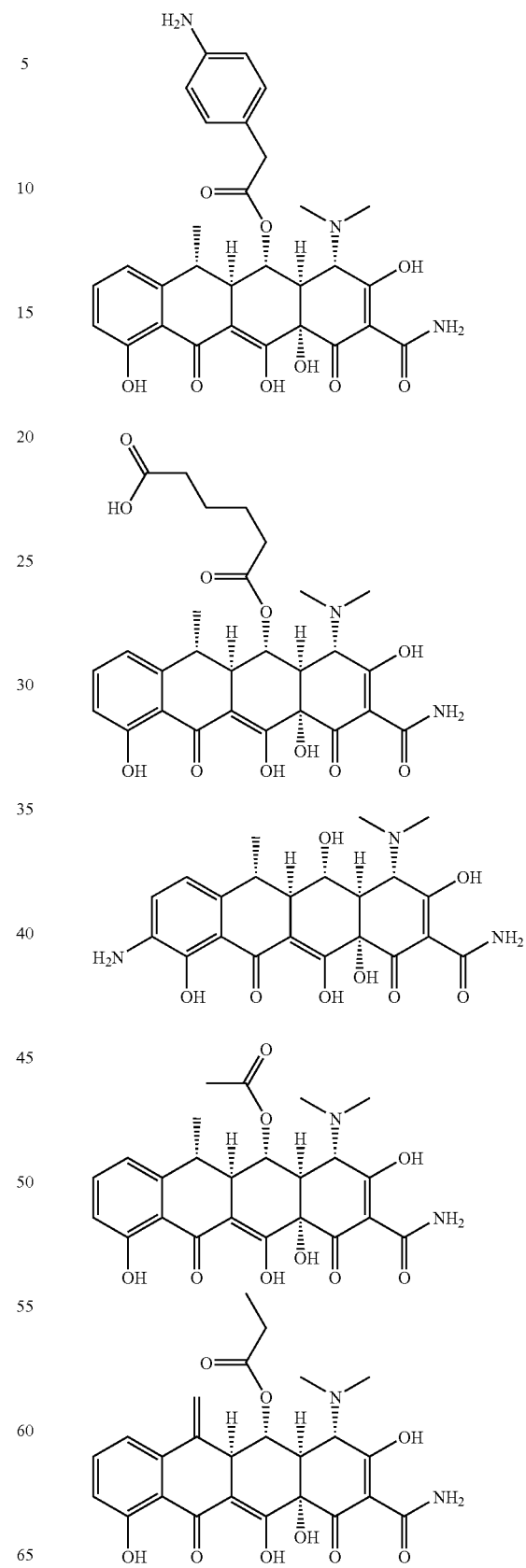

481
-continued
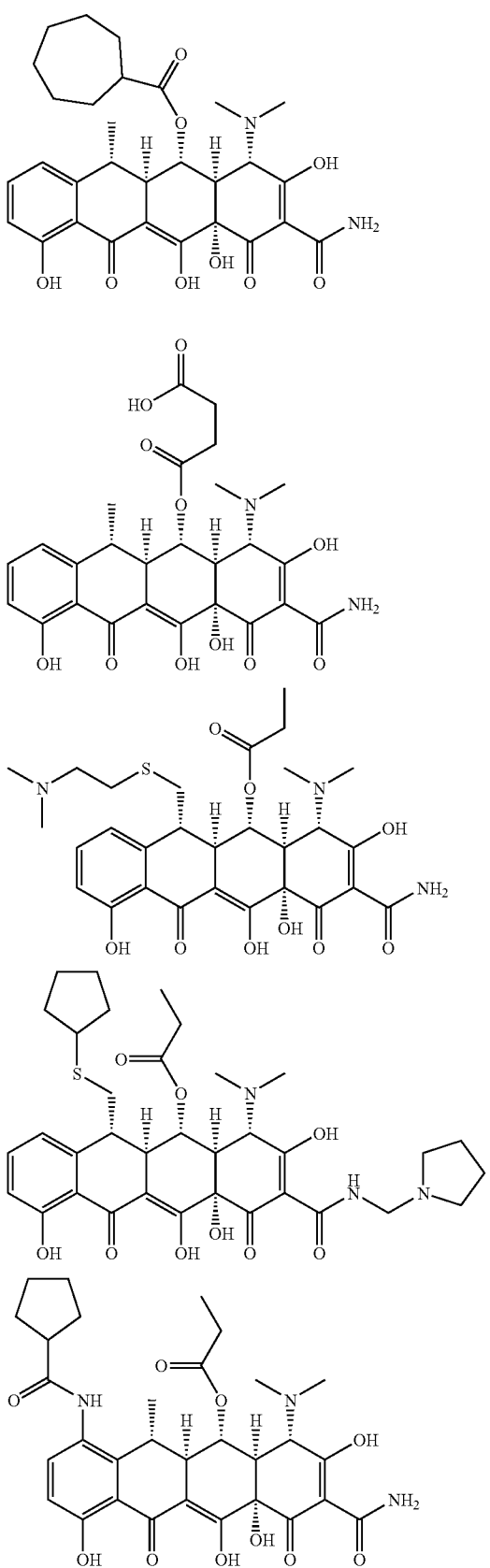
482
-continued
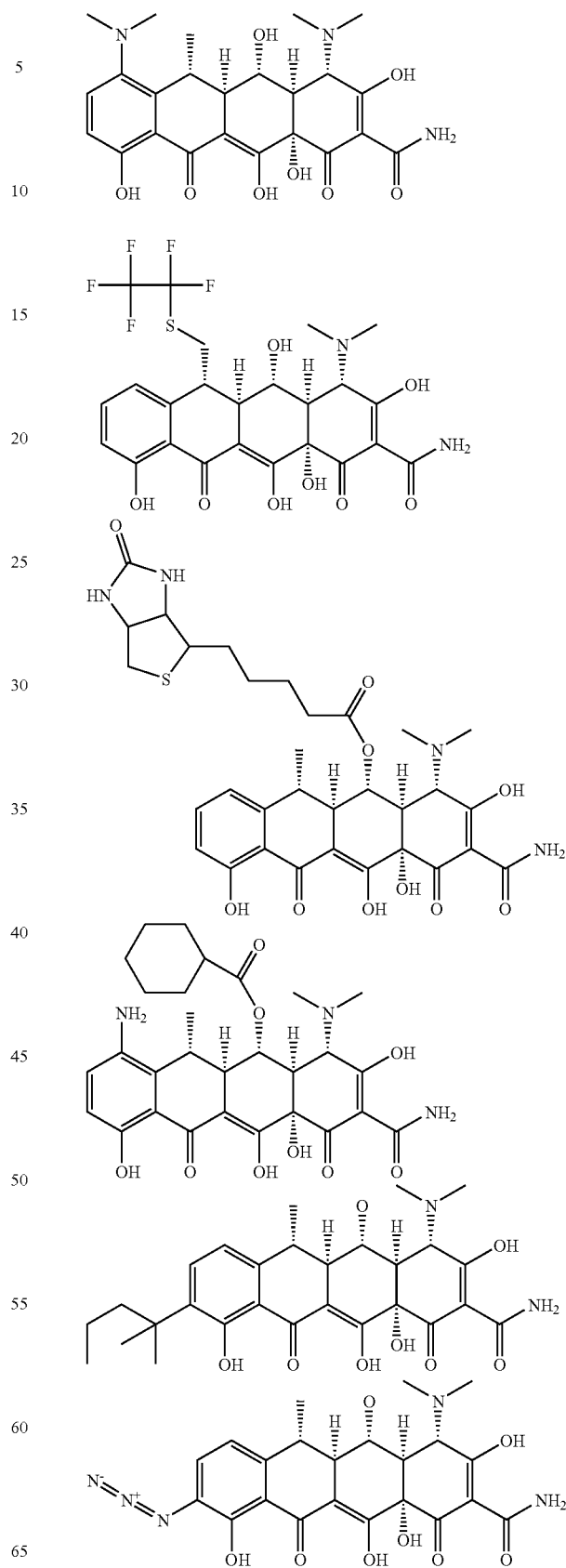

483
-continued
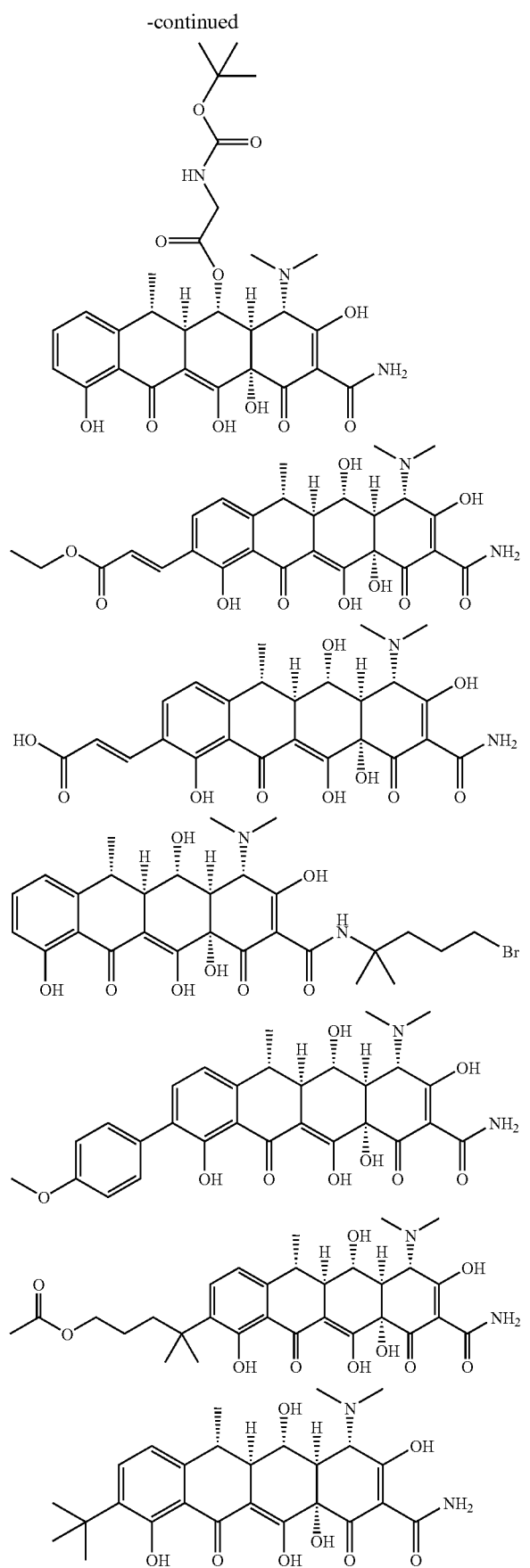
484
-continued
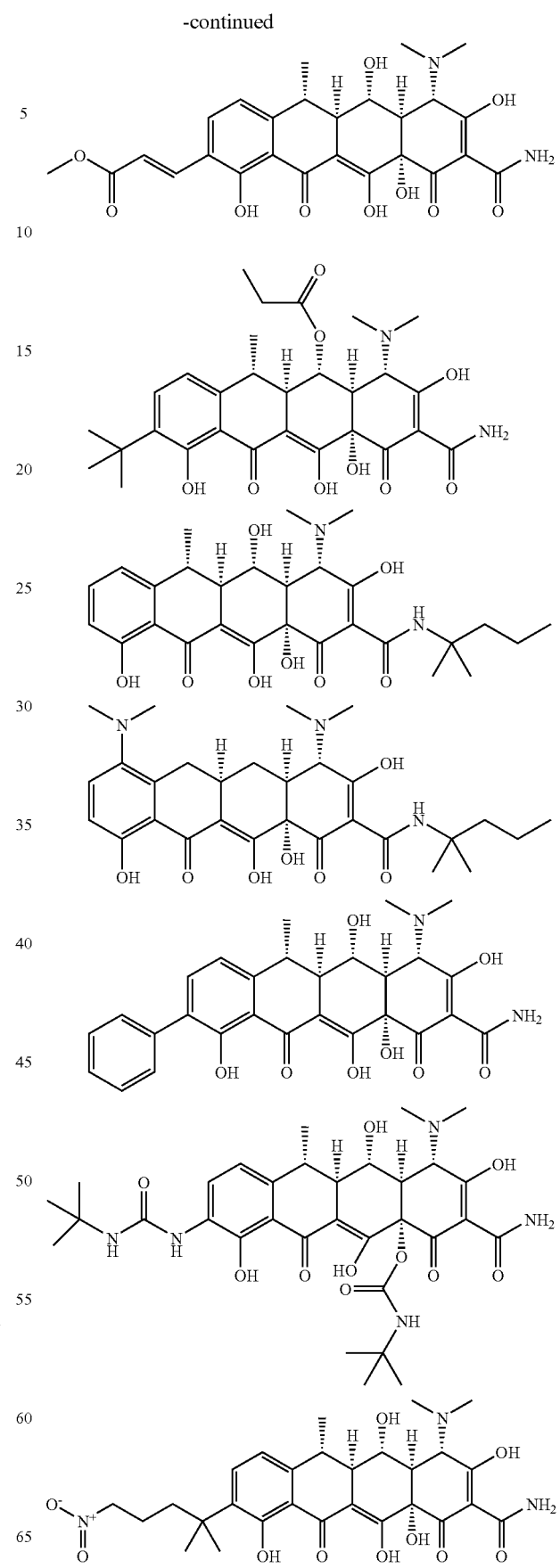

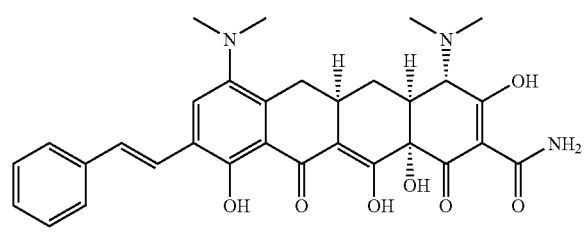
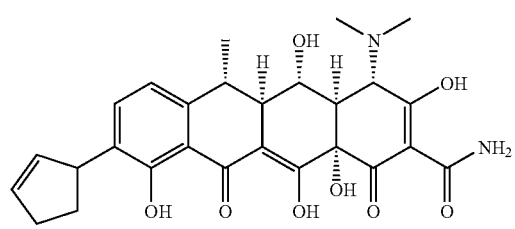
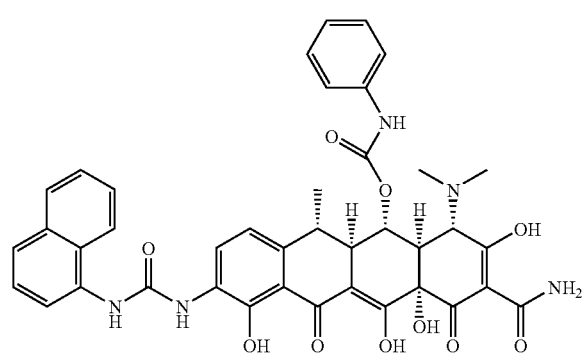
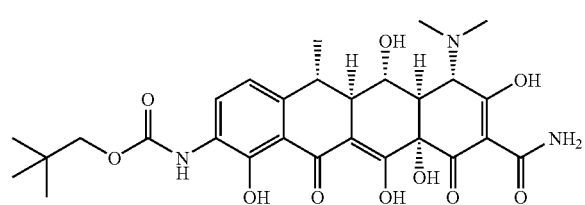
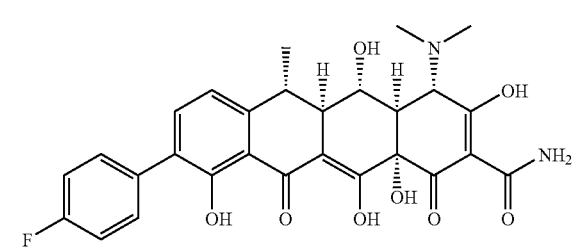
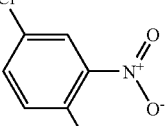
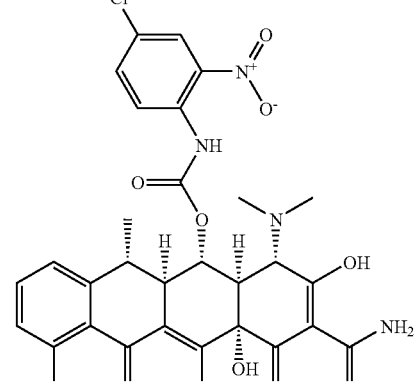
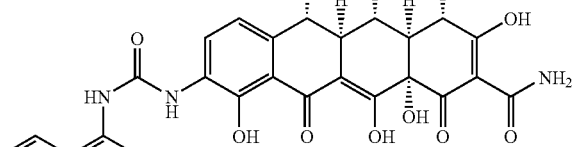
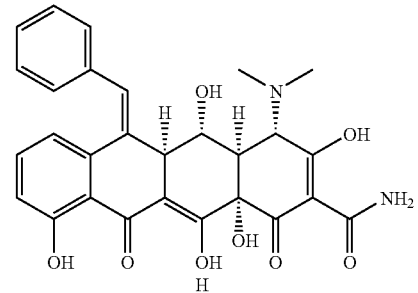
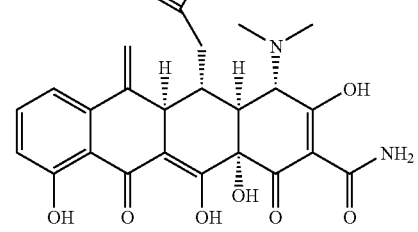
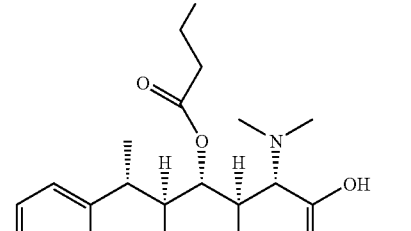
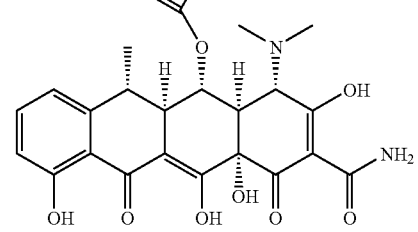

487
-continued
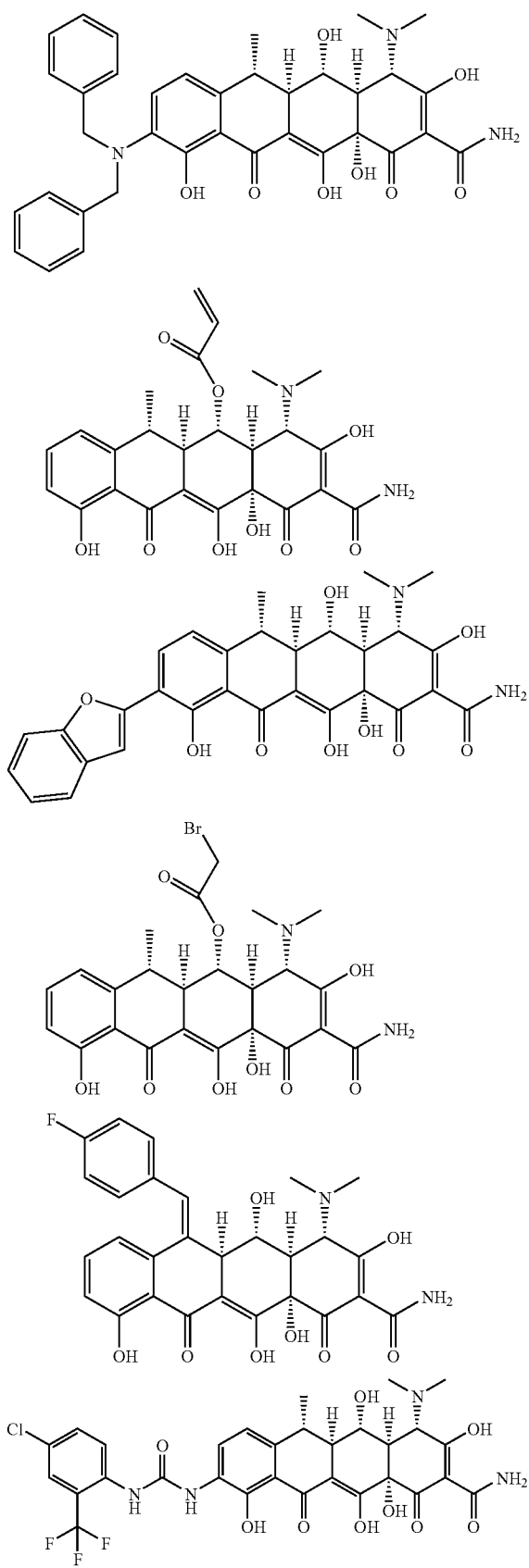
488
-continued
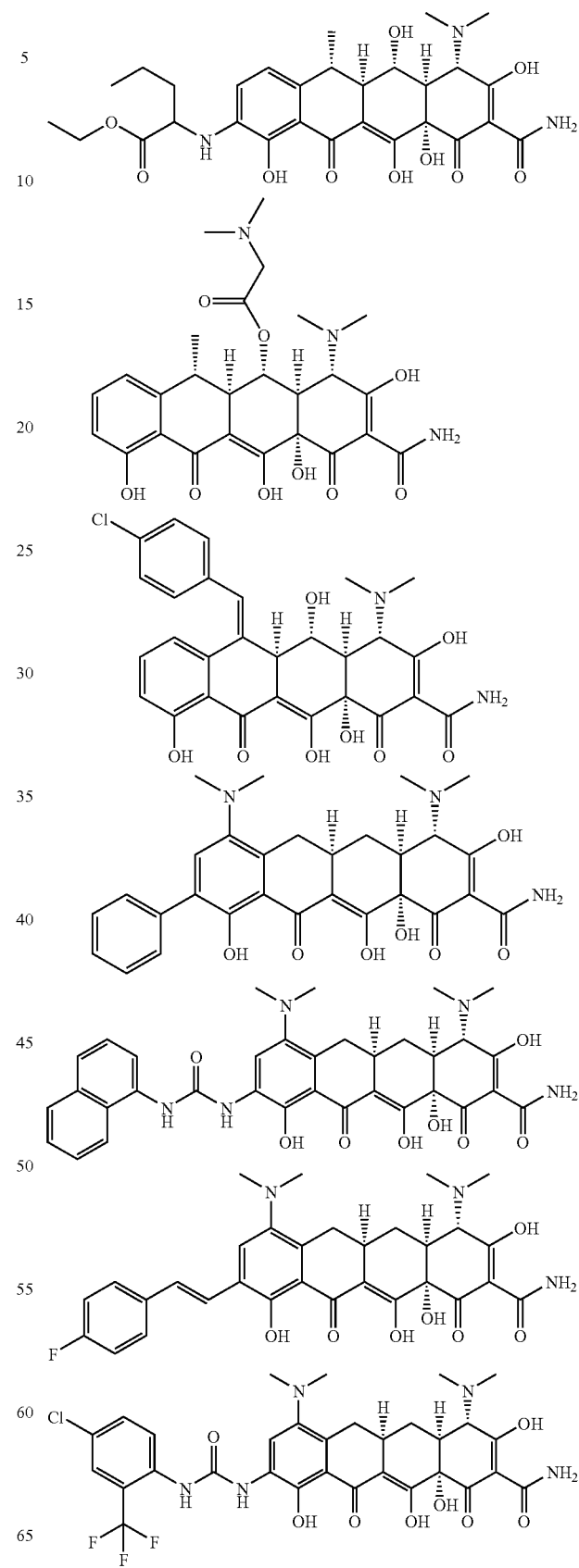

489
-continued
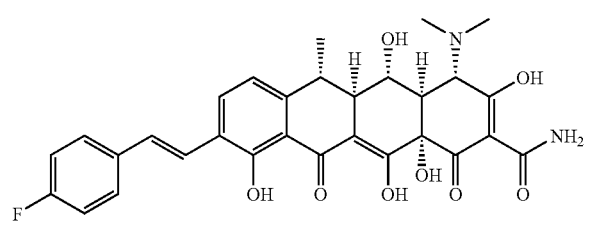
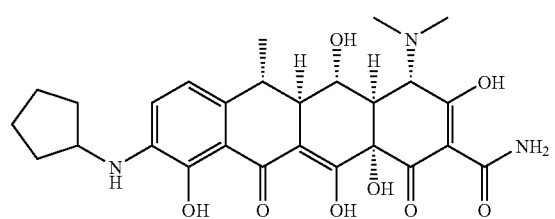
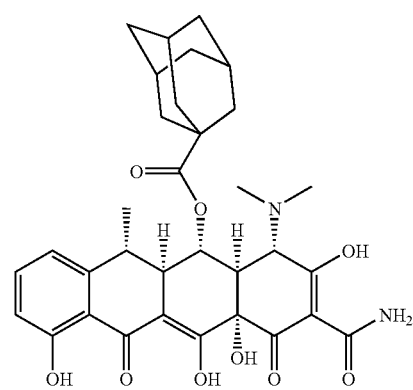
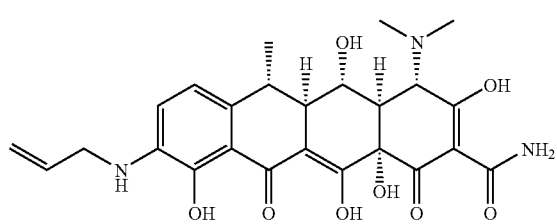
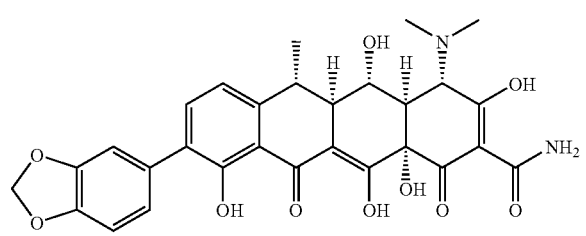
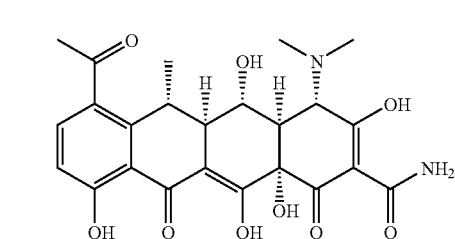
490
-continued
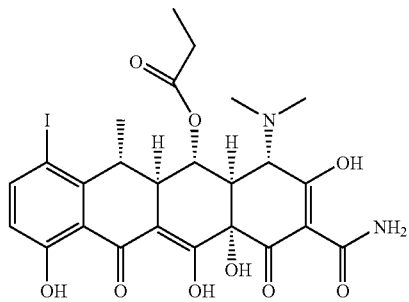
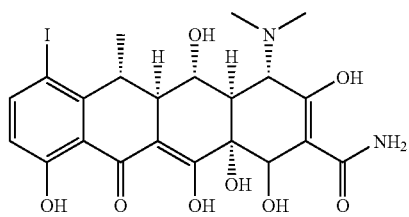
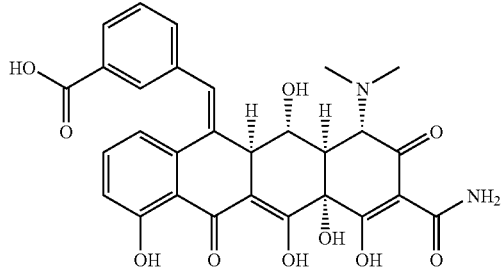
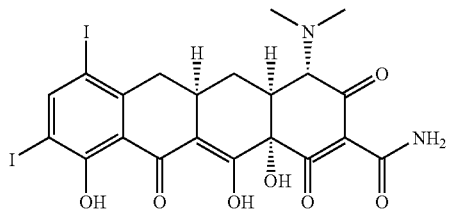
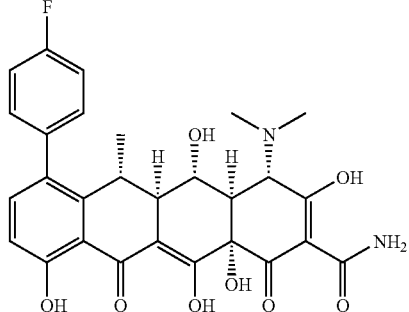
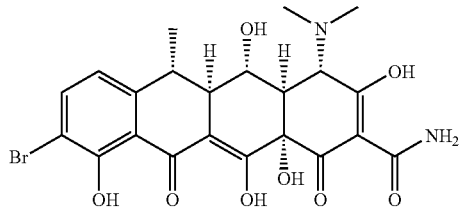

491
-continued
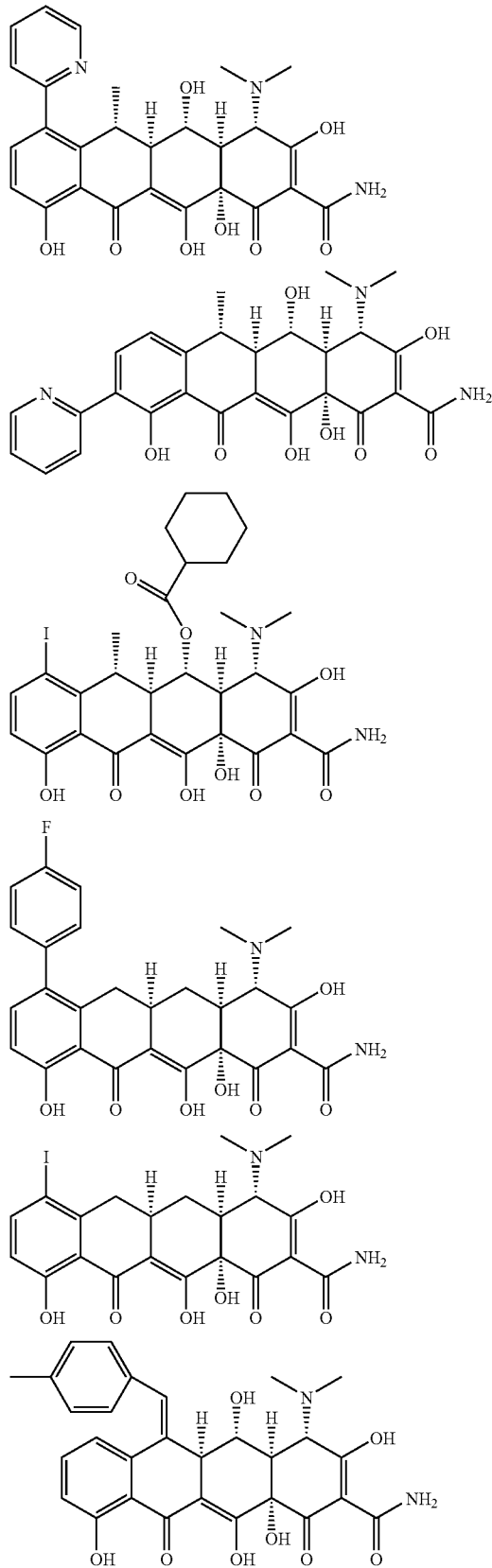
492
-continued
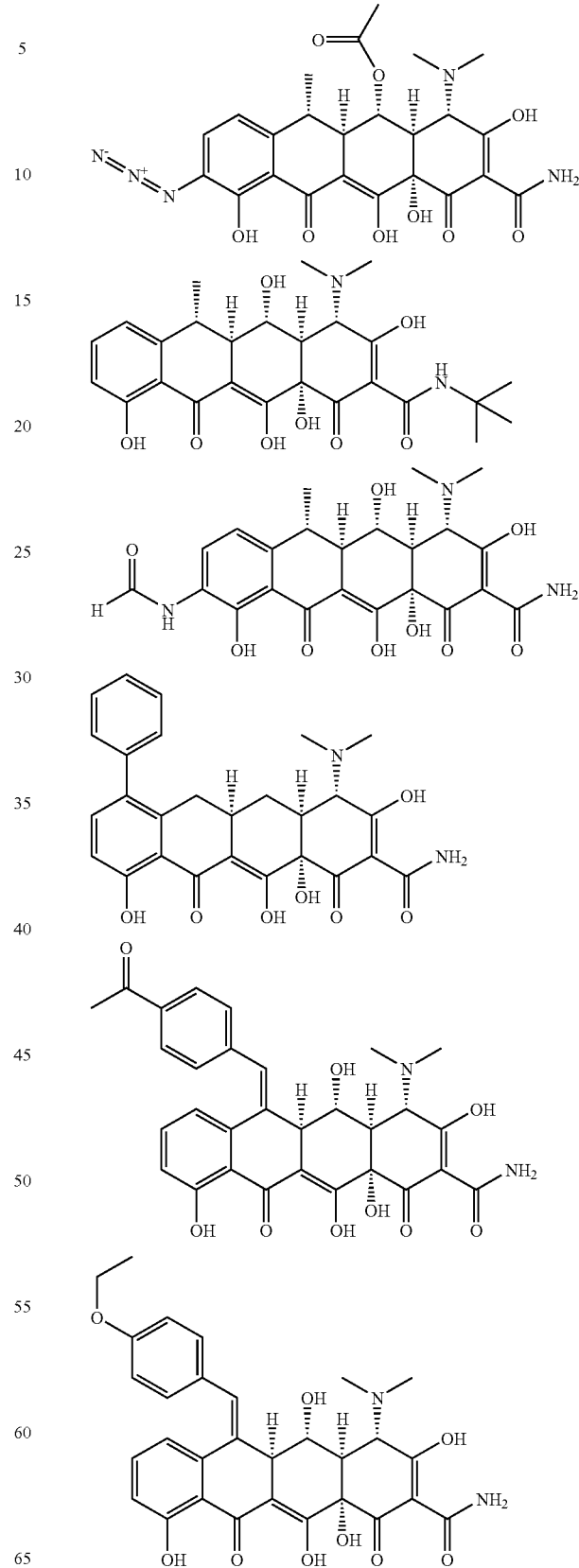

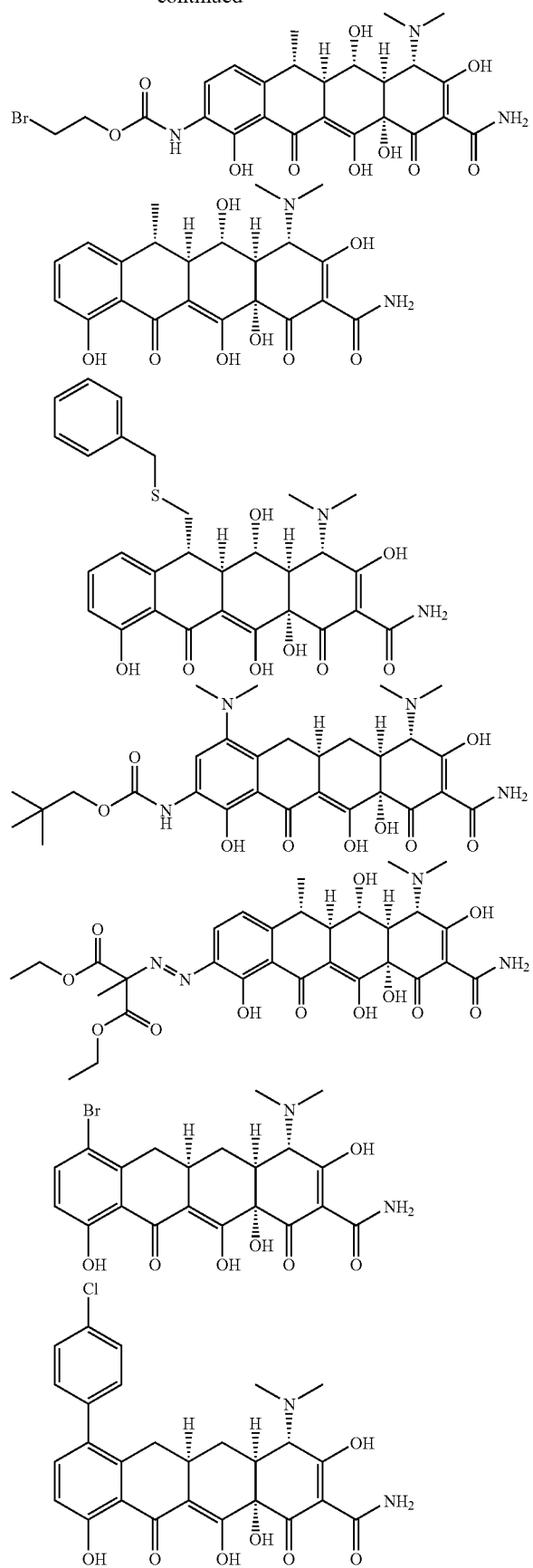
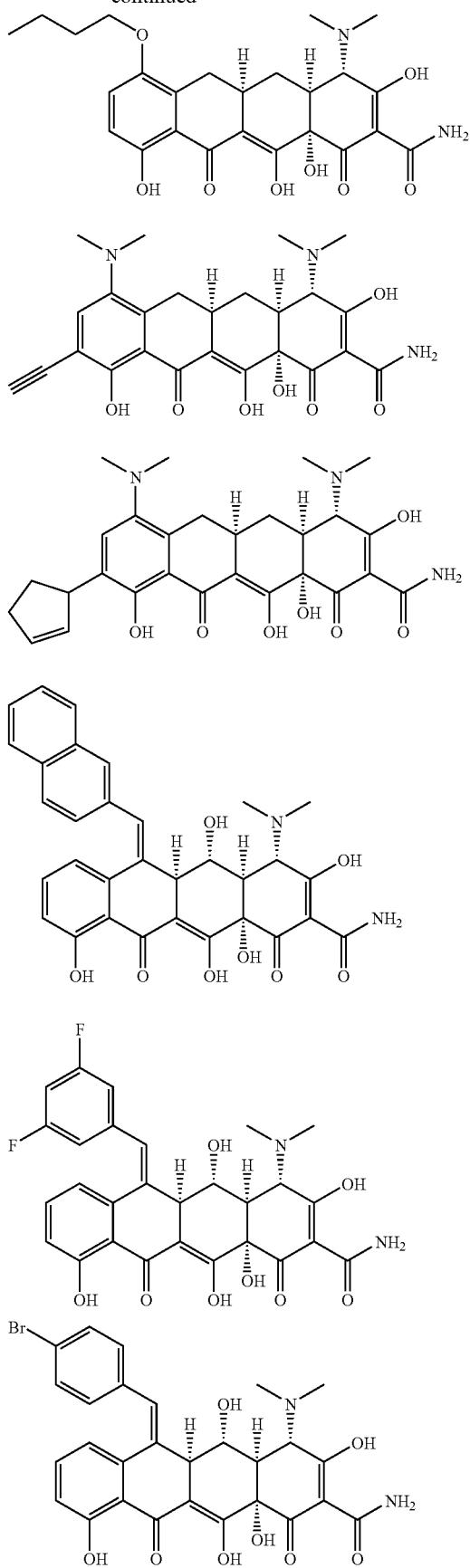

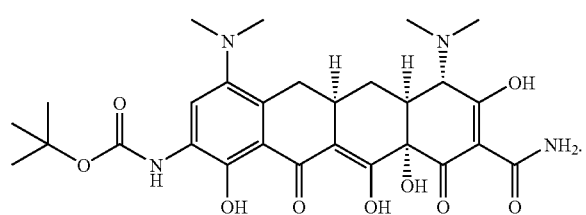
11. A method for increasing the antifungal activity of an antifungal agent, comprising administering said antifungal agent in combination with an effective amount of a substituted tetracycline compound, such that the antifungal activity of said antifungal agent is increased, wherein said tetracycline compound is:
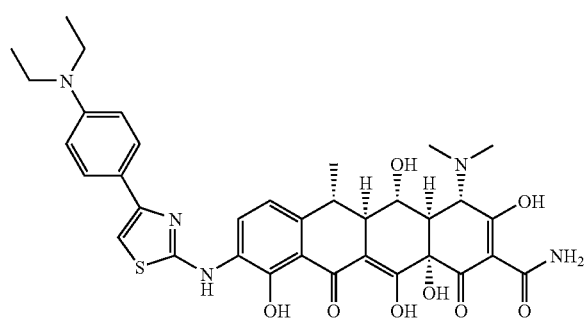
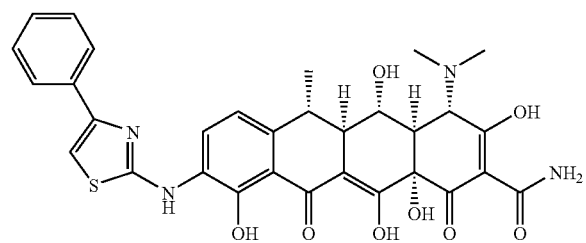
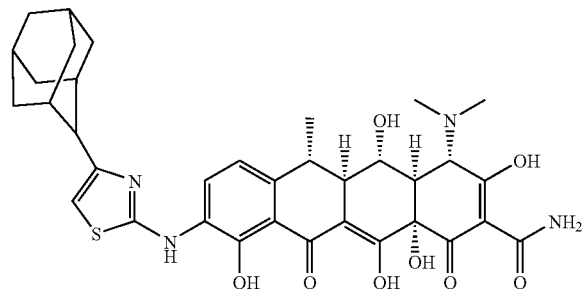
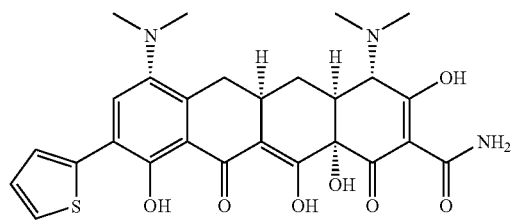
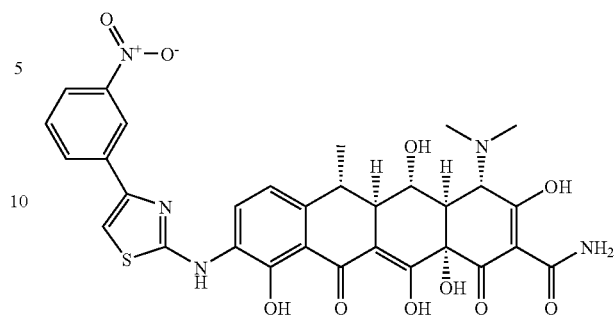
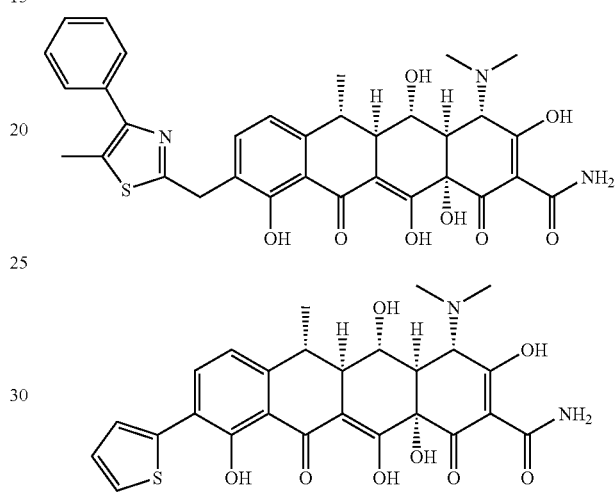
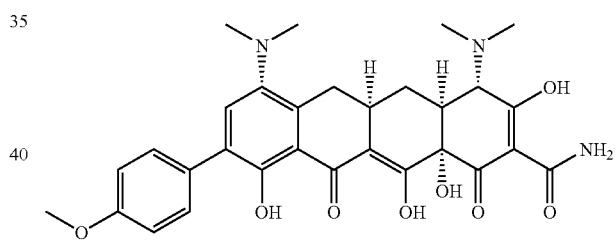
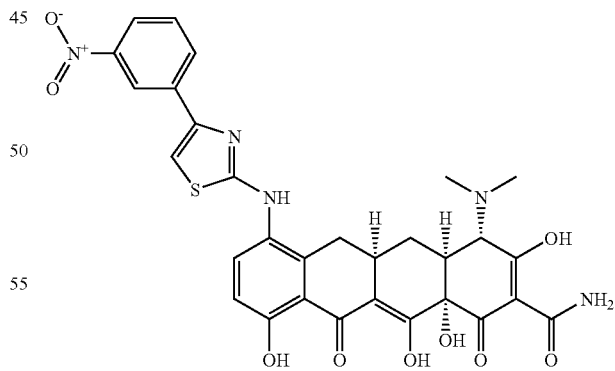
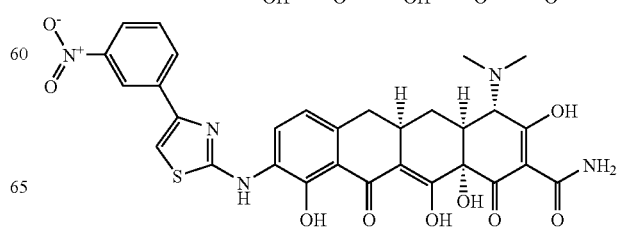

497
-continued
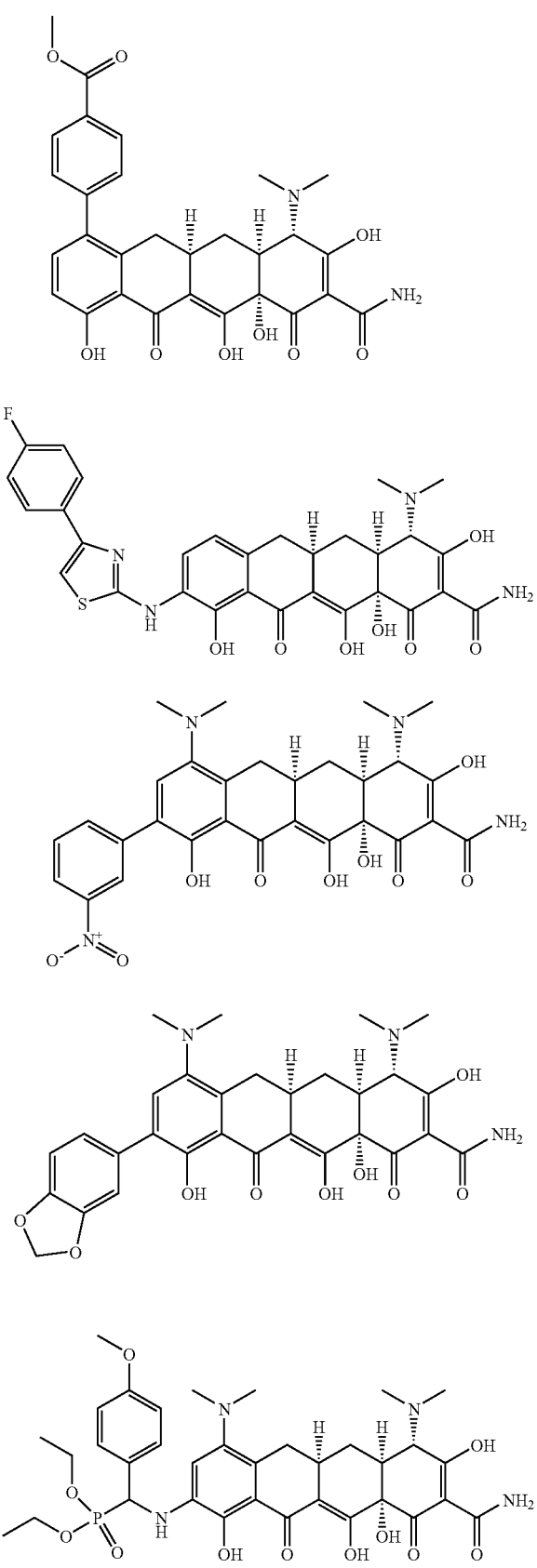
498
-continued
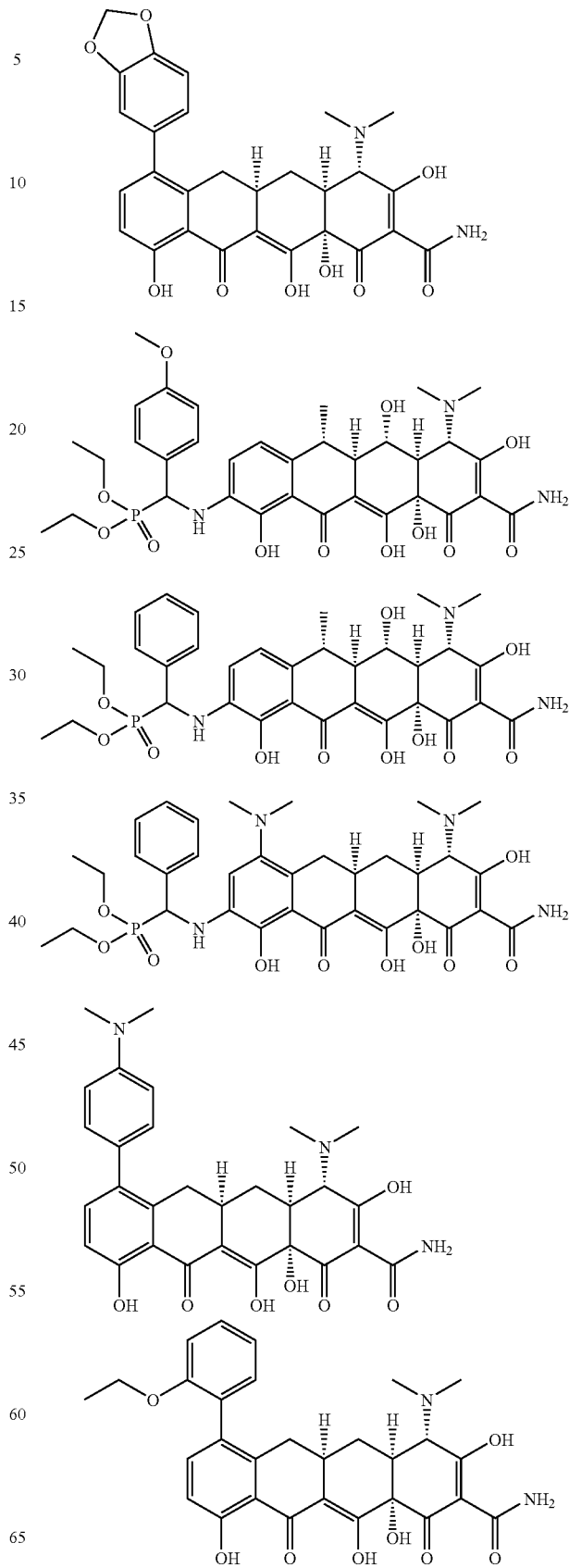

499
-continued
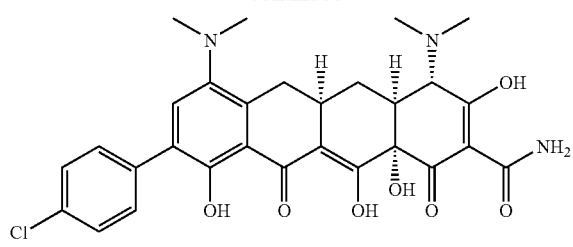
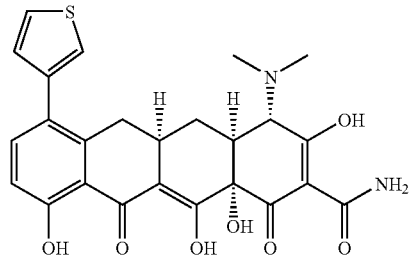
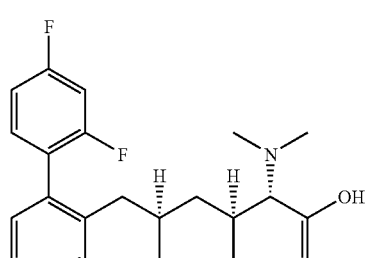
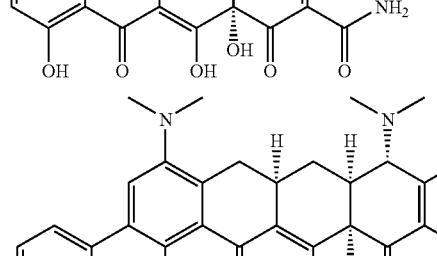
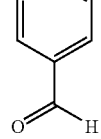
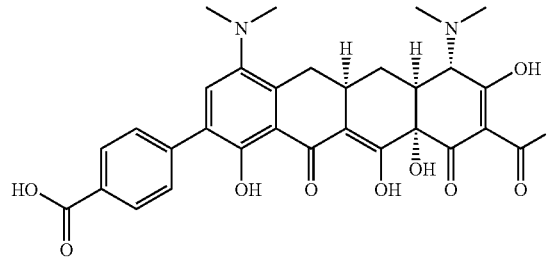
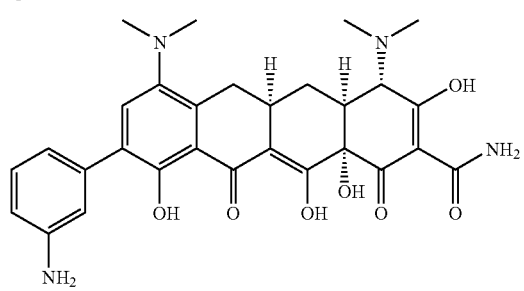
500
-continued
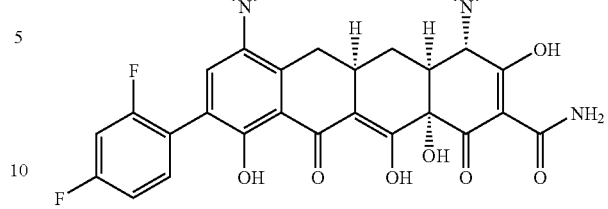
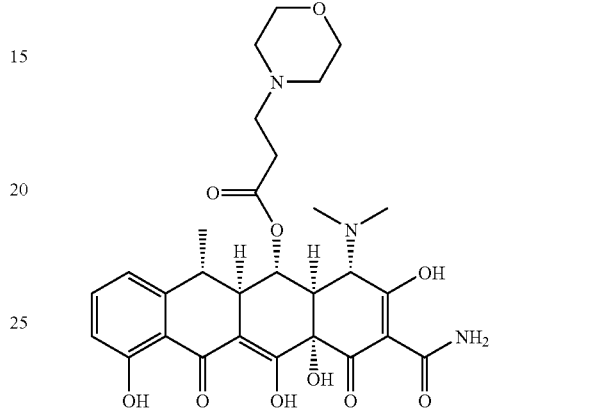
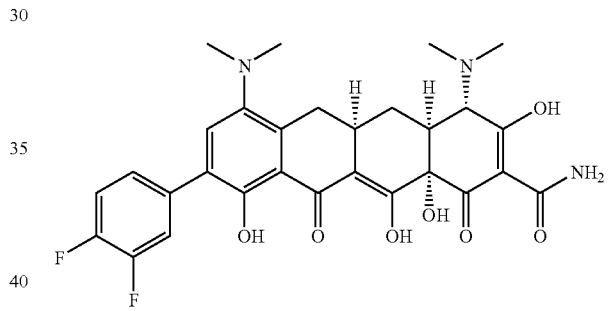
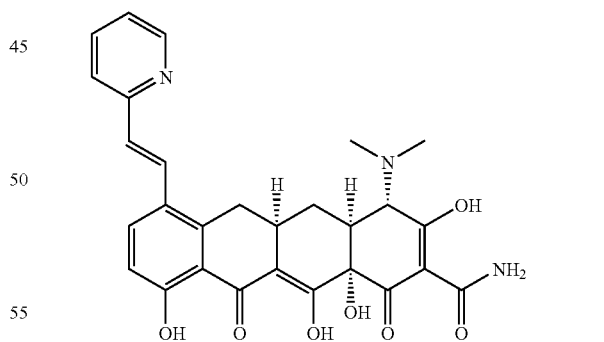
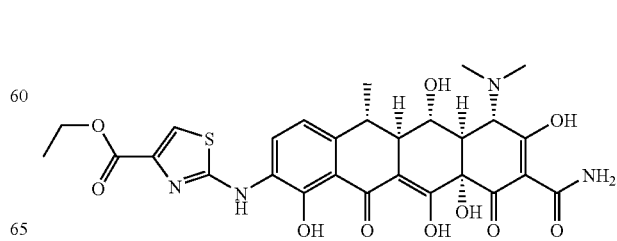

501
-continued
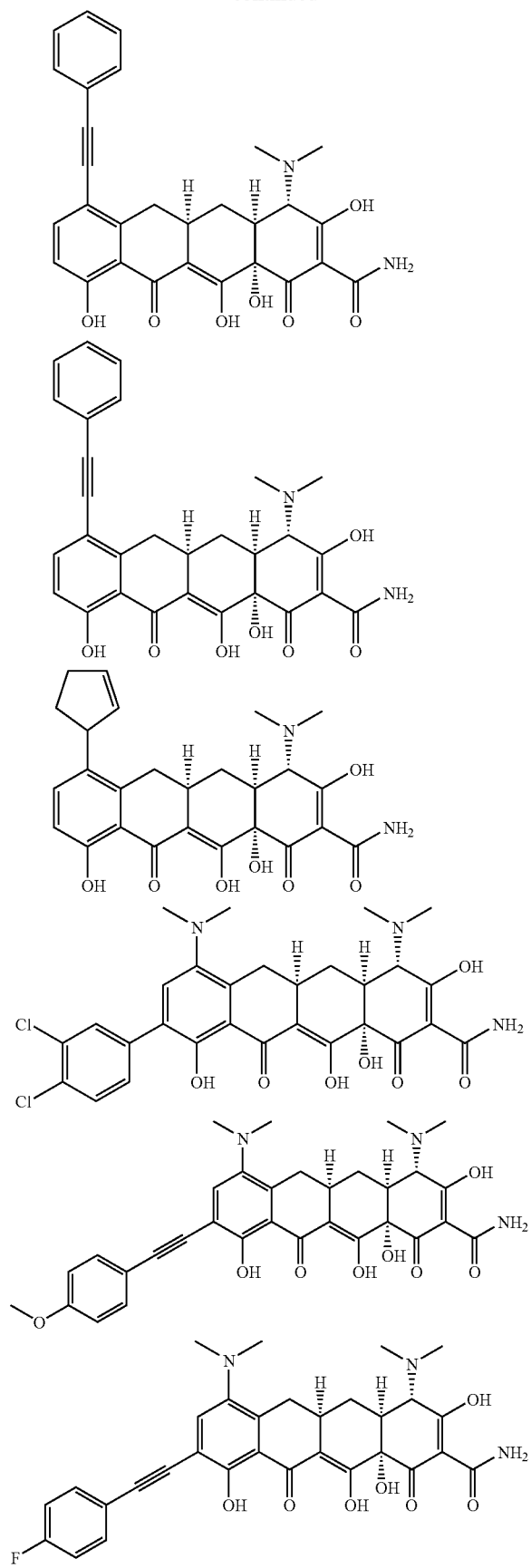
502
-continued
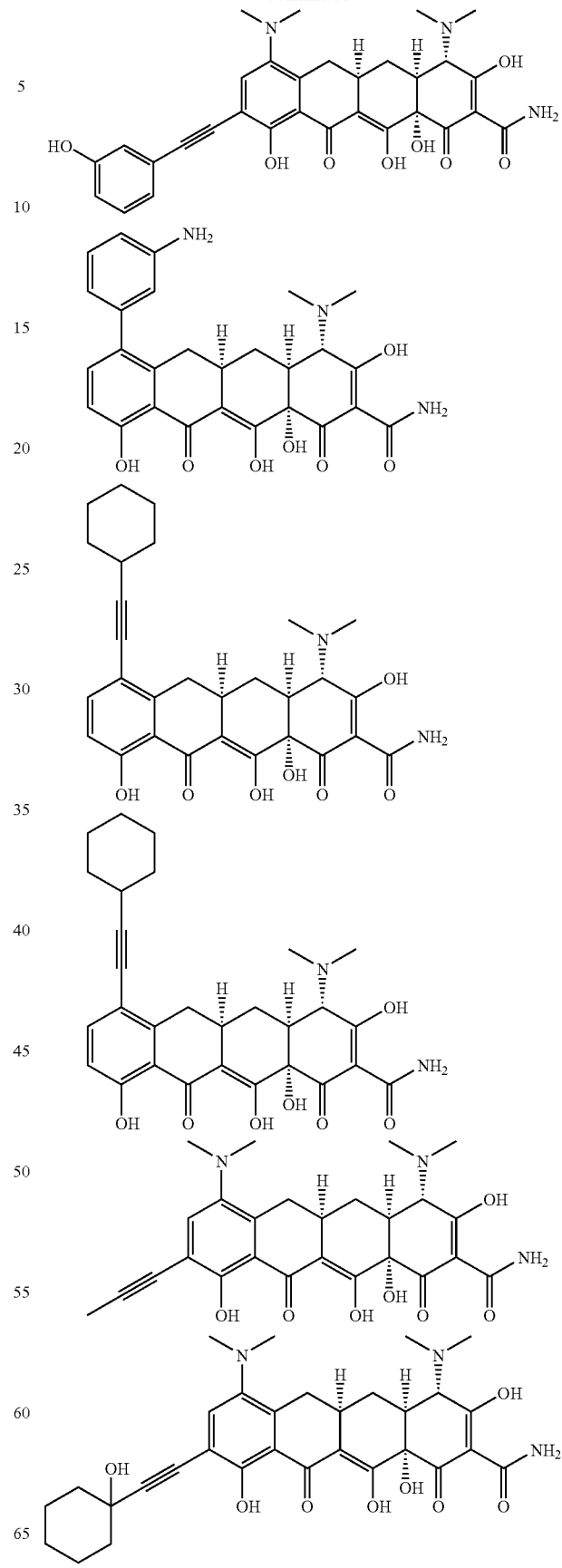

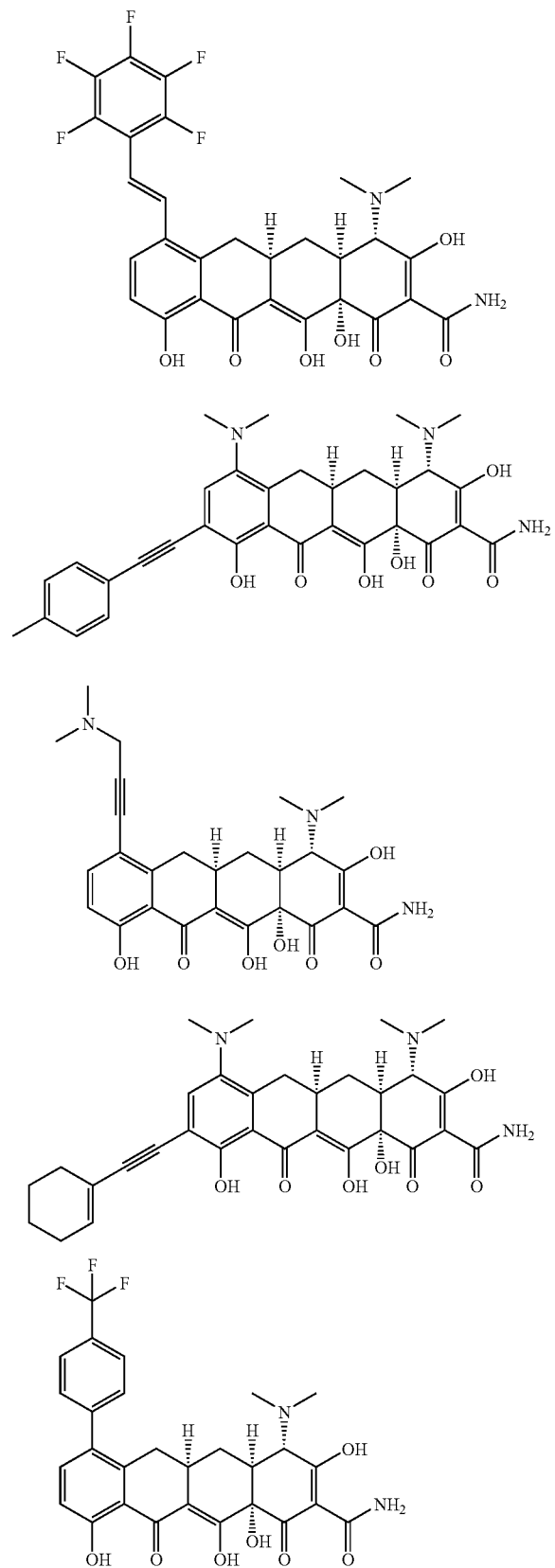
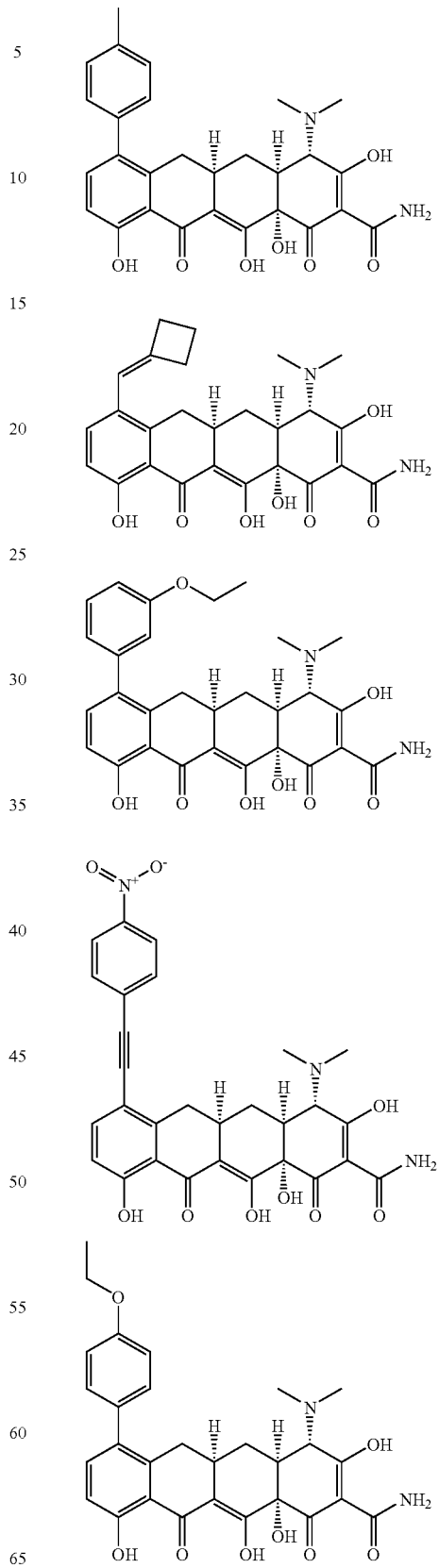

505
-continued
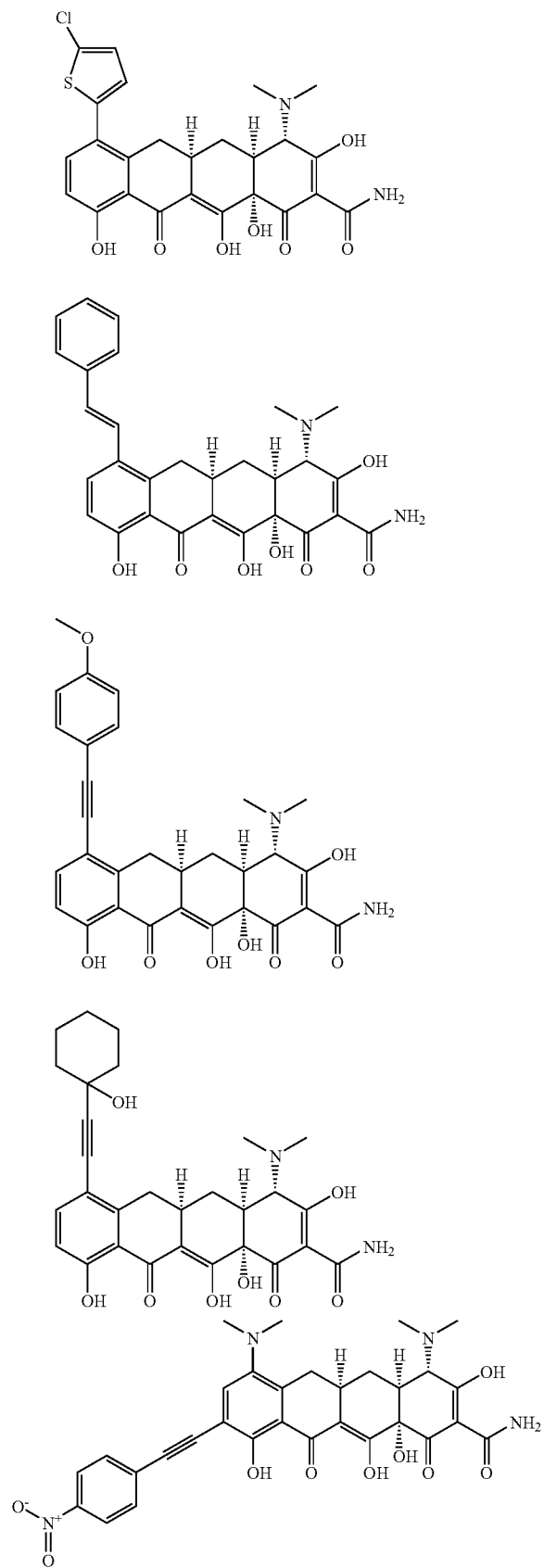
506
-continued
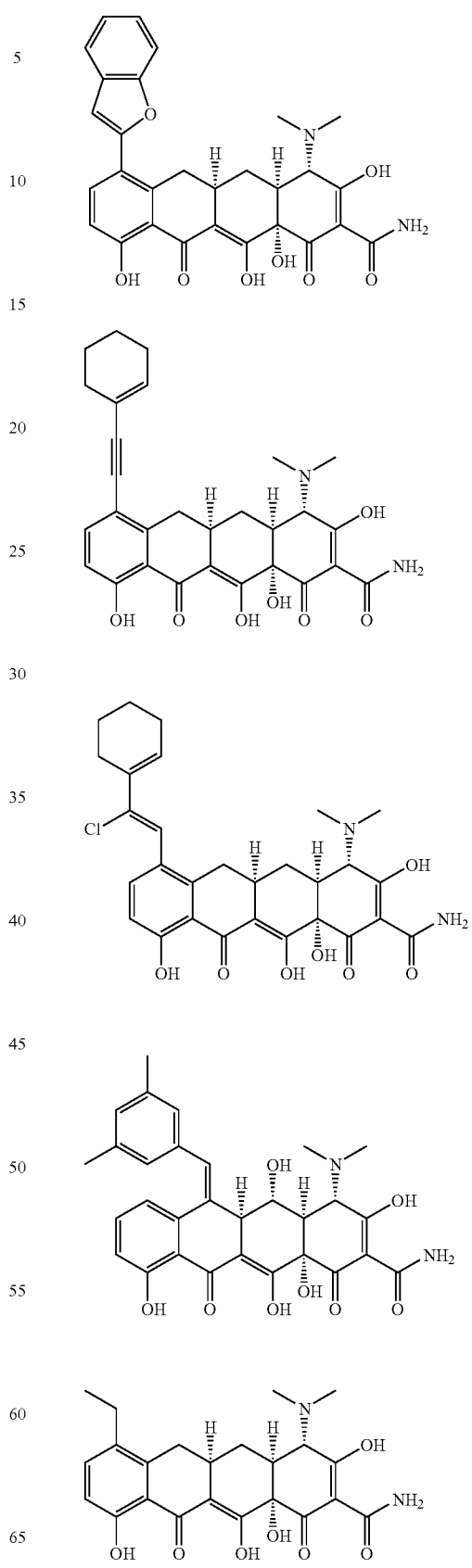

507
-continued
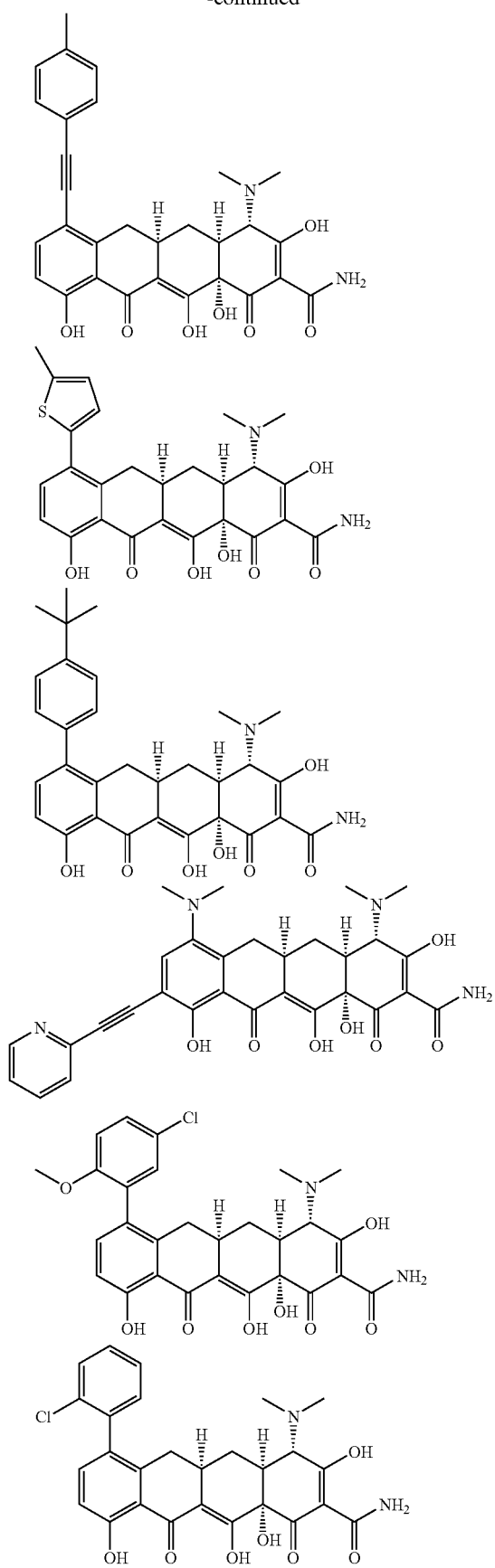
508
-continued
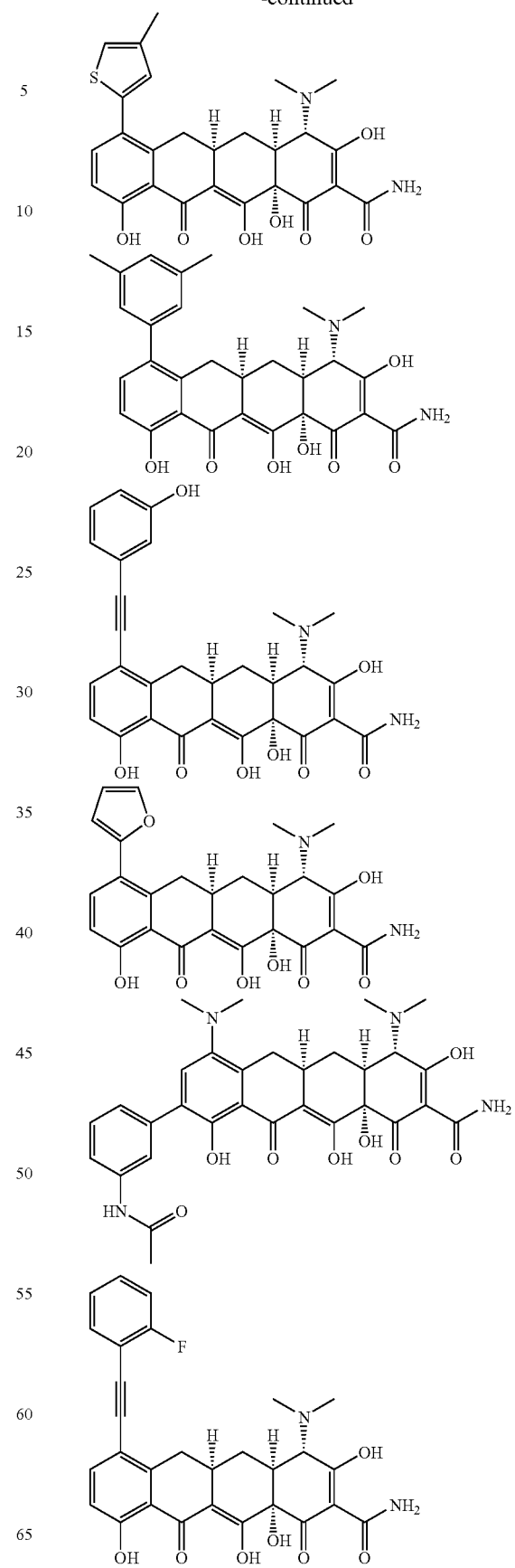

509
-continued
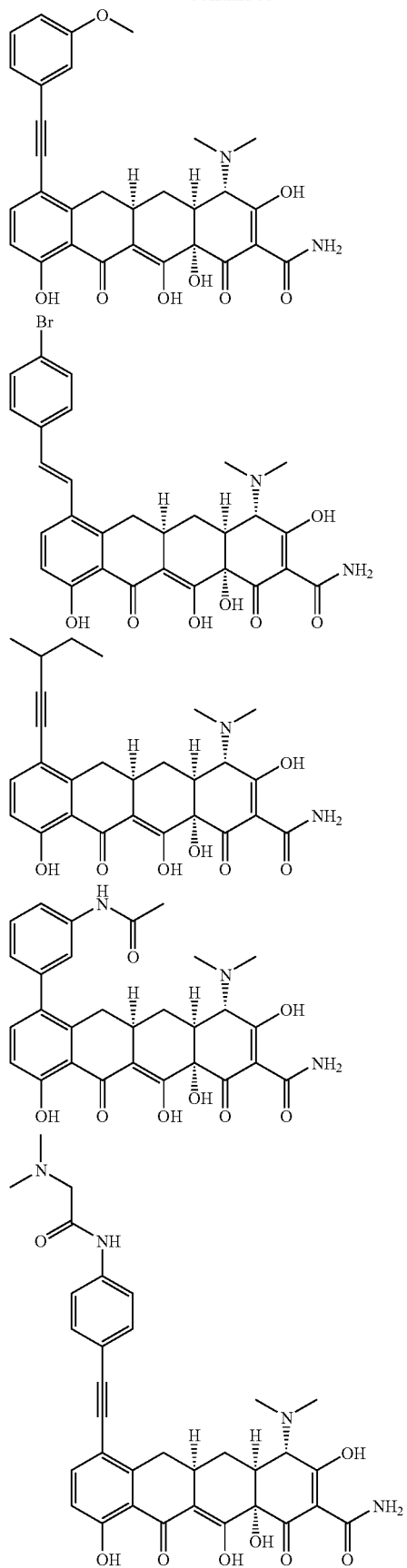
510
-continued
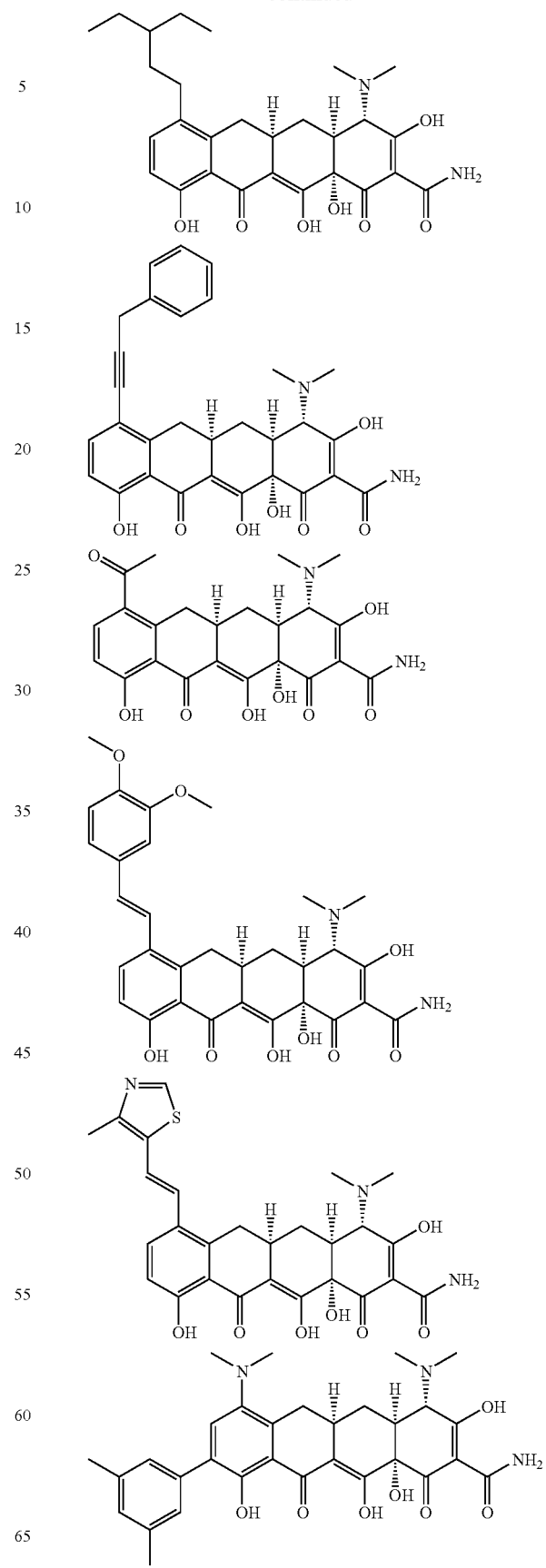

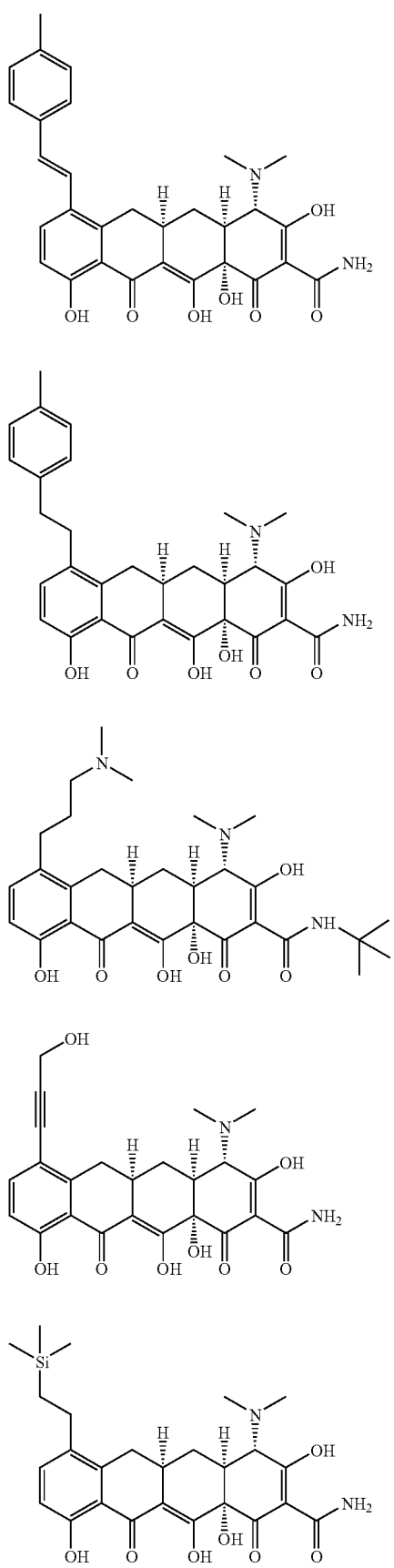

513
-continued
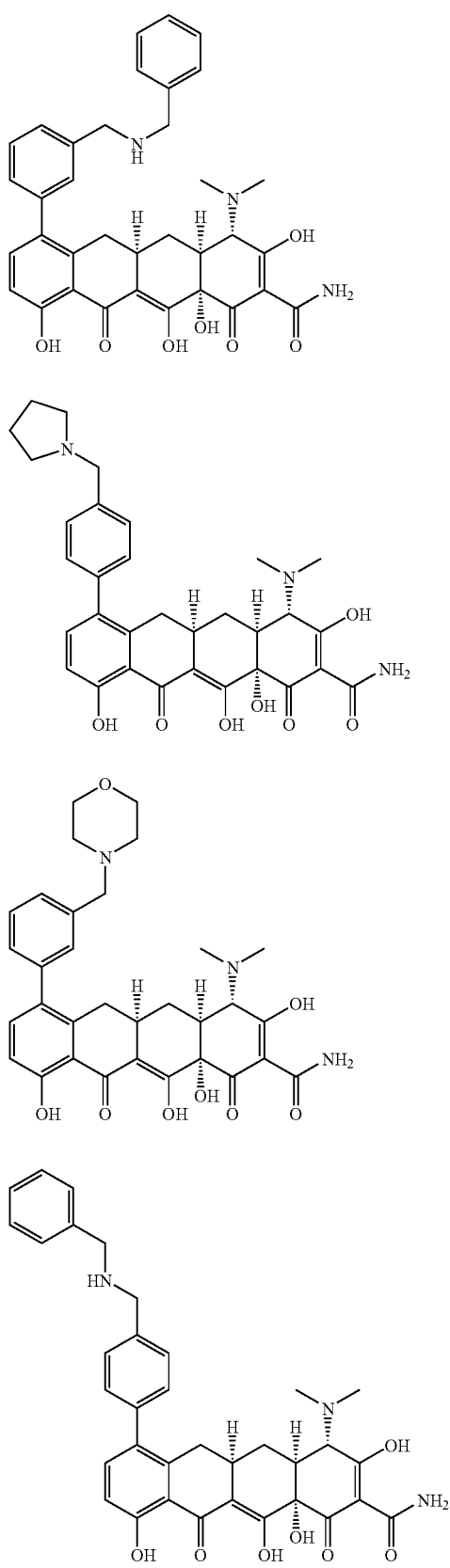
514
-continued
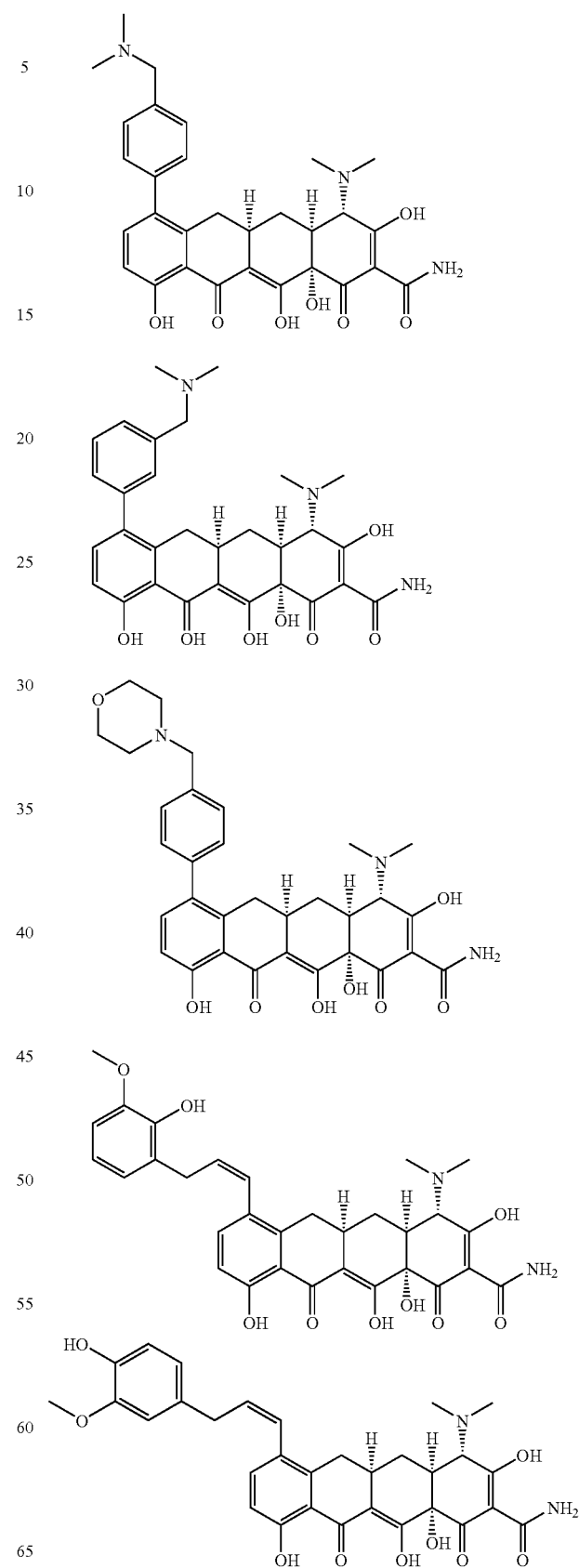

515
-continued
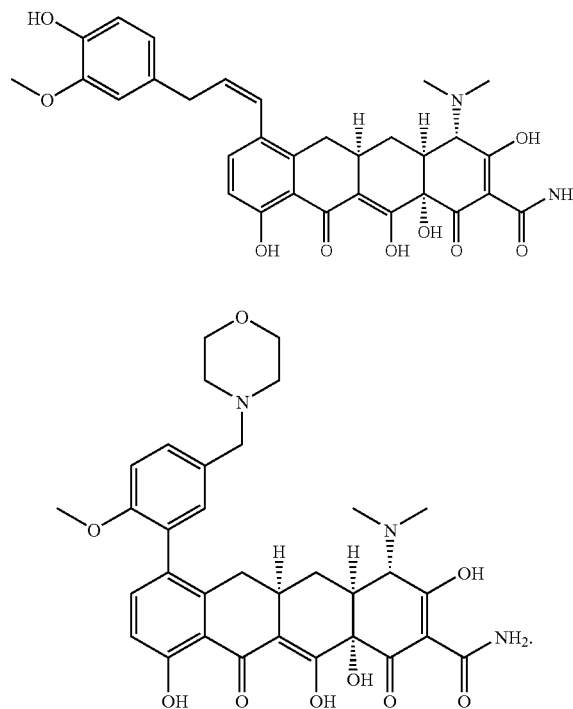
12. A method for increasing the antifungal activity of an antifungal agent, comprising administering said antifungal agent in combination with an effective amount of a substituted tetracycline compound, such that the antifungal activity of said antifungal agent is increased, wherein said tetracycline compound is:
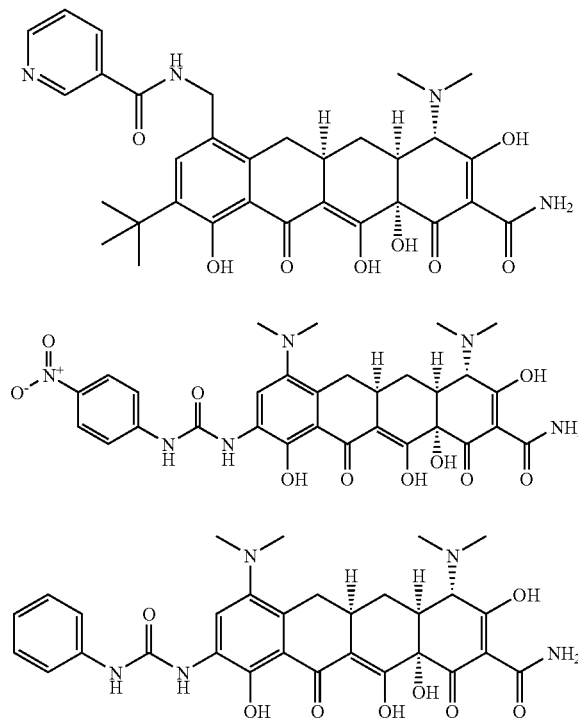
516
-continued
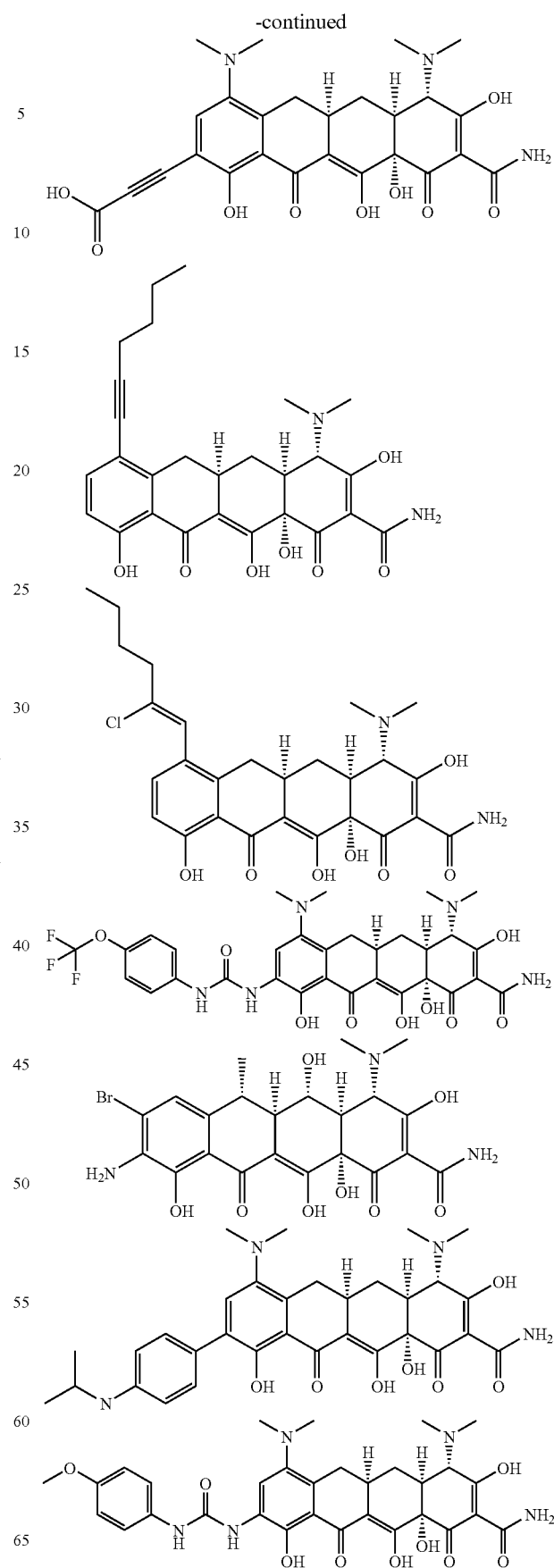

517
-continued
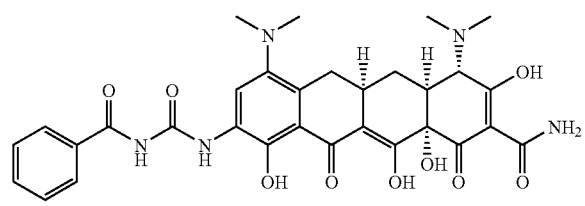
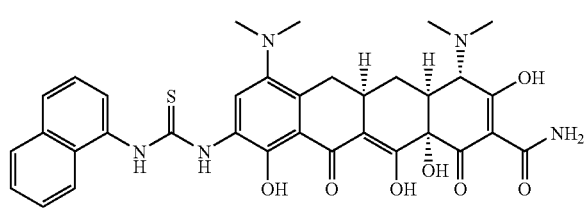
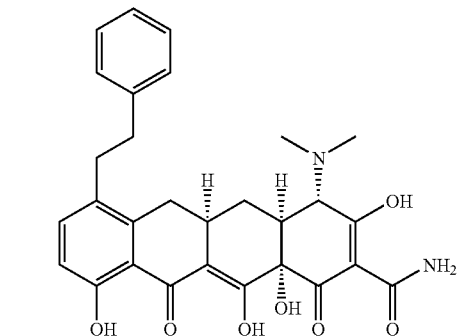
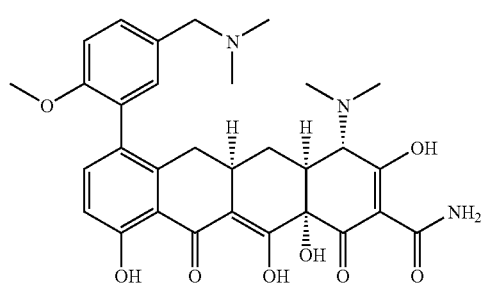
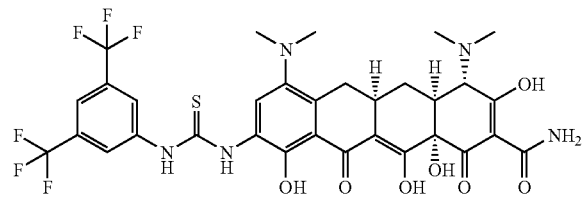
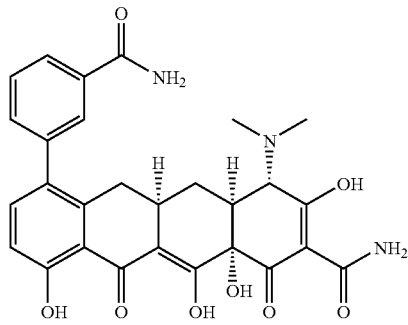
518
-continued
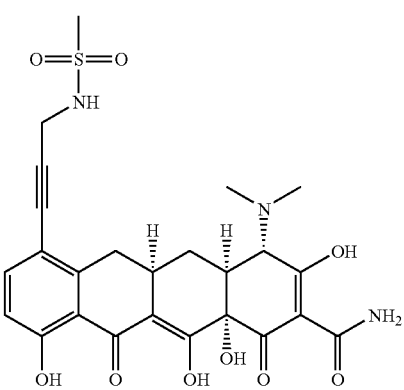
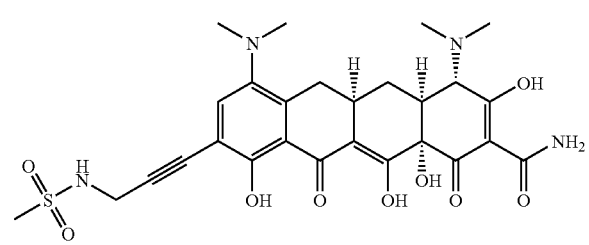
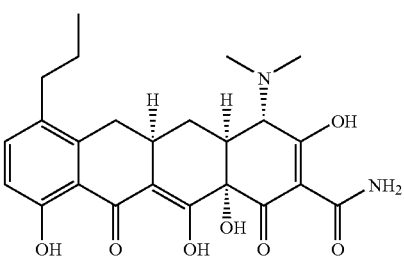
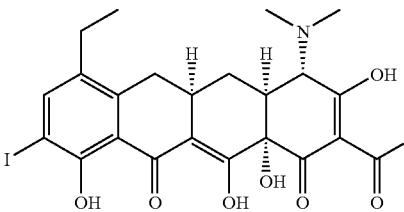
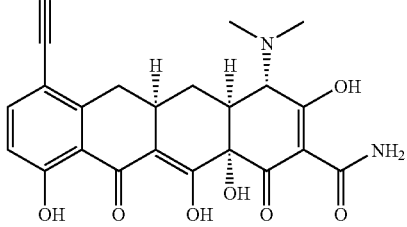

519
-continued
520
-continued
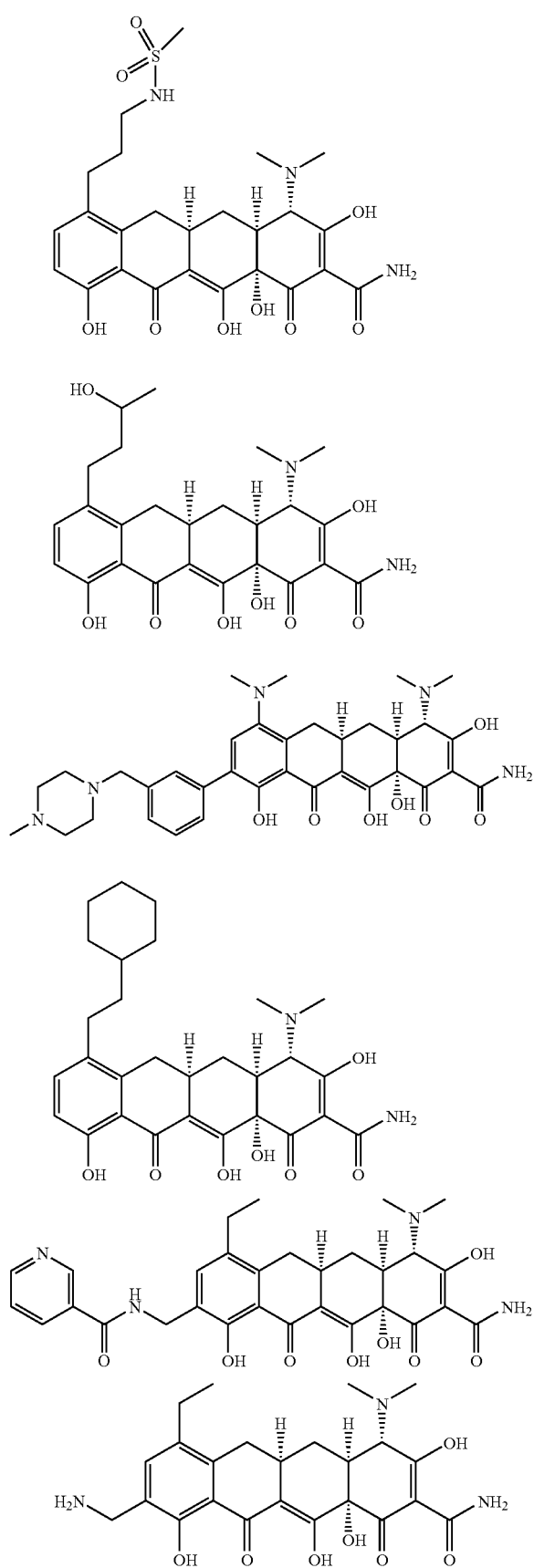
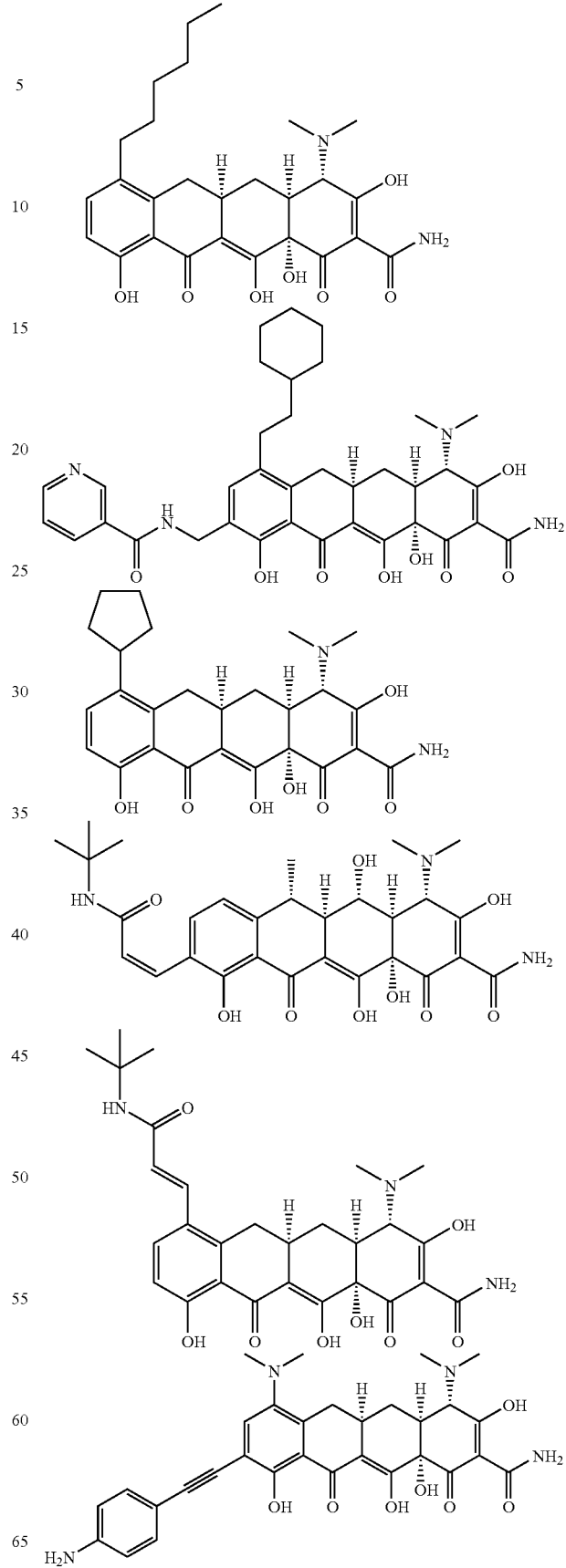

521
-continued
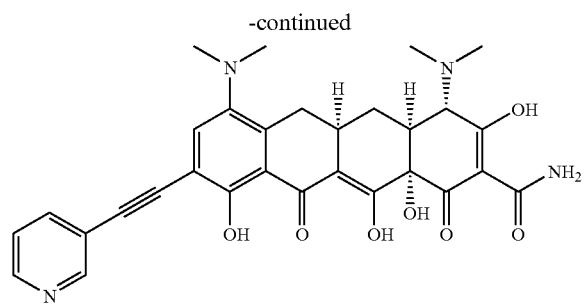
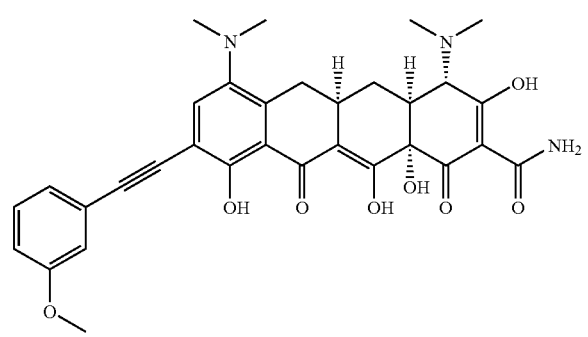
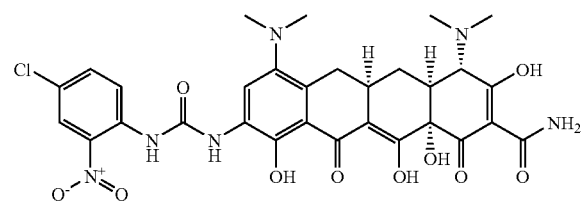
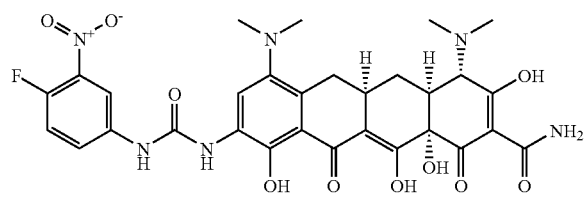
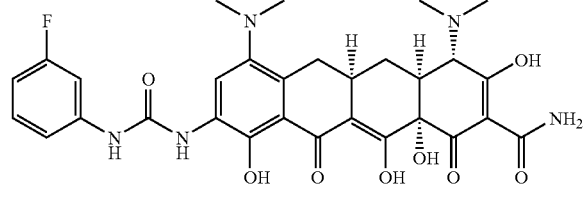
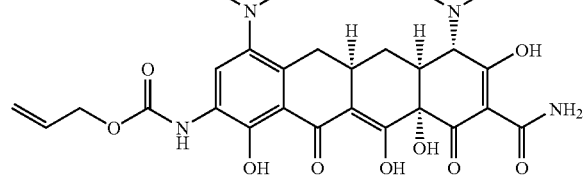
522
-continued
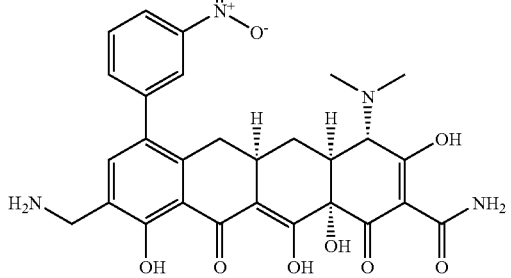
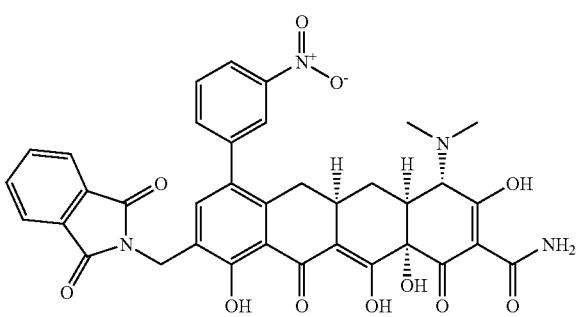
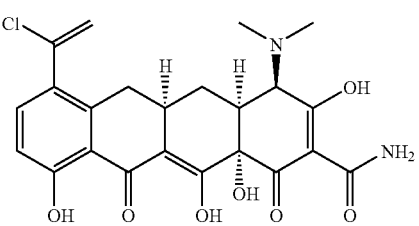
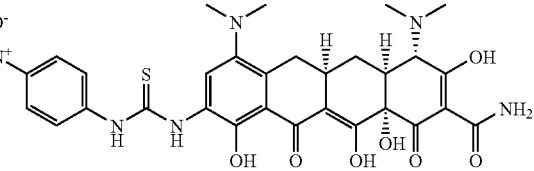
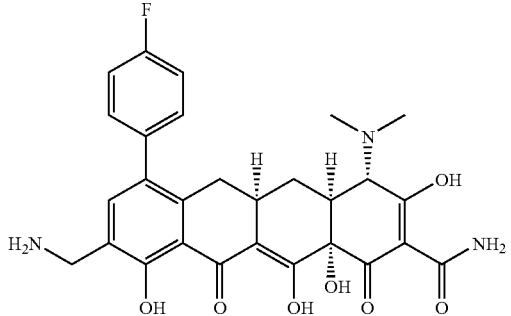
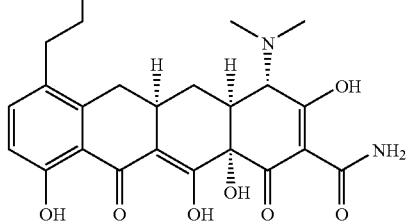

523
-continued
524
-continued
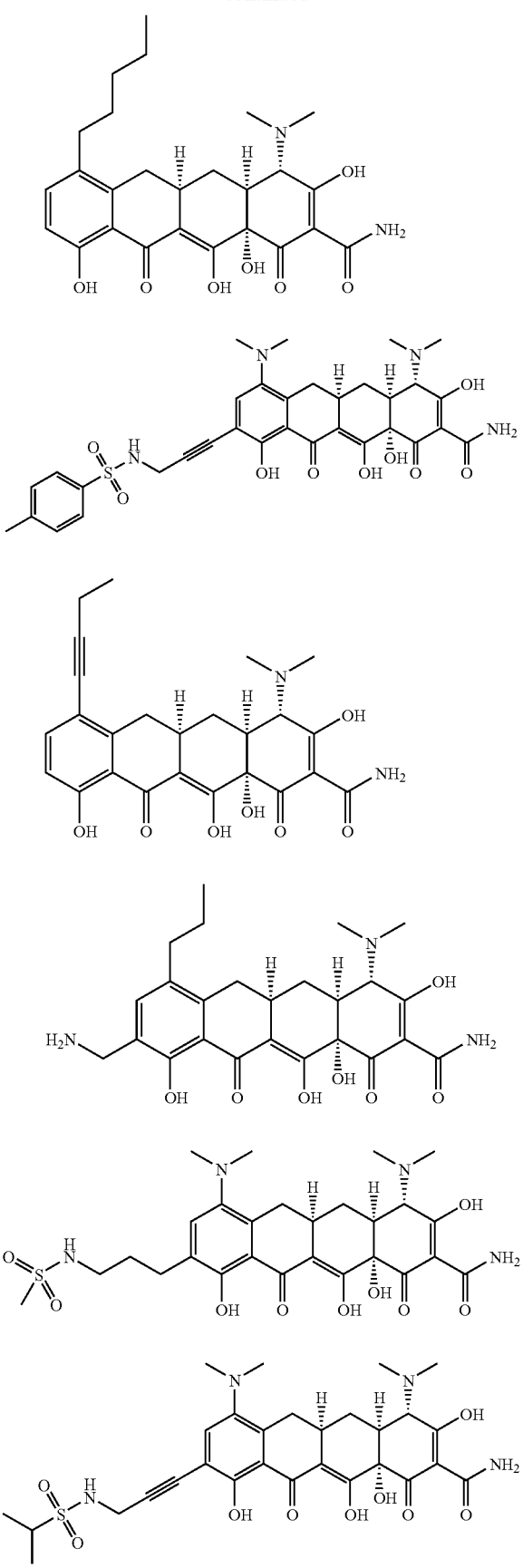
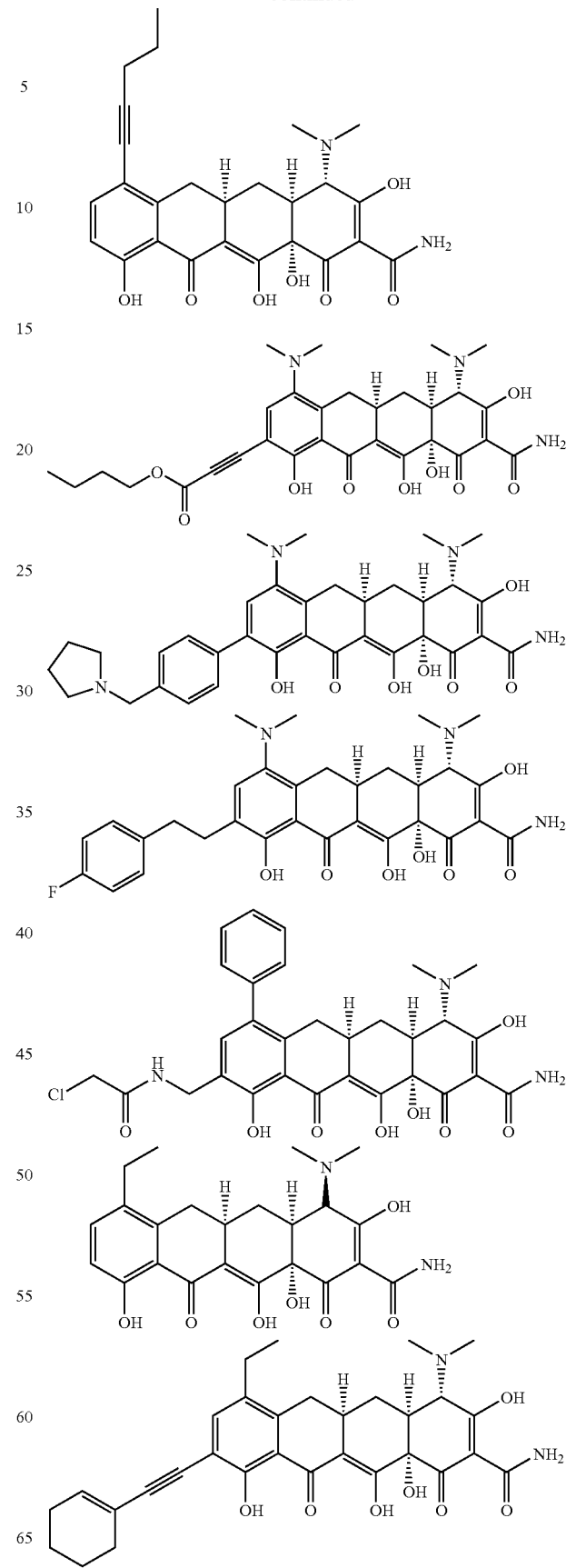

525
-continued
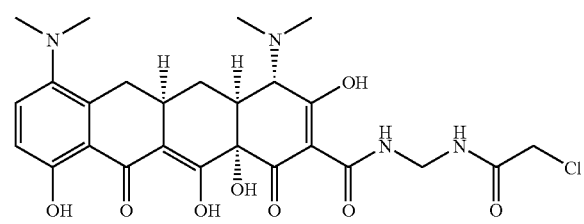
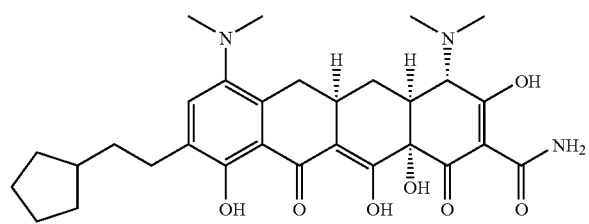
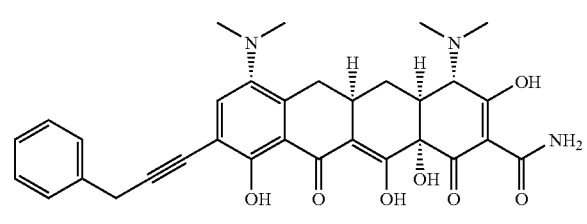
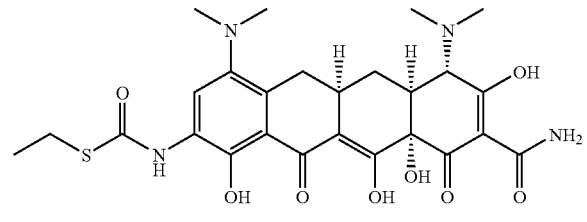
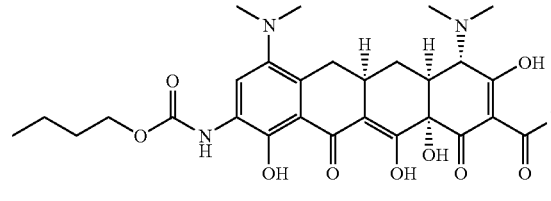
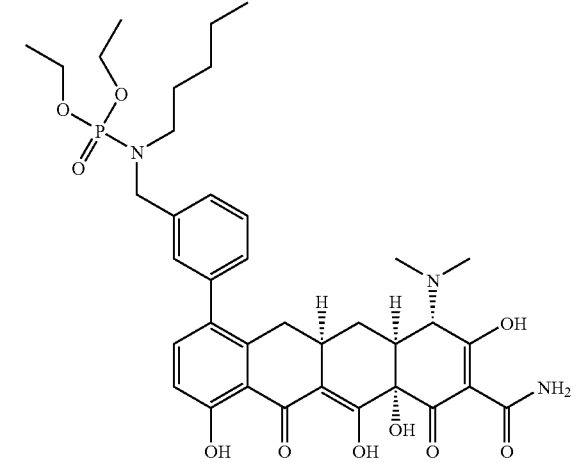
526
-continued
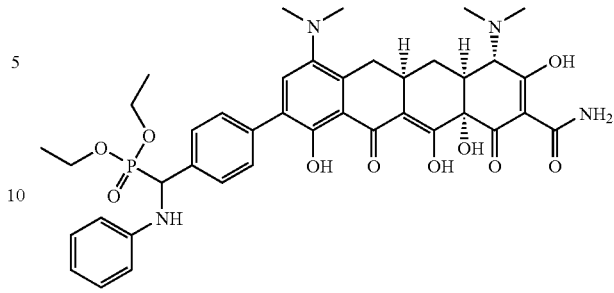
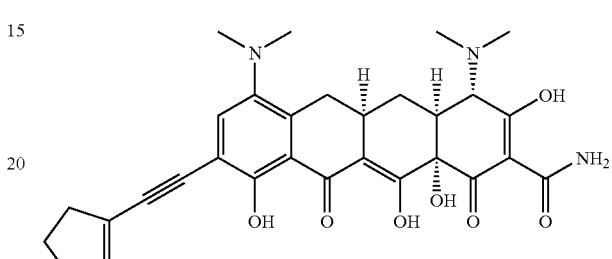
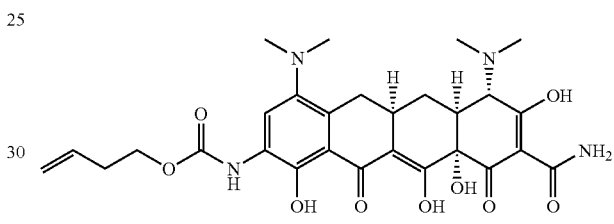
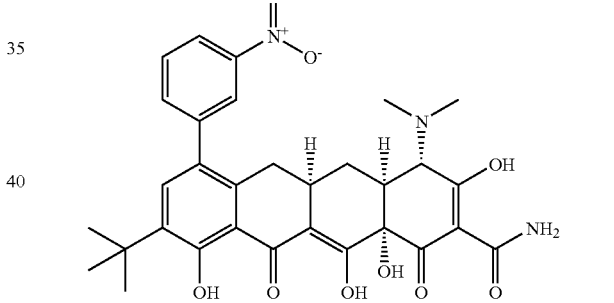
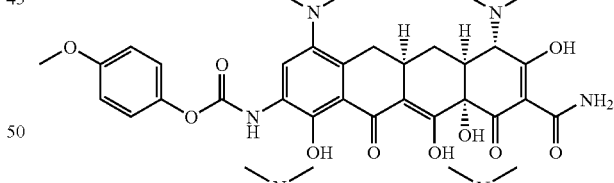
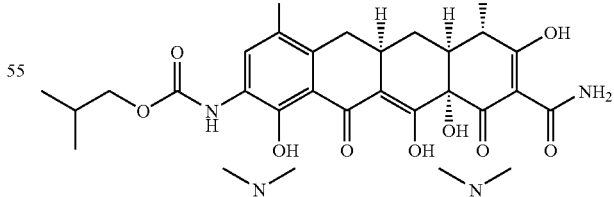
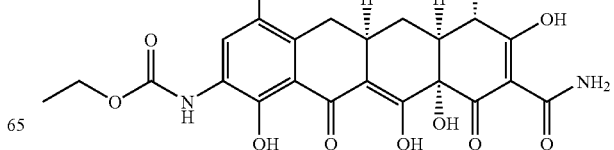

527
-continued
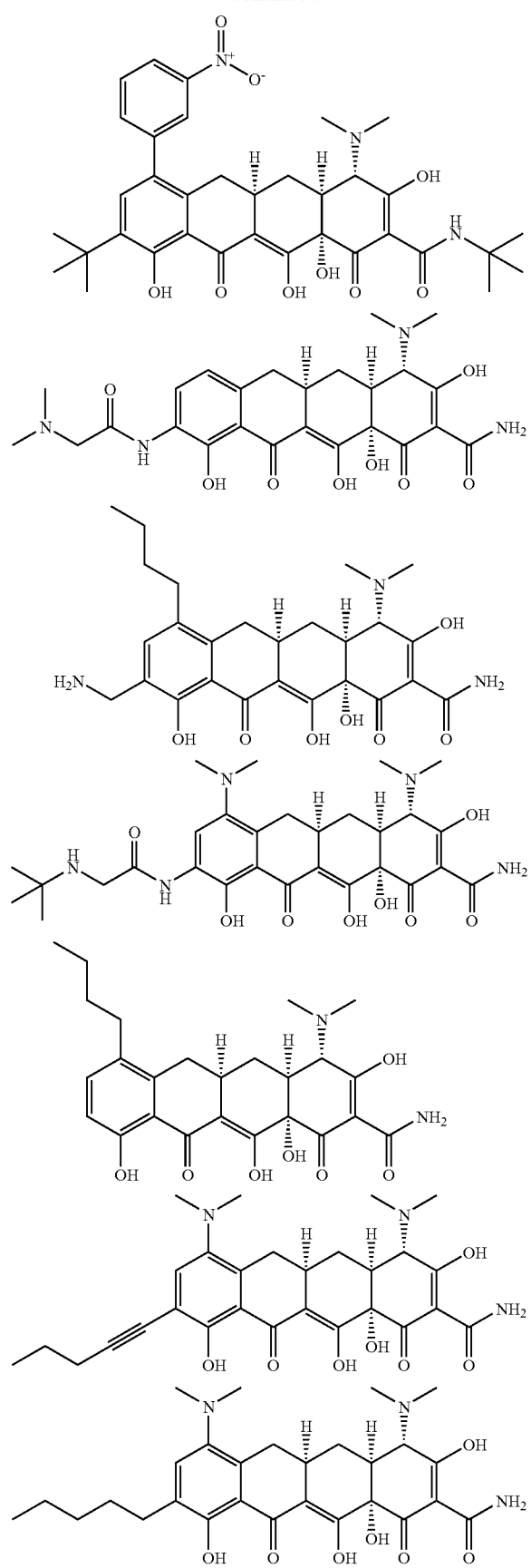
528
-continued
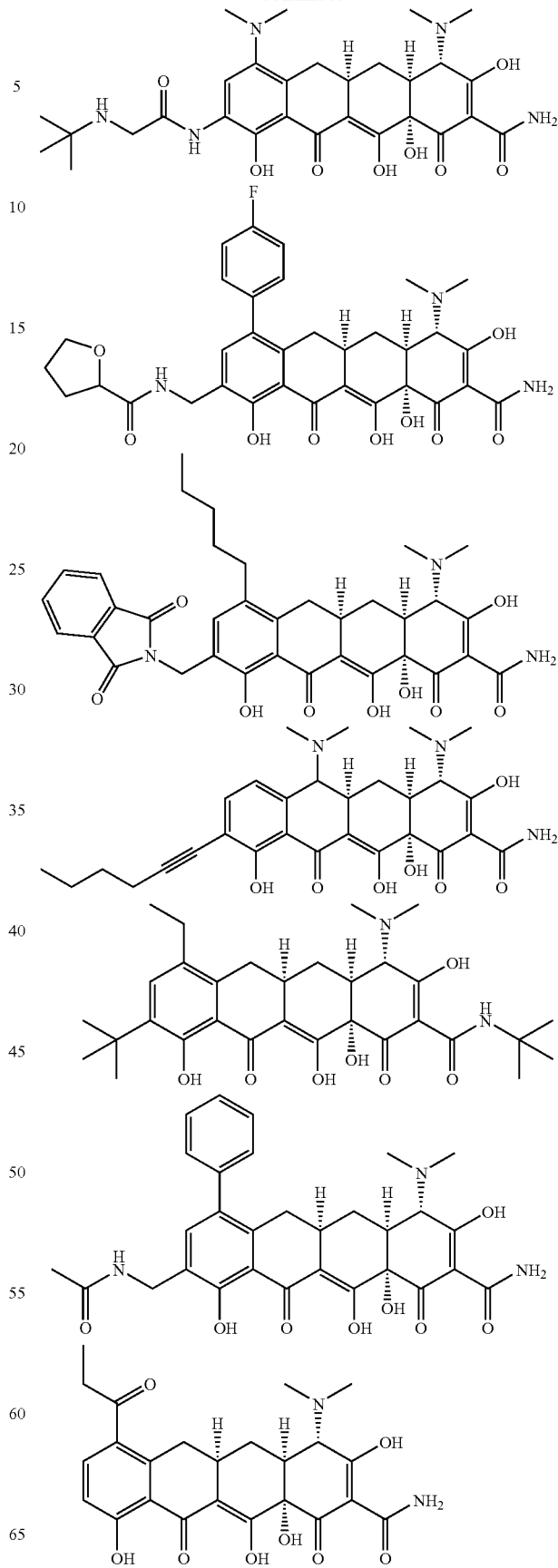

529
-continued
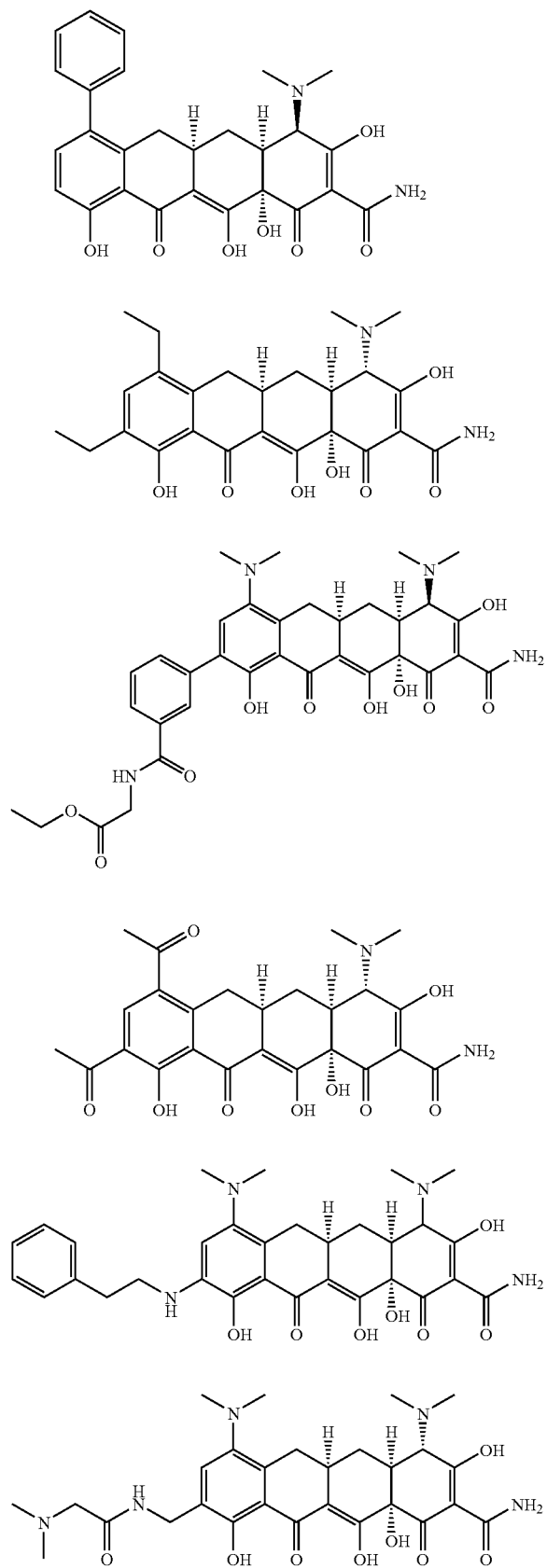
530
-continued
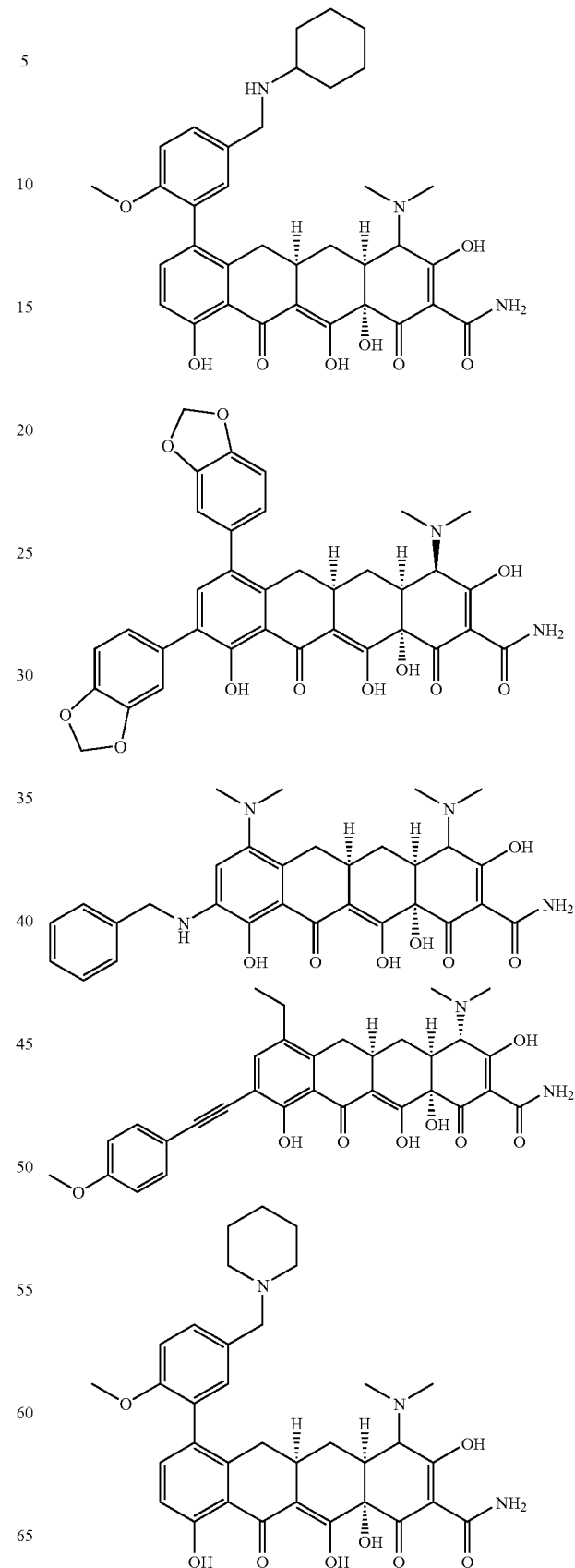

531
-continued
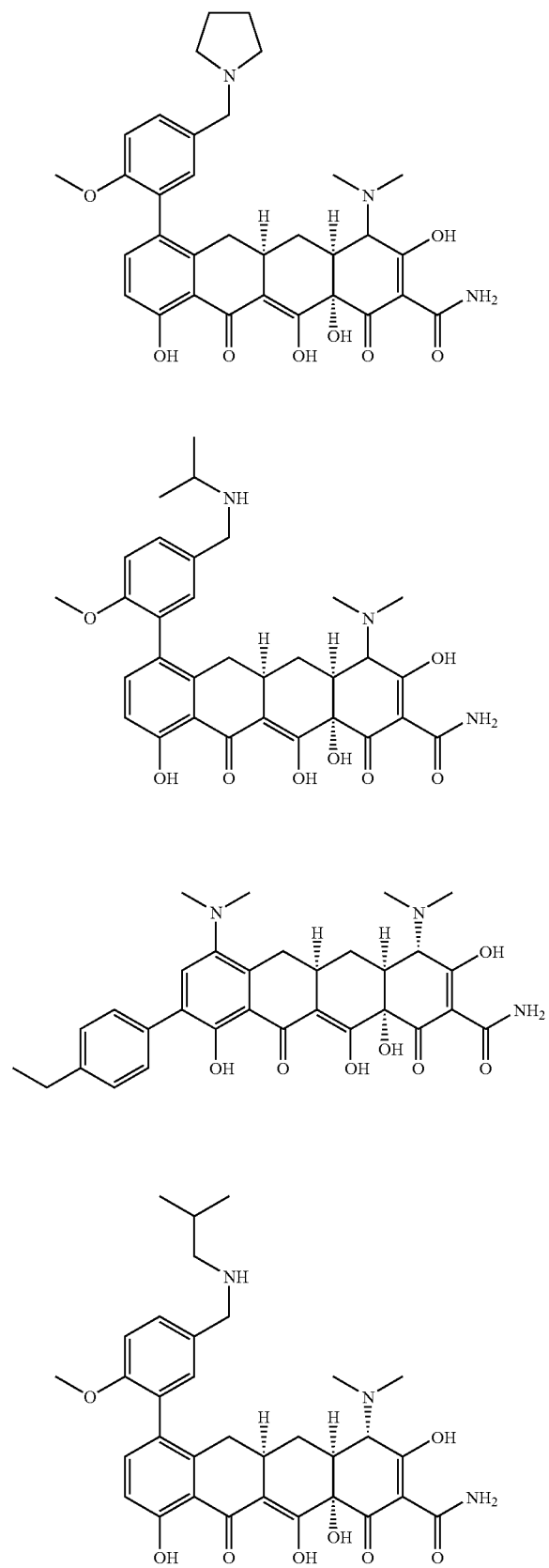
532
-continued
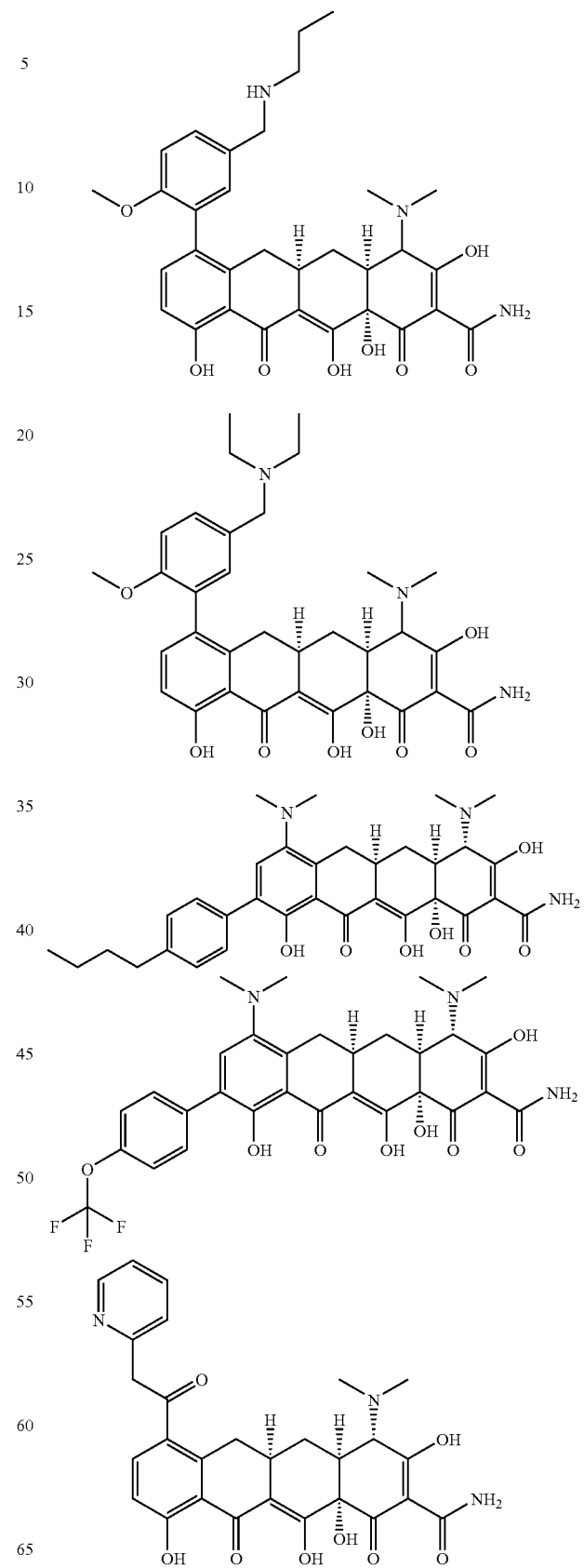

533
-continued
534
-continued
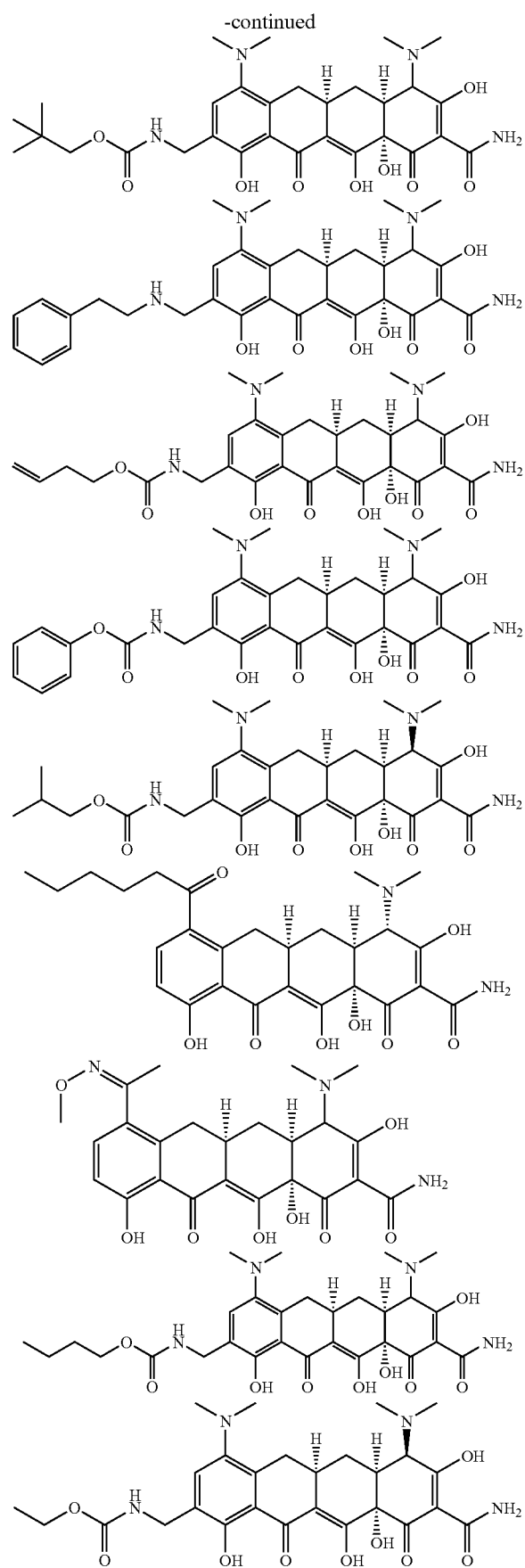
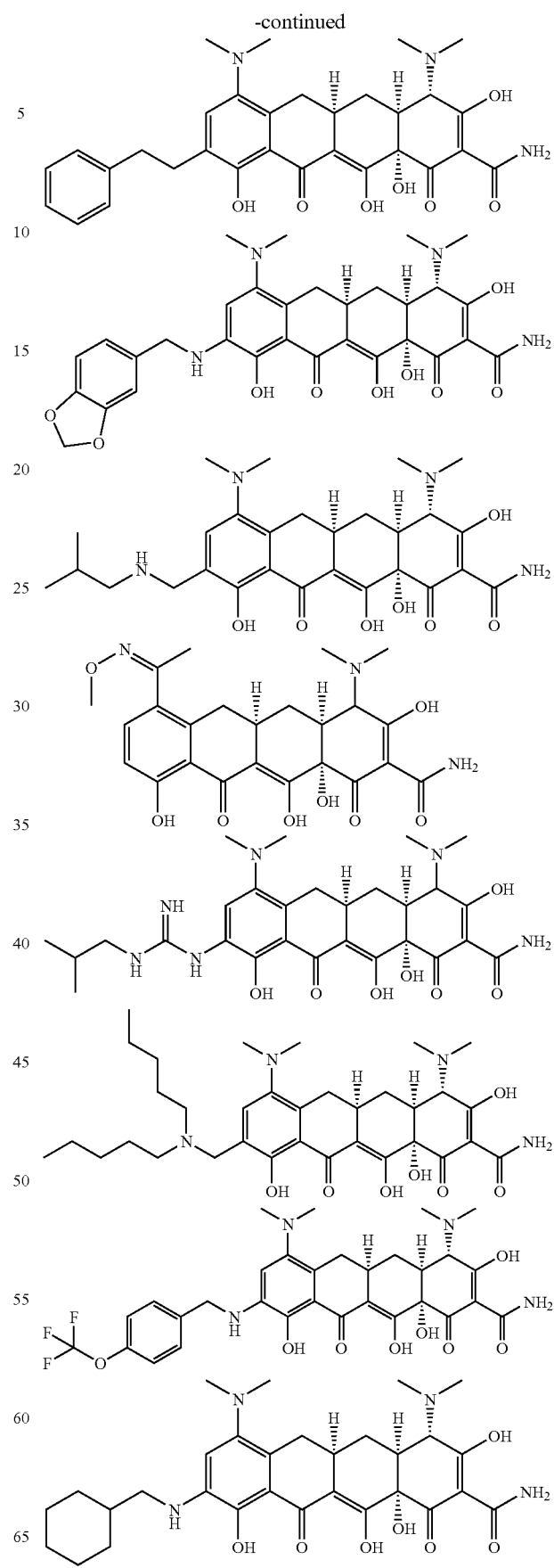

535
-continued
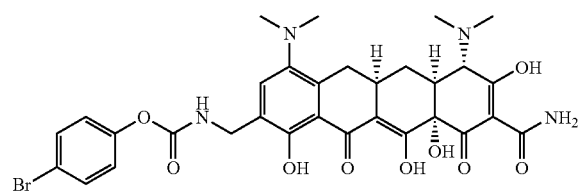
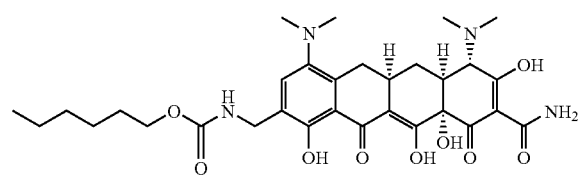
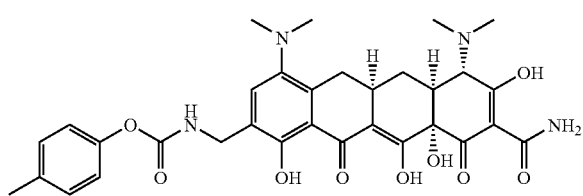
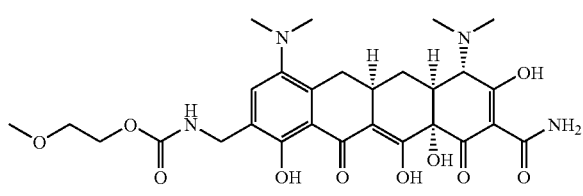
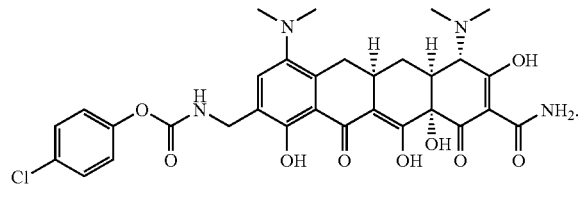
13. A method for increasing the antifungal activity of an antifungal agent, comprising administering said antifungal agent in combination with an effective amount of a substituted tetracycline compound, such that the antifungal activity of said antifungal agent is increased, wherein said tetracycline compound is:
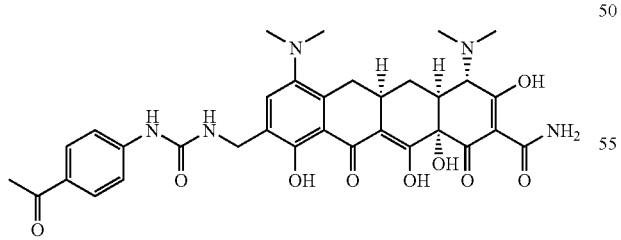
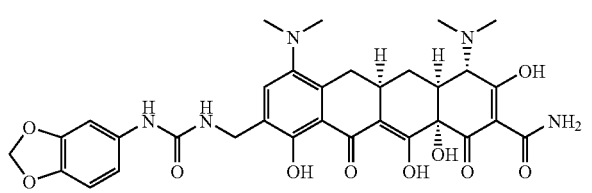
536
-continued
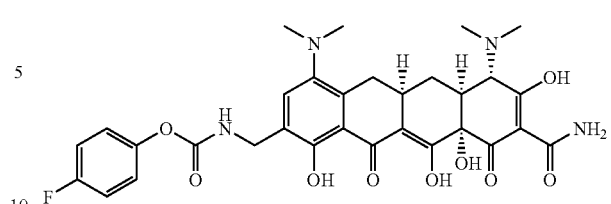
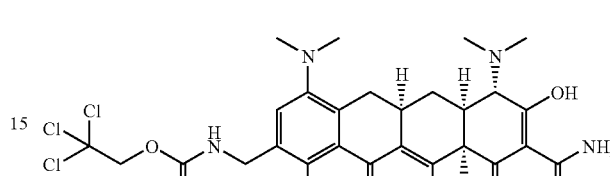
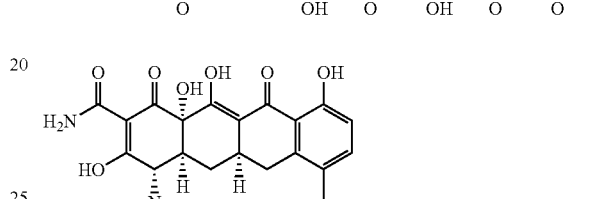
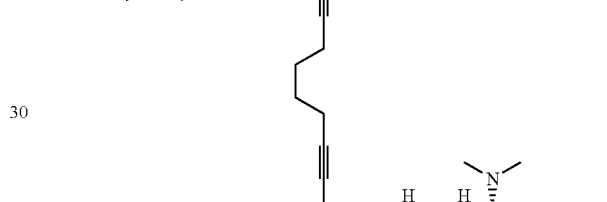
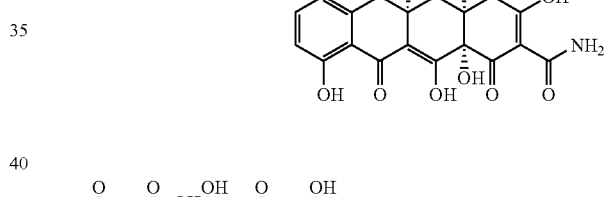
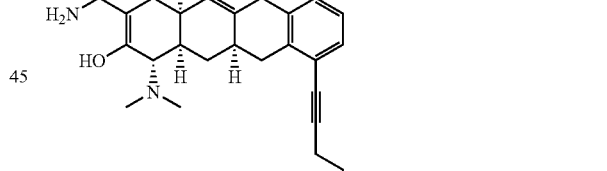
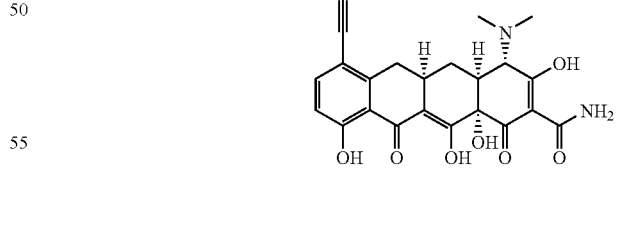
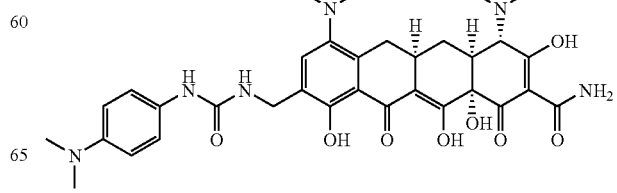

537
-continued
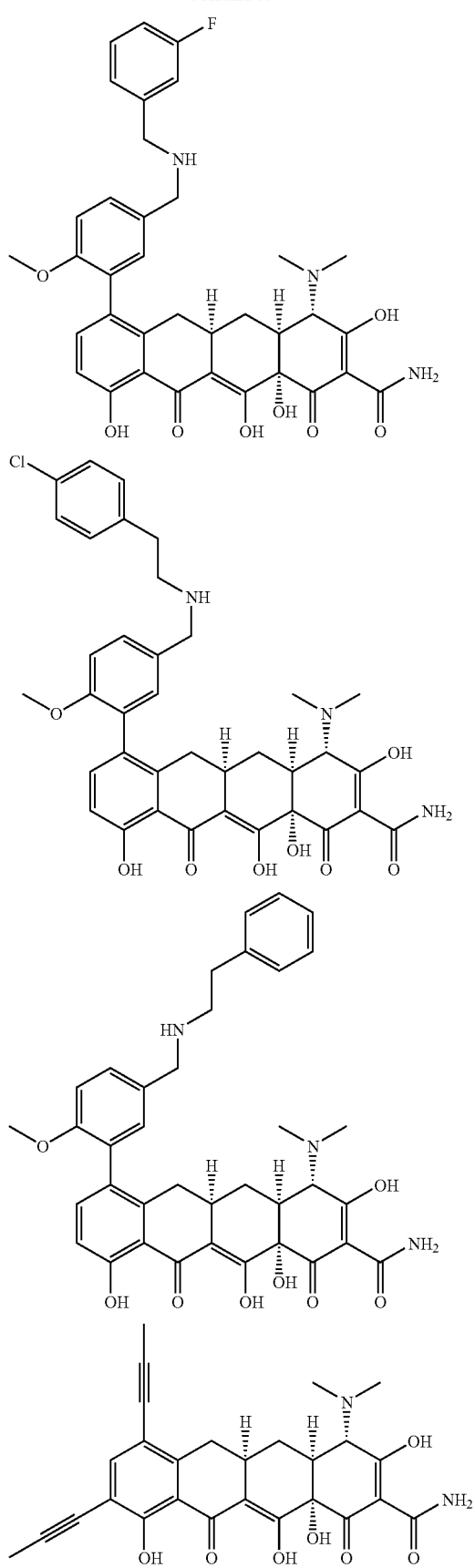
538
-continued
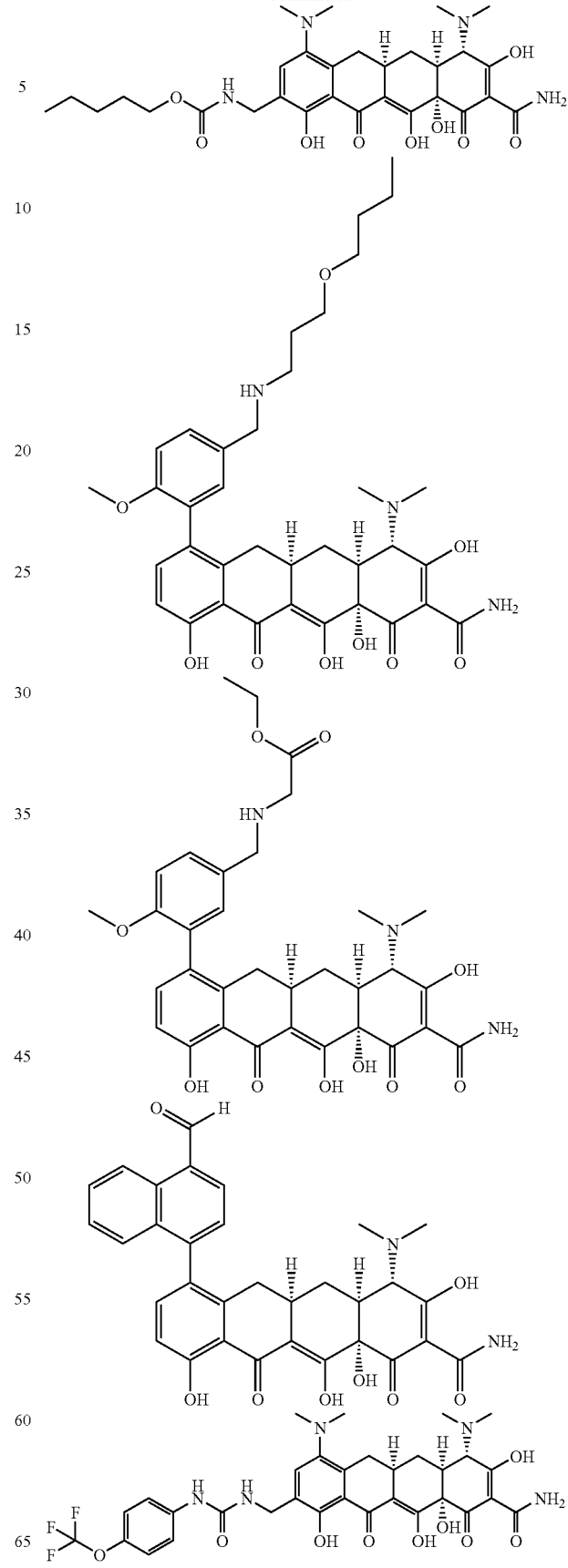

539
-continued
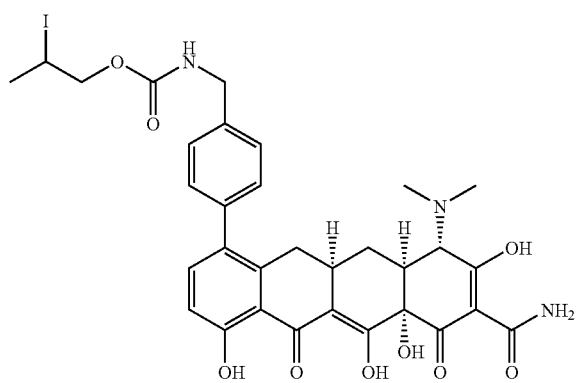
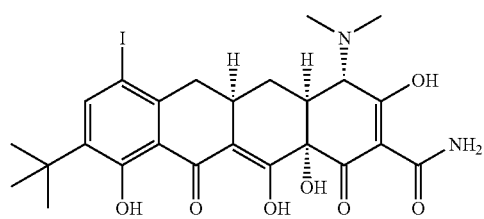
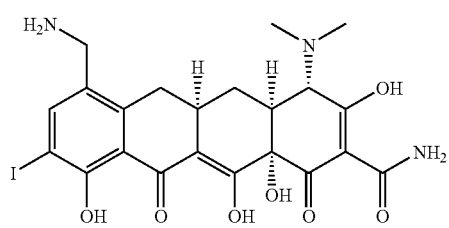
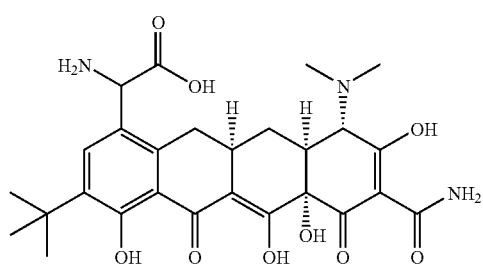
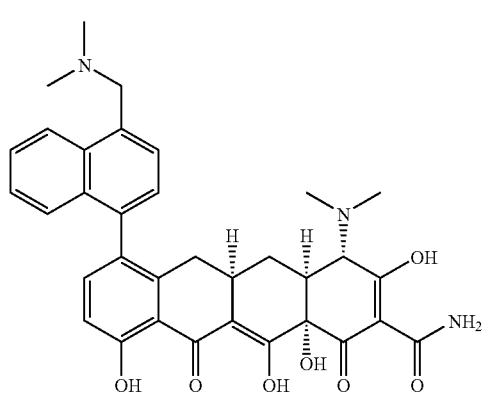
540
-continued
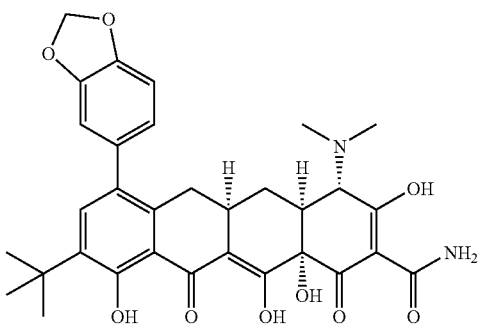
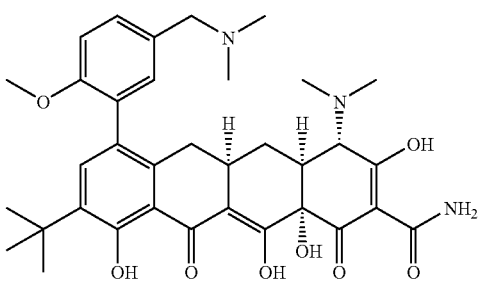
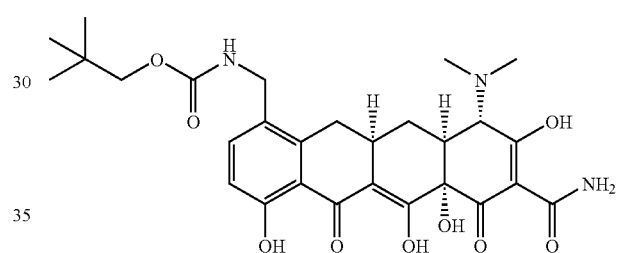
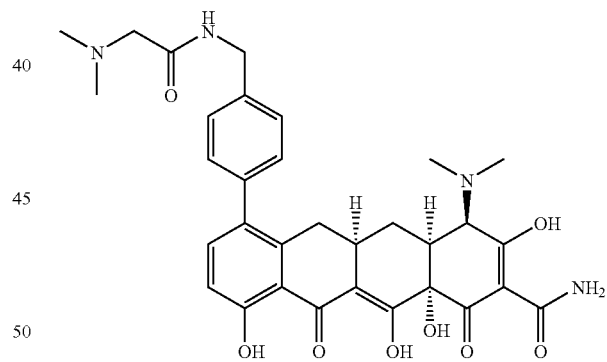
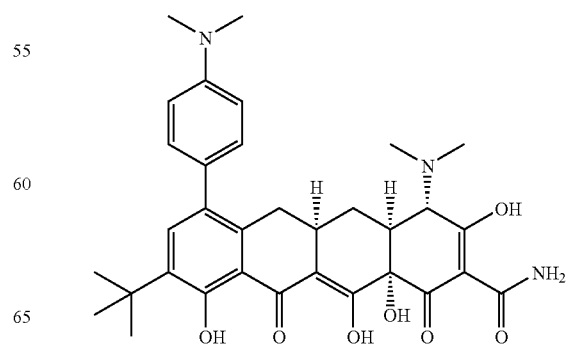

541
-continued
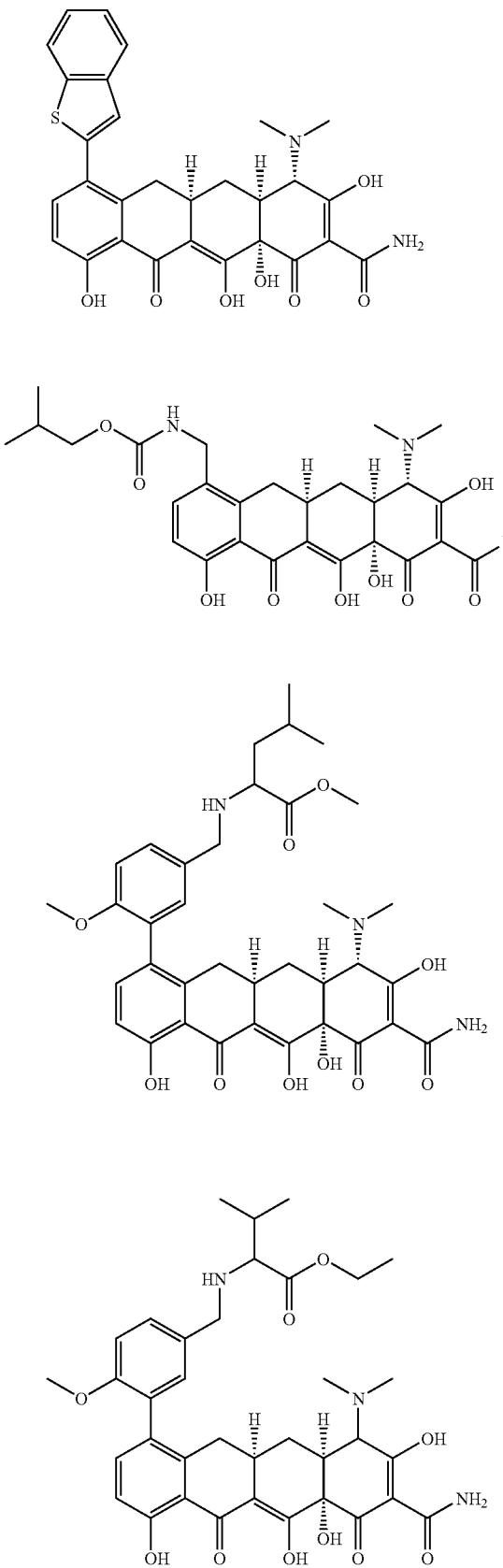
542
-continued
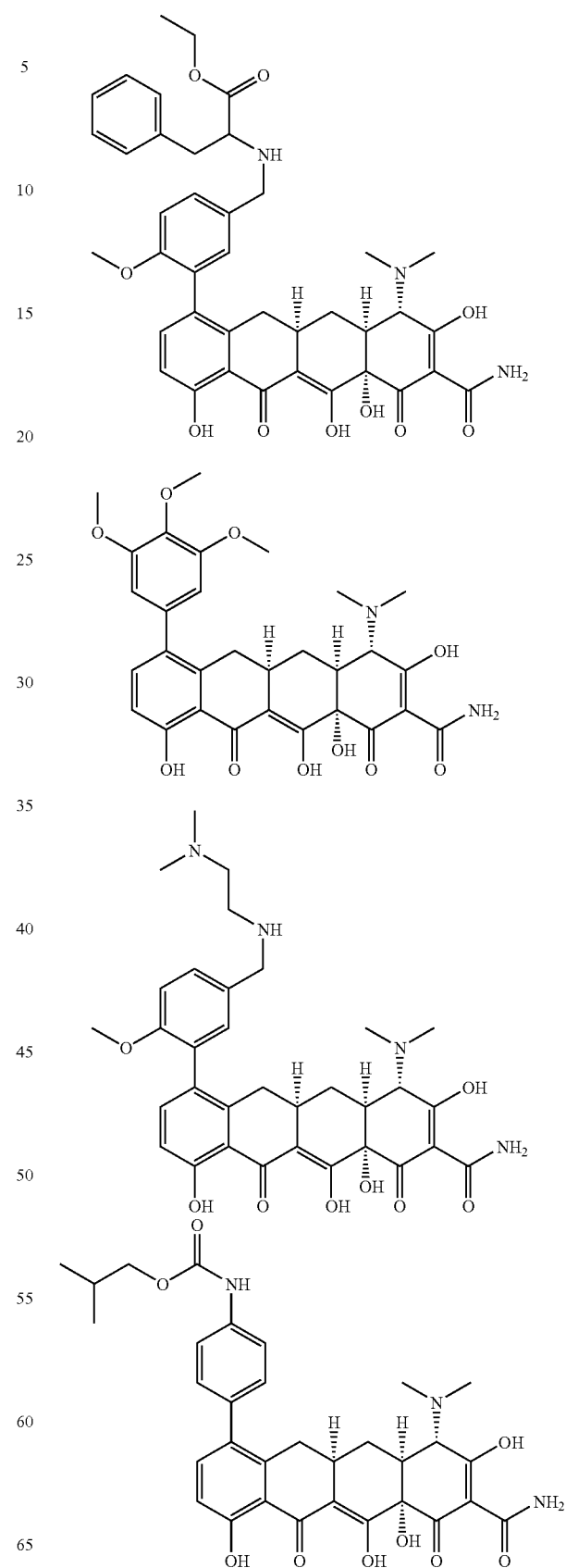

543
-continued
544
-continued
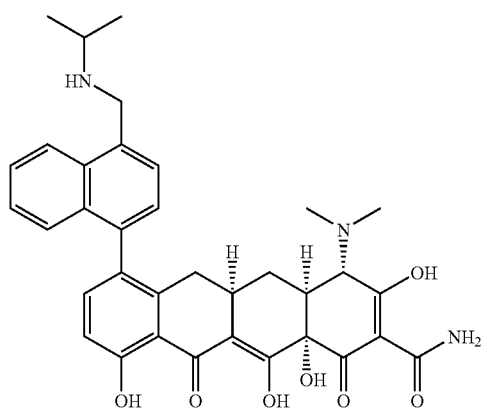
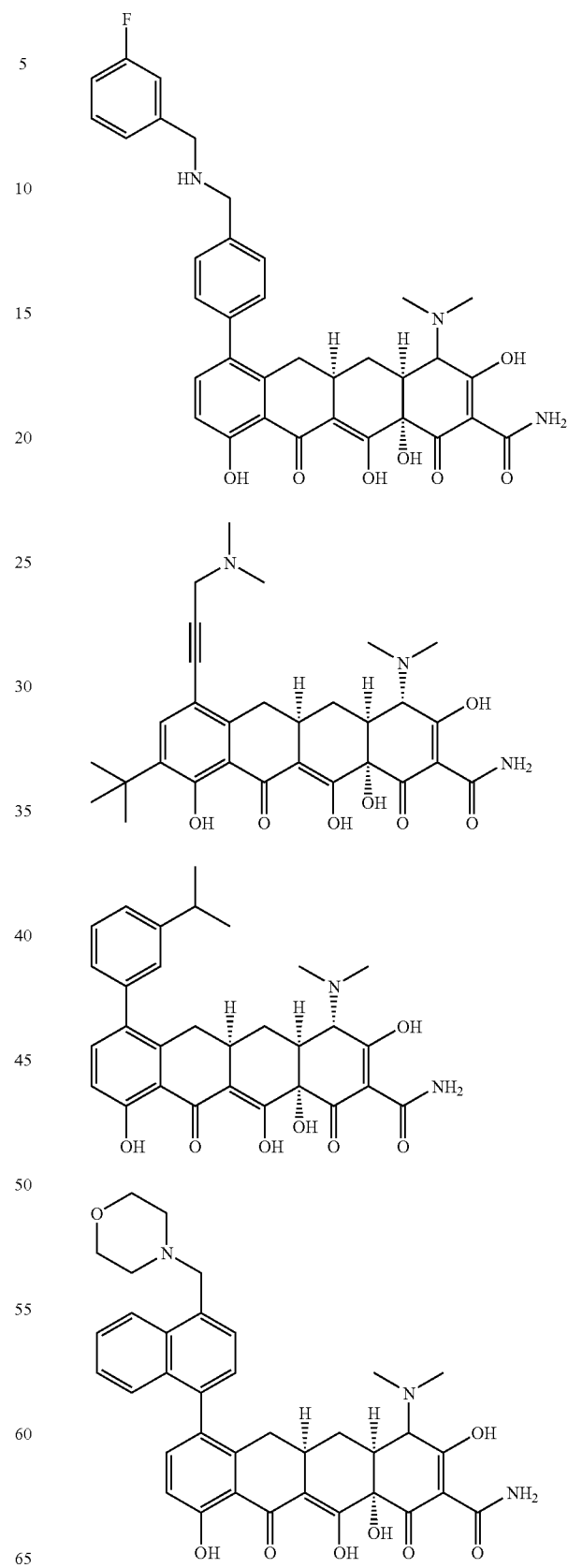

545
-continued
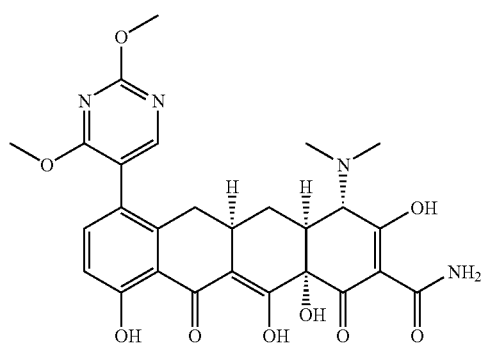
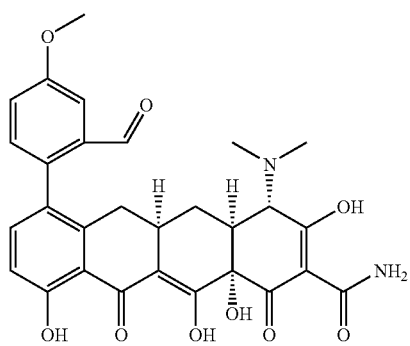
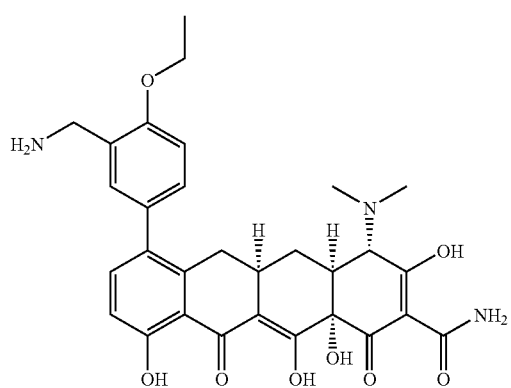
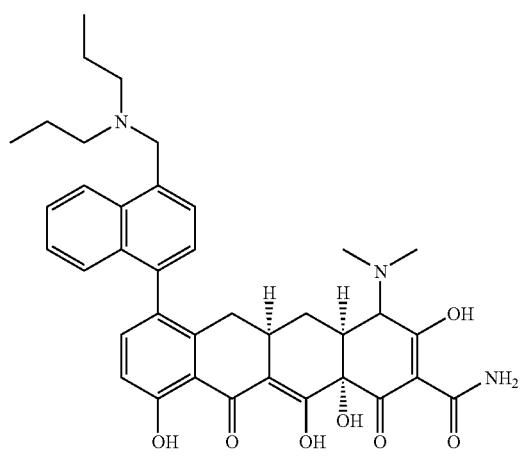
546
-continued
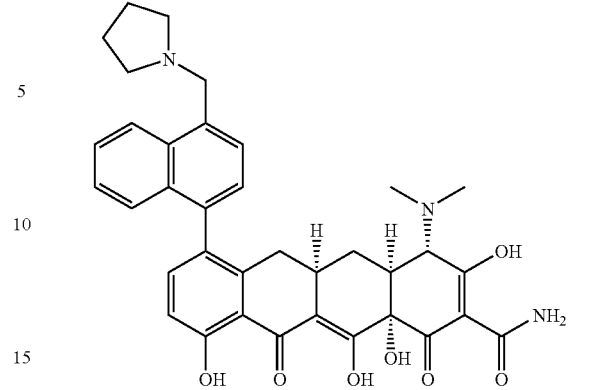
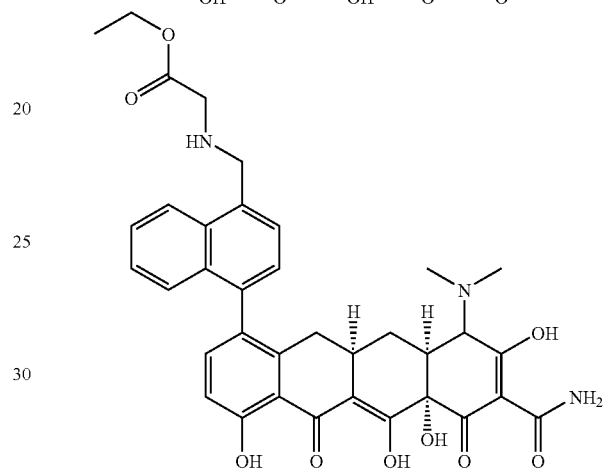
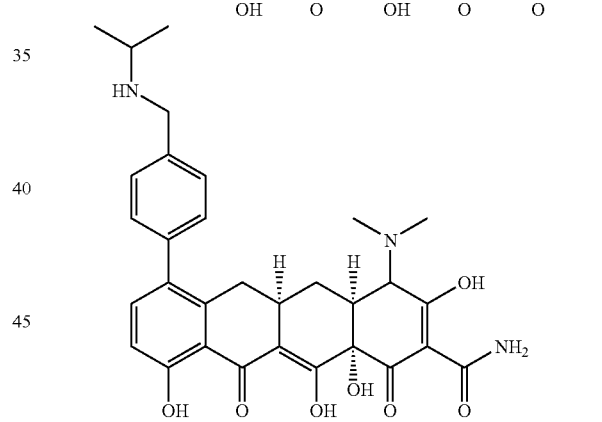
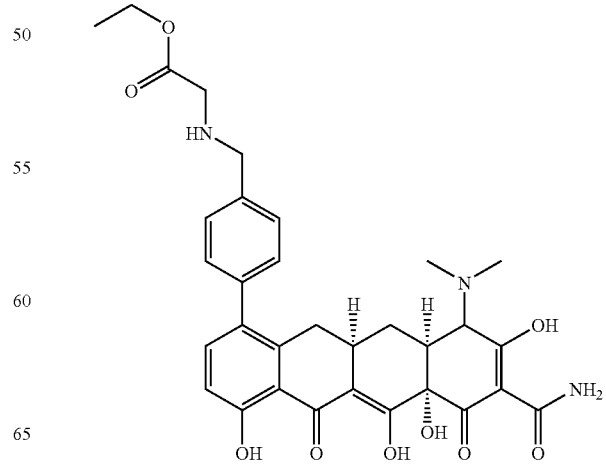

547
-continued
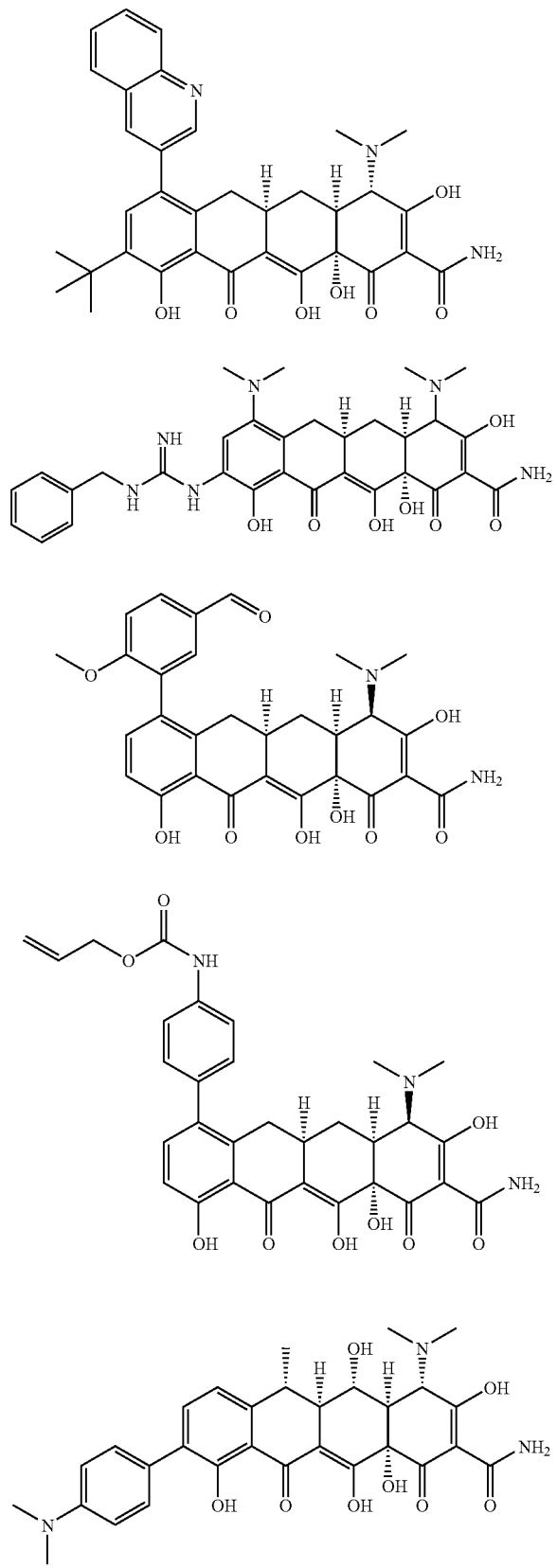
548
-continued
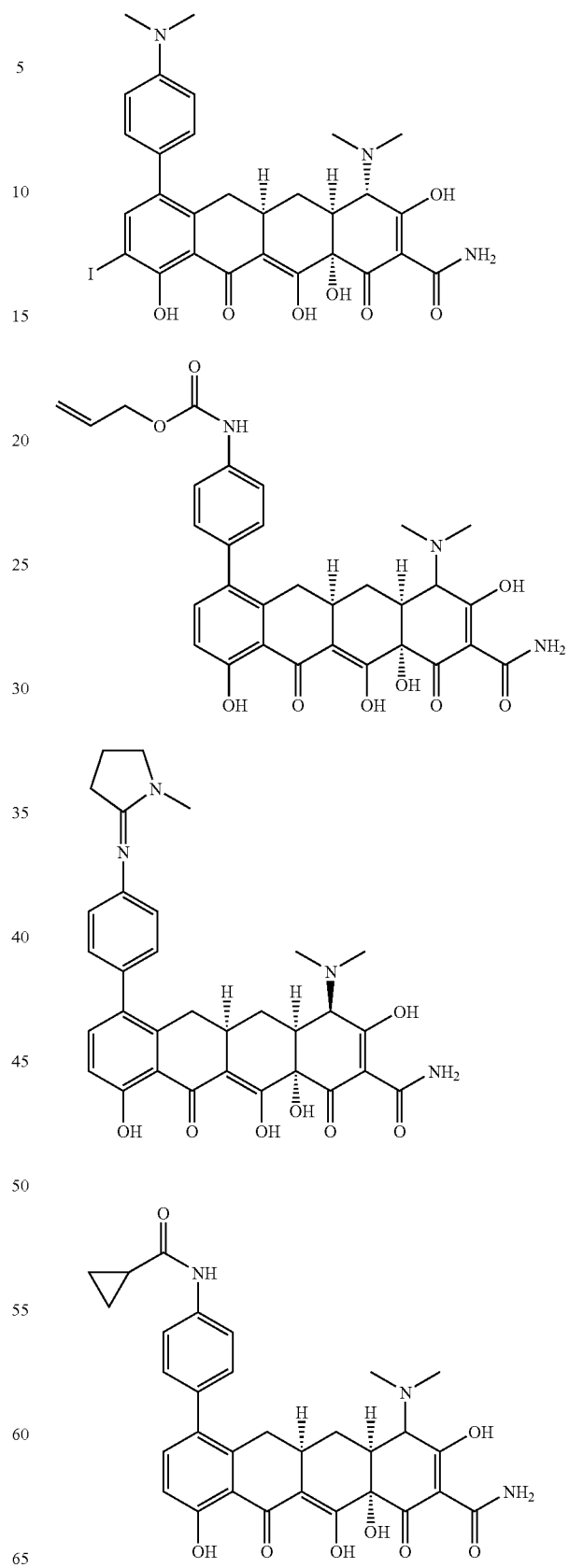

549
-continued
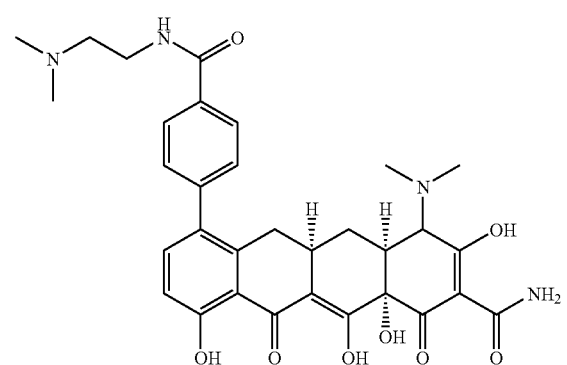
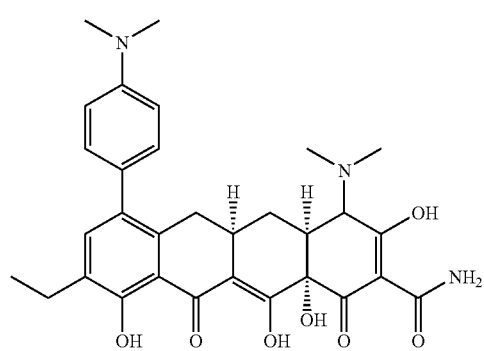
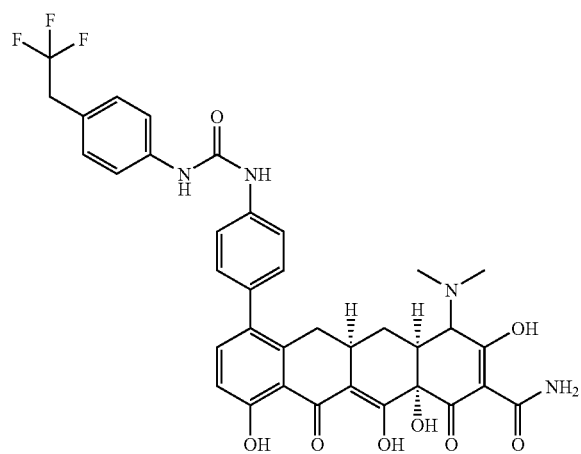
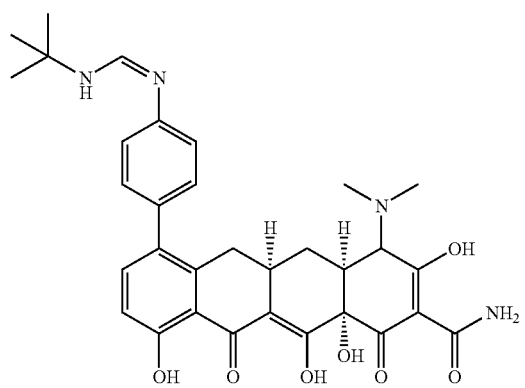
550
-continued
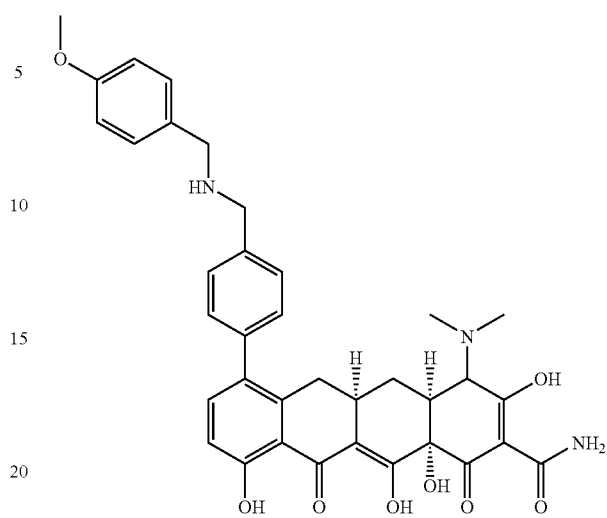
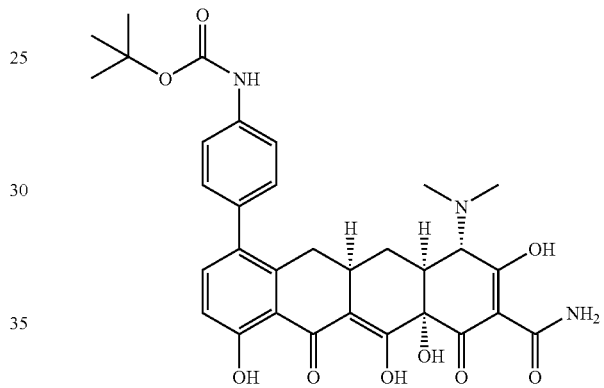
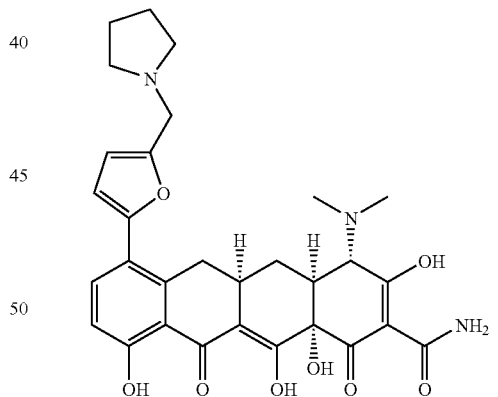
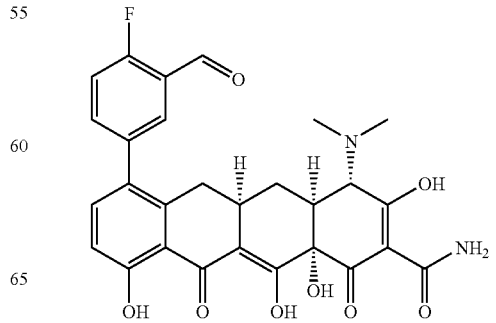

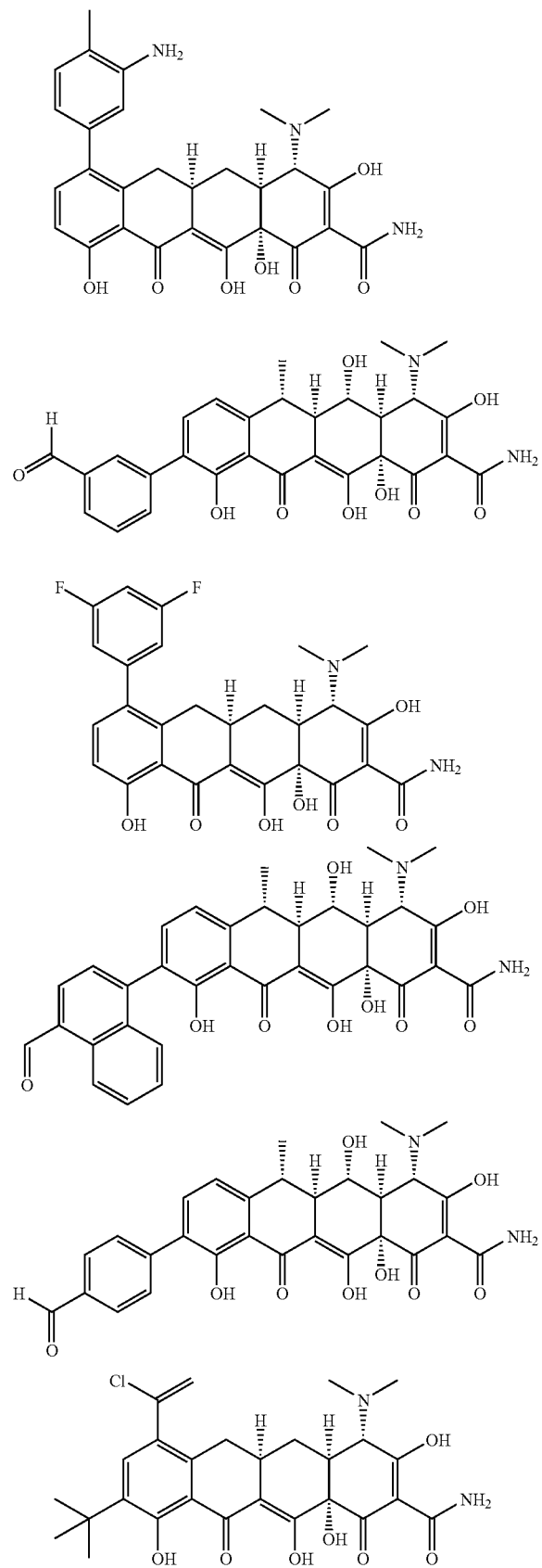
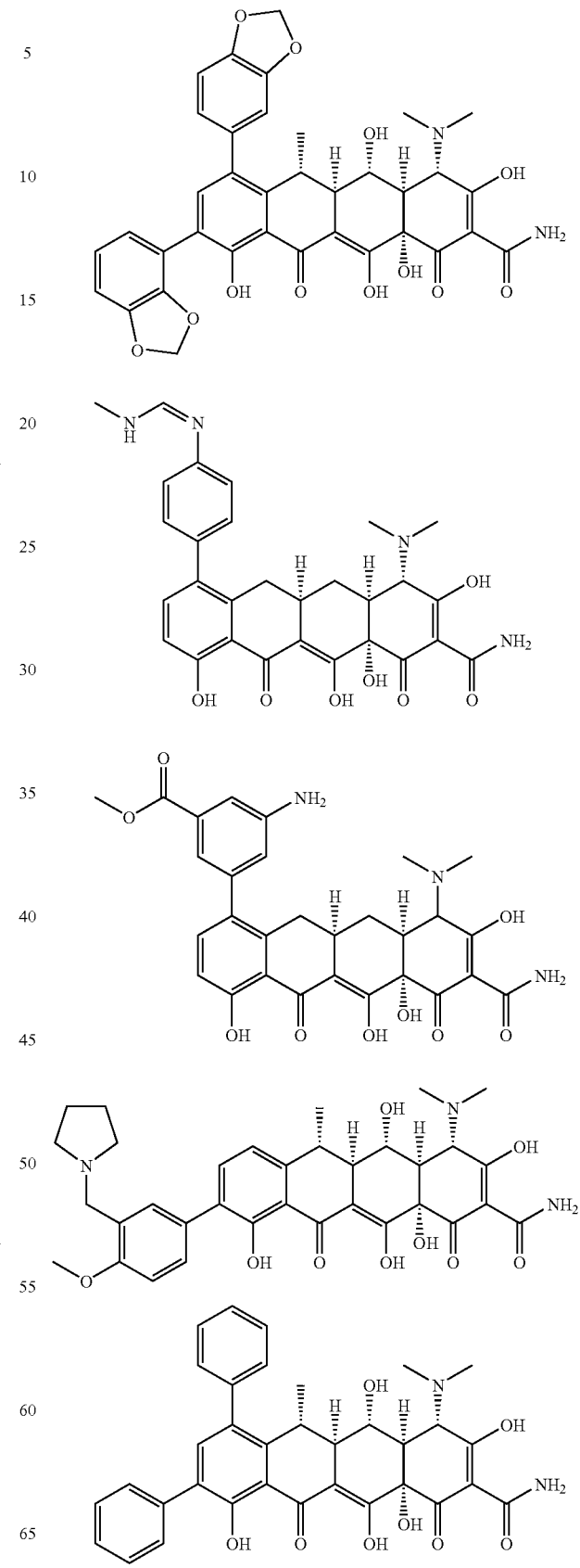

-continued
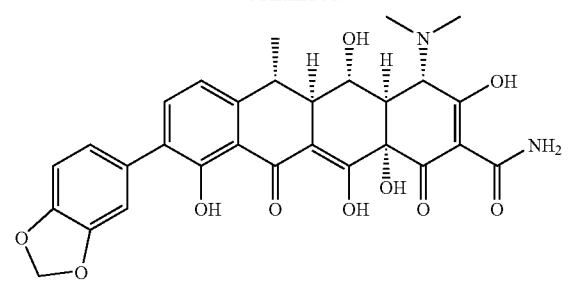
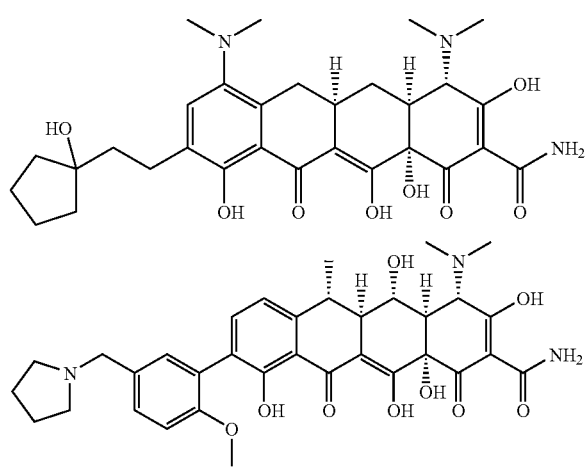
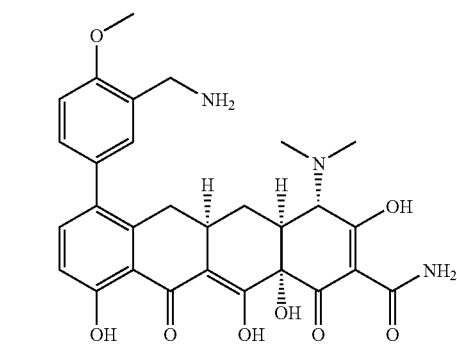
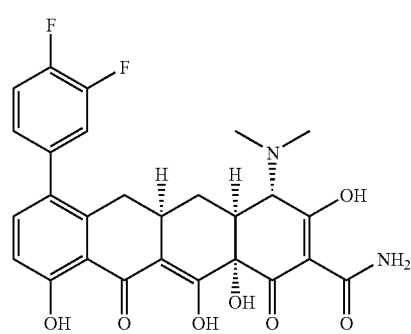
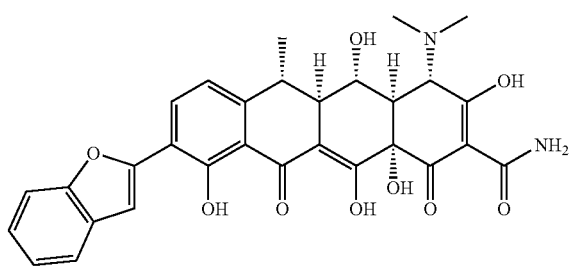
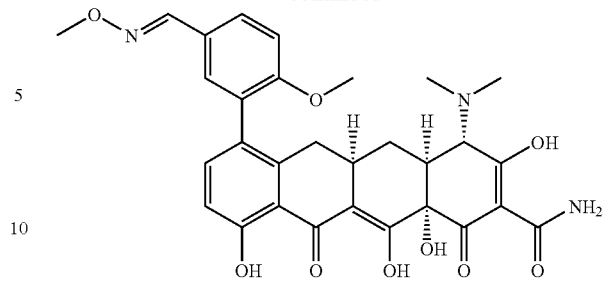
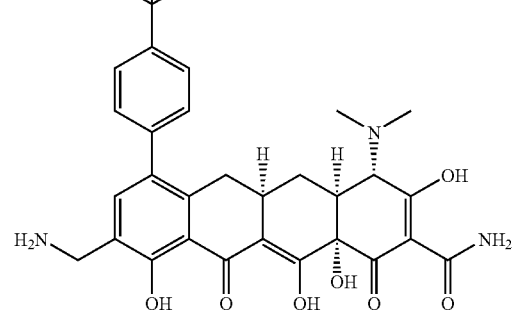
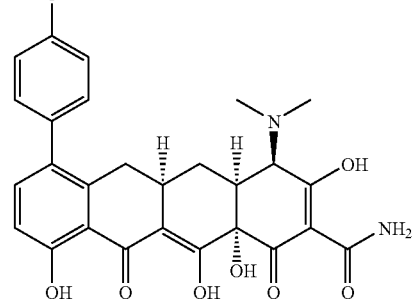
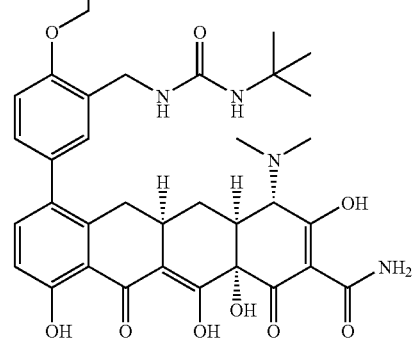
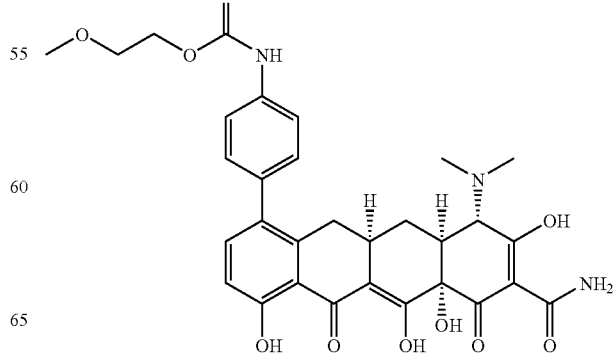

555
-continued
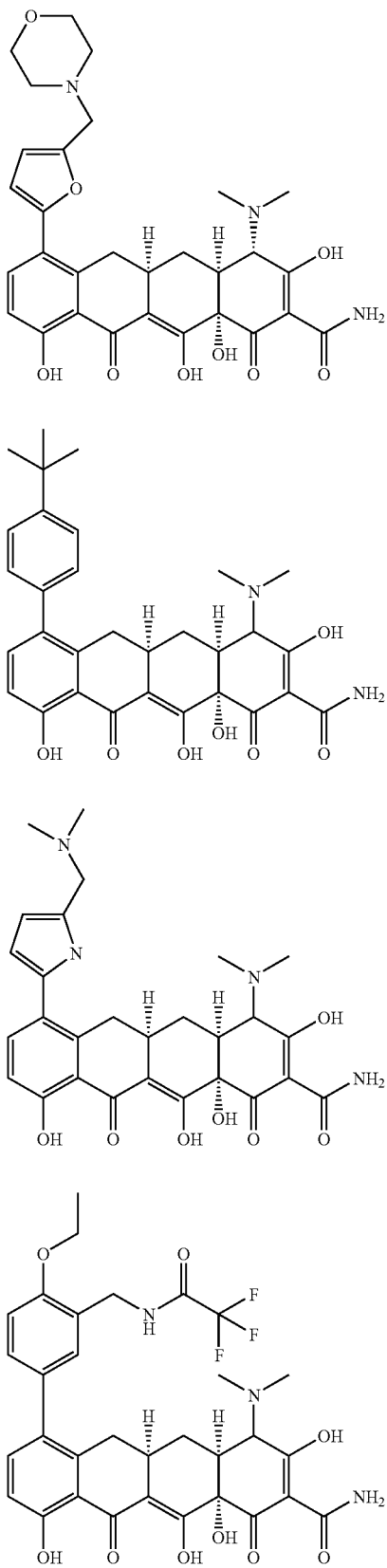
556
-continued
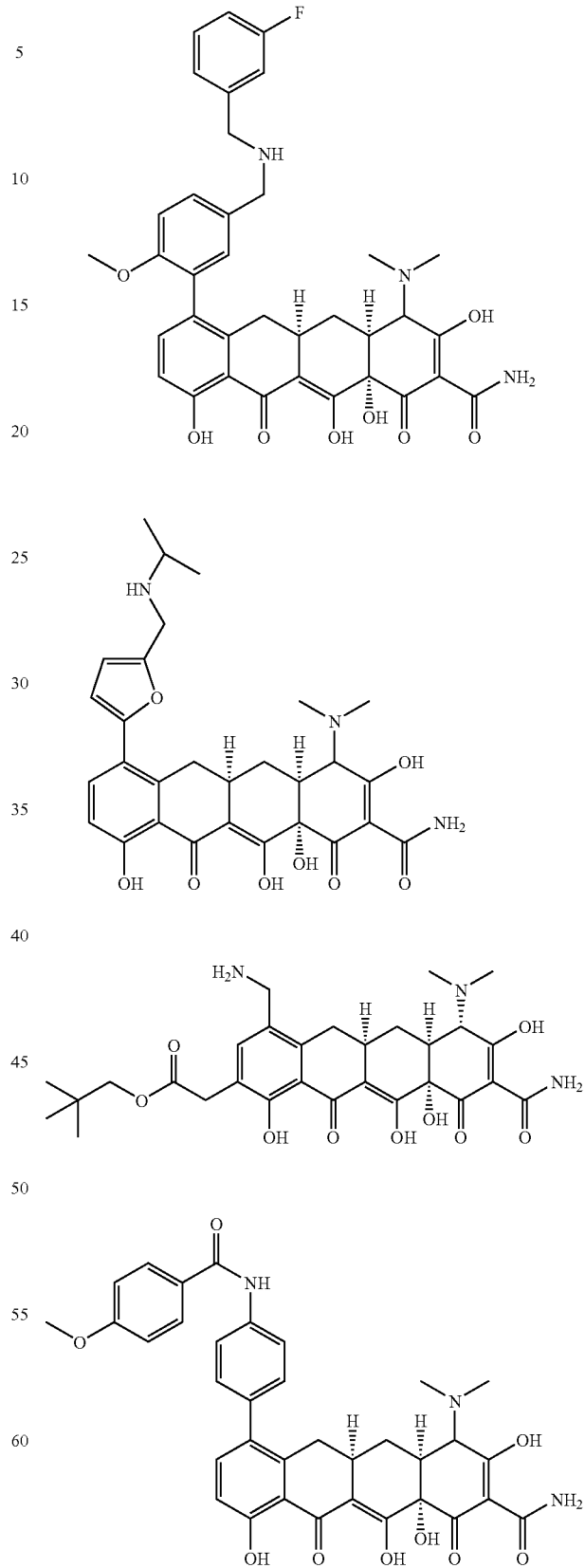

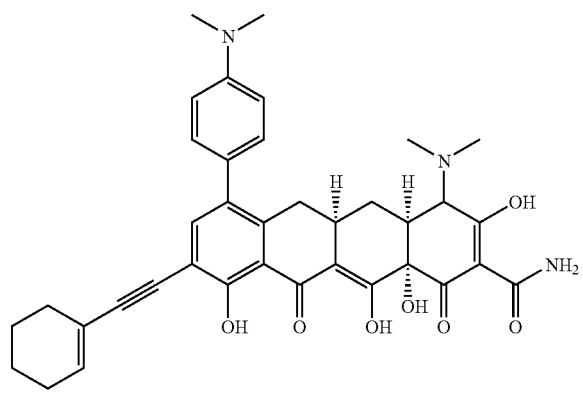
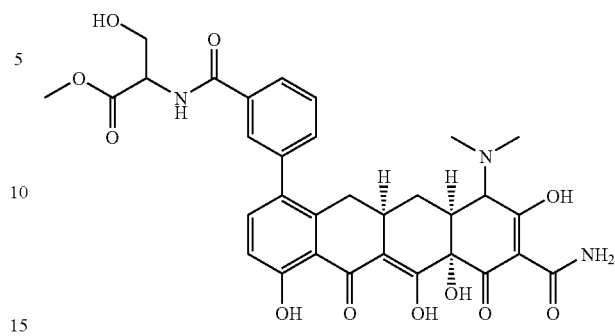
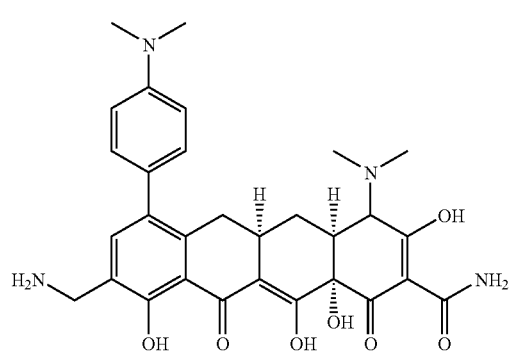
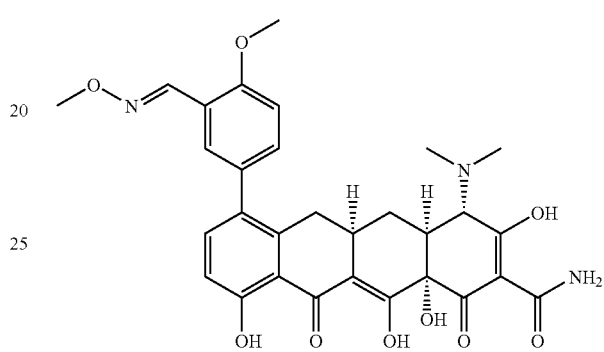
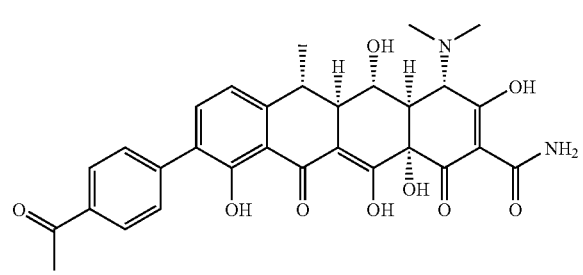
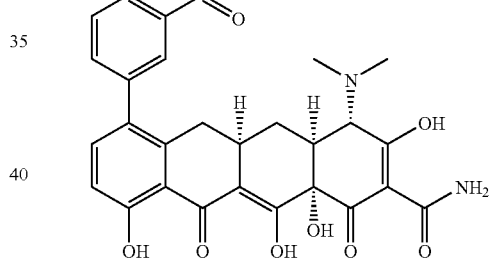
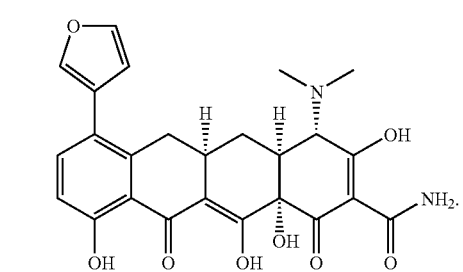
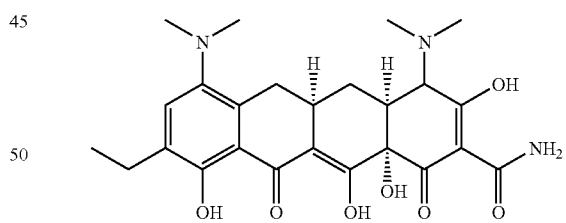
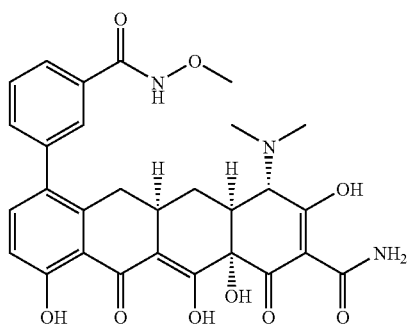
14. A method for increasing the antifungal activity of an antifungal agent, comprising administering said antifungal agent in combination with an effective amount of a substituted tetracycline compound, such that the antifungal activity of said antifungal agent is increased, wherein said tetracycline compound is:

559
-continued
560
-continued
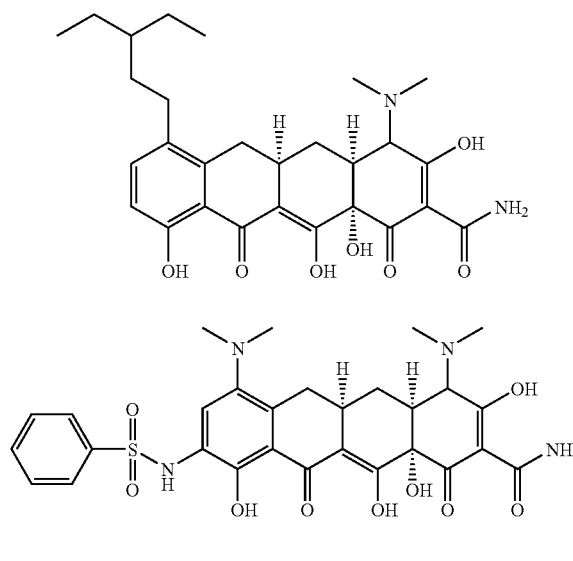
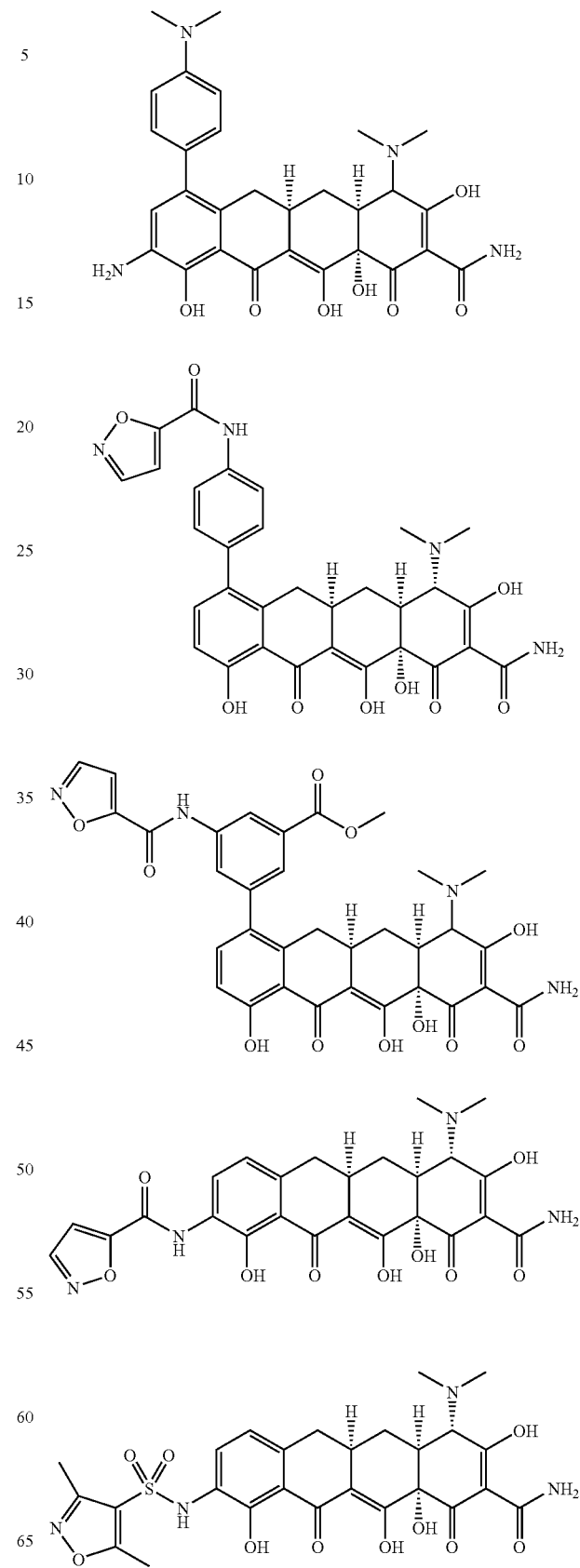

561
-continued
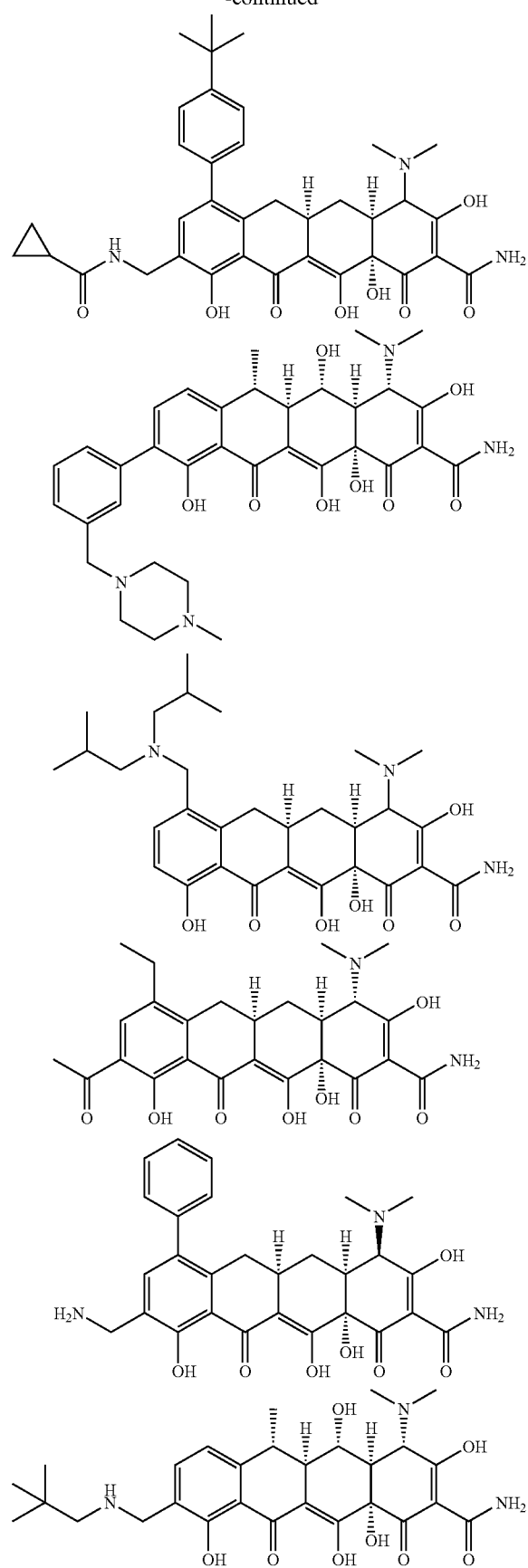
562
-continued
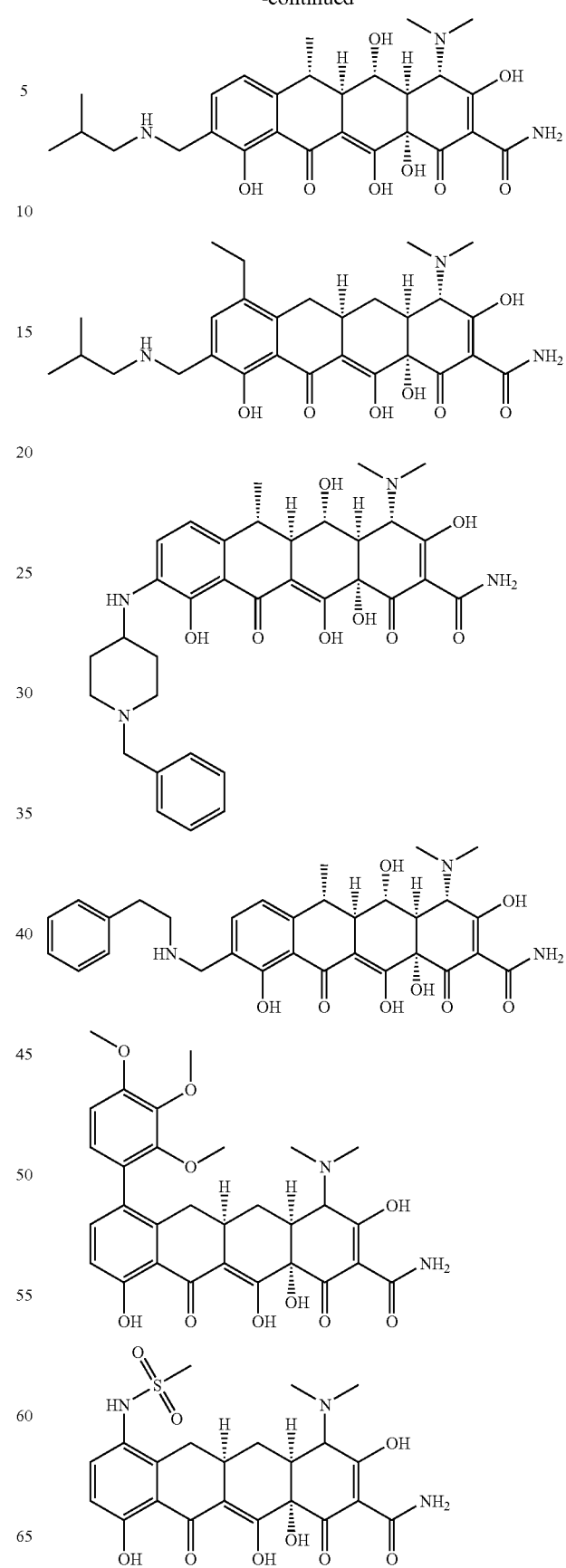

563
-continued
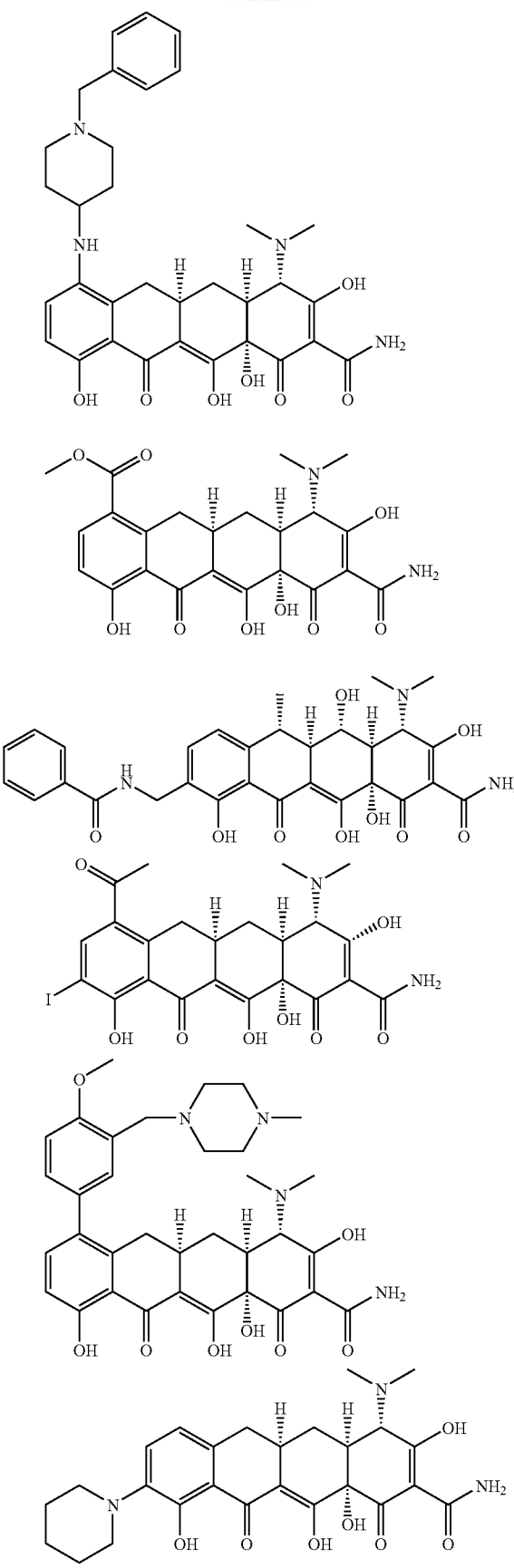
564
-continued
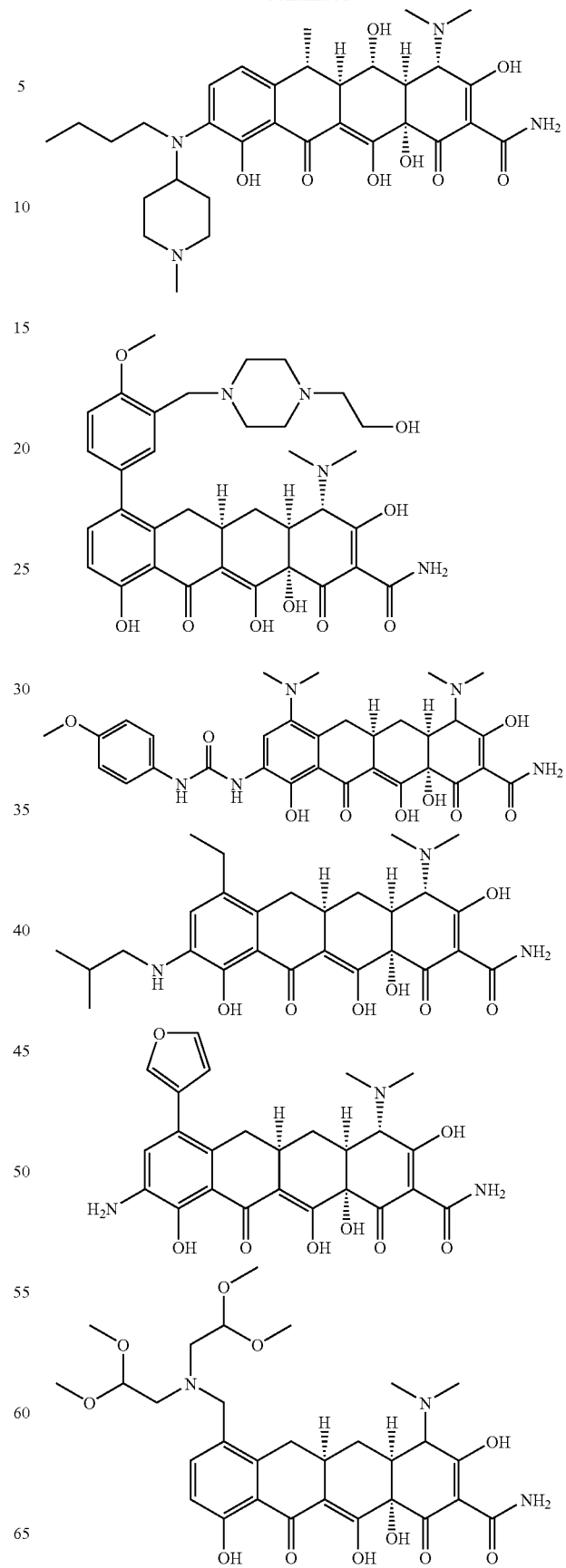

565
-continued
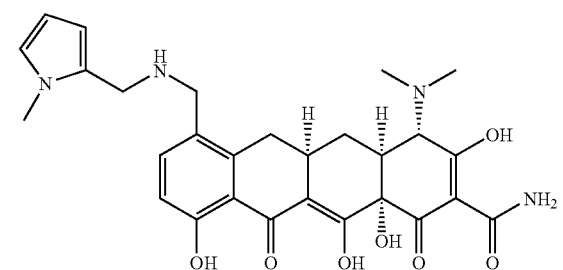
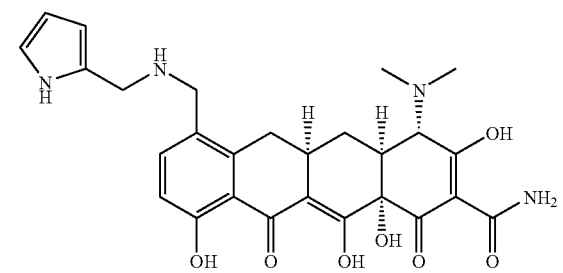
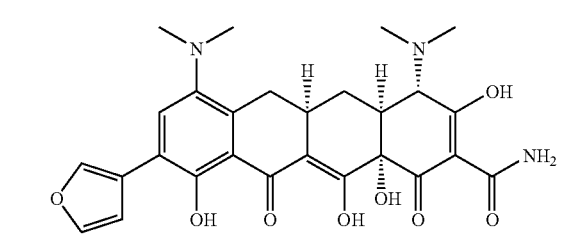
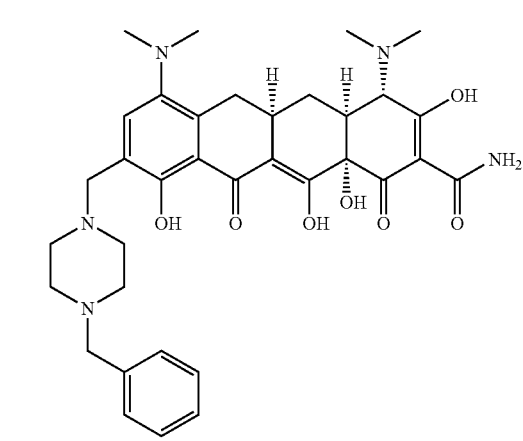
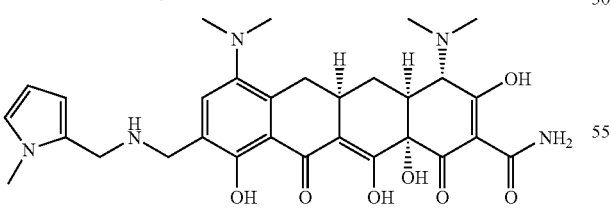
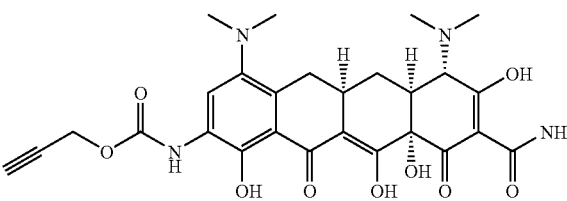
566
-continued
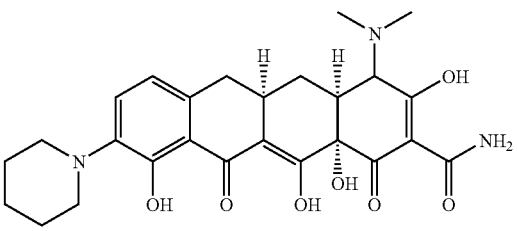
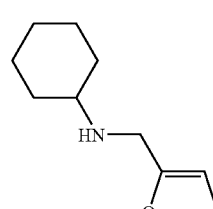
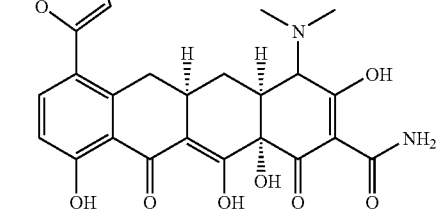
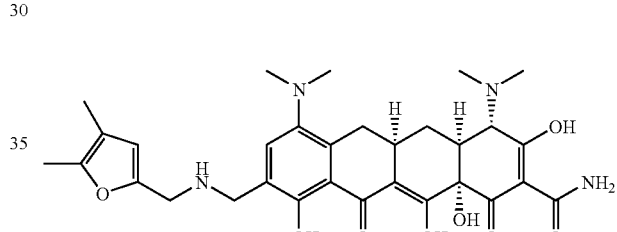
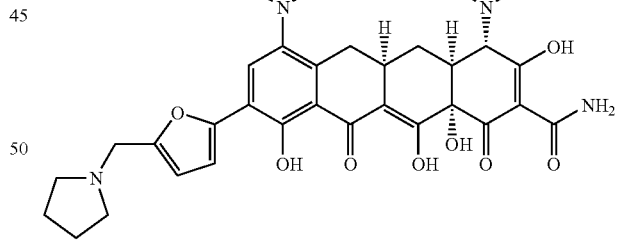
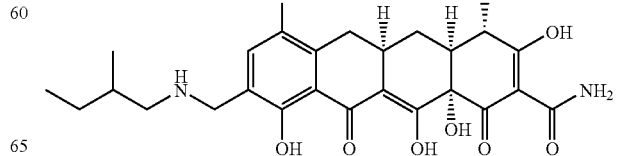
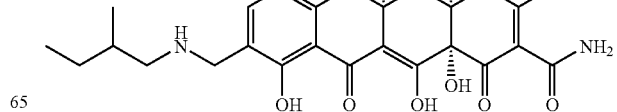

567
-continued
568
-continued
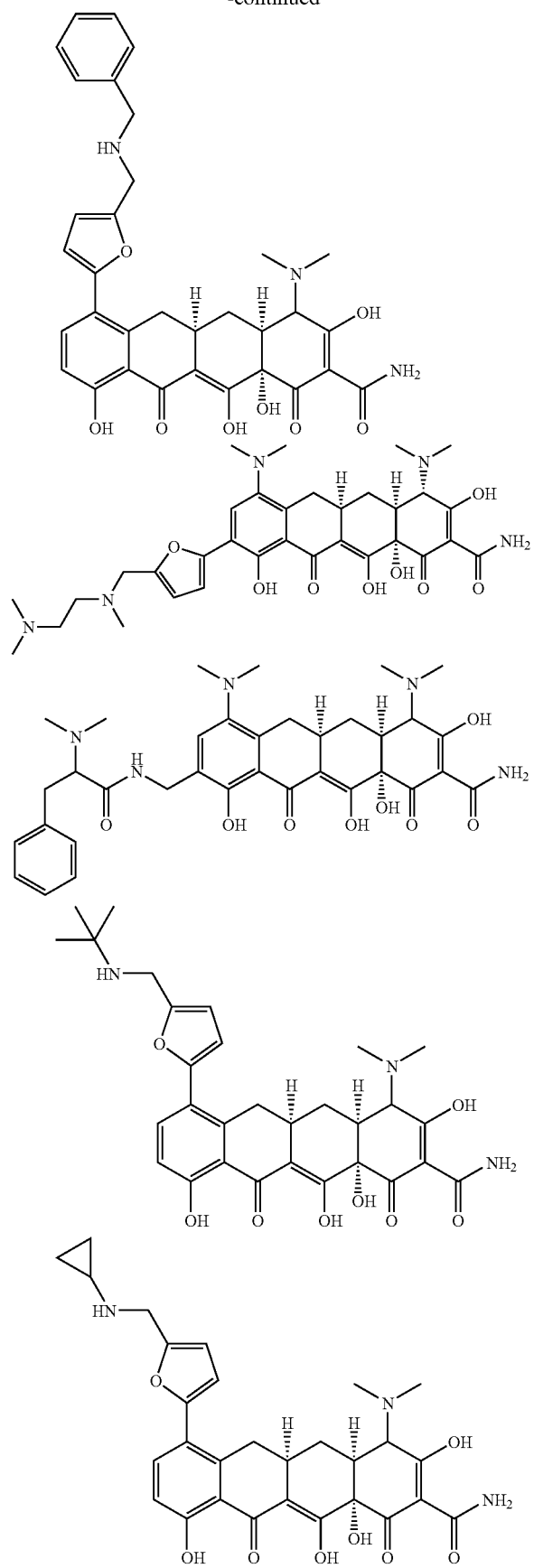
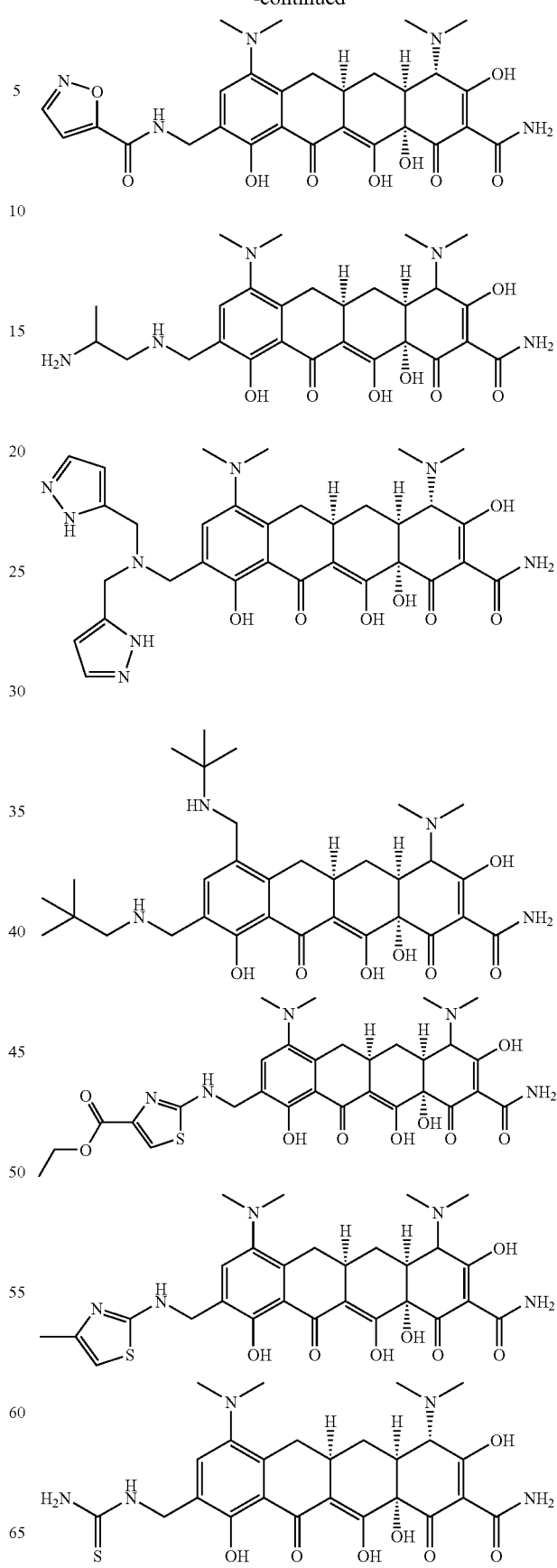

569
-continued
570
-continued
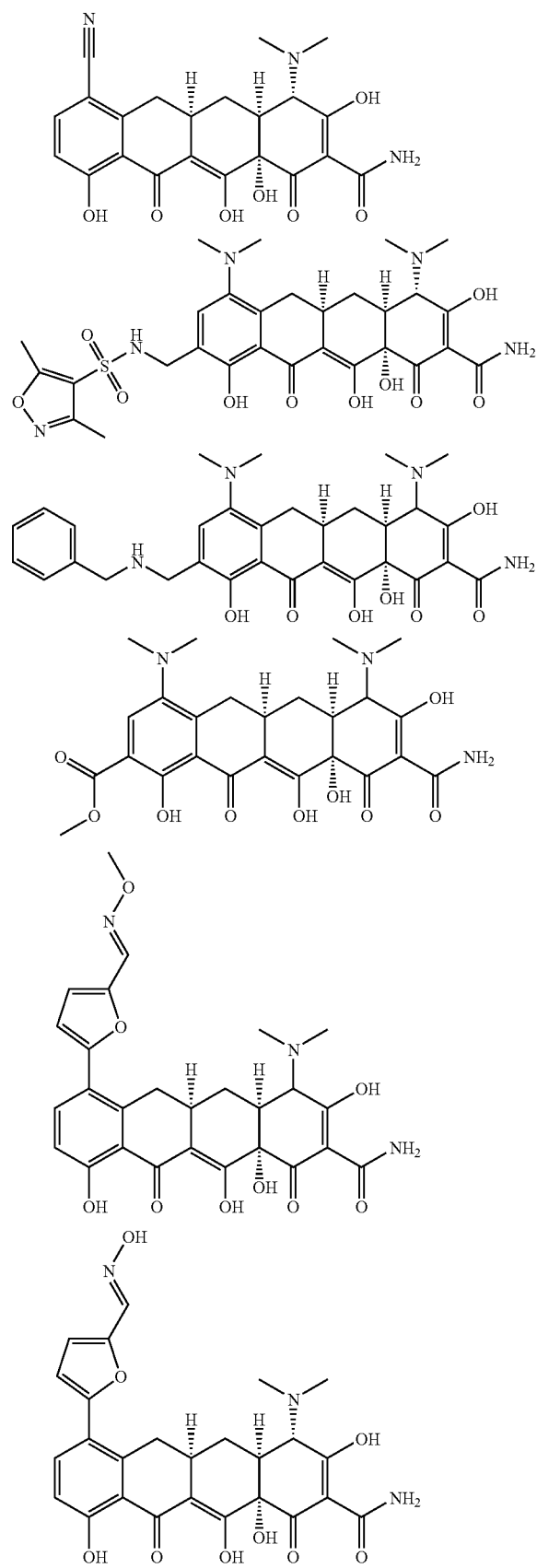
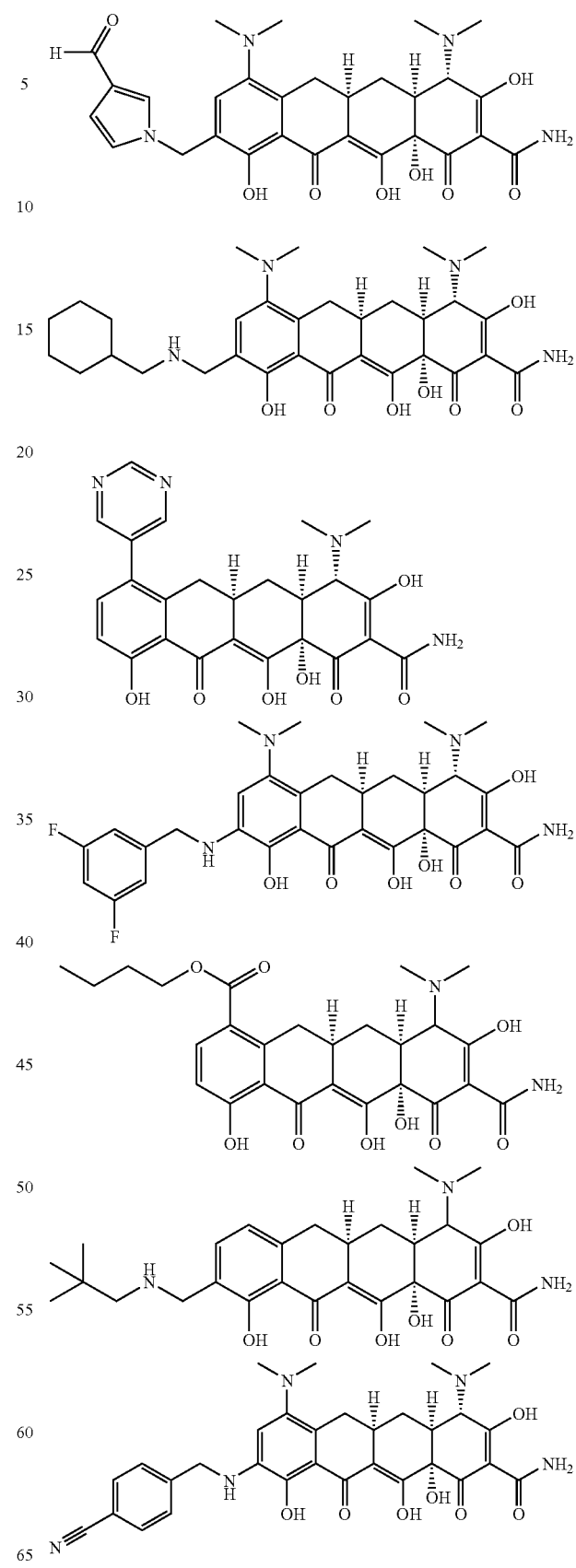

571
-continued
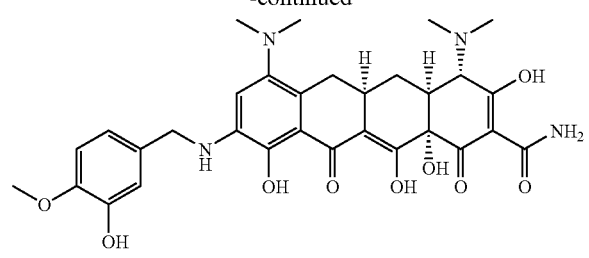
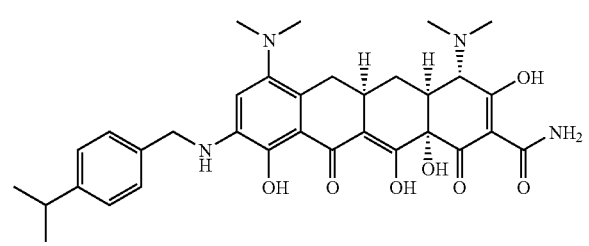
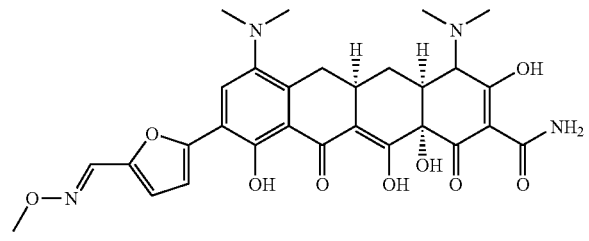
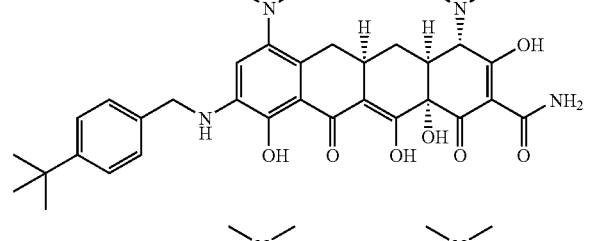
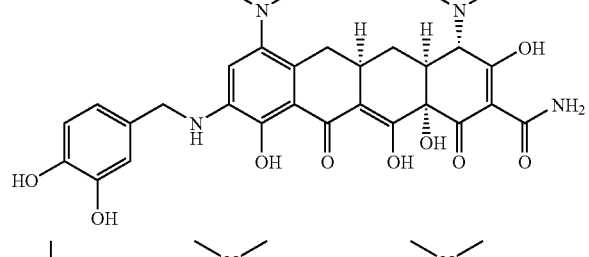
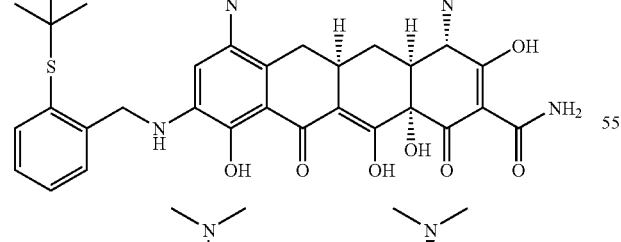
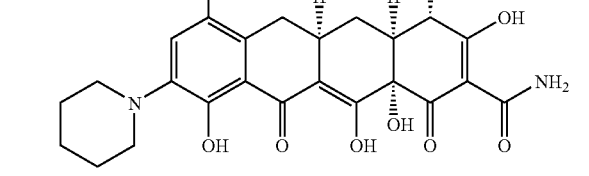
572
-continued
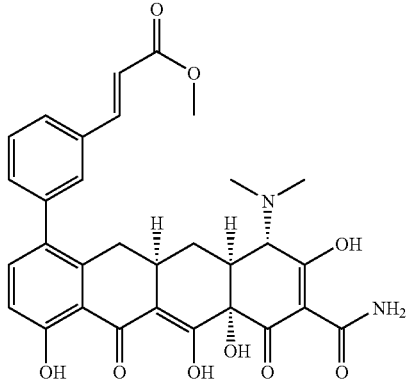
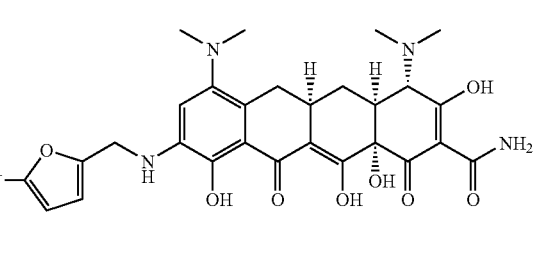
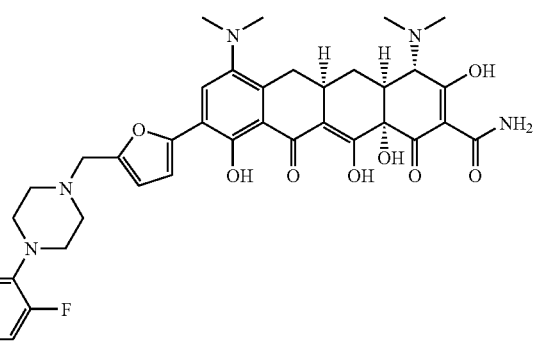
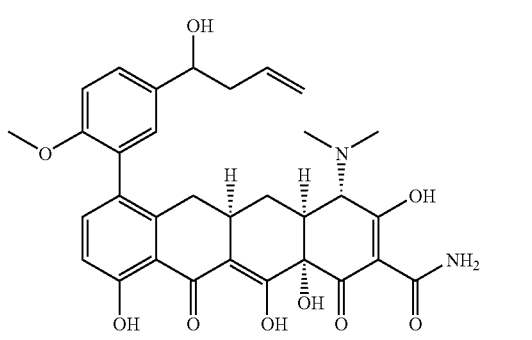
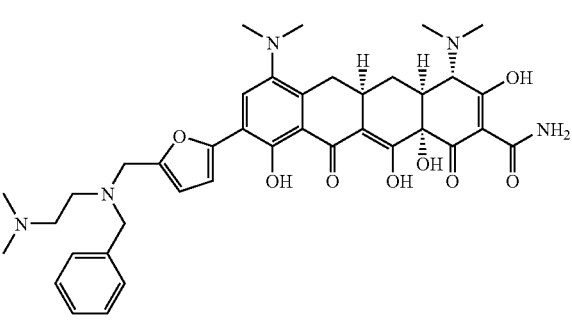

573
-continued
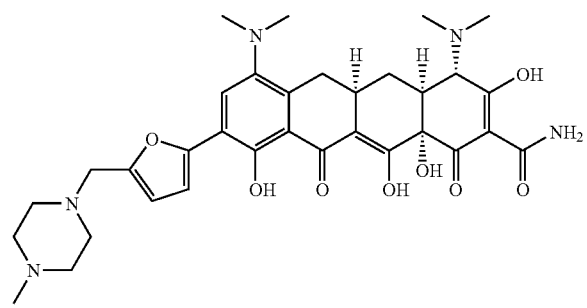
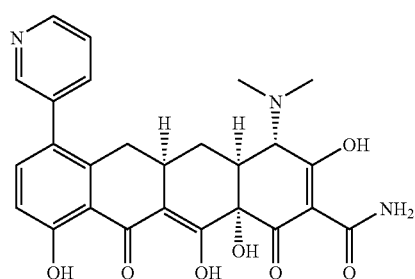
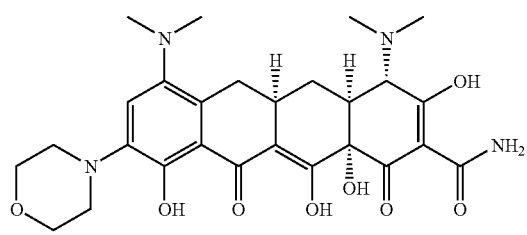
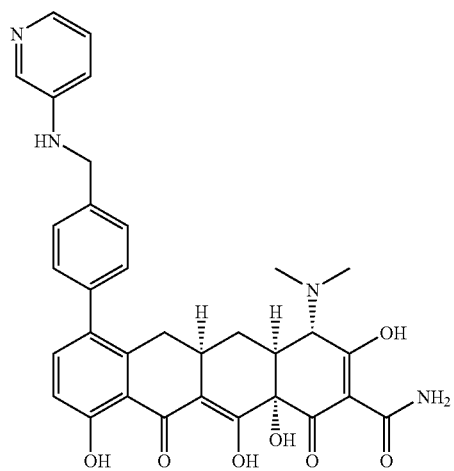
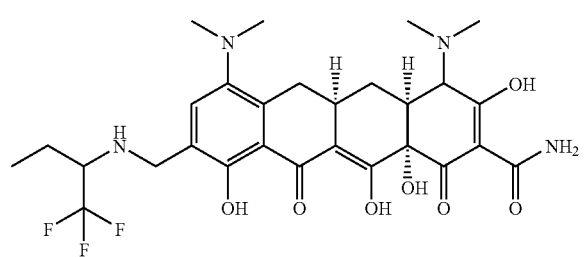
574
-continued
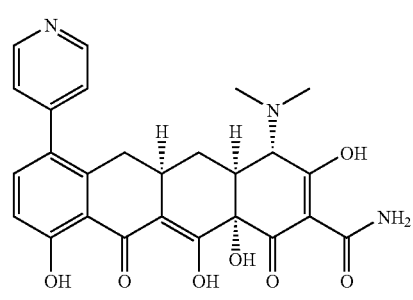
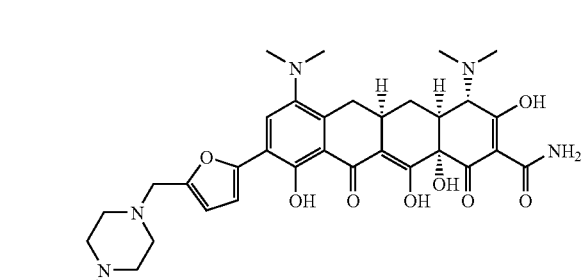
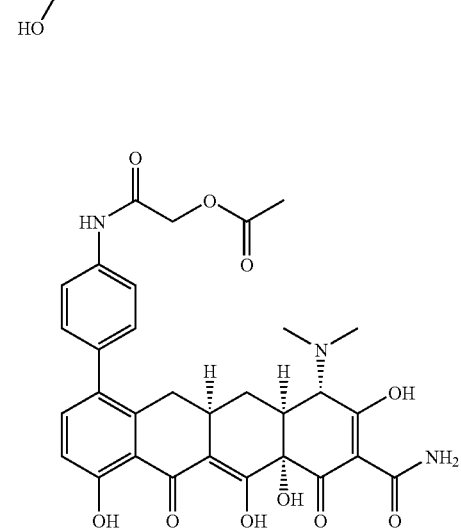
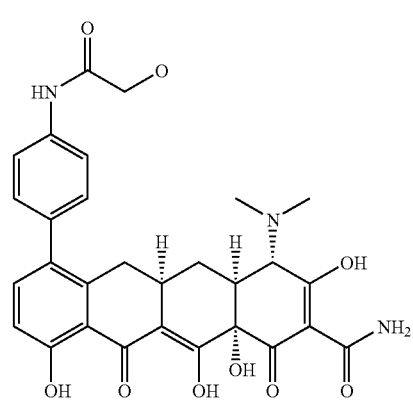

575
-continued
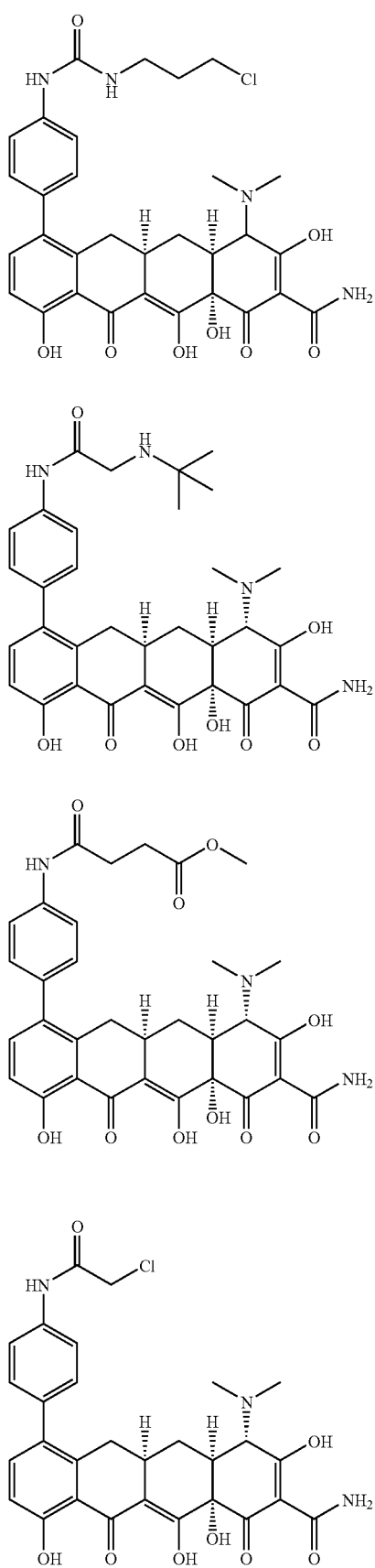
576
-continued
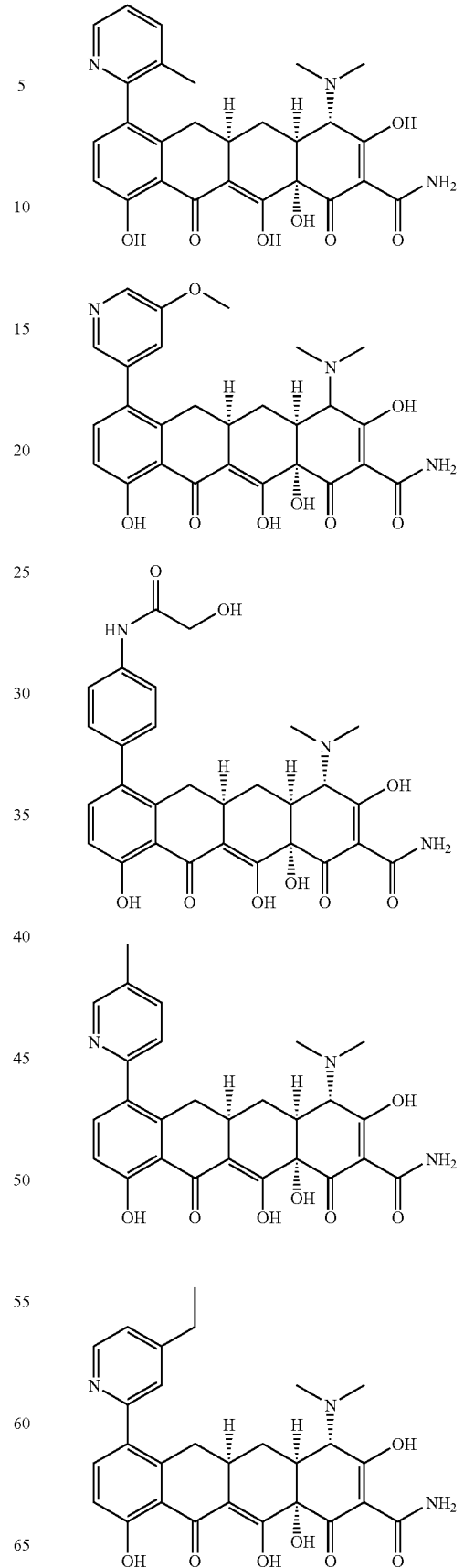

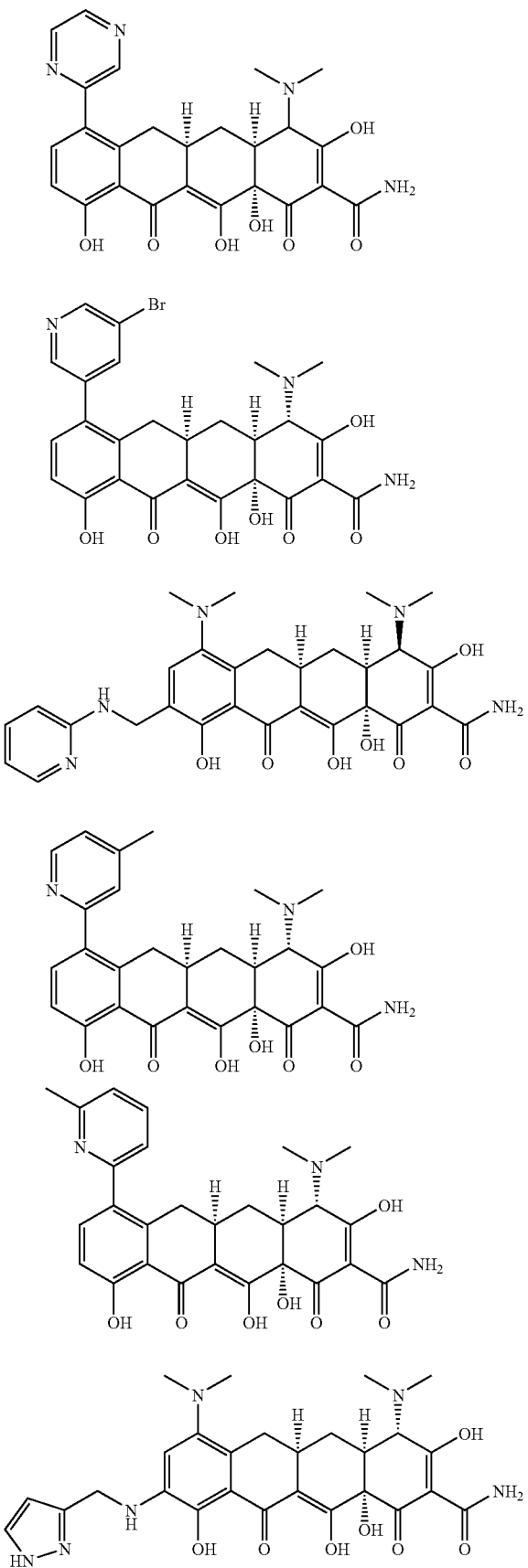

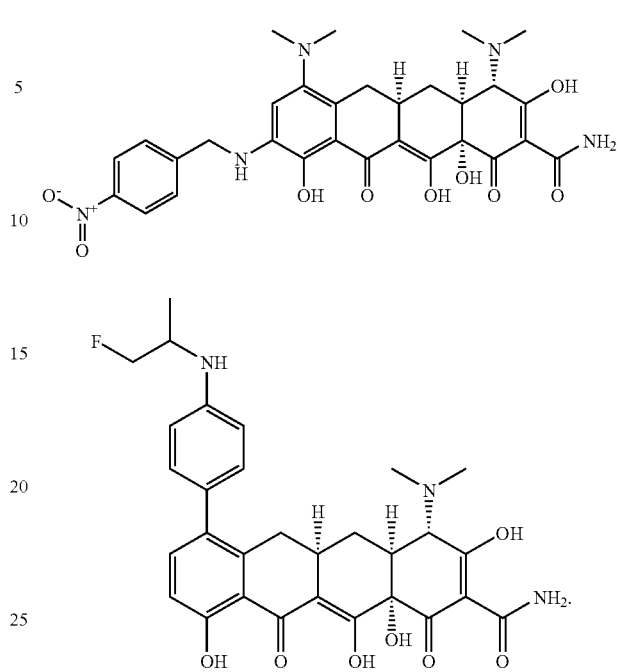

15. The method of claim 1, wherein said antifungal agent is a polyene.
16. The method of claim 15, wherein said antifungal agent is amphotericin B.
17. The method of claim 1, wherein said antifungal activity is inhibiting the growth of a fungus.
18. The method of claim 1, wherein the antifingal activity is killing the fungus.
19. The method of claim 1, wherein the effective amount of said antifungal agent is reduced five fold or greater, from the effective amount when the antifungal agent is administered alone.
20. The method of claim 19, wherein the antifungal activity of said antifungal agent is reduced eight fold or greater.
21. The method of claim 20, wherein the antifungal activity of said antifungal agent is reduced ten fold or greater.
22. The method of claim 1, wherein $R^{2'}$, $R^3$, $R^{10}$, $R^{11}$, and $R^{12}$ are each hydrogen or a prodrug moiety and $R^4$ is dimethyl amino.
23. The method of claim 1, wherein X is $CR^6R^{6'}$; and $R^2$, $R^5$, $R^6$, $R^{6'}$, $R^8$ and $R^9$ are each hydrogen.
24. The method of claim 1, wherein $R^7$ is substituted or unsubstituted aryl.
25. The method of claim 24, wherein $R^7$ is substituted or unsubstituted phenyl.
26. The method of claim 25, wherein said substituted or unsubstituted phenyl is substituted with at least one alkyl, amino, heterocycle, alkoxy, halogen, nitro, alkoxycarbonyl, dialkylamino, or alkylamino.
27. The method of claim 24, wherein $R^7$ is substituted or unsubstituted heteroaryl.
28. The method of claim 27, wherein $R^7$ is thienyl.
29. The method of claim 1, wherein $R^7$ is substituted or unsubstituted alkyl.
30. The method of claim 24, wherein said alkyl is $C_1$–$C_{10}$.
31. The method of claim 29, wherein said alkyl is substituted with a substituted or unsubstituted heterocycle, a substituted or unsubstituted phenyl, a hydroxy, or combinations thereof.

32. The method of claim 1, wherein $R^7$ is substituted or unsubstituted alkenyl.

33. The method of claim 32, wherein said substituted alkenyl is substituted with substituted or unsubstituted cyclic moiety.

34. The method of claim 33, wherein said cyclic moiety is heterocyclic, cycloalkenyl, cycloalkyl, or aryl.

35. The method of claim 34, wherein said cyclic moiety is substituted or unsubstituted phenyl.

36. The method of claim 1, wherein $R^7$ is substituted or unsubstituted alkynyl.

37. The method of claim 36, wherein said substituted alkynyl is substituted with a cyclic moiety or a tetracycline dimer moiety.

38. The method of claim 37, wherein said cyclic moiety is heterocyclic, cycloalkenyl, cycloalkyl, or aryl.

39. The method of claim 38, wherein said cyclic moiety is substituted or unsubstituted phenyl or substituted or unsubstituted cycloalkyl.

40. The method of claim 1, wherein $R^7$ is substituted or unsubstituted alkyl carbonyl or substituted or unsubstituted amino.

41. The method of claim 1, wherein X is $CR^6R^{6'}$; and $R^2$, $R^5$, $R^6$, $R^{6'}$, and $R^8$ are each hydrogen.

42. The method of claim 41, wherein $R^9$ is alkyl and $R^7$ is substituted or unsubstituted aminomethyl.

43. The method of claim 41, wherein $R^7$ is alkyl and $R^9$ is substituted or unsubstituted aminomethyl.

44. The method of claim 1, wherein X is $CR^6R^{6'}$; and $R^2$, $R^5$, $R^6$, $R^{6'}$, and $R^8$ are each hydrogen, and $R^7$ is dimethyl amino.

45. The method of claim 44, wherein $R^9$ is substituted or unsubstituted aryl or araalkyl.

46. The method of claim 45, wherein said aryl is substituted or unsubstituted phenyl.

47. The method of claim 46, wherein said phenyl is substituted with one or more substituents selected from the group consisting of amido, alkyl, aminoalkyl, heterocycle, carboxylic acid, formyl, chlorine, fluorine, or acetyl.

48. The method of claim 44, wherein $R^9$ is substituted or unsubstituted alkenyl or alkynyl.

49. The method of claim 48, wherein said alkynyl is substituted with one or more substituents selected from the group consisting of substituted and unsubstituted aryl, substituted and unsubstituted alkyl, carboxylic acid, cycloalkyl, cycloalkenyl, or alkoxycarbonyl.

50. The method of claim 44, wherein $R^9$ is substituted or unsubstituted alkyl or alkylamino.

51. The method of claim 44, wherein $R^{9c}$ is hydrogen, Z is S or O, and Z' is NH.

52. The method of claim 51, wherein $R^{9a}$ comprises substituted or unsubstituted phenyl.

53. The method of claim 4, wherein X is $C=CR^{13}Y$; and $R^2$, $R^5$, $R^6$, $R^{6'}$, $R^7$, $R^8$, $R^9$ and Y are each hydrogen.

54. The method of claim 53, wherein $R^{13}$ is substituted or unsubstituted aryl.

55. The method of claim 1, wherein said substituted tetracycline compound is selected from the group consisting of:

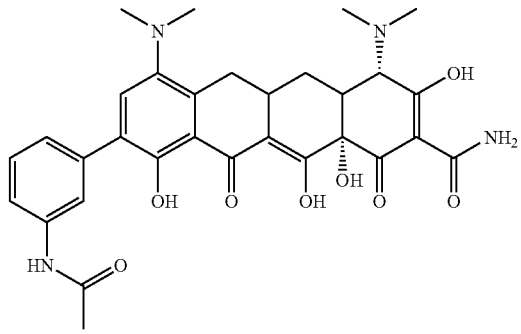

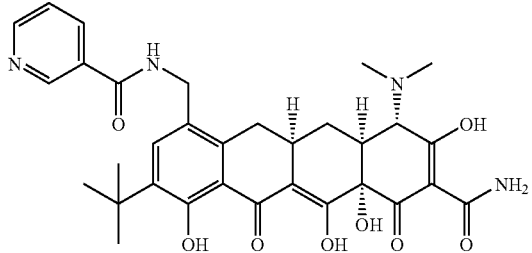

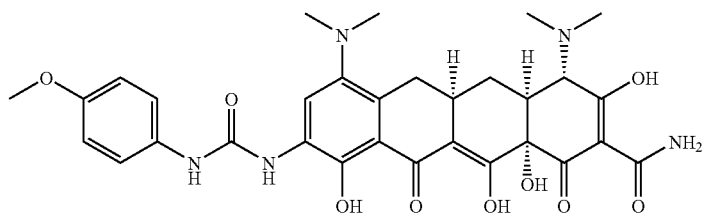

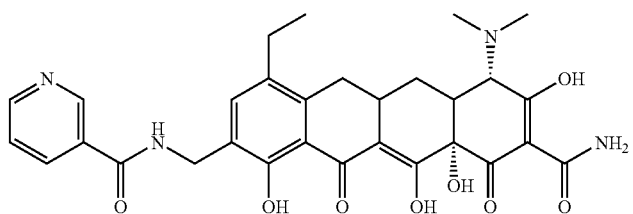

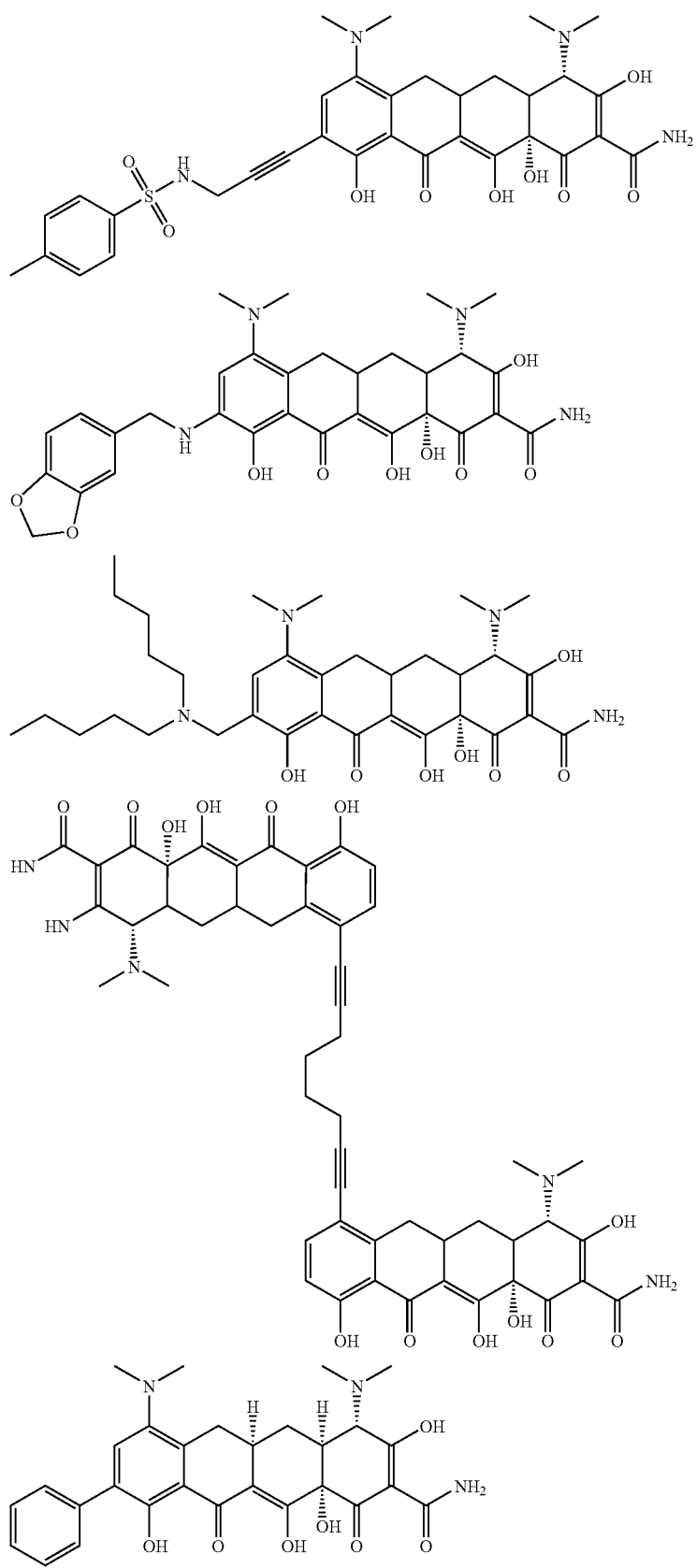

-continued
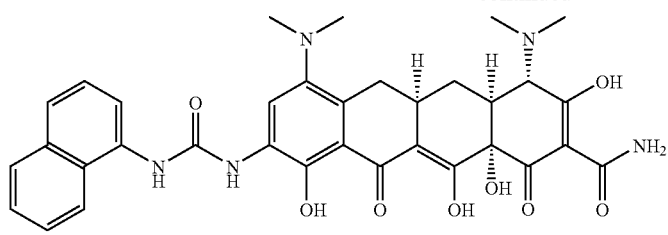
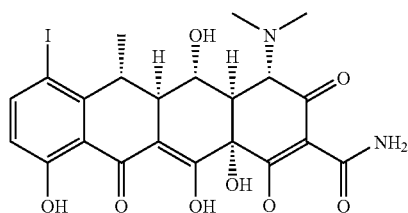
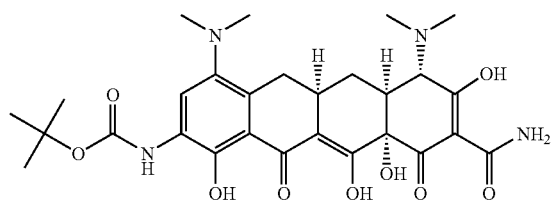
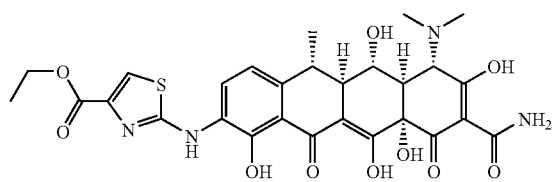
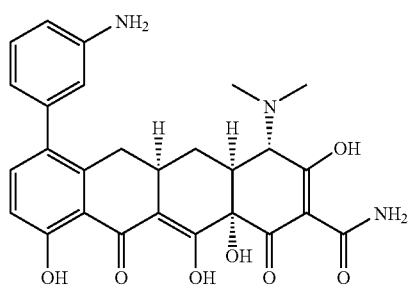
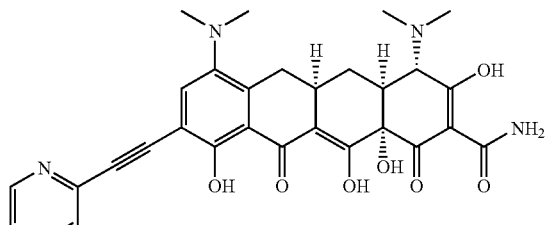
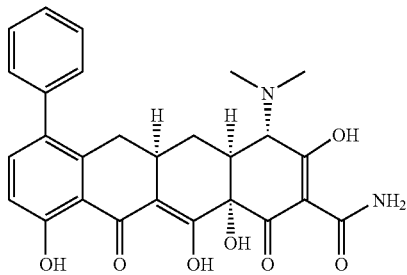
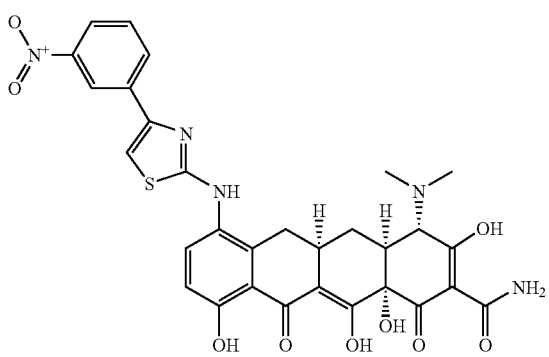
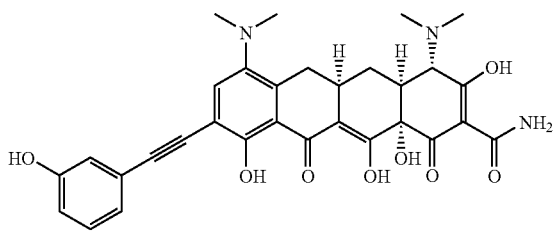
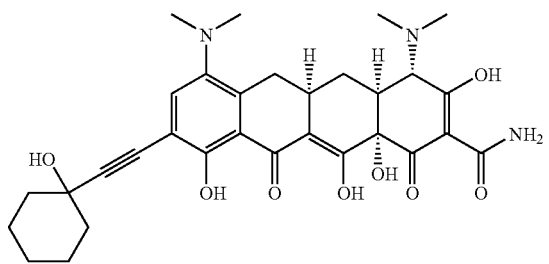
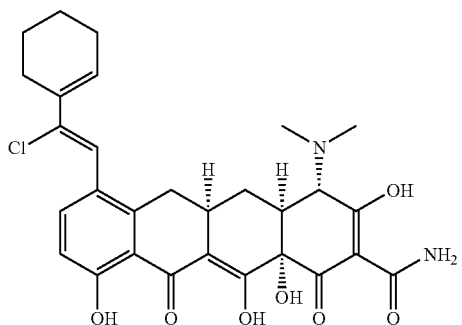

585
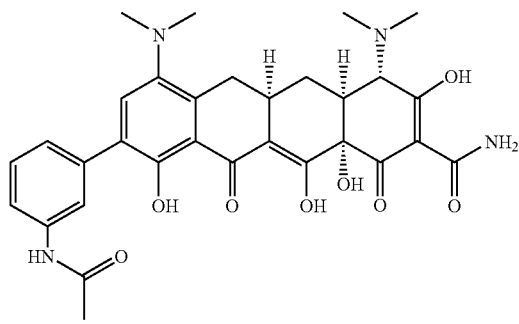
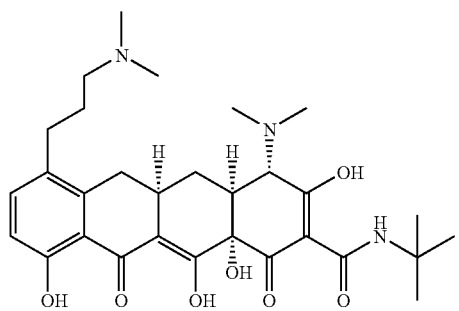
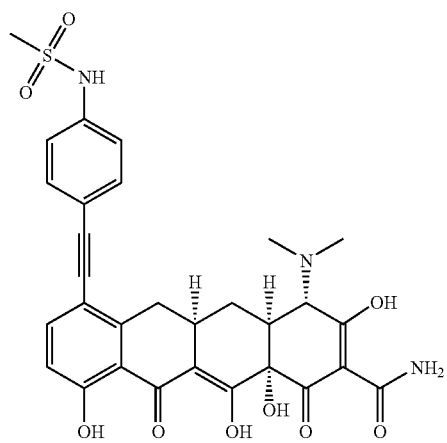
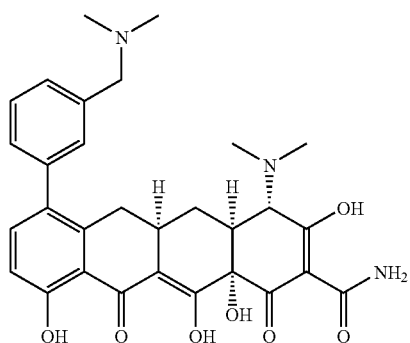
586
-continued
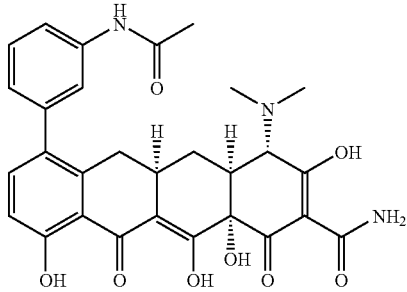
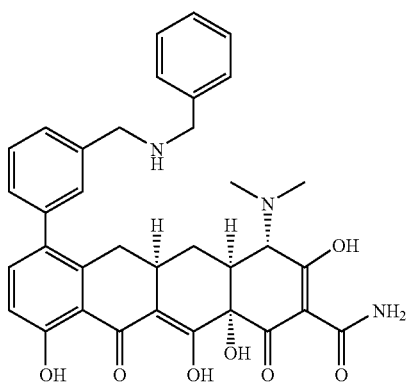
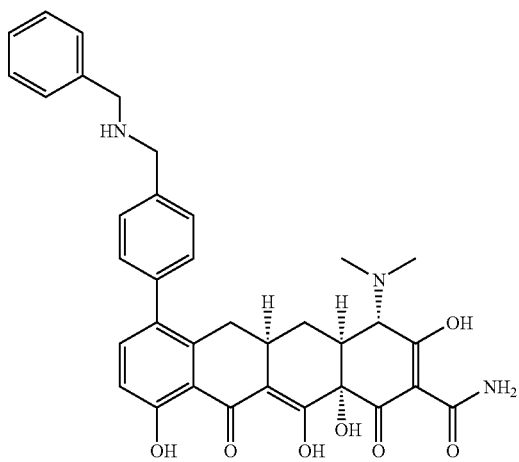
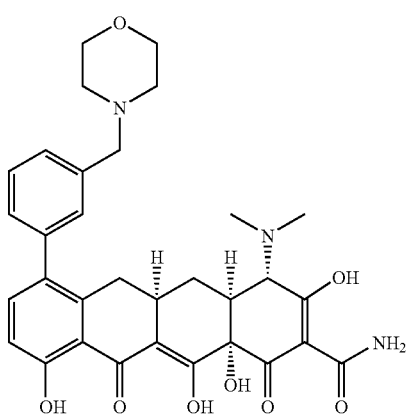

587
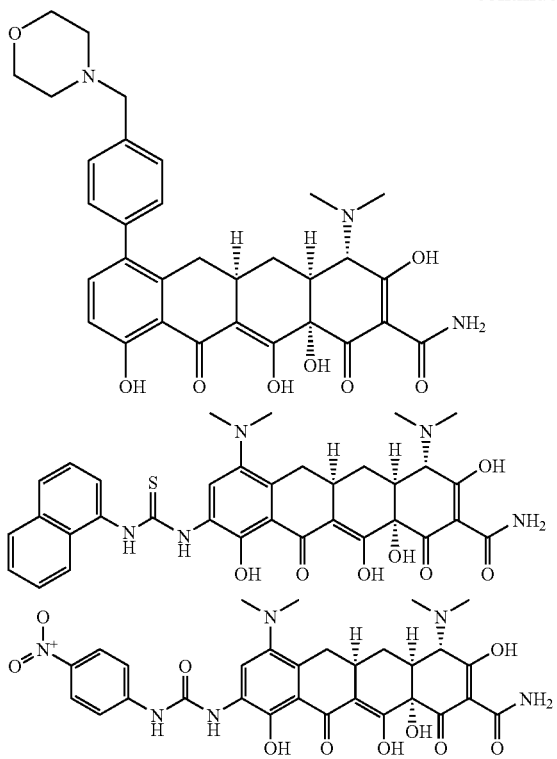
588
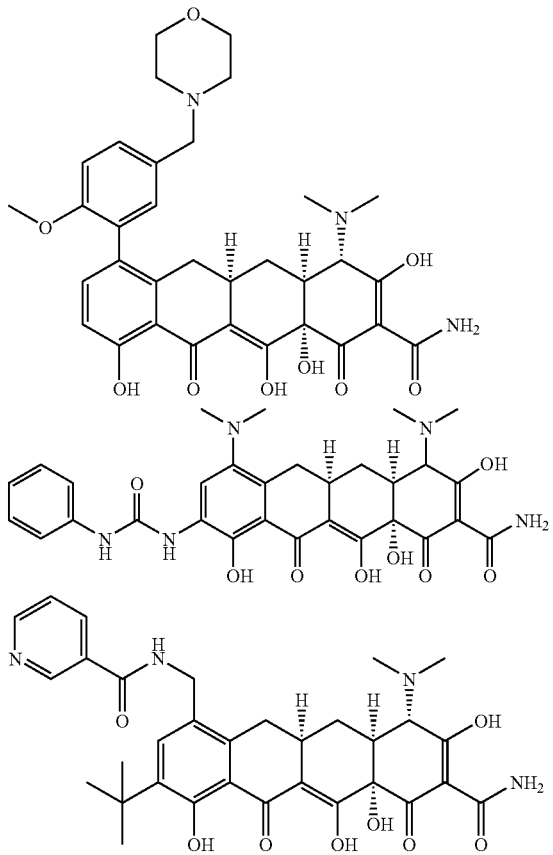
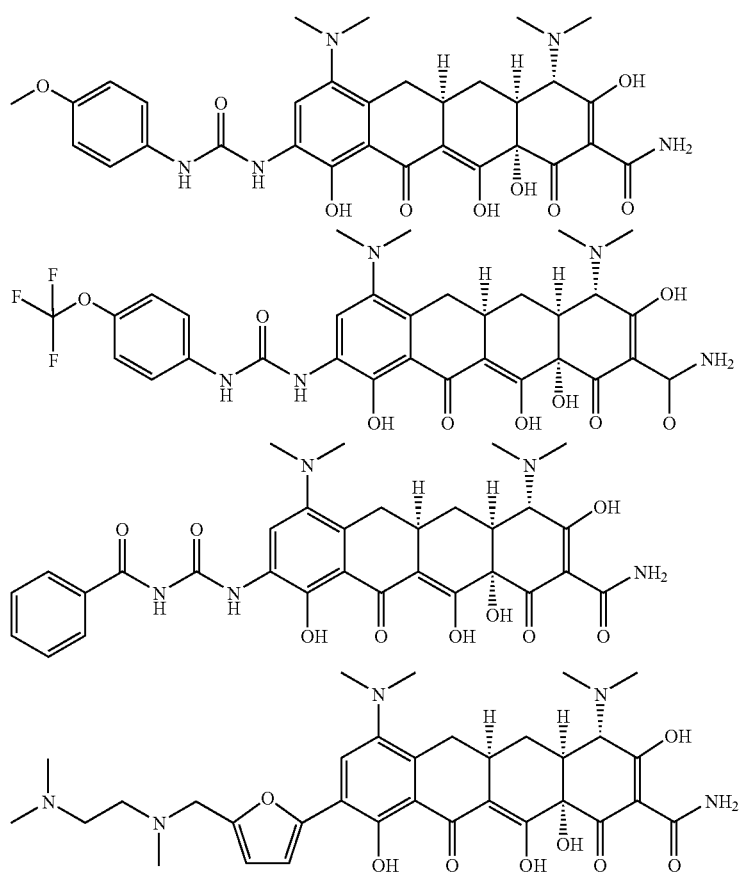

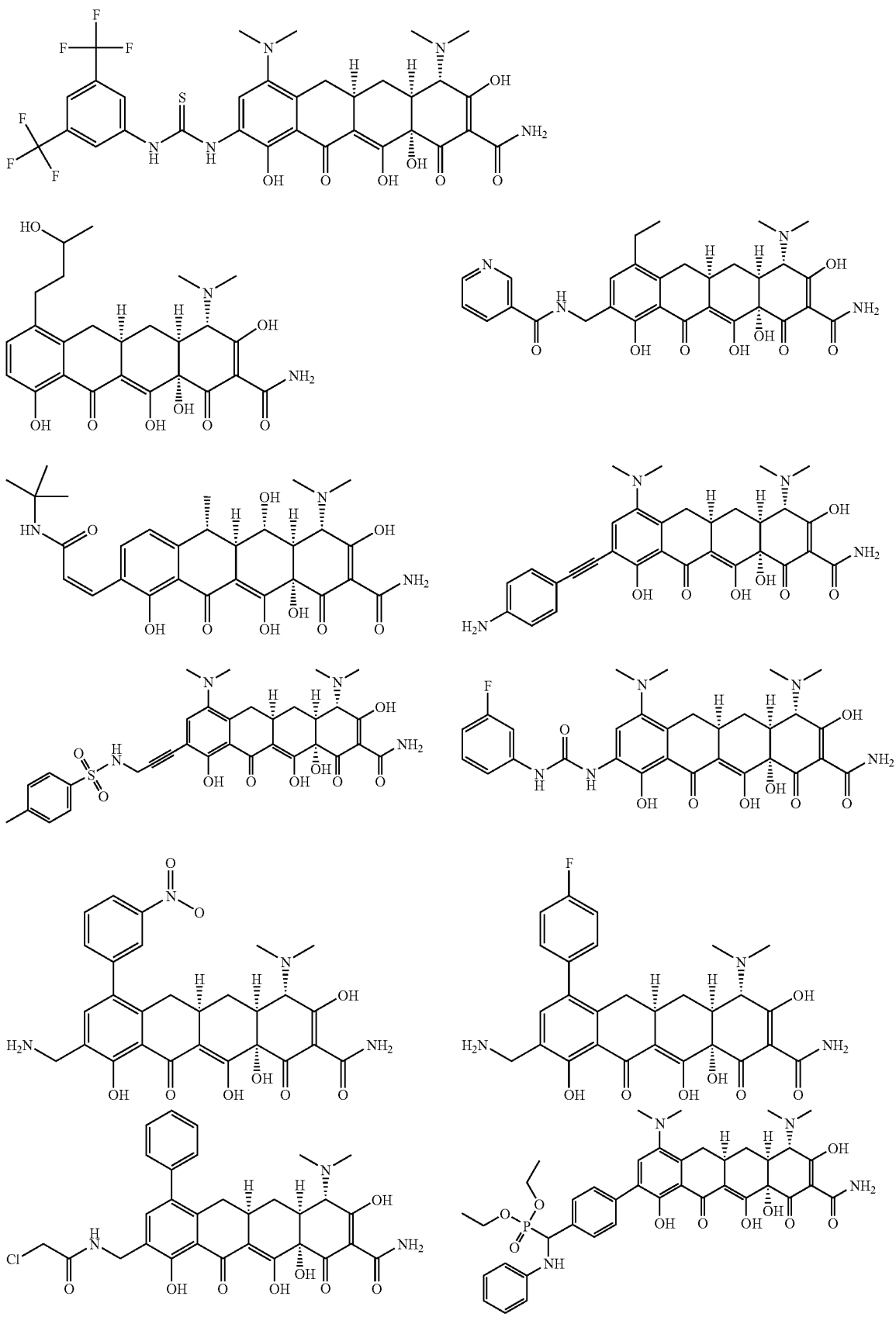

591
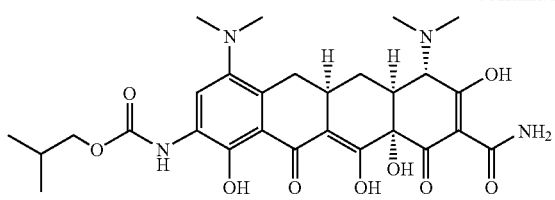
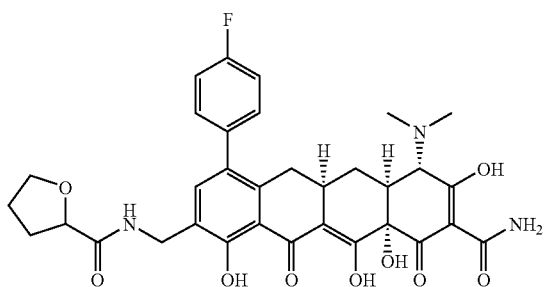
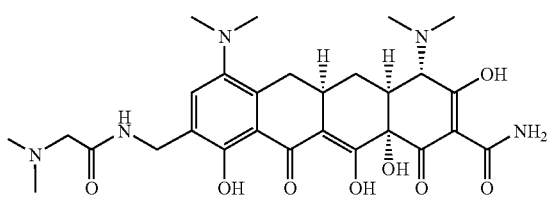
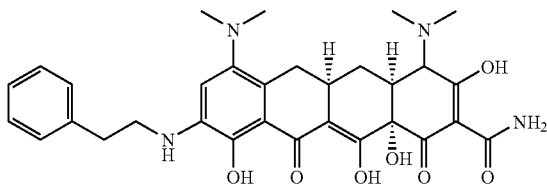
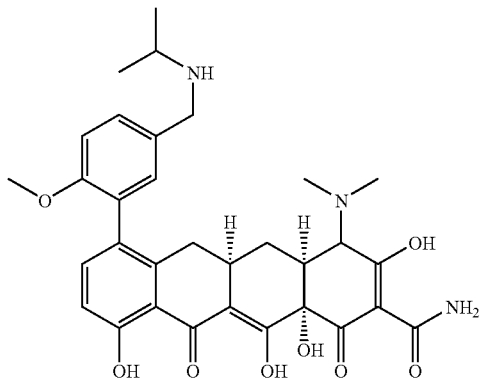
592
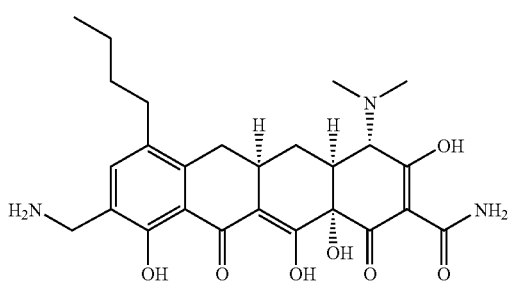
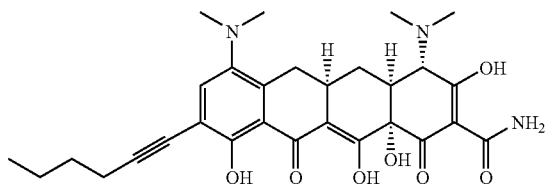
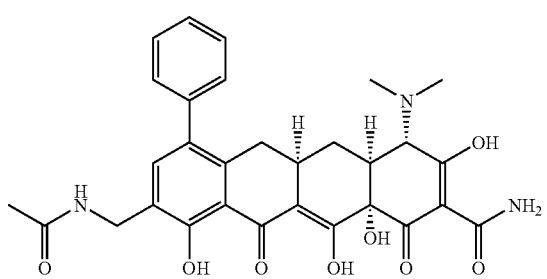
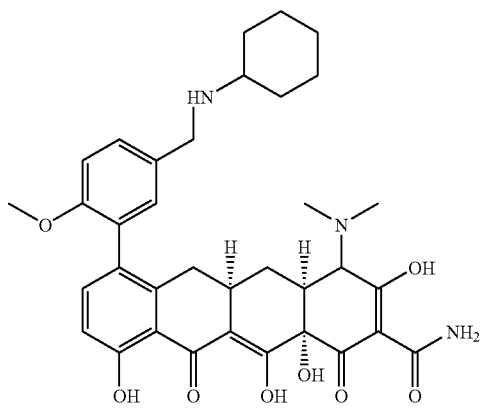
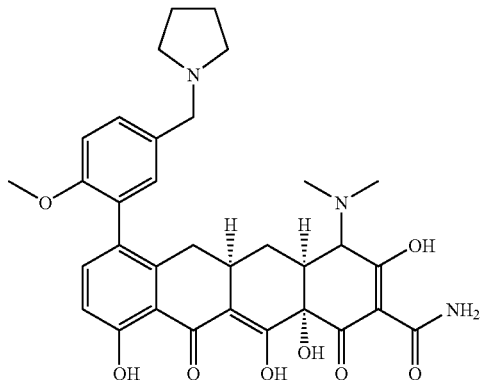

593 594
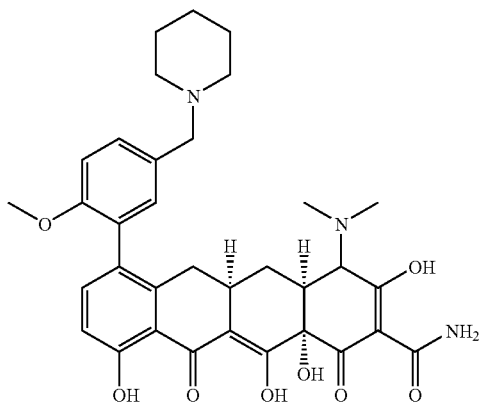
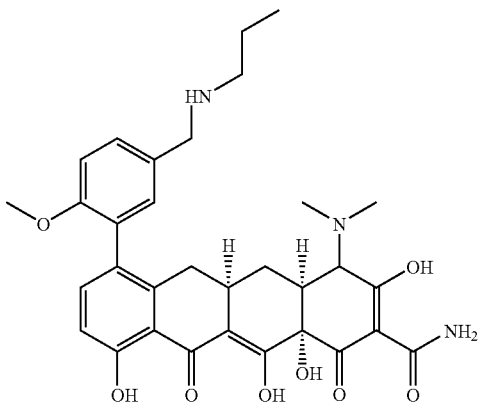
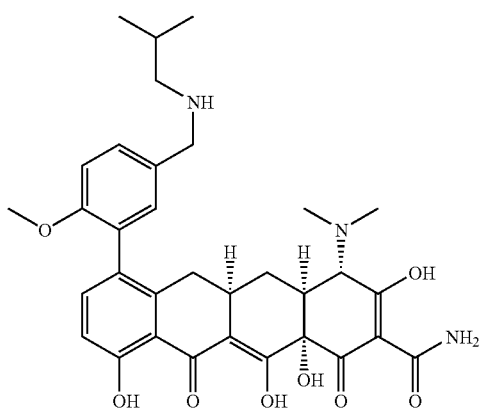
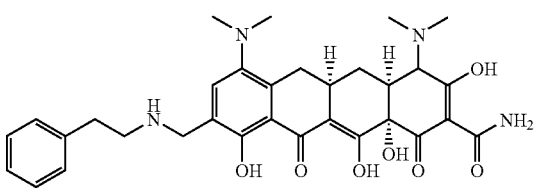
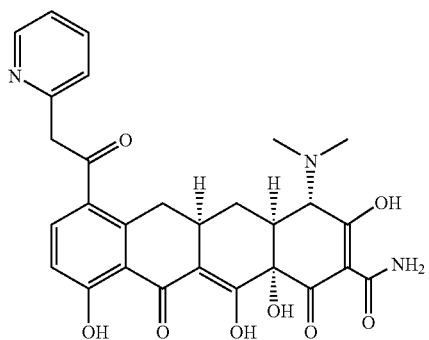
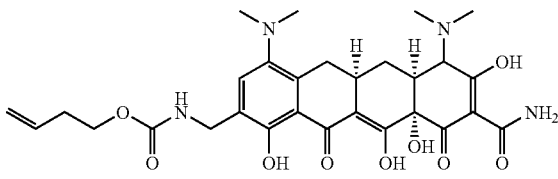
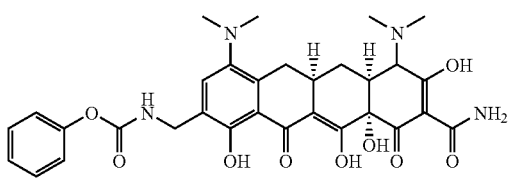
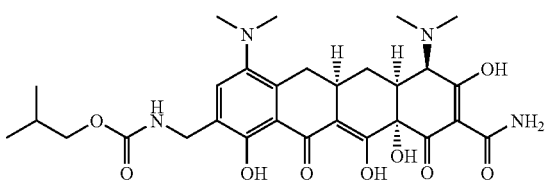
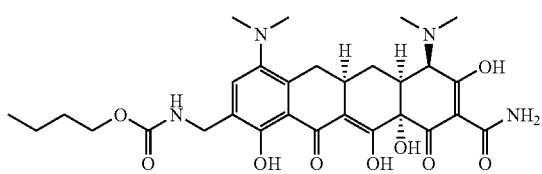
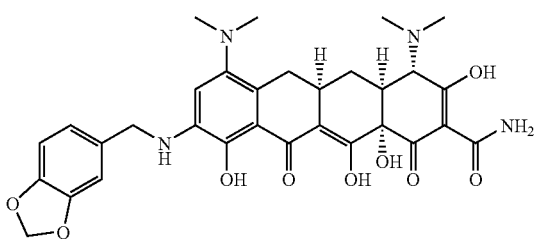

595 596
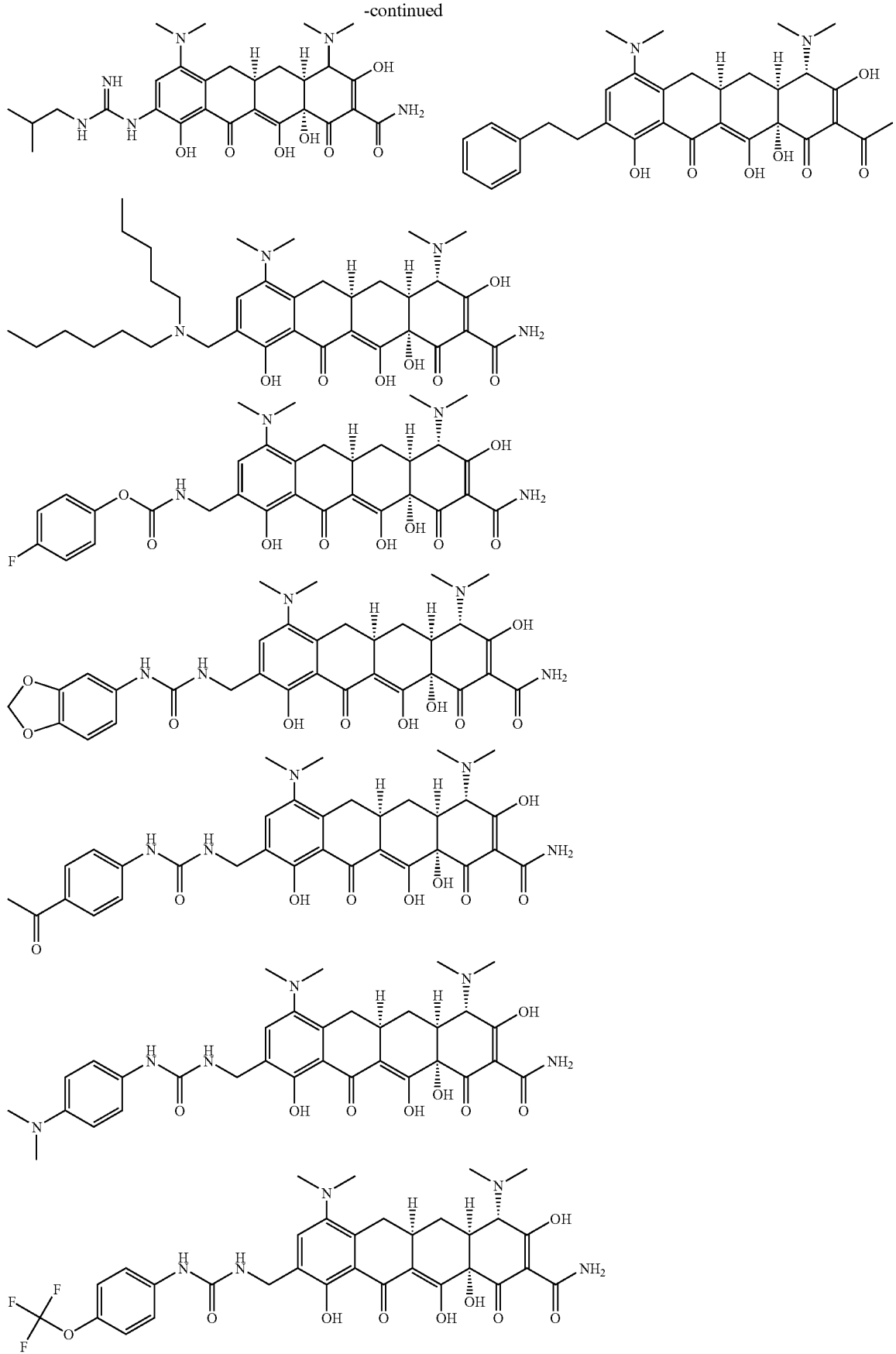
-continued 597 598
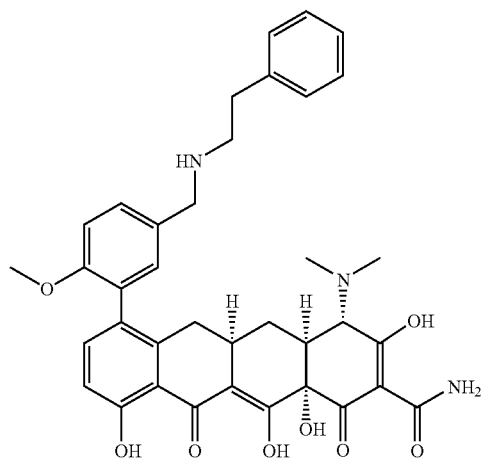
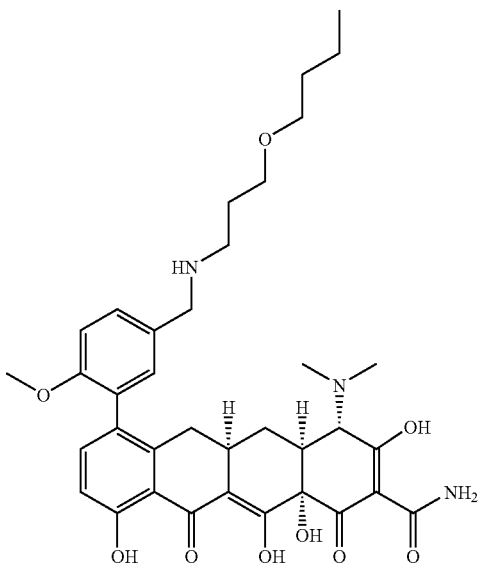
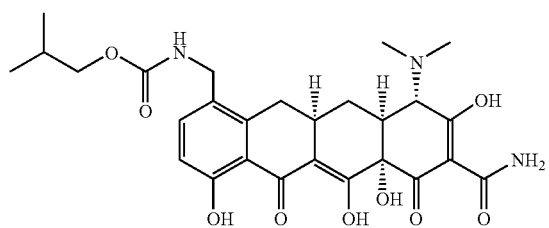
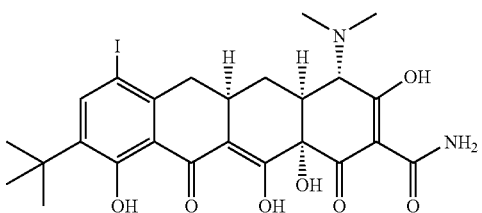
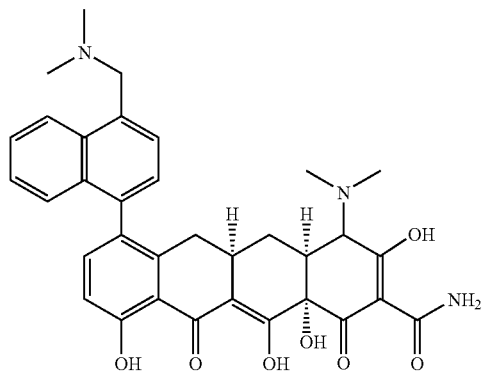
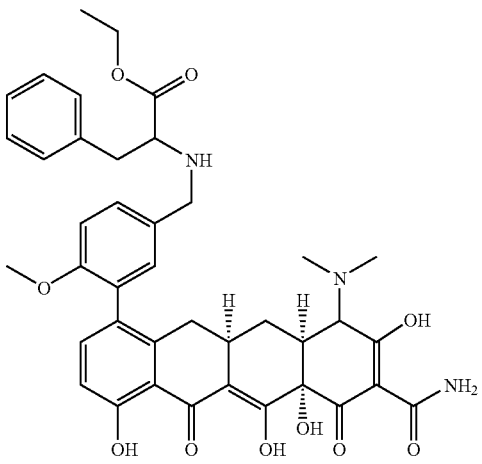
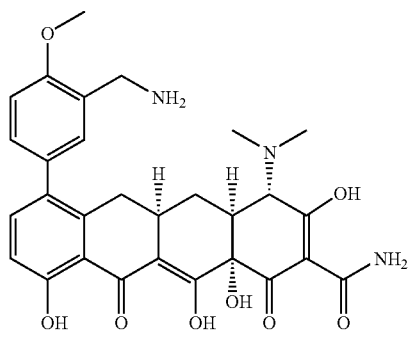
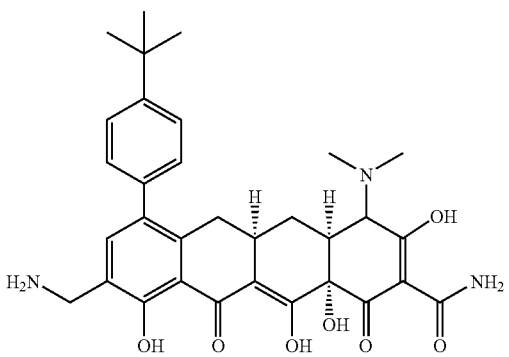

599 600
-continued
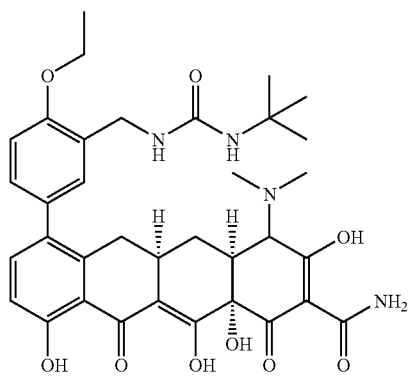
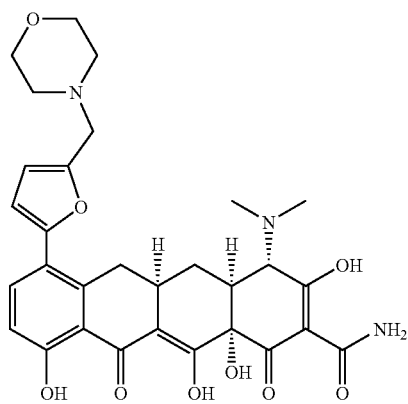
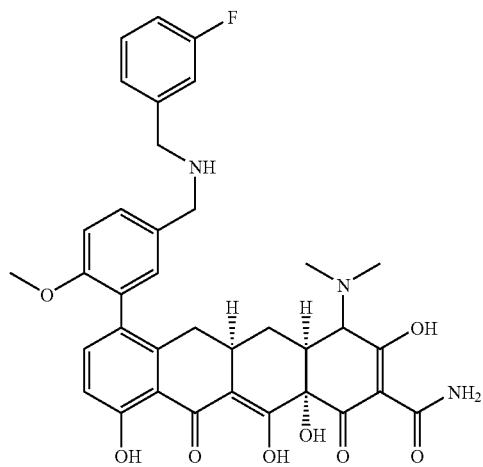
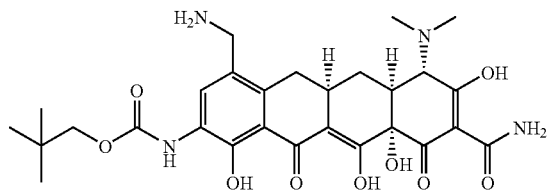
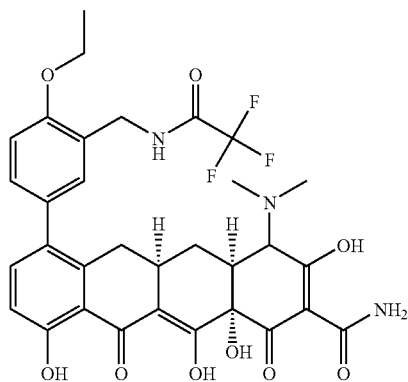
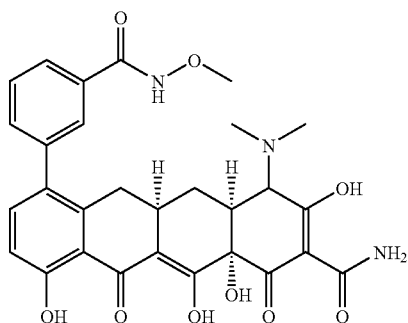
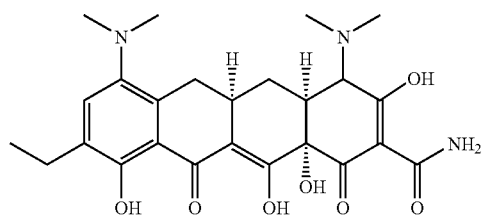
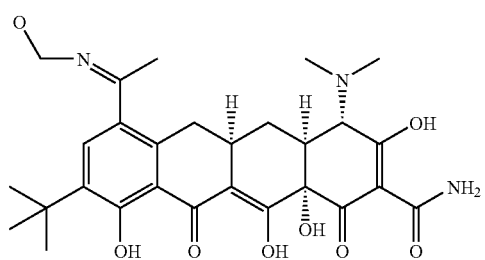

601
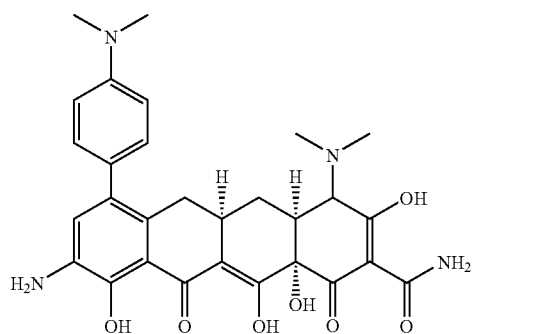
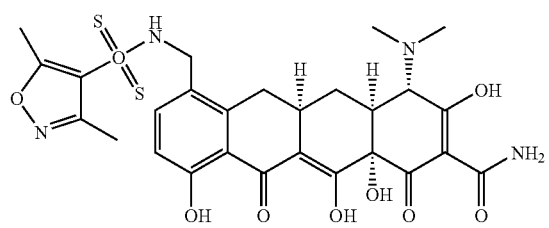
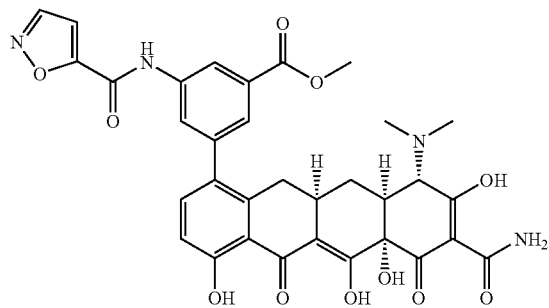
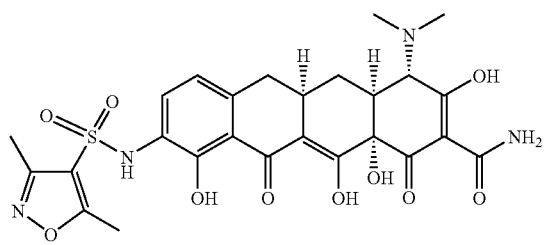
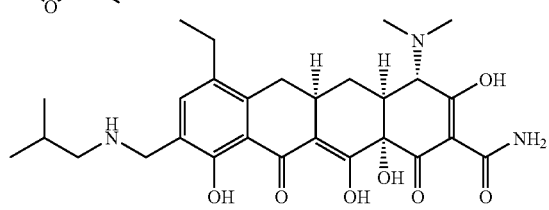
602
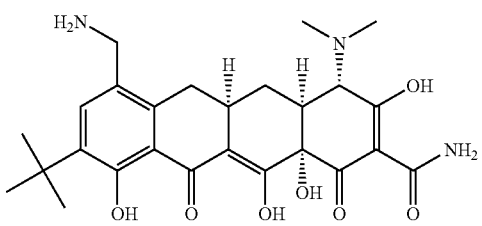
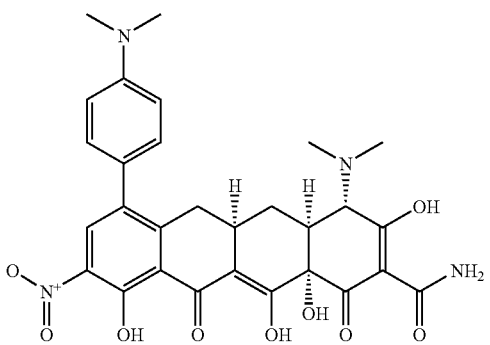
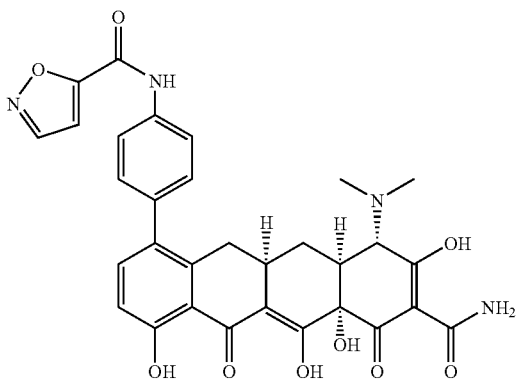
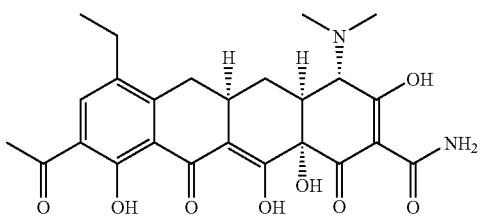
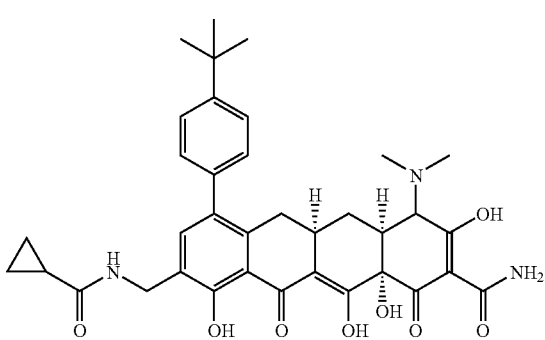

603 604
-continued
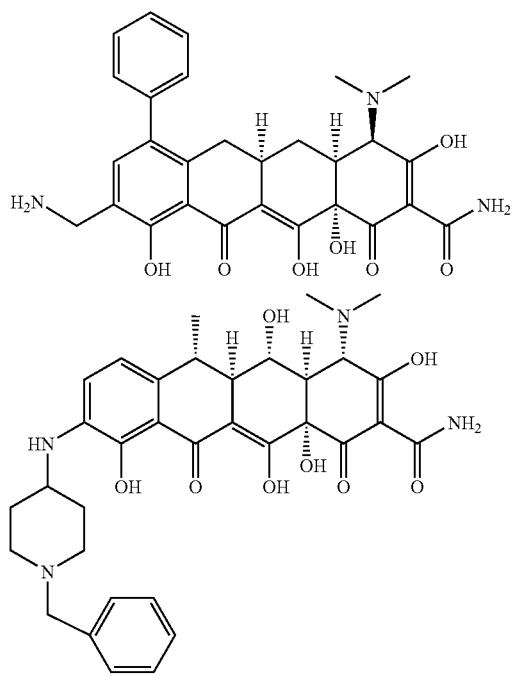
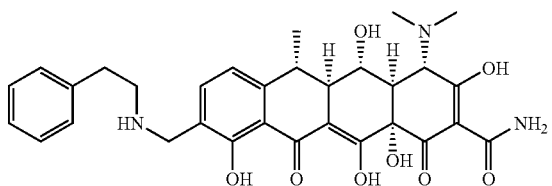
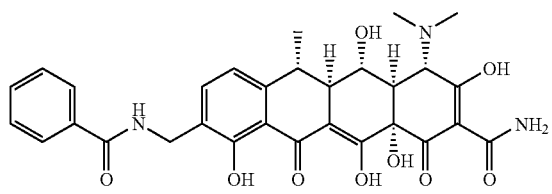
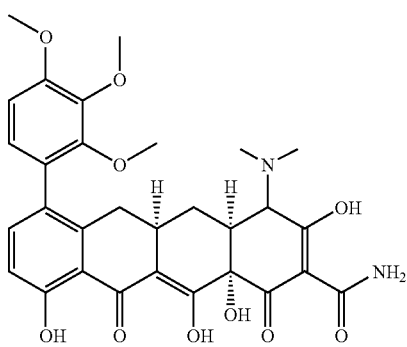
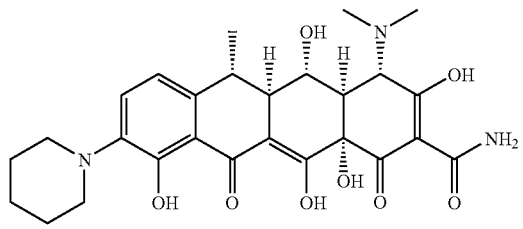
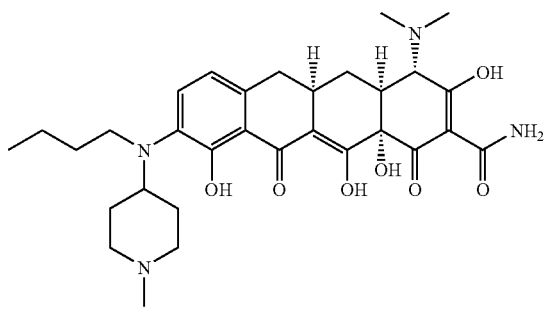
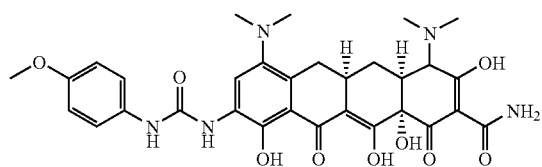
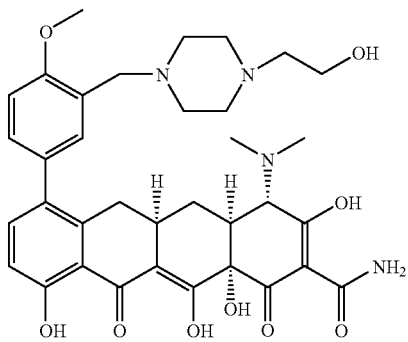
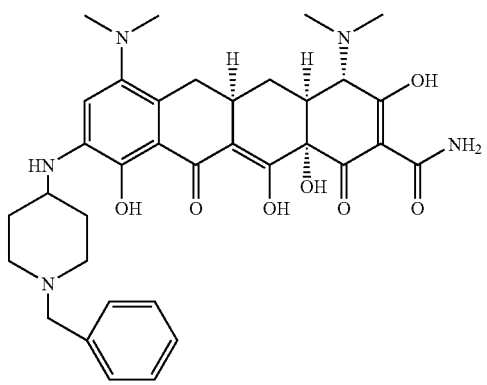

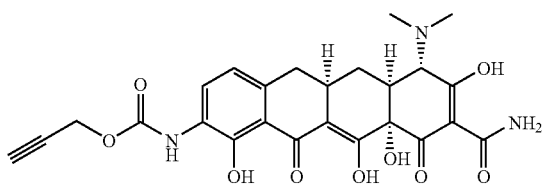
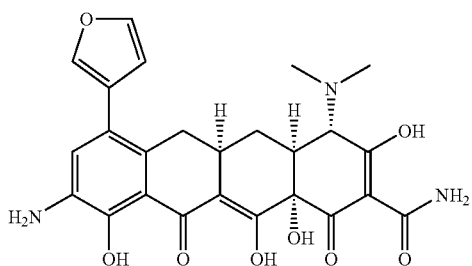
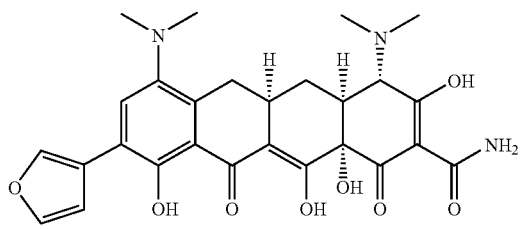
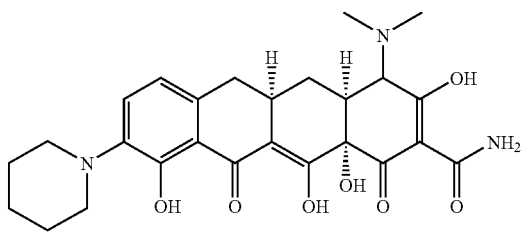
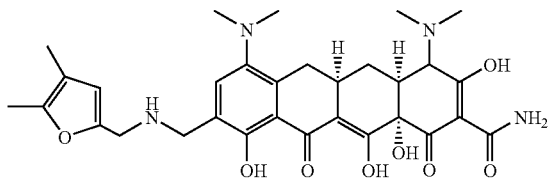
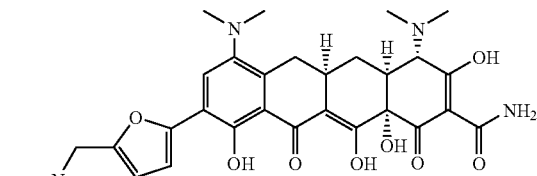
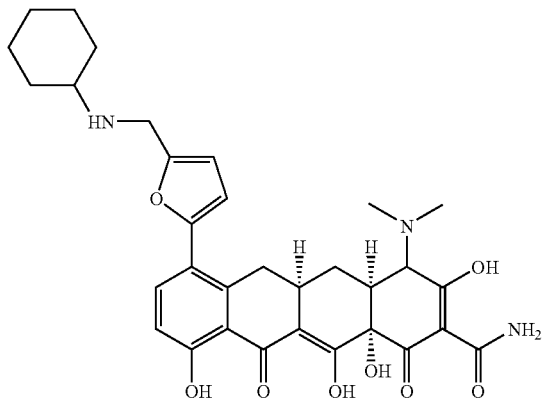
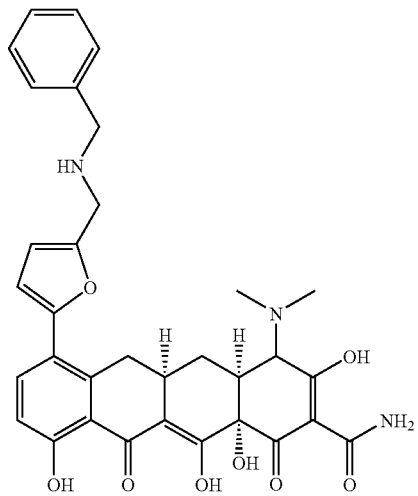

56. The method of claim 1, 4, or 5, wherein said tetracycline compound is non-antibacterial.

57. The method of claim 1, 4, or 5, wherein said tetracycline compound has anti-inflammatory activity.

58. The method of claim 2, 6, or 7, wherein said antifungal agent is a polyene.

59. The method of claim 2, 6, or 7, wherein said antifungal agent is amphotericin B.

60. The method of claim 2, 6, or 7, where said effective amount has a lower cytotoxicity than an effective amount of the antifungal agent when administered alone.

61. The method of claim 2, 6, or 7, wherein said fungal disorder is associated with a fungus selected from the group consisting of *A. nidulans, L. orientalis, C. neoformans, C. tropicalis, C. parapsilosis, C. lusitaniae, C. krusei, C. guilliermondii, C. glabrata, C. dubliniensis*, or *C. albicans*.

62. The method of claim 2, 6, or 7, wherein said fungal associated disorder is histoplasmosis, systemic candidiasis, aspergillosis, blastomycosis, coccidioidomycosis, paracoccidioidomycosis, cryptococcosis, dermatophyte infections, tinea pedis, tinea cruris, candidiasis, actinomycosis, mycoses, aspergillosis, candidosis, chromomycosis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, or sprotrichiosis.

63. The method of claim 2, 6, or 7, wherein said subject is a plant.

64. The method of claim 2, 6, or 7, wherein said subject is a mammal.

65. The method of claim 64, wherein said mammal is a human.

66. The method of claim 64, wherein said mammal is immunocompetent.

67. The method of claim 64, wherein said mammal is immunocompromised.

68. The method of claim 67, wherein said human is immunodeficient.

69. The method of claim 68, wherein said human has AIDS.

70. The method of claim 68, wherein said human has undergone chemotherapy.

71. The method of claim 2, 6, or 7, further comprising the administration of a pharmaceutically acceptable carrier.

72. The method of claim 2, 6, or 7, wherein said tetracycline compound is non-antibacterial.

73. The method of claim 2, 6, or 7, wherein said tetracycline compound has anti-inflammatory activity.

74. The method of claim 3, wherein the amount of said synergistically effective substituted tetracycline compounds and said effective amount of amphotericin B is not toxic to the subject.

75. The method of claim 4, wherein said substituted tetracycline compound is selected from the group consisting of:

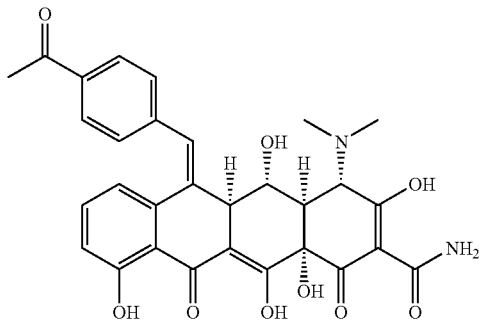

-continued

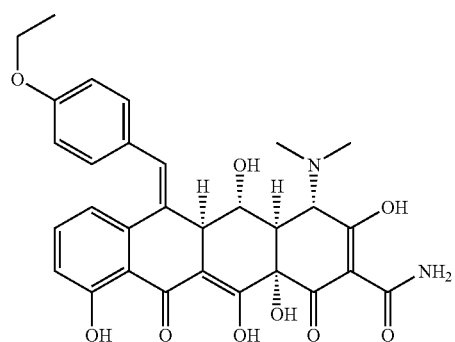

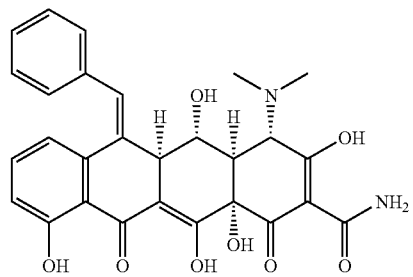

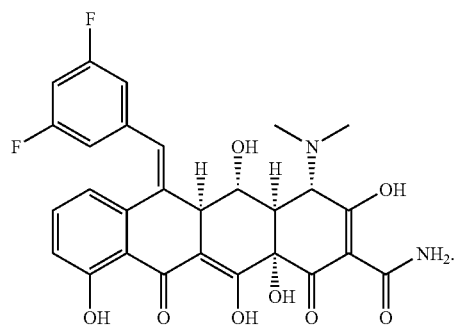

* * * * *

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 15, first compound, replace

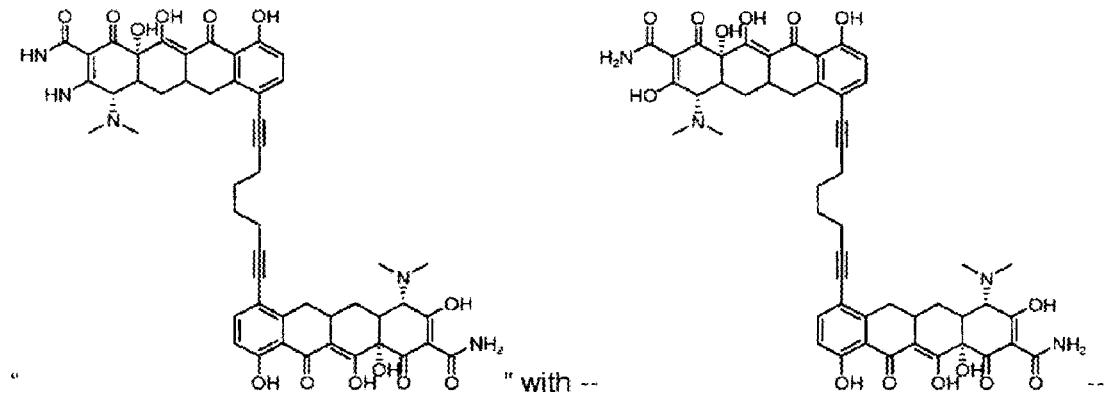

UNITED STATES PATENT AND TRADEMARK OFFICE
CERTIFICATE OF CORRECTION

PATENT NO. : 7,045,507 B2  Page 2 of 53
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 16, third compound, replace

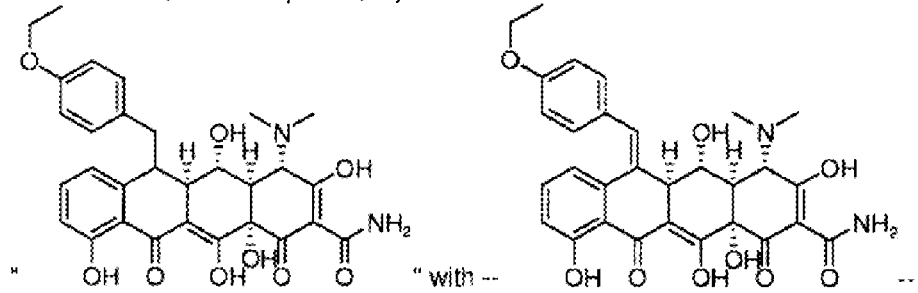

At column 16, third compound, replace

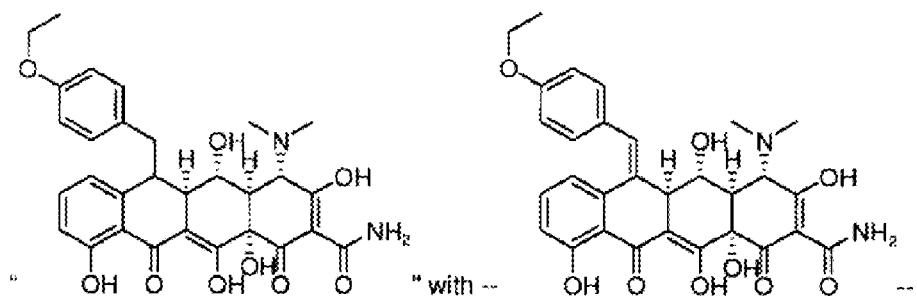

At column 17, second compound, replace

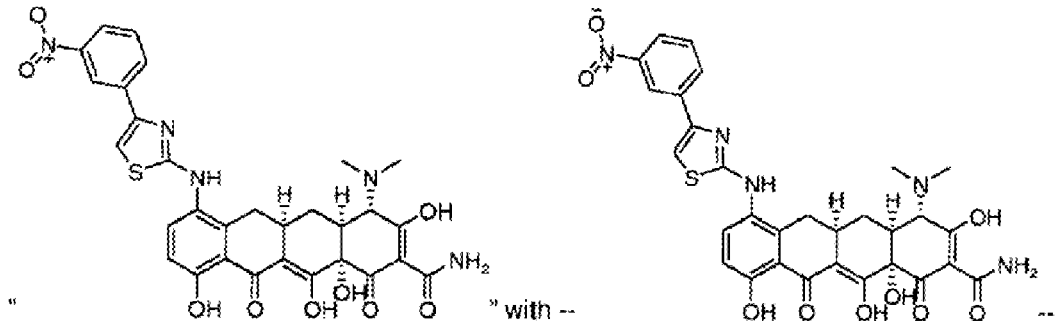

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 18, second compound, replace

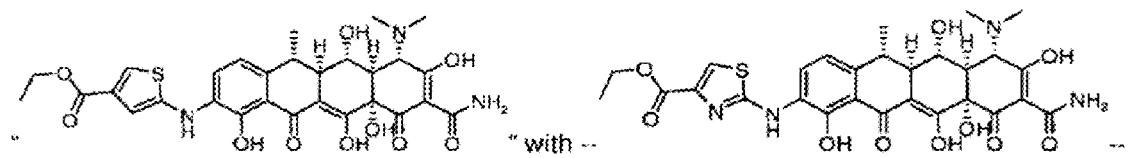

At column 21, third compound, replace

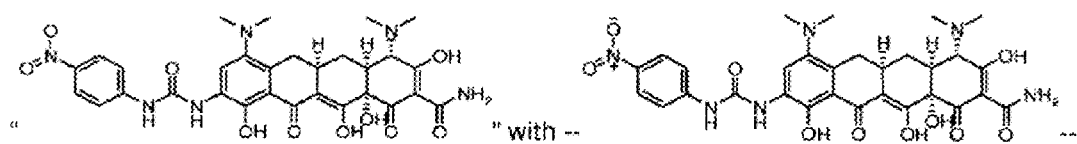

At column 24, third compound, replace

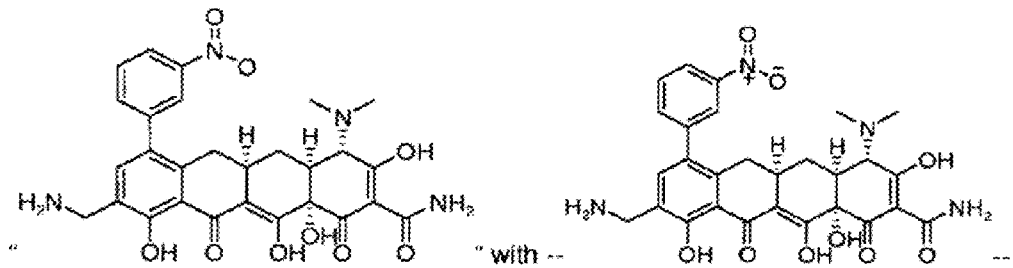

At column 27, second compound, replace

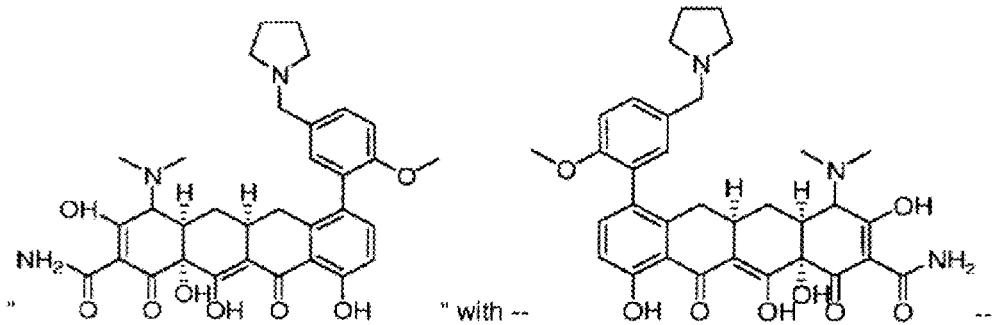

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 28, second compound, replace

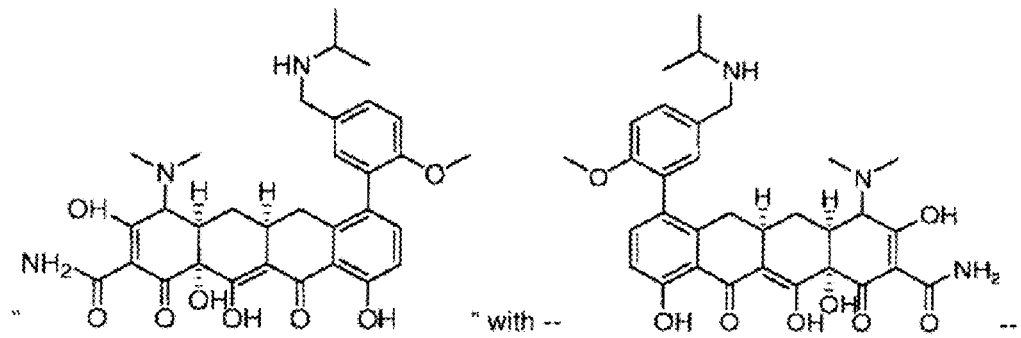

At column 31, second compound, replace

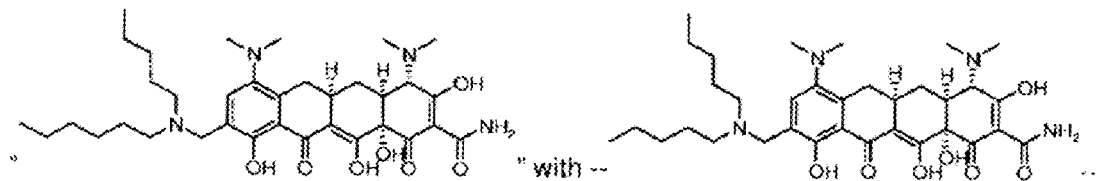

At column 36, fourth compound, replace

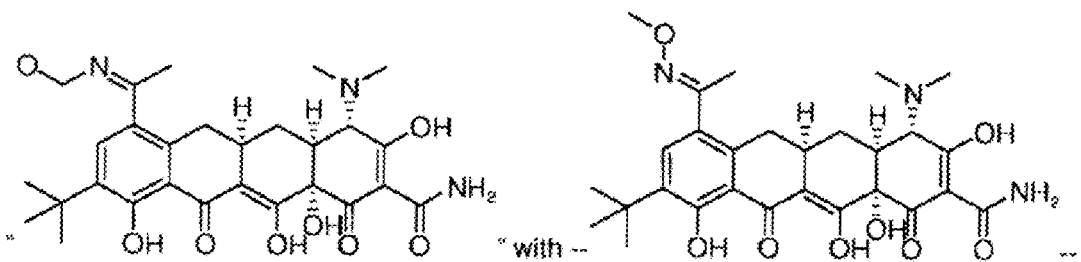

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 38, second compound, replace

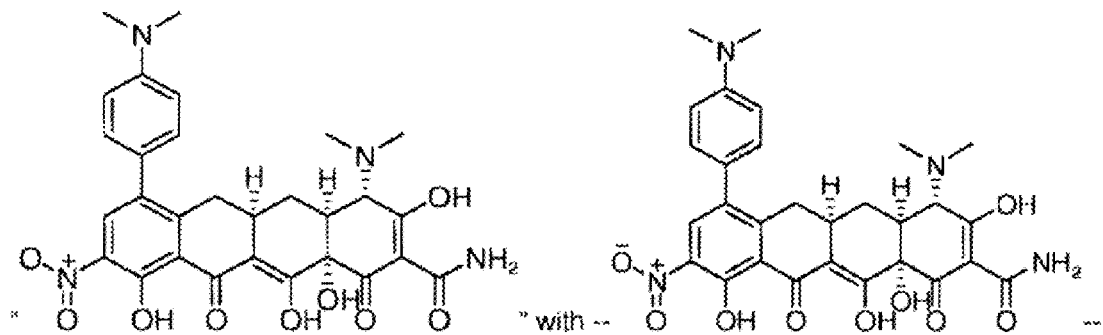

At column 38, third compound, replace

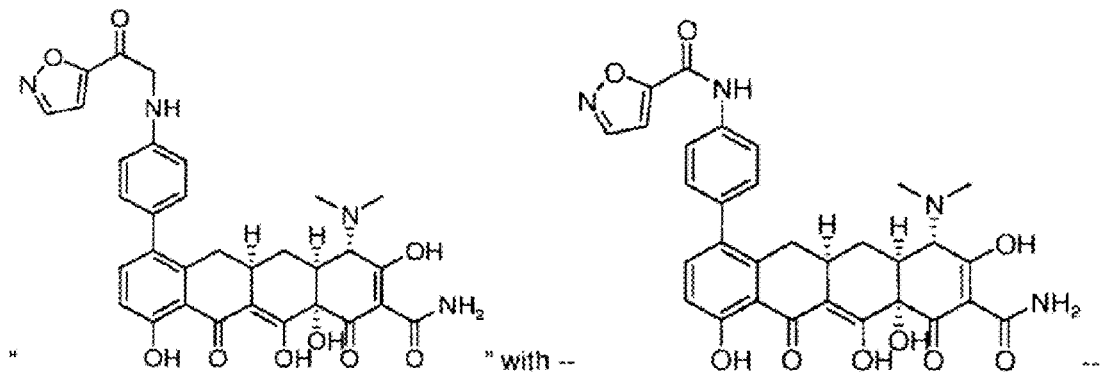

At column 39, fifth compound, replace

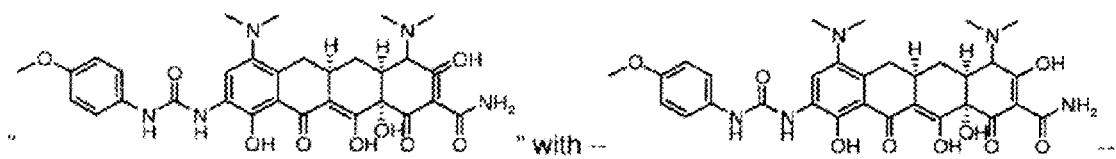

UNITED STATES PATENT AND TRADEMARK OFFICE
CERTIFICATE OF CORRECTION

PATENT NO. : 7,045,507 B2  Page 6 of 53
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 40, fifth compound, replace

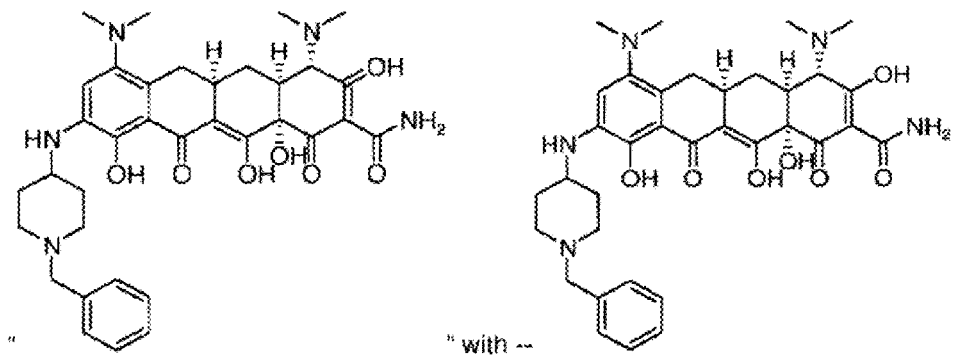

At column 41, first compound, replace

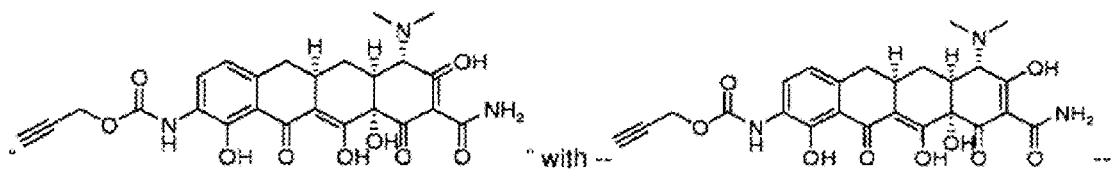

At column 41, second compound, replace

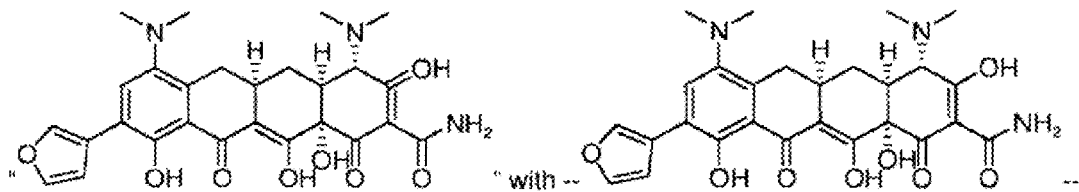

At column 41, third compound, replace

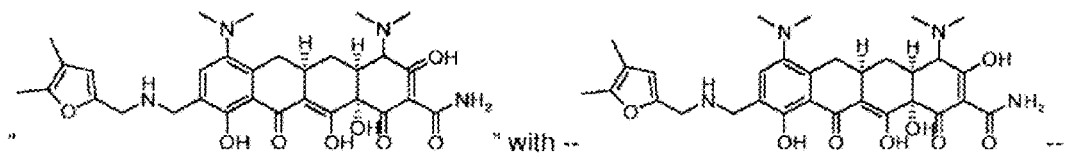

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 41, fourth compound, replace

" 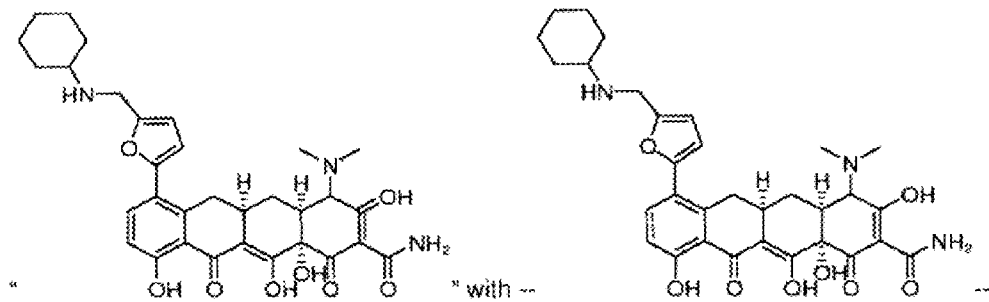 " with --  --

At column 42, first compound, replace

" 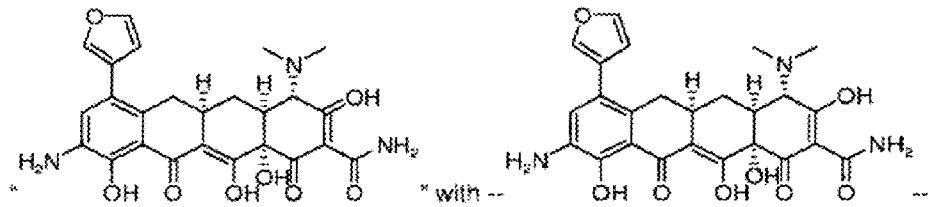 " with --  --

At column 42, second compound, replace

" 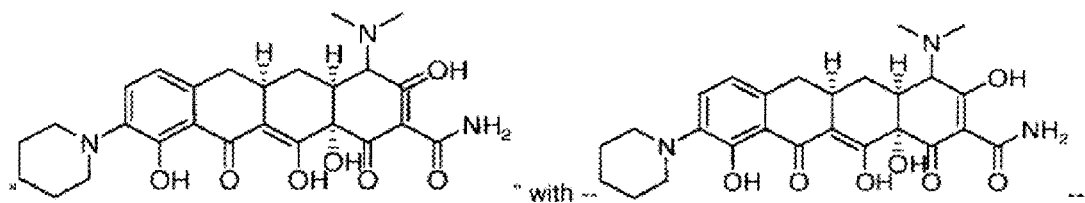 " with --  --

At column 42, third compound, replace

" 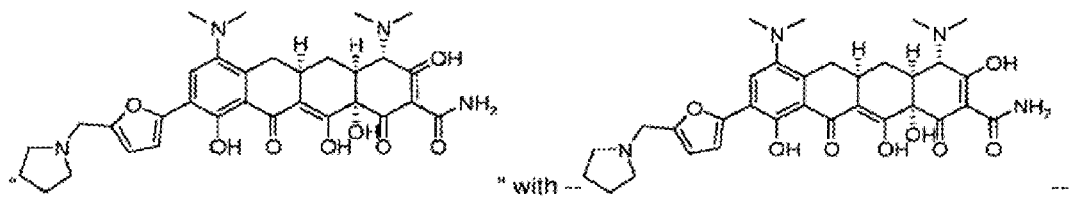 " with --  --

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 42, fourth compound, replace

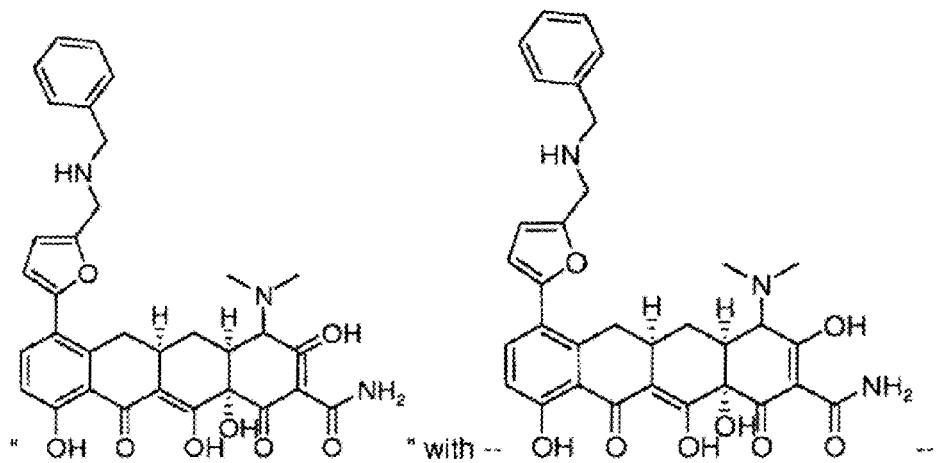

At columns 67-68, Table 2, compound B, replace

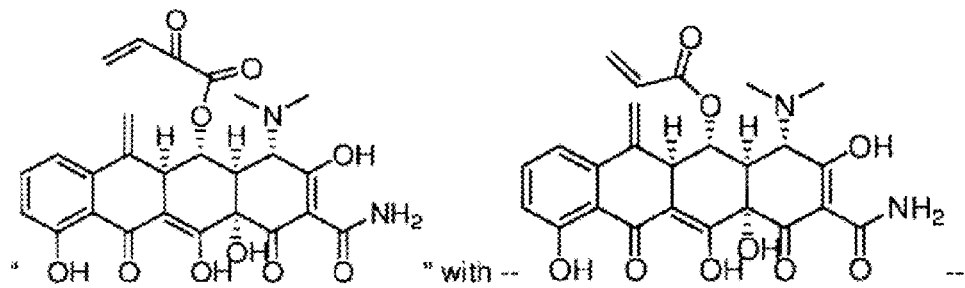

At columns 69-70, Table 2, compound F, replace

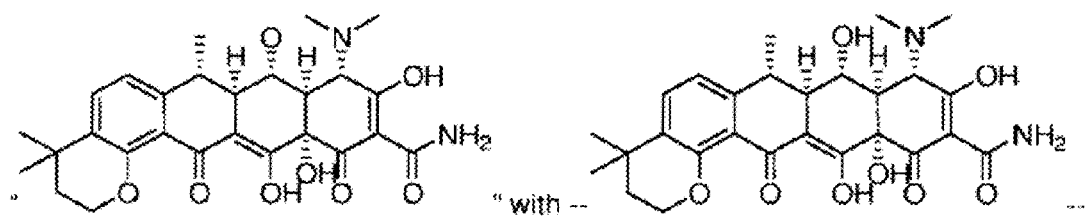

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 70, Table 2, compound G, replace

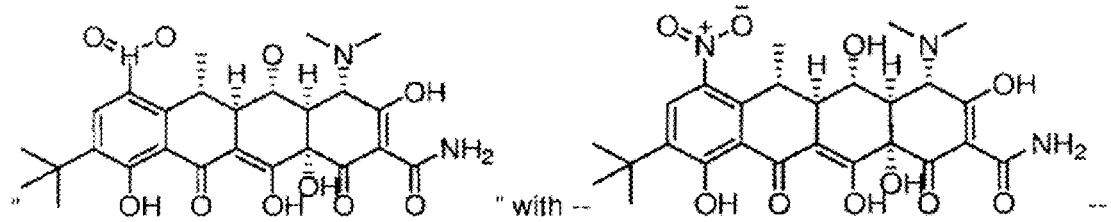

At columns 71-72, Table 2, compound I, replace

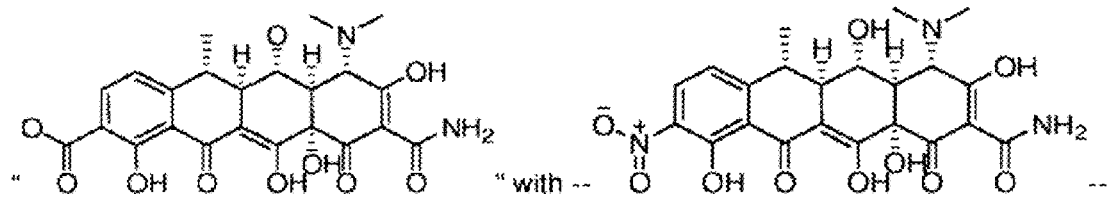

At column 73, Table 2, compound K, replace

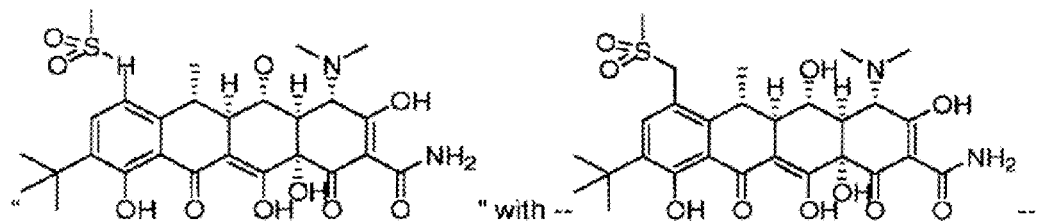

At columns 73-74, Table, 2, compound M, replace

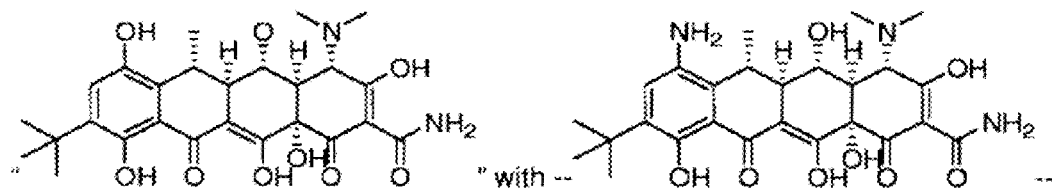

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 74, Table 2, compound N, replace

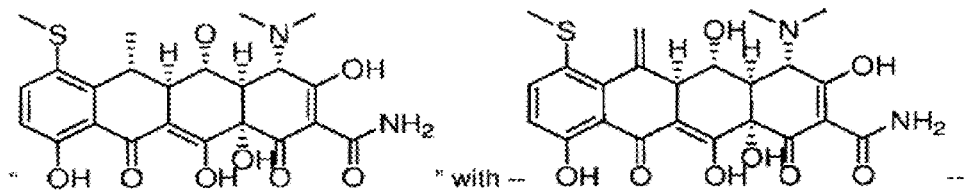

At column 75, Table 2, compound O, replace

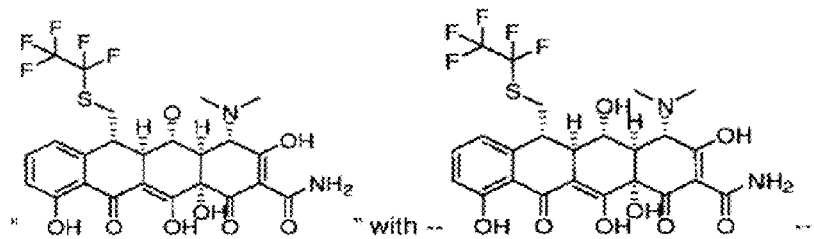

At columns 75-76, Table 2, compound P, replace

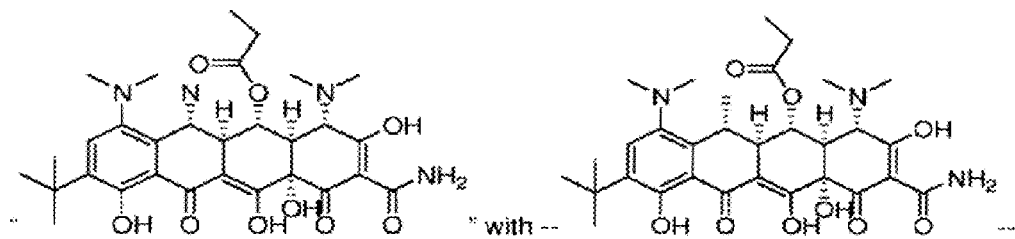

At column 77, Table 2, compound R, replace

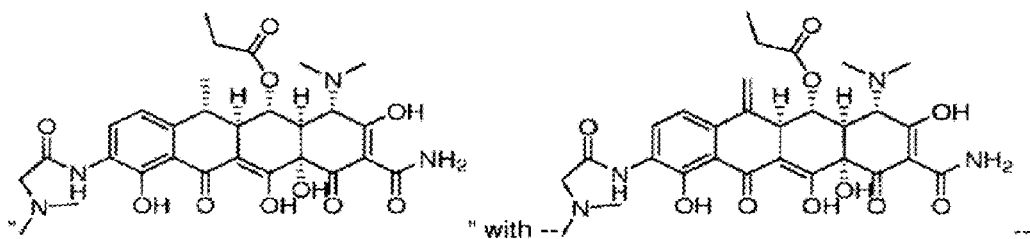

UNITED STATES PATENT AND TRADEMARK OFFICE
CERTIFICATE OF CORRECTION

PATENT NO.         : 7,045,507 B2
APPLICATION NO. : 10/097634
DATED                  : May 16, 2006
INVENTOR(S)        : Michael Draper et al.

It is certified that error appears in the above-identified patent and that said Letters Patent is hereby corrected as shown below:

At columns 85-86, Table 2, compound AE, replace

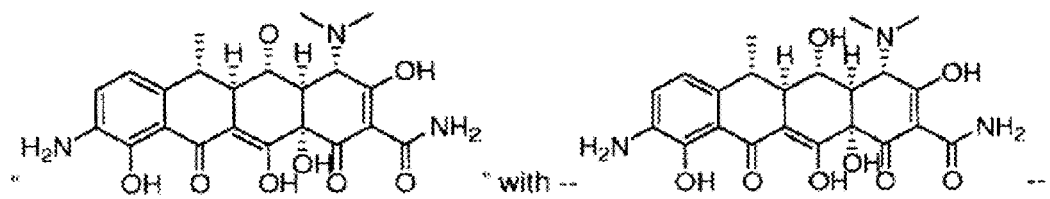

At column 86, Table 2, compound AF, replace

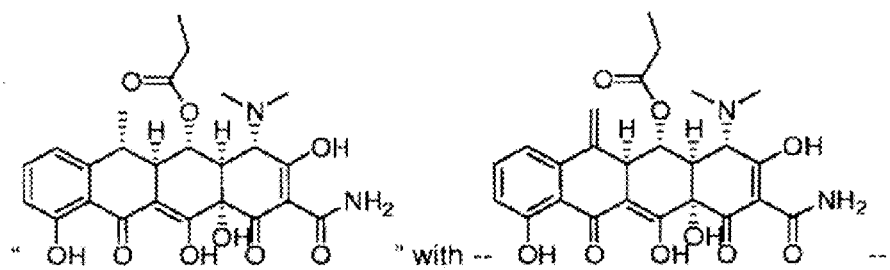

At columns 93-94, Table 2, compound AQ, replace

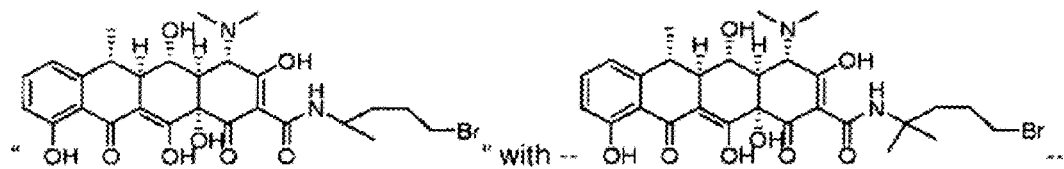

At column 94, Table 2, compound AR, replace

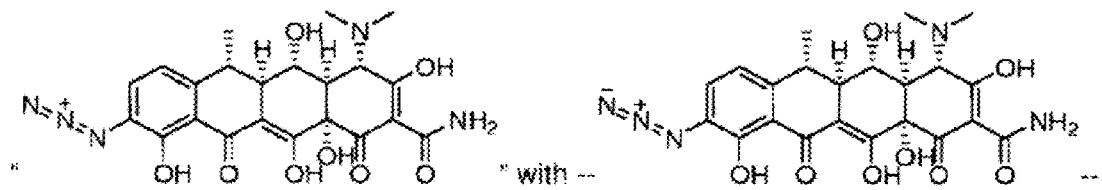

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 101-102, Table 2, compound BF, replace

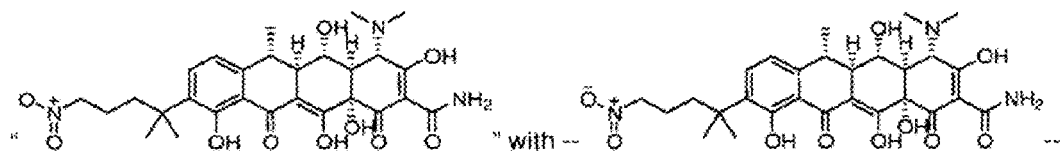

At column 104, Table 2, compound BJ, replace

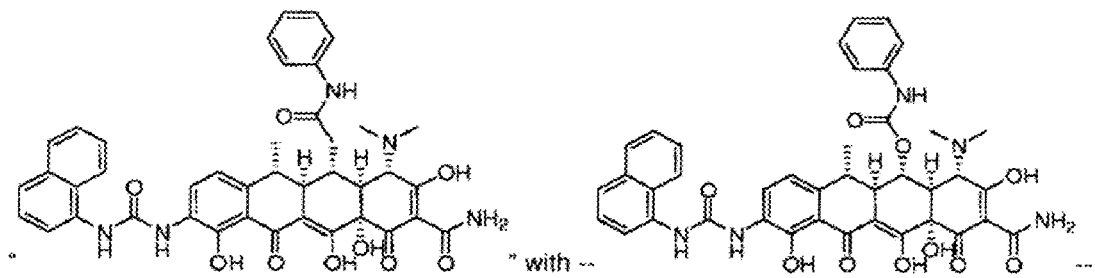

At column 107, Table 2, compound BN, replace

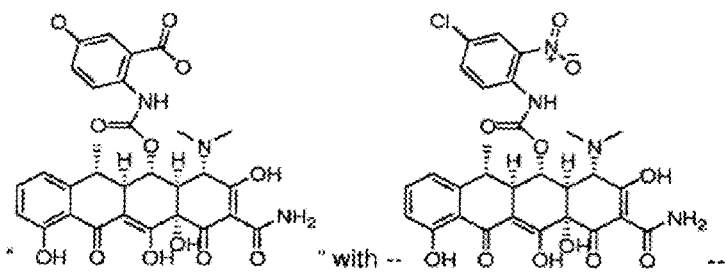

At column 110, Table 2, compound BS, replace

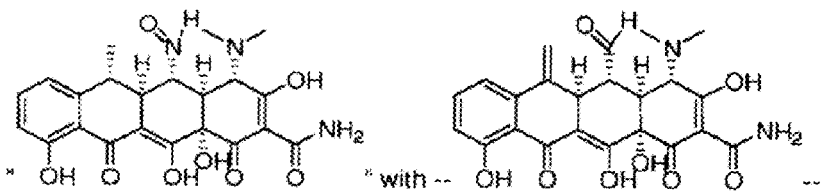

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 120, Table 2, compound CK, replace

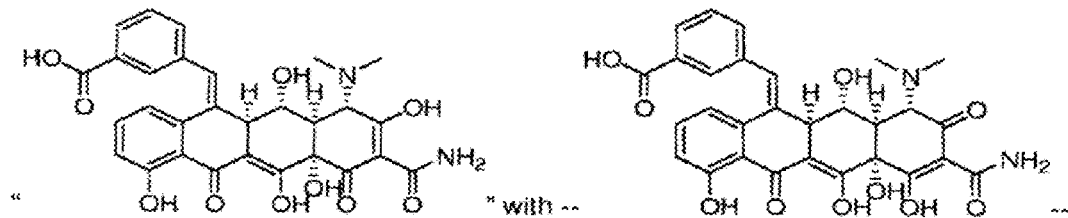

At column 121, Table 2, compound CL, replace

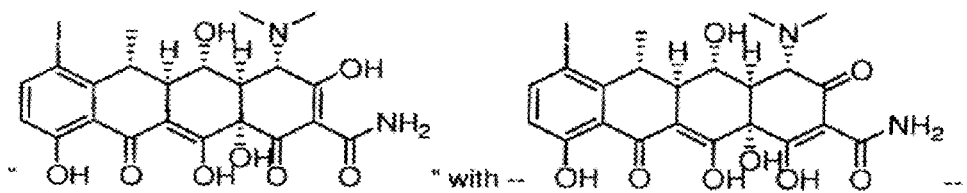

At column 121, Table 2, compound CM, replace

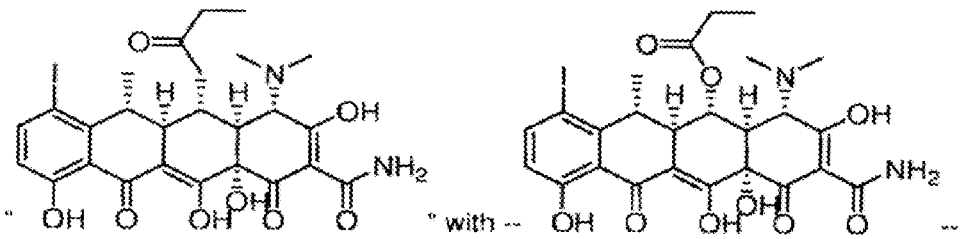

At column 125, Table 2, compound CU, replace

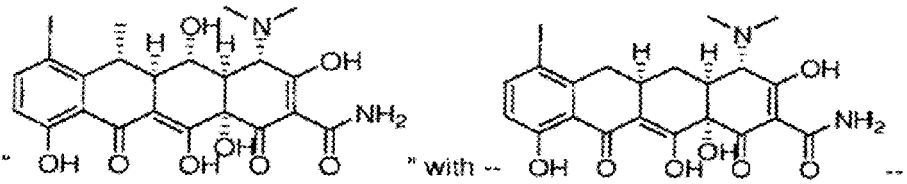

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 128, Table 2, compound CZ, replace

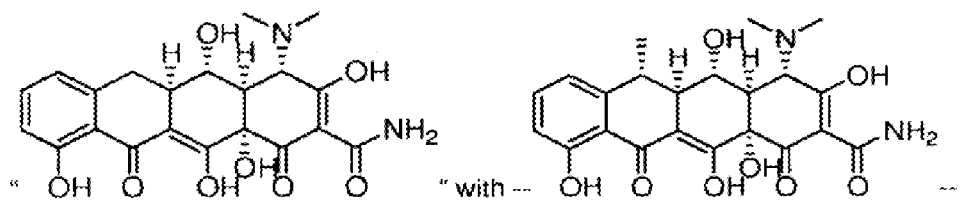

At column 129, Table 2, compound DB, replace

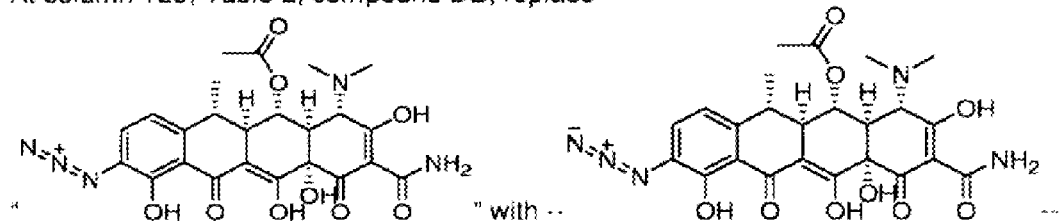

At columns 131-132, Table 2, compound DG, replace

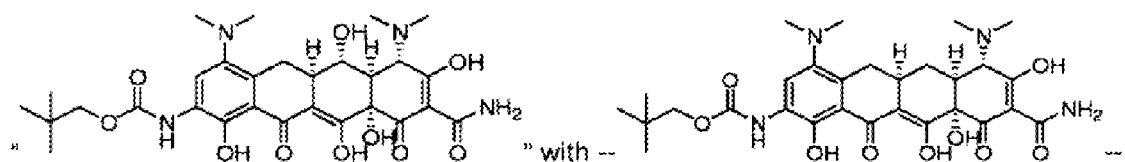

At columns 133-134, Table 2, compound DL, replace

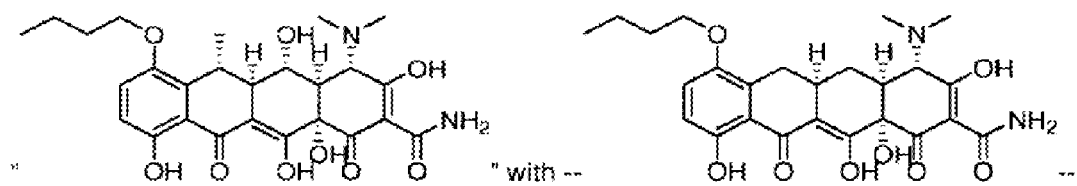

UNITED STATES PATENT AND TRADEMARK OFFICE
CERTIFICATE OF CORRECTION

PATENT NO.         : 7,045,507 B2                                   Page 15 of 53
APPLICATION NO. : 10/097634
DATED              : May 16, 2006
INVENTOR(S)       : Michael Draper et al.

It is certified that error appears in the above-identified patent and that said Letters Patent is hereby corrected as shown below:

At columns 139-140, Table 2, compound DV, replace

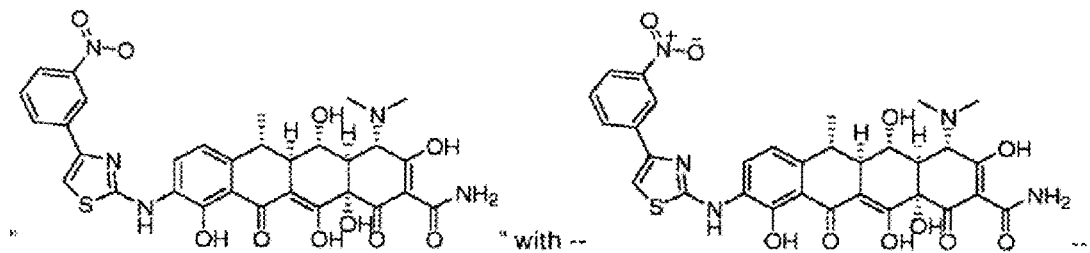

" with --

At column 144, Table 2, compound ED, replace

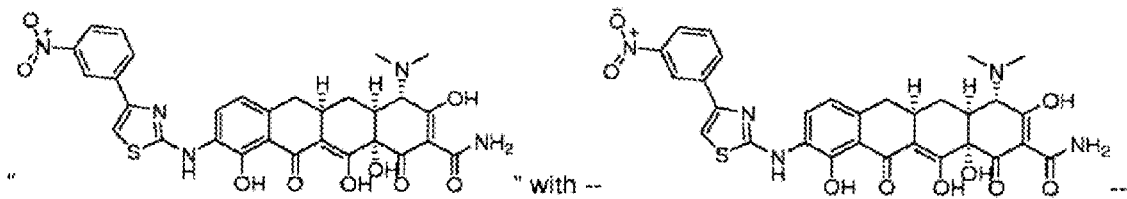

" with --

At columns 145-146, Table 2, compound EG, replace

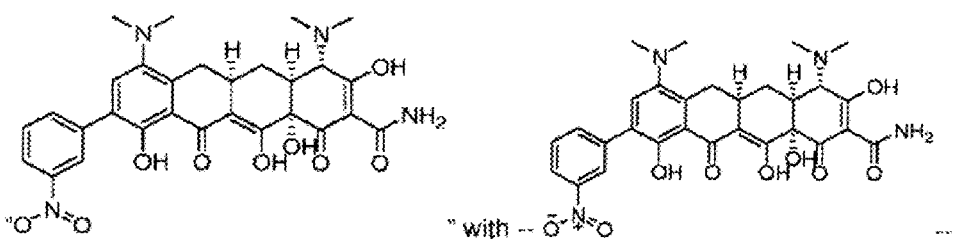

" with --

At column 147, Table 2, compound EI, replace

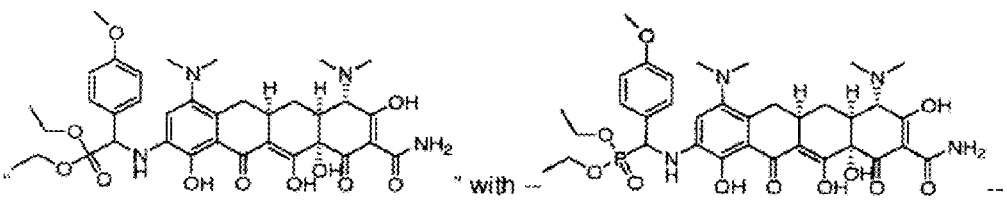

" with --

UNITED STATES PATENT AND TRADEMARK OFFICE
CERTIFICATE OF CORRECTION

PATENT NO.       : 7,045,507 B2
APPLICATION NO.  : 10/097634
DATED            : May 16, 2006
INVENTOR(S)      : Michael Draper et al.

It is certified that error appears in the above-identified patent and that said Letters Patent is hereby corrected as shown below:

At columns 147-148, Table 2, compound EJ, replace

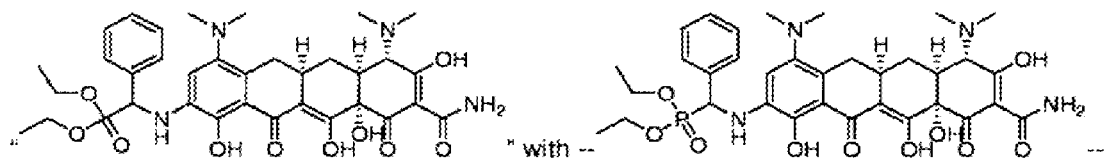

At columns 147-148, Table 2, compound EK, replace

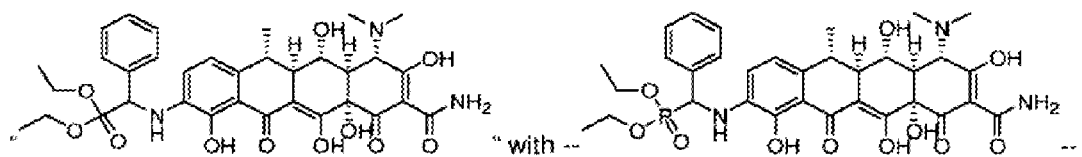

At column 148, Table 2, compound EL, replace

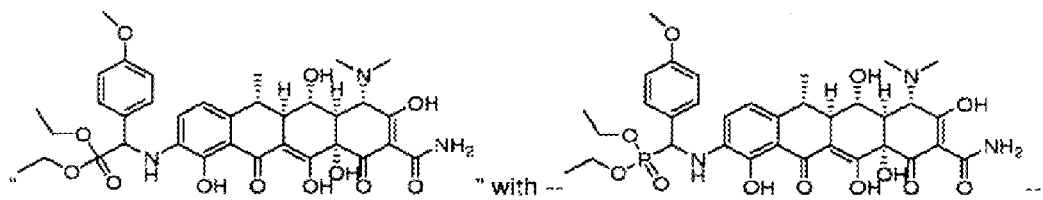

At columns 153-154, Table 2, compound EU, replace

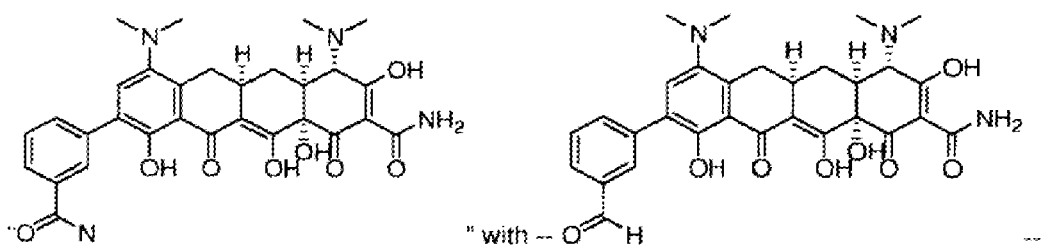

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 170, Table 2, compound FU, replace

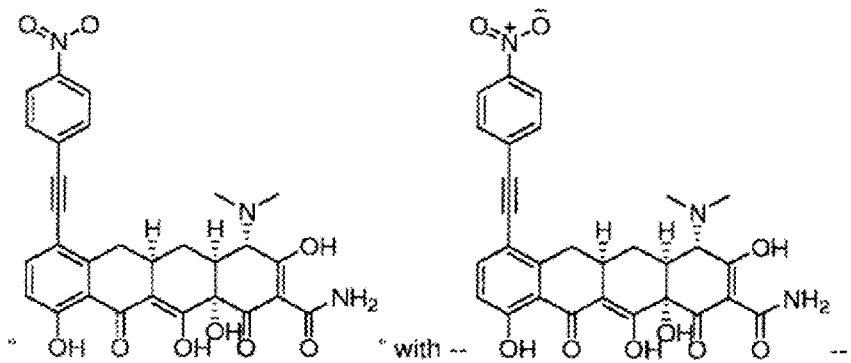

At column 175, Table 2, compound GB, replace

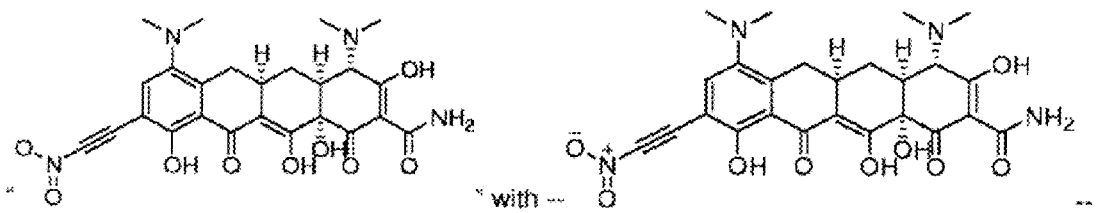

At column 178, Table 2, compound GG, replace

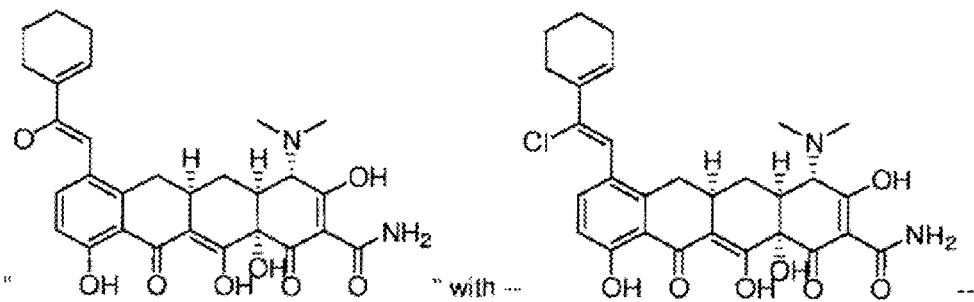

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 193-194, Table 2, compound HB, replace

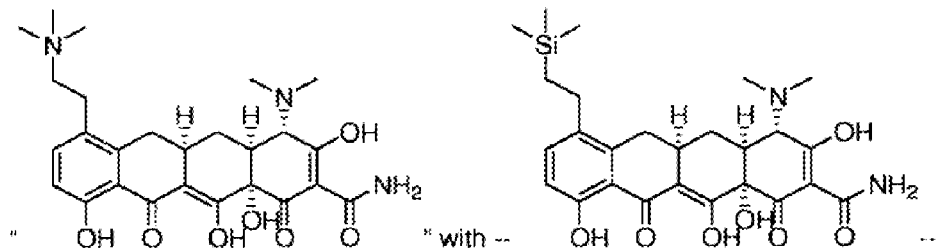

At column 204, Table 2, compound HO, replace

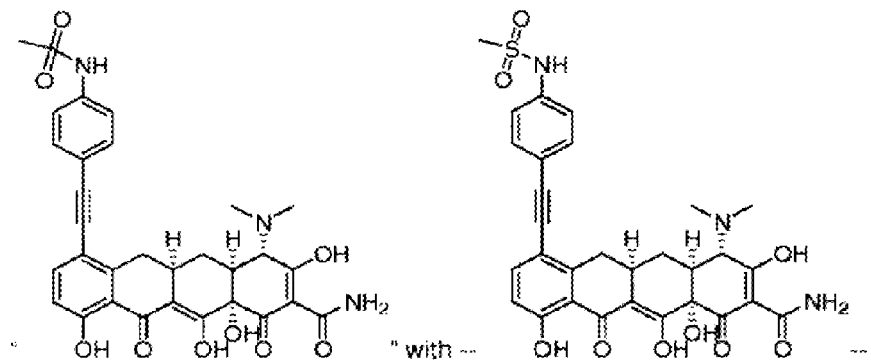

At columns 213-214, Table 2, compound IA, replace

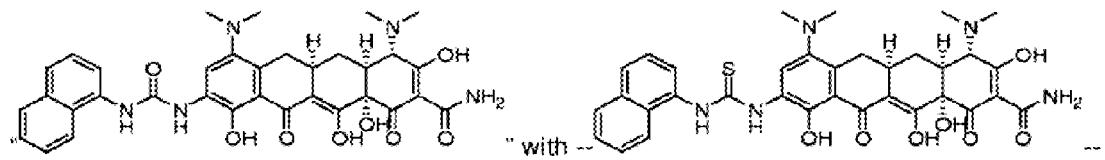

At column 214, Table 2, compound IB, replace

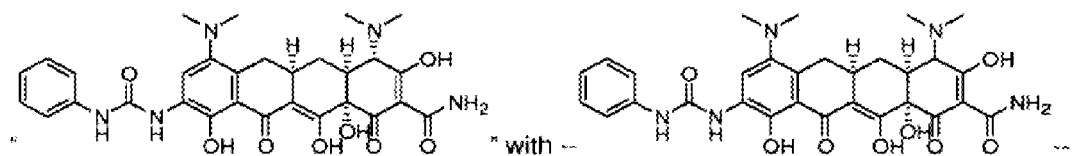

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 215, Table 2, compound IC, replace

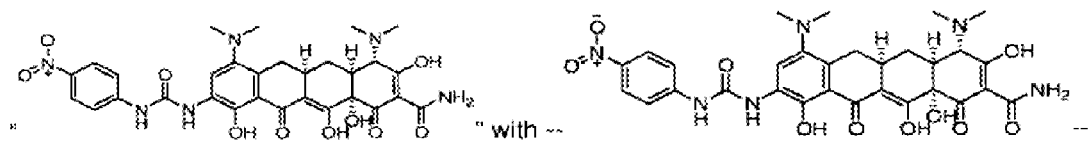

At columns 217-218, Table 2, compound IH, replace

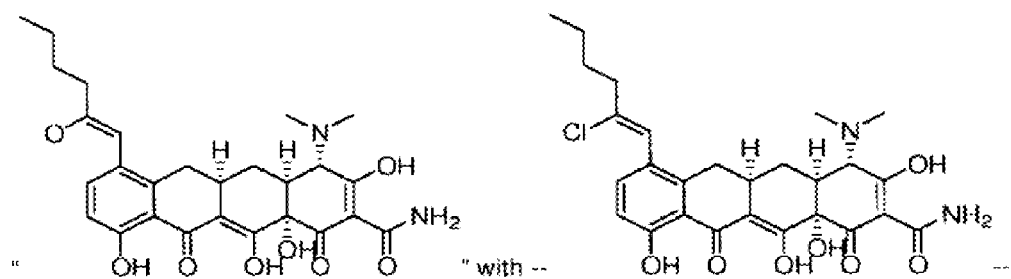

At columns 219-220, Table 2, compound IL, replace

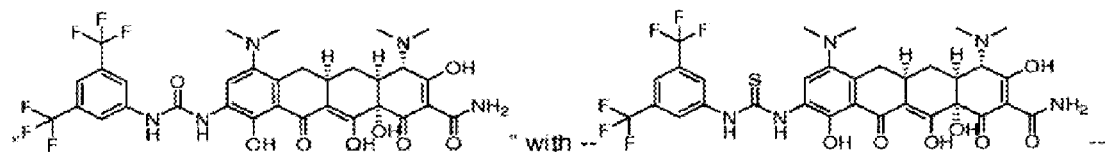

At column 223, Table 2, compound IQ, replace

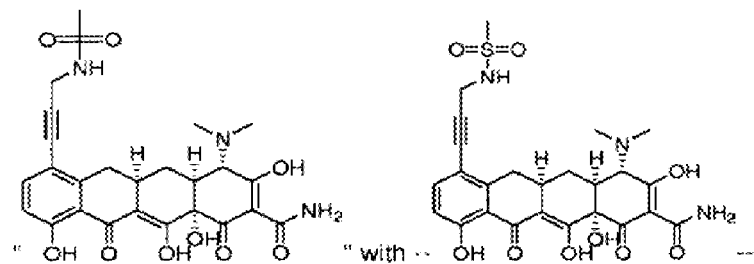

UNITED STATES PATENT AND TRADEMARK OFFICE
CERTIFICATE OF CORRECTION

PATENT NO.        : 7,045,507 B2
APPLICATION NO.   : 10/097634
DATED             : May 16, 2006
INVENTOR(S)       : Michael Draper et al.

It is certified that error appears in the above-identified patent and that said Letters Patent is hereby corrected as shown below:

At column 235, Table 2, compound JJ, replace

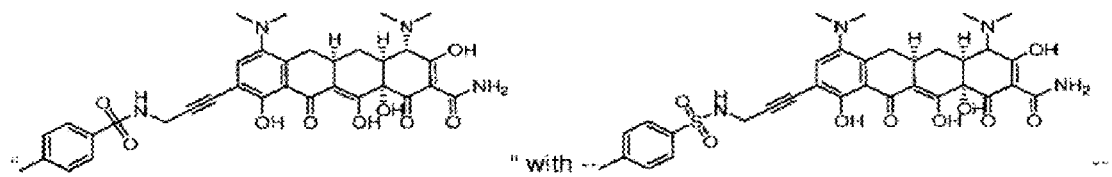

" with --

At columns 235-236, Table 2, compound JK, replace

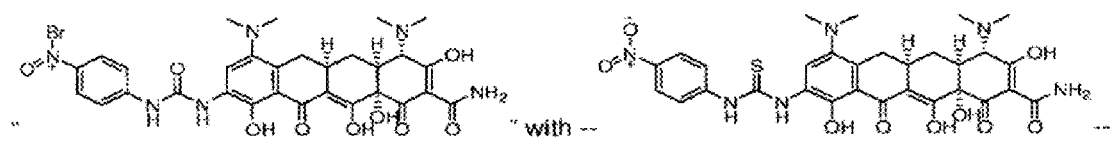

" with --

At column 236, Table 2, compound JM, replace

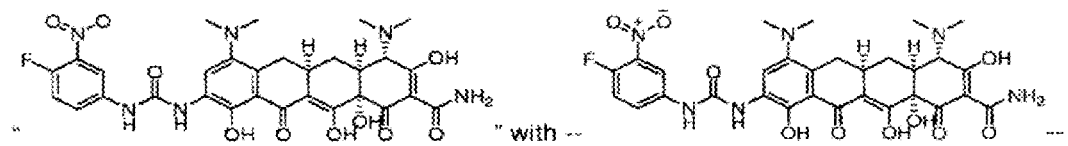

" with --

At column 237, Table 2, compound JN, replace

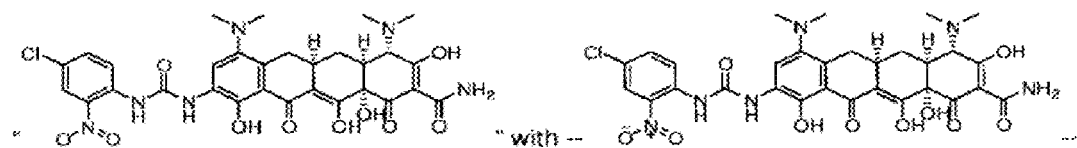

" with --

At columns 237-238, Table 2, compound JP, replace

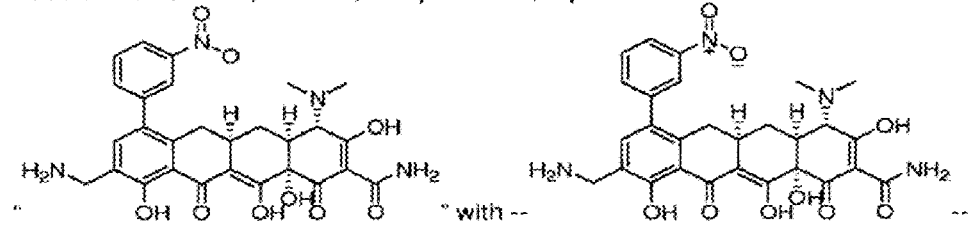

" with --

UNITED STATES PATENT AND TRADEMARK OFFICE
CERTIFICATE OF CORRECTION

PATENT NO. : 7,045,507 B2  Page 21 of 53
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 239, Table 2, compound JQ, replace

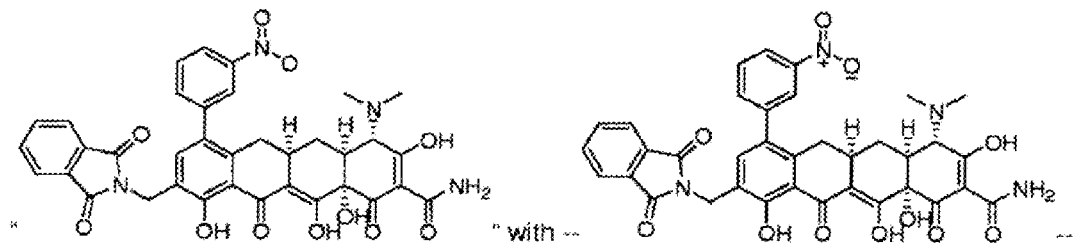

At column 241, Table 2, compound JT, replace

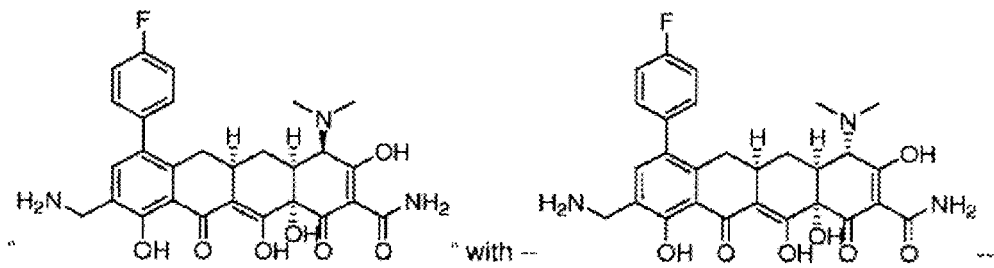

At columns 243-244, Table 2, compound JX, replace

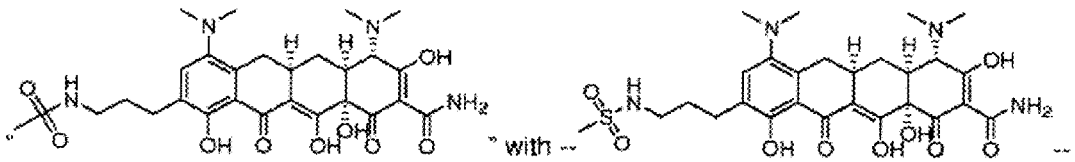

At columns 243-244, Table 2, compound JY, replace

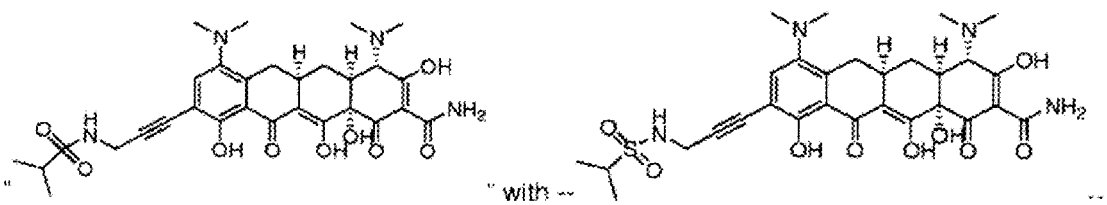

UNITED STATES PATENT AND TRADEMARK OFFICE
CERTIFICATE OF CORRECTION

PATENT NO.      : 7,045,507 B2
APPLICATION NO. : 10/097634
DATED           : May 16, 2006
INVENTOR(S)     : Michael Draper et al.

It is certified that error appears in the above-identified patent and that said Letters Patent is hereby corrected as shown below:

At column 247, Table 2, compound KD, replace

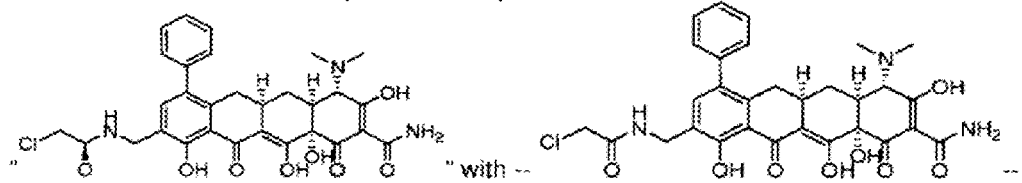

At column 253, Table 2, compound KO, replace

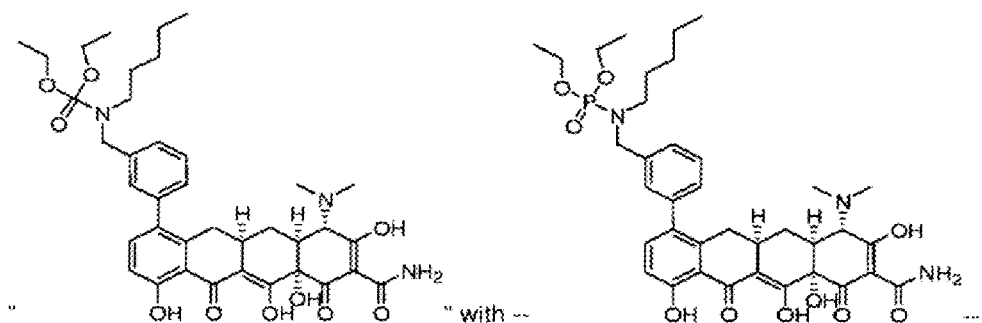

At columns 253-254, Table 2, compound KP, replace

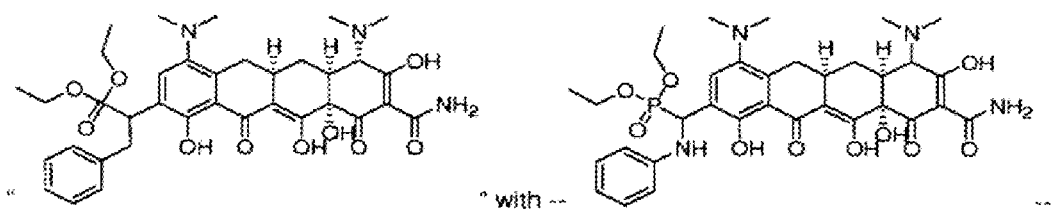

At columns 255-256, Table 2, compound KS, replace

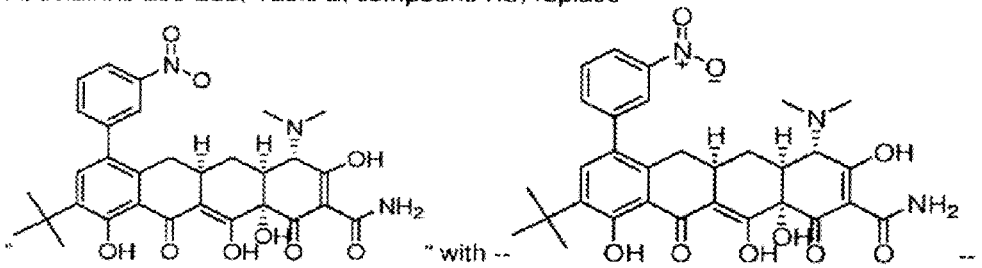

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 256, Table 2, compound KT, replace

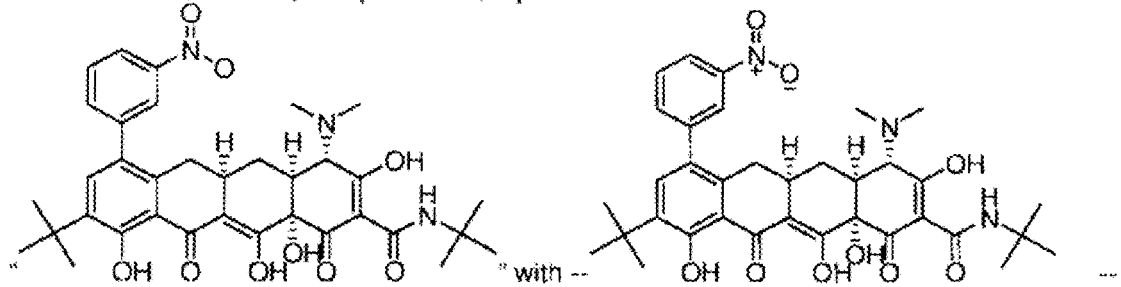

" with --

At column 260, Table 2, compound LA, replace

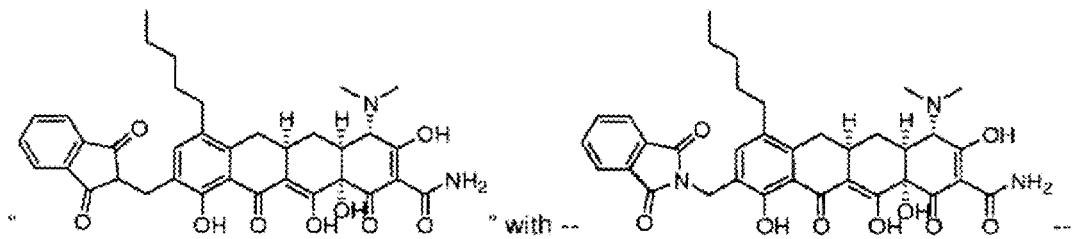

" with --

At column 266, Table 2, compound LL, replace

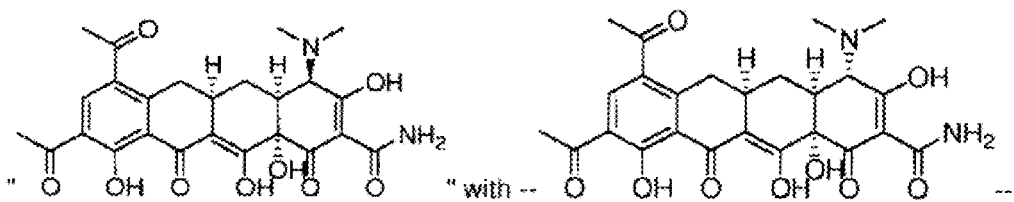

" with --

At column 284, Table 2, compound MM, replace

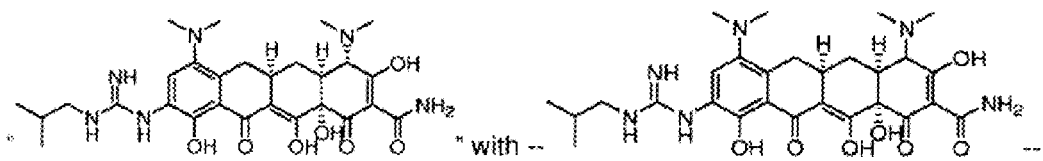

" with --

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 304, Table 2, compound NM, replace

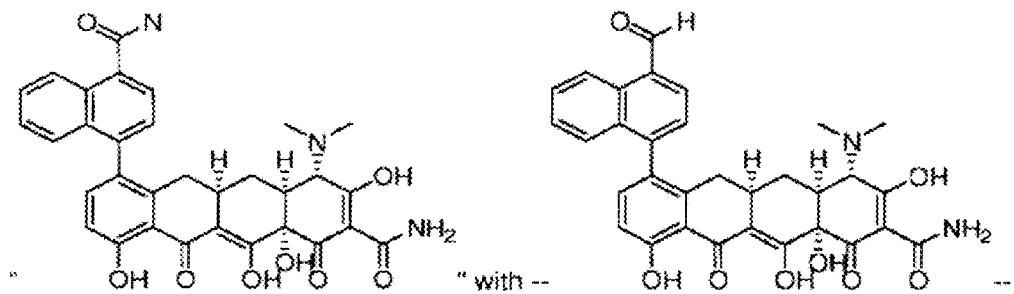

At columns 307-308, Table 2, compound NS, replace

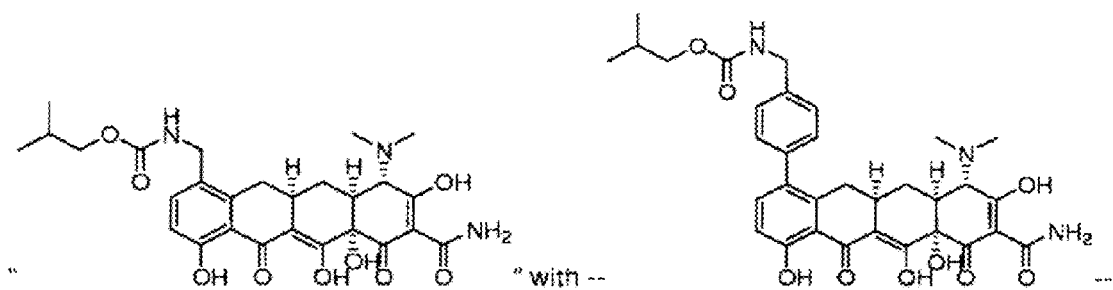

At column 323, Table 2, compound OL, replace

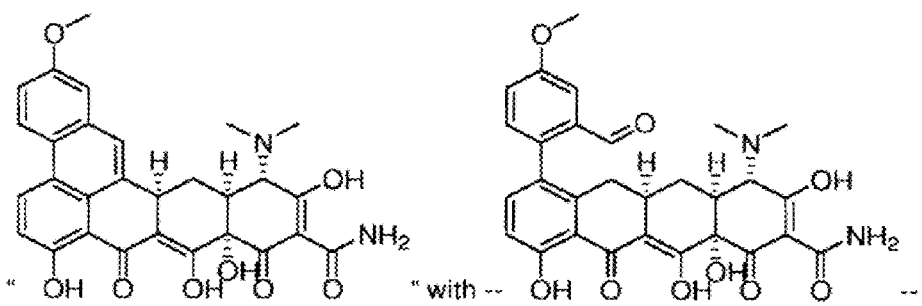

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 323-324, Table 2, compound OM, replace

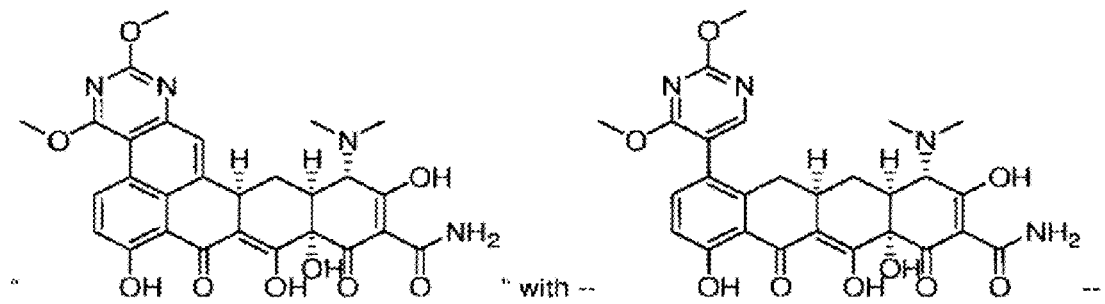

At column 324, Table 2, compound ON, replace

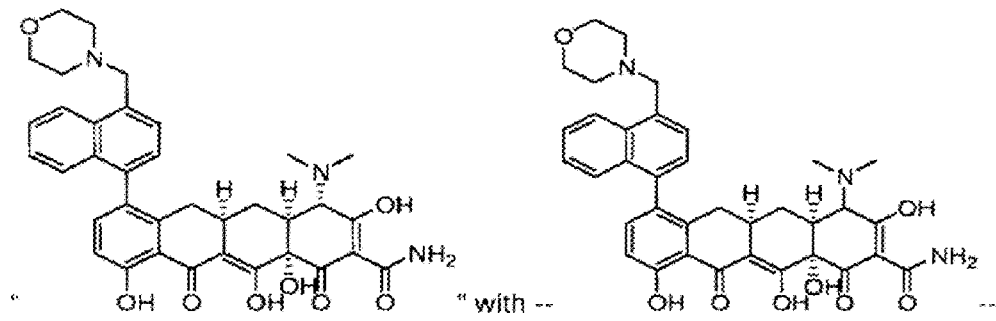

At column 325, Table 2, compound OO, replace

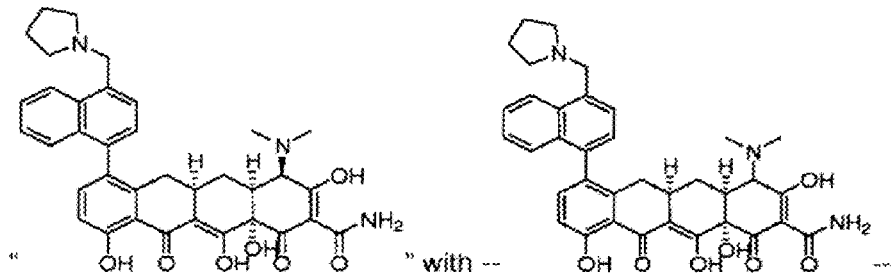

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 326, Table 2, compound OP, replace

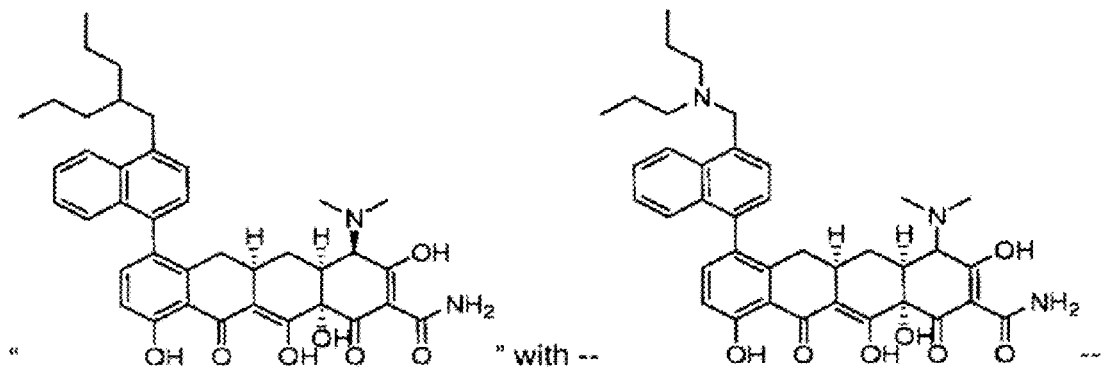

At column 328, Table 2, compound OR, replace

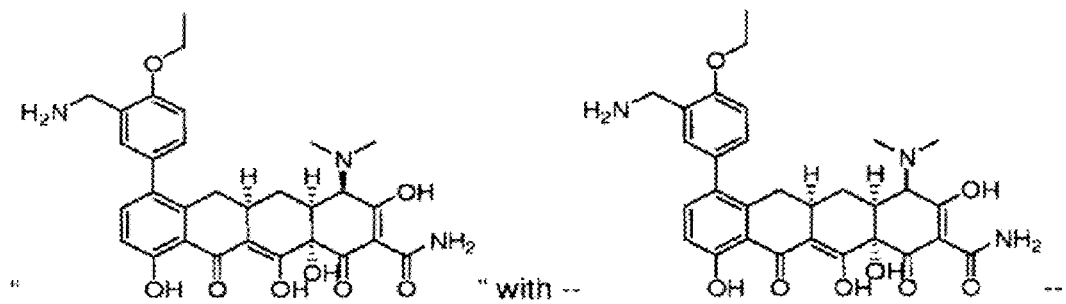

At columns 331-332, Table 2, compound OV, replace

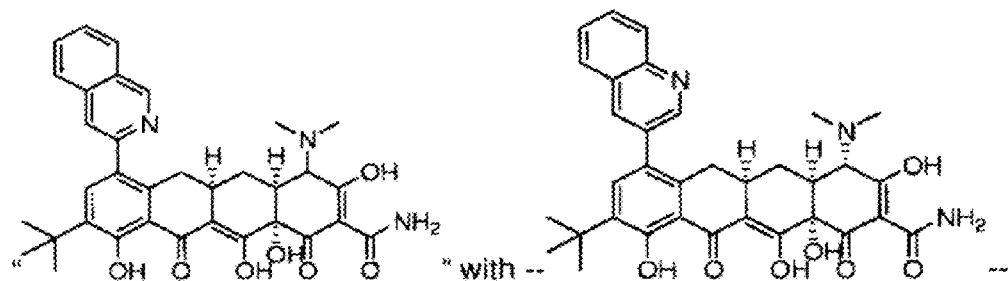

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 332, Table 2, compound OW, replace

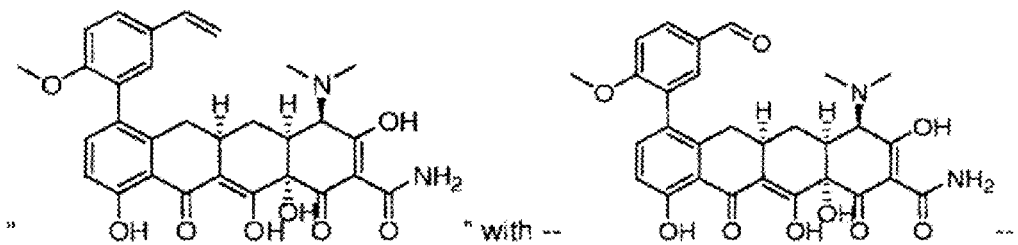

At column 339, Table 2, compound PF, replace

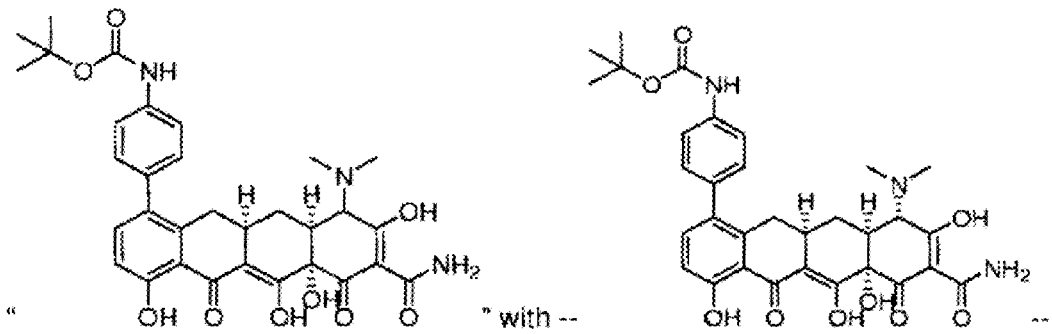

At column 340, Table 2, compound PG, replace

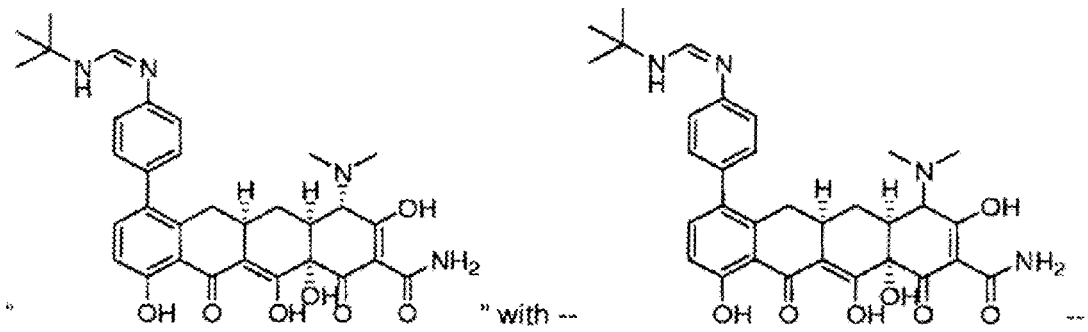

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 341, Table 2, compound PH, replace

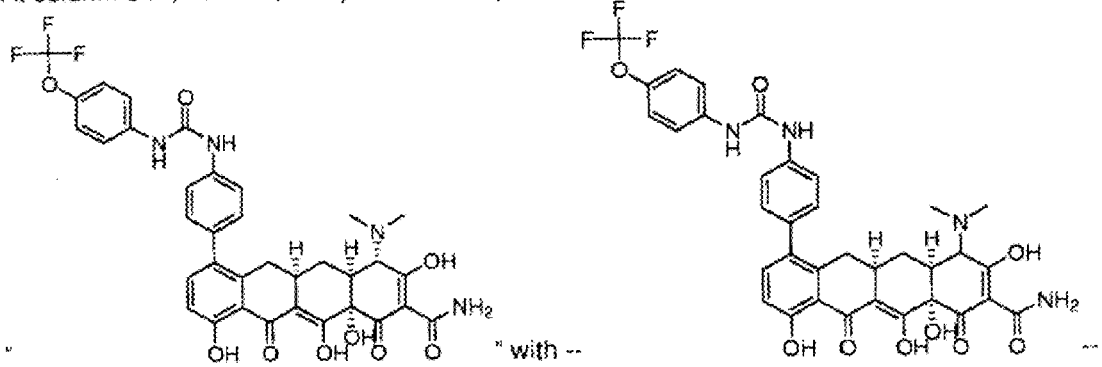

At column 342, Table 2, compound PI, replace

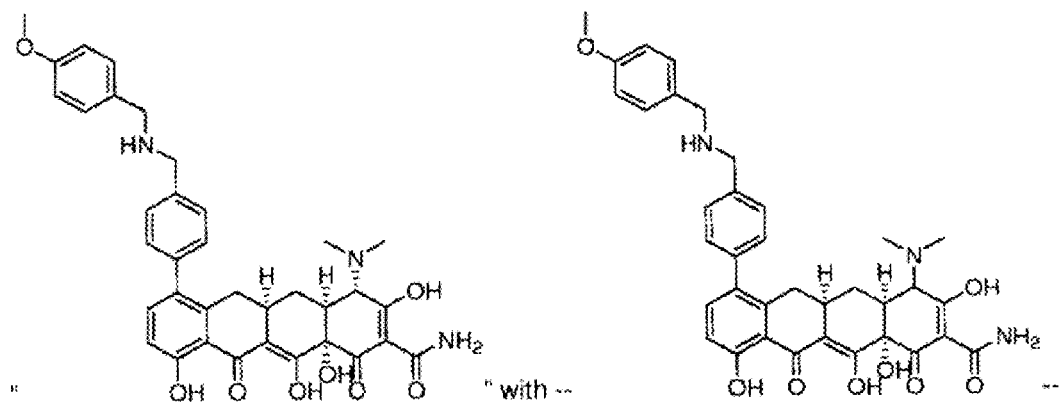

At column 347, Table 2, compound PP, replace

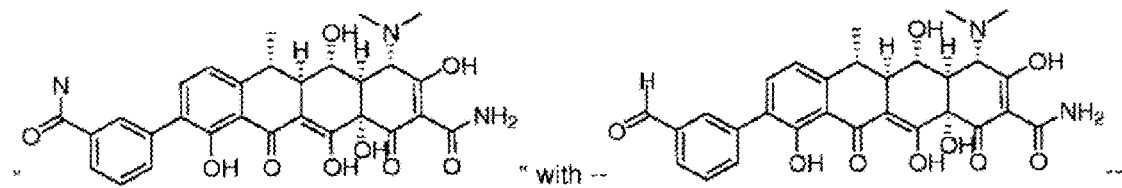

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 349, Table 2, compound PT, replace

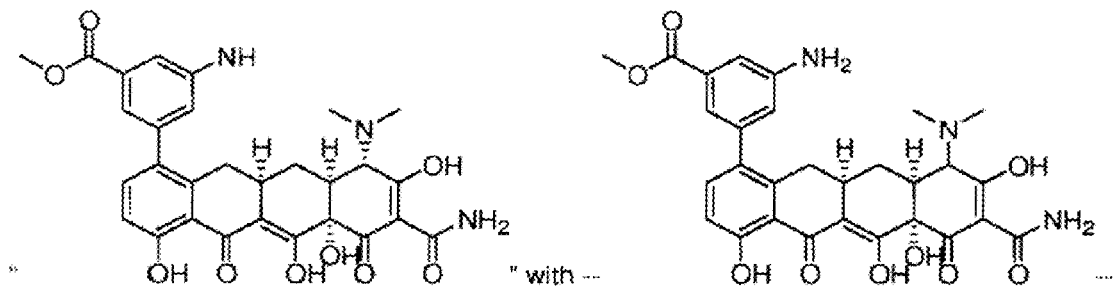

At column 356, Table 2, compound QE, replace

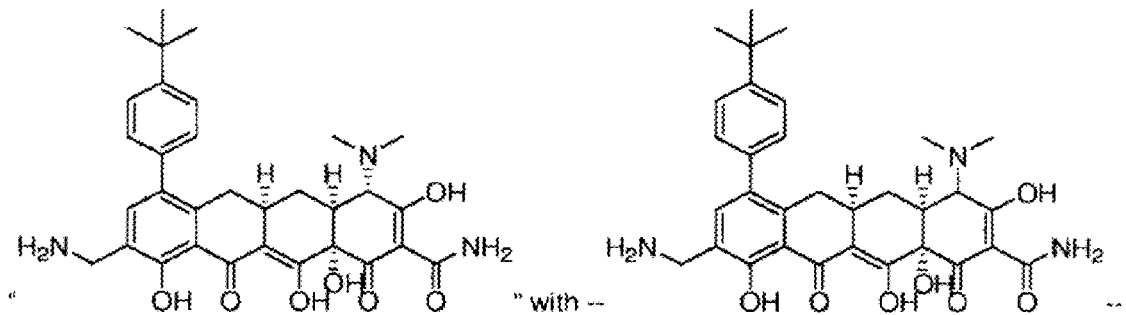

At column 357, Table 2, compound QF, replace

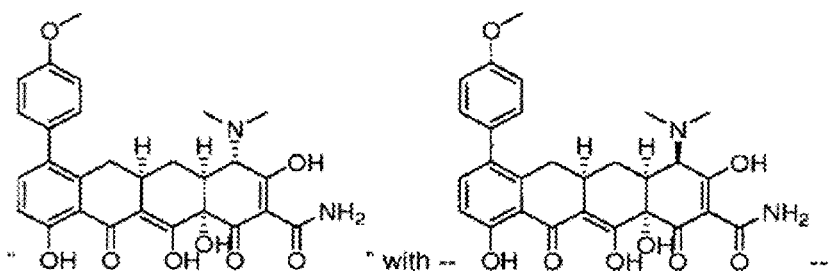

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 357-358, Table 2, compound QG, replace

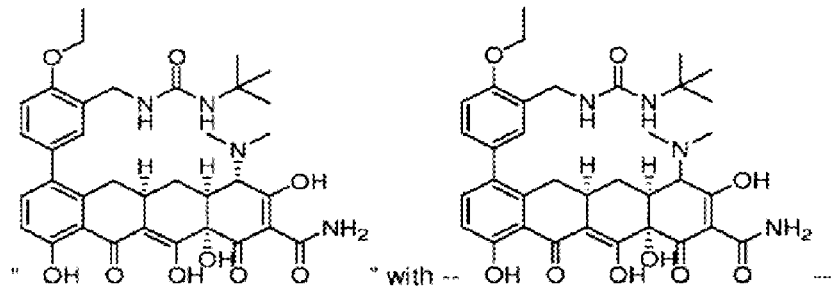

At column 358, Table 2, compound QH, replace

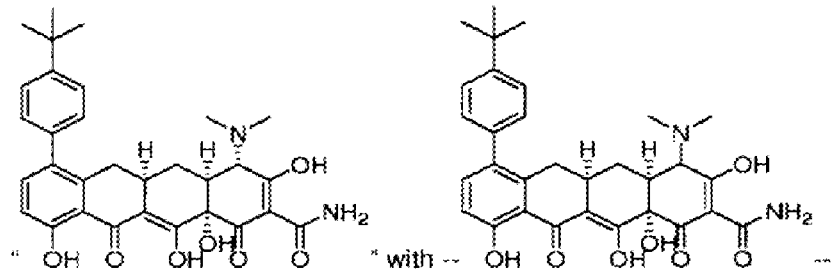

At column 359, Table 2, compound QI, replace

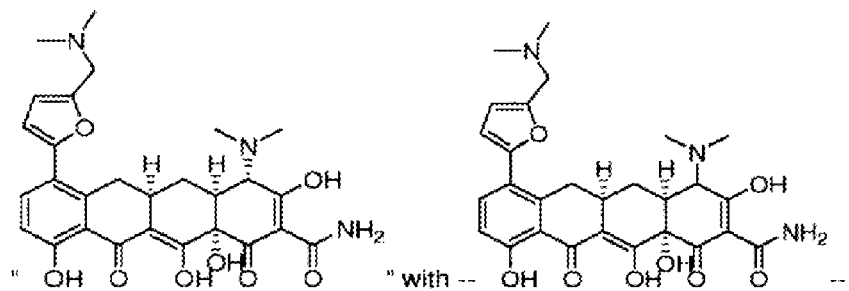

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 361, Table 2, compound QK, replace

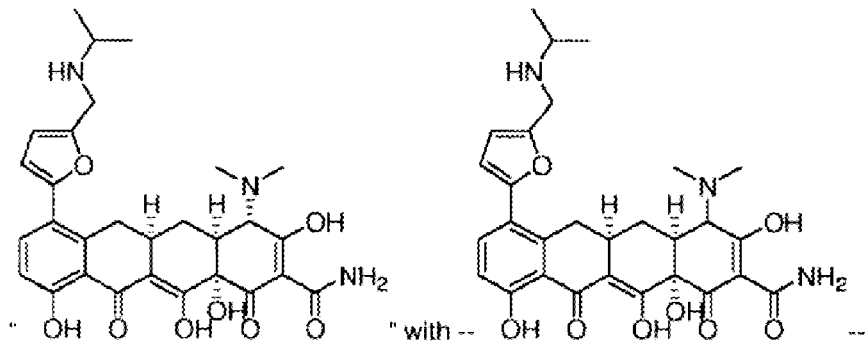

At column 363, Table 2, compound QM, replace

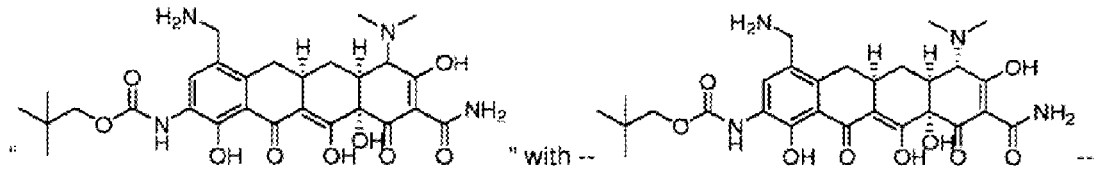

At column 365, Table 2, compound QP, replace

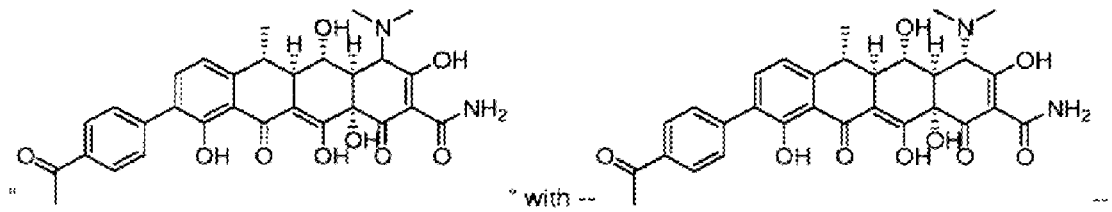

UNITED STATES PATENT AND TRADEMARK OFFICE
CERTIFICATE OF CORRECTION

PATENT NO.        : 7,045,507 B2
APPLICATION NO. : 10/097634
DATED               : May 16, 2006
INVENTOR(S)      : Michael Draper et al.

It is certified that error appears in the above-identified patent and that said Letters Patent is hereby corrected as shown below:

At columns 365-366, Table 2, compound QQ, replace

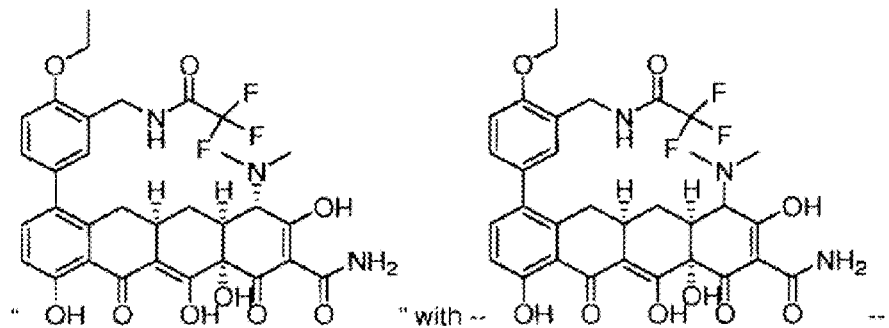

At column 366, Table 2, compound QR, replace

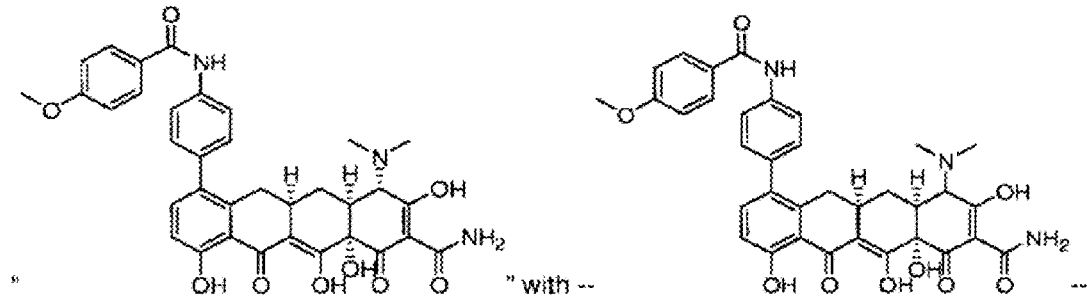

At columns 367-268, Table 2, compound QT, replace

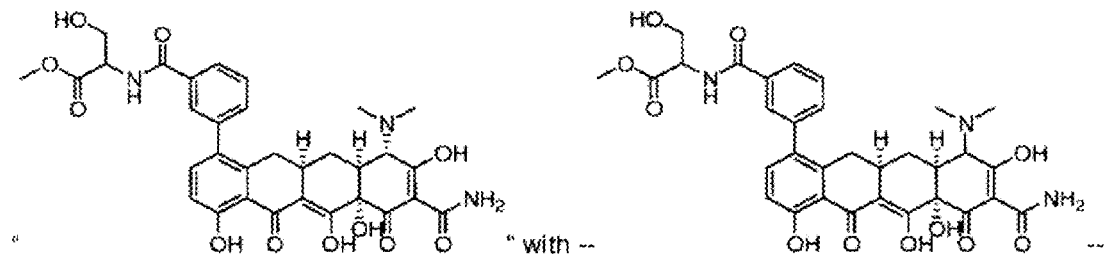

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 368, Table 2, compound QU, replace

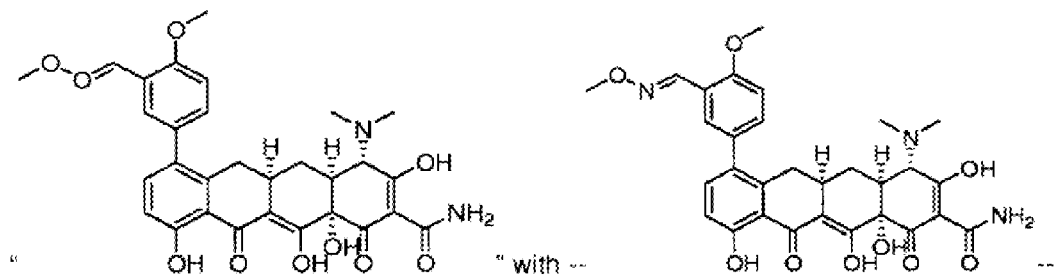

At columns 369-370, Table 2, compound QW, replace

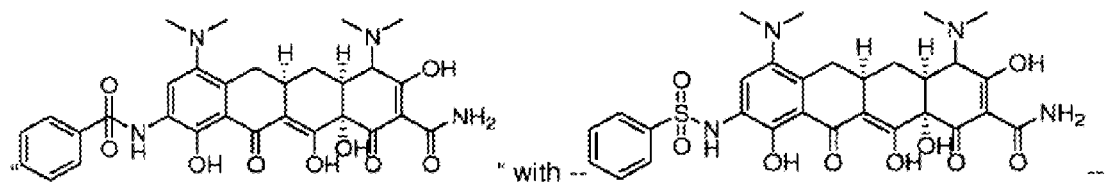

At columns 373-374, Table 2, compound RC, replace

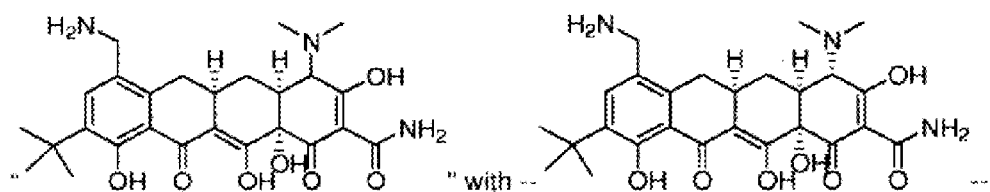

At column 374, Table 2, compound RD, replace

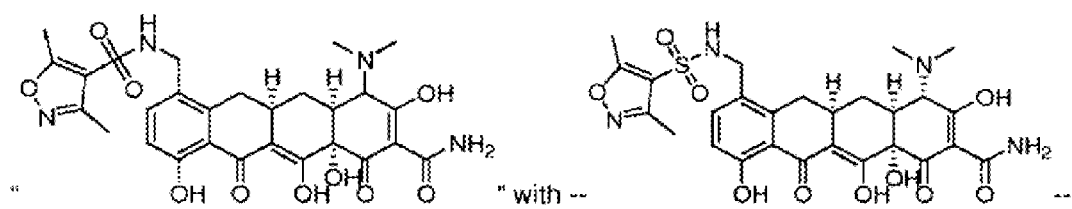

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 375, Table 2, compound RE, replace

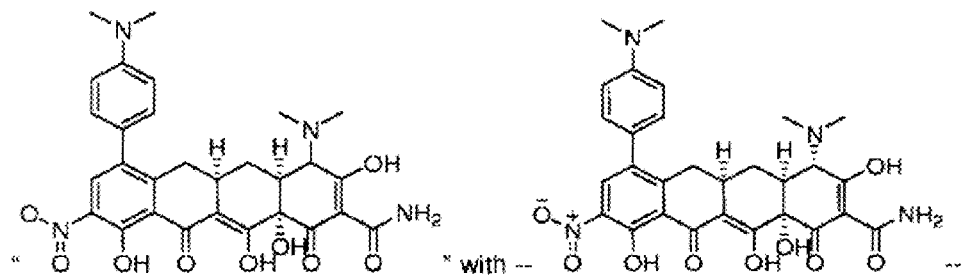

At column 375-376, Table 2, compound RF, replace

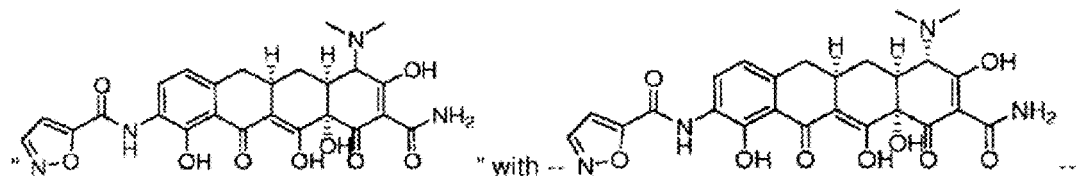

At column 376, Table 2, compound RG, replace

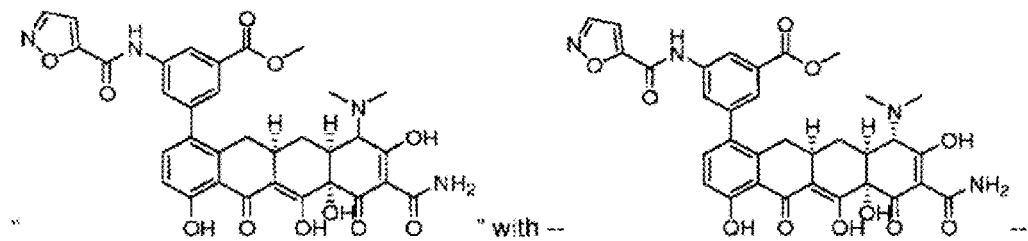

At columns 377-378, Table 2, compound RI, replace

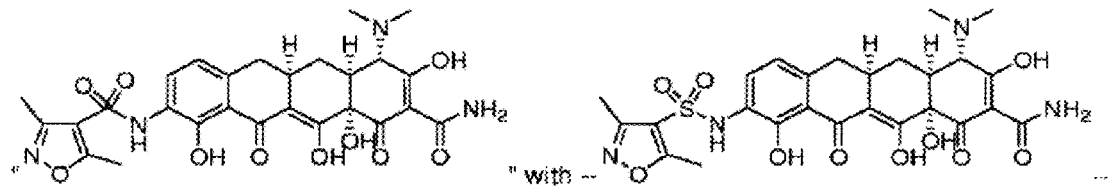

UNITED STATES PATENT AND TRADEMARK OFFICE
CERTIFICATE OF CORRECTION

PATENT NO.        : 7,045,507 B2
APPLICATION NO.   : 10/097634
DATED             : May 16, 2006
INVENTOR(S)       : Michael Draper et al.

It is certified that error appears in the above-identified patent and that said Letters Patent is hereby corrected as shown below:

At column 379, Table 2, compound RL, replace

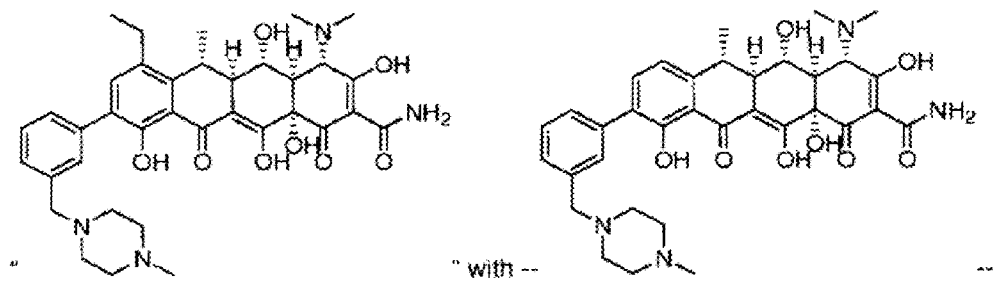

" with --                                                        --

At columns 379-380, Table 2, compound RM, replace

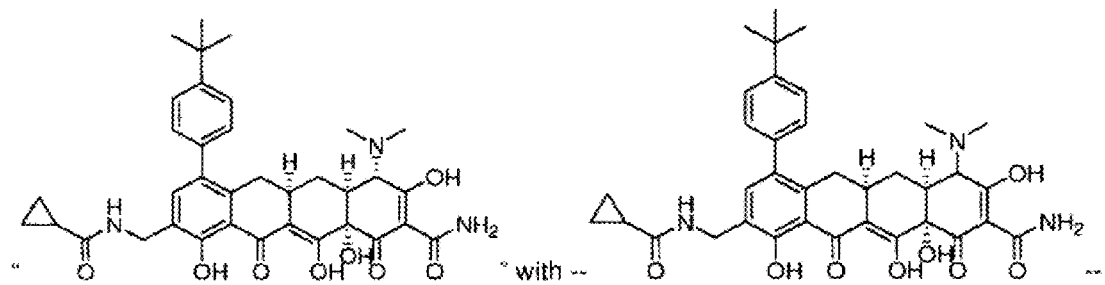

" with --                                                        --

At column 380, Table 2, compound RN, replace

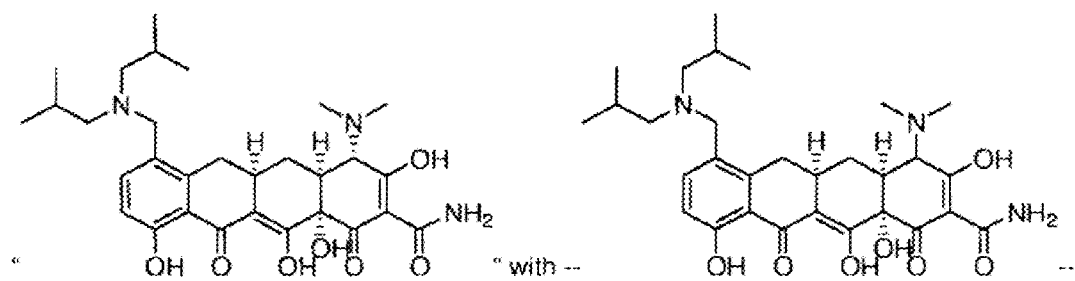

" with --                                                        --

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 383-384, Table 2, compound RT, replace

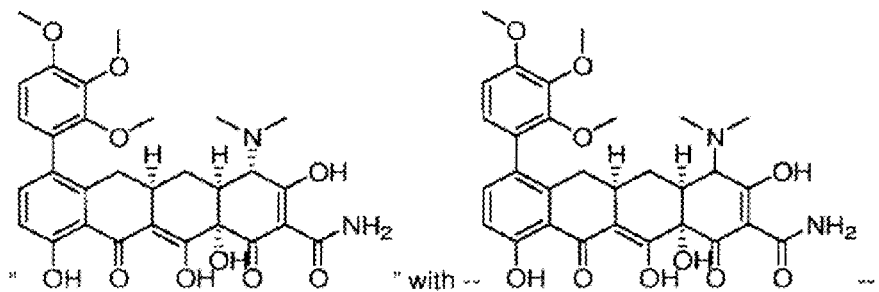

At column 388, Table 2, compound RZ, replace

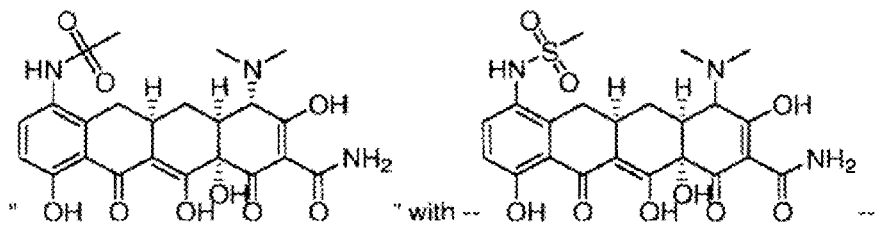

At columns 391-392, Table 2, compound SE, replace

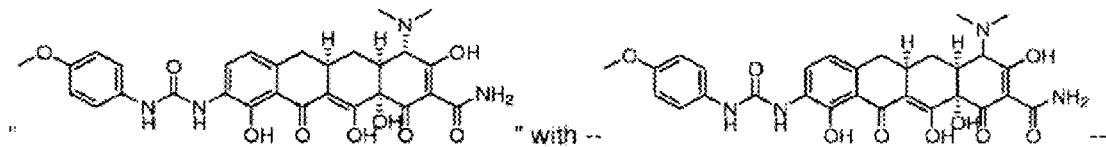

At column 393, Table 2, compound SG, replace

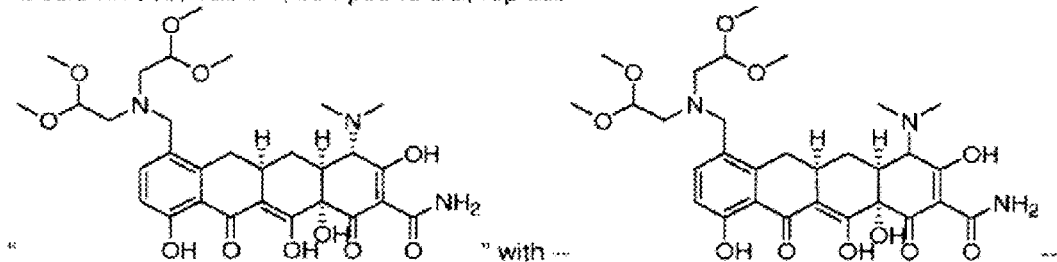

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 397-398, Table 2, compound SN, replace

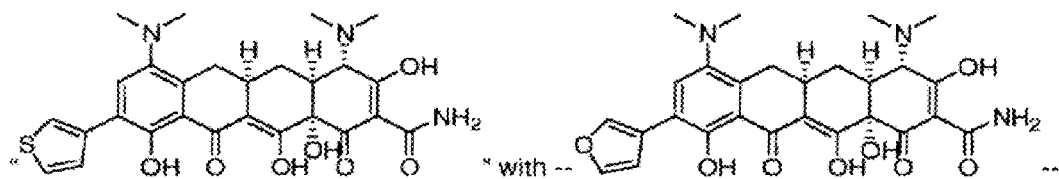

At columns 397-398, Table 2, compound SO, replace

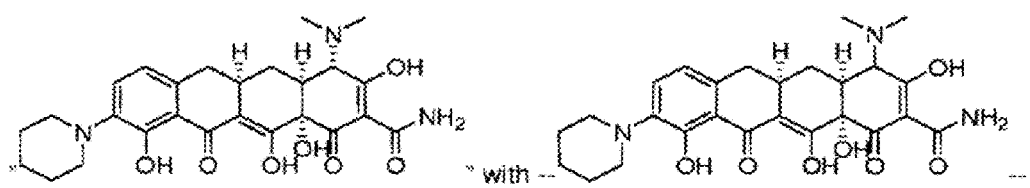

At column 398, Table 2, compound SP, replace

At columns 399-400, Table 2, compound SR, replace

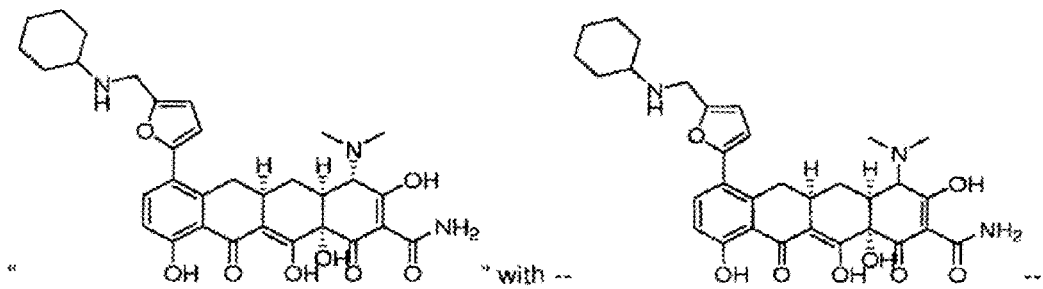

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At column 401, Table 2, compound SS, replace

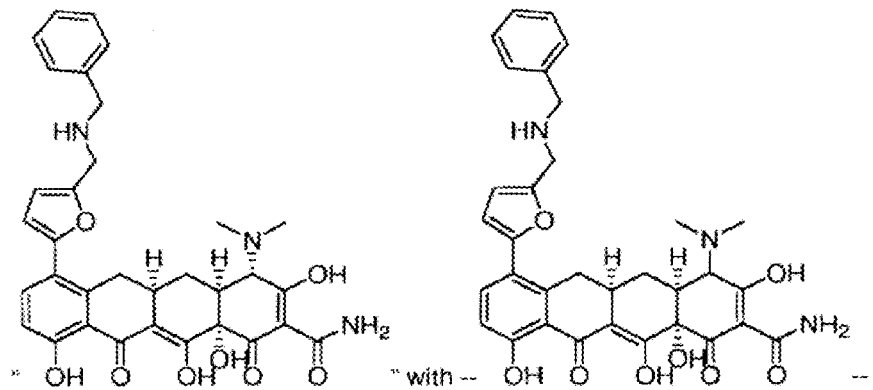

At column 402, Table 2, compound SU, replace

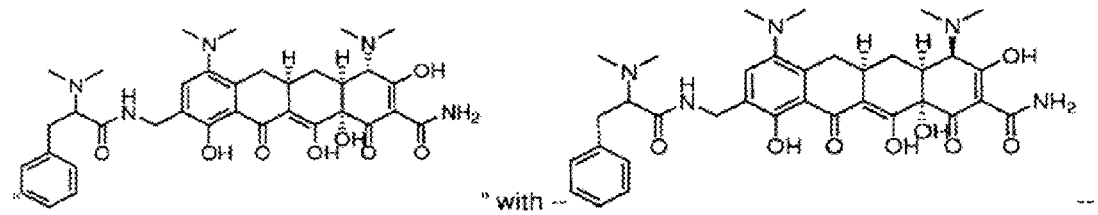

At column 403, Table 2, compound SV, replace

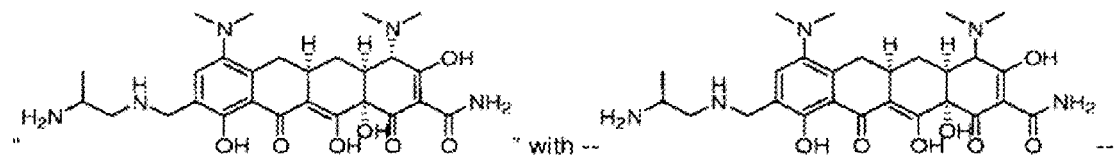

At columns 403-404, Table 2, compound SW, replace

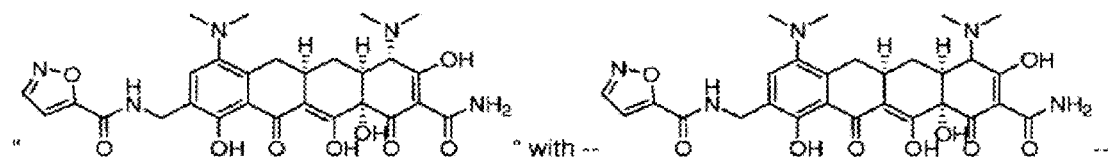

… UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 405-406, Table 2, compound TA, replace

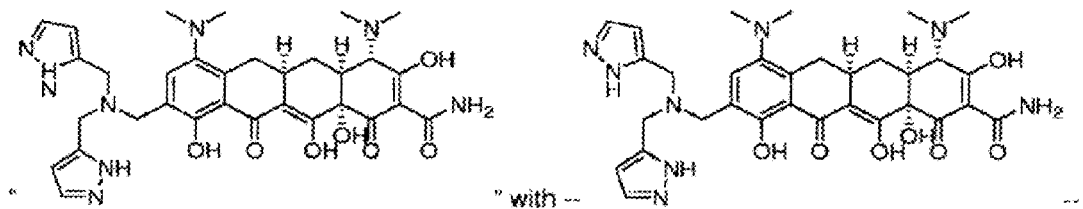

" with --

At column 407, Table 2, compound TC, replace

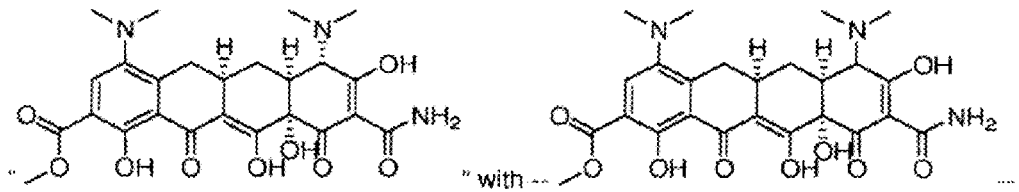

" with --

At columns 407-408, Table 2, compound TE, replace

" with --

At column 408, Table 2, compound TF, replace

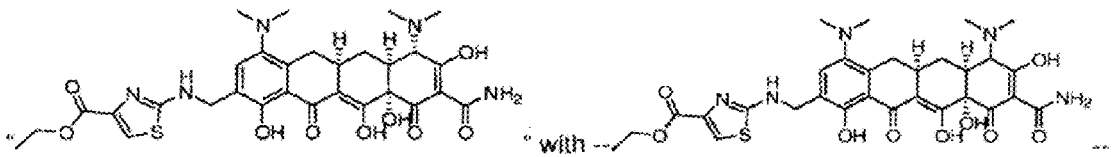

" with --

UNITED STATES PATENT AND TRADEMARK OFFICE
CERTIFICATE OF CORRECTION

PATENT NO.        : 7,045,507 B2
APPLICATION NO.   : 10/097634
DATED             : May 16, 2006
INVENTOR(S)       : Michael Draper et al.

It is certified that error appears in the above-identified patent and that said Letters Patent is hereby corrected as shown below:

At column 409, Table 2, compound TG, replace

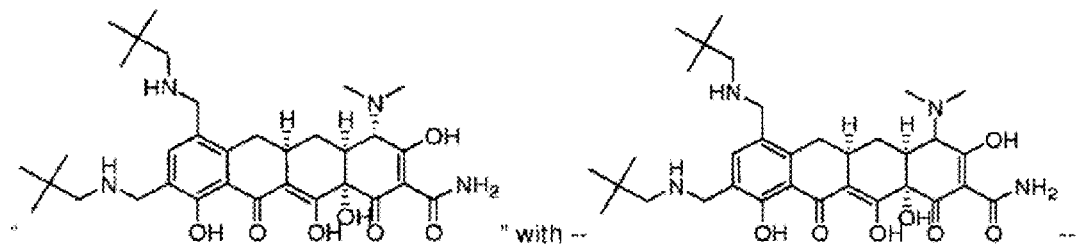

At columns 409-410, Table 2, compound TH, replace

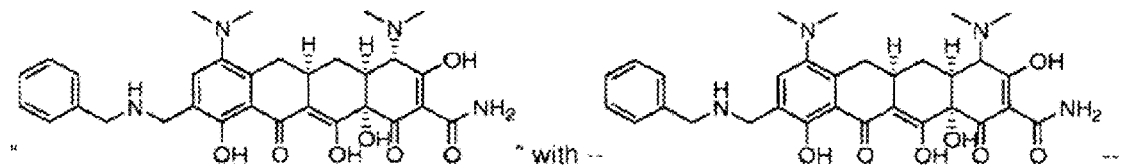

At column 410, Table 2, compound TJ, replace

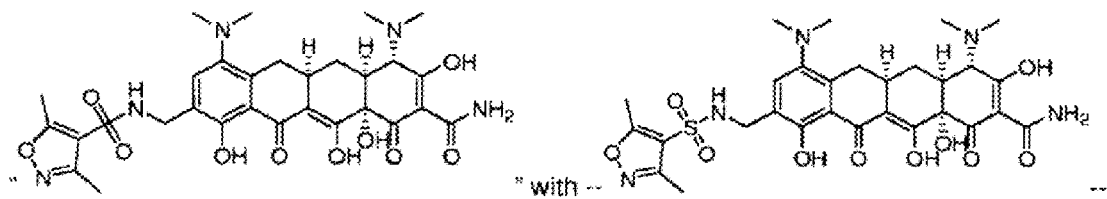

At column 411, Table 2, compound TK, replace

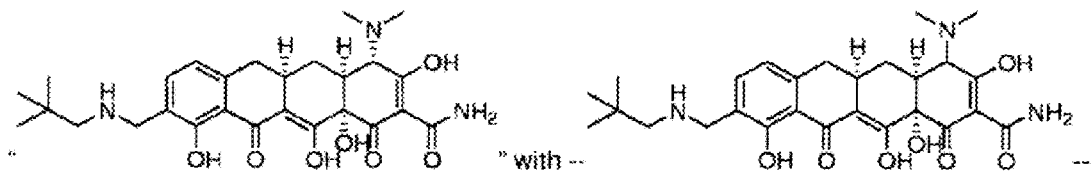

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 411-412, Table 2, compound TL, replace

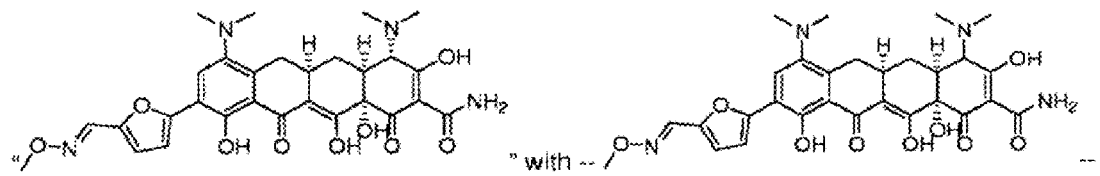

At column 412, Table 2, compound TM, replace

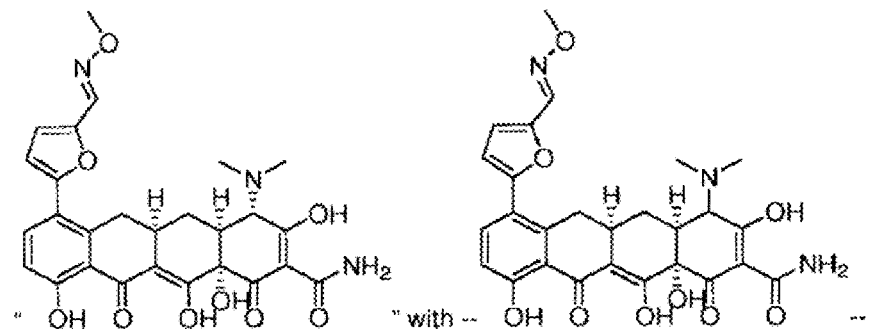

At columns 413-414, Table 2, compound TO, replace

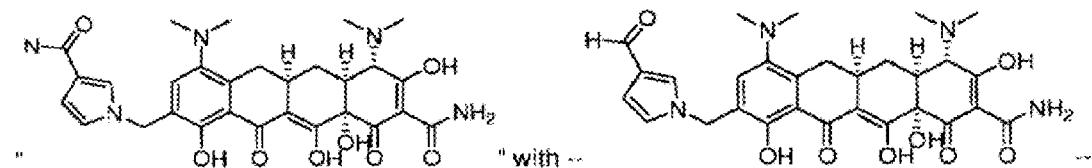

At columns 415-416, Table 2, compound TT, replace

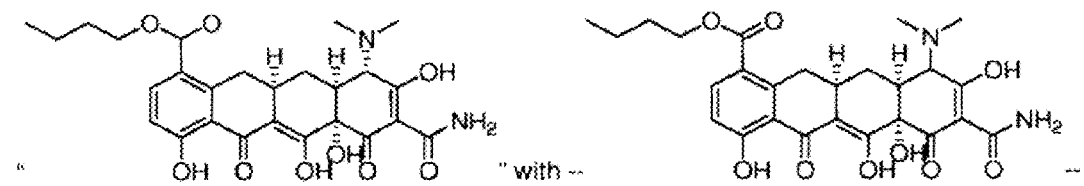

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 417-418, Table 2, compound TW, replace

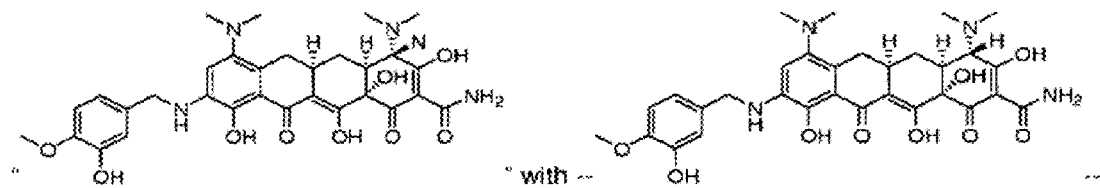
" with --                              --

At column 422, Table 2, compound UH, replace

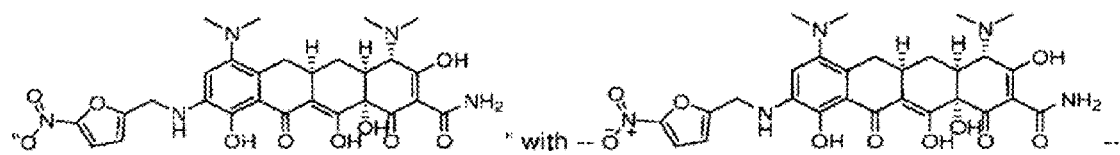
" with --                              --

At column 430, compound UH, replace

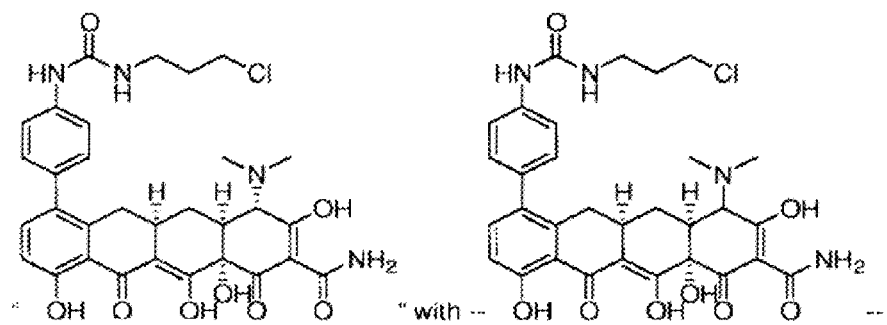
" with --                              --

At column 433, Table 2, compound UX, replace

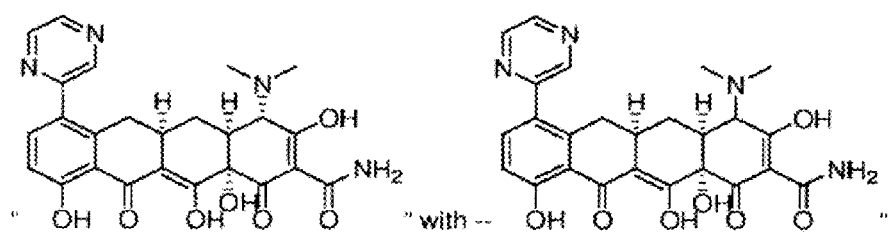
" with --                              "

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At columns 433-434, Table 2, compound UY, replace

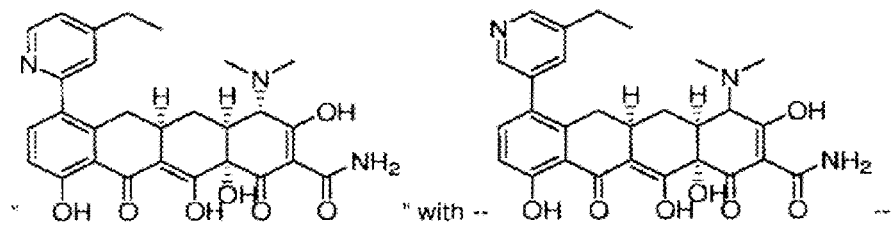

At columns 439-440, Table 2, compound VH, replace

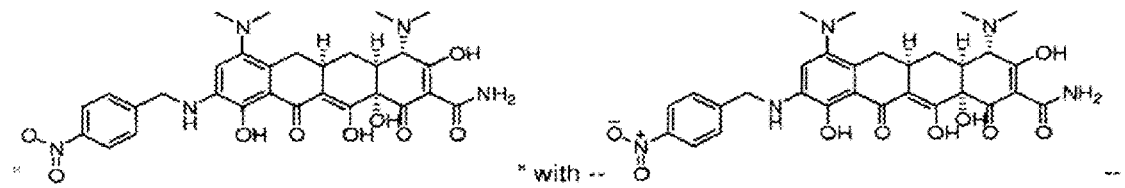

At column 440, Table 2, compound VJ, replace

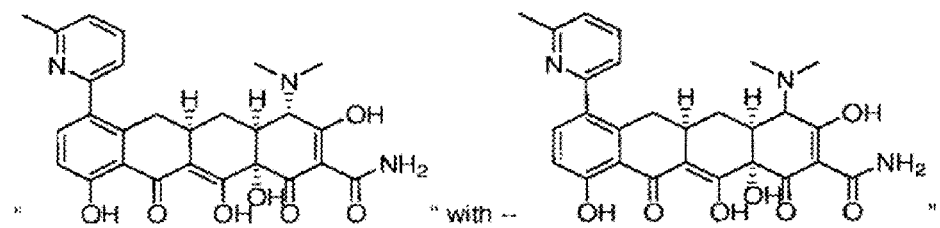

At column 441, Table 2, compound VK, replace

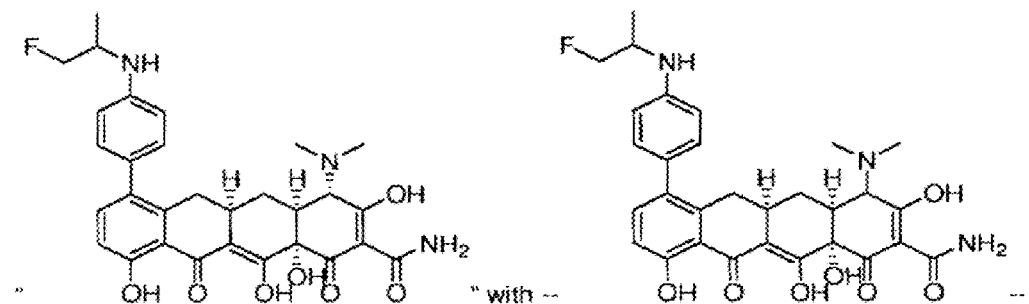

UNITED STATES PATENT AND TRADEMARK OFFICE
CERTIFICATE OF CORRECTION

PATENT NO.       : 7,045,507 B2
APPLICATION NO.  : 10/097634
DATED            : May 16, 2006
INVENTOR(S)      : Michael Draper et al.

It is certified that error appears in the above-identified patent and that said Letters Patent is hereby corrected as shown below:

In the Claims:

At Claim 1, column 466, line 40, replace "Z'is O, S, or $NR^{9f}$;" with --Z' is O, S, or $NR^{9f}$;--

At Claim 1, column 466, line 43, replace "W'is O, $NR^{7f}$ S;" with --W' is O, $NR^{7f}$ or S;--

At Claim 2, column 467, line 40, replace "W' is O, $NR^{7f}$ S;" with --W' is O, $NR^{7f}$ or S;--

At Claim 3, column 468, line 42, replace "W' is O, $NR^{7f}$ S;" with --W' is O, $NR^{7f}$ or S;--

At Claim 4, column 469, line 42, replace "W' is O, $NR^{7f}$ S;" with --W' is O, $NR^{7f}$ or S;--

At Claim 5, column 470, line 40, replace "Z'is O, S, or $NR^{9f}$;" with --Z' is O, S, or $NR^{9f}$;--

At Claim 5, column 470, line 41, replace "W is $CR^{7d}$, $R^{7e}$, S, $NR^{7b}$ or O;" with --W is $CR^{7d}R^{7e}$, S, $NR^{7b}$ or O;--

At Claim 5, column 470, line 42, replace "W' is O, $NR^{7}$ S;" with --W' is O, $NR^{7f}$ or S;--

At Claim 6, column 471, line 40, replace "Z'is O, S, or $NR^{9f}$;" with --Z' is O, S, or $NR^{9f}$;--

At Claim 6, column 471, line 42, replace "W'is O, $NR^{7f}$ S;" with --W' is O, $NR^{7f}$ or S;--

At Claim 7, column 472, line 42, replace "W' is O, $NR^{7f}$ S;" with --W' is O, $NR^{7f}$ or S;--

At Claim 7, column 472, lines 43-48, replace "$R^{7a}$, $R^{7b}$, $R^{7c}R^{7d}$, $R^{7e}$, $R^{7f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;" with
--$R^{7a}$, $R^{7b}$, $R^{7c}$, $R^{7d}$, $R^{7e}$, $R^{7f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;--

UNITED STATES PATENT AND TRADEMARK OFFICE
CERTIFICATE OF CORRECTION

PATENT NO.       : 7,045,507 B2
APPLICATION NO.  : 10/097634
DATED            : May 16, 2006
INVENTOR(S)      : Michael Draper et al.

It is certified that error appears in the above-identified patent and that said Letters Patent is hereby corrected as shown below:

At Claim 8, column 473, line 41, "W' is O, $NR^{7f}$ S;" with --W' is O, $NR^{7f}$ or S;--

At Claim 9, column 474, line 42, replace "W' is O, $NR^{7f}$ S;" with --W' is O, $NR^{7f}$ or S;--

At Claim 10, column 475, lines 25-35, replace

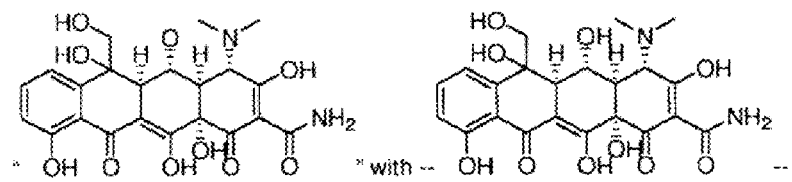

At Claim 10, column 482, lines 50-60, replace

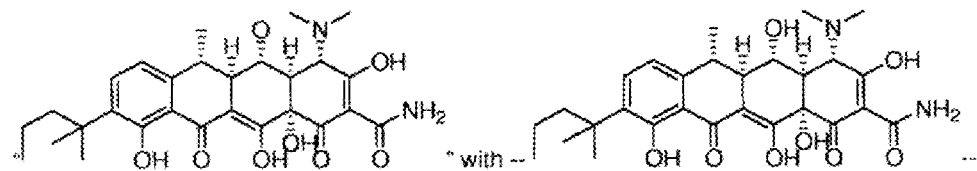

At Claim 10, column 482, lines 60-65, replace

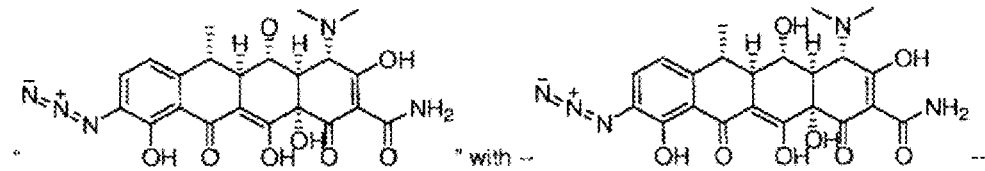

At Claim 10, column 490, lines 15-25, replace

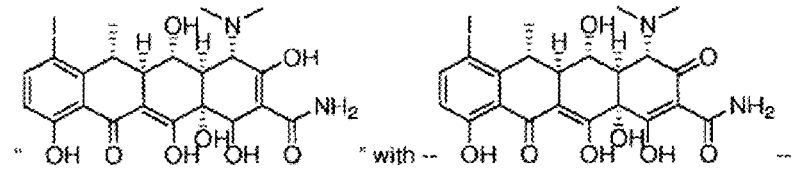

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At Claim 10, column 490, lines 35-45, replace

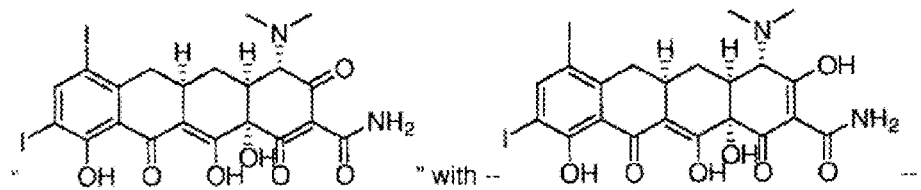

At Claim 11, column 514, lines 5-15, replace

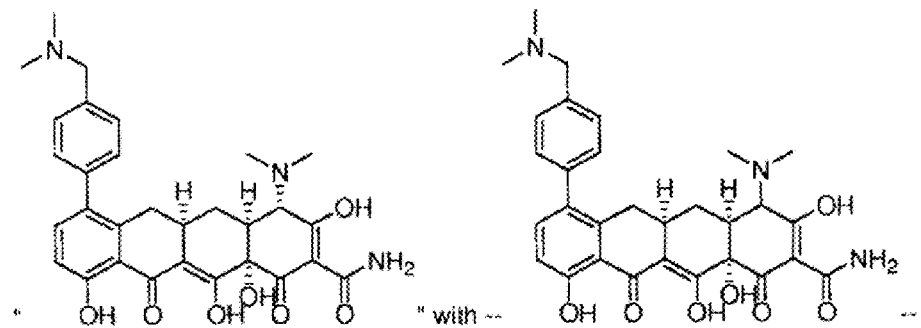

At Claim 12, column 515, lines 60-65, replace

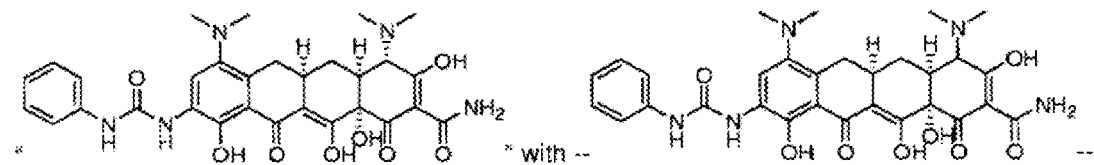

At Claim 12, column 523, lines 15-25, replace

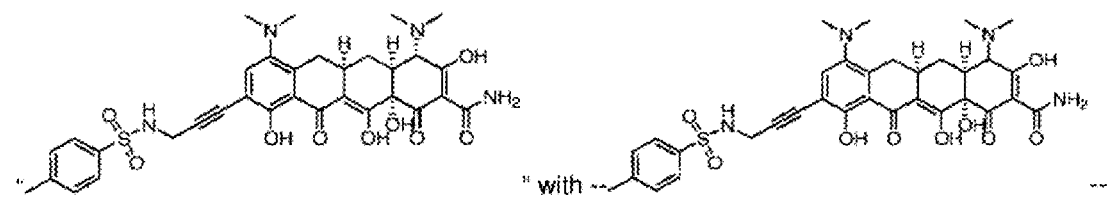

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At Claim 12, column 524, lines 50-55, replace

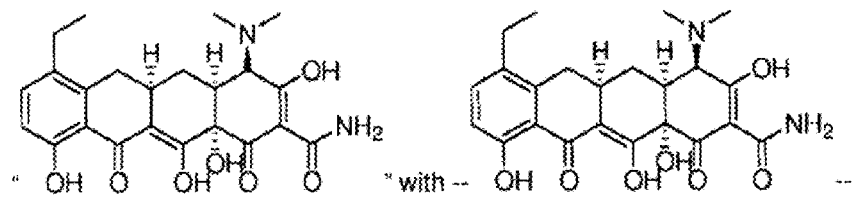

At Claim 12, column 526, lines 5-15, replace

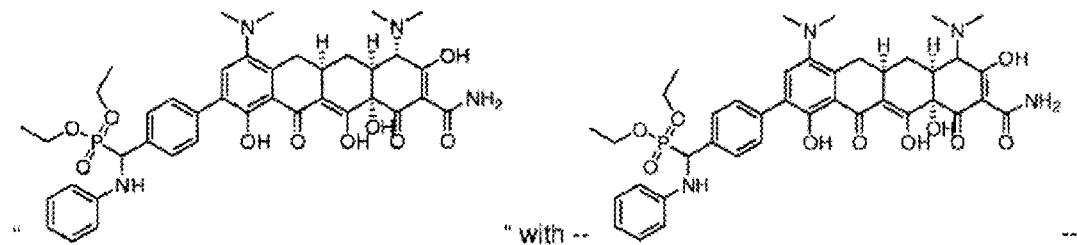

At Claim 12, column 526, lines 45-50, replace

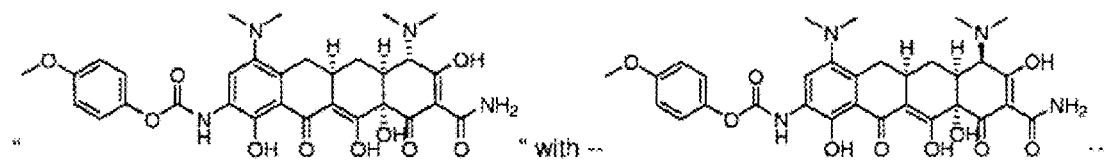

At Claim 12, column 533, lines 55-60, replace

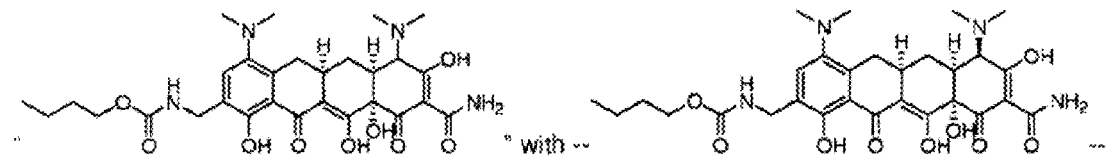

UNITED STATES PATENT AND TRADEMARK OFFICE
CERTIFICATE OF CORRECTION

PATENT NO.       : 7,045,507 B2
APPLICATION NO.  : 10/097634
DATED            : May 16, 2006
INVENTOR(S)      : Michael Draper et al.

It is certified that error appears in the above-identified patent and that said Letters Patent is hereby corrected as shown below:

At Claim 12, column 533, lines 60-65, replace

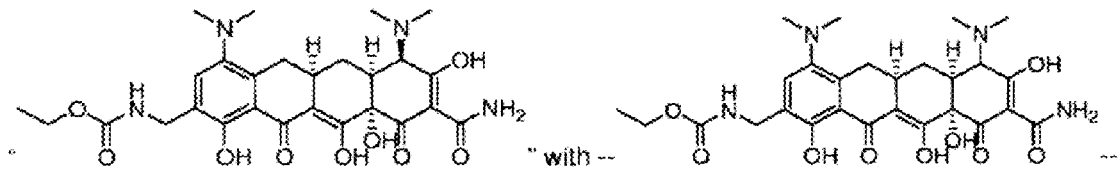

At Claim 13, column 539, lines 5-20, replace

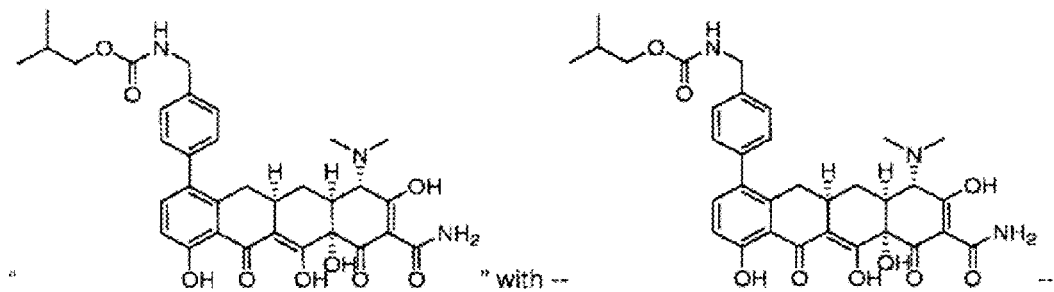

At Claim 13, column 539, lines 55-60, replace

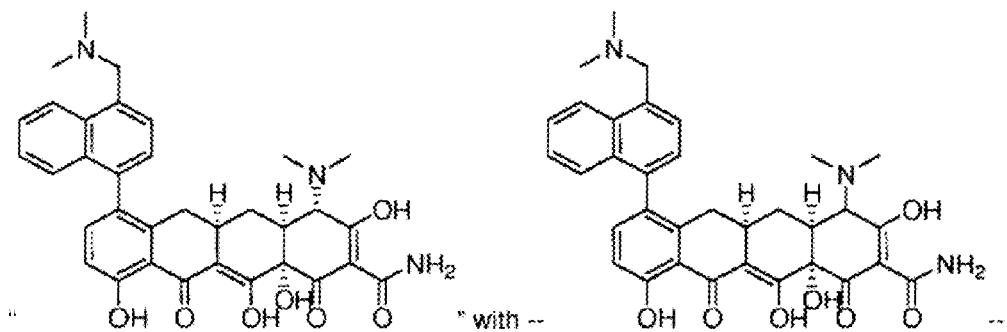

UNITED STATES PATENT AND TRADEMARK OFFICE
CERTIFICATE OF CORRECTION

PATENT NO.       : 7,045,507 B2
APPLICATION NO.  : 10/097634
DATED            : May 16, 2006
INVENTOR(S)      : Michael Draper et al.

It is certified that error appears in the above-identified patent and that said Letters Patent is hereby corrected as shown below:

At Claim 13, column 542, lines 1-20, replace

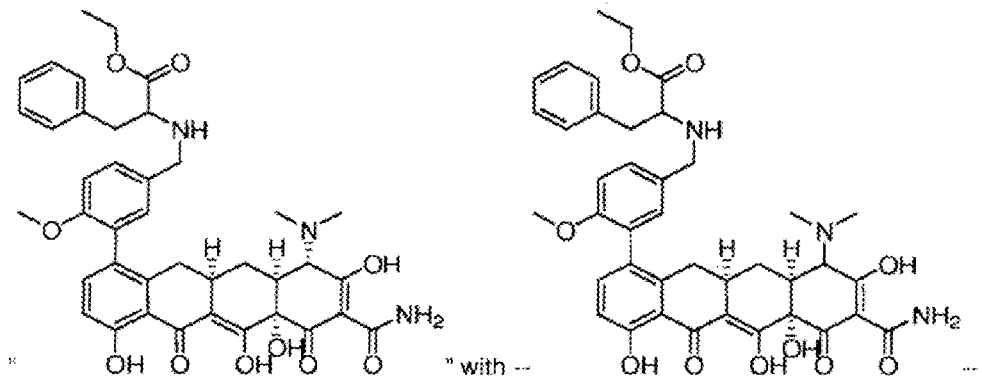

" with --

At Claim 13, column 546, lines 1-15, replace

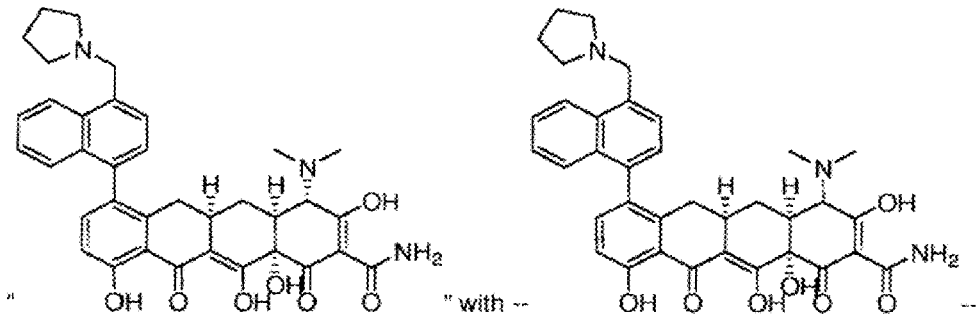

" with --

At Claim 13, column 549, lines 35-50, replace

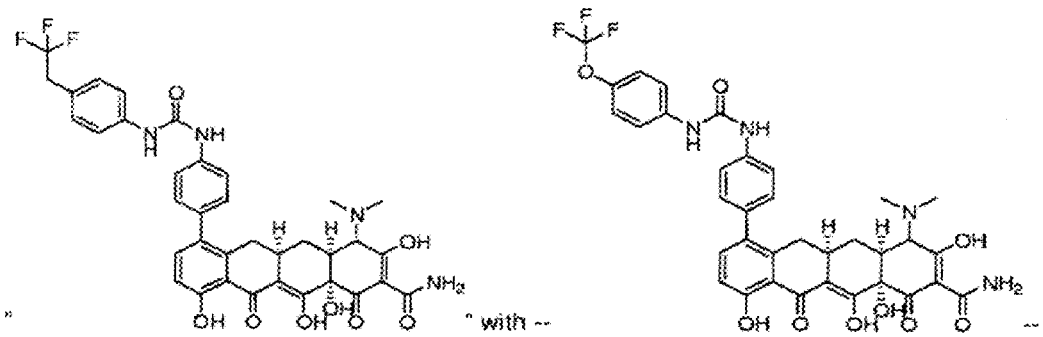

" with --

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At Claim 14, column 564, insert

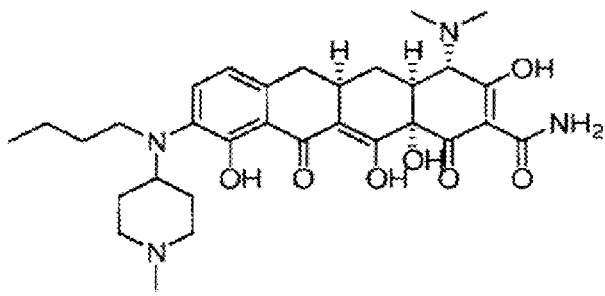

At Claim 14, column 567, lines 40-50, replace

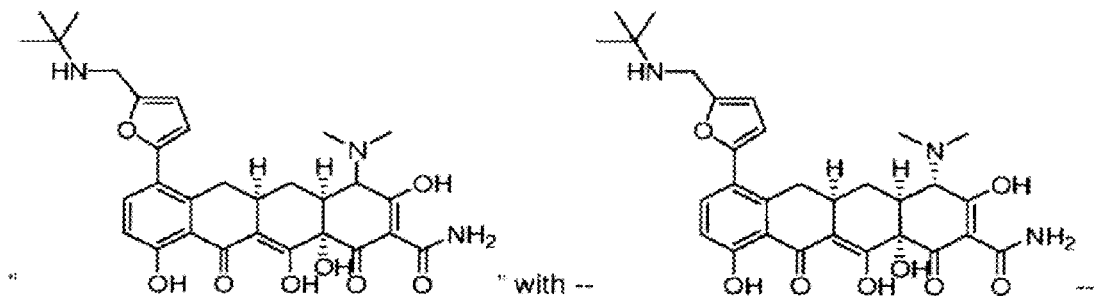

At Claim 14, column 567, lines 55-65, replace

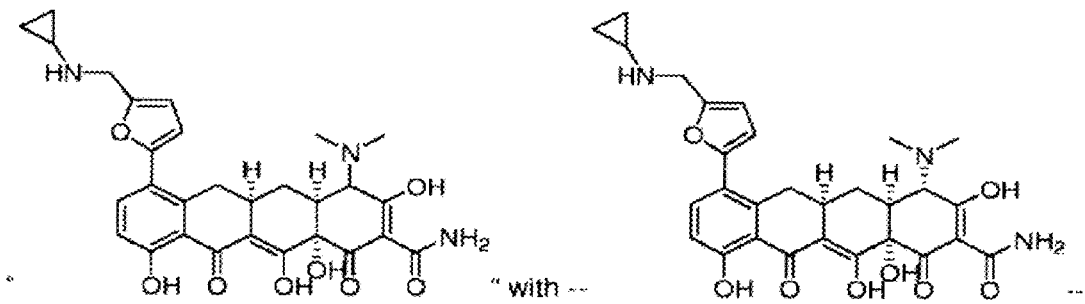

… 
UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At Claim 14, column 574, lines 50-60, replace

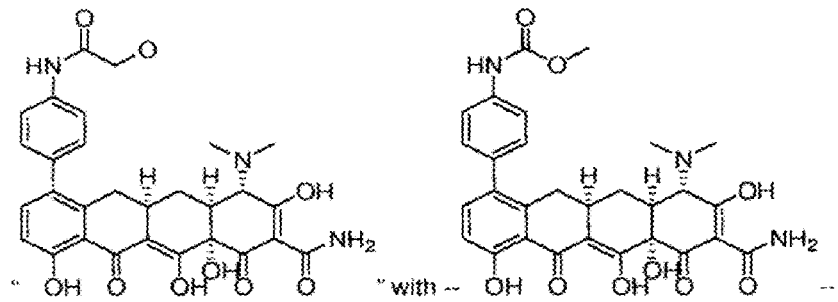

At Claim 55, column 589, fourth compound, replace

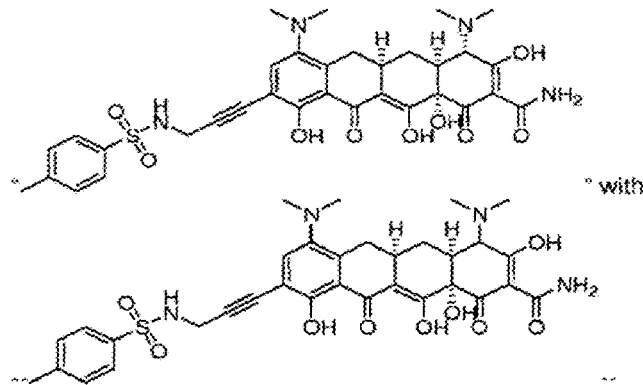

At Claim 55, fifth compound, replace

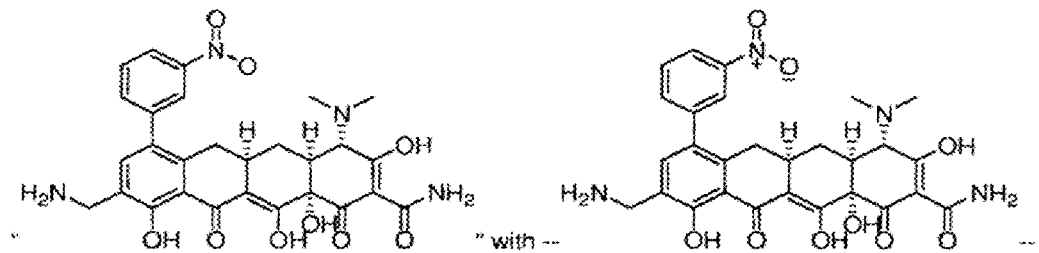

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At Claim 14, column 574, lines 50-60, replace

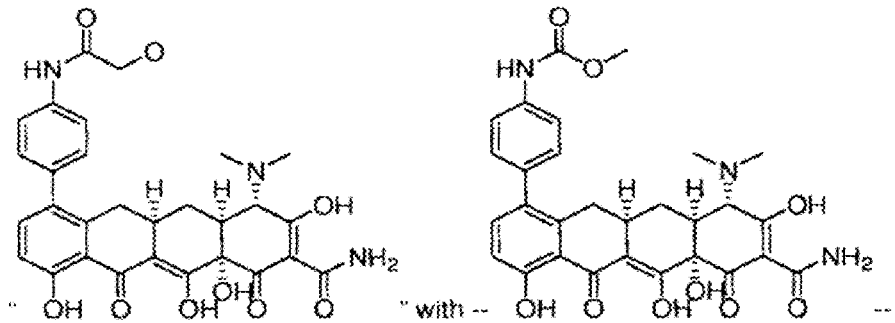

At Claim 55, column 589, fourth compound, replace

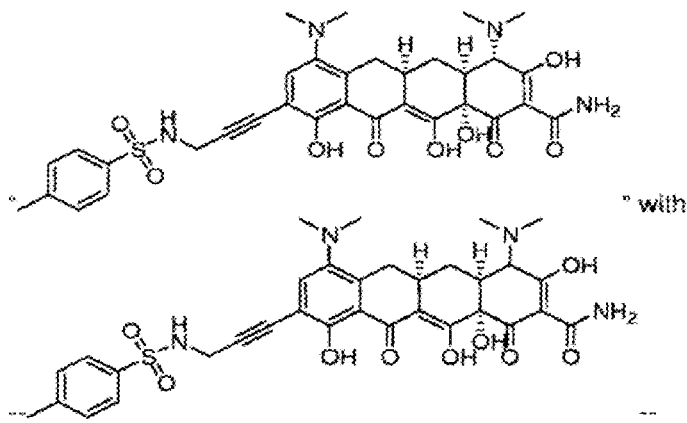

At Claim 55, fifth compound, replace

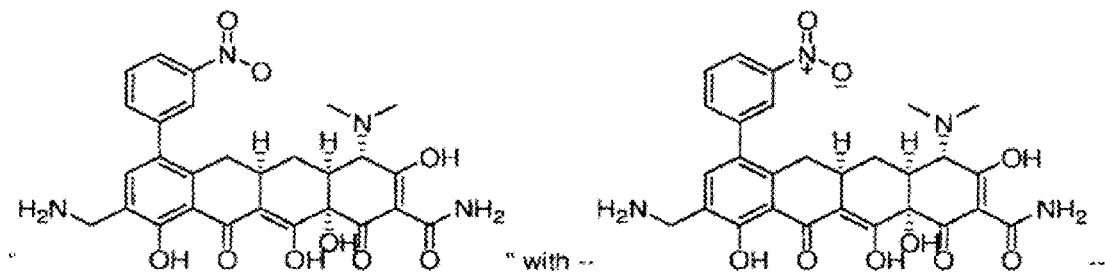

UNITED STATES PATENT AND TRADEMARK OFFICE
CERTIFICATE OF CORRECTION

PATENT NO. : 7,045,507 B2
APPLICATION NO. : 10/097634
DATED : May 16, 2006
INVENTOR(S) : Michael Draper et al.

It is certified that error appears in the above-identified patent and that said Letters Patent is hereby corrected as shown below:

At Claim 55, column 600, fourth compound, replace

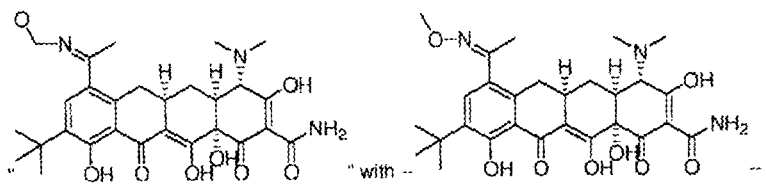

At Claim 55, column 601, second compound, replace

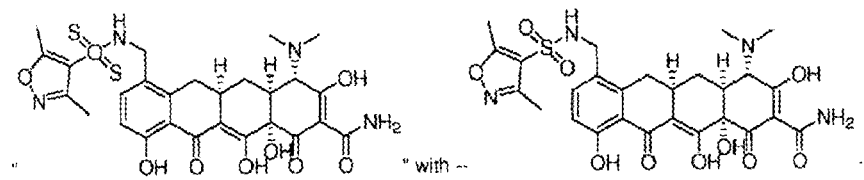

At Claim 55, column 602, second compound, replace

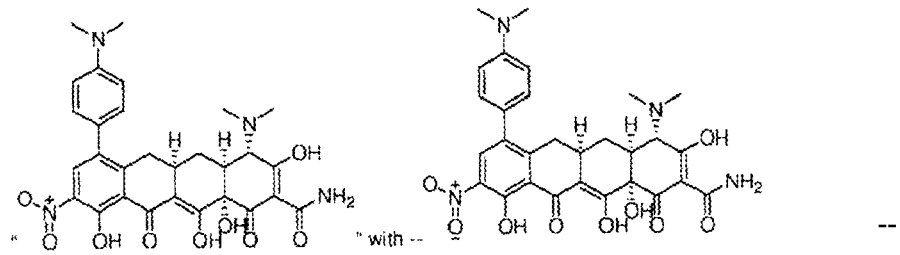

Signed and Sealed this

Twenty-sixth Day of August, 2008

JON W. DUDAS
*Director of the United States Patent and Trademark Office*